(12) United States Patent
Allen et al.

(10) Patent No.: US 11,247,990 B1
(45) Date of Patent: Feb. 15, 2022

(54) BICYCLIC FUSED PYRIDINE COMPOUNDS AS INHIBITORS OF TAM KINASES

(71) Applicant: ARRAY BIOPHARMA INC., Boulder, CO (US)

(72) Inventors: Shelley Allen, Boulder, CO (US); Mark Laurence Boys, Boulder, CO (US); Adam Cook, Boulder, CO (US); John Gaudino, Boulder, CO (US); Ronald Jay Hinklin, Boulder, CO (US); Ellen Laird, Boulder, CO (US); Oren T. McNulty, Boulder, CO (US); Andrew T. Metcalf, Boulder, CO (US); Brad Newhouse, Boulder, CO (US); John E. Robinson, Boulder, CO (US)

(73) Assignee: ARRAY BIOPHARMA INC, Boulder, CO (US)

( * ) Notice: Subject to any disclaimer, the term of this patent is extended or adjusted under 35 U.S.C. 154(b) by 0 days.

(21) Appl. No.: 16/893,784

(22) PCT Filed: Dec. 5, 2018

(86) PCT No.: PCT/US2018/064039
§ 371 (c)(1),
(2) Date: Jun. 5, 2020

(87) PCT Pub. No.: WO2019/113190
PCT Pub. Date: Jun. 13, 2019

Related U.S. Application Data

(60) Provisional application No. 62/595,997, filed on Dec. 7, 2017, provisional application No. 62/724,880, filed on Aug. 30, 2018.

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC .......................... C07D 471/04; C07D 519/00
USPC ................................................... 514/210.21
See application file for complete search history.

(56) References Cited

FOREIGN PATENT DOCUMENTS

| WO | 2005074603 A2 | 8/2005 |
|---|---|---|
| WO | 2013052417 A1 | 4/2013 |
| WO | 2015157123 A1 | 10/2015 |
| WO | 2018026663 A1 | 2/2018 |
| WO | 2018039275 A1 | 3/2018 |

OTHER PUBLICATIONS

Nantka-Namirski et al., Acta Poloniae Pharmaceutica (1961), 18, 449-60.*
Akalu et al., Immunological Reviews 2017; 276:165-177.
Ben-Batalla et al., Blood 2013, 122, 2443-2452.
Brand et al., Cancer Res. 2014, 74:5152-5164.
Brandao et al., Blood Cancer J., 2013, 3, e101.
Chambers et al., 1997, Immunity 7, 885-895.
Cook et al., 2013, The Journal of Clinical Investigation 123, 3231-3242.
Demarest et al., 2013, Biochemistry 52, 3102-3118.
Dufies et al., Oncotarget 2011,2, 874-885.
Elkabets et al., Cancer Cell 2015, 27:533-546.
Feneyrolles et al., 2014, Molecular Cancer Therapeutics 13, 2141-2148.
Giles et al., Mol. Cancer Ther. 2013, 12, 2541-2558.
Gioia et al.. Blood, 2011,118, 2211-2221.
Graham et al., 1995, Oncogene 10, 2349-2359.
Graham et al., 2014, Nature Reviews Cancer 14, 769-785.
Han, Biochem. Biophys. Res. Commun. 2013, 435, 493-500.
Hong et al., Cancer Lett., 2008,268, 314-324.
Huang, Cancer Res. 2010, 70, 7221-7231.
Hutterer et al., Clin. Caner Res. 2008, 14, 130-138.
International Preliminary Report on Patentability Written Opinion for PCT/US2018/064309, dated Jun. 9, 2020.
Keating et al., Mol. Cancer Ther. 2010, 9, 1298-1307.
Keating et al., Oncogene, 2006, 25, 6092-6100.
Kim et al., Mol. Oncol. 2013, 7, 1093-1102.
Koorstra et al., 2009, Cancer Biology & Therapy 8, 618-626.

(Continued)

*Primary Examiner* — Niloofar Rahmani
(74) *Attorney, Agent, or Firm* — Banner & Witcoff, Ltd.

(57) ABSTRACT

Provided herein are compounds of the Formula (I): and stereoisomers, tautomers and pharmaceutically acceptable salts thereof, wherein Ring A, $X^1$, $X^2$, $X^3$, $R^1$, $R^2$ and $R^3$ are as defined herein, which are inhibitors of one or more TAM kinases and are useful in the treatment and prevention of diseases which can be treated with a TAM kinase inhibitor.

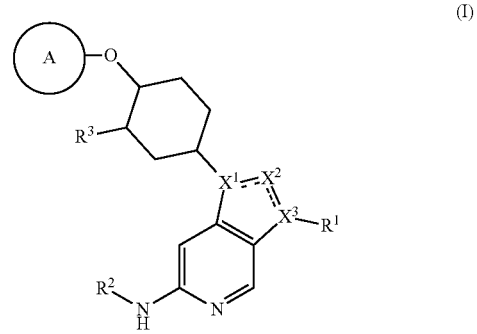

20 Claims, No Drawings

(56) References Cited

OTHER PUBLICATIONS

Lai et al., Neuron 6, 691-70, 1991.
Lay et al., Cancer Res. 2007, 67, 3878-3887.
Lee-Sherick et al., 2013, Oncogene 32, 5359-5368.
Lew et al., 2014. eLife, 3 :e03385.
Li et al., 2009, Oncogene 28, 3442-3455.
Linger et al., 2008, Advances in Cancer Research 100, 35-83.
Linger et al., Blood, 2013, 122, 1599-1609.
Linger et al., Oncogene, 2013, 32, 3420-3431.
Liu et al., Cancer Res. 2009, 69, 6871-6878.
Lu and Lemke, 2001, Science 293, 306-311.
Macleod, Cancer Res. 2005, 65, 6789-6800.
Mahadevan et al., Oncogene, 2007, 26, 3909-3919.
Meyer et al., Sci. Signal 2014, 6(287), ra66.
Miller et al., Cancer Discovery 2016, 6:382-39.
Niederst et al., Sci. Signaling, 2013, 6, re6).
Nishimura et al., 2001, Science 291, 319-322.
O'Bryan et al., 1991, Mol Cell Biol 11, 5016-5031.
Paolino et al., 2014, Nature 507, 508-512.
Pardoll, 2012, Cancer 12, 252-264.
Schlegel et al., 2013.
Schoumacher et al., Curr. Oncol. Rep. 2017; 19(3);19.
Seo et al., Genome Res. 22:2109-2119, 2012.
Shaver et al., Cancer Res. 76(16):4850-4860, 2016.
Shiozawa et al.. Neoplasia, 2010, 12, 116-127.
Song et al.. Cancer, 2011, 117, 734-743.
Tai et al., 2008, Oncogene 27, 4044-4055.
Waizenegger et al., 2014, Leukemia, 1-9.
Wang et al., Oncogene 2013, 32, 872-882.
Wang, Cancer Res. 2013, 73, 6516-6525.
Ware, Oncogenesis 2013, 2, e39.
Wilson et al., Cancer Res. 2014, 74(20), 5878-5890.
Zhang, Nat. Genet. 2013, 44(8), 852-860.
Zhao et al., Cancer Invest, 2012, 30, 287-294.
Zhu et al., Proc. Natl Acad. Sci. USA, 2009, 106, 17025-17030.

* cited by examiner

BICYCLIC FUSED PYRIDINE COMPOUNDS AS INHIBITORS OF TAM KINASES

CROSS-REFERENCE TO RELATED APPLICATIONS

This application is a 35 U.S.C. § 371 application of International Application No. PCT/US2018/064039, filed Dec. 5, 2018, which claims the benefit of U.S. Provisional Application No. 62/595,997, filed Dec. 7, 2017, and U.S. Provisional Application No. 62/724,880, filed Aug. 30, 2018, which applications are herein incorporated by reference in their entirety.

BACKGROUND

Provided herein are novel inhibitors of TAM kinases, pharmaceutical compositions comprising the compounds, processes for making the compounds, and the use of the compounds in therapy. More particularly, provided herein are bicyclic fused pyridine compounds useful in the treatment and prevention of diseases which can be treated with a TAM kinase inhibitor.

Receptor tyrosine kinases (RTKs) are cell surface proteins that transmit signals from the extracellular environment to the cell cytoplasm and nucleus to regulate cellular events such as survival, growth, proliferation, differentiation, adhesion and migration.

The TAM subfamily consists of three RTKs including TYRO3, AXL and Mer (Graham et al., 2014, Nature Reviews Cancer 14, 769-785; Linger et al., 2008, Advances in Cancer Research 100, 35-83). TAM kinases are characterized by an extracellular ligand binding domain consisting of two immunoglobulin-like domains and two fibronectin type III domains. Two ligands, growth arrest specific 6 (GAS6) and protein S (PROS1), have been identified for TAM kinases. GAS6 can bind to and activate all three TAM kinases, while PROS1 is a ligand for Mer and TYRO3 (Graham et al., 2014, Nature Reviews Cancer 14, 769-785).

AXL (also known as UFO, ARK, JTK11 and TYRO7) was originally identified as a transforming gene from DNA of patients with chronic myelogenous leukemia (O'Bryan et al., 1991, Mol Cell Biol 11, 5016-5031; Graham et al., 2014, Nature Reviews Cancer 14, 769-785; Linger et al., 2008, Advances in Cancer Research 100, 35-83). GAS6 binds to AXL and induces subsequent auto-phosphorylation and activation of AXL tyrosine kinase. AXL activates several downstream signaling pathways including PI3K-Akt, Raf-MAPK, PLC-PKC (Feneyrolles et al., 2014, Molecular Cancer Therapeutics 13, 2141-2148; Linger et al., 2008, Advances in Cancer Research 100, 35-83).

MER (also known as MERTK, EYK, RYK, RP38, NYK and TYRO 12) was originally identified as a phosphoprotein from a lymphoblastoid expression library (Graham et al., 1995, Oncogene 10, 2349-2359; Graham et al., 2014, Nature Reviews Cancer 14, 769-785; Linger et al., 2008, Advances in Cancer Research 100, 35-83). Both GAS6 and PROS1 can bind to Mer and induce the phosphorylation and activation of Mer kinase (Lew et al., 2014). Like AXL, MER activation also conveys downstream signaling pathways including PI3K-Akt and Raf-MAPK (Linger et al., 2008, Advances in Cancer Research 100, 35-83).

TYRO3 (also known as DTK, SKY, RSE, BRT, TIF, ETK2) was originally identified through a PCR-based cloning study (Lai et al., Neuron 6, 691-70, 1991; Graham et al., 2014, Nature Reviews Cancer 14, 769-785; Linger et al., 2008, Advances in Cancer Research 100, 35-83). Both ligands, GAS6 and PROS1, can bind to and activate TYRO3. Although the signaling pathways downstream of TYRO3 activation are the least studied among TAM RTKs, it appears that both PI3K-Akt and Raf-MAPK pathways are involved (Linger et al., 2008, Advances in Cancer Research 100, 35-83). AXL, MER and TYRO3 are found to be over-expressed in cancer cells.

Accordingly, there is a need in the art for compounds and methods of use thereof for the modulation of TAM kinases in treatment of cancer.

SUMMARY OF THE INVENTION

Provided herein is a compound of the Formula I.

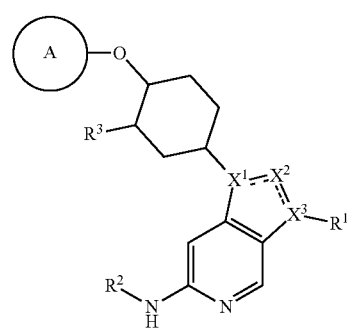

I and stereoisomers, tautomers and pharmaceutically acceptable salts thereof, wherein Ring A, $X^1$, $X^2$, $X^3$, $R^1$, $R^2$ and Rare as defined herein.

Also provided herein is a pharmaceutical composition comprising a compound of Formula I or a pharmaceutically acceptable salt thereof, in admixture with a pharmaceutically acceptable diluent or carrier.

Also provided herein is a method of inhibiting cell proliferation, in vitro or in vivo, the method comprising contacting a cell with an effective amount of a compound of Formula I or a pharmaceutically acceptable salt thereof, or a pharmaceutical composition thereof as defined herein.

Also provided herein is a method of treating cancer and/or inhibiting metastasis associated with a particular cancer in a patient in need of such treatment, the method comprising administering to the patient a therapeutically effective amount of a compound of Formula I or a pharmaceutically acceptable salt thereof or a pharmaceutical composition thereof as defined herein.

Also provided herein is a compound of Formula I or a pharmaceutically acceptable salt thereof, or a pharmaceutical composition thereof as defined herein for use in therapy.

Also provided herein is a compound of Formula I or a pharmaceutically acceptable salt thereof or a pharmaceutical composition thereof as defined herein for use in the treatment of cancer and/or inhibiting metastasis associated with a particular cancer.

Also provided herein is a compound of Formula I or a pharmaceutically acceptable salt thereof for use in the inhibition of TAM kinase activity.

Also provided herein is a compound of Formula I or a pharmaceutically acceptable salt thereof or a pharmaceutical composition thereof as defined herein, for use in the treatment of a TAM-associated disease or disorder such as cancer. In some embodiments, the TAM-associated cancer is a cancer having a chromosomal translocation that results in the expression of a TMEM87B-MERTK fusion protein (e.g., amino acids 1-55 of TMEM87B and amino acids 433-1000 of MERTK) or a AXL-MBIP fusion protein.

Also provided herein is the use of a compound of Formula I or a pharmaceutically acceptable salt thereof, as defined herein in the manufacture of a medicament for the treatment of cancer and/or inhibiting metastasis associated with a particular cancer.

Also provided herein is a use of a compound of Formula I or a pharmaceutically acceptable salt thereof, as defined herein in the manufacture of a medicament for the inhibition of TAM kinase activity.

Also provided herein is the use of a compound of Formula I or a pharmaceutically acceptable salt thereof, as defined herein, in the manufacture of a medicament for the treatment of a TAM-associated disease or disorder such as cancer.

Also provided herein is a pharmaceutical combination for treating cancer (e.g., a TAM-associated cancer) in a patient in need thereof, which comprises (a) a compound of Formula I or a pharmaceutically acceptable salt thereof, and (b) an additional anticancer agent (e.g., any of the additional anticancer agents described herein), wherein the compound of Formula I or the pharmaceutically acceptable salt thereof and the additional therapeutic are formulated as separate compositions or dosages for simultaneous, separate or sequential use for the treatment of cancer, wherein the amounts of the compound of Formula I or a pharmaceutically acceptable salt thereof and of the additional anticancer agent are together effective in treating the cancer. Also provided herein is a pharmaceutical composition comprising such a combination. Also provided herein is the use of such a combination for the preparation of a medicament for the treatment of cancer. Also provided herein is a commercial package or product comprising such a combination as a combined preparation for simultaneous, separate or sequential use; and to a method of treatment of cancer a patient in need thereof.

Also provided are methods of treating an individual with cancer that include administering a compound of Formula I or a pharmaceutically acceptable salt thereof, before, during, or after administration of another anticancer agent (e.g., another anticancer agent to which the subject has previously developed resistance, e.g., any of the additional anticancer agents described herein).

Also provided herein are methods of treating a patient identified or diagnosed as having a TAM-associated cancer that include administering to a patient identified or diagnosed as having a TAM-associated cancer a therapeutically effective amount of a compound of Formula I or a pharmaceutically acceptable salt thereof, or pharmaceutical composition including a therapeutically effective amount of a compound of Formula I or a pharmaceutically acceptable salt thereof.

Also provided herein are methods of treating a patient having a cancer that include (a) identifying the patient as having a TAM-associated cancer, and (b) administering to the patient identified as having a TAM-associated cancer a therapeutically effective amount of a compound of Formula I or a pharmaceutically acceptable salt thereof, or a pharmaceutical composition including a therapeutically effective amount of a compound of Formula I or a pharmaceutically acceptable salt thereof.

Also provided herein are methods of decreasing the risk of developing a metastasis or an additional metastasis in a patient identified or diagnosed as having a TAM-associated cancer that include administering to a patient identified or diagnosed as having a TAM-associated cancer a therapeutically effective amount of a compound of Formula I or a pharmaceutically acceptable salt thereof, or a pharmaceutical composition including a therapeutically effective amount of a compound of Formula I or a pharmaceutically acceptable salt thereof.

Also provided herein are methods of decreasing the risk of developing a metastasis or an additional metastasis in a patient having a cancer that include: (a) identifying a patient having a TAM-associated cancer, and (b) administering to the identified as having a TAM-associated cancer a therapeutically effective amount of a compound of Formula I or a pharmaceutically acceptable salt thereof, or a pharmaceutical composition including a therapeutically effective amount of a compound of Formula I or a pharmaceutically acceptable salt thereof.

Also provided herein are methods of decreasing migration and/or invasion of a cancer cell in a patient identified or diagnosed as having a TAM-associated cancer that include administering to a patient identified or diagnosed as having a TAM-associated cancer a therapeutically effective amount of a compound of Formula I or a pharmaceutically acceptable salt thereof, or a pharmaceutical composition including a therapeutically effective amount of a compound of Formula I or a pharmaceutically acceptable salt thereof.

Also provided herein are methods of decreasing migration and/or invasion of a cancer cell in a patient having a cancer that include (a) identifying the patient as having a TAM-associated cancer; and (b) administering to the patient identified as having a TAM-associated cancer a therapeutically effective amount of a compound of Formula I or a pharmaceutically acceptable salt thereof, or a pharmaceutical composition including a therapeutically effective amount of a compound of Formula I or a pharmaceutically acceptable salt thereof.

Also provided herein are methods of selecting a treatment for a patient identified or diagnosed as having a TAM-associated cancer that include selecting a compound of Formula I or a pharmaceutically acceptable salt thereof, or a pharmaceutical composition including a therapeutically effective amount of a compound of Formula I or a pharmaceutically acceptable salt thereof, for a patient identified or diagnosed as having a TAM-associated cancer.

Also provided herein are methods of selecting a treatment for a patient that include (a) identifying the patient as having a TAM-associated cancer, and (b) selecting a compound of Formula I or a pharmaceutically acceptable salt thereof, or a pharmaceutical composition including a therapeutically effective amount of a compound of Formula I or a pharmaceutically acceptable salt thereof, for the patient identified as having a TAM-associated cancer.

Also provided herein are methods of selecting a treatment for a patient identified or diagnosed as having a cancer that include (a) administering an additional anticancer agent to the patient, (b) after (a), detecting increased expression and/or activity of a TAM kinase in a cancer cell from the patient, and (c) after (b), selecting a compound of Formula I or a pharmaceutically acceptable salt thereof, or a pharmaceutical composition including a therapeutically effective amount of a compound of Formula I or a pharmaceutically acceptable salt thereof, for the patient.

Also provided herein are methods of treating a patient identified or diagnosed as having a cancer that include: (a) administering to the patient identified or diagnosed as having a cancer one or more doses of at least one additional anticancer agent; (b) after (a), detecting an increase in the expression and/or activity of a TAM kinase in a cancer cell or an immune cell from the subject; and (c) after (b), administering to the patient a compound of Formula I or a pharmaceutically acceptable salt thereof, or a pharmaceutical composition including a therapeutically effective amount of a compound of Formula I or a pharmaceutically acceptable salt thereof. In some embodiments of these methods, step (c) further includes administering to the patent the at least one additional anticancer agent.

Also provided are methods of treating a patient identified or diagnosed as having a cancer that include: (a) detecting an increase in the expression and/or activity of a TAM kinase in a cancer cell or an immune cell from a patient identified or diagnosed as having a cancer and previously administered one or more doses of at least one additional anticancer agent; and (b) after (a), administering to the patient a therapeutically effective amount of a compound of Formula I or a pharmaceutically acceptable salt thereof, or a pharmaceutical composition including a therapeutically effective amount of a compound of Formula I or a pharmaceutically acceptable salt thereof. In some embodiments of these methods, step (b) further includes administering to the patient the at least one additional anticancer agent.

Also provided herein are methods of treating a patient identified or diagnosed as having a cancer that has been previously administered one or more doses of at least one additional anticancer agent and has been identified as having a cancer cell or an immune cell that has increased expression and/or activity of a TAM kinase that include administering a therapeutically effective amount of a compound of Formula I or a pharmaceutically acceptable salt thereof, or a pharmaceutical composition including a therapeutically effective amount of a compound of Formula I or a pharmaceutically acceptable salt thereof, to the patient. In some embodiments of these methods, step (b) further includes administering to the patient the at least one additional anticancer agent.

Also provided herein are methods of treating a patient identified or diagnosed as having a cancer that include: (a) selecting a patient identified or diagnosed as having increased expression and/or activity of a TAM kinase in a cancer cell or an immune cell; and (b) after (a) administering to the selected patient a therapeutically effective amount of a compound of Formula I or a pharmaceutically acceptable salt thereof, or a pharmaceutical composition including a therapeutically effective amount of a compound of Formula I or a pharmaceutically acceptable salt thereof. In some embodiments of these methods, step (b) further includes administering to the patient at least one additional anticancer agent.

Also provided herein are methods of treating a patient identified or diagnosed as having a cancer that include: (a) selecting a patient identified or diagnosed as having a cancer that has been previously administered one or more doses of an additional anticancer agent and identified as having a cancer cell or an immune cell having increased expression and/or activity of a TAM kinase; and (b) after (a), administering to the selected patient a therapeutically effective amount of a compound of Formula I or a pharmaceutically acceptable salt thereof, or a pharmaceutical composition including a therapeutically effective amount of a compound of Formula I or a pharmaceutically acceptable salt thereof. In some embodiments of these methods, step (b) further includes administering to the patient at least one additional anticancer agent.

Also provided herein are methods of treating a patient identified or diagnosed as having a TAM-associated cancer that include: (a) administering to the patient identified or diagnosed as having a TAM-associated cancer one or more doses of a TAM kinase inhibitor; (b) after (a), detecting resistance of the TAM-associated cancer in the patient to the TAM kinase inhibitor; and (c) after (b), administering to the patient a therapeutically effective amount of a compound of Formula I or a pharmaceutically acceptable salt thereof, or a pharmaceutical composition including a therapeutically effective amount of a compound of Formula I or a pharmaceutically acceptable salt thereof. In some embodiments of these methods, step (c) further includes administering to the patient at least one additional anticancer agent.

Also provided herein are methods of treating a patient identified or diagnosed as having a TAM-associated cancer that include: (a) detecting resistance of the TAM-associated cancer in the patient to a TAM kinase inhibitor that was previously administered to the patient; and (b) after (a), administering to the patient a therapeutically effective amount of a compound of Formula I or a pharmaceutically acceptable salt thereof, or a pharmaceutical composition including a therapeutically effective amount of a compound of Formula I or a pharmaceutically acceptable salt thereof. In some embodiments of these methods, step (b) further includes administering to the patient at least one additional anticancer agent.

Also provided herein are methods of treating a patient identified or diagnosed as having a TAM-associated cancer and determined to have previously developed resistance to a TAM kinase inhibitor that include administering to the patient a therapeutically effective amount of a compound of Formula I or a pharmaceutically acceptable salt thereof, or a pharmaceutical composition including a therapeutically effective amount of a compound of Formula I or a pharmaceutically acceptable salt thereof. Some embodiments of these methods further include administering to the patient at least one additional anticancer agent.

Also provided herein are methods of decreasing immune tolerance in a subject in need thereof that include administering to the subject a therapeutically effective amount of a compound of Formula I or a pharmaceutically acceptable salt thereof, or a pharmaceutical composition thereof as defined herein.

Also provided herein are methods of inhibiting angiogenesis in a subject in need thereof, the method comprising administering to the subject a therapeutically effective amount of a compound of Formula I or a pharmaceutically acceptable salt thereof, or a pharmaceutical composition thereof as defined herein.

Also provided herein are methods of suppressing resistance to a therapeutic agent in a subject in need thereof that include administering to the subject a therapeutically effective amount of (i) a compound of Formula I or a pharmaceutically acceptable salt thereof, or any of the pharmaceutical compositions thereof described herein, and (ii) the therapeutic agent, where the therapeutic agent is selected from the group consisting of a chemotherapeutic agent, a PI-3 kinase inhibitor, an EGFR inhibitor, a HER2/neu inhibitor, an FGFR inhibitor, an ALK inhibitor, an IGF1R inhibitor, a VEGFR inhibitor, a PDGFR inhibitor, a glucocorticoid, a BRAF inhibitor, a MEK inhibitor, a HER4 inhibitor, a MET inhibitor, a RAF inhibitor, an Akt inhibitor, a FTL-3 inhibitor, and a MAP kinase pathway inhibitor.

Also provided herein are methods of treating a patient identified or diagnosed as having a TAM-associated cancer that include administering radiation therapy before or after administering to the patient a therapeutically effective amount of a compound of Formula I or a pharmaceutically acceptable salt thereof, or a pharmaceutical composition including a therapeutically effective amount of a compound of Formula I or a pharmaceutically acceptable salt thereof.

Also provided herein are methods of treating a patient identified or diagnosed as having a TAM-associated cancer that include administering surgery before or after administering to the patient a therapeutically effective amount of a compound of Formula I or a pharmaceutically acceptable salt thereof, or a pharmaceutical composition including a therapeutically effective amount of a compound of Formula I or a pharmaceutically acceptable salt thereof.

Also provided herein are methods for inhibiting a TAM kinase activity in a mammalian cell in need thereof that include contacting the mammalian cell with a compound of Formula I or a pharmaceutically acceptable salt thereof, or a pharmaceutical composition including a therapeutically effective amount of a compound of Formula I or a pharmaceutically acceptable salt thereof.

Also provided herein is a process for preparing a compound of Formula I or a pharmaceutically acceptable salt thereof.

Also provided herein is a compound of Formula I or a pharmaceutically acceptable salt thereof obtained by a process of preparing the compound as defined herein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION OF THE INVENTION

Provided herein is a compound of the Formula I:

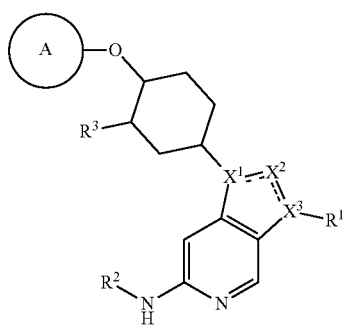

I and stereoisomers, tautomers and pharmaceutically acceptable salts thereof, wherein:

one of the dashed lines in Formula I is a single bond and the other dashed line is a double bond;

$X^1$ is N, $X^2$ is N, and $X^3$ is C, or $X^1$ is C, $X^2$ is N and $X^3$ is N, or $X^1$ is N, $X^2$ is CH and $X^3$ is C;

Ring A is $hetAr^1$, $hetAr^2$ or $Ar^1$;

$hetAr^1$ is a 5-6 membered heteroaryl ring having 1-3 ring nitrogen atoms or a 9-10 membered bicyclic heteroaryl having 1-2 ring nitrogen atoms, wherein one or more ring carbon atoms is optionally substituted with a substituent independently selected from (a) C1-C6 alkyl, (b) C1-C6 fluoroalkyl, (c) C1-C6 alkoxy, (d) C1-C6 fluoroalkoxy, (e) C1-C6 hydroxyalkyl, (f) halogen, (g) cyano, (h) hydroxyl, (i) R'R"N(CH$_2$)$_n$— wherein n is 0 or 1 and R' and R" are independently H or C1-C6 alkyl, (j) (C1-C6 alkoxy)C(=O)—, (k) R'R"NC(=O)— wherein R' and R" are independently H or C1-C6 alkyl, (l) $hetCyc^a$CH$_2$—, (m) C3-C6 cycloalkyl, (n) acetylenyl, and (o) benzyloxy;

$hetAr^2$ is a 6-membered heteroaryl ring having 1-2 ring nitrogen atoms, wherein one ring carbon atom of said heteroaryl ring is substituted with oxo and one of said ring nitrogen atoms is substituted with (a) C1-C6 alkyl, (b) C1-C6 fluoroalkyl, (c) (C1-C6 alkoxy)C1-C6 alkyl-, (d) (R'R"N)C1-C6 alkyl- wherein R' and R" are independently H or C1-C6 alkyl, or (e) $Ar^a$CH$_2$— wherein $Ar^a$ is phenyl optionally substituted with C1-C6 alkoxy, wherein one or more of the remaining ring carbon atoms is optionally substituted with one or two substituents independently selected from C1-C6 alkyl and C1-C6 fluoroalkyl;

$Ar^1$ is phenyl optionally substituted with one or more substituents independently selected from (a) halogen, (b) cyano, (c) C1-C6 alkyl, (d) C1-C6 fluoroalkyl, (e) C1-C6 alkoxy, (f) C3-C6 cycloalkyl, (g) R'R"N(CH$_2$)$_n$— wherein n is 0 or 1 and R' and R" are independently H or C1-C6 alkyl, (h) (C1-C6 alkyl)SO$_2$—, (i) (C1-C6 alkoxy)C(=O)—, (j) HOC(=O)—, and (k) R'R"NC(=O)— wherein R' and R" are independently H, C1-C6 alkyl or (C1-C6 alkoxy)C1-C6 alkyl-, or $Ar^1$ is phenyl fused to a 6-membered heteroaryl ring having a ring nitrogen atom, wherein said ring nitrogen atom is substituted with C1-C6 alkyl and one ring carbon atom of said heteroaryl ring is substituted with oxo, or $Ar^1$ is phenyl fused to a 5-6 membered heterocyclic ring having a ring nitrogen and one ring carbon atom of said heteroaryl ring is substituted with oxo;

when $X^3$ is N, then $R^1$ is $Ar^2$, $hetAr^3$, $hetAr^4$, $hetCyc^1$, $Cyc^1$, or C1-C6 alkyl, and when $X^3$ is C, then $R^1$ is $Ar^2$, $hetAr^3$, $hetAr^4$, $hetCyc^1$, $Cyc^1$, C1-C6 alkyl or Br;

$Ar^2$ is phenyl optionally substituted with one or more substituents independently selected from (a) halogen, (b) CN, (c) C1-C6 hydroxyalkyl, (d) C2-C6 dihydroxyalkyl, (e) C1-C6 alkoxy, (f) $hetCyc^a$(CH$_2$)$_n$— wherein n is 0, 1 or 2, (g) $hetCyc^a$-C(=O)—, (h) $hetCyc^a$-O—, (i) C3-C6 cycloalkyl optionally substituted with cyano or a 5-6 membered heterocyclic ring having 1-2 ring nitrogen atoms wherein said heterocyclic ring is optionally substituted with C1-C6 alkyl, (j) R'R"NC(=O)— wherein R' and R" are independently H, C1-C6 alkyl, C1-C6 hydroxyalkyl, or C3-C6 cycloalkyl, (k) (C1-C6 alkyl)C(=O)NHCH$_2$—, (l) (C1-C6 alkyl)SO$_2$—, and (m) R'R"NSO$_2$— wherein R' and R" are independently H or C1-C6 alkyl, or $Ar^2$ is phenyl fused to a 5-6 membered saturated heterocyclic ring having 1-2 ring heteroatoms independently selected from N and S wherein said S is optionally oxidized to SO$_2$, wherein said heterocyclic ring is optionally substituted with oxo and is further optionally substituted with C1-C6 alkyl;

each $hetCyc^a$ is independently a 5-6 membered heterocyclic ring having 1-2 ring heteroatoms independently selected from N and O, wherein said ring is optionally substituted with one or more substituents independently selected from halogen, cyano, hydroxyl, C1-C6 alkyl, C1-C6 hydroxyalkyl, C1-C6 alkoxy, (C1-C6 alkoxy)C1-C6 alkyl-, (C1-C6 alkoxy)C1-C6 alkoxy-, and R'R"N— wherein R' and R" are independently H or C1-C6 alkyl;

hetAr$^3$ is a 5-6 membered heteroaryl ring having 1-2 ring heteroatoms independently selected from N and O, wherein said heteroaryl ring is optionally substituted with one or more substituents independently selected from (a) halogen, (b) cyano, (c) C1-C6 alkyl, (d) C1-C6 fluoroalkyl, (e) C1-C6 hydroxyalkyl wherein said alkyl portion is optionally substituted with R'R"N— wherein R' and R" are independently H or C1-C6 alkyl, (f) C2-C6 dihydroxyalkyl, (g) C1-C6 cyanoalkyl, (h) C1-C6 alkoxy, (i) R'R"N— wherein R' and R" are independently H, C1-C6 alkyl, or (C1-C6 alkoxy)C1-C6 alkyl-, (k) (C1-C6 alkylSO$_2$)C1-C6 alkyl-, (l) C3-C6 cycloalkyl optionally substituted with hydroxyl, (m) R'R"NC(=O)C1-C6 alkyl- wherein R' and R" are independently H or C1-C6 alkyl, and (n) hetCyc$^b$(CH$_2$)$_n$— wherein n is 0, 1 or 2;

hetCyc$^b$ is a 4-6 membered heterocyclic ring having 1-2 ring heteroatoms independently selected from N, O and S, wherein said S is optionally oxidized to SO$_2$, and wherein said ring is optionally substituted with one or more substituents independently selected from halogen, C1-C6 alkyl, and (C1-C6 alkoxy)C1-C6 alkyl-;

hetAr$^4$ is a 6-membered heteroaryl ring having 1-2 ring nitrogen atoms, wherein a ring carbon atom of said heteroaryl ring is substituted with oxo and wherein one of said ring nitrogen atoms is substituted with C1-C6 alkyl or C1-C6 fluoroalkyl;

hetCyc$^1$ is a 5-6 membered saturated or partially unsaturated monocyclic heterocyclic ring having 1-2 ring heteroatoms independently selected from N and O or a 8-10 membered fused saturated heterocyclic ring having 1-2 ring heteroatoms independently selected from N and O, wherein said heterocyclic rings are optionally substituted with one or more substituents independently selected from (a) halogen, C1-C6 alkyl, (b) C1-C6 alkoxy, (c) (C1-C6 alkoxy)C1-C6 alkyl-, (d) (C1-C6 alkyl)C(=O)—, (e) hydroxyl, and (f) R'R"N— wherein R' and R" are independently H or C1-C6 alkyl;

Cyc$^1$ is 3-6 membered cycloalkyl ring optionally substituted with R'R"N— wherein R' and R" are independently H or C1-C6 alkyl;

R$^2$ is H, C1-C6 alkyl, C1-C6 fluoroalkyl, C3-C6 cycloalkyl, (C3-C6 cycloalkyl)C1-C6 alkyl-, phenyl optionally substituted with one or more substituents independently selected from cyano and halogen, or C1-C6 alkyl wherein 2-5 hydrogens are replaced by deuterium; and R$^3$ is hydrogen or hydroxyl.

In one embodiment, compounds of Formula I are a mixture of cis- and trans-isomers, referring to the configuration of the (Ring A)-O— moiety and the bicyclic ring of Formula I. In one embodiment, compounds of Formula I are a mixture of cis- and trans-isomers, referring to the configuration of the (Ring A)-O— moiety and the bicyclic ring of Formula I. In one embodiment, the (Ring A)-O— moiety and the bicyclic ring of compounds of Formula I are in the cis configuration. In one embodiment, the (Ring A)-O— moiety and the bicyclic ring of compounds of Formula I are in the trans configuration.

For complex chemical names employed herein, the substituent group is named before the group to which it attaches. For example, methoxyethyl comprises an ethyl backbone with a methoxy substituent.

The term "halogen" means —F (sometimes referred to herein as "fluoro" or "fluoros"), —Cl, —Br and —I.

The terms "C1-C6 alkyl" and "C2-C6 alkyl" as used herein refer to saturated linear or branched-chain monovalent hydrocarbon radicals of one to six or two to six carbon atoms, respectively. Examples include, but are not limited to, methyl, ethyl, 1-propyl, isopropyl, 1-butyl, isobutyl, sec-butyl, tert-butyl, 2-methyl-2-propyl, pentyl, neopentyl, and hexyl.

The term "C1-C6 alkoxy" as used herein refers to a saturated linear or branched-chain monovalent alkoxy radical of one to six carbon atoms, wherein the radical is on the oxygen atom. Examples include methoxy, ethoxy, propoxy, isopropoxy, butoxy and tert-butoxy.

The terms "C1-C6 fluoroalkyl" and "C1-C6 fluoroalkoxy" as used herein include C1-C6 alkyl and C1-C6 alkoxy groups, respectively, that are substituted with one or more fluorines, such as, but not limited to, trifluoromethyl, difluoromethyl, 2,2,2-trifluoroethyl, 1-fluoromethyl-2-fluoroethyl, trifluoromethoxy, and the like.

The term "(C1-C6 alkoxy)C1-C6 alkyl-" as used herein refers to saturated linear or branched-chain monovalent radicals of one to six carbon atoms, wherein one of the carbon atoms is substituted with a (C1-C6 alkoxy) group as defined herein. Examples include methoxymethyl (CH$_3$OCH$_2$—) and methoxyethyl (CH$_3$OCH$_2$CH$_2$—).

The term "(C1-C6 alkoxy)C1-C6 alkoxy-" as used herein refers to a C1-C6 alkoxy group as defined herein, wherein one of the carbon atoms is substituted with a (C1-C6 alkoxy) group as defined herein. An examples includes methoxyethoxy (CH$_3$OCH$_2$CH$_2$O—).

The term "C1-C6 hydroxyalkyl-" as used herein refers to a saturated linear or branched-chain monovalent alkyl radicals of one to six carbon atoms, respectively, wherein one of the carbon atoms is substituted with a hydroxyl group.

The term "C2-C6 dihydroxyalkyl-" as used herein refers to a saturated linear or branched-chain monovalent alkyl radical of two to six carbon atoms, wherein two of the carbon atoms are substituted with a hydroxyl group, provided two hydroxyl groups are not on the same carbon atom.

The term "C1-C6 cyanoalkyl" as used herein refers to a saturated linear or branched-chain monovalent alkyl radicals of one to six carbon atoms, respectively, wherein one of the carbon atoms is substituted with cyano (—CN).

The term "C3-C6 cycloalkyl" as used herein refers to cyclopropyl, cyclobutyl, cyclopentyl or cyclohexyl.

The term "(R'R"N)C1-C6 alkyl-" as used herein refers to a saturated linear or branched-chain monovalent alkyl radicals of one to six carbon atoms, respectively, wherein one of the carbon atoms is substituted with a R'R"N— radical, wherein R' and R" are independently H or C1-C6 alkyl.

The term "(C1-C6 alkylSO$_2$)C1-C6 alkyl-" as used herein refers to a saturated linear or branched-chain monovalent alkyl radicals of one to six carbon atoms, respectively, wherein one of the carbon atoms is substituted with a C1-C6 alkylSO$_2$— radical.

The term "R'R"NC(=O)C1-C6 alkyl-" as used herein refers to a saturated linear or branched-chain monovalent alkyl radicals of one to six carbon atoms, respectively, wherein one of the carbon atoms is substituted with a R'R"NC(=O)— radical, wherein R' and R" are independently H or C1-C6 alkyl.

The term "oxo" or "oxo group" as used herein means an oxygen that is double bonded to a carbon atom, i.e., =O. For example, The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The term "tautomer" as used herein refers to compounds whose structures differ markedly in arrangement of atoms, but which exist in easy and rapid equilibrium, and it is to be understood that compounds provided herein may be depicted as different tautomers, and when compounds have tautomeric forms, all tautomeric forms are intended to be within the scope of the invention, and the naming of the compounds does not exclude any tautomer. Exemplary tautomerizations include, but are not limited to, keto-to-enol; amide-to-imide; lactam-to-lactim; enamine-to-imine; and enamine-to-(a different) enamine tautomerizations. A specific example of phenol-keto tautomerization is the interconversion of pyridin-2-ol and pyridin-2(1H)-one tautomers, for example:

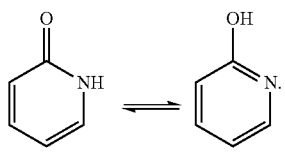

It will be appreciated that certain compounds provided herein may contain one or more centers of asymmetry and may therefore be prepared and isolated in a mixture of isomers such as a racemic mixture, or in an enantiomerically pure form.

In certain embodiments of Formula I, $X^1$ is N, $X^2$ is N, and $X^3$ is C, such that Formula I has the structure of Formula I-a:

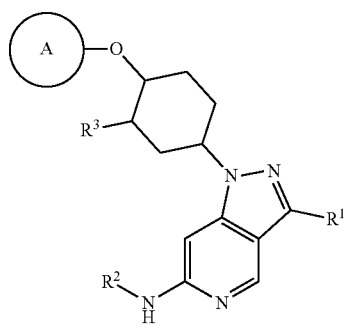

I-a wherein Ring A, $R^1$, $R^2$ and $R^3$ are as defined for Formula I. In one embodiment, compounds of Formula I-a are a mixture of cis- and trans-isomers, referring to the configuration of the (Ring A)-O— moiety and the bicyclic ring of Formula I-a. In one embodiment, the (Ring A)-O— moiety and the bicyclic ring of compounds of Formula I-a are in the cis configuration. In one embodiment, the (Ring A)-O— moiety and the bicyclic ring of compounds of Formula I-a are in the trans configuration.

In certain embodiments of Formula I, $X^1$ is C, $X^2$ is N, and $X^3$ is N, such that Formula I has the structure of Formula I-b:

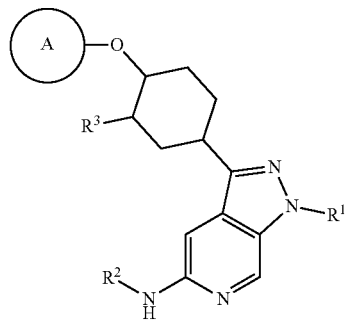

I-b wherein Ring A, $R^1$, $R^2$ and $R^3$ are as defined for Formula I. In one embodiment, compounds of Formula I-b are a mixture of cis- and trans-isomers, referring to the configuration of the (Ring A)-O— moiety and the bicyclic ring of compounds of Formula I-b. In one embodiment, the (Ring A)-O— moiety and the bicyclic ring of compounds of Formula I-b are in the cis configuration. In one embodiment, the (Ring A)-O— moiety and the bicyclic ring of Formula I-b are in the trans configuration.

In certain embodiments of Formula I, $X^1$ is N, $X^2$ is CH, and $X^3$ is C, such that Formula I has the structure of Formula I-c

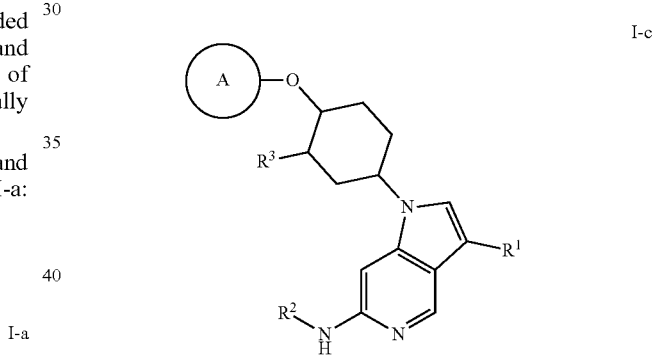

I-c wherein Ring A, $R^1$, $R^2$ and $R^3$ are as defined for Formula I. In one embodiment, compounds of Formula I-c are a mixture of cis- and trans-isomers, referring to the configuration of the (Ring A)-O— moiety and the bicyclic ring of compounds of Formula I-c. In one embodiment, the (Ring A)-O— moiety and the bicyclic ring of compounds of Formula I-c are in the cis configuration. In one embodiment, the (Ring A)-O— moiety and the bicyclic ring of Formula I-c are in the trans configuration.

In certain embodiments of Formula I, Ring A is hetAr$^1$, wherein hetAr$^1$ is a 5-6 membered heteroaryl ring having 1-3 ring nitrogen atoms or a 9-10 membered bicyclic heteroaryl having 1-2 ring nitrogen atoms, wherein one or more ring carbon atoms is optionally substituted with a substituent independently selected from (a) C1-C6 alkyl, (b) C1-C6 fluoroalkyl, (c) C1-C6 alkoxy, (d) C1-C6 fluoroalkoxy, (e) C1-C6 hydroxyalkyl, (f) halogen, (g) cyano, (h) hydroxyl, (i) R'R"N(CH$_2$)$_n$— wherein n is 0 or 1 and R' and R" are independently H or C1-C6 alkyl, (j) (C1-C6 alkoxy)C(=O)—, (k) R'R"NC(=O)— wherein R' and R" are independently H or C1-C6 alkyl, (l) hetCyc$^a$CH$_2$—, (m) C3-C6 cycloalkyl, (n) acetylenyl, and (o) benzyloxy.

Non-limiting examples when Ring A is hetAr¹ include the structures:
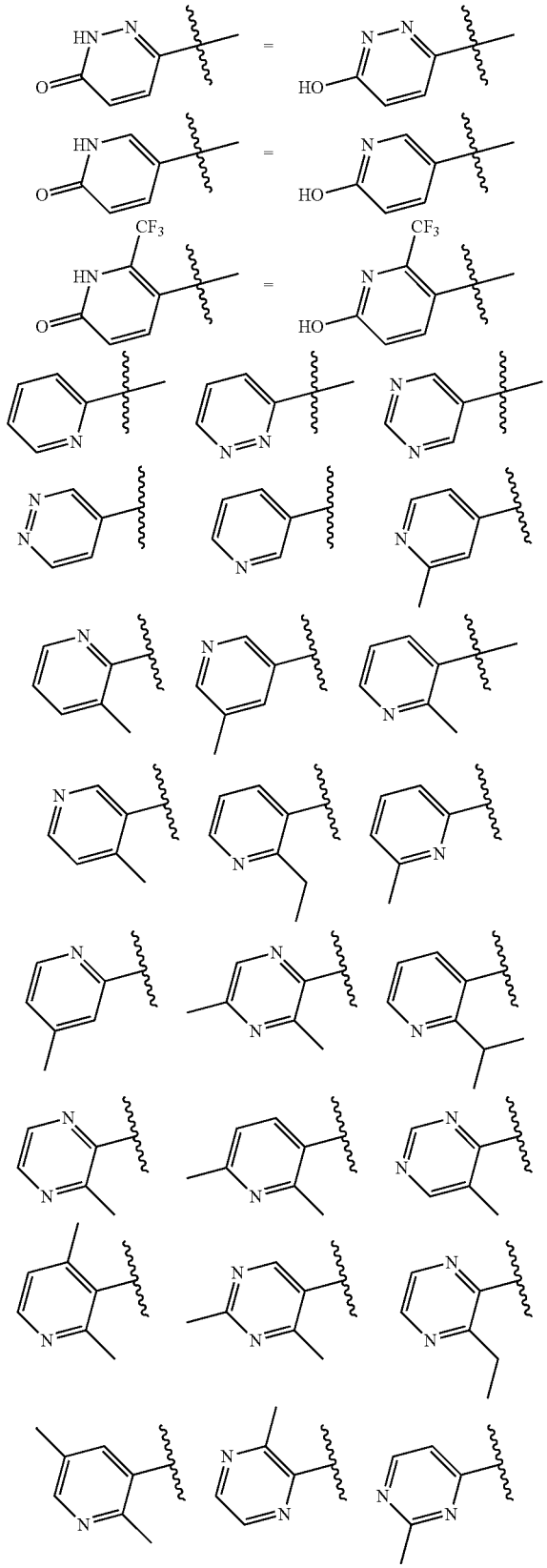
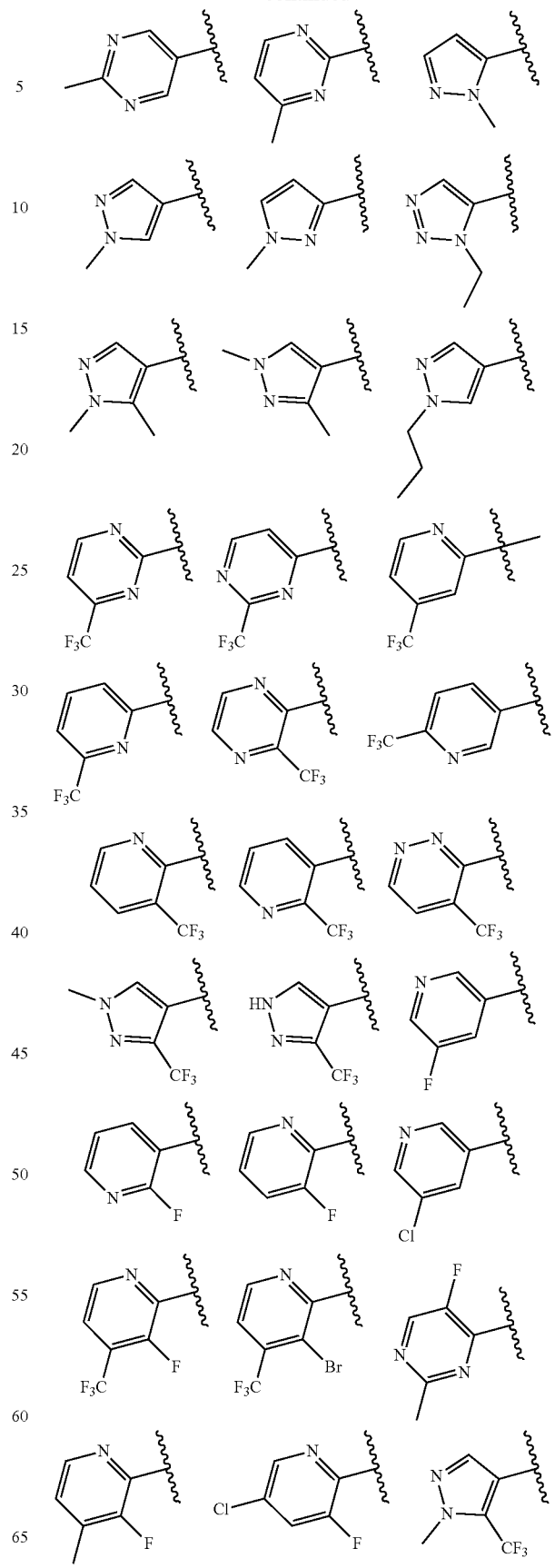

-continued

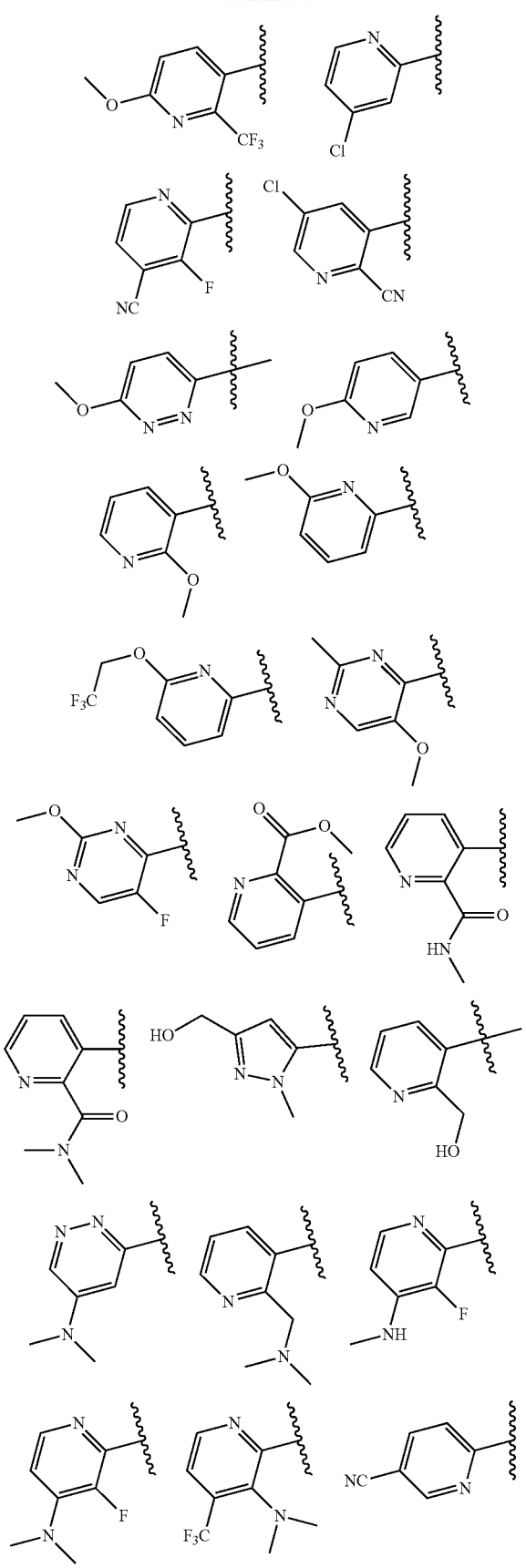

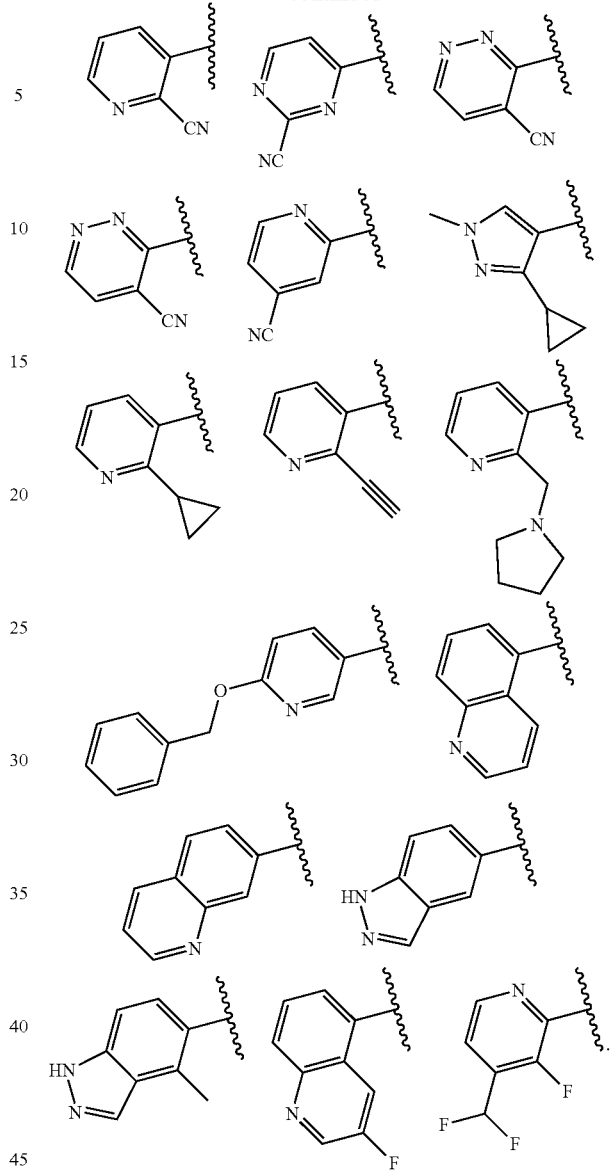

In certain embodiments of Formula I when Ring A is hetAr¹, Formula I is Formula I-a.

In certain embodiments of Formula I when Ring A is hetAr¹, Formula I is Formula I-b.

In certain embodiments of Formula I when Ring A is hetAr¹, Formula I is Formula I-c.

In certain embodiments of Formula I, Ring A is hetAr², wherein hetAr² is a 6-membered heteroaryl ring having 1-2 ring nitrogen atoms, wherein one ring carbon atom of said heteroaryl ring is substituted with oxo and one of said ring nitrogen atoms is substituted with (a) C1-C6 alkyl, (b) C1-C6 fluoroalkyl, (c) (C1-C6 alkoxy)C1-C6 alkyl-, (d) (R'R"N)C1-C6 alkyl- wherein R' and R" are independently H or C1-C6 alkyl, or (e) Ar$^a$CH$_2$— wherein Ar$^a$ is phenyl optionally substituted with C1-C6 alkoxy, wherein one or more of the remaining ring carbon atoms is optionally substituted with one or two substituents independently selected from C1-C6 alkyl and C1-C6 fluoroalkyl.

Non-limiting examples when Ring A is hetAr² include the structures:

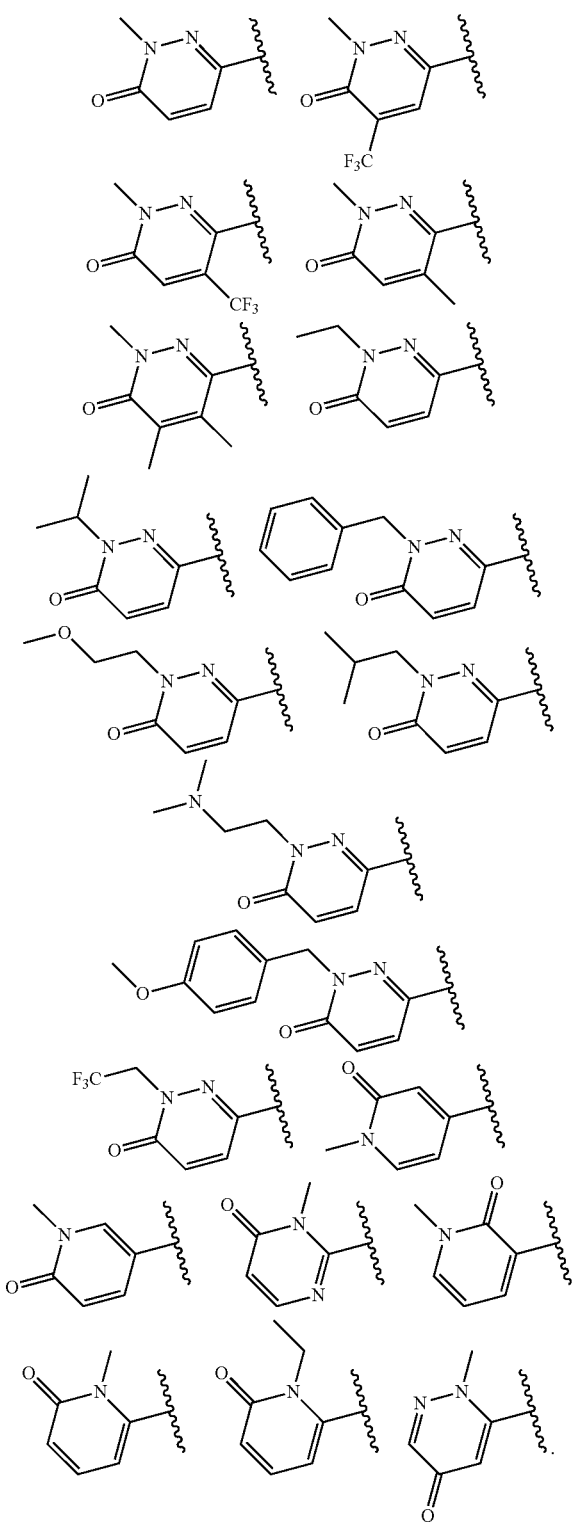

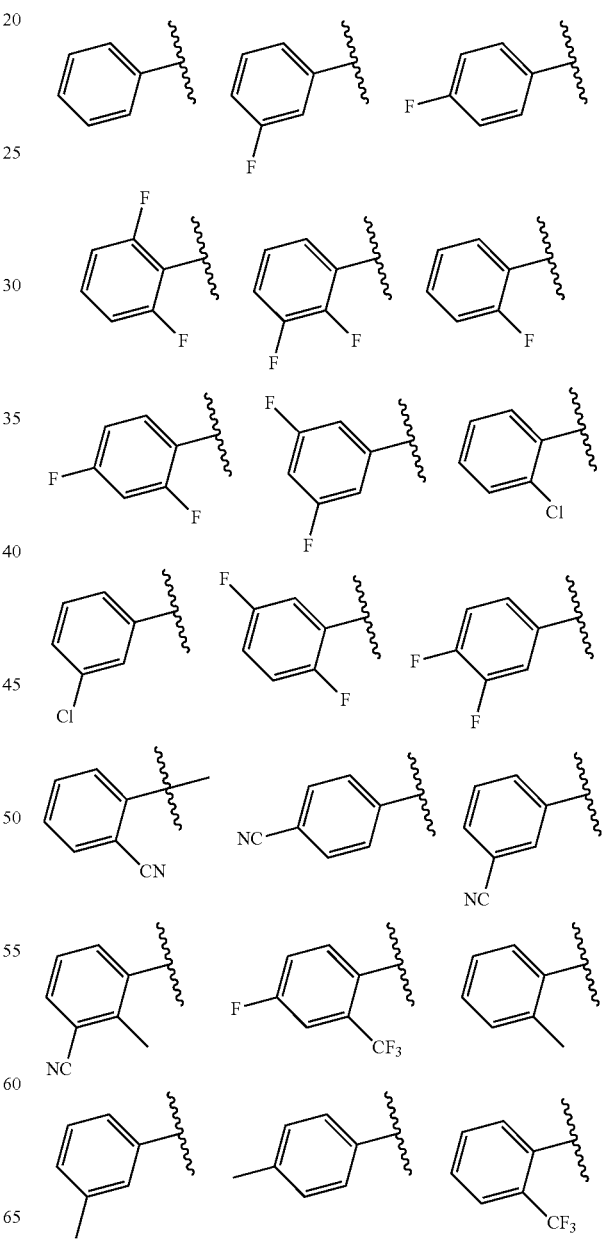

more substituents independently selected from (a) halogen, (b) cyano, (c) C1-C6 alkyl, (d) C1-C6 fluoroalkyl, (e) C1-C6 alkoxy, (f) C3-C6 cycloalkyl, (g) R'R"N(CH$_2$)$_n$— wherein n is 0 or 1 and R' and R" are independently H or C1-C6 alkyl, (h) (C1-C6 alkyl)SO$_2$—, (i) (C1-C6 alkoxy)C(=O)—, (j) HOC(=O)—, and (k) R'R"NC(=O)— wherein R' and R" are independently H, C1-C6 alkyl or (C1-C6 alkoxy)C1-C6 alkyl-, or Ar$^1$ is phenyl fused to a 6-membered heteroaryl ring having a ring nitrogen atom, wherein said ring nitrogen atom is substituted with C1-C6 alkyl and one ring carbon atom of said heteroaryl ring is substituted with oxo, or Ar$^1$ is phenyl fused to a 5-6 membered heterocyclic ring having a ring nitrogen and one ring carbon atom of said heteroaryl ring is substituted with oxo.

Non-limiting examples when Ring A is Ar$^1$ include the structures:

In certain embodiments of Formula I when Ring A is hetAr$^2$, Formula I is Formula I-a.

In certain embodiments of Formula I when Ring A is hetAr$^2$, Formula I is Formula I-b.

In certain embodiments of Formula I when Ring A is hetAr$^2$, Formula I is Formula I-c.

In certain embodiments of Formula I, Ring A is Ar$^1$, wherein Ar$^1$ is phenyl optionally substituted with one or -continued
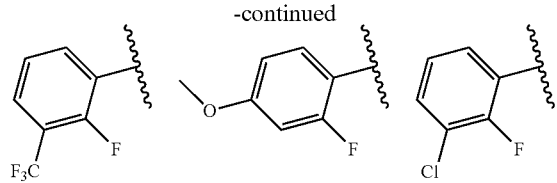
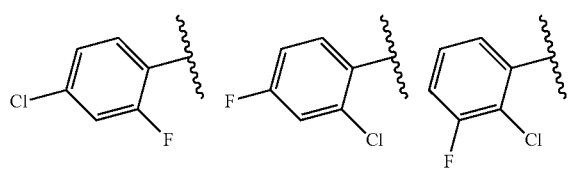
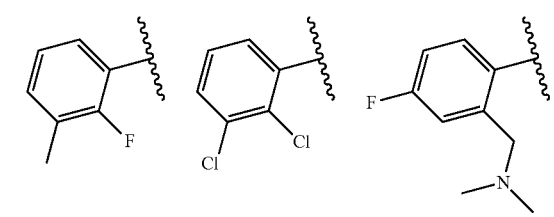
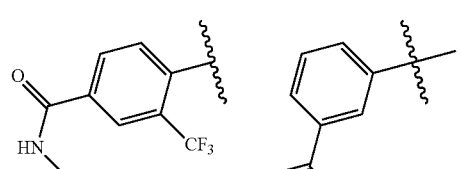
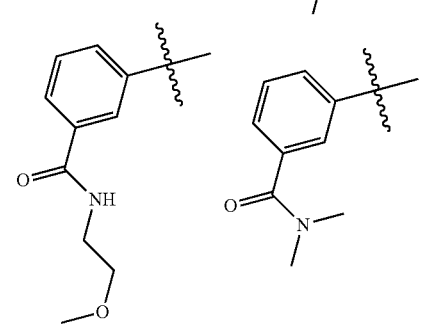
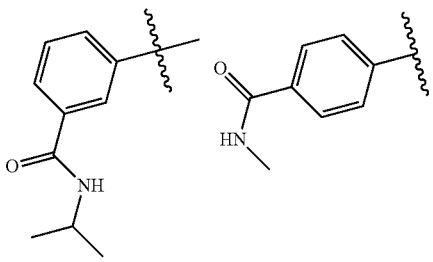
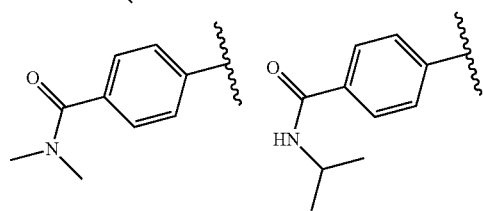
-continued
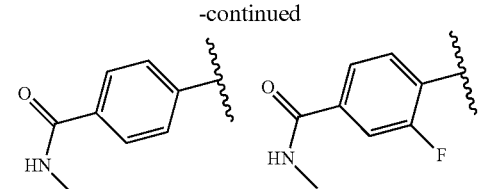
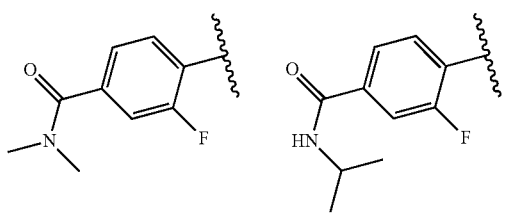
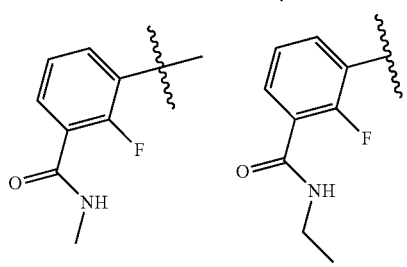
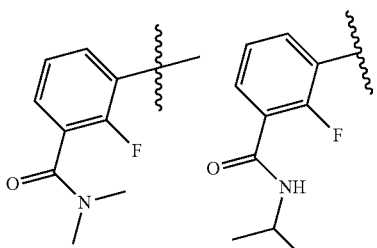
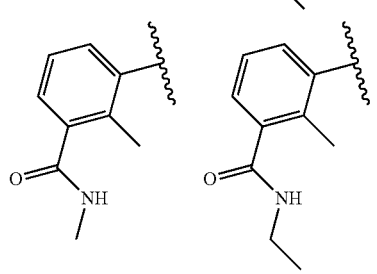
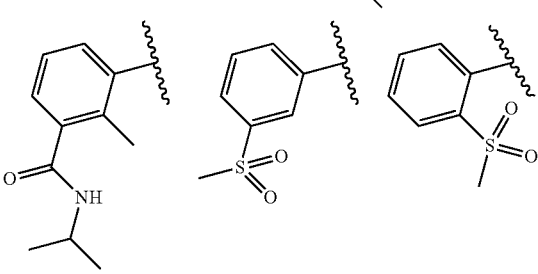
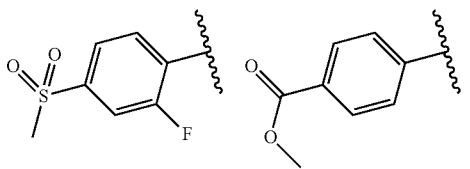

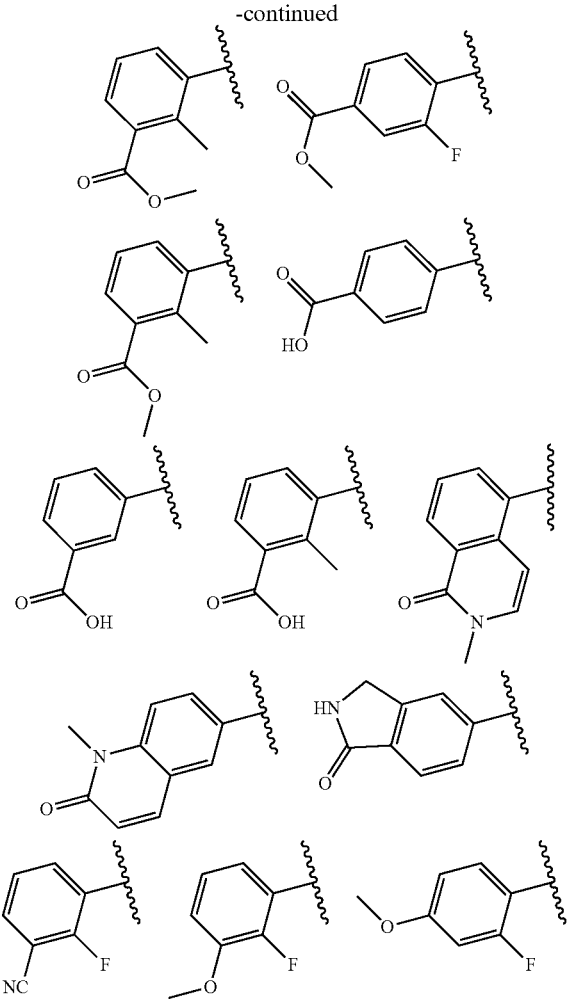

In certain embodiments of Formula I when Ring A is Ar¹, Formula I is Formula I-a.

In certain embodiments of Formula I when Ring A is Ar¹, Formula I is Formula I-b.

In certain embodiments of Formula I when Ring A is Ar¹, Formula I is Formula I-C.

In certain embodiments of Formula I, R¹ is Ar², wherein Ar² is phenyl optionally substituted with one or more substituents independently selected from (a) halogen, (b) CN, (c) C1-C6 hydroxyalkyl, (d) C2-C6 dihydroxyalkyl, (e) C1-C6 alkoxy, (f) hetCyc$^a$(CH$_2$)$_n$— wherein n is 0, 1 or 2, (g) hetCyc$^a$-C(=O)—, (h) hetCyc$^a$-O—, (i) C3-C6 cycloalkyl optionally substituted with cyano or a 5-6 membered heterocyclic ring having 1-2 ring nitrogen atoms wherein said heterocyclic ring is optionally substituted with C1-C6 alkyl, (j) R'R"NC(=O)— wherein R' and R" are independently H, C1-C6 alkyl, C1-C6 hydroxyalkyl, or C3-C6 cycloalkyl, (k) (C1-C6 alkyl)C(=O)NHCH$_2$—, (l) (C1-C6 alkyl)SO$_2$—, and (m) R'R"NSO$_2$— wherein R' and R" are independently H or C1-C6 alkyl, or Ar² is phenyl fused to a 5-6 membered saturated heterocyclic ring having 1-2 ring heteroatoms independently selected from N and S wherein said S is optionally oxidized to SO$_2$, wherein said heterocyclic ring is optionally substituted with oxo and is further optionally substituted with C1-C6 alkyl.

In certain embodiments of Formula I, R¹ is Ar², wherein Ar² is phenyl optionally substituted with one or more substituents independently selected from (a) halogen, (b) CN, (c) C1-C6 hydroxyalkyl, (d) C2-C6 dihydroxyalkyl, (e) C1-C6 alkoxy, (f) hetCyc$^a$(CH$_2$)$_n$— wherein n is 0, 1 or 2, (g) hetCyc$^a$-C(=O)—, (h) hetCyc$^a$-O—, (i) C3-C6 cycloalkyl optionally substituted with cyano or a 5-6 membered heterocyclic ring having 1-2 ring nitrogen atoms wherein said heterocyclic ring is optionally substituted with C1-C6 alkyl, (j) R'R"NC(=O)— wherein R' and R" are independently H, C1-C6 alkyl, C1-C6 hydroxyalkyl, or C3-C6 cycloalkyl, (k) (C1-C6 alkyl)C(=O)NHCH$_2$—, (l) (C1-C6 alkyl)SO$_2$—, and (m) R'R"NSO$_2$— wherein R' and R" are independently H or C1-C6 alkyl. In certain embodiments of Formula I, R¹ is Ar², wherein Ar² is phenyl optionally substituted with 1-2 substituents independently selected from (a) halogen, (b) CN, (c) C1-C6 hydroxyalkyl, (d) C2-C6 dihydroxyalkyl, (e) C1-C6 alkoxy, (f) hetCyc$^a$(CH$_2$)$_n$— wherein n is 0, 1 or 2, (g) hetCyc$^a$-C(=O)—, (h) hetCyc$^a$-O—, (i) C3-C6 cycloalkyl optionally substituted with cyano or a 5-6 membered heterocyclic ring having 1-2 ring nitrogen atoms wherein said heterocyclic ring is optionally substituted with C1-C6 alkyl, (j) R'R"NC(=O)— wherein R' and R" are independently H, C1-C6 alkyl, C1-C6 hydroxyalkyl, or C3-C6 cycloalkyl, (k) (C1-C6 alkyl)C(=O)NHCH$_2$—, (l) (C1-C6 alkyl)SO$_2$—, and (m) R'R"NSO$_2$— wherein R' and R" are independently H or C1-C6 alkyl. Non-limiting examples include the structures:

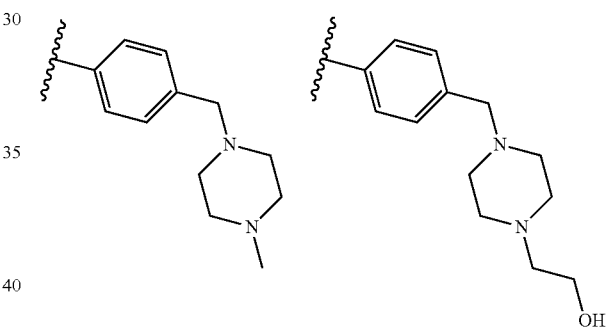

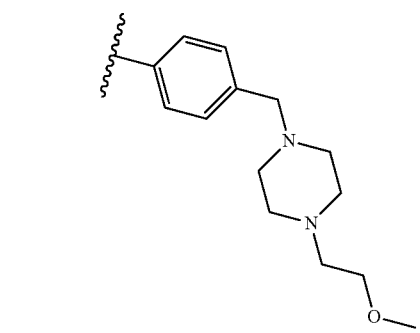

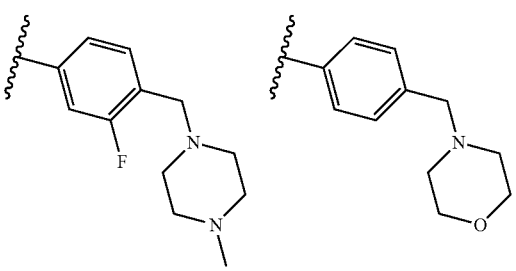

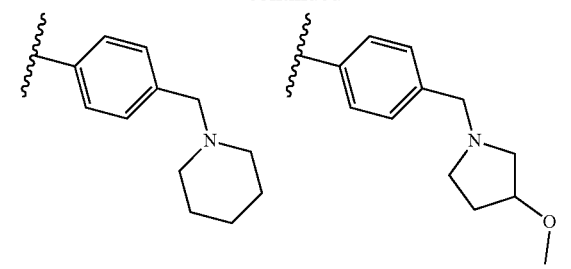
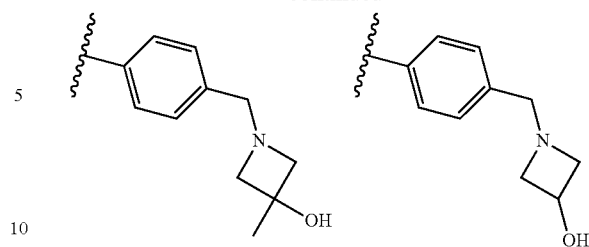
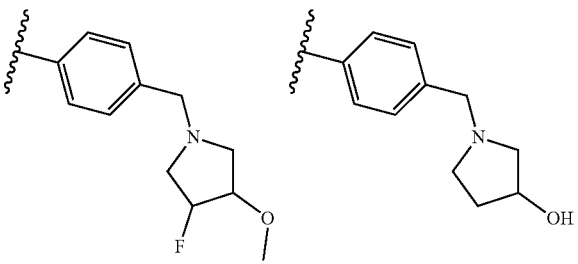
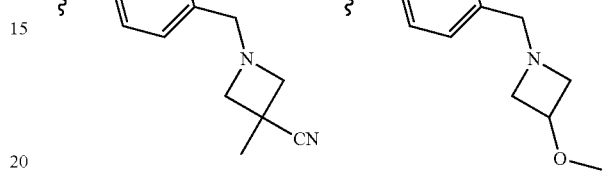
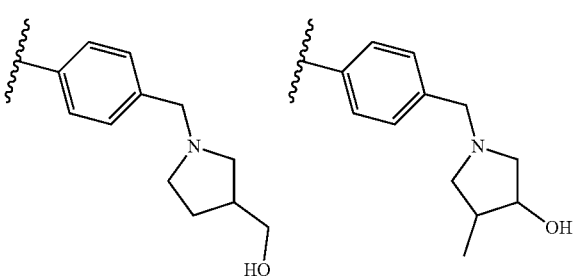
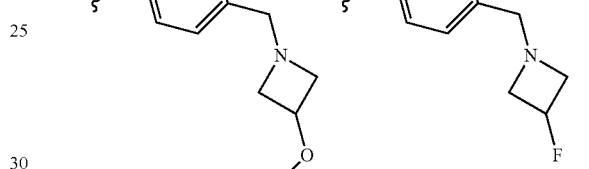
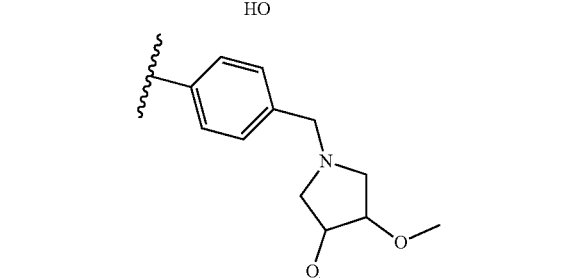
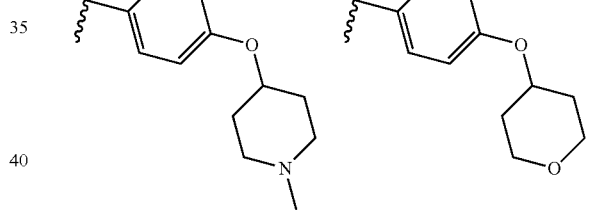
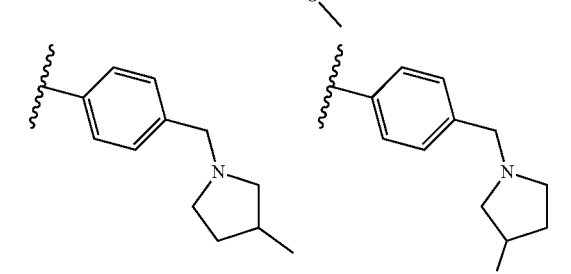
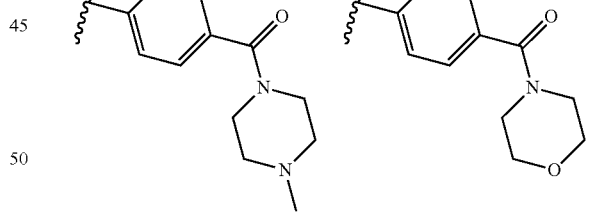
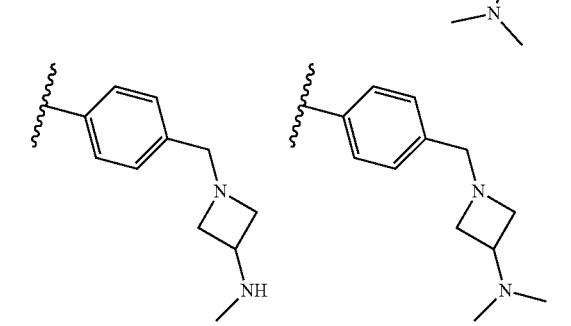
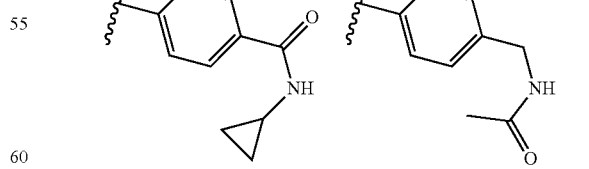
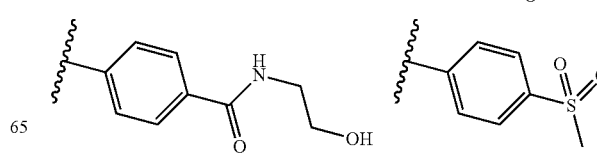
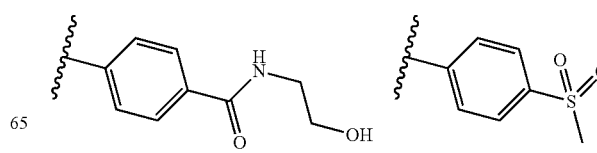

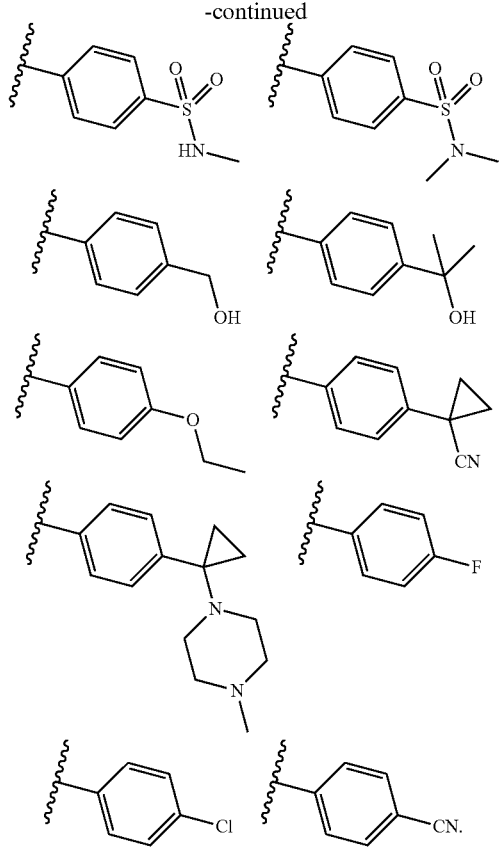

In certain embodiments of Formula I, $R^1$ is $Ar^2$, wherein $Ar^2$ is phenyl fused to a 5-6 membered saturated heterocyclic ring having 1-2 ring heteroatoms independently selected from N and S wherein said S is optionally oxidized to $SO_2$, wherein said heterocyclic ring is optionally substituted with oxo and is further optionally substituted with C1-C6 alkyl. Non-limiting examples include the structures:

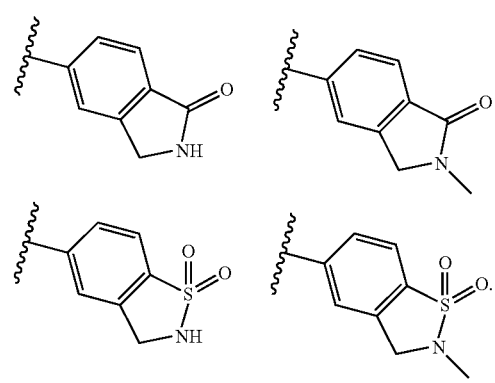

In certain embodiments of Formula I, $R^1$ is $hetAr^3$, where $hetAr^3$ is a 5-6 membered heteroaryl ring having 1-2 ring heteroatoms independently selected from N and O, wherein said heteroaryl ring is optionally substituted with one or more substituents independently selected from (a) halogen, (b) cyano, (c) C1-C6 alkyl, (d) C1-C6 fluoroalkyl, (e) C1-C6 hydroxyalkyl wherein said alkyl portion is optionally substituted with R'R"N— wherein R' and R" are independently H or C1-C6 alkyl, (f) C2-C6 dihydroxyalkyl, (g) C1-C6 cyanoalkyl, (h) C1-C6 alkoxy, (i) R'R"N— wherein R' and R" are independently H, C1-C6 alkyl, or (C1-C6 alkoxy)C1-C6 alkyl-, (k) (C1-C6 alkylSO$_2$)C1-C6 alkyl-, (l) C3-C6 cycloalkyl optionally substituted with hydroxyl, (m) R'R"NC(=O)C1-C6 alkyl- wherein R' and R" are independently H or C1-C6 alkyl, and (n) hetCyc$^b$(CH$_2$)$_n$— wherein n is 0, 1 or 2. Non-limiting examples include the structures:

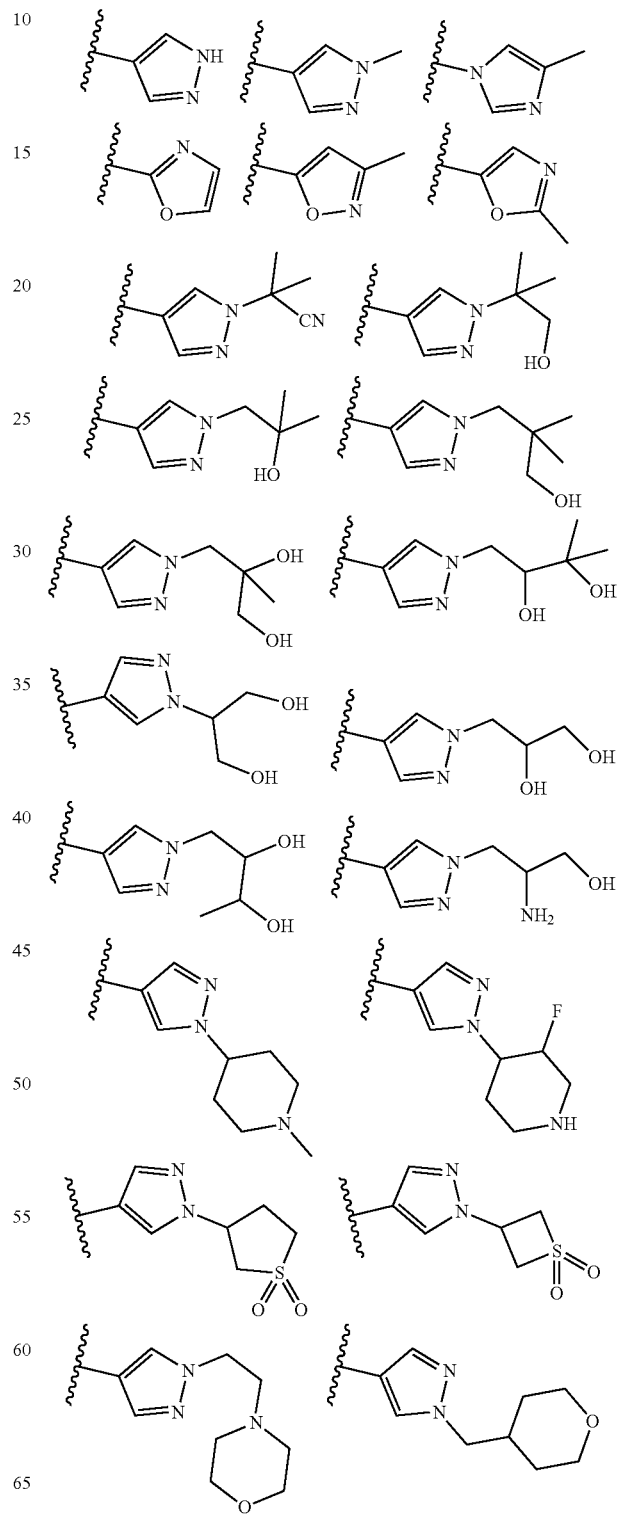

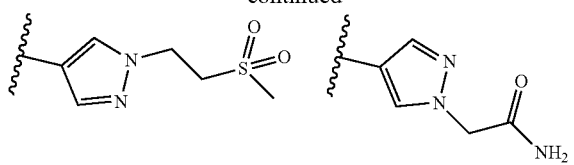
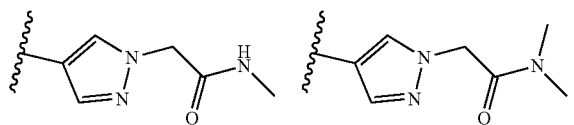
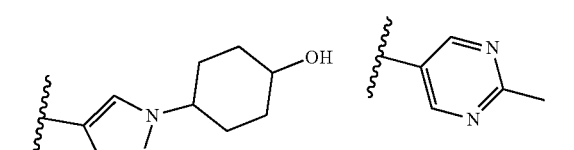
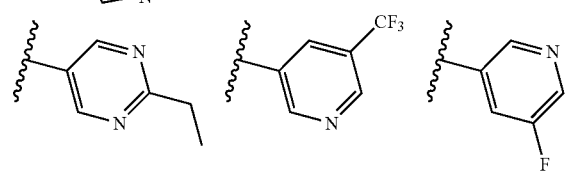
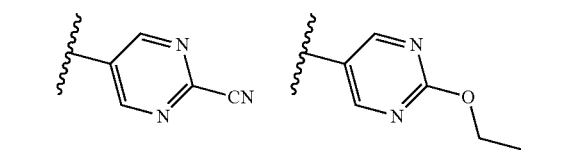
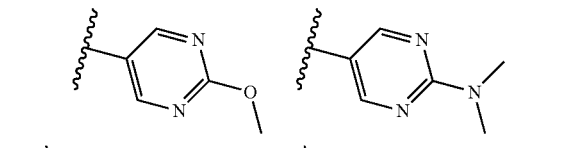
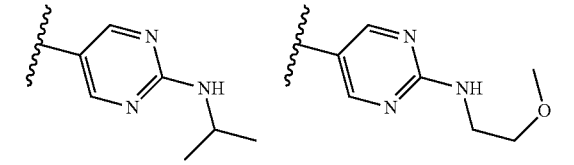
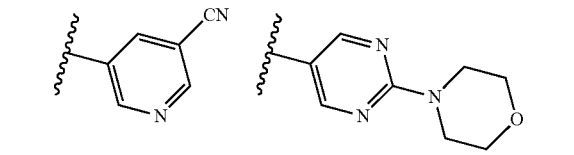
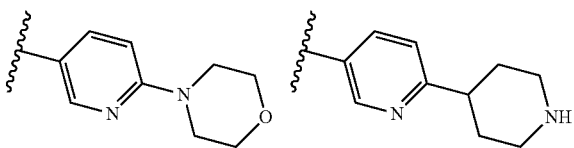
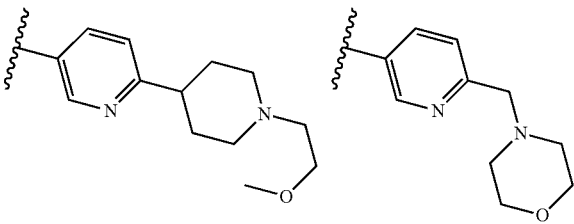

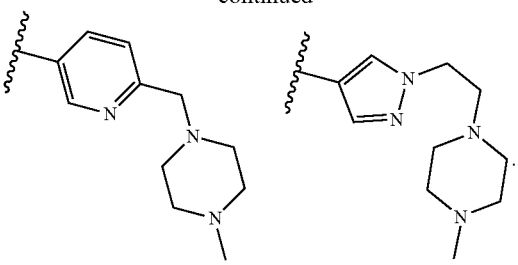

In certain embodiments of Formula I, $R^1$ is hetAr$^4$, wherein hetAr$^4$ is a 6-membered heteroaryl ring having 1-2 ring nitrogen atoms, wherein a ring carbon atom of said heteroaryl ring is substituted with oxo and wherein one of said ring nitrogen atoms is substituted with C1-C6 alkyl or C1-C6 fluoroalkyl. Non-limiting examples include the structures:

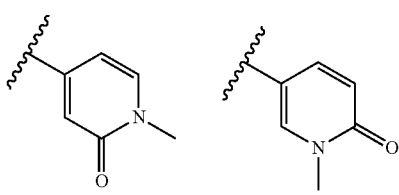
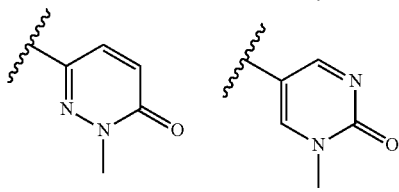
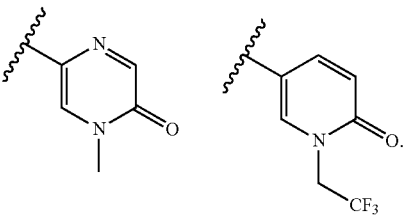

In certain embodiments of Formula I, $R^1$ is hetCyc$^1$, wherein hetCyc$^1$ is a 5-6 membered saturated or partially unsaturated monocyclic heterocyclic ring having 1-2 ring heteroatoms independently selected from N and O or a 8-10 membered fused saturated heterocyclic ring having 1-2 ring heteroatoms independently selected from N and O, wherein said heterocyclic rings are optionally substituted with one or more substituents independently selected from (a) halogen, C1-C6 alkyl, (b) C1-C6 alkoxy, (c) (C1-C6 alkoxy)C1-C6 alkyl-, (d) (C1-C6 alkyl)C(=O)—, (e) hydroxyl, and (f) R'R"N— wherein R' and R" are independently H or C1-C6 alkyl. Non-limiting examples include the structures:

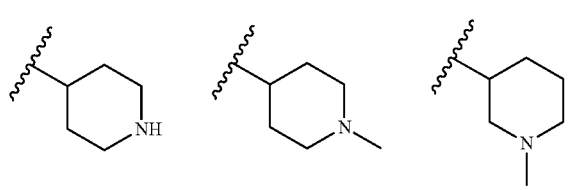

-continued

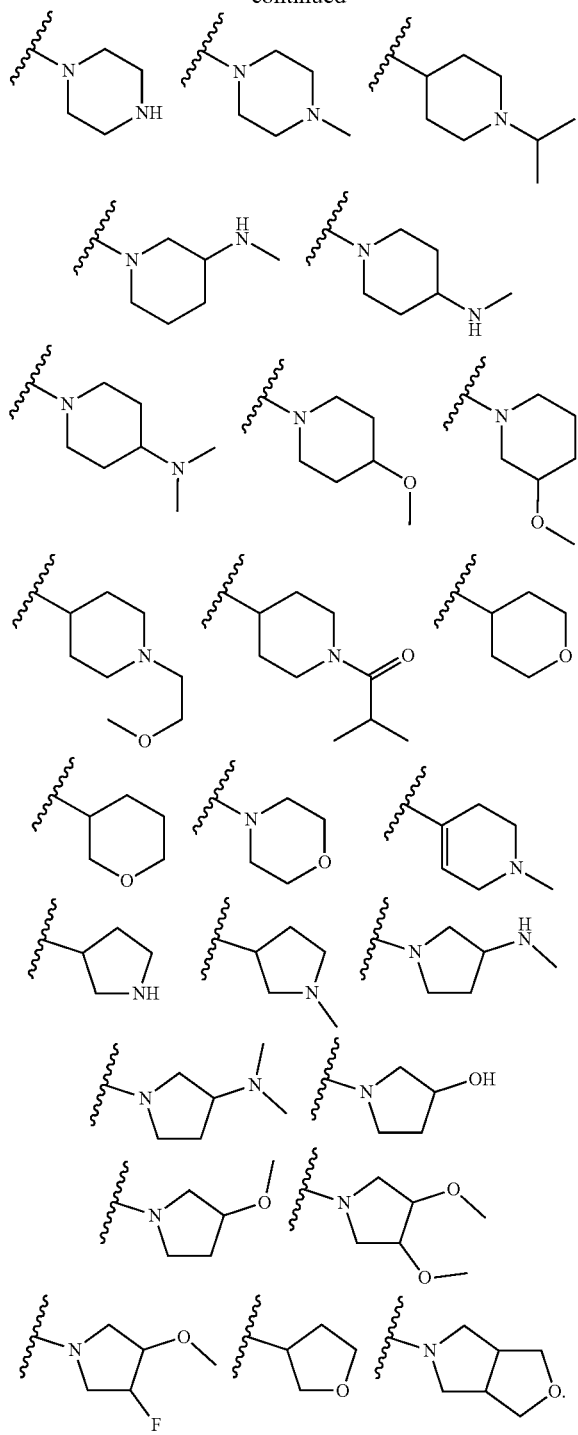

In certain embodiments of Formula I, R¹ is Cyc¹, wherein Cyc¹ is a 3-6 membered cycloalkyl ring optionally substituted with R'R"N— wherein R' and R" are independently H or C1-C6 alkyl. Non-limiting examples include cyclopentyl, cyclohexyl, and 4-(N,N-dimethylamino)cyclohexyl.

In certain embodiments of Formula I, R¹ is C1-C6 alkyl. In certain embodiments of Formula I, R¹ is isopropyl.

In certain embodiments of Formula I, R¹ is bromo.

In certain embodiments of Formula I, R² is hydrogen.

In certain embodiments of Formula I, R² is C1-C6 alkyl. Non-limiting examples include methyl, ethyl, propyl, isopropyl, 2,2,2-triethyl, In certain embodiments of Formula I, R² is C1-C6 fluoroalkyl. Non-limiting examples 3-fluropropyl and 4-fluorobutyl.

In certain embodiments of Formula I, R² is C1-C6 alkyl wherein 2-5 hydrogens are replaced by deuterium. A non-limiting example is CD₃-.

In certain embodiments of Formula I, R² is C3-C6 cycloalkyl. A non-limiting example is cyclobutyl.

In certain embodiments of Formula I, R² is (C3-C6 cycloalkyl)C1-C6 alkyl-. A non-limiting example is 2-cyclopropylethyl.

In certain embodiments of Formula I, R² is phenyl optionally substituted with one or more substituents independently selected from cyano and halogen. Non-limiting examples include phenyl, 2-fluorophenyl, 3-fluorophenyl, 4-fluorophenyl, and 4-cyanophenyl.

In certain embodiments of Formula I, R³ is hydrogen.

In certain embodiments of Formula I, R³ is hydroxyl.

In one embodiment, the (Ring A)-O— moiety and the bicyclic ring of Formula I are in the cis configuration.

In one embodiment, the (Ring A)-O— moiety and the bicyclic ring of Formula I are in the trans configuration.

In one embodiment, provided are compounds of Formula wherein:

X¹ is N, X² is N, and X³ is C, such that Formula I has the structure of Formula I-a:

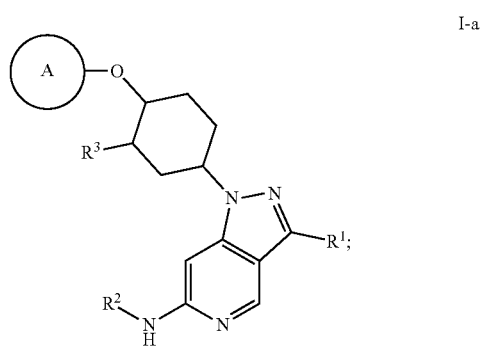

I-a wherein Ring A is hetAr¹, Ar¹ or hetAr²;

R¹ is Ar², hetAr³, hetAr⁴, hetCyc¹, Cyc¹, C1-C6 alkyl, or Br;

R² is H, C1-C6 alkyl, C1-C6 fluoroalkyl, C3-C6 cycloalkyl, (C3-C6 cycloalkyl)C1-C6 alkyl-, phenyl optionally substituted with one or more substituents independently selected from cyano and halogen, or C1-C6 alkyl wherein 2-5 hydrogens are replaced by deuterium;

R³ is hydrogen or hydroxyl;

and hetAr¹, Ar¹, hetAr², Ar², hetAr³, hetAr⁴, hetCyc¹ and Cyc¹ are as defined for Formula I.

In one embodiment, the (Ring A)-O— moiety and the bicyclic ring of Formula I-a are in the cis configuration.

In one embodiment, the (Ring A)-O— moiety and the bicyclic ring of Formula I-a are in the trans configuration.

In one embodiment, provided are compounds of Formula I wherein:

$X^1$ is N, $X^2$ is N, and $X^3$ is C, such that Formula I has the structure of Formula I-a:

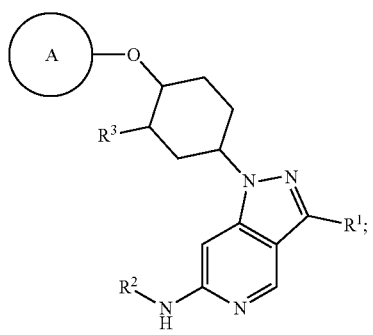

I-a wherein Ring A is $Ar^1$; and $Ar^1$, $R^1$, $R^2$ and $R^3$ are as defined for Formula I. In one embodiment, Ring A is $Ar^1$; $R^1$ is $Ar^2$; and $Ar^1$, $Ar^2$, $R^2$ and $R^3$ are as defined for Formula I. In one embodiment, Ring A is $Ar^1$; $R^1$ is $Ar^2$; $R^3$ is hydrogen; and $R^2$, $Ar^1$ and $Ar^2$ are as defined for Formula I. In one embodiment, Ring A is $Ar^1$; $R^1$ is $Ar^2$; $R^3$ is hydroxyl; and $R^2$, $Ar^1$ and $Ar^2$ are as defined for Formula I. In one embodiment, the (Ring A)-O— moiety and the bicyclic ring of Formula I-a are in the cis configuration. In one embodiment, the (Ring A)-O— moiety and the bicyclic ring of Formula I-a are in the trans configuration. In one of any of said embodiments, $R^2$ is H. In one of any of said embodiments, $R^2$ is C1-C6 alkyl. In one of any of said embodiments, $R^2$ is C1-C6 fluoroalkyl. In one of any of said embodiments, $R^2$ is C3-C6 cycloalkyl. In one of any of said embodiments, $R^2$ is (C3-C6 cycloalkyl)C1-C6 alkyl-. In one of any of said embodiments, $R^2$ is phenyl optionally substituted with one or more substituents independently selected from cyano and halogen. In one of any of said embodiments, $R^2$ is C1-C6 alkyl wherein 2-5 hydrogens are replaced by deuterium.

In one embodiment, provided are compounds of Formula I wherein:

$X^1$ is N, $X^2$ is N, and $X^3$ is C, such that Formula I has the structure of Formula I-a:

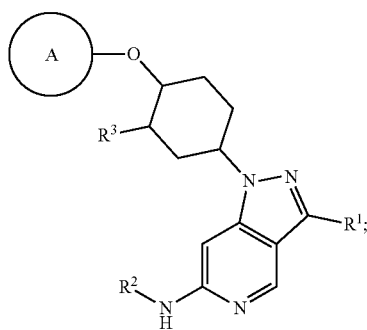

I-a wherein Ring A is $Ar^1$; $R^1$ is $hetAr^3$; and $Ar^1$, $R^2$, $R^3$ and $hetAr^3$ are as defined for Formula I. In one embodiment, Ring A is $Ar^1$; $R^1$ is $hetAr^3$; $R^3$ is hydrogen; and $Ar^1$, $R^2$ and $hetAr^3$ are as defined for Formula I. In one embodiment, Ring A is $Ar^1$; $R^1$ is $hetAr^3$; $R^3$ is hydroxyl; and $Ar^1$, $R^2$ and $hetAr^3$ are as defined for Formula I. In one embodiment, the (Ring A)-O— moiety and the bicyclic ring of Formula I-a are in the cis configuration. In one embodiment, the (Ring A)-O— moiety and the bicyclic ring of Formula I-a are in the trans configuration. In one of any of said embodiments, $R^2$ is H. In one of any of said embodiments, $R^2$ is C1-C6 alkyl. In one of any of said embodiments, $R^2$ is C1-C6 fluoroalkyl. In one of any of said embodiments, $R^2$ is C3-C6 cycloalkyl. In one of any of said embodiments, $R^2$ is (C3-C6 cycloalkyl)C1-C6 alkyl-. In one of any of said embodiments, $R^2$ is phenyl optionally substituted with one or more substituents independently selected from cyano and halogen. In one of any of said embodiments, $R^2$ is C1-C6 alkyl wherein 2-5 hydrogens are replaced by deuterium.

In one embodiment, provided are compounds of Formula I wherein:

$X^1$ is N, $X^2$ is N, and $X^3$ is C, such that Formula I has the structure of Formula I-a:

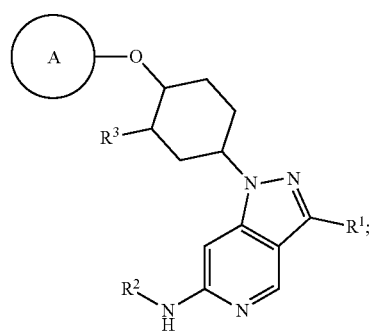

I-a wherein Ring A is $hetAr^1$; and $R^1$, $R^2$, $R^3$ and $hetAr^1$ are as defined for Formula I. In one embodiment, Ring A is $hetAr^1$; $R^1$ is $Ar^2$; and $R^2$, $R^3$ and $hetAr^1$ are as defined for Formula I. In one embodiment, Ring A is $hetAr^1$; $R^1$ is $Ar^2$; $R^3$ is hydrogen; and $R^2$ and $hetAr^1$ are as defined for Formula I. In one embodiment, Ring A is $hetAr^1$; $R^1$ is $Ar^2$; $R^3$ is hydroxyl; and $R^2$ and $hetAr^1$ are as defined for Formula I. In one embodiment, the (Ring A)-O— moiety and the bicyclic ring of Formula I-a are in the cis configuration. In one embodiment, the (Ring A)-O— moiety and the bicyclic ring of Formula I-a are in the trans configuration. In one of any of said embodiments, $R^2$ is H. In one of any of said embodiments, $R^2$ is C1-C6 alkyl. In one of any of said embodiments, $R^2$ is C1-C6 fluoroalkyl. In one of any of said embodiments, $R^2$ is C3-C6 cycloalkyl. In one of any of said embodiments, $R^2$ is (C3-C6 cycloalkyl)C1-C6 alkyl-. In one of any of said embodiments, $R^2$ is phenyl optionally substituted with one or more substituents independently selected from cyano and halogen. In one of any of said embodiments, $R^2$ is C1-C6 alkyl wherein 2-5 hydrogens are replaced by deuterium.

In one embodiment, provided are compounds of Formula I wherein:

$X^1$ is N, $X^2$ is N, and $X^3$ is C, such that Formula I has the structure of Formula I-a:

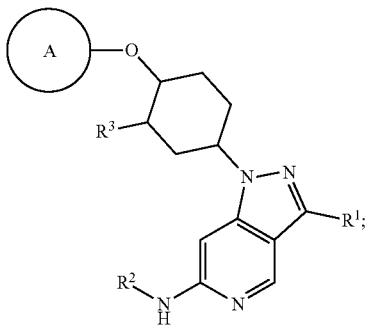

I-a wherein Ring A is hetAr$^1$; R$^1$ is hetAr$^3$; and R$^2$, R$^3$ hetAr$^1$ and hetAr$^3$ are as defined for Formula I. In one embodiment, Ring A is hetAr$^1$; R$^1$ is hetAr$^3$; R$^3$ is hydrogen; and R$^2$, hetAr$^1$ and hetAr$^3$ are as defined for Formula I. In one embodiment, hetAr$^1$; R$^1$ is hetAr$^3$; R$^3$ is hydroxyl; and R$^2$, hetAr$^1$ and hetAr$^3$ are as defined for Formula I. In one embodiment, the (Ring A)-O— moiety and the bicyclic ring of Formula I-a are in the cis configuration. In one embodiment, the (Ring A)-O— moiety and the bicyclic ring of Formula I-a are in the trans configuration. In one of any of said embodiments, R$^2$ is H. In one of any of said embodiments, R$^2$ is C1-C6 alkyl. In one of any of said embodiments, R$^2$ is C1-C6 fluoroalkyl. In one of any of said embodiments, R$^2$ is C3-C6 cycloalkyl. In one of any of said embodiments, R$^2$ is (C3-C6 cycloalkyl)C1-C6 alkyl-. In one of any of said embodiments, R$^2$ is phenyl optionally substituted with one or more substituents independently selected from cyano and halogen. In one of any of said embodiments, R$^2$ is C1-C6 alkyl wherein 2-5 hydrogens are replaced by deuterium.

In one embodiment, provided are compounds of Formula I wherein:

$X^1$ is N, $X^2$ is N, and $X^3$ is C, such that Formula I has the structure of Formula I-a:

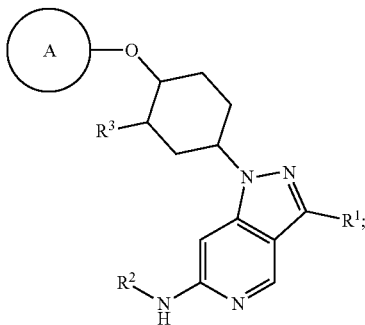

I-a wherein Ring A is hetAr$^1$; R$^1$ is hetAr$^4$; and R$^2$, R$^3$, hetAr$^1$ and hetAr$^4$ are as defined for Formula I. In one embodiment, Ring A is hetAr$^1$; R$^1$ is hetAr$^4$; R$^3$ is hydrogen; and R$^2$, hetAr$^1$ and hetAr$^4$ are as defined for Formula I. In one embodiment, Ring A is hetAr$^1$; R$^1$ is hetAr$^4$; R$^3$ is hydroxyl; and R$^2$, hetAr$^1$ and hetAr$^4$ are as defined for Formula I. In one embodiment, the (Ring A)-O— moiety and the bicyclic ring of Formula I-a are in the cis configuration. In one embodiment, the (Ring A)-O— moiety and the bicyclic ring of Formula I-a are in the trans configuration. In one of any of said embodiments, R$^2$ is H. In one of any of said embodiments, R$^2$ is C1-C6 alkyl. In one of any of said embodiments, R$^2$ is C1-C6 fluoroalkyl. In one of any of said embodiments, R$^2$ is C3-C6 cycloalkyl. In one of any of said embodiments, R$^2$ is (C3-C6 cycloalkyl)C1-C6 alkyl-. In one of any of said embodiments, R$^2$ is phenyl optionally substituted with one or more substituents independently selected from cyano and halogen. In one of any of said embodiments, R$^2$ is C1-C6 alkyl wherein 2-5 hydrogens are replaced by deuterium.

In one embodiment, provided are compounds of Formula I wherein:

$X^1$ is N, $X^2$ is N, and $X^3$ is C, such that Formula I has the structure of Formula I-a:

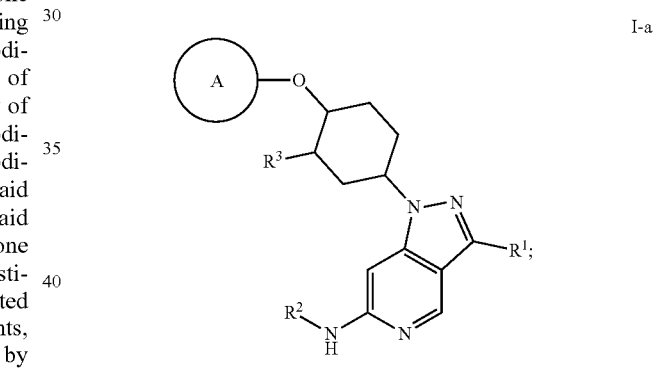

I-a wherein Ring A is hetAr$^1$; R$^1$ is Cyc$^1$; and R$^2$, R$^3$, hetAr$^1$ and Cyc$^1$ are as defined for Formula I. In one embodiment, Ring A is hetAr$^1$; R$^1$ is Cyc$^1$; R$^3$ is hydrogen; and R$^2$, hetAr$^1$ and Cyc$^1$ are as defined for Formula I. In one embodiment, Ring A is hetAr$^1$; R$^1$ is Cyc$^1$; R$^3$ is hydroxyl; and R$^2$, hetAr$^1$ and Cyc$^1$ are as defined for Formula I. In one embodiment, the (Ring A)-O— moiety and the bicyclic ring of Formula I-a are in the cis configuration. In one embodiment, the (Ring A)-O— moiety and the bicyclic ring of Formula I-a are in the trans configuration. In one of any of said embodiments, R$^2$ is H. In one of any of said embodiments, R$^2$ is C1-C6 alkyl. In one of any of said embodiments, R$^2$ is C1-C6 fluoroalkyl. In one of any of said embodiments, R$^2$ is C3-C6 cycloalkyl. In one of any of said embodiments, R$^2$ is (C3-C6 cycloalkyl)C1-C6 alkyl-. In one of any of said embodiments, R$^2$ is phenyl optionally substituted with one or more substituents independently selected from cyano and halogen. In one of any of said embodiments, R$^2$ is C1-C6 alkyl wherein 2-5 hydrogens are replaced by deuterium.

In one embodiment, provided are compounds of Formula I wherein:

$X^1$ is N, $X^2$ is N, and $X^3$ is C, such that Formula I has the structure of Formula I-a:

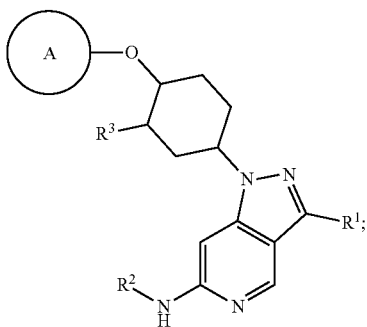

I-a wherein Ring A is hetAr$^1$; R$^1$ is hetCyc$^1$; and R$^2$, R$^3$, hetAr$^1$ and hetCyc$^1$ are as defined for Formula I. In one embodiment, Ring A is hetAr$^1$; R$^1$ is hetCyc$^1$; R$^3$ is hydrogen; and R$^2$, hetAr$^1$ and hetCyc$^1$ are as defined for Formula I. In one embodiment, Ring A is hetAr$^1$; R$^1$ is hetCyc$^1$; R$^3$ is hydroxyl; and R$^2$, hetAr$^1$ and hetCyc$^1$ are as defined for Formula I. In one embodiment, the (Ring A)-O— moiety and the bicyclic ring of Formula I-a are in the cis configuration. In one embodiment, the (Ring A)-O— moiety and the bicyclic ring of Formula I-a are in the trans configuration. In one of any of said embodiments, R$^2$ is H. In one of any of said embodiments, R$^2$ is C1-C6 alkyl. In one of any of said embodiments, R$^2$ is C1-C6 fluoroalkyl. In one of any of said embodiments, R$^2$ is C3-C6 cycloalkyl. In one of any of said embodiments, R$^2$ is (C3-C6 cycloalkyl)C1-C6 alkyl-. In one of any of said embodiments, R$^2$ is phenyl optionally substituted with one or more substituents independently selected from cyano and halogen. In one of any of said embodiments, R$^2$ is C1-C6 alkyl wherein 2-5 hydrogens are replaced by deuterium.

In one embodiment, provided are compounds of Formula I wherein:

X$^1$ is N, X$^2$ is N, and X$^3$ is C, such that Formula I has the structure of Formula I-a:

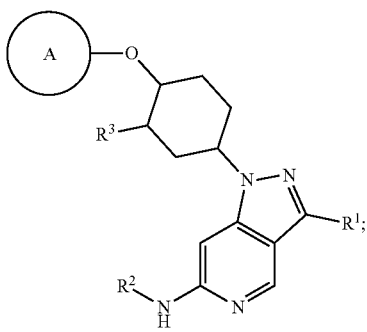

I-a wherein Ring A is hetAr$^1$; R$^1$ is C1-C6 alkyl; and R$^2$, R$^3$, and hetAr$^1$ are as defined for Formula I. In one embodiment, Ring A is hetAr$^1$; R$^1$ is C1-C6 alkyl; R$^3$ is hydrogen; and R$^2$ and hetAr$^1$ are as defined for Formula I. In one embodiment, Ring A is hetAr$^1$; R$^1$ is C1-C6 alkyl; R$^3$ is hydroxyl; and R$^2$ and hetAr$^1$ are as defined for Formula I. In one embodiment, the (Ring A)-O— moiety and the bicyclic ring of Formula I-a are in the cis configuration. In one embodiment, the (Ring A)-O— moiety and the bicyclic ring of Formula I-a are in the trans configuration. In one of any of said embodiments, R$^2$ is H. In one of any of said embodiments, R$^2$ is C1-C6 alkyl. In one of any of said embodiments, R$^2$ is C1-C6 fluoroalkyl. In one of any of said embodiments, R$^2$ is C3-C6 cycloalkyl. In one of any of said embodiments, R$^2$ is (C3-C6 cycloalkyl)C1-C6 alkyl-. In one of any of said embodiments, R$^2$ is phenyl optionally substituted with one or more substituents independently selected from cyano and halogen. In one of any of said embodiments, R$^2$ is C1-C6 alkyl wherein 2-5 hydrogens are replaced by deuterium.

In one embodiment, provided are compounds of Formula I wherein:

X$^1$ is N, X$^2$ is N, and X$^3$ is C, such that Formula I has the structure of Formula I-a.

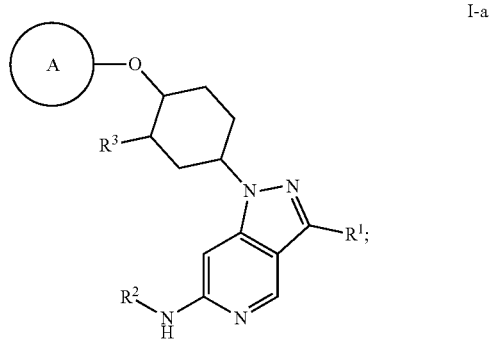

I-a wherein Ring A is hetAr$^1$; R$^1$ is Br; and R$^2$, R$^3$, and hetAr$^1$ are as defined for Formula I. In one embodiment, Ring A is hetAr$^1$; R$^1$ is Br; R$^3$ is hydrogen; and R$^2$ and hetAr$^1$ are as defined for Formula I. In one embodiment, Ring A is hetAr$^1$; R$^1$ is Br; R$^3$ is hydroxyl; and R$^2$ and hetAr$^1$ are as defined for Formula I. In one embodiment, the (Ring A)-O— moiety and the bicyclic ring of Formula I-a are in the cis configuration. In one embodiment, the (Ring A)-O— moiety and the bicyclic ring of Formula I-a are in the trans configuration. In one of any of said embodiments, R$^2$ is H. In one of any of said embodiments, R$^2$ is C1-C6 alkyl. In one of any of said embodiments, R$^2$ is C1-C6 fluoroalkyl. In one of any of said embodiments, R$^2$ is C3-C6 cycloalkyl. In one of any of said embodiments, R$^2$ is (C3-C6 cycloalkyl)C1-C6 alkyl-. In one of any of said embodiments, R$^2$ is phenyl optionally substituted with one or more substituents independently selected from cyano and halogen. In one of any of said embodiments, R$^2$ is C1-C6 alkyl wherein 2-5 hydrogens are replaced by deuterium.

In one embodiment, provided are compounds of Formula I wherein:

X$^1$ is N, X$^2$ is N, and X$^3$ is C, such that Formula I has the structure of Formula I-a.

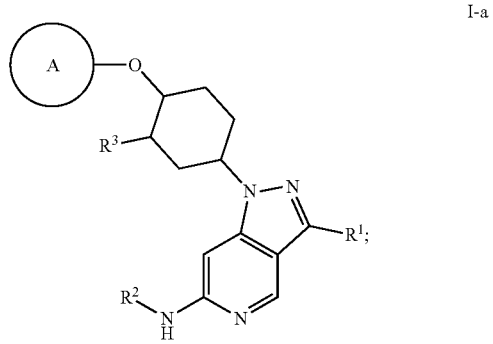

I-a wherein Ring A is hetAr², and R¹, R², R³ and hetAr² are as defined for Formula I. In one embodiment, Ring A is hetAr²; R¹ is hetAr³; and R², R³, hetAr² and hetAr³ are as defined for Formula I. In one embodiment, Ring A is hetAr²; R¹ is hetAr³; R³ is hydrogen; and R², hetAr² and hetAr³ are as defined for Formula I. In one embodiment, Ring A is hetAr²; R¹ is hetAr³; R³ is hydroxyl; and R², hetAr² and hetAr³ are as defined for Formula I. In one embodiment, the (Ring A)-O— moiety and the bicyclic ring of Formula I-a are in the cis configuration. In one embodiment, the (Ring A)-O— moiety and the bicyclic ring of Formula I-a are in the trans configuration. In one of any of said embodiments, R² is H. In one of any of said embodiments, R² is C1-C6 alkyl. In one of any of said embodiments, R² is C1-C6 fluoroalkyl. In one of any of said embodiments, R² is C3-C6 cycloalkyl. In one of any of said embodiments, R² is (C3-C6 cycloalkyl)C1-C6 alkyl-. In one of any of said embodiments, R² is phenyl optionally substituted with one or more substituents independently selected from cyano and halogen. In one of any of said embodiments, R² is C1-C6 alkyl wherein 2-5 hydrogens are replaced by deuterium.

In one embodiment, provided are compounds of Formula I wherein:

X¹ is N, X² is N, and X³ is C, such that Formula I has the structure of Formula I-a:

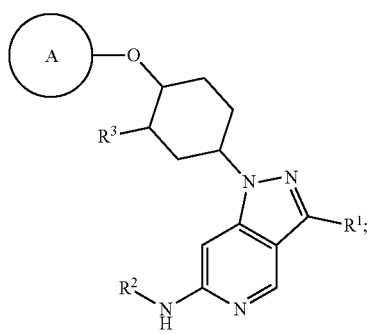

I-a wherein Ring A is hetAr²; R¹ is hetCyc¹; and R², R³, hetAr² and hetCyc¹ are as defined for Formula I. In one embodiment, Ring A is hetAr²; R¹ is hetCyc¹; R³ is hydrogen; and R², hetAr² and hetCyc¹ are as defined for Formula I. In one embodiment, Ring A is hetAr²; R¹ is hetCyc¹; R³ is hydroxyl; and R², hetAr² and hetCyc¹ are as defined for Formula I. In one embodiment, the (Ring A)-O— moiety and the bicyclic ring of Formula I-a are in the cis configuration. In one embodiment, the (Ring A)-O— moiety and the bicyclic ring of Formula I-a are in the trans configuration. In one of any of said embodiments, R² is H. In one of any of said embodiments, R² is C1-C6 alkyl. In one of any of said embodiments, R² is C1-C6 fluoroalkyl. In one of any of said embodiments, R² is C3-C6 cycloalkyl. In one of any of said embodiments, R² is (C3-C6 cycloalkyl)C1-C6 alkyl-. In one of any of said embodiments, R² is phenyl optionally substituted with one or more substituents independently selected from cyano and halogen. In one of any of said embodiments, R² is C1-C6 alkyl wherein 2-5 hydrogens are replaced by deuterium.

In one embodiment, provided are compounds of Formula I wherein X¹ is C, X² is N, and X³ is N, such that Formula I has the structure of Formula I-b:

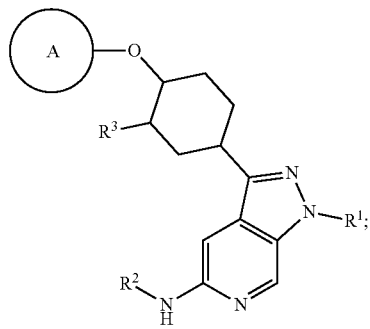

I-b wherein Ring A is Ar¹ or hetAr²;
R¹ is Ar², hetAr³ or hetCyc¹;
R² is H, C1-C6 alkyl, C1-C6 fluoroalkyl, C3-C6 cycloalkyl, (C3-C6 cycloalkyl)C1-C6 alkyl-, phenyl optionally substituted with one or more substituents independently selected from cyano and halogen, or C1-C6 alkyl wherein 2-5 hydrogens are replaced by deuterium;
R³ is hydrogen or hydroxyl; and
Ar¹, hetAr², Ar², hetAr³ and hetCyc¹ are as defined for Formula I.

In one embodiment, the (Ring A)-O— moiety and the bicyclic ring of Formula I-b are in the cis configuration. In one embodiment, the (Ring A)-O— moiety and the bicyclic ring of Formula I-b are in the trans configuration.

In one embodiment, provided are compounds of Formula I wherein X¹ is C, X² is N, and X³ is N, such that Formula I has the structure of Formula I-b:

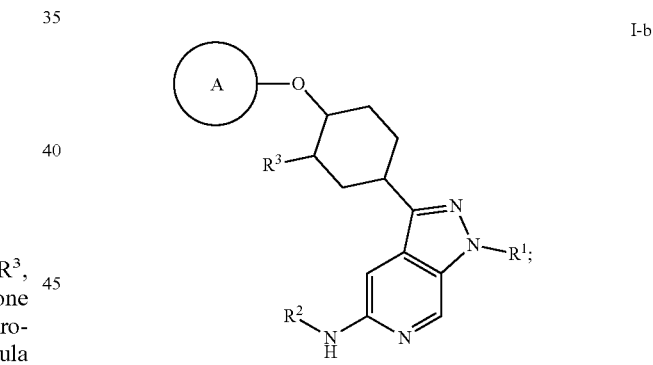

I-b wherein Ring A is Ar¹; and R¹, R², R³, and Ar¹ are as defined for Formula I. In one embodiment, Ring A is Ar¹; R¹ is Ar²; and R², R³, Ar¹ and Ar² are as defined for Formula I. In one embodiment, Ring A is Ar¹; R¹ is Ar²; R³ is hydrogen; and R², Ar¹ and Ar² are as defined for Formula I. In one embodiment, Ring A is Ar¹; R¹ is Ar²; R³ is hydroxyl; and R², Ar¹ and Ar² are as defined for Formula I. In one embodiment, the (Ring A)-O— moiety and the bicyclic ring of Formula I-b are in the cis configuration. In one embodiment, the (Ring A)-O— moiety and the bicyclic ring of Formula I-b are in the trans configuration. In one of any of said embodiments, R² is H. In one of any of said embodiments, R² is C1-C6 alkyl. In one of any of said embodiments, R² is C1-C6 fluoroalkyl. In one of any of said embodiments, R² is C3-C6 cycloalkyl. In one of any of said embodiments, R² is (C3-C6 cycloalkyl)C1-C6 alkyl-. In one of any of said embodiments, R² is phenyl optionally substituted with one or more substituents independently selected from cyano and halogen. In one of any of said embodiments, R² is C1-C6 alkyl wherein 2-5 hydrogens are replaced by deuterium.

In one embodiment, provided are compounds of Formula I wherein X¹ is C, X² is N, and X³ is N, such that Formula I has the structure of Formula I-b:

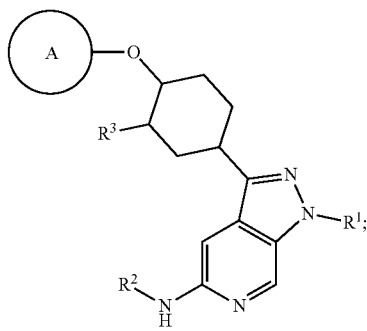

I-b wherein Ring A is Ar¹; R¹ is hetAr³; and R², R³, Ar¹ and hetAr³ are as defined for Formula I. In one embodiment, Ring A is Ar¹; R¹ is hetAr³; R³ is hydrogen; and R², Ar¹ and hetAr³ are as defined for Formula I. In one embodiment, Ring A is Ar¹; R¹ is hetAr³; R³ is hydroxyl; and R², Ar¹ and hetAr³ are as defined for Formula I. In one embodiment, the (Ring A)-O— moiety and the bicyclic ring of Formula I-b are in the cis configuration. In one embodiment, the (Ring A)-O— moiety and the bicyclic ring of Formula I-b are in the trans configuration. In one of any of said embodiments, R² is H. In one of any of said embodiments, R² is C1-C6 alkyl. In one of any of said embodiments, R² is C1-C6 fluoroalkyl. In one of any of said embodiments, R² is C3-C6 cycloalkyl. In one of any of said embodiments, R² is (C3-C6 cycloalkyl)C1-C6 alkyl-. In one of any of said embodiments, R² is phenyl optionally substituted with one or more substituents independently selected from cyano and halogen. In one of any of said embodiments, R² is C1-C6 alkyl wherein 2-5 hydrogens are replaced by deuterium.

In one embodiment, provided are compounds of Formula I wherein X¹ is C, X² is N, and X³ is N, such that Formula I has the structure of Formula I-b:

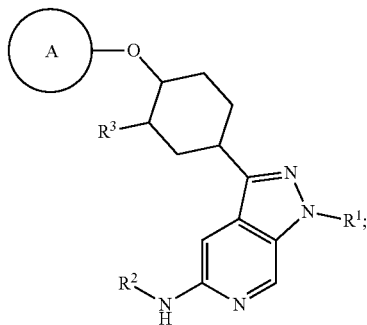

I-b wherein Ring A is Ar¹; R¹ is hetCyc¹; and R², R³, Ar¹ and hetCyc¹ are as defined for Formula I. In one embodiment, Ring A is Ar¹; R¹ is hetCyc¹; R³ is hydrogen; and R², Ar¹ and hetCyc¹ are as defined for Formula I. In one embodiment, Ring A is Ar¹; R¹ is hetCyc¹; R³ is hydroxyl; and R², Ar¹ and hetCyc¹ are as defined for Formula I. In one embodiment, the (Ring A)-O— moiety and the bicyclic ring of Formula I-b are in the cis configuration. In one embodiment, the (Ring A)-O— moiety and the bicyclic ring of Formula I-b are in the trans configuration. In one of any of said embodiments, R² is H. In one of any of said embodiments, R² is C1-C6 alkyl. In one of any of said embodiments, R² is C1-C6 fluoroalkyl. In one of any of said embodiments, R² is C3-C6 cycloalkyl. In one of any of said embodiments, R² is (C3-C6 cycloalkyl)C1-C6 alkyl-. In one of any of said embodiments, R² is phenyl optionally substituted with one or more substituents independently selected from cyano and halogen. In one of any of said embodiments, R² is C1-C6 alkyl wherein 2-5 hydrogens are replaced by deuterium.

In one embodiment, provided are compounds of Formula I wherein X¹ is C, X² is N, and X³ is N, such that Formula I has the structure of Formula I-b:

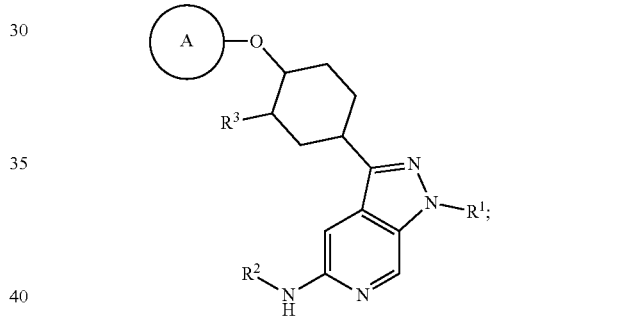

I-b wherein Ring A is hetAr²; and R¹, R², R³ and hetAr² are as defined for Formula I. In one embodiment, Ring A is hetAr²; R¹ is Ar²; and R², R³ and hetAr² are as defined for Formula I. In one embodiment, Ring A is Ar¹; R¹ is Ar²; R³ is hydrogen; and R², hetAr² and Ar² are as defined for Formula I. In one embodiment, Ring A is Ar¹; R¹ is Ar²; R³ is hydroxyl; and R², hetAr² and Ar² are as defined for Formula I. In one embodiment, the (Ring A)-O— moiety and the bicyclic ring of Formula I-b are in the cis configuration. In one embodiment, the (Ring A)-O— moiety and the bicyclic ring of Formula I-b are in the trans configuration. In one of any of said embodiments, R² is H. In one of any of said embodiments, R² is C1-C6 alkyl. In one of any of said embodiments, R² is C1-C6 fluoroalkyl. In one of any of said embodiments, R² is C3-C6 cycloalkyl. In one of any of said embodiments, R² is (C3-C6 cycloalkyl)C1-C6 alkyl-. In one of any of said embodiments, R² is phenyl optionally substituted with one or more substituents independently selected from cyano and halogen. In one of any of said embodiments, R² is C1-C6 alkyl wherein 2-5 hydrogens are replaced by deuterium.

In one embodiment, provided are compounds of Formula I wherein X¹ is C, X² is N, and X³ is N, such that Formula I has the structure of Formula I-b:

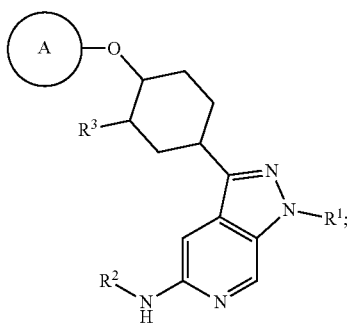

I-b wherein Ring A is hetAr²; R¹ is hetAr³; and R², R³, hetAr² and hetAr³ are as defined for Formula I. In one embodiment, Ring A is Ar¹; R¹ is hetAr³; R³ is hydrogen; and R², hetAr² and hetAr³ are as defined for Formula I. In one embodiment, Ring A is Ar¹; R¹ is hetAr³; R³ is hydroxyl; and R², hetAr² and hetAr³ are as defined for Formula I. In one embodiment, the (Ring A)-O— moiety and the bicyclic ring of Formula I-b are in the cis configuration. In one embodiment, the (Ring A)-O— moiety and the bicyclic ring of Formula I-b are in the trans configuration. In one of any of said embodiments, $R^2$ is H. In one of any of said embodiments, $R^2$ is C1-C6 alkyl. In one of any of said embodiments, $R^2$ is C1-C6 fluoroalkyl. In one of any of said embodiments, $R^2$ is C3-C6 cycloalkyl. In one of any of said embodiments, $R^2$ is (C3-C6 cycloalkyl)C1-C6 alkyl-. In one of any of said embodiments, $R^2$ is phenyl optionally substituted with one or more substituents independently selected from cyano and halogen. In one of any of said embodiments, $R^2$ is C1-C6 alkyl wherein 2-5 hydrogens are replaced by deuterium.

In one embodiment, provided are compounds of Formula I wherein $X^1$ is C, $X^2$ is N, and $X^3$ is N, such that Formula I has the structure of Formula I-b:

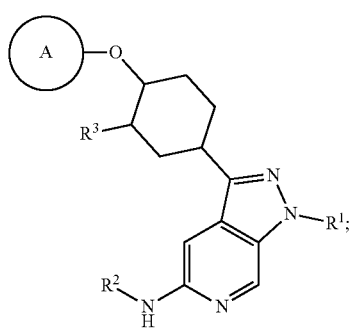

wherein Ring A is hetAr²; R¹ is hetCyc¹; and R², R³, hetAr² and hetCyc¹ are as defined for Formula I. In one embodiment, Ring A is Ar¹; R¹ is hetCyc¹; R³ is hydrogen; and R², hetAr² and hetCyc¹ are as defined for Formula I. In one embodiment, Ring A is Ar¹; R¹ is hetCyc¹; R³ is hydroxyl; and R², hetAr² and hetCyc¹ are as defined for Formula I. In one embodiment, the (Ring A)-O— moiety and the bicyclic ring of Formula I-b are in the cis configuration. In one embodiment, the (Ring A)-O— moiety and the bicyclic ring of Formula I-b are in the trans configuration. In one of any of said embodiments, $R^2$ is H. In one of any of said embodiments, $R^2$ is C1-C6 alkyl. In one of any of said embodiments, $R^2$ is C1-C6 fluoroalkyl. In one of any of said embodiments, $R^2$ is C3-C6 cycloalkyl. In one of any of said embodiments, $R^2$ is (C3-C6 cycloalkyl)C1-C6 alkyl-. In one of any of said embodiments, $R^2$ is phenyl optionally substituted with one or more substituents independently selected from cyano and halogen. In one of any of said embodiments, $R^2$ is C1-C6 alkyl wherein 2-5 hydrogens are replaced by deuterium.

In one embodiment, provided are compounds of Formula I wherein $X^1$ is N, $X^2$ is CH, and $X^3$ is C, such that Formula I has the structure of Formula I-c

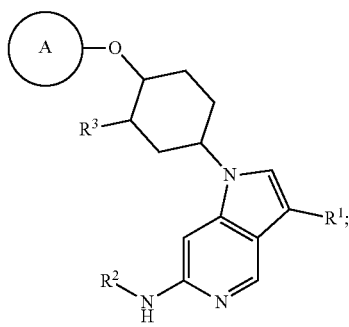

I-c wherein $X^1$ is N, $X^2$ is CH, and $X^3$ is C;
Ring A is hetAr¹ or hetAr²;
R¹ is hetAr³.
R² is H, C1-C6 alkyl, C1-C6 fluoroalkyl, C3-C6 cycloalkyl, (C3-C6 cycloalkyl)C1-C6 alkyl-, phenyl optionally substituted with one or more substituents independently selected from cyano and halogen, or C1-C6 alkyl wherein 2-5 hydrogens are replaced by deuterium;
R³ is hydrogen or hydroxyl; and
hetAr¹, hetAr² and hetAr³ are as defined for Formula I.

In one embodiment, the (Ring A)-O— moiety and the bicyclic ring of Formula I-c are in the cis configuration. In one embodiment, the (Ring A)-O— moiety and the bicyclic ring of Formula I-bc are in the trans configuration.

In one embodiment, provided are compounds of Formula I wherein $X^1$ is N, $X^2$ is CH, and $X^3$ is C, such that Formula I has the structure of Formula I-c

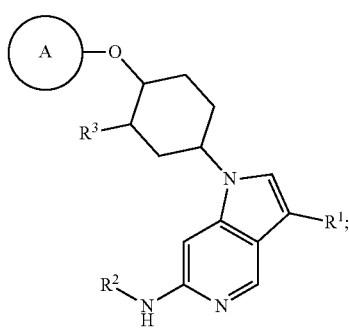

I-c wherein Ring A is hetAr¹; and R¹, R², R³ and hetAr¹ are as defined for Formula I. In one embodiment, Ring A is hetAr¹; R¹ is hetAr³; and R², R³, hetAr¹ and hetAr³ are as defined for Formula I. In one embodiment, Ring A is hetAr¹; R¹ is hetAr³; R³ is hydrogen; and R², hetAr¹ and hetAr³ are as defined for Formula I. In one embodiment, Ring A is Ar¹; R¹ is hetAr³; R³ is hydroxyl; and R², hetAr¹ and hetAr³ are as defined for Formula I. In one embodiment, the (Ring A)-O— moiety and the bicyclic ring of Formula I-c are in the cis configuration. In one embodiment, the (Ring A)-O— moiety and the bicyclic ring of Formula I-bc are in the trans configuration. In one of any of said embodiments, R² is H. In one of any of said embodiments, R² is C1-C6 alkyl. In one of any of said embodiments, R² is C1-C6 fluoroalkyl. In one of any of said embodiments, R² is C3-C6 cycloalkyl. In one of any of said embodiments, R² is (C3-C6 cycloalkyl)C1-C6 alkyl-. In one of any of said embodiments, R² is phenyl optionally substituted with one or more substituents independently selected from cyano and halogen. In one of any of said embodiments, R² is C1-C6 alkyl wherein 2-5 hydrogens are replaced by deuterium.

In one embodiment, provided are compounds of Formula I wherein $X^1$ is N, $X^2$ is CH, and $X^3$ is C, such that Formula I has the structure of Formula I-c

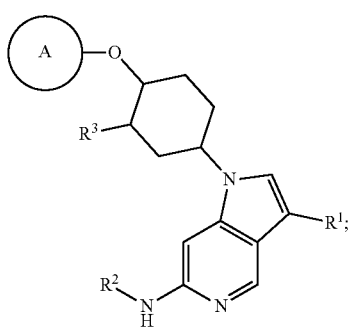

I-c wherein Ring A is hetAr²; and $R^1$, $R^2$, $R^3$ and hetAr² are as defined for Formula I. In one embodiment, Ring A is hetAr²; $R^1$ is hetAr³; and $R^2$, $R^3$, hetAr² and hetAr³ are as defined for Formula I. In one embodiment, Ring A is hetAr²; $R^1$ is hetAr³; $R^3$ is hydrogen; and $R^2$, hetAr² and hetAr³ are as defined for Formula I. In one embodiment, Ring A is Ar¹; $R^1$ is hetAr³; $R^3$ is hydroxyl; and $R^2$, hetAr² and hetAr³ are as defined for Formula I. In one embodiment, the (Ring A)-O— moiety and the bicyclic ring of Formula I-c are in the cis configuration. In one embodiment, the (Ring A)-O— moiety and the bicyclic ring of Formula I-c are in the trans configuration. In one of any of said embodiments, R² is H. In one of any of said embodiments, R² is C1-C6 alkyl. In one of any of said embodiments, R² is C1-C6 fluoroalkyl. In one of any of said embodiments, R² is C3-C6 cycloalkyl. In one of any of said embodiments, R² is (C3-C6 cycloalkyl)C1-C6 alkyl-. In one of any of said embodiments, R² is phenyl optionally substituted with one or more substituents independently selected from cyano and halogen. In one of any of said embodiments, R² is C1-C6 alkyl wherein 2-5 hydrogens are replaced by deuterium.

The compounds of Formula I include pharmaceutically acceptable salts thereof. In addition, the compounds of Formula I also include other salts of such compounds which are not necessarily pharmaceutically acceptable salts, and which may be useful as intermediates for preparing and/or purifying compounds of Formula I and/or for separating enantiomers of compounds of Formula I. Non-limiting examples of pharmaceutically acceptable salts of compounds of Formula I include hydrochloride salts.

It will further be appreciated that the compounds of Formula I or their salts may be isolated in the form of solvates, and accordingly that any such solvate is included within the scope of the present invention. For example, compounds of Formula I and salts thereof can exist in unsolvated as well as solvated forms with pharmaceutically acceptable solvents such as water, ethanol, and the like.

In one embodiment, the compounds of Formula I include the compounds of Examples 1-470, 471A, 471B, 472-510 and stereoisomers and pharmaceutically acceptable salts and solvates thereof. In one embodiment, the compounds of Examples 1-470, 471A, 471B, and 472-510 are in the free base form. In one embodiment, one or more compounds of Examples 1-470, 471A, 471B, and 472-510 are hydrochloride acid salts.

The term "pharmaceutically acceptable" indicates that the compound, or salt or composition thereof is compatible chemically and/or toxicologically with the other ingredients comprising a formulation and/or the patient being treated therewith.

Compounds provided herein may also contain unnatural proportions of atomic isotopes at one or more of the atoms that constitute such compounds. That is, an atom, in particular when mentioned in relation to a compound according to Formula I, comprises all isotopes and isotopic mixtures of that atom, either naturally occurring or synthetically produced, either with natural abundance or in an isotopically enriched form. For example, when hydrogen is mentioned, it is understood to refer to $^1$H, $^2$H, $^3$H or mixtures thereof; when carbon is mentioned, it is understood to refer to $^{11}$C, $^{12}$C, $^{13}$C, $^{14}$C or mixtures thereof; when nitrogen is mentioned, it is understood to refer to $^{13}$N, $^{14}$N, $^{15}$N or mixtures thereof; when oxygen is mentioned, it is understood to refer to $^{14}$O, $^{15}$O, $^{16}$O, $^{17}$O, $^{18}$O or mixtures thereof; and when fluoro is mentioned, it is understood to refer to $^{18}$F, $^{19}$F or mixtures thereof. The compounds provided herein therefore also comprise compounds with one or more isotopes of one or more atoms, and mixtures thereof, including radioactive compounds, wherein one or more non-radioactive atoms has been replaced by one of its radioactive enriched isotopes. Radiolabeled compounds are useful as additional anticancer agents, e.g., cancer therapeutic agents, research reagents, e.g., assay reagents, and diagnostic agents, e.g., in vivo imaging agents. All isotopic variations of the compounds provided herein, whether radioactive or not, are intended to be encompassed within the scope of the present invention.

For illustrative purposes, Schemes 1-13 show general methods for preparing the compounds provided herein as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Scheme 1

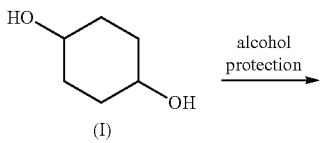

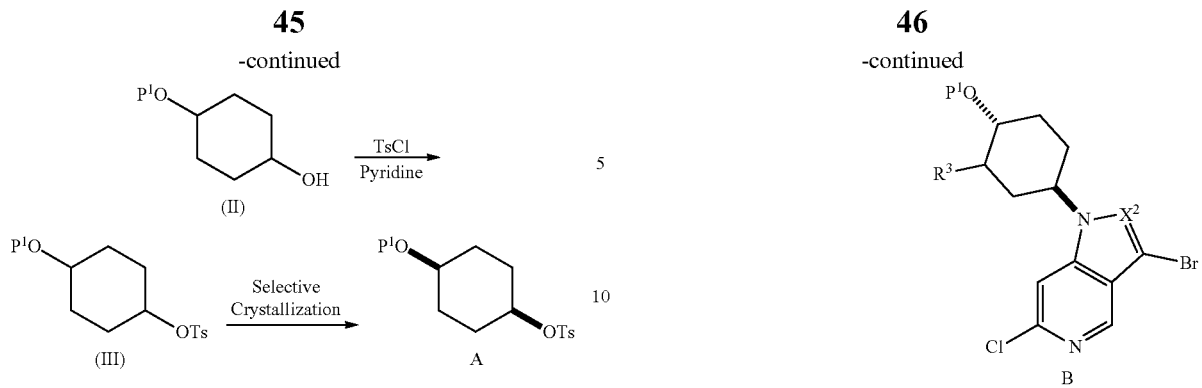

Scheme 1 shows a general scheme for the synthesis of intermediate A which is useful for preparing compounds of Formula I. Cyclohexane-1,4-diol (i) may be mono-protected with a suitable alcohol protecting group under suitable reaction conditions to provide the mono-protected compound (ii) where $P^1$ is an alcohol protecting group, such as a silyl protecting group, for example a t-butyldimethylsilyl group. For example, (i) can be treated with t-butylchlorodimethylsilane in the presence of a base such as imidazole to provide the mono-protected compound (ii) where $P^1$ is t-butyldimethylsilyl. The hydroxyl group of compound (ii) may be converted to a tosylate group by treating (ii) with 4-methylbenzenesulfonyl chloride in the presence of base, such as pyridine, to provide a mixture of compound (iii) as a mixture of the cis- and trans-isomers. The cis-isomer of intermediate A may be isolated by selective crystallization of compound (iii). As used herein, the term "selective crystallization" refers to a process in which individual compounds may be separated from a solution containing two or more crystallizable compounds. In one embodiment for isolating compound (iii) by selective crystallization (i.e., under conditions that favor crystallization of cis-isomer over the trans-isomer), the mixture of cis- and trans-compound (iii) is suspended in hexanes and warmed to reflux, and then allowed to cool to room temperature. Filtration of the resultant solids provides cis- and trans-compound (iii) which is enriched in the cis-isomer (e.g., about a 8:1 mixture of cis/trans). One or more additional crystallizations from hexanes provides Intermediate A as >99:1 cis/trans.

Scheme 2 shows a general scheme for the synthesis of intermediate B which is useful for the preparation of compounds of Formula I, wherein $X^1$ is N, $X^2$ is N or CH, $X^3$ is C, $R^3$ is H, and $P^1$ is an alcohol protecting group, wherein the $P^1$—O— moiety and bicyclic ring of intermediate B are in the trans-configuration. Compound 1, where $X^2$ is N or CH, may be treated with N-bromosuccinimide to provide compound 2. Compound 2 may be treated with intermediate A in the presence of a base, such as an inorganic base, such as an alkali metal carbonate (e.g. potassium carbonate or sodium carbonate) to provide intermediate B.

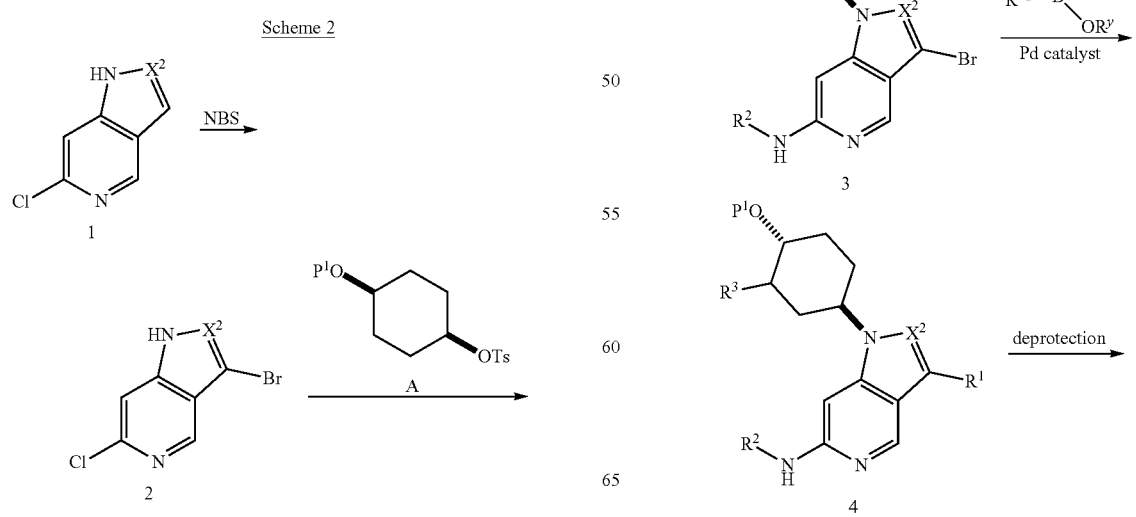

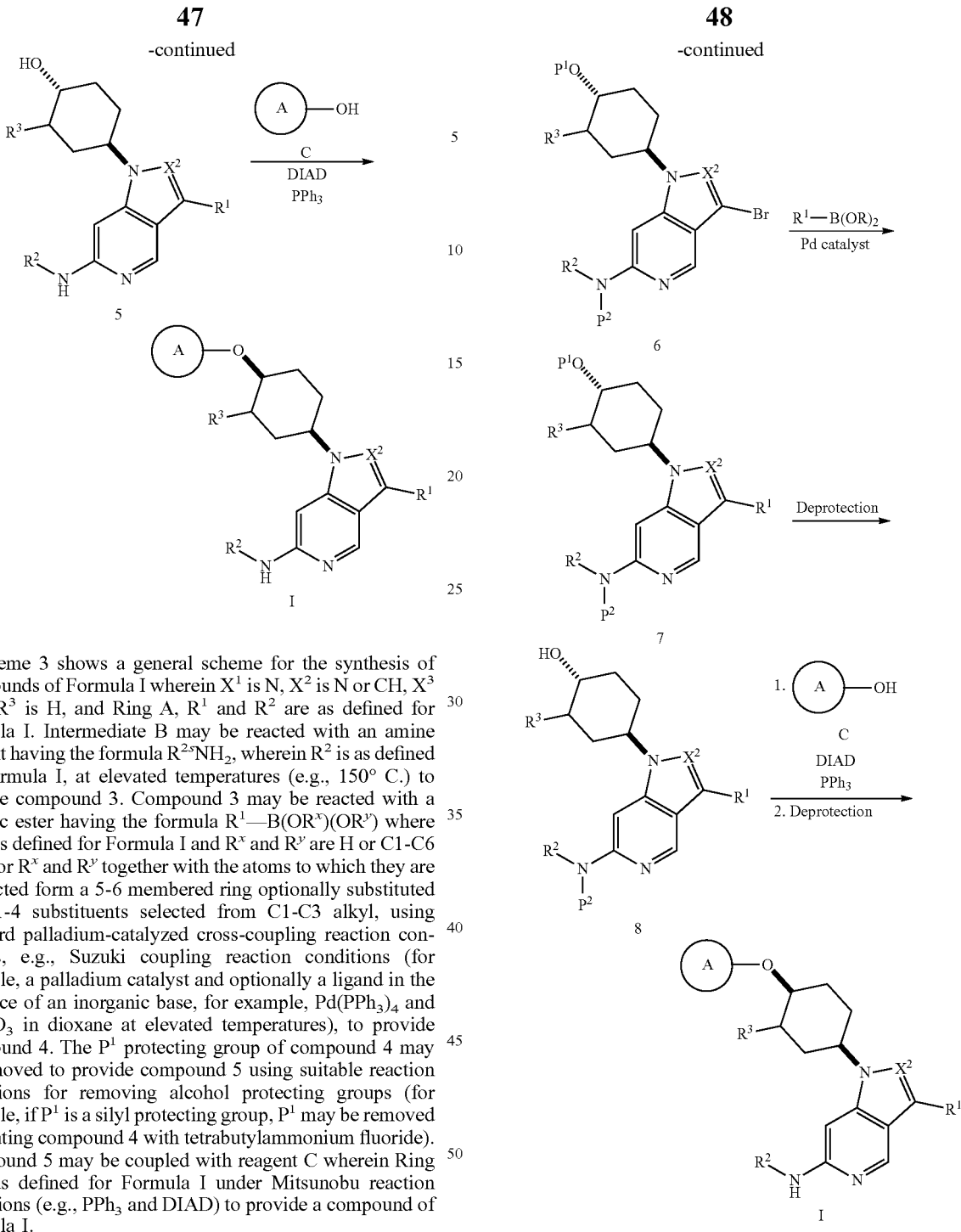

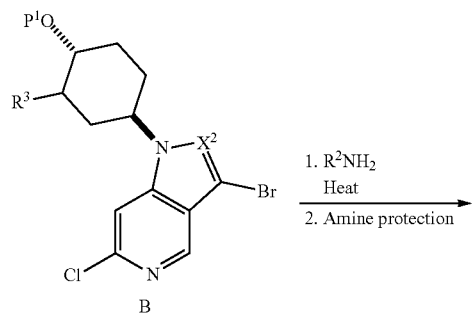

Scheme 3 shows a general scheme for the synthesis of compounds of Formula I wherein $X^1$ is N, $X^2$ is N or CH, $X^3$ is C, $R^3$ is H, and Ring A, $R^1$ and $R^2$ are as defined for Formula I. Intermediate B may be reacted with an amine reagent having the formula $R^{2s}NH_2$, wherein $R^2$ is as defined for Formula I, at elevated temperatures (e.g., 150° C.) to provide compound 3. Compound 3 may be reacted with a boronic ester having the formula $R^1$—B(OR$^x$)(OR$^y$) where $R^1$ is as defined for Formula I and $R^x$ and $R^y$ are H or C1-C6 alkyl, or $R^x$ and $R^y$ together with the atoms to which they are connected form a 5-6 membered ring optionally substituted with 1-4 substituents selected from C1-C3 alkyl, using standard palladium-catalyzed cross-coupling reaction conditions, e.g., Suzuki coupling reaction conditions (for example, a palladium catalyst and optionally a ligand in the presence of an inorganic base, for example, Pd(PPh$_3$)$_4$ and Na$_2$CO$_3$ in dioxane at elevated temperatures), to provide compound 4. The $P^1$ protecting group of compound 4 may be removed to provide compound 5 using suitable reaction conditions for removing alcohol protecting groups (for example, if $P^1$ is a silyl protecting group, $P^1$ may be removed by treating compound 4 with tetrabutylammonium fluoride). Compound 5 may be coupled with reagent C wherein Ring A is as defined for Formula I under Mitsunobu reaction conditions (e.g., PPh$_3$ and DIAD) to provide a compound of Formula I.

Scheme 4 shows another general scheme for the synthesis of compounds of Formula I where $X^1$ is N, $X^2$ is N or CH, $X^3$ is C, $R^3$ is H, and Ring A, $R^1$ and $R^2$ are as defined for Formula I. Intermediate B may be reacted with an amine reagent having the formula $R^2NH_2$, wherein $R^2$ is as defined for Formula I, with heating, followed by protection of the reaction product with an appropriate amino protecting group (e.g., a Boc protecting group) to provide compound 6 where $P^2$ is an amino protecting group. Compound 6 may be coupled with a boronic ester having the formula $R^1$—B (OR$^x$)(OR$^y$), where $R^1$ is as defined for Formula I and $R^x$ and $R^y$ are H or C1-C6 alkyl, or $R^x$ and $R^y$ together with the atoms to which they are connected form a 5-6 membered ring optionally substituted with 1-4 substituents selected from C1-C3 alkyl, using standard palladium-catalyzed cross-coupling reaction conditions such as described in Scheme 3, to provide compound 7. The $P^1$ alcohol protecting group of compound 7 may be removed using suitable reaction conditions and reagents (for example, if $P^1$ is a silyl protecting group, $P^1$ may be removed by treating compound 4 with tetrabutylammonium fluoride) to provide compound 8. Compound 8 may be coupled with reagent C wherein Ring A is as defined for Formula I under Mitsunobu reaction conditions (e.g., $PPh_3$ and DIAD), followed by removal of the amino protecting group under standard conditions (e.g., HCl or TFA) to provide a compound of Formula I.

Scheme 5

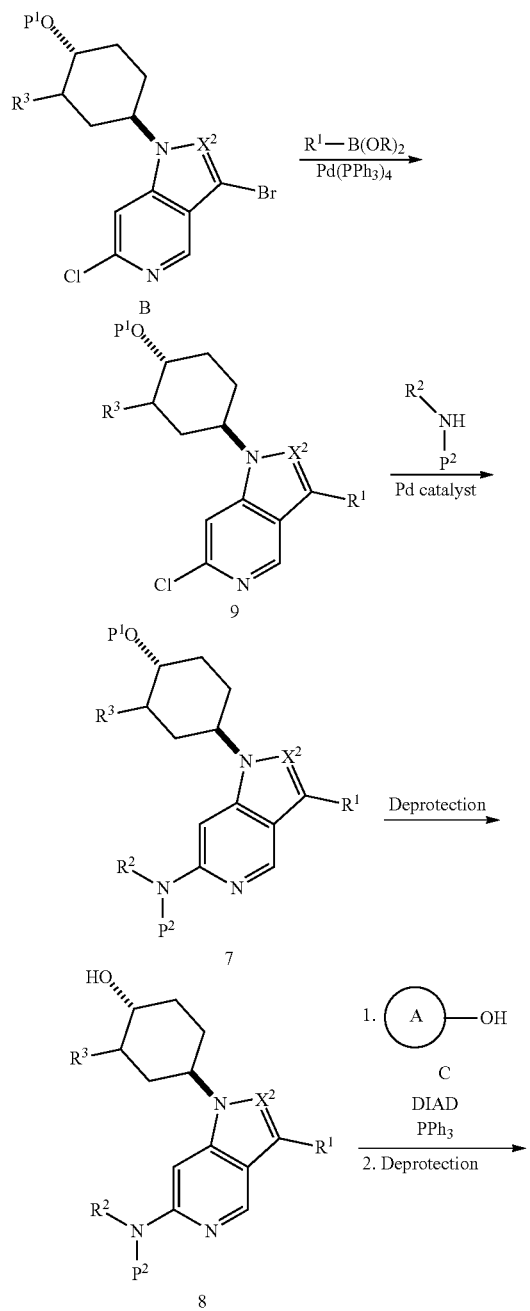

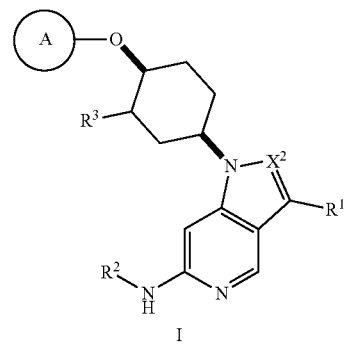

Scheme 5 shows another general scheme for the synthesis of compounds of Formula I where $X^1$ is N, $X^2$ is N or CH, $X^3$ is C, $R^3$ is H, and Ring A, $R^1$ and $R^2$ are as defined for Formula I. Intermediate B may be reacted with a boronic ester having the formula $R^1$—$B(OR^x)(OR^y)$, where $R^1$ is as defined for Formula I and $R^x$ and $R^y$ are H or C1-C6 alkyl, or $R^x$ and $R^y$ together with the atoms to which they are connected form a 5-6 membered ring optionally substituted with 1-4 substituents selected from C1-C3 alkyl, using standard palladium-catalyzed cross-coupling reaction conditions such as described in Scheme 3, to provide compound 9. Compound 9 may be reacted with a reagent having the formula $R^2$—NH—$P^2$ wherein $R^2$ is as defined for Formula I and $P^2$ is an amino protecting group (e.g., a Boc group) using standard palladium-catalyzed cross-coupling reaction conditions (e.g., using a palladium catalyst such as $Pd(PPh_3)$, $PdCl_2(dppf).CH_2Cl_2$, or $Pd(OAc)_2$, and a alkaline base such as an alkaline carbonate, for example potassium carbonate) to provide compound 7. The $P^1$ alcohol protecting group of compound 7 may be removed using suitable reaction conditions for removing alcohol protecting groups (for example, if $P^1$ is a silyl protecting group, $P^1$ may be removed by treating compound 7 with tetrabutylammonium fluoride) to provide compound 8. Compound 8 may be coupled with reagent C wherein Ring A is as defined for Formula I under Mitsunobu reaction conditions (e.g., $PPh_3$ and DIAD), followed by removal of the amino protecting group $P^2$ under standard reaction conditions (e.g., HCl or TFA), to provide a compound of Formula I.

Scheme 6

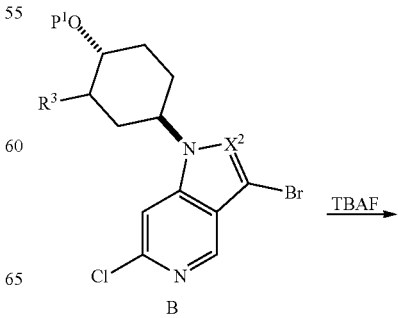

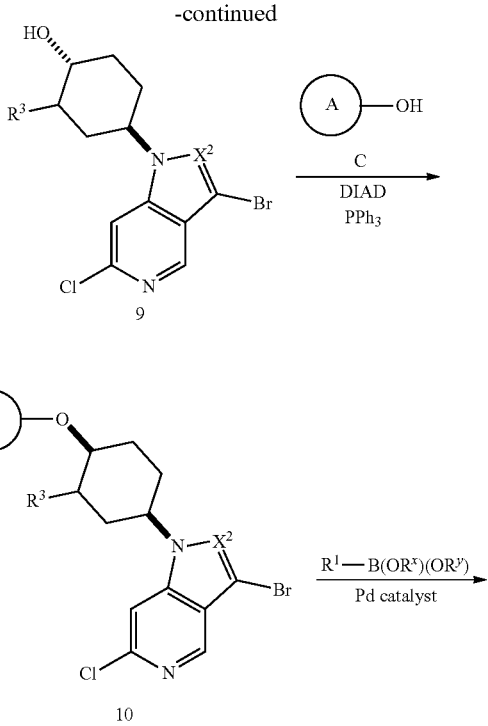

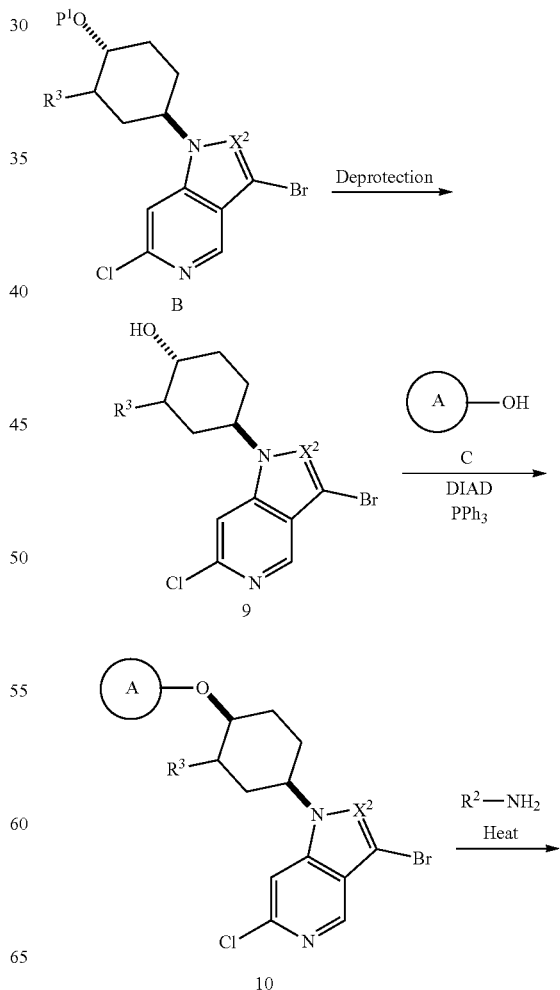

PPh$_3$ and DIAD) to provide compound 10. Compound 10 may be coupled with a boronic ester having the formula R$^1$—B(OR$^x$)(OR$^y$), where R$^1$ is as defined for Formula I and R$^x$ and R$^y$ are H or C1-C6 alkyl, or R$^x$ and R$^y$ together with the atoms to which they are connected form a 5-6 membered ring optionally substituted with 1-4 substituents selected from C1-C3 alkyl, using standard palladium-catalyzed cross-coupling reaction conditions such as described in Scheme 3, to provide compound 11. A compound of Formula I may be prepared by reacting compound 11 with an amine reagent having the formula R$^2$NH$_2$, wherein R$^2$ is as defined for Formula I, at elevated temperatures (e.g., 150° C.) to provide a compound of Formula I. Alternatively, a compound of Formula I may be prepared by reacting compound 11 with an amine reagent having the formula R$^2$—NH—P$^2$ wherein R$^2$ is as defined for Formula I and P$^2$ is an amino protecting group, (e.g., a Boc group) using standard palladium-catalyzed cross-coupling reaction conditions (e.g., using a palladium catalyst such as Pd(PPh$_3$), PdCl$_2$(dppf), or Pd(OAc)$_2$, and a alkaline base such as an alkaline carbonate, for example potassium carbonate), followed by removal the amino protecting group under standard reaction conditions (e.g., HCl or TFA), to provide a compound of Formula I.

Scheme 6 shows another general scheme for the synthesis of compounds of Formula I where X$^1$ is N, X$^2$ is N or CH, X$^3$ is C, R$^3$ is H, and Ring A, R$^1$ and R$^2$ are as defined for Formula I. The alcohol protecting group P$^1$ of intermediate B may be removed using suitable reaction conditions and reagents to provide compound 9 (for example, if P$^1$ is a silyl protecting group, P$^1$ may be removed by treating intermediate B with tetrabutylammonium fluoride). Compound 9 may be coupled with reagent C wherein Ring A is as defined for Formula I under Mitsunobu reaction conditions (e.g.,

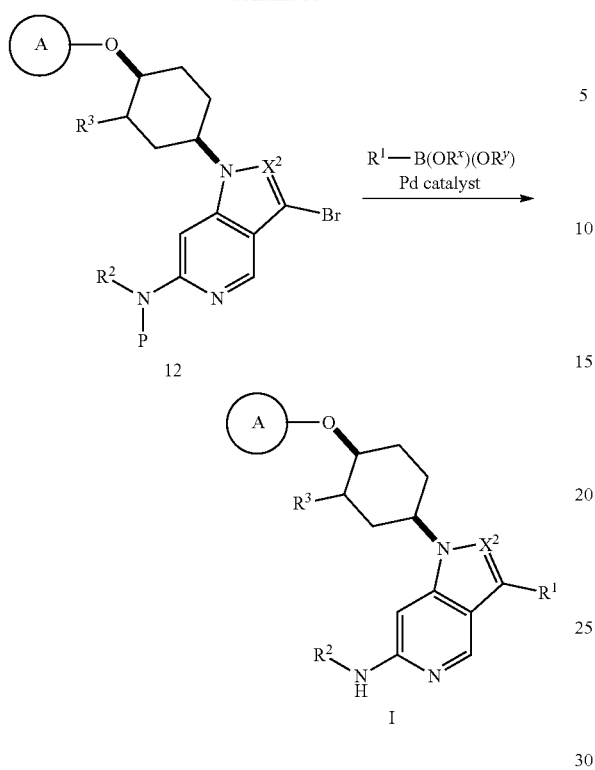

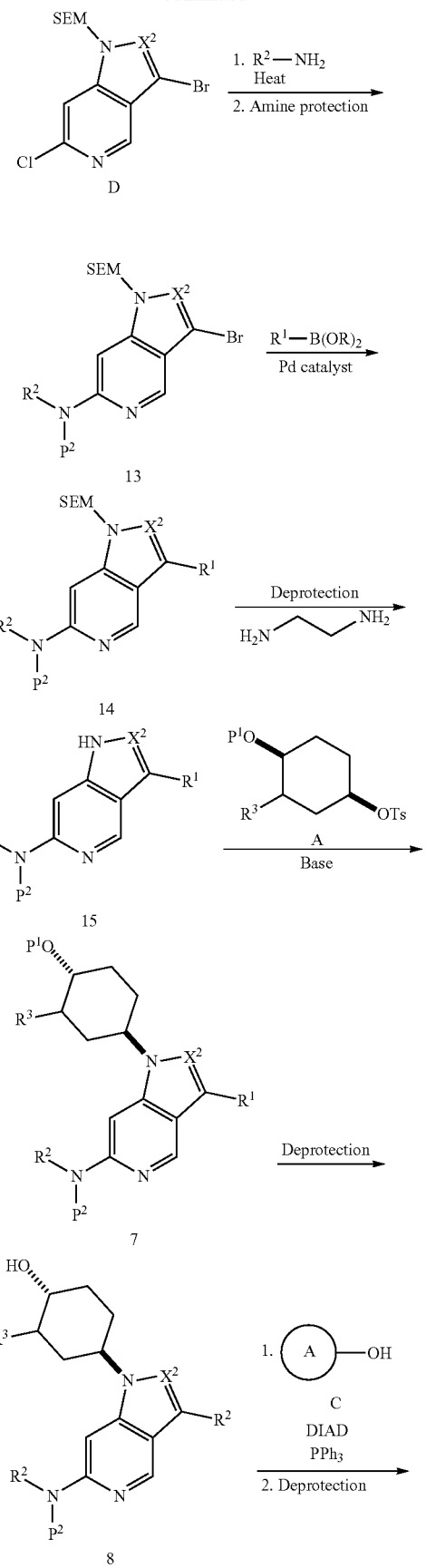

Scheme 7 shows another general scheme for the synthesis of compounds of Formula I where $X^1$ is N, $X^2$ is N or CH, $X^3$ is C, $R^3$ is H, and Ring A, $R^1$ and $R^2$ are as defined for Formula I. The alcohol protecting group $P^1$ of intermediate B may be removed using suitable reaction conditions and reagents to provide compound 9 (for example, if $P^1$ is a silyl protecting group, $P^1$ may be removed by treating intermediate B with tetrabutylammonium fluoride). Compound 9 may be coupled with reagent C wherein Ring A is as defined for Formula I under Mitsunobu reaction conditions (e.g., PPh₃ and DIAD) to provide compound 10. A compound of formula 12, wherein P is hydrogen, may be prepared by reacting compound 10 with an amine reagent having the formula $R^2NH_2$, wherein $R^2$ is as defined for Formula I, at elevated temperatures (e.g., 150° C.) to provide a compound of Formula I. A compound of Formula I may be prepared by coupling compound 12 with a boronic ester having the formula $R^1$—B(OR$^x$)(OR$^y$), where $R^1$ is as defined for Formula I and $R^x$ and $R^y$ are H or C1-C6 alkyl, or $R^x$ and $R^y$ together with the atoms to which they are connected form a 5-6 membered ring optionally substituted with 1-4 substituents selected from C1-C3 alkyl, using standard palladium-catalyzed cross-coupling reaction conditions such as described in Scheme 3.

Scheme 8

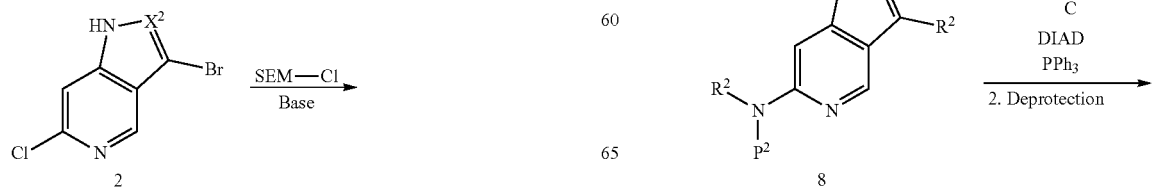

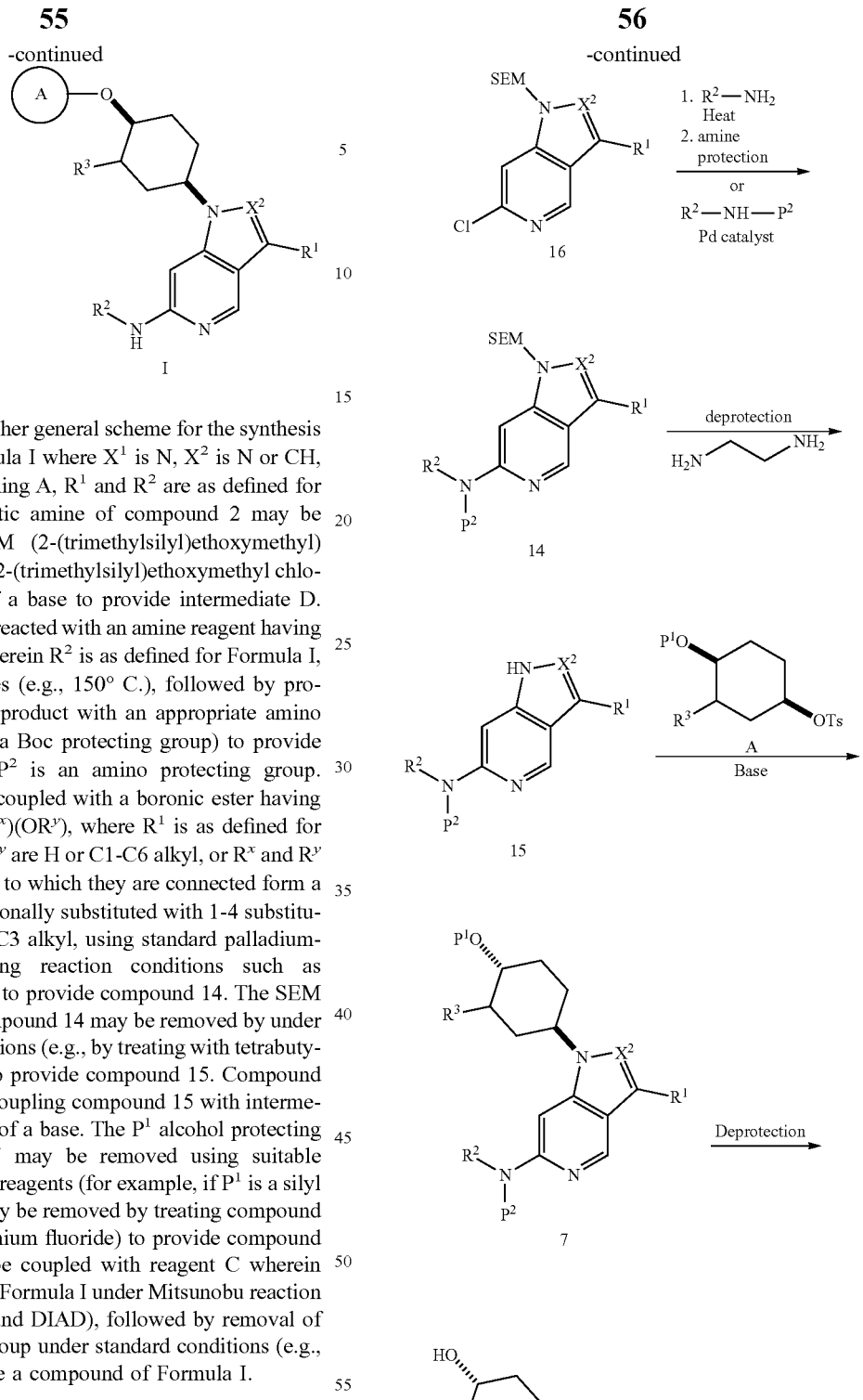

Scheme 8 shows another general scheme for the synthesis of compounds of Formula I where $X^1$ is N, $X^2$ is N or CH, $X^3$ is C, $R^3$ is H, and Ring A, $R^1$ and $R^2$ are as defined for Formula I. The aromatic amine of compound 2 may be protected with a SEM (2-(trimethylsilyl)ethoxymethyl) group by reaction with 2-(trimethylsilyl)ethoxymethyl chloride in the presence of a base to provide intermediate D. Intermediate D may be reacted with an amine reagent having the formula $R^2NH_2$, wherein $R^2$ is as defined for Formula I, at elevated temperatures (e.g., 150° C.), followed by protection of the reaction product with an appropriate amino protecting group (e.g., a Boc protecting group) to provide compound 13 where $P^2$ is an amino protecting group. Compound 13 may be coupled with a boronic ester having the formula $R^1$—$B(OR^x)(OR^y)$, where $R^1$ is as defined for Formula I and $R^x$ and $R^y$ are H or C1-C6 alkyl, or $R^x$ and $R^y$ together with the atoms to which they are connected form a 5-6 membered ring optionally substituted with 1-4 substituents selected from C1-C3 alkyl, using standard palladium-catalyzed cross-coupling reaction conditions such as described in Scheme 3, to provide compound 14. The SEM protecting group of compound 14 may be removed by under standard reaction conditions (e.g., by treating with tetrabutylammonium fluoride) to provide compound 15. Compound 7 may be prepared by coupling compound 15 with intermediate A in the presence of a base. The $P^1$ alcohol protecting group of compound 7 may be removed using suitable reaction conditions and reagents (for example, if $P^1$ is a silyl protecting group, $P^1$ may be removed by treating compound 4 with tetrabutylammonium fluoride) to provide compound 8. Compound 8 may be coupled with reagent C wherein Ring A is as defined for Formula I under Mitsunobu reaction conditions (e.g., $PPh_3$ and DIAD), followed by removal of the amino protecting group under standard conditions (e.g., HCl or TFA) to provide a compound of Formula I.

Scheme 9

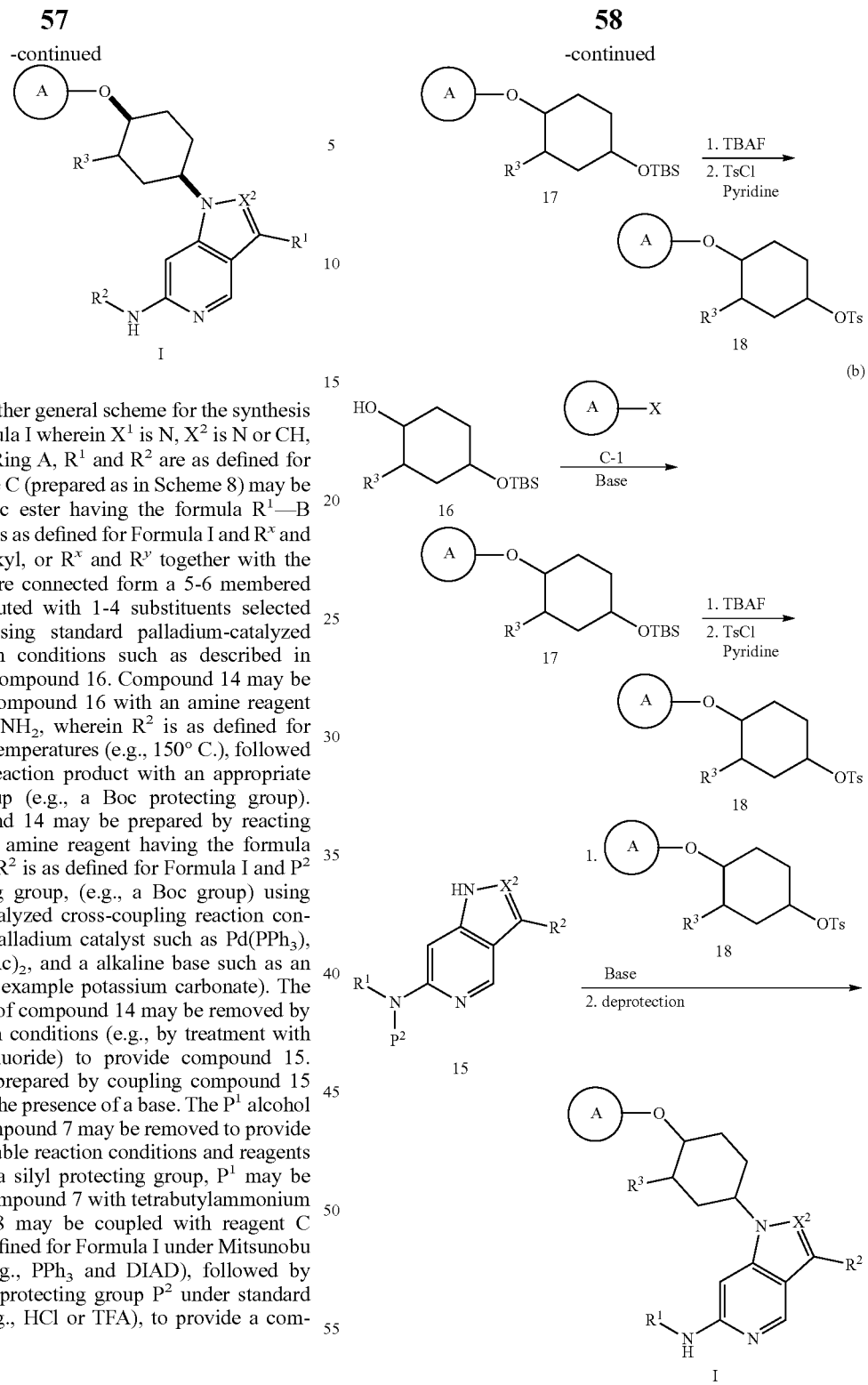

Scheme 9 shows another general scheme for the synthesis of compounds of Formula I wherein $X^1$ is N, $X^2$ is N or CH, $X^3$ is C, $R^3$ is H, and Ring A, $R^1$ and $R^2$ are as defined for Formula I. Intermediate C (prepared as in Scheme 8) may be coupled with a boronic ester having the formula $R^1$—B$(OR^x)(OR^y)$, where $R^1$ is as defined for Formula I and $R^x$ and $R^y$ are H or C1-C6 alkyl, or $R^x$ and $R^y$ together with the atoms to which they are connected form a 5-6 membered ring optionally substituted with 1-4 substituents selected from C1-C3 alkyl, using standard palladium-catalyzed cross-coupling reaction conditions such as described in Scheme 3, to provide compound 16. Compound 14 may be prepared by reacting compound 16 with an amine reagent having the formula $R^2NH_2$, wherein $R^2$ is as defined for Formula I, at elevated temperatures (e.g., 150° C.), followed by protection of the reaction product with an appropriate amino protecting group (e.g., a Boc protecting group). Alternatively, compound 14 may be prepared by reacting compound 16 with an amine reagent having the formula $R^2$—NH—$P^2$ wherein $R^2$ is as defined for Formula I and $P^2$ is an amino protecting group, (e.g., a Boc group) using standard palladium-catalyzed cross-coupling reaction conditions (e.g., using a palladium catalyst such as Pd(PPh$_3$), PdCl$_2$(dppf), or Pd(OAc)$_2$, and a alkaline base such as an alkaline carbonate, for example potassium carbonate). The SEM protecting group of compound 14 may be removed by under standard reaction conditions (e.g., by treatment with tetrabutylammonium fluoride) to provide compound 15. Compound 7 may be prepared by coupling compound 15 with intermediate A in the presence of a base. The $P^1$ alcohol protecting group of compound 7 may be removed to provide compound 8 using suitable reaction conditions and reagents (for example, if $P^1$ is a silyl protecting group, $P^1$ may be removed by treating compound 7 with tetrabutylammonium fluoride). Compound 8 may be coupled with reagent C wherein Ring A is as defined for Formula I under Mitsunobu reaction conditions (e.g., PPh$_3$ and DIAD), followed by removal of the amino protecting group $P^2$ under standard reaction conditions (e.g., HCl or TFA), to provide a compound of Formula I.

Scheme 10

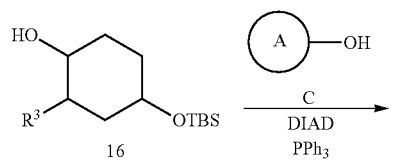

Scheme 10 shows another general scheme for the synthesis of compounds of Formula I wherein $X^1$ is N, $X^2$ is N or CH, $X^3$ is C, $R^3$ is H, and Ring A, $R^1$ and $R^2$ are as defined for Formula I. A general scheme for preparing intermediate compound 18 is shown in process (a). According to process (a), compound 16 may be coupled with reagent C wherein Ring A is as defined for Formula I under Mitsunobu reaction conditions (e.g., PPh$_3$ and DIAD) to provide compound 17. Removal of the alcohol protecting group followed by addition of a tosylate group by reaction with p-toluenesulfonyl chloride in the presence of a base such as pyridine provides compound 18. Alternatively, intermediate compound 18 can be made according to process (b). According to process (b), compound 16 may be coupled reagent C-1 wherein Ring A is as defined for Formula I and X can be, for example, a halogen such as F or Cl. Compound 18 prepared by either method (a) or (b) may then be coupled with compound 15 (prepared, for example, as shown in Scheme 8) wherein $X^2$ is N, $P^2$ is an amino protecting group, and $R^1$ and $R^2$ are as defined for Formula I, in the presence of a base, followed by removal of the amino protecting group $P^2$ under standard reaction conditions (e.g., HCl or TFA), to provide a compound of Formula I. In one embodiment, the starting material (compound 16) or either of the intermediates (e.g., compounds 17 or 18), which are represented as mixtures of the cis- and trans-isomers in Scheme 10, may be purified to isolate the cis- or trans-isomer, e.g., by column chromatography, prior to proceeding with the subsequent reaction step. Alternatively, the cis- and/or trans-isomer of a compound of Formula I may be isolated upon purification of a compound of Formula I that has been prepared as a mixture of cis- and trans isomers, e.g., by column chromatography.

Scheme 11

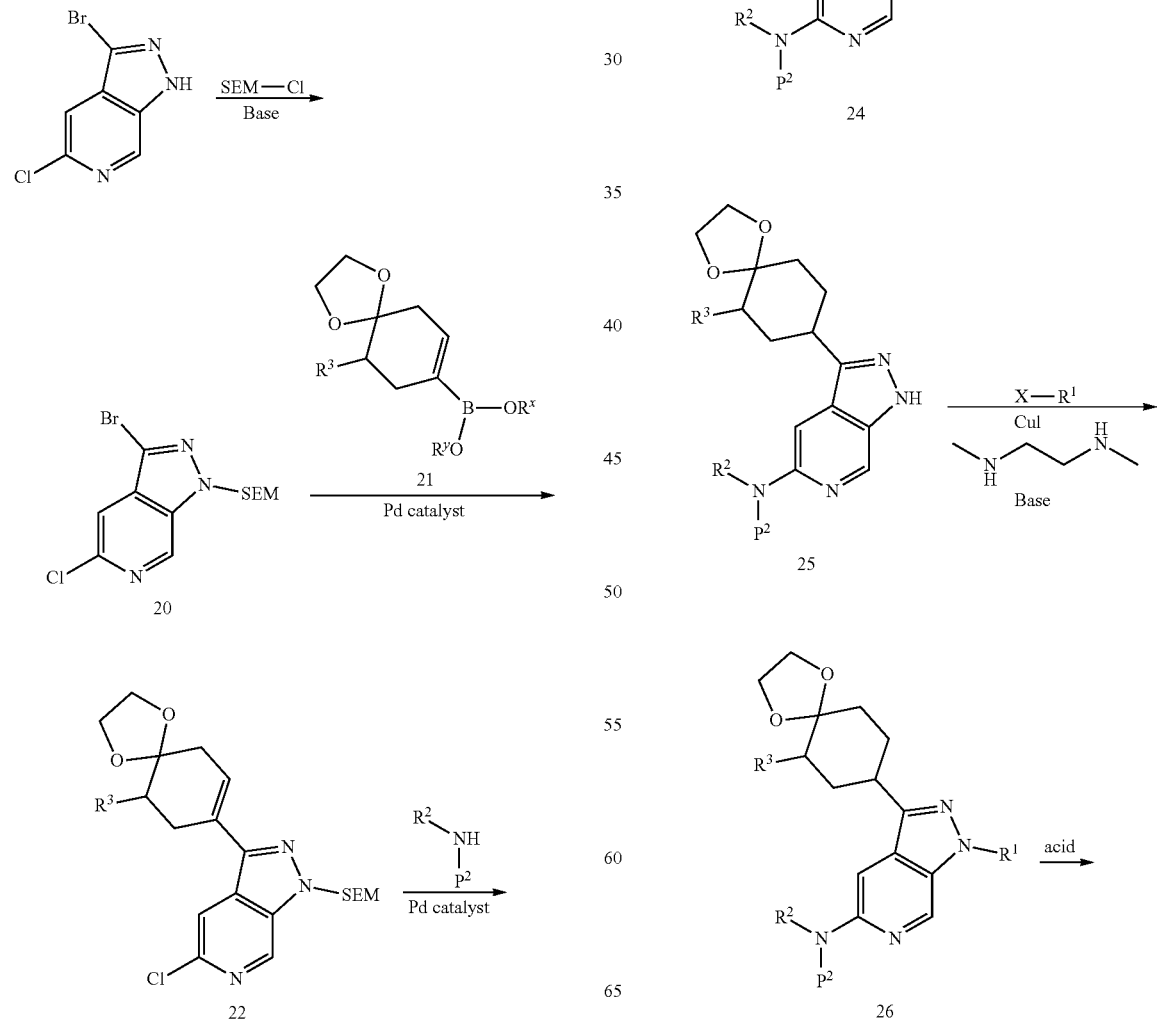

-continued

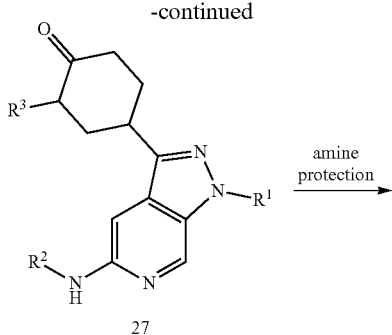

27

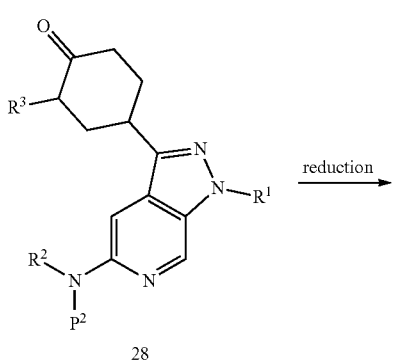

28

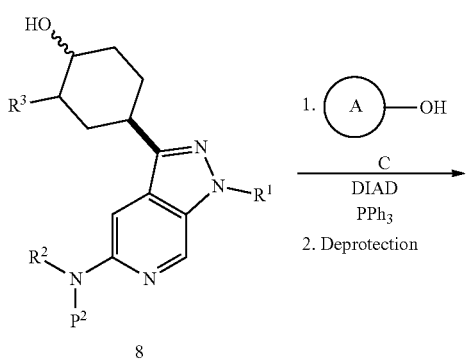

8

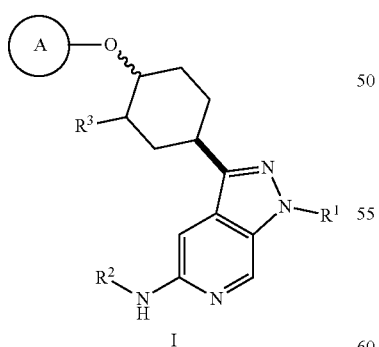

I

Scheme 11 shows a general scheme for the synthesis of compounds of Formula I wherein $X^1$ is C, $X^2$ is N, $X^3$ is N, $R^1$ is $Ar^2$ or $hetAr^3$, $R^3$ is hydrogen, and $Ar^2$, $hetAr^3$, $R^2$ and Ring A are as defined for Formula I. 3-Bromo-5-chloro-1H-pyrazolo[3,4-c]pyridine may be treated with 2-(trimethylsilyl)ethoxymethyl chloride in the presence of the base to provide the SEM-protected compound 20. Compound 20 may be reacted with the boronic ester compound 21 where $R^3$ is hydrogen and $R^x$ and $R^y$ are H or C1-C6 alkyl, or $R^x$ and $R^y$ together with the atoms to which they are connected form a 5-6 membered ring optionally substituted with 1-4 substituents selected from C1-C3 alkyl, using standard palladium-catalyzed cross-coupling reaction conditions, e.g., Suzuki coupling reaction conditions (for example, a palladium catalyst and optionally a ligand in the presence of an inorganic base, for example, $Pd(PPh_3)_4$ and $Na_2CO_3$ in dioxane at elevated temperatures), to provide compound 22. Compound 22 may be treated with a reagent having the formula $R^2$—NH—$P^2$ wherein $R^2$ is as defined for Formula I and $P^2$ is an amino protecting group (e.g., a Boc group) using standard palladium-catalyzed cross-coupling reaction conditions (e.g., using a palladium catalyst such as $Pd(PPh_3)$, $PdCl_2(dppf)$, or $Pd(OAc)_2$, and a alkaline base such as an alkaline carbonate, for example potassium carbonate) to provide compound 23. Compound 23 may be treated to hydrogenation conditions (e.g., under a hydrogen atmosphere in the presence of a catalyst, e.g., a palladium catalyst, e.g., palladium on carbon) to provide compound 24. The amino protecting group $P^2$ of compound 24 may be removed under standard reaction conditions (e.g., by treatment with tetrabutylammonium fluoride) to provide compound 25. Compound 26 may be prepared by reacting compound 25 with a reagent having the formula X—$R^1$ where $R^1$ is as defined for Formula I and X is a leaving group or leaving atom, such as a halogen atom, for example iodo, using standard N-arylation reaction conditions, for example, with a copper catalyst (e.g., copper (I) iodide) in the presence of a base and optionally in the presence of a diamine ligand (e.g., ethane-1,2-diamine). The oxo protecting group of compound 26 may be removed by treating compound 26 with acid, for example HCl, to provide compound 27. The amino group of compound 27 may be protected with a suitable protecting group $P^2$ (for example a Boc protecting group) to provide compound 28. The oxo moiety of compound 28 may be reduced with a suitable reducing agent (e.g., a hydride reagent, for example sodium borohydride or lithium aluminum hydride) to provide compound 8. Compound 8 may be coupled with reagent C wherein Ring A is as defined for Formula I under Mitsunobu reaction conditions (e.g., $PPh_3$ and DIAD), followed by removal of the amino protecting group $P^2$ under standard reaction conditions (e.g., HCl or TFA), to provide a compound of Formula I.

Scheme 12

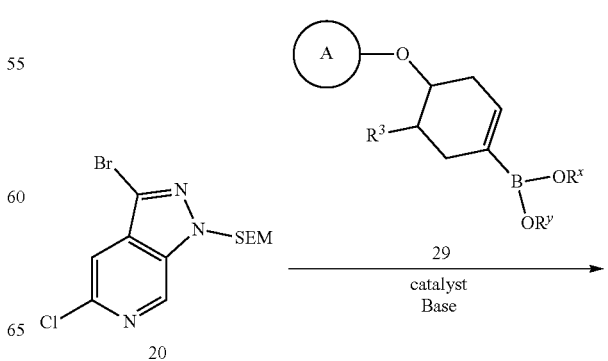

20

-continued

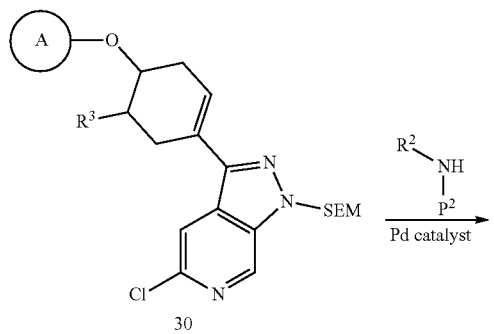

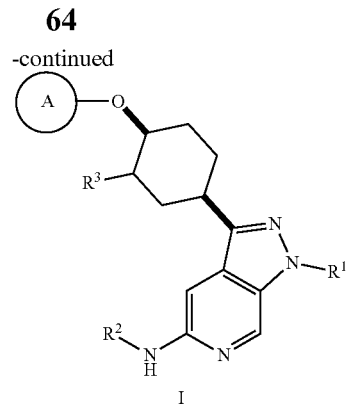

Scheme 12 shows a general scheme for the synthesis of compounds of Formula I wherein $X^1$ is C, $X^2$ is N, $X^3$ is N, $R^3$ is hydrogen, and $R^1$, $R^2$, and Ring A are as defined for Formula I. Compound 20 (prepared, for example, according to the process shown in Scheme 11) may be coupled with the boronic ester compound 29 where $R^3$ is hydrogen, Ring A is as defined for Formula I, and $R^x$ and $R^y$ are H or C1-C6 alkyl, or $R^x$ and $R^y$ together with the atoms to which they are connected form a 5-6 membered ring optionally substituted with 1-4 substituents selected from C1-C3 alkyl, using standard palladium-catalyzed cross-coupling reaction conditions, e.g., Suzuki coupling reaction conditions (for example, a palladium catalyst and optionally a ligand in the presence of an inorganic base, for example, Pd(PPh$_3$)$_4$ and Na$_2$CO$_3$ in dioxane at elevated temperatures), to provide compound 30. Compound 30 may be reacted with a reagent having the formula $R^2$—NH—$P^2$ wherein $R^2$ is as defined for Formula I and $P^2$ is an amino protecting group (e.g., a Boc group) using standard palladium-catalyzed cross-coupling reaction conditions (e.g., using a palladium catalyst such as Pd(PPh$_3$), PdCl$_2$(dppf), or Pd(OAc)$_2$, and a alkaline base such as an alkaline carbonate, for example potassium carbonate) to provide compound 31. Compound 31 may be treated to hydrogenation conditions (e.g., under a hydrogen atmosphere in the presence of a catalyst, e.g., a palladium catalyst, e.g., palladium on carbon) to provide compound 32. The SEM protecting group of compound 32 may be removed by under standard reaction conditions (e.g., by treating with tetrabutylammonium fluoride) to provide compound 33. Compound 33 may be reacted with a reagent having the formula X—$R^1$ where $R^1$ is as defined for Formula I and X is a leaving group, such as a halogen atom, for example iodo, using standard N-arylation reaction conditions, for example, with a copper catalyst (e.g., copper (I) iodide) in the presence of a base (e.g., K$_3$PO$_4$ or Cs$_2$CO$_3$) and optionally in the presence of a diamine ligand (e.g., ethane-1,2-diamine), followed by removal of the amino protecting group $P^2$ under standard reaction conditions (e.g., HCl or TFA), to provide a compound of Formula I. Alternatively, compound 33 may be reacted with a reagent having the formula X—$R^1$ where $R^1$ is as defined for Formula I and X is a leaving group, such as a halogen atom, using standard S$_N$Ar or alkylation reaction conditions, for example, with a base (e.g., K$_3$PO$_4$ or Cs$_2$CO$_3$) at elevated temperatures, followed by removal of the amino protecting group $P^2$ under standard reaction conditions (e.g., HCl or TFA), to provide a compound of Formula I.

Scheme 13

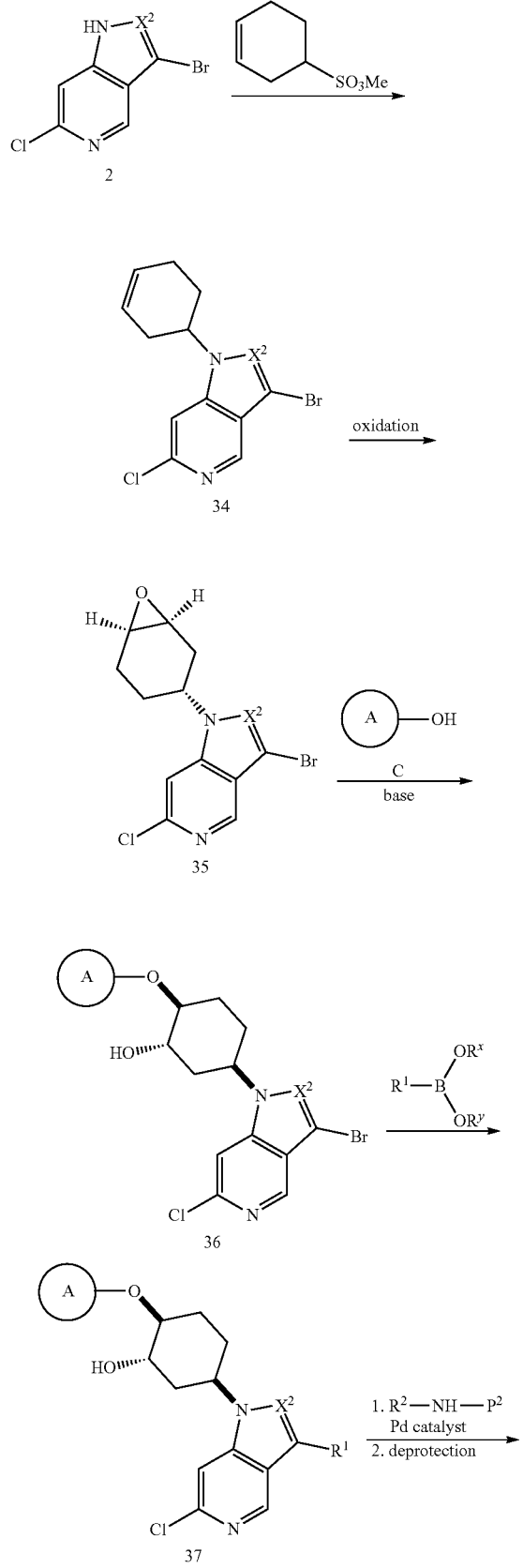

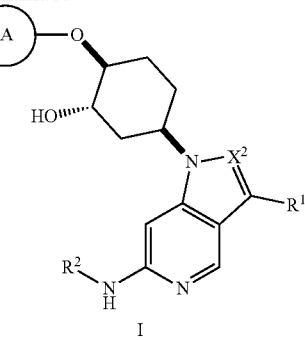

Scheme 13 shows a general scheme for the synthesis of compounds of Formula I wherein $X^1$ is N, $X^2$ is N or CH, $X^3$ is C, $R^3$ is hydroxyl, and $R^1$, $R^2$, and Ring A are as defined for Formula I. Compound 2 (prepared, for example, as shown in Scheme 2), may be reacted with methyl cyclohex-3-ene-1-sulfonate in the presence of a base (for example an alkaline carbonate such as cesium carbonate) to provide compound 34. Oxidation of the cyclohexenyl ring of compound 34 under standard oxidation conditions (e.g., using mCPBA) to provide compound 35. Ring opening of the epoxide of compound 35 by reacting compound 35 reagent C wherein Ring A is as defined for Formula I in the presence of a base provides compound 36. Compound 36 may be reacted with a boronic ester having the formula $R^1$—$B(OR^x)(OR^y)$ where $R^1$ is as defined for Formula I and $R^x$ and $R^y$ are H or C1-C6 alkyl, or $R^x$ and $R^y$ together with the atoms to which they are connected form a 5-6 membered ring optionally substituted with 1-4 substituents selected from C1-C3 alkyl, using standard palladium-catalyzed cross-coupling reaction conditions, e.g., Suzuki coupling reaction conditions (for example, a palladium catalyst and optionally a ligand in the presence of an inorganic base, for example, $Pd(PPh_3)_4$ and $Na_2CO_3$ in dioxane at elevated temperatures), to provide compound 36. Compound 36 may be reacted with a reagent having the formula $R^2$—NH—$P^2$ wherein $R^2$ is as defined for Formula I and $P^2$ is an amino protecting group (e.g., a Boc group) using standard palladium-catalyzed cross-coupling reaction conditions (e.g., using a palladium catalyst such as $Pd(PPh_3)$, $PdCl_2(dppf)$, or $Pd(OAc)_2$, and a alkaline base such as an alkaline carbonate, for example potassium carbonate), followed by removal of the amino protecting group under standard reaction conditions (e.g., HCl or TFA), to provide a compound of Formula I.

The term "amino protecting group" as used herein refers to a derivative of the groups commonly employed to block or protect an amino group while reactions are carried out on other functional groups on the compound. Examples of suitable protecting groups for use in any of the processes described herein include carbamates, amides, alkyl and aryl groups, imines, as well as many N-heteroatom derivatives which can be removed to regenerate the desired amine group. Non-limiting examples of amino protecting groups are acetyl, trifluoroacetyl, t-butyloxycarbonyl ("Boc"), benzyloxycarbonyl ("CBz") and 9-fluorenylmethyleneoxycarbonyl ("Fmoc"). Further examples of these groups, and other protecting groups, are found in T. W. Greene, et al., Greene's Protective Groups in Organic Synthesis. New York: Wiley Interscience, 2006.

Hydroxyl groups may be protected with any convenient hydroxyl protecting group, for example as described in T. W. Greene, et al., Greene's Protective Groups in Organic Synthesis. New York: Wiley Interscience, 2006. Examples include benzyl, trityl, silyl ethers, and the like.

Nitrogen atoms in compounds described in any of the above methods may be protected with any convenient nitrogen protecting group, for example as described in Greene & Wuts, eds., "Protecting Groups in Organic Synthesis", 2$^{nd}$ ed. New York; John Wiley & Sons, Inc., 1991. Examples of nitrogen protecting groups include acyl and alkoxycarbonyl groups, such as t-butoxycarbonyl (BOC), phenoxycarbonyl, and [2-(trimethylsilyl)ethoxy]methyl (SEM).

In one embodiment, provided herein is a process for preparing a compound of Formula I, comprising:

(a) for a compound of Formula I wherein $X^1$ is N, $X^2$ is N or CH, $X^3$ is C, $R^3$ is H, and Ring A, $R^1$ and $R^2$ are as defined for Formula I, reacting a corresponding compound of formula 5

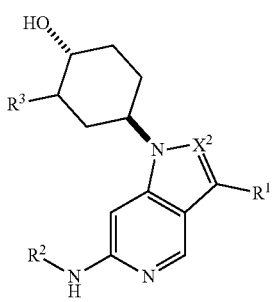

5 wherein $X^2$ is N, $R^3$ is hydrogen, and $R^1$ and $R^2$ are as defined for Formula I, with a reagent having the formula C

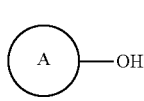

C wherein Ring A is a defined for Formula I, in the presence of triphenylphosphine and diisopropyl azodicarboxylate; or (b) for a compound of Formula I wherein $X^1$ is N, $X^2$ is N or CH, $X^3$ is C, $R^3$ is H, and Ring A, $R^1$ and $R^2$ are as defined for Formula I, reacting a corresponding compound of formula 11

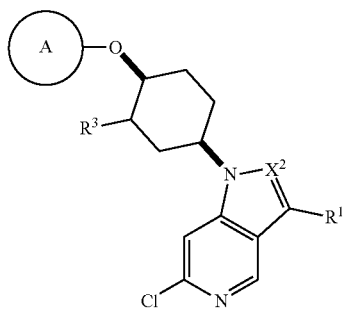

11 wherein $X^2$ is N, $R^3$ is hydrogen, and $R^1$, $R^2$ and Ring A are as defined for Formula I, with a reagent having the formula $R^2$—$NH_2$ wherein $R^2$ is as defined for Formula I, at elevated temperature; or (c) for a compound of Formula I wherein $X^1$ is N, $X^2$ is N or CH, $X^3$ is C, $R^3$ is H, and Ring A, $R^1$ and $R^2$ are as defined for Formula I, reacting a corresponding compound of formula 11

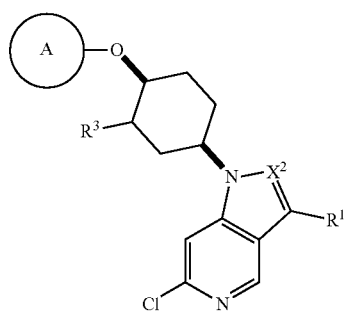

11 wherein $X^2$ is N, $R^3$ is hydrogen, and $R^1$, $R^2$ and Ring A are as defined for Formula I, with a reagent having the formula $R^2$—NH—$P^2$ wherein $P^2$ is an amino protecting group and $R^2$ is as defined for Formula I, in the presence of a palladium catalyst, followed by removal of the amino protecting group $P^2$; or (d) for a compound of Formula I wherein $X^1$ is N, $X^2$ is N or CH, $X^3$ is C, $R^3$ is H, and Ring A, $R^1$ and $R^2$ are as defined for Formula I, reacting a corresponding compound of formula 12a

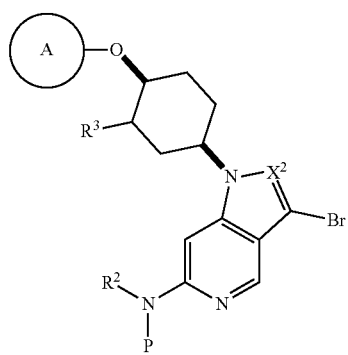

12a

P = H wherein P of compound 12a is hydrogen, $P^2$ of compound 12b is an amino protecting group, $R^3$ is hydrogen, $X^2$ is nitrogen, and Ring A and $R^2$ are as defined for Formula I, with a boronic ester having the formula $R^1$—B(OR$^x$)(OR$^y$), where $R^1$ is as defined for Formula I and $R^x$ and $R^y$ are H or C1-C6 alkyl, or $R^x$ and $R^y$ together with the atoms to which they are connected form a 5-6 membered ring optionally substituted with 1-4 substituents selected from C1-C3 alkyl, in the presence of a palladium catalyst; or (e) for a compound of Formula I wherein $X^1$ is N, $X^2$ is N or CH, $X^3$ is C, $R^3$ is H, and Ring A, $R^1$ and $R^2$ are as defined for Formula I, reacting a corresponding compound of formula 12b

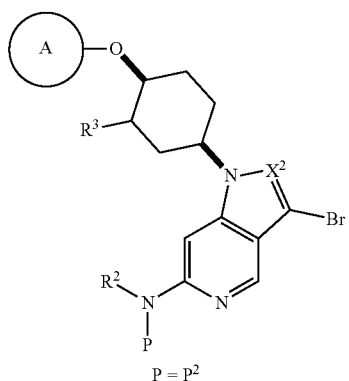

12b $P = P^2$ wherein $P^2$ is an amino protecting group, $R^3$ is hydrogen, $X^2$ is nitrogen, and Ring A and $R^2$ are as defined for Formula I, with a boronic ester having the formula $R^1$—B(OR$^x$)(OR$^y$), where $R^1$ is as defined for Formula I and $R^x$ and $R^y$ are H or C1-C6 alkyl, or $R^x$ and $R^y$ together with the atoms to which they are connected form a 5-6 membered ring optionally substituted with 1-4 substituents selected from C1-C3 alkyl, in the presence of a palladium catalyst, followed by removal of the amino protecting group; or (f) for a compound of Formula I wherein $X^1$ is N, $X^2$ is N or CH, $X^3$ is C, $R^3$ is H, and Ring A, $R^1$ and $R^2$ are as defined for Formula I, reacting a compound of formula 15

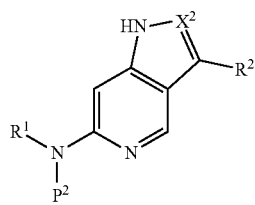

15 wherein $X^2$ is N, $P^2$ is an amino protecting group, and $R^1$ and $R^2$ are as defined for Formula I, with a compound having the formula 18

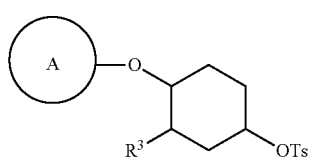

18 wherein $R^3$ is hydrogen and Ring A is as defined for Formula I, in the presence of a base, followed by removal of the amino protecting group $P^2$; or (g) for a compound of Formula I wherein $X^1$ is C, $X^2$ is N, $X^3$ is N, $R^3$ is H, and Ring A, $R^1$ and $R^2$ are as defined for Formula I, reacting a compound of formula 33

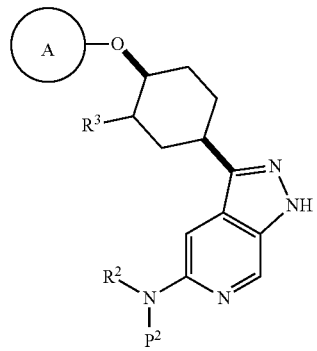

33 wherein $P^2$ is an amino protecting group, $R^3$ is hydrogen and $R^3$ and Ring A are as defined for Formula I, with a reagent having the formula X—$R^1$ wherein X is a leaving group or atom, in the presence of a copper catalyst and a base, followed by removal of the $P^2$ protecting group; or (h) for a compound of Formula I wherein $X^1$ is N, $X^2$ is N or CH, $X^3$ is C, $R^3$ is hydroxyl, and $R^1$, $R^2$, and Ring A are as defined for Formula I, reacting a compound of formula 37

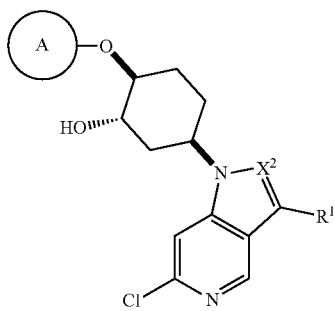

wherein $X^2$ is N or CH, and $R^1$ and Ring A are as defined for Formula I, with a reagent having the formula $R^2$—NH—$P^2$ wherein $R^2$ is as defined for Formula I and $P^2$ is an amino protecting group, in the presence of a palladium catalyst, followed by removal of the $P^2$ protecting group; and removing any additional protecting groups if present and optionally forming a pharmaceutically acceptable salt thereof.

Compounds of Formula I or pharmaceutically acceptable salts thereof can modulate or inhibit the activity of one or more TAM kinases. The ability of compounds of Formula I to act as inhibitors of one or more TAM kinases may be demonstrated by the assays described in Examples A, B and C. $IC_{50}$ values are shown in Table 1.

In some embodiments, the compounds provided herein exhibit potent and selective inhibition of one or more TAM kinases. For example, the compounds provided herein exhibit nanomolar potency against TAM, with minimal activity against other kinases.

As used herein, the term "a TAM kinase" refers to one, two or all three of the TAM receptor tyrosine kinases, i.e., TYRO3, AXL and MER.

As used herein, the term "a TAM kinase inhibitor" refers any compound exhibiting inhibition activity against one, two or all three of the TAM receptor kinases, i.e., the compounds exhibit inhibitory activity against AXL and/or MER and/or TYRO3.

In some embodiments, compounds of Formula I or pharmaceutically acceptable salts thereof have inhibitory activity against AXL. In some embodiments, compounds of Formula I or pharmaceutically acceptable salts thereof have inhibitory activity against MER. In some embodiments, a compound of Formula I has inhibitory activity against AXL and MER. In some embodiments, compounds of Formula I or pharmaceutically acceptable salts thereof have inhibitory activity against AXL, MER and TYRO3.

In one embodiment, compounds of Formula I or pharmaceutically acceptable salts thereof exhibit inhibition activity ($IC_{50}$) against a TAM kinase of less than about 1000 nM, less than about 500 nM, less than about 200 nM, less than about 100 nM, less than about 50 nM, less than about 25 nM, less than about 10 nM, or less than about 1 nM as measured in an assay as described herein. In some embodiments, compounds of Formula I or pharmaceutically acceptable salts thereof exhibit inhibition activity ($IC_{50}$) against a TAM kinase of less than about 25 nM, less than about 10 nM, less than about 5 nM, or less than about 1 nM as measured in an assay as provided herein.

In one embodiment, exemplary compounds of Formula I or pharmaceutically acceptable salts thereof exhibit inhibition activity ($IC_{50}$) against AXL of less than about 1000 nM, less than about 500 nM, less than about 200 nM, less than about 100 nM, less than about 50 nM, less than about 25 nM, less than about 10 nM, or less than about 1 nM as measured in an assay as described herein. In some embodiments, compounds of Formula I or pharmaceutically acceptable salts thereof exhibit inhibition activity ($IC_{50}$) against AXL of less than about 25 nM, less than about 10 nM, less than about 5 nM, or less than about 1 nM as measured in an assay as provided herein.

In one embodiment, compounds of Formula I or pharmaceutically acceptable salts thereof exhibit inhibition activity ($IC_{50}$) against MER of less than about 1000 nM, less than about 500 nM, less than about 200 nM, less than about 100 nM, less than about 50 nM, less than about 25 nM, less than about 10 nM, or less than about 1 nM as measured in an assay as described herein. In some embodiments, compounds of Formula I or pharmaceutically acceptable salts thereof exhibit inhibition activity ($IC_{50}$) against MER of less than about 25 nM, less than about 10 nM, less than about 5 nM, or less than about 1 nM as measured in an assay as provided herein.

In some embodiments, compounds of Formula I or pharmaceutically acceptable salts thereof inhibit all of three of the TAM kinases (i.e., AXL, MER and TYRO3).

In some embodiments, compounds of Formula I or pharmaceutically acceptable salts thereof are selective for AXL over MER. In some embodiments, a compound of Formula I or a pharmaceutically acceptable salt thereof, exhibits at least a 3-fold selectivity; at least a 5-fold selectivity; at least a 10-fold selectivity; or at least a 20-fold selectivity for AXL over MER. In some embodiments, selectivity for AXL and MER is measured in an enzyme assay (e.g., an enzyme assay as provided herein.

In some embodiments, a compound of Formula I or a pharmaceutically acceptable salt thereof, exhibits at least a 10-fold selectivity; at least a 20-fold selectivity; at least a 30-fold selectivity; at least a 40-fold selectivity; at least a 50-fold selectivity; at least a 60-fold selectivity; at least a 70-fold selectivity; at least a 80-fold selectivity; at least a 90-fold selectivity; or at least a 100-fold selectivity for AXL over TYRO3. In some embodiments, selectivity for AXL and TYRO3 is measured in an enzyme assay (e.g., an enzyme assay as provided herein).

In some embodiments, compounds of Formula I or a pharmaceutically acceptable salt thereof exhibit at least a 20-fold selectivity; at least a 30-fold selectivity; at least a 40-fold selectivity; at least a 50-fold selectivity; at least a 60-fold selectivity; at least a 70-fold selectivity; at least a 80-fold selectivity; at least a 90-fold selectivity; or at least a 100-fold selectivity for MER over AXL. In some embodiments, selectivity for AXL and MER is measured in an enzyme assay (e.g., an enzyme assay as provided herein.

In some embodiments, compounds of Formula I or a pharmaceutically acceptable salt thereof exhibit at least a 20-fold selectivity; at least a 30-fold selectivity; at least a 40-fold selectivity; at least a 50-fold selectivity; at least a 60-fold selectivity; at least a 70-fold selectivity; at least a 80-fold selectivity; at least a 90-fold selectivity; or at least a 100-fold selectivity for MER over TYRO3. In some embodiments, selectivity for MER and TYRO3 is measured in an enzyme assay (e.g., an enzyme assay as provided herein.

In some embodiments, provided herein is a method for inhibiting AXL kinase, which comprises contacting the AXL kinase with compound of Formula I, or a pharmaceutically acceptable salt thereof.

In some embodiments, provided herein is a method for inhibiting MER kinase, which comprises contacting the MER kinase with compound of Formula I, or a pharmaceutically acceptable salt thereof.

In some embodiments, provided herein is a method for inhibiting AXL and MER kinases, which comprises contacting the AXL and MER kinases with compound of Formula I, or a pharmaceutically acceptable salt thereof.

Compounds of Formula I or pharmaceutically acceptable salts thereof are useful in the treatment of various diseases associated with increased (e.g., at least 1%, at least 2%, at least 4%, at least 6%, at least 8%, at least 10%, at least 12%, at least 14%, at least 16%, at least 18%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, at least 160%, at least 170%, at least 180%, at least 190%, at least 200%, at least 210%, at least 220%, at least 230%, at least 240%, at least 250%, at least 260%, at least 270%, at least 280%, at least 290%, or at least 300%) expression and/or activity of one or more of the TAM kinases (e.g., in a cancer cell or in an immune cell) (e.g., as compared to a control, e.g., a non-cancerous tissue or cell, or a corresponding tissue or cell from a control subject that does not have cancer). In one embodiment, compounds of Formula I or pharmaceutically acceptable salts thereof are useful in treating or preventing proliferative disorders such as cancers. In one embodiment, tumors with an activating mutation (e.g., a point mutation or a chromosomal translocation) in a gene encoding a receptor tyrosine kinase and/or upregulation of the expression of a receptor tyrosine kinase (e.g., any of the TAM kinases described herein) may be particularly sensitive to compounds of Formula I.

As used herein, terms "treat" or "treatment" refer to therapeutic or palliative measures. Beneficial or desired clinical results include, but are not limited to, alleviation, in whole or in part, of symptoms associated with a disease or disorder or condition, diminishment of the extent of disease, stabilized (i.e., not worsening) state of disease, delay or slowing of disease progression, amelioration or palliation of the disease state (e.g., one or more symptoms of the disease), and remission (whether partial or total), whether detectable or undetectable. "Treatment" can also mean prolonging survival as compared to expected survival if not receiving treatment.

As used herein, the terms "subject," "individual," or "patient," are used interchangeably, refers to any animal, including mammals such as mice, rats, other rodents, rabbits, dogs, cats, swine, cattle, sheep, horses, primates, and humans. In some embodiments, the patient is a human. In some embodiments, the subject has experienced and/or exhibited at least one symptom of the disease or disorder to be treated and/or prevented. In some embodiments, the subject has been identified or diagnosed as having a TAM-associated disease or disorder (e.g., a TAM-associated cancer) (e.g., as determined using a regulatory agency-approved, e.g., FDA-approved, assay or kit). In some embodiments, the subject has been identified or diagnosed as having a cancer associated with one or more TAM kinases (e.g., a TAK-associated cancer) (e.g., as determined using a regulatory agency-approved, e.g., FDA-approved, assay or kit). In some embodiments, the subject has a tumor that is associated with one or more TAM kinases (e.g., an increase in the expression and/or activation of one or more TAM kinases in a cell (e.g., a cancer cell or an immune cell) as compared to a control, e.g., a non-cancerous tissue or a corresponding tissue from a control subject that does not have cancer) (e.g., as determined using a regulatory agency-approved assay or kit). In some embodiments, the subject is suspected of having a TAM-associated cancer. In some embodiments, the subject has a clinical record indicating that the subject has a tumor is associated with one or more TAM kinases (e.g., a TAM-associated cancer) (and optionally the clinical record indicates that the subject should be treated with any of the compositions provided herein). In some embodiments, the patient is a pediatric patient.

The term "pediatric patient" as used herein refers to a patient under the age of 21 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E. Nelson *Textbook of Pediatrics,* 15th Ed. Philadelphia: W.B. Saunders Company, 1996; Rudolph A M, et al. *Rudolph's Pediatrics,* 21st Ed. New York: McGraw-Hill, 2002; and Avery M D, First L R. *Pediatric Medicine,* 2nd Ed. Baltimore: Williams & Wilkins; 1994. In some embodiments, a pediatric patient is from birth through the first 28 days of life, from 29 days of age to less than two years of age, from two years of age to less than 12 years of age, or 12 years of age through 21 years of age (up to, but not including, the twenty-second birthday). In some embodiments, a pediatric patient is from birth through the first 28 days of life, from 29 days of age to less than 1 year of age, from one month of age to less than four months of age, from three months of age to less than seven months of age, from six months of age to less than 1 year of age, from 1 year of age to less than 2 years of age, from 2 years of age to less than 3 years of age, from 2 years of age to less than seven years of age, from 3 years of age to less than 5 years of age, from 5 years of age to less than 10 years of age, from 6 years of age to less than 13 years of age, from 10 years of age to less than 15 years of age, or from 15 years of age to less than 22 years of age.

The phrase "therapeutically effective amount" means an amount of compound that, when administered to a patient in need of such treatment, is sufficient to (i) treat a TAM kinase-associated disease or disorder (e.g., a TAM-associated cancer), (ii) attenuate, ameliorate, or eliminate one or more symptoms of the particular disease, condition, or disorder, or (iii) delay the onset of one or more symptoms of the particular disease, condition, or disorder described herein. The amount of a compound of Formula I that will correspond to such an amount will vary depending upon factors such as the particular compound, disease condition and its severity, the identity (e.g., weight) of the patient in need of treatment, but can nevertheless be routinely determined by one skilled in the art.

The term "regulatory agency" refers to a country's agency for the approval of the medical use of pharmaceutical agents with the country. For example, a non-limiting example of a regulatory agency is the U.S. Food and Drug Administration (FDA).

The term "TAM-associated disease or disorder" as used herein refers to diseases or disorders associated with or having increased expression and/or activity of one or more of the TAM kinases in a cell (e.g., a cancer cell or an immune cell) (e.g., as compared to a control, e.g., a non-cancerous tissue or cell, or a corresponding tissue or cell from a control subject that does not have cancer) and/or where activation of a TAM kinase expressed on non-cancer cells contributes to disease. Non-limiting examples of a TAM-associated disease or disorder include, for example, cancer (a TAM-associated cancer), e.g., any of the cancers described herein. In one embodiment, the disease is a cancer that overexpresses one or more TAM kinases after treatment with at least one additional anticancer agent (e.g., one or more of any of the additional anticancer agents described herein), e.g., a kinase-targeted therapeutic agent and/or a chemotherapeutic agent as described herein). In one embodiment, the disease is associated with signaling through one or more TAM kinases expressed in cells of the immune system (e.g., immune cells selected from the group of tumor-associated macrophages, natural killer (NK) cells, and subsets of tumor associated dendritic cells), wherein the expression of one or more TAM kinases in the immune cells may limit the ability of the patient's immune system to make an effective anti-tumor response.

The term "TAM-associated cancer" as used herein refers to cancers associated with or having increased expression and/or activity of one or more of the TAM kinases in a cancer cell or an immune cell (e.g., as compared to a control, e.g., a non-cancerous tissue or cell, or a corresponding tissue or cell from a control subject that does not have cancer). Non-limiting examples of a TAM-associated cancer are described herein. In some embodiments, the TAM-associated cancer is a cancer having a chromosomal translocation that results in the expression of a TMEM87B-MERTK fusion protein (e.g., amino acids 1-55 of TMEM87B and amino acids 433-1000 of MERTK) or a AXL-MBIP fusion protein. A description of an exemplary chromosomal translocation that results in the expression of a TMEM87B-MERTK fusion protein is provided in Shaver et al. (Cancer Res. 76(16):4850-4860, 2016). A description of an exemplary chromosomal translocation that results in the expression of an AXL-MBIP fusion protein is provided in Seo et al. (*Genome Res.* 22:2109-2119, 2012). Chromosomal translocations or the resulting expression of TMEM87B-MERTK or AXL-MBIP fusion proteins can be detected using In Situ Hybridization (e.g., Fluorescent In Situ Hybridization (FISH)). Chromosomal translocations that result in the expression of TMEM87B-MERTK or AXL-MBIP can be detected by sequencing DNA from a sample obtained from the subject (e.g., blood, plasma, urine, cerebrospinal fluid, saliva, sputum, bronchoalveolar lavage, bile, lymphatic fluid, cyst fluid, stool ascites, or a tumor biopsy obtained from the subject). Exemplary methods that can be used to sequence DNA are known in the art and include, e.g., next-generation sequencing (NGS), traditional PCR, digital PCR, and microarray analysis. Additional methods that can be used to detect chromosomal translocations that result in the expression of TMEM87B-MERTK or AXL-MBIP fusion proteins, or the expression of TMEM87B-MERTK or AXL-MBIP fusion proteins, are known in the art. Receptor tyrosine kinases (RTKs) are cell surface proteins that transmit signals from the extracellular environment to the cell cytoplasm and nucleus to regulate cellular events such as survival, growth, proliferation, differentiation, adhesion, and migration. All RTKs contain an extracellular ligand binding domain and a cytoplasmic protein tyrosine kinase domain. Ligand binding leads to the dimerization of RTKs, which triggers the activation of the cytoplasmic kinase and initiates downstream signal transduction pathways. RTKs can be classified into distinct subfamilies based on their sequence similarity. The TAM receptor tyrosine kinases (TYRO3, AXL (also known as UFO) and MER) is an emerging class of innate immune checkpoints that participate in key steps of anti-tumoral immunity (Akalu, T, et al., Immunological Reviews 2017; 276:165-177). TAM kinases are characterized by an extracellular ligand binding domain consisting of two immunoglobulin-like domains and two fibronectin type III domains. Two ligands, growth arrest specific 6 (GAS6) and protein S (ProS), have been identified for TAM kinases. GAS6 can bind to and activate all three TAM kinases, while ProS is a ligand for MER and TYRO3 (Graham et al., 2014, Nature reviews Cancer 14, 769-785).

TAM kinases are ectopically expressed or over-expressed in a wide variety of cancers, including breast, colon, renal, skin, lung, liver, brain, ovarian, prostate, and thyroid malignancies (Graham et al., 2014, Nature Reviews Cancer 14, 769-785; and Linger et al., 2008, Oncogene 32, 3420-3431) and play important roles in tumor initiation and maintenance. When activated, AXL and MER can regulate tumor cell survival, proliferation, migration and invasion, angiogenesis, and tumor-host interactions (Schoumacher, M. et al., Curr. Oncol. Rep. 2017; 19(3); 19) Accordingly, blocking TAM signaling may promote engagement of adaptive immunity and complement T-cell checkpoint blockade (Akalu, T, et al., Immunological Reviews 2017; 276:165-177). Therefore, TAM inhibition represents an attractive approach for targeting another class of oncogenic RTKs (Graham et al., 2014, Nature Reviews Cancer 14, 769-785; and Linger et al., 2008, Oncogene 32, 3420-3431).

AXL was originally identified as a transforming gene from DNA of patients with chronic myelogenous leukemia (O'Bryan et al., 1991, Molecular and Cellular Biology 11, 5016-5031). GAS6 binds to AXL and induces subsequent auto-phosphorylation and activation of AXL tyrosine kinase. AXL activates several downstream signaling pathways including PI3K-AKT, RAF-MAPK, PLC-PKC (Feneyrolles et al., 2014, Molecular Cancer Therapeutics 13, 2141-2148; Linger et al., 2008, Oncogene 32, 3420-3431). Over-expression or overactivation of the AXL protein has been correlated with the promotion of multiple tumorigenic processes. High levels of AXL expression have been associates with poor prognosis in different cancers such as glioblastoma multiforme (Hutterer, M., et al., Clin. Caner Res. 2008, 14, 130-138), breast cancer (Wang, X., Cancer Res. 2013, 73, 6516-6525), lung cancer (Niederst, M. et al, Sci. Signaling, 2013, 6, re6), osteosarcoma (Han, J., Biochem. Biophys. Res. Commun. 2013, 435, 493-500), and acute myeloid leukemia (Ben-Batalla, L., et al., Blood 2013, 122, 2443-2452). AXL is over-expressed or amplified in a variety of malignancies including lung cancer, prostate cancer, colon cancer, breast cancer, melanoma, and renal cell carcinoma (Linger et al., 2008, Oncogene 32, 3420-3431), and overexpression of AXL is correlated with poor prognosis (Linger et al., 2008, Oncogene 32, 3420-3431). AXL activation promotes cancer cell survival, proliferation, angiogenesis, metastasis, and resistance to chemotherapy and targeted therapies. AXL knockdown or AXL antibody can inhibit the migration of breast cancer and NSCLC cancer in vitro, and blocked tumor growth in xenograft tumor models (Li et al., 2009, Oncogene 28, 3442-3455). In pancreatic cancer cells, inhibition of AXL decreased cell proliferation and survival (Koorstra et al., 2009, Cancer Biology & Therapy 8, 618-626). In prostate cancer, AXL inhibition decreased cell migration, invasion, and proliferation (Tai et al., 2008, Oncogene 27, 4044-4055). In triple-negative breast cancer, patients typically present a significant clinical challenge, as they do not respond to the various targeted cancer therapies due to an apparent lack of RTK activation. However, patients with triple-negative breast cancer do show some response to taxane-based chemotherapy and studies have suggested that combining anti-mitotic drugs (e.g., docetaxol) with an AXL inhibitor sensitized cancer cells to the anti-mitotic drug, and AXL in combination with an anti-mitotic drug may be an appropriate combination therapy in this disease setting (Wilson, et al., Cancer Res. 2014, 74(20), 5878-5890).

TAM kinases can contribute to therapeutic resistance by at least three mechanisms: intrinsic survival signaling in tumor cells, induction of TAM kinases as an escape mechanism for tumors that have been treated with oncogene-targeted agents, and immunosuppression in the tumor microenvironment (Graham, et al, Nature Reviews Cancer, 2014, 14, 769-785).

TAM kinases were found to promote resistance to cytotoxic chemotherapies (chemoresistance) in leukemia cells and solid tumor cells (Graham, et al, Nature Reviews Cancer, 2014, 14, 769-785). Transgenic lymphocytes ectopically expressing MER were found to be more resistant to dexamethasone than wild-type lymphocytes (Keating, A. K., et al., Oncogene, 2006, 25, 6092-6100), and stimulation of B-ALL cells with GAS6 increased resistance to cytarabine (Shiozawa, Y., et al., Neoplasia, 2010, 12, 116-127). AXL is induced in acute myeloid leukemia (AML) cells that have been treated with cytotoxic chemotherapies, and it mediates increased chemoresistance (Hong, C. C., et al., Cancer Lett., 2008, 268, 314-324). Chemotherapy-resistant chronic myeloid leukemia (CML) cell lines have upregulated levels of AXL, and shRNA-mediated knockdown of AXL increases chemosensitivity in CML cells and xenograft models (Zhao, Y., et al., Cancer Invest. 2012, 30, 287-294). Similarly, shRNA-mediated MER knock-down sensitizes B-cell acute lymphoblastic leukemia (B-ALL) and T-lineage acute lymphoblastic leukemia (T-ALL) cells to a range of chemotherapies (Linger, R. M., et al., Blood, 2013, 122, 1599-1609; Brandao, L. N., et al., Blood Cancer J., 2013, 3, e101). In solid tumors such as non-small cell lung cancer, pancreatic ductal adenocarcinoma, astrocytoma, lung adenocarcinoma, ovarian cancer, melanoma, and gloibalstoma multiforme, overexpression of AXL or MER promotes chemoresistance, and shRNA-mediated inhibition sensitizes cells to treatment with cytotoxic chemotherapies (Linger, R. N., et al., Oncogene, 2013, 32, 3420-3431; Song, X., et al., Cancer, 2011, 117, 734-743; Keating, A. K., et al., Mol. Cancer Ther. 2010, 9, 1298-1307; Lay, J. D., et al., Cancer Res. 2007, 67, 3878-3887; Zhao, Y., et al., Cancer Invest, 2012, 30, 287-294; Macleod, K., Cancer Res. 2005, 65, 6789-6800; Zhu, S., et al., Proc. Natl Acad. Sci. USA, 2009, 106, 17025-17030; Wang, Y., et al., Oncogene 2013, 32, 872-882).

In contrast to chemoresistance, examples of acquired resistance are currently limited to AXL. AXL is upregulated in imatinib-resistant CML and gastrointestinal stromal tumor (GIST) cell lines and tumor samples (Mahadevan, D., et al., Oncogene, 2007, 26, 3909-3919; Dufies, M., et al., Oncotarget 2011, 2, 874-885; Gioia, R., et al., Blood, 2011, 118, 2211-2221), and siRNA-mediated knockdown of AXL restored imatinib sensitivity to resistant cell lines (Dufies, M., et al.). Similarly, AXL is induced in lapatinib-resistant HER2 (also known as ERBB2)-positive breast cancer cell lines, and AXL inhibition restored lapatinib sensitivity (Liu, L., et al., Cancer Res. 2009, 69, 6871-6878). AXL has been associated with acquired resistance to epidermal growth factor receptor (EGFR) tyrosine kinase inhibitors (e.g., lapatinib and erlotinib) and therapeutic antibodies (e.g., cetuximab) in triple-negative breast cancer (Meyer, A. S. et al., Sci. Signal 2013, 6, ra66), colorectal cancer (Brand, et al., Cancer Res. 2014, 74:5152-5164), head and neck cancer (Kiles, K. M, et al., Mol. Cancer Ther. 2013, 12, 2541-2558) cell lines, and non-small cell lung cancer (Zhang, Nat. Genet. 2013, 44(8), 852-860). AXL has also been associated with acquired resistance to inhibitors targeting other kinases, including PI3Kα inhibitors such as alpesib (BYL719) in head and neck and esophageal squamous cell carcinomas (Elkabets, et al., Cancer Cell 2015, 27:533-546), MEK inhibitors (e.g., U0126 (1,4-Diamino-2,3-dicyano-1,4-bis(o-aminophenylmercapto)butadiene) and PD 325901 (1,4-Diamino-2,3-dicyano-1,4-bis(o-aminophenylmercapto)butadiene) in triple-negative breast cancer cell lines and melanoma cell lines (Miller, et al., Cancer Discovery 2016, 6:382-39), fibroblast growth factor (FGFR) (Ware, K. E., Oncogenesis 2013, 2, e39), anaplastic lymphoma kinase (ALK) (Kim, H. R., et al., Mol. Oncol. 2013, 7, 1093-1102) and insulin-like growth factor 1 receptor (IGF1R) (Huang, R., Cancer Res. 2010, 70, 7221-7231), and AXL inhibition has been demonstrated to overcome or delay resistance to these inhibitors. AXL is upregulated in NSCLC cell lines and xenografts that are resistant to EGFR tyrosine kinase inhibitors (erlotinib) and antibody drugs (cetuximab) (Brad, T. M., et al., Cancer Res. 2014, 74, 5152-5164; Zhang, Z., et al., Nature Genet. 2012, 44, 852-860), and it is induced in 20% of matched tumor samples taken from patients with NSCLC after development of resistance to the EGFR inhibitor erlotinib.

Regarding MER and AXL dual inhibitors, the normal roles of MER and AXL in preventing or terminating innate immune-mediated inflammation and natural killer (NK) cell responses are subverted in the tumor microenvironment. MER and AXL decrease NK cell antitumor activity, which allows increased metastases.

MER was originally identified as a phospho-protein from a lymphoblastoid expression library (Graham et al., 1995, Oncogene 10, 2349-2359). Both GAS6 and ProS can bind to MER and induce the phosphorylation and activation of MER kinase (Lew et al., 2014. eLife, 3:e03385). Like AXL, MER activation also conveys downstream signaling pathways including PI3K-Akt and Raf-MAPK (Linger et al., 2008, Oncogene 32, 3420-3431). MER is over-expressed in many cancers including multiple myeloma, gastric, prostate, breast, melanoma and rhabdomyosarcoma (Linger et al., 2008, Oncogene 32, 3420-3431). MER knockdown inhibits multiple myeloma cell growth in vitro and in xenograft models (Waizenegger et al., 2014, Leukemia, 1-9). In acute myeloid leukemia, MER knockdown induced apoptosis, decreased colony formation, and increased survival in a mouse model (Lee-Sherick et al., 2013, Oncogene 32, 5359-5368). MER inhibition increased apoptosis, decreased colony formation, increased chemo-sensitivity, and decreased tumor growth in NSCLC (Linger et al., 2013, Oncogene 32, 3420-3431). Similar effects are observed for MER knockdown in melanoma (Schlegel et al., 2013) and glioblastoma (Wang et al., 2013, Oncogene 32, 872-882).

TYRO3 was originally identified through a PCR-based cloning study (Lai and Lemke, 1991, Neuron 6, 691-704). Both ligands, GAS6 and ProS, can bind to and activate Tyro3. TYRO3 also plays a role in cancer growth and proliferation. TYRO3 is over-expressed in melanoma cells, and knockdown of TYRO3 induces apoptosis in these cells (Demarest et al., 2013, Biochemistry 52, 3102-3118).

TAM kinases have emerged as potential immune-oncology targets. The durable clinical responses to immune checkpoint blockade observed in cancer patients clearly indicate that the immune system plays a critical role in tumor initiation and maintenance. Genetic mutations from cancer cells can provide a diverse set of antigens that the immune cells can use to distinguish tumor cells from their normal counterpart. However, cancer cells have evolved multiple mechanisms to evade host immune surveillance. In fact, one hallmark of human cancer is its ability to avoid immune destruction. Cancer cells can induce an immune-suppressive microenvironment by promoting the formation of M2 tumor associated macrophages, myeloid derived suppressor cells (MDSC), and regulatory T cells. Cancer cells can also produce high levels of immune checkpoint proteins such as PD-L1 to induce T cell anergy or exhaustion. It is now clear that tumors co-opt certain immune-checkpoint pathways as a major mechanism of immune resistance (Pardoll, 2012, Cancer 12, 252-264). Antagonizing these negative regulators of T-cell function with antibodies has shown striking efficacy in clinical trials of a number of malignancies including advanced melanoma, non-small cell lung and bladder cancer. While these therapies have shown encouraging results, not all patients mount an anti-tumor response suggesting that other immune-suppressive pathways may also be important.

TAM kinases have been shown to function as checkpoints for immune activation in the tumor milieu. All TAM kinases are expressed in NK cells, and TAM kinases inhibit the antitumor activity of NK cells. LDC1267, a small molecule TAM kinase inhibitor, activates NK cells, and blocks metastasis in tumor models with different histologies (Paolino et al., 2014, Nature 507, 508-512). In addition, MER kinase decreases the activity of tumor associated macrophages through the increased secretion of immune suppressive cytokines such as IJIO and IL4, and decreased production of immune activating cytokines such as IL12 (Cook et al., 2013, The Journal of Clinical Investigation 123, 3231-3242). MER inhibition has been shown to reverse this effect. As a result, MER knockout mice are resistant to PyVmT tumor formation (Cook et al., 2013, Journal of Clinical Investigation 123, 3231-3242). The role of TAM kinases in the immune response is also supported by knockout mouse studies. TAM triple knockout mice (TKO) are viable. However, these mice displayed signs of autoimmune disease including enlarged spleen and lymph nodes, autoantibody production, swollen footpad and joints, skin lesions, and systemic lupus erythematosus (Lu and Lemke, 2001, Science 293, 306-311). This is consistent with the knockout phenotype for approved immune-oncology targets such as CTLA4 and PD-1. Both CTLA-4 and PD-1 knockout mice showed signs of autoimmune disease, and these mice die within a few weeks after birth (Chambers et al., 1997, Immunity 7, 885-895; and Nishimura et al., 2001, Science 291, 319-322). Therefore inhibition of TAM kinases alone or in combination with other immune therapies may increase the ability of the immune system to make a therapeutically beneficial immune response against the cancer.

Accordingly, in one embodiment, provided herein is a method for treating a TAM-associated disease or disorder (e.g., a TAM-associated cancer) in a patient in need thereof, the method comprising administering to the patient a therapeutically effective amount of a compound of Formula I or a pharmaceutically acceptable salt thereof or a pharmaceutical composition thereof.

Also provided herein are methods of treating a patient having a cancer that include: (a) identifying the patient as having a TAM-associated cancer, and (b) administering to the patient identified as having a TAM-associated cancer a therapeutically effective amount of a compound of Formula I or a pharmaceutically acceptable salt thereof or a pharmaceutical composition thereof.

Also provided herein are methods of decreasing the risk of developing a metastasis or an additional metastasis in a patient identified or diagnosed as having a TAM-associated cancer that include administering to the patient identified or diagnosed as having a TAM-associated cancer a therapeutically effective amount of a compound of Formula I or a pharmaceutically acceptable salt thereof or a pharmaceutical composition thereof. In some embodiments, the methods result in at least a 1% reduction (e.g., at least a 2% reduction, at least a 3% reduction, at least a 4% reduction, at least a 5% reduction, at least a 6% reduction, at least a 8% reduction, at least a 10% reduction, at least a 12% reduction, at least a 14% reduction, at least a 16% reduction at least a 18% reduction, at least a 20% reduction, at least a 25% reduction, at least a 30% reduction, at least a 35% reduction, at least a 40% reduction, at least a 45% reduction, at least a 50% reduction, at least a 55% reduction, at least a 60% reduction, at least a 65% reduction, at least a 70% reduction, at least a 75% reduction, at least a 80% reduction, at least a 85% reduction, at least a 90% reduction, at least a 95% reduction, or at least a 99% reduction) in the patient's risk of developing a metastasis or an additional metastasis, e.g., as compared to a population of subjects having a similar TAM-associated cancer but receiving a different treatment or no treatment.

Also provided are methods of decreasing the risk of developing a metastasis or an additional metastasis in a patient having a cancer that include: (a) identifying the patient as having a TAM-associated cancer; and (b) administering to the patient identified as having a TAM-associated cancer a therapeutically effective amount of a compound of Formula I or a pharmaceutically acceptable salt thereof or a pharmaceutical composition thereof. In some embodiments, the methods result in at least a 1% reduction (e.g., at least a 2% reduction, at least a 3% reduction, at least a 4% reduction, at least a 5% reduction, at least a 6% reduction, at least a 8% reduction, at least a 10% reduction, at least a 12% reduction, at least a 14% reduction, at least a 16% reduction, at least a 18% reduction, at least a 20% reduction, at least a 25% reduction, at least a 30% reduction, at least a 35% reduction, at least a 40% reduction, at least a 45% reduction, at least a 50% reduction, at least a 55% reduction, at least a 60% reduction, at least a 65% reduction, at least a 70% reduction, at least a 75% reduction, at least a 80% reduction, at least a 85% reduction, at least a 90% reduction, at least a 95% reduction, or at least a 99% reduction) in the patient's risk of developing a metastasis or an additional metastasis, e.g., as compared to a population of subjects having a similar TAM-associated cancer but receiving a different treatment or no treatment.

Also provided are methods of decreasing migration and/or invasion of a cancer cell in a patient identified as having a TAM-associated cancer that include administering to a patient identified or diagnosed as having a TAM-associated cancer a therapeutically effective amount of a compound of Formula I or a pharmaceutically acceptable salt thereof or a pharmaceutical composition thereof. In some embodiments, the methods result in at least a 1% decrease (e.g., at least a 2% decrease, at least a 3% decrease, at least a 4% decrease, at least a 5% decrease, at least a 6% decrease, at least a 8% decrease, at least a 10% decrease, at least a 12% decrease, at least a 14% decrease, at least a 16% decrease, at least a 18% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, at least a 95% decrease, or at least a 99% decrease) in the migration and/or invasion of a cancer cell in the patient, e.g., as compared to the migration and/or invasion of a cancer cell or a population of cancer cells in a subject having a similar TAM-associated cancer but receiving a different treatment or no treatment.

Also provided herein are methods of decreasing migration and/or invasion of a cancer cell in a patient having a cancer that include: (a) identifying the patient as having a TAM-associated cancer; and (b) administering to the patient identified as having a TAM-associated cancer a therapeutically effective amount of a compound of Formula I or a pharmaceutically acceptable salt thereof or a pharmaceutical composition thereof. In some embodiments, the methods result in at least a 1% decrease (e.g., at least a 2% decrease, at least a 3% decrease, at least a 4% decrease, at least a 5% decrease, at least a 6% decrease, at least a 8% decrease, at least a 10% decrease, at least a 12% decrease, at least a 14% decrease, at least a 16% decrease, at least a 18% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, at least a 95% decrease, or at least a 99% decrease) in the migration and/or invasion of a cancer cell in the patient, e.g., as compared to the migration and/or invasion of a cancer cell or a population of cancer cells in a subject having a similar TAM-associated cancer but receiving a different treatment or no treatment.

Some embodiments of these methods further include administering to the patient at least one additional anticancer agent (e.g., any of the exemplary additional anticancer agents described herein or known in the art). For example, in some examples, the at least one anticancer agent or therapy can be selected from the group of: a kinase inhibitor, a chemotherapy, radiation and surgery.

In some embodiments of any of the methods described herein, the patient was previously treated with at least one additional anticancer agent (e.g., any of the additional anticancer agents described herein) and the previous treatment with the at least one additional anticancer agent was unsuccessful (e.g., the patient previously developed resistance to one or more of the at least one additional anticancer agent).

In some embodiments of any of the methods described herein, the at least one additional anticancer agent is selected from the group of: a chemotherapeutic agent, a PI-3 kinase inhibitor, an EGFR inhibitor, a HER2/neu inhibitor, an FGFR inhibitor, an ALK inhibitor, an IGF1R inhibitor, a VEGFR inhibitor, a PDGFR inhibitor, a glucocorticoid, a BRAF inhibitor, a MEK inhibitor, a HER4 inhibitor, a MET inhibitor, a RAF inhibitor, an Akt inhibitor, a FTL-3 inhibitor, and a MAP kinase pathway inhibitor.

In some embodiments of any of the methods described herein, the at least one additional anticancer agent can include a kinase inhibitor, and the patient previously developed resistance to the kinase inhibitor. In some embodiments of any of the methods described herein, the at least one anticancer agent includes a kinase inhibitor selected from the group of: bosutinib, BGB324, crizotinib, foretinib, BMS-777607, LY2801653, amuvatinib, BMS-796302, cabozantinib, MGCD265, NPS-1034, LDC1267, gilteritinib, SGI-7079, TP-0903, UNC2025, S49076, sunitinib, 12A11, Mab173, YW327.6S2, D9, E8, merestinib, ASLAN002, SGI-7079, TP-0903, and LDC1267.

In some embodiments of any of the methods described herein, the at least one additional anticancer agent includes dexamethasone, and the patient previously developed resistance to dexamethasone. In some embodiments of any of the methods described herein, the at least one additional anticancer agent includes cytarabine, and the patient previously developed resistance to cytarabine. In some embodiments of any of the methods described herein, the at least one additional anticancer agent includes imatinib, and the patient previously developed resistance to imatinib. In some embodiments of any of the methods described herein, the at least one additional anticancer agent includes lapatinib, and the patient previously developed resistance to lapatinib. In some embodiments of any of the methods described herein, the at least one additional anticancer agent includes cetuximab, and the patient previously developed resistance to cetuximab. In some embodiments of any of the methods described herein, the at least one additional anticancer agent includes erlotinib, and the patient previously developed resistance to erlotinib. In some embodiments of any of the methods described herein, the at least one additional anticancer agent includes alpelisib, and the patient previously developed resistance to alpelisib. In some embodiments of any of the methods described herein, the at least one additional anticancer agent includes cisplatin, and the patient previously developed resistance to cisplatin. In some embodiments of any of the methods described herein, the at least one additional anticancer agent includes sunitinib, and the patient previously developed resistance to sunitinib. In some embodiments of any of the methods described herein, the at least one additional anticancer agent includes metformin, and the patient previously developed resistance to metformin.

In some embodiments of any of the methods described herein, the at least one additional anticancer agent includes an anti-PD1 antibody, and the patient previously developed resistance to the anti-PD1 antibody. In some embodiments of any of the methods described herein, the at least one additional anticancer agent includes docetaxel, and the patient previously developed resistance to docetaxel. In some embodiments of any of the methods described herein, the at least one additional anticancer agent includes an EGFR inhibitor, and the patient previously developed resistance to the EGFR inhibitor.

Also provided herein are methods of selecting a treatment for a patient identified as having a TAM-associated cancer that include selecting a compound of Formula I or a pharmaceutically acceptable salt thereof or a pharmaceutical composition thereof for the patient identified or diagnosed as having a TAM-associated cancer. Some embodiments further comprise administering the selected compound of Formula I or the pharmaceutically acceptable salt thereof or the pharmaceutical composition thereof to the patient.

Also provided herein are methods of selecting a treatment for a patient that include: (a) identifying the patient as having a TAM-associated cancer; and (b) selecting a compound of Formula I or a pharmaceutically acceptable salt thereof or a pharmaceutical composition thereof for the patient identified as having a TAM-associated cancer. Some embodiments further comprise administering the selected compound of Formula I or the pharmaceutically acceptable salt thereof or the pharmaceutical composition thereof to the patient identified as having a TAM-associated cancer.

Also provided herein are methods of selecting a treatment for a patient identified or diagnosed as having a cancer that include: (a) administering an additional anticancer agent to the patient (e.g., any of the additional anticancer agents described herein); (b) after (a), detecting increased expression and/or activity of a TAM kinase in a cancer cell or an immune cell from the patient; and (c) after (b), selecting a compound of Formula I or a pharmaceutically acceptable salt thereof or a pharmaceutical composition thereof for the patient.

Also provided herein are methods of treating a patient identified or diagnosed as having a cancer that include: (a) administering to the patient identified or diagnosed as having a cancer one or more doses of at least one additional anticancer agent (e.g., at least one of any of the additional anticancer agents described herein); (b) after (a), detecting an increase in the expression and/or activity of a TAM kinase in a cancer cell or an immune cell from the patient; and (c) after (b), administering to the patient a therapeutically effective amount of a compound of Formula I or a pharmaceutically acceptable salt thereof or a pharmaceutical composition thereof. In some embodiments, step (c) further includes administering to the patient the at least one additional anticancer agent.

Also provided herein are methods of treating a patient identified or diagnosed as having a cancer that include: (a) detecting an increase in the expression/or activity of a TAM kinase in a cancer cell or an immune cell from a patient identified or diagnosed as having a cancer and previously administered one or more doses of the at least on additional anticancer agent (e.g., any of the additional anticancer agents described herein); and (b) after (a), administering to the patient a therapeutically effective amount of a compound of Formula I or a pharmaceutically acceptable salt thereof or a pharmaceutical composition thereof. In some embodiments, step (b) further includes administering to the patient the at least one additional anticancer agent.

Also provided herein are methods of treating a patient identified or diagnosed as having a cancer that has been previously administered one or more doses of at least one additional anticancer agent and has been identified as having a cancer cell or an immune cell that has increased expression and/or activity of a TAM kinase that include administering a therapeutically effective amount of a compound of Formula I or a pharmaceutically acceptable salt thereof or a pharmaceutical composition thereof to the patient. In some embodiments, the method further includes administering to the patient that at least one additional anticancer agent.

Also provided herein are methods of treating a patient identified or diagnosed as having a cancer that include: (a) selecting a patient identified or diagnosed as having increased expression and/or activity of a TAM kinase in a cancer cell or an immune cell; and (b) after (a) administering to the selected patient a therapeutically effective amount of a compound of Formula I or a pharmaceutically acceptable salt thereof or a pharmaceutical composition thereof. In some embodiments, step (b) further includes administering to the patient at least one additional anticancer agent (e.g., any of the additional anticancer agents described herein).

Also provided are methods of treating a patient identified or diagnosed as having a cancer that include: (a) selecting a patient identified or diagnosed as having a cancer that has been previously administered one or more doses of an additional anticancer agent (e.g., any of the additional anticancer agents described herein) and identified as having a cancer cell or an immune cell having increased expression and/or activity of a TAM kinase; and (b) after (a), administering to the selected patient a therapeutically effective amount of a compound of Formula I or a pharmaceutically acceptable salt thereof or a pharmaceutical composition thereof. In some embodiments, step (b) further includes administering to the patient the at least one additional anticancer agent.

Also provided are methods of treating a patient identified or diagnosed as having a TAM-associated cancer that include: (a) administering to the patient identified or diagnosed as having a TAM-associated cancer one or more doses of a TAM kinase inhibitor; (b) after (a), detecting resistance of the TAM-associated cancer in the patient to the TAM kinase inhibitor; and (c) after (b), administering to the patient a therapeutically effective amount of a compound of Formula I or a pharmaceutically acceptable salt thereof or a pharmaceutical composition thereof. In some embodiments, step (c) further includes administering to the patient at least one additional anticancer agent (e.g., any of the additional anticancer agents described herein).

Also provided are methods of treating a patient identified or diagnosed as having a TAM-associated cancer that include: (a) detecting resistance of the TAM-associated cancer in the patient to a TAM kinase inhibitor that was previously administered to the patient; and (b) after (a), administering to the patient a therapeutically effective amount of a compound of Formula I or a pharmaceutically acceptable salt thereof or a pharmaceutical composition thereof. In some embodiments, step (b) further includes administering to the patient at least one additional anticancer agent.

Also provided herein are methods of treating a patient identified or diagnosed as having a TAM-associated cancer and determined to have a previously developed resistance to a TAM kinase inhibitor that include administering to the patient a therapeutically effective amount of a compound of Formula I or a pharmaceutically acceptable salt thereof or a pharmaceutical composition thereof. Some embodiments of these methods further include administering to the patient at least one additional anticancer agent (e.g., any of the additional anticancer agents described herein or known in the art).

In some embodiments of any of the methods described herein, the step of identifying the patient as having a TAM-associated cancer includes performing an assay on a biopsy sample obtained from the patient. In some embodiments, the assay is selected from the group of sequencing, immunohistochemistry, enzyme-linked immunosorbent assay, and fluorescence in situ hybridization (FISH). In some embodiments, the assay is selected from the group of: denaturing gradient gel electrophoresis (DGGE), temperature gradient electrophoresis (TGGE), temperature gradient capillary electrophoresis, a single strand conformational polymorphism assay, a molecular beacon assay, a dynamic hybridization assay, a PCR-based assay and denaturing high performance liquid chromatography. Some embodiments of these methods can further include: obtaining the biopsy sample from the patient.

In some embodiments of any of the methods described herein, a compound of Formula I is selected from the compounds described in Example Nos. 1-471A, 471B and 472-480, or pharmaceutically acceptable salts thereof. In some embodiments, a compound of Formula I is selected from i) Example Nos. 1-20; ii) Example Nos. 21-40; iii) Example Nos. 41-60; iv) Example Nos. 61-80; v) Example Nos. 81-100; vi) Example Nos. 101-120; vii) Example Nos. 121-140; viii) Example Nos. 141-160; ix) Example Nos. 161-180; x) Example Nos. 181-200; xi) Example Nos. 201-220; xii) Example Nos. 221-240; xiii) Example Nos. 241-260; xiv) Example Nos. 261-280; xv) Example Nos. 281-300; xvi) Example Nos. 301-320; xvii) Example Nos. 321-340; xviii) Example Nos. 341-360; xix) Example Nos. 361-380; xx) Example Nos. 381-400; xxi) Example Nos. 401-420; xxii) Example Nos. 421-440; xxiii) Example Nos. 441-460; xxiii) Example Nos. 461-471A; xxiv) Example Nos. 471B-480; xxiv) Example Nos. 481-490; xxv) Example Nos. 491-500; or xxvi) Example Nos. 501-510,or pharmaceutically acceptable salts thereof.

The compounds and methods described herein are useful for the treatment of tumors and cancers (e.g., TAM-associated cancers). The TAM-associated cancer treated can be a primary tumor or a metastatic tumor. In one aspect, the methods described herein are used to treat a solid TAM-associated tumor, for example, melanoma, lung cancer (including lung adenocarcinoma, basal cell carcinoma, squamous cell carcinoma, large cell carcinoma, bronchioloalveolar carcinoma, bronchiogenic carcinoma, non-small-cell carcinoma, small cell carcinoma, mesothelioma); breast cancer (including ductal carcinoma, lobular carcinoma, inflammatory breast cancer, clear cell carcinoma, mucinous carcinoma, serosal cavities breast carcinoma); colorectal cancer (colon cancer, rectal cancer, colorectal adenocarcinoma); anal cancer; pancreatic cancer (including pancreatic adenocarcinoma, islet cell carcinoma, neuroendocrine tumors); prostate cancer; prostate adenocarcinoma; urinary tract cancer; ovarian cancer or carcinoma (ovarian epithelial carcinoma or surface epithelial-stromal tumor including serous tumor, endometrioid tumor and mucinous cystadenocarcinoma); liver and bile duct carcinoma (including hepatocellular carcinoma, cholangiocarcinoma. hemangioma); esophageal carcinoma or cancer (including esophageal adenocarcinoma and squamous cell carcinoma); oral and oropharyngeal squamous cell carcinoma; salivary gland adenoid cystic carcinoma: bladder cancer; bladder carcinoma; carcinoma of the uterus (including endometrial cancer or endometrial adenocarcinoma, ocular, uterine papillary serous carcinoma, uterine clear-cell carcinoma, uterine sarcomas and leiomyosarcomas, mixed mullerian tumors); glioma, glioblastoma. medulablastoma, and other tumors of the brain; kidney cancers (including renal cancer, renal cell carcinoma, clear cell carcinoma, Wilm's tumor); pituitary adenoma; cancer of the head and neck (including squamous cell carcinomas); cancer of the stomach (gastric cancers, stomach adenocarcinoma, gastrointestinal stromal tumor (GIST)); testicular cancer; germ cell tumor; neuroendocrine tumor; cervical cancer; carcinoids of the gastrointestinal tract, breast, and other organs; signet ring cell carcinoma; mesenchymal tumors including sarcomas (e.g., Kaposi's sarcoma), fibrosarcomas, haemangioma, angiomatosis, haemangiopericytoma, pseudoangiomatous stromal hyperplasia, myofibroblastoma, fibromatosis, inflammatory myofibroblastic tumor, lipoma, angiolipoma, granular cell tumor, neurofibroma, schwannoma, angiosarcoma, liposarcoma. rhabdomyosarcoma, osteosarcoma, leiomyoma, leiomysarcoma, skin (e.g., squamous cell skin cancer), including melanoma, cervical, retinoblastoma, head and neck cancer, pancreatic, brain, thyroid, testicular, renal, bladder, soft tissue, adrenal gland, urethra, cancers of the penis, myxosarcoma, chondrosarcoma, osteosarcoma, chordoma. malignant fibrous histiocytoma, lymphangiosarcoma. mesothelioma, squamous cell carcinoma; epidermoid carcinoma. malignant skin adnexal tumors, adenocarcinoma, hepatoma, hepatocellular carcinoma, renal cell carcinoma, hypernephroma, cholangiocarcinoma. transitional cell carcinoma, choriocarcinoma, seminoma, embryonal cell carcinoma, glioma anaplastic; glioblastoma multiforme, neuroblastoma, medulloblastoma. malignant meningioma, malignant schwannoma, neurofibrosarcoma, parathyroid carcinoma, medullary carcinoma of thyroid, bronchial carcinoid, pheochromocytoma. Islet cell carcinoma, malignant carcinoid, malignant paraganglioma, melanoma, Merkel cell neoplasm, eystosarcoma phylloide, salivary cancers, thymic carcinomas, and cancers of the vagina among others.

The compounds of Formula I or pharmaceutically acceptable salts thereof can also be used for treating lymphoma or lymphocytic or myelocytic proliferation disorder or abnormality (e.g., a TAM-associated lymphoma or lymphocytic or myelocytic proliferation disorder or abnormality). For example, the TAM-associated cancer can be a Hodgkin Lymphoma of a Non-Hodgkin Lymphoma. For example, the subject can be suffering from a TAM-associated Non-Hodgkin Lymphoma such as, but not limited to: an AIDS-Related Lymphoma; Anaplastic Large-Cell Lymphoma; Angioimmunoblastic Lymphoma; Blastic N-Cell Lymphoma; Burkitt's Lymphoma: Burkitt-like Lymphoma (Small Non-Cleaved Cell Lymphoma); Chronic Lymphocytic Leukemia/Small Lymphocytic Lymphoma: Cutaneous T-Cell Lymphoma; Diffuse Large B-Cell Lymphoma; Entcropathy-Type T-Cell Lymphoma; Follicular Lymphoma; Hepatosplenic Gamma-Delta T-Cell Lymphoma; Lymphoblastic Lymphoma: Mantle Cell Lymphoma; Marginal Zone Lymphoma; Nasal T-Cell Lymphoma; Pediatric Lymphoma; Peripheral T-Cell Lymphomas; Primary Central Nervous System Lymphoma; T-Cell Leukemias; Transformed Lymphomas; Treatment-Related T-Cell Lymphomas; or Waldenstrom's Macroglobulinemia.

Alternatively, the subject may be suffering from a TAM-associated Hodgkin Lymphoma, such as, but not limited to: Nodular Sclerosis Classical Hodgkin's Lymphoma (CHL); Mixed Cellularity CHL; Lymphocyte-depletion CHL; Lymphocyte-rich CHL; Lymphocyte Predominant Hodgkin Lymphoma; or Nodular Lymphocyte Predominant HL.

In one embodiment, the methods as described herein may be useful to treat a patient suffering from a specific TAM-associated T-cell, a B-cell, or a NK-cell based lymphoma, proliferative disorder, or abnormality. For example, the patient can be suffering from a specific TAM-associated T-cell or NK-cell lymphoma, for example, but not limited to: Peripheral T-cell lymphoma, for example, peripheral T-cell lymphoma and peripheral T-cell lymphoma not otherwise specified (PTCL-NOS); anaplastic large cell lymphoma, for example anaplastic lymphoma kinase (ALK) positive. ALK negative anaplastic large cell lymphoma, mantle cell lymphoma, or primary cutaneous anaplastic large cell lymphoma; angioimmunoblastic lymphoma; cutaneous T-cell lymphoma, for example mycosis fungoides, Sezary syndrome, primary cutaneous anaplastic large cell lymphoma, primary cutaneous CD30+ T-cell lymphoproliferative disorder; primary cutaneous aggressive epidermolropic CD8+ cytotoxic T-cell lymphoma; primary cutaneous gamma-delta T-cell lymphoma; primary cutaneous small/medium CD4+ T-cell lymphoma, and lymphomatoid papulosis; Adult T-cell Leukemia/Lymphoma (ATLL); Blastic NK-cell Lymphoma: Enteropathy-type T-cell lymphoma; Hematosplenic gamma-delta T-cell Lymphoma: Lymphoblastic Lymphoma; Nasal NK/T-cell Lymphomas; Treatment-related T-cell lymphomas; for example lymphomas that appear after solid organ or bone marrow transplantation; T-cell prolymphocyte leukemia; T-cell large granular lymphocytic leukemia; Chronic lymphoproliferative disorder of NK-cells; Aggressive NK cell leukemia; Systemic EBV+ T-cell lymphoproliferative disease of childhood (associated with chronic active EBV infection); Hydroa vacciniforme-like lymphoma; Adult T-cell leukemia/lymphoma; Enteropathy-associated T-cell lymphoma; Hepatosplenic T-cell lymphoma; or Subcutaneous panniculitis-like T-cell lymphoma.

In one embodiment, the methods as described herein may be useful to treat a patient suffering from a specific TAM-associated B-cell lymphoma or proliferative disorder such as, but not limited to: multiple myeloma; Diffuse large B cell lymphoma; Follicular lymphoma; Mucosa-Associated Lymphatic Tissue lymphoma (MALT); Small cell lymphocytic lymphoma; Mantle cell lymphoma (MCL); Burkitt lymphoma; Mediastinal large B cell lymphoma; Waldenstrom macroglobulinemia; Nodal marginal zone B cell lymphoma (NMZL); Splenic marginal zone lymphoma (SMZL); Intravascular large B-cell lymphoma; Primary effusion lymphoma; or Lymphomatoid granulomatosis; Chronic lymphocytic leukemia/small lymphocytic lymphoma; B-cell prolymphocyte leukemia; Hairy cell leukemia; Splenic lymphoma/leukemia, unclassifiable; Splenic diffuse red pulp small B-cell lymphoma; Hairy cell leukemia-variant; Lymphoplasmacytic lymphoma; Heavy chain diseases, for example, Alpha heavy chain disease, Gamma heavy chain disease, Mu heavy chain disease; Plasma cell myeloma; Solitary plasmacytoma of bone; Extraosseous plasmacytoma; Primary cutaneous follicle center lymphoma; cell/histiocytc rich large B-cell lymphoma; DLBCL associated with chronic inflammation; Epstein-Barr virus (EBV)+ DLBCL of the elderly; Primary mediastinal (thymic) large B-cell lymphoma; Primary cutaneous DLBCL, leg type; ALK+ large B-cell lymphoma; Plasmablastic lymphoma; Large B-cell lymphoma arising in HHV8-associated multicentric; Castleman disease; B-cell lymphoma, unclassifiable, with features intermediate between diffuse large B-cell lymphoma and Burkitt lymphoma; B-cell lymphoma, unclassifiable, with features intermediate between diffuse large B-cell lymphoma and classical Hodgkin lymphoma; Nodular sclerosis classical Hodgkin lymphoma; Lymphocyte-rich classical Hodgkin lymphoma; Mixed cellularity classical Hodgkin lymphoma; or Lymphocyte-depleted classical Hodgkin lymphoma.

In one embodiment, the methods as described herein may be useful to treat a patient suffering from a TAM-associated leukemia. For example, the subject may be suffering from an acute or chronic TAM-associated leukemia of a lymphocytic or myelogenous origin, such as, but not limited to: Acute lymphoblastic leukemia (ALL); Acute myelogenous leukemia (AML); Chronic lymphocytic leukemia (CLL); Chronic myelogenous leukemia (CML); juvenile myelomonocytic leukemia (JMML); hairy cell leukemia (HCL); acute promyelocyte leukemia (a subtype of AML); T-cell prolymphocyte leukemia (TPLL); large granular lymphocytic leukemia; or Adult T-cell chronic leukemia; large granular lymphocytic leukemia (LGL). In one embodiment, the patient suffers from an acute myelogenous leukemia, for example an undifferentiated AML (M0); myeloblasts leukemia (M1; with/without minimal cell maturation); myeloblastic leukemia (M2; with cell maturation); promyelocytic leukemia (M3 or M3 variant [M3V]); myelomonocytic leukemia (M4 or M4 variant with eosinophilia [M4E]); monocytic leukemia (M5); erythroleukemia (M6); or megakaryoblastic leukemia (M7).

In one embodiment, the compounds and methods described herein are useful for treating a TAM-associated cancer in a patient, wherein the cancer overexpresses AXL, MER, or TYRO3, or a combination thereof, e.g., as compared to a control non-cancerous tissue or a control cell (e.g., from the same or a different subject). In one embodiment, the cancer overexpresses AXL. In one embodiment, the cancer overexpresses MER. In an alternative embodiment, the cancer ectopically expresses MER. In one embodiment, the TAM-associated cancer is breast, colon, renal, skin, lung (including non-small cell lung cancer), liver, gastric, brain (including glioblastoma), ovarian, pancreatic, prostate, glioblastoma multiforme, osteosarcoma, thyroid malignancies, rhabdomyosarcoma, melanoma. acute myeloid leukemia, T-cell acute lymphoid leukemia, B-cell acute lymphoid leukemia, schwannoma, and mantle cell lymphoma.

In one embodiment, the TAM-associated cancer is selected from breast, colon, renal, skin, lung (including non-small cell lung cancer), liver, gastric, brain (including glioblastoma), ovarian, pancreatic, prostate, glioblastoma multiforme, osteosarcoma, thyroid malignancies, rhabdomyosarcoma, and melanoma.

In one embodiment, the TAM-associated cancer is selected from leukemias (including acute myeloid leukemia and chronic myeloid leukemia, B-cell myeloid leukemia (B-CLL), B-cell acute lymphoblastic leukemia, erythroid leukemia, and T-lineage acute lymphoblastic leukemia), non-small cell lung cancer, pancreatic ductal adenocarcinoma, astrocytoma, lung adenocarcinoma, ovarian cancer, melanoma, and gloibalstoma multiforme.

In one embodiment, the TAM-associated cancer is selected from chronic myeloid leukemia, gastrointestinal stromal tumors (GIST), breast cancer (e.g., HER2 positive breast cancer and triple negative breast cancer), head and neck cancer, and non-small cell lung cancer.

In some embodiments of any of the methods described herein, the TAM-associated cancer is a cancer having overexpression of a TAM kinase, e.g., as compared to a non-cancerous tissue or cell in the same patient or a different subject. In some embodiments of any of the methods described herein, the TAM-associated cancer is a cancer having ectopic expression of a TAM kinase.

In some embodiments of any of the methods described herein, the TAM-associated cancer is a cancer having overexpression or ectopic expression of a TYRO3 protein. In some embodiments of any of the methods described herein, the TAM-associated cancer has one or more point mutations in a gene encoding TYRO3 that results in the expression of a TYRO3 that includes one or more amino acid substitutions. In some embodiments of any of the methods described herein, the TAM-associated cancer has a chromosomal translocation which results in the expression of a fusion protein including the kinase domain of TYRO3 and a fusion partner. Non-limiting examples of a TAM-associated cancer having overexpression or ectopic expression of TYRO3, or a mutation in a TYRO3 gene that results in the expression of TYRO3 having one or more point mutations or a TYRO3 fusion protein include: AML, multiple myeloma, lung cancer, melanoma, prostate cancer, endometrial cancer, thyroid cancer, schwannoma, pancreatic cancer, and brain cancer. Non-limiting aspects of TAM-associated cancers having increased expression and/or activity of TYRO3 are listed below.

TABLE A

TAM-Associated Cancers Having with Increased Expression and/or Activity of TYRO3

| | |
|---|---|
| Melanoma | Amino acid substitutions at: Q67 and/or R462Q, and/or W708fs*5 |
| Lung Cancer | Amino acid substitution at E340 or N615K in TYRO3 |
| Pancreatic Cancer | Amino acid substitution R514Q in TYRO3 |
| Colon Cancer | Amino acid substitution G809D and/or M592I in TYRO3 |
| Brain Cancer | Amino acid substitution A709T in TYRO3 |
| AML, multiple myeloma, lung cancer, melanoma, prostate cancer, endometrial cancer, thyroid cancer, and schwannoma | Overexpression or ectopic expression of TYRO3 |

Additional anticancer agents that are TYRO3 inhibitors include, e.g., 6 g, merestinib (LY2801653), ASLAN002 (BMS-777607), LDC1267, and UNC2025.

In some embodiments of any of the methods described herein, the TAM-associated cancer is a cancer having overexpression or ectopic expression of a AXL protein. In some embodiments of any of the methods described herein, the TAM-associated cancer has one or more point mutations in a gene encoding AXL that results in the expression of a AXL that includes one or more amino acid substitutions. In some embodiments of any of the methods described herein, the TAM-associated cancer has a chromosomal translocation which results in the expression of a fusion protein including the kinase domain of AXL and a fusion partner. Non-limiting examples of a TAM-associated cancer having overexpression or ectopic expression of AXL, or a mutation in a AXL gene that results in the expression of AXL having one or more point mutations or a AXL fusion protein include: AML, CML, B-CLL, lung cancer, glioblastoma, breast cancer, colorectal cancer, gastric cancer, pancreatic cancer, oesophageal cancer, melanoma, squamous cell skin cancer, prostate cancer, endometrial cancer, ovarian cancer, oral squamous cell carcinoma, thyroid cancer, bladder cancer, renal cancer, schwannoma, mesothelioma, Kaposi's sarcoma, osteosarcoma, erythroid leukemia, colon cancer, liver cancer, renal cell carcinoma, osteosarcoma, kidney cancer, PH+ CML, non-small cell lung cancer, triple-negative metastatic breast cancer, and HER2+ breast cancer. Non-limiting aspects of TAM-associated cancers having increased expression and/or activity of AXL are listed below.

TABLE B

TAM-Associated Cancers Having with Increased Expression and/or Activity of AXL

| Cancer | Mutations |
|---|---|
| Ovarian Cancer | Amino acid substitutions C24G and/or A358V in AXL |
| Melanoma | One or more of the amino acid substitutions of P36L, R236C, G413W, E431K, A451T, E535K, G829E, I610V, A666T, S685F, and R784Q in AXL |
| Colon Cancer | One or more of the amino acid substitutions of N43T, M580K, and L684P in AXL |
| Skin Cancer | An amino acid substitution of P238L in AXL |
| Gastric Cancer | One or more of the amino acid substitutions of V289M, R492C, S842F, and P636H in AXL |
| Lung Cancer | One or more of the amino acid substitutions of R295W, L423Q, K526N, and S599F in AXL |
| Breast Cancer | One or more of the amino acid substitutions of T343M, E745K, and S747R in AXL |
| Prostate Cancer | An amino acid substitution of R368Q in AXL |
| Pancreatic Cancer | An amino acid substitution of E484D in AXL |
| Kidney Cancer | An amino acid substitution of P742T in AXL |
| AML, CIVIL, B-CLL, lung cancer, glioblastoma, breast cancer, colorectal cancer, gastric cancer, pancreatic cancer, esophageal cancer, melanoma, squamous cell skin cancer, prostate cancer, endometrial cancer, ovarian cancer, oral squamous cell carcinoma, thyroid cancer, bladder cancer, renal cancer, schwannoma, mesothelioma, Kaposi's sarcoma, and osteosarcoma | Overexpression or ectopic expression of AXL |

Additional anticancer agents that are AXL inhibitors include, e.g., bosutinib (SKI-606, PF-5208765, Bosulif), BGB324 (R428), crizotinib (PF-2341066, Xalkon), foretinib (GSK1363089, XL880), BMS-777607 (ASLAN002), LY2801653 (merestinib), amuvatinib (MP-470), cabozantinib (XL184, BMS-907351, Cometriq), MGCD265, NPS-1034, LDC1267, gilteritinib (ASP2215), SGI-7079, TP-0903, UNC2025, S49076, sunitinib (SU11248, Sutent), and the monoclonal antibodies of 12A11, Mab173, YW327.6S2, D9, and E8.

In some embodiments of any of the methods described herein, the TAM-associated cancer is a cancer having overexpression or ectopic expression of a MER protein. In some embodiments of any of the methods described herein, the TAM-associated cancer has one or more point mutations in a gene encoding MER that results in the expression of a MER that includes one or more amino acid substitutions. In some embodiments of any of the methods described herein, the TAM-associated cancer has a chromosomal translocation which results in the expression of a fusion protein including the kinase domain of MER and a fusion partner. Non-limiting examples of a TAM-associated cancer having overexpression or ectopic expression of MER, or a mutation in a MER gene that results in the expression of MER having one or more point mutations or a MER fusion protein include: AML, ALL (B-ALL, T-ALL), lung cancer, glioma, melanoma, prostate cancer, schwannoma, mantle cell lymphoma, rhabdomyosarcoma, pancreatic cancer, breast cancer, gastric cancer, pituitary adenoma, urinary tract cancer, kidney cancer, liver cancer, colon cancer, and breast cancer. Non-limiting aspects of MER-associated cancers having increased expression and/or activity of MER are listed below.

TABLE C

TAM-Associated Cancers Having with Increased Expression and/or Activity of MER

| Cancer | Mutations |
|---|---|
| Melanoma | One or more amino acid substitutions of P40S, V861I, K923R, and P802S in MER |
| Lung Cancer | One or more amino acid substitutions of S159F, I431F, S905F, P672S, N718Y, and M790V in MER |
| Urinary Tract Cancer | One or more amino acid substitutions of E204K, L586F, and S626C in MER |
| Gastic Cancer | An amino acid substitutions of S428G in MER |
| Kidney Cancer | Amino acid substitutions of A446G and/or P958L in MER |
| Liver Cancer | One or more amino acid substitutions of N454S, V873I, and D983N in MER |
| Lymphoma | An amino acid substitution of W485S/C in MER |
| Colon Cancer | One or more amino acid substitutions of D990N, L688M, and R722 in MER |
| Breast Cancer | An amino acid substitution of G594R in MER |
| Head and Neck Cancer | An amino acid substitution of A708S in MER |
| AML, ALL, lung cancer, glioma, melanoma, prostate cancer, schwannoma, mantle cell lymphoma, and rhabdomyosarcoma | Overexpression or ectopic expression of MER |

Additional anticancer agents that are MER inhibitors include, e.g., foretinib, merestinib (LY2801653), ASLAN002 (BMS-777607), SGI-7079, TP-0903, UNC2025, and 549076.

Also provided are methods for treating a cancer (e.g., a TAM-associated cancer0 in a patient in need thereof, the method comprising: (a) determining if the cancer in the patient is a TAM-associated cancer; and (b) if the cancer is determined to be a TAM-associated cancer, administering to the patient a therapeutically effective amount of a compound of Formula I or a pharmaceutically acceptable salt thereof or a pharmaceutical composition thereof. Some embodiments of these methods further include administering to the subject at least one additional anticancer agent (e.g., an immunotherapy). In some embodiments, the subject was previously treated with at least one additional anticancer agent or therapy, e.g., a kinase inhibitor, an immunotherapy, chemotherapy, radiation therapy and/or surgery. In some embodiments the patient has a cancer that is resistant to the at least one additional anticancer agent. In one embodiment, the at least one additional anticancer agent does not include a compound of Formula I.

Also provided herein is a method for treating a patient diagnosed with or identified as having a TAM-associated cancer, e.g., any of the exemplary TAM-associated cancers disclosed herein, comprising administering to the patient a therapeutically effective amount of a compound of Formula I or a pharmaceutically acceptable salt thereof, or a pharmaceutical composition thereof as defined herein. Some embodiments of these methods further include administering to the subject at least one additional anticancer agent (e.g., an immunotherapy). In some embodiments, the subject was previously treated with at least one additional anticancer agent or therapy, e.g., a kinase inhibitor, an immunotherapy, chemotherapy, radiation therapy and or surgery. In one embodiment the patient has a cancer that is resistant to the previously administered at least one additional anticancer agent. In some embodiments, the at least one additional anticancer agent does not include a compound of Formula I.

In one embodiment, provided herein are methods for treating a patient diagnosed with (or identified as having) a cancer (e.g., a TAM-associated cancer) that include administering to the patient a therapeutically effective amount of a compound of Formula I or a pharmaceutically acceptable salt thereof. Also provided herein are methods for treating a patient identified or diagnosed as having a TAM-associated cancer that include administering to the patient a therapeutically effective amount of a compound of Formula I or a pharmaceutically acceptable salt thereof or a pharmaceutical composition thereof. In some embodiments, the patient that has been identified or diagnosed as having a TAM-associated cancer through the use of a regulatory agency-approved, e.g., FDA-approved test or assay for identifying abnormal (e.g., increased) expression and/or activity of one or more of the TAM kinases, in a patient or a biopsy sample from the patient or by performing any of the non-limiting examples of assays described herein. In some embodiments, the test or assay is provided as a kit. Some embodiments of these methods further include administering to the patient at least one additional anticancer agent (e.g., an immunotherapy). In some embodiments, the patient was previously treated with at least one additional anticancer agent or therapy, e.g., a kinase inhibitor, an immunotherapy, chemotherapy, radiation therapy and or surgery. In some embodiments, the patient has a cancer that is resistant to the at least one additional anticancer agent. In some embodiments, the at least one additional anticancer agent does not include a compound of Formula I.

Also provided is a compound of Formula I or a pharmaceutically acceptable salt thereof, for use in the treatment of a cancer in a patient in need thereof or a patient identified or diagnosed as having a TAM-associated cancer (e.g., any of the TAM-associated cancers described herein). Also provided is the use of a compound of Formula I or a pharmaceutically acceptable salt thereof for the manufacture of a medicament for treating a cancer in a patient identified or diagnosed as having a TAM-associated cancer. In some embodiments, the cancer is a TAM-associated cancer. In some embodiments, a patient is identified or diagnosed as having a TAM-associated cancer through the use of a regulatory agency-approved, e.g., FDA-approved, kit for identifying abnormal (e.g., increased) expression and/or activity of one or more of the TAM kinases, e.g., as compared to a non-cancerous tissue or cell from the same or a different subject. Some embodiments of these methods further include administering to the patient at least one additional anticancer agent (e.g., immunotherapy). In some embodiments, the subject was previously treated with at least one additional anticancer agent or therapy, e.g., a kinase inhibitor, an immunotherapy, chemotherapy, radiation therapy and/or surgery. In some embodiments, the patient has a cancer that is resistant to one or more of the at least one additional anticancer agents. In one embodiment, the at least one additional anticancer agent does not include a compound of Formula I.

In some embodiments of any of the methods or uses described herein, the patient has been identified or diagnosed as having a cancer associated with or having abnormal (e.g., increased) expression and/or activity of one or more of the TAM kinases, e.g., as compared to a non-cancerous tissue or cell in the same or a different subject. In some embodiments, provided herein are methods for treating a TAM-associated cancer in a patient in need of such treatment, the method comprising a) detecting abnormal (e.g., increased) expression and/or activity of one or more of the TAM kinases, e.g., as compared to a non-cancerous tissue or cell in the same or a different subject; and b) after a), administering a therapeutically effective amount of a compound of Formula I or a pharmaceutically acceptable salt thereof. Some embodiments of these methods further include administering to the patient at least one additional anticancer agent (e.g., immunotherapy). In some embodiments, the patient was previously treated with at least one additional anticancer agent or therapy, e.g., a kinase inhibitor, an immunotherapy, chemotherapy, radiation therapy and/or surgery. In some embodiments, the patient has a cancer that is resistant to one or more of the at least one additional anticancer agent. In one embodiment, the at least one additional anticancer agent does not include a compound of Formula I.

In some embodiments of any of the methods or uses described herein, the patient has a clinical record indicating that the patient has a tumor associated with or having abnormal (e.g., increased) expression and/or activity of one or more of the TAM kinases, e.g., as compared to a non-cancerous tissue or cell in the same patient or a different subject). In some embodiments, the clinical record indicates that the patient should be treated with one or more of the compounds of Formula I or a pharmaceutically acceptable salts thereof or compositions provided herein. Some embodiments of these methods further include administering to the patient at least one additional anticancer agent (e.g., an immunotherapy). In some embodiments, the subject was previously treated with at least one additional anticancer agent or therapy, e.g., a kinase inhibitor, an immunotherapy, chemotherapy, radiation therapy and/or surgery. In some embodiments, the patient has a cancer that is resistant to one or more of the at least one additional anticancer agent. In one embodiment, the at least one additional anticancer agent does not include a compound of Formula I.

Also provided are methods of treating a patient that include administering a therapeutically effective amount of a compound of Formula I or a pharmaceutically acceptable salt thereof to a patient having a clinical record that indicates that the patient has a cancer associated with or having abnormal (e.g., increased) expression and/or activity of one or more of the TAM kinases, e.g., as compared to a non-cancerous tissue or cell from the patient or a different subject. Also provided is the use of a compound of Formula I or a pharmaceutically acceptable salt thereof for the manufacture of a medicament for treating a TAM-associated cancer in a patient having a clinical record that indicates that the patient has a cancer associated with or having abnormal (e.g., increased) expression and/or activity of one or more of the TAM kinases, e.g., as compared to a non-cancerous tissue or cell from the patient or a different subject. Some embodiments of these methods and uses can further include: a step of performing an assay on a sample (e.g., a biopsy sample) obtained from the patient to determine whether the patient has abnormal (e.g., increased) expression and/or activity of one or more of the TAM kinases (e.g., as compared to a non-cancerous tissue or cell from the patient or a different subject), and recording the information in a patient's clinical file (e.g., a computer readable medium) that the patient has been identified to have abnormal (e.g., increased) expression and/or activity of one or more of the TAM kinases. In some embodiments, the assay is an in vitro assay. Some embodiments of these methods further include administering to the patient at least one additional anticancer agent (e.g., an immunotherapy). In some embodiments, the subject was previously treated with at least one additional anticancer agent or therapy, e.g., a kinase inhibitor, an immunotherapy, chemotherapy, radiation therapy and/or surgery. In some embodiments, the patient has a cancer that is resistant to one or more of the at least one additional anticancer agent. In one embodiment, the at least one additional anticancer agent does not include a compound of Formula I.

Also provided herein is a method of treating a patient in need thereof. The method includes performing an assay on a sample obtained from the patient to determine whether the subject has abnormal (e.g., increased) expression and/or activity of one or more of the TAM kinases, e.g., as compared to a non-cancerous tissue or cell from the same patient or a different subject). The method also includes administering to a patient determined to have abnormal (e.g., increased) expression and/or activity of one or more of the TAM kinases (e.g., as compared to a non-cancerous tissue or cell from the same patient or a different subject) a therapeutically effective amount of a compound of Formula I or a pharmaceutically acceptable salt thereof. Some embodiments of these methods further include administering to the patient at least one additional anticancer agent (e.g., an immunotherapy). In some embodiments, the patient was previously treated with at least one additional anticancer agent or therapy, e.g., a kinase inhibitor, an immunotherapy, chemotherapy, radiation therapy and/or surgery. In some embodiments, the patient has a cancer that is resistant to one or more of the at least one additional anticancer agent. In some embodiments, the at least one additional anticancer agent does not include a compound of Formula I.

Also provided are methods (e.g., in vitro methods) of selecting a treatment for a patient identified or diagnosed as having a TAM-associated cancer. Some embodiments can further include administering the selected treatment to the patient identified or diagnosed as having a TAM-associated cancer. For example, the selected treatment can include administration of a therapeutically effective amount of a compound of Formula I or a pharmaceutically acceptable salt thereof. Some embodiments can further include a step of performing an assay on a sample (e.g., a biopsy sample) obtained from the patient to determine whether the patient has abnormal (e.g., increased) expression and/or activity of one or more of the TAM kinases (e.g., as compared to a non-cancerous tissue or cell from the same patient or a different subject), and identifying and diagnosing a patient determined to have abnormal (e.g., increased) expression and/or activity of one or more of the TAM kinases, as having a TAM-associated cancer. In some embodiments, the patient has been identified or diagnosed as having a TAM-associated cancer through the use of a regulatory agency-approved, e.g., FDA-approved, kit for identifying abnormal (e.g., increased) expression and/or activity of one or more of the TAM kinases in a patient or a biopsy sample from the patient. In some embodiments, the TAM-associated cancers is a cancer described herein or known in the art. In some embodiments, the assay is an in vitro assay. For example, an assay that utilizes the next generation sequencing, immunohistochemistry, or break apart FISH analysis. In some embodiments, the assay is a regulatory agency-approved, e.g., FDA-approved, kit. Some embodiments of these methods further include administering to the patient at least one additional anticancer agent (e.g., an immunotherapy). Some embodiments of these methods further include administering to the subject at least one additional anticancer agent (e.g., an immunotherapy). In some embodiments, the patient was previously treated with at least one additional anticancer agent or therapy, e.g., a kinase inhibitor, an immunotherapy, chemotherapy, radiation therapy and/or surgery. In one embodiment the patient has a cancer that is resistant to one or more of the at least one anticancer agent. In one embodiment, the at least one additional anticancer agent does not include a compound of Formula I.

Also provided herein are methods of selecting a treatment for a patient, wherein the methods include a step of performing an assay on a sample obtained from the patient to determine whether the patient has abnormal (e.g., increased) expression and/or activity of one or more of the TAM kinases, e.g., as compared to a non-cancerous tissue or cell from the patient or a different subject. Some embodiments further include administering the selected treatment to the patient identified or diagnosed as having a TAM-associated cancer. For example, the selected treatment can include administration of a therapeutically effective amount of a compound of Formula I or a pharmaceutically acceptable salt thereof to the patient identified or diagnosed as having a TAM-associated cancer. In some embodiments, the assay is an in vitro assay. Some embodiments of these methods further include administering to the patient at least one additional anticancer agent (e.g., an immunotherapy). In some embodiments, the patient was previously treated with at least one additional anticancer agent or therapy, e.g., a kinase inhibitor, an immunotherapy, chemotherapy, radiation therapy and/or surgery. In some embodiments, the patient has a cancer that is resistant to one or more of the at least one additional anticancer agent. In one embodiment, the at least one additional anticancer agent does not include a compound of Formula I.

Also provided are methods of selecting a patient for treatment, wherein the methods include selecting, identifying, or diagnosing a patient having a TAM-associated cancer, and selecting the patient for treatment including administration of a therapeutically-effective amount of a compound of Formula I or a pharmaceutically acceptable salt thereof. In some embodiments, identifying or diagnosing a patient as having a TAM-associated cancer can include a step of performing an assay on a sample obtained from the patient to determine whether the patient has abnormal (e.g., increased) expression and/or activity of one or more of the TAM kinases (e.g., as compared to a non-cancerous tissue or cell from the patient or a different subject), as having a TAM-associated cancer. In some embodiments, the method of selecting a treatment can be used as a part of a clinical study that includes administration of various treatments of a TAM-associated cancer. In some embodiments, the assay is an in vitro assay. Some embodiments of these methods further include administering to the subject at least one additional anticancer agent (e.g., an immunotherapy). In some embodiments, the patient was previously treated with at least one additional anticancer agent or therapy, e.g., a kinase inhibitor, an immunotherapy, chemotherapy, radiation therapy and/or surgery. In some embodiments, the patient has a cancer that is resistant to one or more of the at least one additional anticancer agent. In some embodiments, the at least one additional anticancer agent does not include a compound of Formula I.

In some embodiments of any of the methods or uses described herein, an assay can be used to determine whether the patient has abnormal (e.g., increased) expression and/or activity of one or more of the TAM kinases. In some embodiments, the sample is a biological sample or a biopsy sample (e.g., a paraffin-embedded biopsy sample) from the patient. In some embodiments, the patient is a patient suspected of having a TAM-associated cancer, a patient having one or more symptoms of a TAM-associated cancer, and/or a patient that has an increased risk of developing a TAM-associated cancer).

In some embodiments of any the methods described herein, the compound of Formula I or a pharmaceutically acceptable salt thereof is administered in combination with a therapeutically effective amount of at least one additional anticancer agent selected from one or more additional therapies or therapeutic agents, for example an agent that works by the same or by a different mechanism of action. In one embodiment, the compound of Formula I is selected from i) Example No. 1-20; ii) Example No. 21-40; iii) Example No. 41-60; iv) Example No. 61-80; v) Example No. 81-100; vi) Example No. 101-120; vii) Example No. 121-140; viii) Example No. 141-160; ix) Example No. 161-180; x) Example No. 181-200; xi) Example No. 201-220; xii) Example No. 221-240; xiii) Example No. 241-260; xiv) Example No. 261-280; xv) Example No. 281-300; xvi) Example No. 301-320; xvii) Example No. 321-340; xviii) Example No. 341-360; xix) Example No. 361-380; xx) Example No. 381-400; xxi) Example No. 401-420; xxii) Example No. 421-440; xxiii) Example No. 441-460; xxiii) Example No. 461-471A; xxiv) Example No. 471B-480; 481-490; xxv) Example Nos. 491-500; or xxvi) Example Nos. 501-510.

Non-limiting examples of additional anticancer agents include immune-targeted agents including immunotherapy agents, anti-viral agents, kinase-targeted therapeutic agents, anti-viral vaccines, anti-hormonal agents, signal transduction pathway inhibitors, chemotherapeutics or other anticancer agents, angiogenesis inhibitors, and radiotherapy.

One or more of any of the additional anticancer agents described herein can be combined with the present compounds in a single dosage form, or the present compounds and the at least one additional anticancer agents can be administered simultaneously or sequentially as separate dosage forms.

In one embodiment the compound of Formula I or a pharmaceutically acceptable salt thereof is administered daily for 28 consecutive days in a 28 days cycle.

In one embodiment, compounds of Formula I or pharmaceutically acceptable salts thereof may be combined with immune-targeted agents including immunotherapy drugs.

The term "immunotherapy agents" refers to an agent that modulates the immune system. In some embodiments, an immunotherapy can increase the expression and/or activity of a regulator of the immune system. In some embodiments, an immunotherapy can decrease the expression and/or activity of a regulator of the immune system. In some embodiments, an immunotherapy can recruit and/or enhance the activity of an immune cell.

In some embodiments, the immunotherapy agent is an immune checkpoint inhibitor. As used herein, the term "immune checkpoint inhibitor" or "checkpoint inhibitor" refers to molecules that totally or partially reduce, inhibit, interfere with, or modulate the expression and/or activity of one or more checkpoint proteins. In some embodiments, the immunotherapy includes one or more immune checkpoint inhibitors. In some embodiments, the immune checkpoint inhibitor is a CTLA-4 inhibitor (e.g., an anti-CTLA-4 antibody), a PD-1 inhibitor (e.g., an anti-PD-1 monoclonal antibody) or a PD-L1 inhibitor (e.g., an anti-III PD-L1 monoclonal antibody). In some embodiments, the CTLA-4 inhibitor is ipilimumab (Yervoy®) or tremelimumab (CP-675,206). In some embodiments, the PD-1 inhibitor is pembrolizumab (Keytruda®), nivolumab (Opdivo®), or pidilizumab. In some embodiments, the anti-PD-1 monoclonal antibody is nivolumab or pembrolizumab. In some embodiments, the anti-PD1 antibody is pembrolizumab. In some embodiments, the PD-L1 inhibitor is atezolizumab (Tecentriq®), avelumab (Bavencio®), durvalumab (Imfinzi™) MEDI4736, or MPDL3280A. In some embodiments, the PD-L1 inhibitor is atezolizumab (Tecentriq®), avelumab (Bavencio®), or durvalumab (Imfinzi™). In some embodiments, a checkpoint inhibitor can target 4-1BB (e.g., urelumab (BMS-663513) and PF-05082566 (PF-2566)), CD27 (e.g., varlilumab (CDX-1127), CD40 (e.g., CP-870, 893), OX40, TIM-3, ICOS, BTLA, A2AR, B7-H3, B7-H4, BTLA, IDO, KIR, LAG3, TIM-3, and VISTA. Additional non-limiting examples of immune checkpoint inhibitors include ulocuplumab, urelumab, PF 05082566, TRX518, varlilumab, CP 870893, PDROOIMEDI4736, avelumab, BMS 986016, MGA271, IPH2201, emactuzumab, INCB024360, MEDI6469, galunisertib, BKT140, bavituximab, lirilumab, bevacizumab, MNRP1685A, lambroizumab, CC 90002, BMS-936559, and MGA271.

In some embodiments, a compound of Formula I or pharmaceutically acceptable salt thereof is combined with an immune checkpoint inhibitor, wherein the immune checkpoint inhibitor is administered on one or more days in a 28 days cycle. In one embodiment the compound of Formula I or a pharmaceutically acceptable salt thereof is administered daily for 28 consecutive days in a 28 days cycle.

In some embodiments, a compound of Formula I or pharmaceutically acceptable salt thereof is combined with an immune checkpoint inhibitor, wherein the immune checkpoint inhibitor is administered one a week. In one embodiment, the immune checkpoint inhibitor is administered every two weeks. the immune checkpoint inhibitor is administered every three weeks. the immune checkpoint inhibitor is administered every 4 weeks. In one embodiment, the immune checkpoint inhibitor is administered on day 1 of a 28 day cycle. In one embodiment, the immune checkpoint inhibitor is administered on days 1 and 7 in a 28 day cycle. In one embodiment, the immune checkpoint inhibitor is administered in days 1, 7 and 14 in a 28 day cycle. In one embodiment, the immune checkpoint inhibitor is administered on days 1, 7, 14 and 21 in a 28 day cycle. In one embodiment, the immune checkpoint inhibitor is administered on days 1, 7, 14 and 28 in a 28 day cycle. In one embodiment the compound of Formula I or a pharmaceutically acceptable salt thereof is administered daily for 28 consecutive days in a 28 days cycle. In one embodiment, the immune checkpoint inhibitor is administered by intravenous infusion.

In some embodiments, a compound of Formula I or pharmaceutically acceptable salt thereof is combined with an immune checkpoint inhibitor, wherein the immune checkpoint inhibitor is administered on day 1 of cycles 1 through 13. In one embodiment the compound of Formula I or a pharmaceutically acceptable salt thereof is administered daily for 28 consecutive days in a 28 days cycle.

In some embodiments, the immunotherapy agent is a cellular immunotherapy (e.g., adoptive T-cell therapy, dendritic cell therapy, or a natural killer cell therapy). In some embodiments, the cellular immunotherapy is sipuleucel-T (APC8015; Provenge™; Plosker (2011) Drugs 71(1): 101-108). In some embodiments, the cellular immunotherapy includes cells that express a chimeric antigen receptor (CAR). In some embodiments, the cellular immunotherapy is a CAR-T cell therapy. In some embodiments, the CAR-T cell therapy is tisagenlecleucel (Kymriah™).

In some embodiments, the immunotherapy agent is an antibody therapy (e.g., a monoclonal antibody, a conjugated antibody). In some embodiments, the antibody therapy is bevacizumab (Mvasti™, Avastin®), trastuzumab (Herceptin®), avelumab (Bavencio®), rituximab (MabThera™, Rituxan®), edrecolomab (Panorex), daratumuab (Darzalex®), olaratumab (Lartruvo™), ofatumumab (Arzerra®), alemtuzumab (Campath®), cetuximab (Erbitux®), oregovomab, pembrolizumab (Keytruda®), dinutiximab (Unituxin®), obinutuzumab (Gazyva®), tremelimumab (CP-675,206), ramucirumab (Cyramza®), ublituximab (TG-1101), panitumumab (Vectibix®), elotuzumab (Empliciti™), avelumab (Bavencio®), necitumumab (Portrazza™), cirmtuzumab (UC-961), ibritumomab (Zevalin®), isatuximab (SAR650984), nimotuzumab, fresolimumab (GC1008), lirilumab (INN), mogamulizumab (Poteligeo®), ficlatuzumab (AV-299), denosumab (Xgeva®), ganitumab, urelumab, pidilizumab, or amatuximab.

In some embodiments, the immunotherapy agent is an antibody-drug conjugate. In some embodiments, the antibody-drug conjugate is gemtuzumab ozogamicin (Mylotarg™), inotuzumab ozogamicin (Besponsa®), brentuximab vedotin (Adcetris®), ado-trastuzumab emtansine (TDM-1; Kadcyla®), mirvetuximab soravtansine (IMGN853), or anetumab ravtansine In some embodiments, the immunotherapy includes blinatumomab (AMG103; Blincyto®) or midostaurin (Rydapt).

In some embodiments, the immunotherapy agent includes a toxin. In some embodiments, the immunotherapy is denileukin diftitox (Ontak®).

In some embodiments, the immunotherapy agent is a cytokine therapy. In some embodiments, the cytokine therapy is an interleukin 2 (IL-2) therapy, an interferon alpha (IFNα) therapy, a granulocyte colony stimulating factor (G-CSF) therapy, an interleukin 12 (IL-12) therapy, an interleukin 15 (IL-15) therapy, an interleukin 7 (IL-7) therapy or an erythropoietin-alpha (EPO) therapy. In some embodiments, the IL-2 therapy is aldesleukin (Proleukin®). In some embodiments, the IFNα therapy is IntronA® (Roferon-A®). In some embodiments, the G-CSF therapy is filgrastim (Neupogen®).

In some embodiments, the immunotherapy agent is an inhibitory nucleic acid-based immunotherapy agent (e.g., antisense oligonucleotides, small interfering RNAs (siRNAs), and short hairpin RNAs (shRNAs). In some embodiments, the inhibitory nucleic acid-based immunotherapy is CV9104 (see, e.g., Rausch et al. (2014) Human Vaccine Immunother. 10(11): 3146-52; and Kubler et al. (2015) J. Immunother. Cancer 3:26).

In some embodiments, the immunotherapy agent is bacillus Calmette-Guerin (BCG) therapy. In some embodiments, the immunotherapy agent is an oncolytic virus therapy. In some embodiments, the oncolytic virus therapy is talimogene alherparepvec (T-VEC; Imlygic®).

In some embodiments, the immunotherapy agent is a cancer vaccine. In some embodiments, the cancer vaccine is a human papillomavirus (HPV) vaccine. In some embodiments, the HPV vaccine is Gardasil®, Gardasil9@ or Cervarix®. In some embodiments, the cancer vaccine is a hepatitis B virus (HBV) vaccine. In some embodiments, the HBV vaccine is Engerix-B®, Recombivax HB® or GI-13020 (Tarmogen®). In some embodiments, the cancer vaccine is Twinrix® or Pediarix®. In some embodiments, the cancer vaccine is BiovaxID®, Oncophage®, GVAX, ADXS11-001, ALVAC-CEA, PROSTVAC®, Rindopepimut®, CimaVax-EGF, lapuleucel-T (APC8024; Neuvenge™), GRNVAC1, GRNVAC2, GRN-1201, hepcortespenlisimut-L (Hepko-V5), DCVAX®, SCIB1, BMT CTN 1401, PrCa VBIR, PANVAC, ProstAtak®, DPX-Survivac, or viagenpumatucel-L (HS-110).

In some embodiments, the immunotherapy agent is a peptide vaccine. In some embodiments, the peptide vaccine is nelipepimut-S (E75) (NeuVax™), IMA901, or SurVaxM (SVN53-67). In some embodiments, the cancer vaccine is an immunogenic personal neoantigen vaccine (see, e.g., Ott et al. (2017) Nature 547: 217-221; Sahin et al. (2017) Nature 547: 222-226). In some embodiments, the cancer vaccine is RGSH4K or NEO-PV-01. In some embodiments, the cancer vaccine is a DNA-based vaccine. In some embodiments, the DNA-based vaccine is a mammaglobin-A DNA vaccine (see, e.g., Kim et al. (2016) OncoImmunology 5(2): e1069940).

In some embodiments, immune-targeted agents are selected from aldesleukin, interferon alfa-2b, ipilimumab, lambrolizumab, nivolumab, prednisone, and sipuleucel-T.

Suitable antiviral agents contemplated for use in combination with a compound of Formula I or a pharmaceutically acceptable salt thereof can comprise nucleoside and nucleotide reverse transcriptase inhibitors (RTIs), non-nucleoside reverse transcriptase inhibitors (NRTIs), protease inhibitors, and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(-)—FTC]; beta-L-FD4 (also called beta-L-D4C and named beta-L-2', 3'-dicleoxy-5-fluoro-cytidene); DAPD, ((-)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside, and Yissum Project No. 11607.

Compounds of Formula I and pharmaceutically acceptable salts thereof can be used in combination with one or more other kinase inhibitors for the treatment of diseases, such as cancer, that are impacted by one or more signaling pathways.

In certain embodiments, the patient to be treated with a combination therapy described herein has not been treated with an additional anticancer agent prior to the administration the combination therapy. In certain embodiments, the patient to be treated with a combination therapy described herein has been treated with at least one additional anticancer agent prior to administration of a compound of Formula I for use alone or in a combination therapy described herein. In certain embodiments, the patient to be treated with a compound of Formula I as monotherapy or in a combination therapy described herein has developed drug resistance to, or has a cancer that is refractory to, at least one additional anticancer agent.

In one embodiment, compounds of Formula I and pharmaceutically acceptable salts thereof can be combined with one or more inhibitors of the following kinases for the treatment of cancer: PIM (PIM 1, PIM 2, PIM 3), IDO, AKT 1, AKT2 and AKT3, TGFR, PKA, PKG, PKC, CaM-kinase, phosphorylase kinase, MEKK, ERK, MAPK, mTOR, EGFR, HER2, HER3, HER4, INS-R, IGF-1R, IR-R, PDG-FaR, PDGF R, CSFIR, KIT, FLK-II, KDR/FLK-1, FLK-4, fit-1, FGFR, FGFR1, FGFR2, FGFR3, FGFR4, c-MET, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, FAK, SYK, FRK, JAK, ABL, ALK, and B-Raf.

Compounds of Formula I and pharmaceutically acceptable salts thereof can also be used in combination with one or more additional anticancer agents, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate.

In some embodiments, signal transduction pathway inhibitors include kinase inhibitors of the Ras-Raf-MEK-ERK pathway (e.g., binimetinib, selumetinib, encorafinib, sorafenib, trametinib, and vemurafenib), kinase inhibitors of the PI3K-AKT-mTOR-S6K pathway (e.g. everolimus, rapamycin, perifosine, temsirolimus), and other kinase inhibitors, such as baricitinib, brigatinib, capmatinib, danusertib, ibrutinib, milciclib, quercetin, regorafenib, ruxolitinib, semaxanib, ((R)-amino-N-[5,6-dihydro-2-(1-methyl-1H-pyrazol-4-yl)-6-oxo-1H-pyrrolo[4,3,2-ef][2,3]benzodiazepin-8-yl]-cyclohexaneacetamide), and TG101209 (N-tert-butyl-3-(5-methyl-2-(4-(4-methylpiperazin-1-yl)phenylamino)pyrimidin-4-ylamino)benzenesulfonamide).

Angiogenesis inhibitors may be efficacious in some tumors in combination with compounds of Formula I or pharmaceutically acceptable salts thereof. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib.

Non-limiting examples of radiotherapy include radioiodide therapy, external-beam radiation, and radium 223 therapy.

Non-limiting examples of surgery include, e.g., open surgery or minimally invasive surgery. Surgery can include, e.g., removing an entire tumor, debulking of a tumor, or removing a tumor that is causing pain or pressure in the subject. Methods for performing open surgery and minimally invasive surgery on a subject having a cancer are known in the art.

Accordingly, also provided herein is a method of treating cancer, comprising administering to a patient in need thereof a pharmaceutical combination for treating cancer which comprises (a) a compound of Formula I or a pharmaceutically acceptable salt thereof, and (b) an additional anticancer agent, for simultaneous, separate or sequential use for the treatment of cancer, wherein the amounts of the compound of Formula I or a pharmaceutically acceptable salt thereof and the additional anticancer agent are together effective in treating the cancer.

Also provided herein is a method of treating cancer, comprising administering to a patient in need thereof a pharmaceutical combination for treating cancer which comprises (a) a compound of Formula I or a pharmaceutically acceptable salt thereof, and (b) an additional anticancer therapy, wherein the therapy is selected from radiation therapy and surgery. In one embodiment, the additional anticancer therapy is radiation therapy. In one embodiment, the additional anticancer therapy is surgery.

In some embodiments, the additional anticancer agent(s) includes any one of the above listed therapies or therapeutic agents which are standards of care in cancers wherein the cancer is a TAM-associated cancer. In one embodiment, the compound of Formula I the additional anticancer agent is an immunotherapy agent. In one embodiment, the immunotherapy agent is a CTLA-4 inhibitor (e.g., an anti-CTLA-4 antibody), a PD-1 inhibitor (e.g., an anti-PD-1 monoclonal antibody) or a PD-L1 inhibitor (e.g., an anti-PD-L1 monoclonal antibody).

In one embodiment, provided herein is a method for treating cancer, comprising administering a compound of Formula I in combination with an immune checkpoint inhibitor. In some embodiments, the immunotherapy includes one or more immune checkpoint inhibitors. In some embodiments, the immune checkpoint inhibitor is a CTLA-4 inhibitor (e.g., an anti-CTLA-4 antibody), a PD-1 inhibitor (e.g., an anti-PD-1 monoclonal antibody) or a PD-L1 inhibitor (e.g., an anti-PD-L1 monoclonal antibody). In some embodiments, the CTLA-4 inhibitor is ipilimumab (Yervoy®) or tremelimumab (CP-675,206). In some embodiments, the PD-1 inhibitor is pembrolizumab (Keytruda®) or nivolumab (Opdivo®), or pidilizumab. In some embodiments, the anti-PD-1 monoclonal antibody is nivolumab or pembrolizumab. In some embodiments, the anti-PD1 antibody is pembrolizumab. In some embodiments, the PD-L1 inhibitor is atezolizumab (Tecentriq®), avelumab (Bavencio®), durvalumab (Imfinzi™). In some embodiments, the PD-L1 inhibitor is atezolizumab (Tecentriq®), avelumab (Bavencio®) or durvalumab (Imfinzi™) In one embodiment, the compound of Formula I is selected from i) Example No. 1-20; ii) Example No. 21-40; iii) Example No. 41-60; iv) Example No. 61-80; v) Example No. 81-100; vi) Example No. 101-120; vii) Example No. 121-140; viii) Example No. 141-160; ix) Example No. 161-180; x) Example No. 181-200; xi) Example No. 201-220; xii) Example No. 221-240; xiii) Example No. 241-260; xiv) Example No. 261-280; xv) Example No. 281-300; xvi)

Example No. 301-320; xvii) Example No. 321-340; xviii) Example No. 341-360; xix) Example No. 361-380; xx) Example No. 381-400; xxi) Example No. 401-420; xxii) Example No. 421-440; xxiii) Example No. 441-460; xxiii) Example No. 461-471A; xxiv) Example No. 471B-480; 481-490; xxv) Example Nos. 491-500; or xxvi) Example Nos. 501-510. In some embodiments, provided herein is a method for treating cancer, comprising administering to a patient in need thereof a compound of Formula I in combination with an immune checkpoint inhibitor, wherein the patient is further treated with ionizing radiation. In one embodiment, the cancer overexpresses AXL. In one embodiment, the cancer does not have a B-RAF mutation. In one embodiment, the cancer has a B-RAF mutation. In one embodiment, the cancer has a RAS mutation. In one embodiment, the cancer has a EGFR mutation. In one embodiment, the cancer overexpresses MER. In one embodiment, the cancer is lung cancer. In one embodiment, the cancer is non-small cell lung carcinoma (NSCLC). In one embodiment, the cancer is colon cancer. In one embodiment, the cancer is prostate cancer. In one embodiment, the cancer is melanoma. In one embodiment, the cancer is Acute Lymphoblastic Leukemia (ALL). In one embodiment, the cancer is Acute Myeloid Leukemia (AML).

Combination therapies as described herein may be administered without restriction on the order in which therapies are administered to a patient with a disease or disorder described herein. Thus, in one embodiment, a compound of Formula I or pharmaceutically acceptable salt thereof can be administered prior to (e.g., 5 minutes, 15 minutes, 30 minutes, 45 minutes, 1 hour, 2 hours, 4 hours, 6 hours, 12 hours, 24 hours, 36 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 36 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent (e.g., any of the additional anticancer agents described herein) to the subject. In another embodiment, a compound of Formula I or pharmaceutically acceptable salt thereof can be administered prior to (e.g., 5 minutes, 15 minutes, 30 minutes, 45 minutes, 1 hour, 2 hours, 4 hours, 6 hours, 12 hours, 24 hours, 36 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 36 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent (e.g., any of the anticancer agents described herein).

In one embodiment, provided herein is a method for treating cancer, comprising sensitizing said cancer to an anti-mitotic drug by administration of a compound of Formula I. In one embodiment, the anti-mitotic drug is a taxane-based chemotherapeutic, such as docetaxel.

In one embodiment, compounds of Formula I may be used in combination with other agents to treat patients who have primary or acquired resistance to at least one additional anticancer agent.

In one embodiment of methods disclosed herein for treating cancer, compounds of Formula I may be used as monotherapy to treat patients who have developed primary or acquired resistance to at least one additional anticancer agent.

In one embodiment, compounds of Formula I may be used to overcome resistance to at least one additional anticancer agent in a cancer. In one embodiment, a compound of Formula I is used in combination with the at least one additional anticancer agent to which the cancer has developed resistance.

In one embodiment, compounds of Formula I may be used to delay resistance to at least one additional anticancer agent. In one embodiment, a compound of Formula I is used in combination with the at least one additional anticancer agent.

As used herein, the term "resistance" refers to a clinical scenario where a cancer fails to respond to a targeted therapy or immunotherapy. For example, resistance of a cancer can be observed by, e.g., a decrease in the rate of increase of tumor burden in the subject, a lack of a decrease in the tumor burden in the subject, an increase in the dosage of a therapeutic agent over time required to achieve the same therapeutic effect in a patient, and the requirement of co-administration of an additional anticancer agent to achieve the same therapeutic effect as the previous administration of the therapeutic agent as a monotherapy.

As used herein, the term "primary resistance", also known as intrinsic resistance, refers to a clinical scenario where a cancer fails to respond to a targeted therapy or immunotherapy, that is, the cancer is resistant to a therapy without having been previously exposed to the therapy.

As used herein, the term "acquired resistance" refers to a clinical scenario in which a cancer initially responded to a targeted therapy or immunotherapy but after a period of time the cancer stops responding to the treatment (e.g., the cancer relapses and progresses).

In one embodiment of methods disclosed herein for treating cancer, compounds of Formula I may be used as monotherapy to treat patients who have developed primary or acquired resistance to at least one additional anticancer agent.

In one embodiment of methods disclosed herein for treating cancer, compounds of Formula I may be used as in combination with at least one additional anticancer agent to treat patients who have developed primary or acquired resistance to one or more of the at least one additional anticancer agent (e.g., a targeted therapeutic agent).

Targeted therapeutic agents include inhibitors or antibodies against EGFR, HER2, VEGFR, c-Met, Ret, IGFR1, PDGFR, FGFR1, FGFR2, FGFR3, FGFR4, TrkA, TrkB, TrkC, ROS, c-Kit, or Flt-3 and against cancer-associated fusion protein kinases such as Bcr-Abl and EML4-Alk. Inhibitors against EGFR include gefitinib and erlotinib, and inhibitors against EGFR/Her2 include but are not limited to dacomitinib, afatinib, lapitinib and neratinib. Antibodies against the EGFR include but are not limited to cetuximab, panitumumab and necitumumab. Inhibitors of c-Met may be used in combination with compounds of Formula I of pharmaceutically acceptable salts thereof c-MET inhibitors include onartumzumab, tivantnib, and INC-280. Inhibitors against FGFRs include but not limited to AZD4547, BAY1187982, ARQ087, BGJ398, BIBF1120, TKI258, lucitanib, dovitinib, TAS-120, JNJ-42756493, and Debiol347. Inhibitors against Trks include but not limited to larotrectinib (LOXO-101), and entrectinib (RXDX-101). Inhibitors against Abl (or Bcr-Abl) include imatinib, dasatinib, nilotinib, and ponatinib and those against Alk (or EML4-ALK) include crizotinib.

In one embodiment, provided herein are methods of treating a patient having cancer who has been previously treated with a first kinase inhibitor, wherein the first kinase inhibitor is not a compound of Formula I, comprising administering to said patient a therapeutically effective amount of a compound of Formula I or a pharmaceutically acceptable salt thereof. In one embodiment, the patient is treated with a compound of Formula I as a single agent. In one embodiment, the patient is treated with a combination of a compound of Formula I and the previously administered first kinase inhibitor. In one embodiment, the patient is treated with a combination of a compound of Formula I and the previously administered first kinase inhibitor. In one embodiment, the compound of Formula I and the previously administered first kinase inhibitor are administered as separate dosages sequentially in any order. In one embodiment, the kinase inhibitor is an EGFR inhibitor. In one embodiment, the EGFR inhibitor is erlotinib or lapatinib. In one embodiment, the kinase inhibitor is a PI3Kα inhibitor. In one embodiment, the PI3Kα inhibitor is alpesib. In one embodiment, the kinase inhibitor is a MEK inhibitor. In one embodiment, the MEK inhibitor is binimetinib, U0126, or PD 325901. In one embodiment, the kinase inhibitor is an FGFR inhibitor. In one embodiment, the kinase inhibitor is an ALK inhibitor. In one embodiment, the kinase inhibitor is an IGFR1 inhibitor. In one embodiment, the cancer is breast cancer (e.g., triple negative breast cancer), head and neck cancer (e.g., squamous cell head and neck cancer), non-small cell lung cancer, colorectal cancer, esophageal squamous cell carcinoma, or melanoma.

In one embodiment, provided herein are methods of treating a patient having cancer who has been previously treated with an EGFR antibody, comprising administering to said patient a therapeutically effective amount of a compound of Formula I or a pharmaceutically acceptable salt thereof. In one embodiment, the patient is treated with a compound of Formula I as a single agent. In one embodiment, the patient is treated with a combination of a compound of Formula I and the previously administered EGFR antibody. In one embodiment, the compound of Formula I and the previously administered EGFR antibody are administered as separate dosages sequentially in any order. In one embodiment, the EGFR antibody is cetuximab. In one embodiment, In one embodiment, the cancer is breast cancer, head and neck cancer, or non-small cell lung cancer In one embodiment, provided herein are methods of treating a patient having cancer who has been previously treated with a first kinase inhibitor, wherein the first kinase inhibitor is not a compound of Formula I, comprising (a) determining that said cancer overexpresses a TAM kinase (e.g., as compared to a non-cancerous tissue or a cell in the patient or a different subject), and (b) after (a), administering to said patient a therapeutically effective amount of a compound of Formula I or a pharmaceutically acceptable salt thereof. In one embodiment, the step of determining if the cancer overexpresses a TAM kinase includes a step of performing an assay on a sample obtained from the patient to determine whether the patient has abnormal (e.g., increased) expression and/or activity of one or more of the TAM kinases (e.g., as compared to a non-cancerous tissue or cell in the patient or a different subject), e.g., AXL and/or MER and/or TYRO3. In one embodiment, the cancer that was previously treated with the first kinase inhibitor overexpresses AXL. In one embodiment, the cancer that was previously treated with the first kinase inhibitor overexpresses MER. In one embodiment, the method further comprises obtaining a sample from the patient. In one embodiment, the sample is a biopsy sample. In one embodiment, the assay is selected from the group consisting of sequencing, immunohistochemistry, enzyme-linked immunosorbent assay, and fluorescence in situ hybridization (FISH). In one embodiment, the first kinase inhibitor is an EGFR inhibitor. In one embodiment, the EGFR inhibitor is erlotinib or lapatinib. In one embodiment, the first kinase inhibitor is a PI3Kα inhibitor. In one embodiment, the PI3Kα inhibitor is alpesib. In one embodiment, the first kinase inhibitor is a MEK inhibitor. In one embodiment, the MEK inhibitor is binimetinib, U0126, or PD 325901. In one embodiment, the first kinase inhibitor is an FGFR inhibitor. In one embodiment, the first kinase inhibitor is an ALK inhibitor. In one embodiment, the first kinase inhibitor is an IGFR1 inhibitor. In one embodiment, the cancer is breast cancer (e.g., triple negative breast cancer), head and neck cancer (e.g., squamous cell head and neck cancer), non-small cell lung cancer, colorectal cancer, esophageal squamous cell carcinoma, or melanoma. In one embodiment, the patient is treated with a compound of Formula I as a single agent. In one embodiment, the patient is treated with a combination of a compound of Formula I and the first kinase inhibitor. In one embodiment, the compound of Formula I and the previously prescribed kinase inhibitor are administered as separate dosages sequentially in any order.

In one embodiment, provided herein is a method of treating a subject having cancer, wherein the method comprises (a) determining that a cancer cell in a sample obtained from a subject having a cancer and previously administered one or more doses of a first kinase inhibitor, wherein the first kinase inhibitor is not a compound of Formula I, overexpresses one or more TAM kinases (e.g., as compared to a non-cancerous tissue or cell in the subject or a different subject); and (b) administering a compound of Formula I or a pharmaceutically acceptable salt or solvate thereof as a monotherapy or in conjunction with the previously administered first kinase inhibitor to the subject. In one embodiment, the cancer that was previously treated with the first kinase inhibitor overexpresses AXL. In one embodiment, the cancer that was previously treated with the first kinase inhibitor overexpresses MER. In one embodiment, the first kinase inhibitor is an EGFR inhibitor. In one embodiment, the EGFR inhibitor is erlotinib or lapatinib. In one embodiment, the first kinase inhibitor is a PI3Kα inhibitor. In one embodiment, the PI3Kα inhibitor is alpesib. In one embodiment, the first kinase inhibitor is a MEK inhibitor. In one embodiment, the MEK inhibitor is binimetinib, U0126, or PD 325901. In one embodiment, the first kinase inhibitor is an FGFR inhibitor. In one embodiment, the first kinase inhibitor is an ALK inhibitor. In one embodiment, the first kinase inhibitor is an IGFR1 inhibitor. In one embodiment, the cancer is breast cancer (e.g., triple negative breast cancer), head and neck cancer (e.g., squamous cell head and neck cancer), non-small cell lung cancer, colorectal cancer, esophageal squamous cell carcinoma, or melanoma. In one embodiment, the patient is treated with a compound of Formula I as a single agent. In one embodiment, the patient is treated with a combination of a compound of Formula I and the first kinase inhibitor. In one embodiment, the compound of Formula I and the previously prescribed kinase inhibitor are administered as separate dosages sequentially in any order.

In one embodiment of methods disclosed herein for treating cancer, compounds of Formula I may be used as monotherapy to treat patients who have developed primary or acquired resistance to chemotherapy.

In one embodiment of methods disclosed herein for treating cancer, compounds of Formula I may be used as in combination with a chemotherapeutic agent to treat patients who have developed primary or acquired resistance to the chemotherapeutic agent.

In one embodiment, provided herein are methods of treating a patient having cancer who has been previously treated with a chemotherapeutic, comprising administering to said patient a therapeutically effective amount of a compound of Formula I or a pharmaceutically acceptable salt thereof. In one embodiment, the patient is treated with a compound of Formula I as a single agent. In one embodiment, the patient is treated with a combination of a compound of Formula I and the previously administered chemotherapeutic. In one embodiment, the chemotherapeutic is selected from taxane-based chemotherapies (e.g., docetaxol), dexamethasone, and cytarabine. In one embodiment, the patient is treated with a compound of Formula I as a single agent. In one embodiment, the patient is treated with a compound of Formula I in combination with the previously administered chemotherapeutic. In one embodiment, the compound of Formula I and the previously administered chemotherapeutic are administered as separate dosages sequentially in any order. In one embodiment, the cancer is selected from leukemias (including acute myeloid leukemia and chronic myeloid leukemia, B-cell acute lymphoblastic leukemia, and T-lineage acute lymphoblastic leukemia), non-small cell lung cancer, pancreatic ductal adenocarcinoma, astrocytoma, lung adenocarcinoma, ovarian cancer, melanoma, and gloibalstoma multiforme.

In one embodiment, provided herein are methods of treating a patient having cancer who has been previously treated with a chemotherapeutic, comprising (a) determining that said cancer overexpresses a TAM kinase (e.g., as compared to a non-cancerous tissue or cell in the patient or a different subject), and (b) after (a), administering to said patient a therapeutically effective amount of a compound of Formula I or a pharmaceutically acceptable salt thereof. In one embodiment, the step of determining if the cancer overexpresses a TAM kinase includes a step of performing an assay on a sample obtained from the patient to determine whether the patient has abnormal expression and/or activity of one or more of the TAM kinases, e.g., AXL and/or MER and/or TYRO3. In one embodiment, the method further comprises obtaining a sample from the patient. In one embodiment, the sample is a biopsy sample. In one embodiment, the assay is selected from the group consisting of sequencing, immunohistochemistry, enzyme-linked immunosorbent assay, and fluorescence in situ hybridization (FISH). In one embodiment, the patient is treated with a compound of Formula I as a single agent. In one embodiment, the patient is treated with a combination of a compound of Formula I and the previously administered chemotherapeutic. In one embodiment, the chemotherapeutic is selected from taxane-based chemotherapies (e.g., docetaxol), dexamethasone, and cytarabine. In one embodiment, the patient is treated with a compound of Formula I as a single agent. In one embodiment, the patient is treated with a compound of Formula I in combination with the previously administered chemotherapeutic. In one embodiment, the compound of Formula I and the previously administered chemotherapeutic are administered as separate dosages sequentially in any order. In one embodiment, the cancer is selected from leukemias (including acute myeloid leukemia and chronic myeloid leukemia, B-cell acute lymphoblastic leukemia, and T-lineage acute lymphoblastic leukemia), non-small cell lung cancer, pancreatic ductal adenocarcinoma, astrocytoma, lung adenocarcinoma, ovarian cancer, melanoma, and gloibalstoma multiforme.

In one embodiment, provided herein is a method of treating a subject having cancer, wherein the method comprises (a) determining that a cancer cell in a sample obtained from a subject having a cancer and previously administered one or more doses of a chemotherapeutic, overexpresses one or more TAM kinases (e.g., as compared to a non-cancerous tissue or cell in the subject or a different subject); and (b) administering a compound of Formula I or a pharmaceutically acceptable salt or solvate thereof as a monotherapy or in conjunction with the previously administered chemotherapeutic or a different chemotherapeutic. In one embodiment, the cancer that was previously treated with the chemotherapeutic overexpresses AXL. In one embodiment, the cancer that was previously treated with the chemotherapeutic overexpresses MER. In one embodiment, the patient is treated with a compound of Formula I as a single agent. In one embodiment, the patient is treated with a combination of a compound of Formula I and the previously administered chemotherapeutic. In one embodiment, the chemotherapeutic is selected from taxane-based chemotherapies (e.g., docetaxol), dexamethasone, and cytarabine. In one embodiment, the patient is treated with a compound of Formula I as a single agent. In one embodiment, the patient is treated with a compound of Formula I in combination with the previously administered chemotherapeutic. In one embodiment, the compound of Formula I and the previously administered chemotherapeutic are administered as separate dosages sequentially in any order. In one embodiment, the cancer is selected from leukemias (including acute myeloid leukemia and chronic myeloid leukemia, B-cell acute lymphoblastic leukemia, and T-lineage acute lymphoblastic leukemia), non-small cell lung cancer, pancreatic ductal adenocarcinoma, astrocytoma, lung adenocarcinoma, ovarian cancer, melanoma, and gloibalstoma multiforme.

Also provided herein is (i) a pharmaceutical combination for treating a cancer in a patient in need thereof, which comprises (a) a compound of Formula I or a pharmaceutically acceptable salt thereof, and (b) at least one additional anticancer agent (e.g., any of the exemplary additional anticancer agents described herein or known in the art), for simultaneous, separate or sequential use for the treatment of cancer, wherein the amounts of the compound of Formula I or pharmaceutically acceptable salt thereof and of the additional anticancer agent are together effective in treating the cancer; (ii) a pharmaceutical composition comprising such a combination; (iii) the use of such a combination for the preparation of a medicament for the treatment of cancer; and (iv) a commercial package or product comprising such a combination as a combined preparation for simultaneous, separate or sequential use; and to a method of treatment of cancer in a patient in need thereof. In one embodiment the patient is a human. In some embodiments, the cancer is a TAM-associated cancer.

The term "pharmaceutical combination", as used herein, refers to a pharmaceutical therapy resulting from the mixing or combining of more than one active ingredient and includes both fixed and non-fixed combinations of the active ingredients. The term "fixed combination" means that a compound of Formula I or a pharmaceutically acceptable salt thereof and at least one additional anticancer agent (e.g., a chemotherapeutic agent), are both administered to a patient simultaneously in the form of a single composition or dosage. The term "non-fixed combination" means that a compound of Formula I or a pharmaceutically acceptable salt thereof and at least one additional anticancer agent (e.g., chemotherapeutic agent) are formulated as separate compositions or dosages such that they may be administered to a patient in need thereof simultaneously, separately or sequentially with variable intervening time limits, wherein such administration provides effective levels of the two or more compounds in the body of the patient. These also apply to cocktail therapies, e.g. the administration of three or more active ingredients Accordingly, also provided herein is a method of treating a cancer, comprising administering to a patient in need thereof a pharmaceutical combination for treating cancer which comprises (a) a compound of Formula I or pharmaceutically acceptable salt thereof, and (b) an additional anticancer agent for simultaneous, separate or sequential use for the treatment of cancer, wherein the amounts of the compound of Formula I or pharmaceutically acceptable salt thereof and the additional anticancer agent are together effective in treating the cancer. In one embodiment, the compound of Formula I or pharmaceutically acceptable salt thereof, and the additional anticancer agent are administered simultaneously as separate dosages. In one embodiment, the compound of Formula I or pharmaceutically acceptable salt thereof, and the additional anticancer agent are administered as separate dosages sequentially in any order, in jointly therapeutically effective amounts, e.g. in daily or intermittently dosages. In one embodiment, the compound of Formula I or pharmaceutically acceptable salt thereof, and the additional anticancer agent are administered simultaneously as a combined dosage.

Accordingly, also provided herein are methods for inhibiting, preventing, aiding in the prevention, or decreasing the symptoms of metastasis of a cancer in a patient in need thereof, the method comprising administering to the patient a therapeutically effective amount of a compound of Formula I or a pharmaceutically acceptable salt thereof or a pharmaceutical composition thereof. Such methods can be used in the treatment of one or more of the cancers described herein. In some embodiments, the cancer is a TAM-associated cancer. In some embodiments, the compound of Formula I or a pharmaceutically acceptable salt thereof is used in combination with an additional anticancer agent, including an immunotherapy.

The term "metastasis" is an art known term and means the formation of an additional tumor (e.g., a solid tumor) at a site distant from a primary tumor in a subject or patient, where the additional tumor includes the same or similar cancer cells as the primary tumor.

Also provided are methods of decreasing the risk of developing a metastasis or an additional metastasis in a patient having a TAM-associated cancer that include: selecting, identifying, or diagnosing a patient as having a TAM-associated cancer, and administering a therapeutically effective amount of a compound of Formula I or a pharmaceutically acceptable salt thereof to the patient selected, identified, or diagnosed as having a TAM-associated cancer. Also provided are methods of decreasing the risk of developing a metastasis or an additional metastasis in a patient having a TAM-associated cancer that includes administering a therapeutically effective amount of a compound of Formula I or a pharmaceutically acceptable salt or solvent thereof to a patient having a TAM-associated cancer. The decrease in the risk of developing a metastasis or an additional metastasis in a patient having a TAM-associated cancer can be compared to the risk of developing a metastasis or an additional metastasis in the patient prior to treatment, or as compared to a patient or a population of patients having a similar or the same TAM-associated cancer that has received no treatment or a different treatment.

The phrase "risk of developing a metastasis" means the risk that a subject or patient having a primary tumor will develop an additional tumor (e.g., a solid tumor) at a site distant from a primary tumor in a subject or patient over a set period of time, where the additional tumor includes the same or similar cancer cells as the primary tumor. Methods for reducing the risk of developing a metastasis in a subject or patient having a cancer are described herein.

The phrase "risk of developing additional metastases" means the risk that a subject or patient having a primary tumor and one or more additional tumors at sites distant from the primary tumor (where the one or more additional tumors include the same or similar cancer cells as the primary tumor) will develop one or more further tumors distant from the primary tumor, where the further tumors include the same or similar cancer cells as the primary tumor. Methods for reducing the risk of developing additional metastasis are described herein.

Also provided is a method for inhibiting TAM kinase activity in a cell (e.g., a mammalian cell), comprising contacting the cell with a compound of Formula I or a pharmaceutically acceptable salt thereof, or a pharmaceutical composition thereof. In one embodiment, the contacting is in vitro. In one embodiment, the contacting is in vivo. In one embodiment, the contacting is in vivo, wherein the method comprises administering an effective amount of a compound of Formula I or a pharmaceutically acceptable salt thereof to a subject having a cell having TAM kinase activity. In some embodiments, the cell is a cancer cell (e.g., a human cancer cell). In one embodiment, the cancer cell is any cancer as described herein. In some embodiments, the cancer cell is a TAM-associated cancer cell.

In some embodiments, the mammalian cell is in vitro. In some embodiments, the mammalian cell is in vivo. In some embodiments, the mammalian cell is ex vivo.

Also provided herein is a method of inhibiting cell proliferation, in vitro or in vivo, the method comprising contacting a cell with an effective amount of a compound of Formula I or a pharmaceutically acceptable salt thereof, or a pharmaceutical composition thereof as defined herein.

Also provided herein are methods of decreasing immune tolerance in a subject in need thereof that include administering to the subject a therapeutically effective amount of a compound of Formula I or a pharmaceutically acceptable salt thereof, or a pharmaceutical composition thereof as defined herein. As used herein, the term "immune tolerance" refers to a decrease (e.g., a 1% to about 99% decrease, or any of the subranges of this range described herein) in one or more of: the processing of tumor-associated antigens by antigen-presenting cells (e.g., dendritic cells), presentation of antigens to tumor antigen-specific T cells, activation and proliferation of tumor antigen-specific T cells, and maintenance of the T-cell response in a subject (e.g., in a solid tumor in a subject), e.g., as compared to a control (e.g., a corresponding level in a similar subject that does not have a cancer)). In some embodiments of these methods, the subject has been identified or diagnosed as having a cancer (e.g., a TAM-associated cancer (e.g., any of the exemplary TAM-associated cancers described herein)). In some examples, a decrease in immune tolerance in a subject can be detected by observing an about 1% to about 99% (e.g., about 1% to about 95%, about 1% to about 90%, about 1% to about 85%, about 1% to about 80%, about 1% to about 75%, about 1% to about 70%, about 1% to about 65%, about 1% to about 60%, about 1% to about 55%, about 1% to about 50%, about 1% to about 45%, about 1% to about 40%, about 1% to about 35%, about 1% to about 30%, about 1% to about 25%, about 1% to about 20%, about 1% to about 15%, about 1% to about 10%, about 1% to about 5%, about 5% to about 99%, about 5% to about 90%, about 5% to about 85%, about 5% to about 80%, about 5% to about 75%, about 5% to about 70%, about 5% to about 65%, about 5% to about 60%, about 5% to about 55%, about 5% to about 50%, about 5% to about 45%, about 5% to about 40%, about 5% to about 35%, about 5% to about 30%, about 5% to about 25%, about 5% to about 20%, about 5% to about 10%, about 10% to about 99%, about 10% to about 95%, about 10% to about 90%, about 10% to about 85%, about 10% to about 80%, about 10% to about 75%, about 10% to about 70%, about 10% to about 65%, about 10% to about 60%, about 10% to about 55%, about 10% to about 50%, about 10% to about 45%, about 10% to about 40%, about 10% to about 35%, about 10% to about 30%, about 10% to about 25%, about 10% to about 20%, about 10% to about 15%, about 15% to about 99%, about 15% to about 95%, about 15% to about 90%, about 15% to about 85%, about 15% to about 80%, about 15% to about 75%, about 15% to about 70%, about 15% to about 65%, about 15% to about 60%, about 15% to about 55%, about 15% to about 50%, about 15% to about 45%, about 15% to about 40%, about 15% to about 35%, about 15% to about 30%, about 15% to about 25%, about 15% to about 20%, about 20% to about 99%, about 20% to about 95%, about 20% to about 90%, about 20% to about 85%, about 20% to about 80%, about 20% to about 75%, about 20% to about 70%, about 20% to about 65%, about 20% to about 60%, about 20% to about 55%, about 20% to about 50%, about 20% to about 45%, about 20% to about 40%, about 20% to about 35%, about 20% to about 30%, about 20% to about 25%, about 25% to about 99%, about 25% to about 95%, about 25% to about 90%, about 25% to about 85%, about 25% to about 80%, about 25% to about 75%, about 25% to about 70%, about 25% to about 65%, about 25% to about 60%, about 25% to about 55%, about 25% to about 50%, about 25% to about 45%, about 25% to about 40%, about 25% to about 35%, about 25% to about 30%, about 30% to about 99%, about 30% to about 95%, about 30% to about 90%, about 30% to about 85%, about 30% to about 80%, about 30% to about 75%, about 30% to about 70%, about 30% to about 65%, about 30% to about 60%, about 30% to about 55%, about 30% to about 50%, about 30% to about 45%, about 30% to about 40%, about 30% to about 35%, about 35% to about 99%, about 35% to about 95%, about 35% to about 90%, about 35% to about 85%, about 35% to about 80%, about 35% to about 75%, about 35% to about 70%, about 35% to about 65%, about 35% to about 60%, about 35% to about 55%, about 35% to about 50%, about 35% to about 45%, about 35% to about 40%, about 40% to about 99%, about 40% to about 95%, about 40% to about 90%, about 40% to about 85%, about 40% to about 80%, about 40% to about 75%, about 40% to about 70%, about 40% to about 65%, about 40% to about 60%, about 40% to about 55%, about 40% to about 50%, about 40% to about 45%, about 45% to about 99%, about 45% to about 95%, about 45% to about 90%, about 45% to about 85%, about 45% to about 80%, about 45% to about 75%, about 45% to about 70%, about 45% to about 65%, about 45% to about 60%, about 45% to about 55%, about 45% to about 50%, about 50% to about 99%, about 50% to about 95%, about 50% to about 90%, about 50% to about 85%, about 50% to about 80%, about 50% to about 75%, about 50% to about 70%, about 50% to about 65%, about 50% to about 60%, about 50% to about 55%, about 55% to about 99%, about 55% to about 95%, about 55% to about 90%, about 55% to about 85%, about 55% to about 80%, about 55% to about 75%, about 55% to about 70%, about 55% to about 65%, about 55% to about 60%, about 60% to about 99%, about 60% to about 95%, about 60% to about 90%, about 60% to about 85%, about 60% to about 80%, about 60% to about 75%, about 60% to about 70%, about 60% to about 65%, about 65% to about 99%, about 65% to about 95%, about 65% to about 90%, about 65% to about 85%, about 65% to about 80%, about 65% to about 75%, about 65% to about 70%, about 70% to about 99%, about 70% to about 95%, about 70% to about 90%, about 70% to about 85%, about 70% to about 80%, about 70% to about 75%, about 75% to about 99%, about 75% to about 95%, about 75% to about 90%, about 75% to about 85%, about 75% to about 80%, about 80% to about 99%, about 80% to about 95%, about 80% to about 90%, about 80% to about 85%, about 85% to about 99%, about 85% to about 95%, about 85% to about 90%, about 90% to about 99%, about 90% to about 95%, or about 95% to about 99%) decrease in the level of myeloid-derived suppressor cells (MDSCs) (e.g., cells characterized by expression of CD33, CD14, and low levels of HLA DR) in the subject (e.g., in a sample comprising blood or a biopsy sample obtained from the subject) (e.g., as compared to the level of MDSCs in the subject prior to administration of treatment (e.g., prior to administration of any of the compounds of Formula I or any of the pharmaceutical compositions described herein).

In some examples, a decrease in immune tolerance in a subject can be detected by observing an about 1% to about 99% (or any of the subranges of this range described herein) decrease in the level of Treg cells (e.g., cells characterized by expression of CD4, FOXP3, and CD25) in the subject (e.g., in a sample comprising blood or a biopsy sample obtained from the subject) (e.g., as compared to the level of Tregs in the subject prior to administration of treatment (e.g., prior to administration of any of the compounds of Formula I or any of the pharmaceutical compositions described herein).

In some examples, a decrease in immune tolerance in a subject can be detected by observing an about 1% to about 99% (or any of the subranges of this range described herein) decrease in the level of dendritic cells with reduced expression of CD80/CD86 in the subject (e.g., in a sample comprising blood or a biopsy sample obtained from the subject) (e.g., as compared to the level of dendritic cells with reduced expression of CD80/CD86 in the subject prior to administration of treatment (e.g., prior to administration of any of the compounds of Formula I or any of the pharmaceutical compositions described herein). Exemplary methods for detecting the levels of MDSCs, Tregs, and dendritic cells with reduced expression of CD80/CD86 include, fluorescence-assisted cell sorting and immunofluorescence microscopy.

Also provided herein are methods of inhibiting angiogenesis in a subject in need thereof, the method comprising administering to the subject a therapeutically effective amount of a compound of Formula I or a pharmaceutically acceptable salt thereof, or a pharmaceutical composition thereof as defined herein. In some embodiments, the angiogenesis is tumor angiogenesis and the subject has been identified or diagnosed as having a cancer (e.g., a TAM-associated cancer). In some embodiments, these methods result in a decrease (e.g., a 1% to about 99% decrease, or any of the subranges of this range described herein) in the rate of development of new blood vessels (e.g., as compared to the rate of development of new blood vessels in a similar subject administered a placebo or a different treatment over a similar period of time). Exemplary methods for detecting the formation of new blood vessels include Doppler ultrasound (e.g., Color Dopler Flow Imaging), Ultrasound-Guided Diffus Optical Tomography, MRI, perfusion CT (also called functional multi-detector row CT (f-MDCT)), positron emission tomography (PET), dynamic MRI, dynamic susceptibility contrast enhanced MRI (DSC-MRI), and T1-weighted dynamic MRI (DCE-MRI). Non-limiting methods that can be used to detect the formation of new blood vessels (angiogenesis) are described in Jeswani et al., *Cancer Imaging* 5(1):131-138, 2005.

Also provided herein are methods of suppressing (e.g., decreasing, e.g., a 1% to about 99% decrease, or any of the subranges of this range described herein) resistance to a therapeutic agent in a subject in need thereof that include administering to the subject a therapeutically effective amount of (i) a compound of Formula I or a pharmaceutically acceptable salt thereof, or any of the pharmaceutical compositions thereof described herein, and (ii) the therapeutic agent, where the therapeutic agent is selected from the group consisting of a chemotherapeutic agent, a PI-3 kinase inhibitor, an EGFR inhibitor, a HER2/neu inhibitor, an FGFR inhibitor, an ALK inhibitor, an IGF1R inhibitor, a VEGFR inhibitor, a PDGFR inhibitor, a glucocorticoid, a BRAF inhibitor, a MEK inhibitor, a HER4 inhibitor, a MET inhibitor, a RAF inhibitor, an Akt inhibitor, a FTL-3 inhibitor, and a MAP kinase pathway inhibitor. In some examples of these methods, the compound of Formula I or a pharmaceutically acceptable salt thereof, or a pharmaceutical composition thereof, and the therapeutic agent, are administered to the subject at substantially the same time. In some embodiments of these methods, the compound of Formula I or a pharmaceutically acceptable salt thereof, or a pharmaceutical composition thereof, and the therapeutic agent, are formulated in a single dosage form.

In some embodiments of these methods, the compound of Formula I or a pharmaceutically acceptable salt thereof, or a pharmaceutical composition thereof, is administered to the subject prior to administration of the therapeutic agent to the subject. In some embodiments of these methods, the therapeutic agent is administered to the subject prior to administration of the compound of Formula I or a pharmaceutically acceptable salt thereof, or a pharmaceutical composition thereof, to the subject.

As used herein, the term "resistance to a therapeutic agent" refers to a reduced or decreased level of sensitivity to treatment with a therapeutic agent (e.g., a chemotherapeutic agent, a PI-3 kinase inhibitor, an EGFR inhibitor, a HER2/neu inhibitor, an FGFR inhibitor, an ALK inhibitor, an IGF1R inhibitor, a VEGFR inhibitor, a PDGFR inhibitor, a glucocorticoid, a BRAF inhibitor, a MEK inhibitor, a HER4 inhibitor, a MET inhibitor, a RAF inhibitor, an Akt inhibitor, a FTL-3 inhibitor, and a MAP kinase pathway inhibitor) in a subject (e.g., as compared to a similar subject or as compared to the level of sensitivity to the therapeutic agent at an earlier time point). For example, resistance to an therapeutic agent in a subject can be observed by a physician, e.g., by observing the requirement of a increasing dosage amounts of a therapeutic agent over time in order to achieve the same therapeutic effect in a subject, observing the requirement for an increased number of doses and/or an increased frequency of doses of a therapeutic agent over time in order to achieve the same therapeutic effect in a subject, a decrease in the observed therapeutic response to treatment with the same dosage of a therapeutic agent over time, or an observed progression of disease or disease relapse in a subject administered a therapeutic agent.

When employed as pharmaceuticals, the compounds of Formula I can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Oral administration can include a dosage form formulated for once-daily or twice-daily (BID) administration. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. In one embodiment, a compound of Formula I is formulated as a tablet. In one embodiment, a compound of Formula I is formulated as a capsule. In one embodiment, a compound of Formula I is administered orally. In one embodiment, a compound of Formula I is administered orally once a day. In one embodiment, a compound of Formula I is administered orally twice a day.

Also provided herein are pharmaceutical compositions which contain, as the active ingredient, a compound of Formula I or a pharmaceutically acceptable salt thereof, in combination with one or more pharmaceutically acceptable carriers (excipients). In some embodiments, the composition is suitable for topical administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In one embodiment, the composition is formulated for oral administration. In one embodiment, the composition is formulated as a tablet or capsule.

The compositions comprising a compound of Formula I or a pharmaceutically acceptable salt thereof can be formulated in a unit dosage form, each dosage containing from about 5 to about 1,000 mg (1 g), more usually about 100 mg to about 500 mg, of the active ingredient. The term "unit dosage form" refers to physically discrete units suitable as unitary dosages for human subjects and other patients, each unit containing a predetermined quantity of active material (i.e., a compound for Formula I as provided herein) calculated to produce the desired therapeutic effect, in association with a suitable pharmaceutical excipient.

In some embodiments, the compositions provided herein contain from about 5 mg to about 50 mg of the active ingredient. One having ordinary skill in the art will appreciate that this embodies compounds or compositions containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient.

In some embodiments, the compositions provided herein contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient.

In some embodiments, the compositions provided herein contain from about 500 mg to about 1,000 mg of the active ingredient. One having ordinary skill in the art will appreciate that this embodies compounds or compositions containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of the active ingredient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

In some embodiments, the compounds provided herein can be administered in an amount ranging from about 1 mg/kg to about 100 mg/kg. In some embodiments, the compound provided herein can be administered in an amount of about 1 mg/kg to about 20 mg/kg, about 5 mg/kg to about 50 mg/kg, about 10 mg/kg to about 40 mg/kg, about 15 mg/kg to about 45 mg/kg, about 20 mg/kg to about 60 mg/kg, or about 40 mg/kg to about 70 mg/kg. For example, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg. In some embodiments, such administration can be once-daily or twice-daily (BID) administration.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

EXAMPLES

The following examples illustrate the invention.

Biological Examples

Example A

AXL Enzyme Assay

Compounds of Formula I were screened for their ability to inhibit AXL kinase using Invitrogen's LanthaScreen™ Eu Kinase Binding technology. His-tagged recombinant human AXL cytoplasmic domain was incubated with 20 nM Alexa-Fluor® Tracer 236 (PR9078A), 2 nM biotinylated anti-His (Cat. No. M4408), and 2 nM europium-labeled Streptavidin (Cat. No. PV5899) along with test compound in a buffer consisting of 25 mM HEPES, pH 7.4, 10 mM $MgCl_2$, 0.01% Triton X-100, and 2% DMSO. Compounds were typically prepared in a threefold serial dilution in DMSO and added to the assay to give the appropriate final concentration. After a 60-minute incubation at 22° C., the reaction was measured using a PerkinElmer EnVision multimode plate reader via TR-FRET dual wavelength detection, and the percent of control (POC) was calculated using a ratiometric emission factor. 100 POC was determined using no test compounds and 0 POC was determined using a concentration of control compound that completely inhibits the enzyme. The POC values are fit to a 4 parameter logistic curve and the $IC_{50}$ value is point where the curve crosses 50 POC.

Example B

MER Enzyme Assay

Compounds of Formula I were screened for their ability to inhibit MER kinase using Invitrogen's LanthaScreen™ Eu Kinase Binding technology. His-tagged recombinant human MER cytoplasmic domain (5 nM) was incubated with 20 nM Alexa-Fluor® Tracer 236 (PR9078A), 2 nM biotinylated anti-His (Cat. No. M4408), and 2 nM europium-labeled Streptavidin (Cat. No. PV5899) along with test compound in a buffer consisting of 25 mM HEPES, pH 7.4, 10 mM $MgCl_2$, 0.01% Triton X-100, and 2% DMSO. Compounds were typically prepared in a threefold serial dilution in DMSO and added to the assay to give the appropriate final concentration. After a 60-minute incubation at 22° C., the reaction was measured using a PerkinElmer EnVision multimode plate reader via TR-FRET dual wavelength detection, and the percent of control (POC) was calculated using a ratiometric emission factor. 100 POC was determined using no test compounds and 0 POC was determined using a concentration of control compound that completely inhibits the enzyme. The POC values are fit to a 4 parameter logistic curve and the $IC_{50}$ value is point where the curve crosses 50 POC.

Example C

TYRO3 Enzyme Assay

Compounds of Formula I were screened for their ability to inhibit TYRO3 kinase using Invitrogen's LanthaScreen™ Eu Kinase Binding technology. GST-tagged recombinant human TYRO3 kinase domain from Carna (5 nM; Cat. No. PR7480A) was incubated with 20 nM Alexa-Fluor® Tracer 236 (PR9078A) and 2 nM Europium-anti-GST (Cat. No. A15116) along with test compound in a buffer consisting of 25 mM HEPES, pH 7.4, 10 mM $MgCl_2$, 0.01% Triton X-100, and 2% DMSO. Compounds are typically prepared in a threefold serial dilution in DMSO and added to the assay to give the appropriate final concentration. After a 60-minute incubation at 22° C., the reaction was measured using a PerkinElmer EnVision multimode plate reader via TR-FRET dual wavelength detection, and the percent of control (POC) calculated using a ratiometric emission factor. 100 POC was determined using no test compounds and 0 POC was determined using a concentration of control compound that completely inhibits the enzyme. The POC values were fit to a 4 parameter logistic curve and the IC50 value is point where the curve crosses 50 POC.

The averaged $IC_{50}$'s of compounds tested in the assay of Examples A, B and C are shown in Table 1, where "A" represents compounds having an averaged $IC_{50}$ <10 nM, "B" represents compounds having an averaged $IC_{50}$ between ≥10 nM and 100 nM, "C" represents compounds having an averaged $IC_{50}$ between ≥100 nM and 1000 nM, and "D" represents compounds having an averaged $IC_{50}$ between ≥1000 nM and ≤10,000 nM.

TABLE 1

| Ex. | | AXL enzyme $IC_{50}$ | MER enzyme $IC_{50}$ | TYRO3 enzyme $IC_{50}$ |
|---|---|---|---|---|
| 1 | 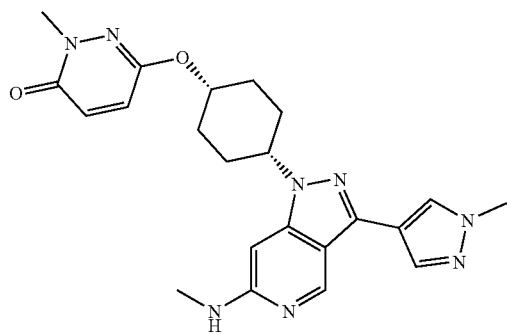 [SMILES: CNc1cc2c(cn1)c(-c1cnn(C)c1)nn2[C@H]1CC[C@@H](Oc2ccc(=O)n(C)n2)CC1] | B | B | C |
| 2 | 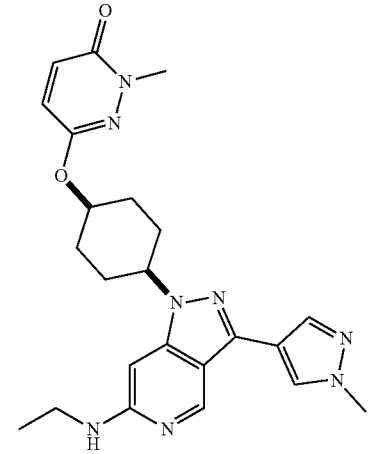 | C | B | C |
| 3 | 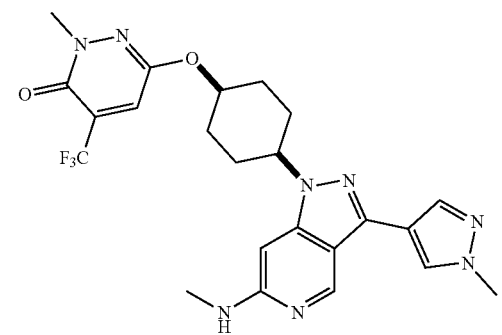 | B | B | C |

TABLE 1-continued

| Ex. | Structure | AXL enzyme IC$_{50}$ | MER enzyme IC$_{50}$ | TYRO3 enzyme IC$_{50}$ |
|---|---|---|---|---|
| 4 | | B | B | C |
| 5 | | B | B | B |
| 6 | | B | B | D |
| 7 | | B | B | C |

TABLE 1-continued
| Ex. | | AXL enzyme IC$_{50}$ | MER enzyme IC$_{50}$ | TYRO3 enzyme IC$_{50}$ |
|---|---|---|---|---|
| 8 | 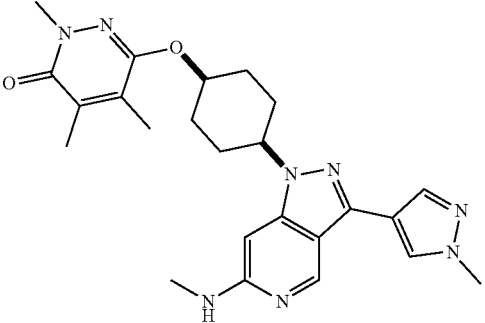 | B | B | D |
| 9 | 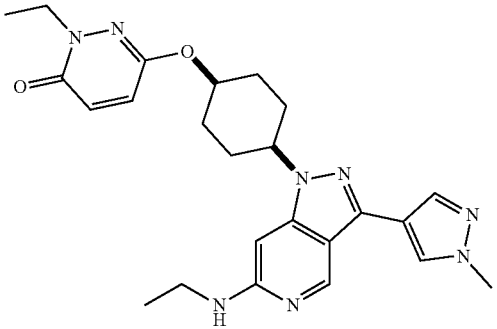 | C | C | C |
| 10 | 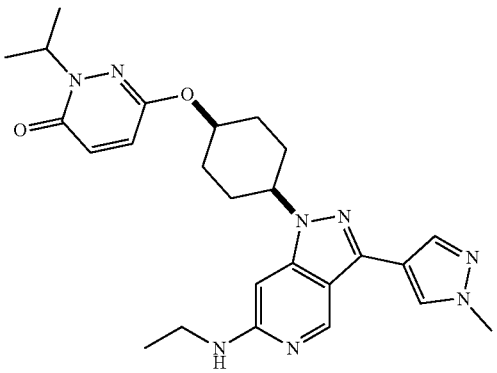 | C | B | C |
| 11 | 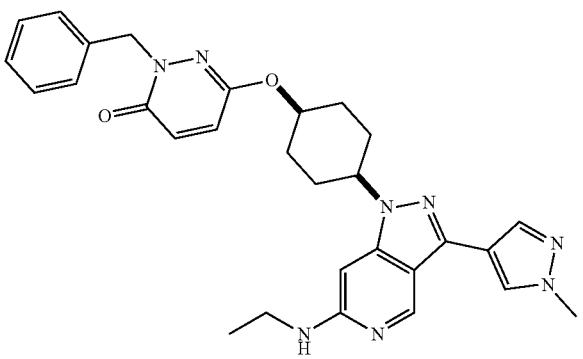 | C | B | C |

TABLE 1-continued
| Ex. | | AXL enzyme IC$_{50}$ | MER enzyme IC$_{50}$ | TYRO3 enzyme IC$_{50}$ |
|---|---|---|---|---|
| 12 | 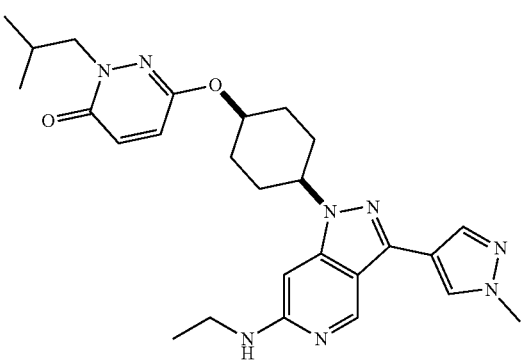 | C | C | C |
| 13 | 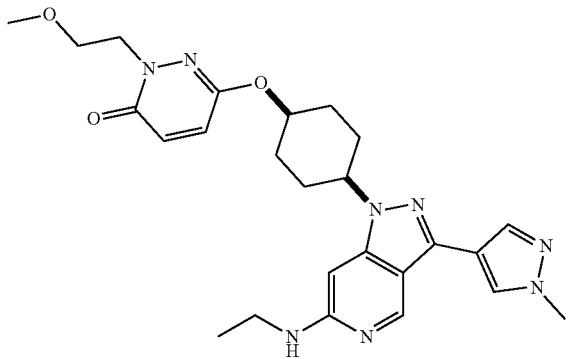 | C | C | D |
| 14 | 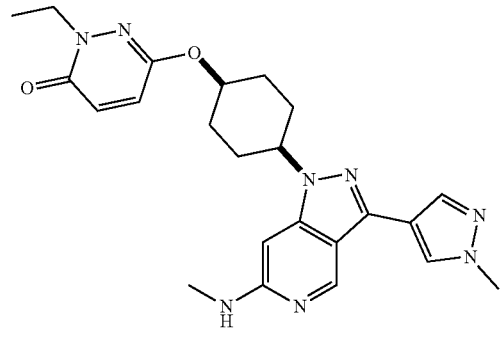 | B | B | D |
| 15 | 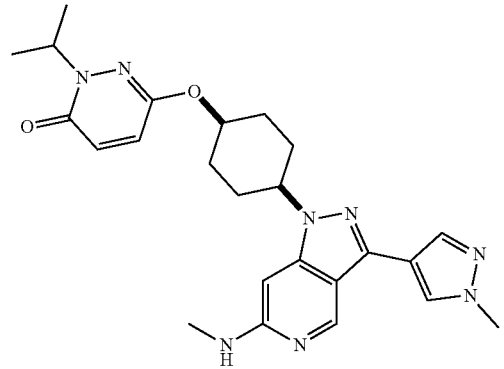 | B | B | C |

TABLE 1-continued
| Ex. | | AXL enzyme IC$_{50}$ | MER enzyme IC$_{50}$ | TYRO3 enzyme IC$_{50}$ |
|---|---|---|---|---|
| 16 | 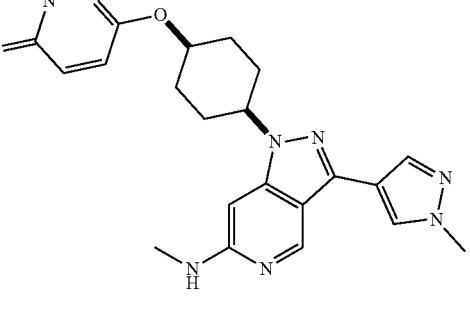 | B | B | D |
| 17 | 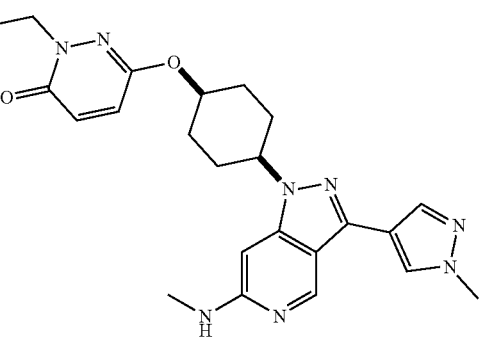 | B | B | D |
| 18 | 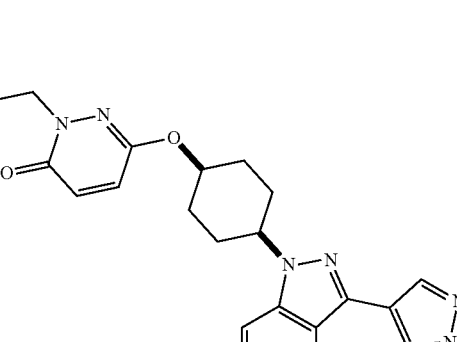 | B | B | D |
| 19 | 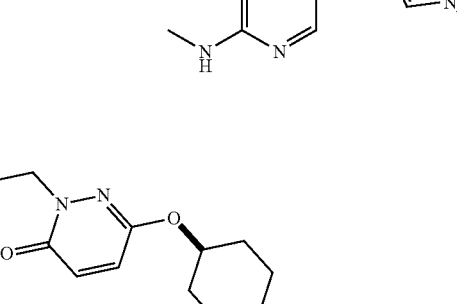 | C | B | C |

TABLE 1-continued
| Ex. | | AXL enzyme IC$_{50}$ | MER enzyme IC$_{50}$ | TYRO3 enzyme IC$_{50}$ |
|---|---|---|---|---|
| 20 | 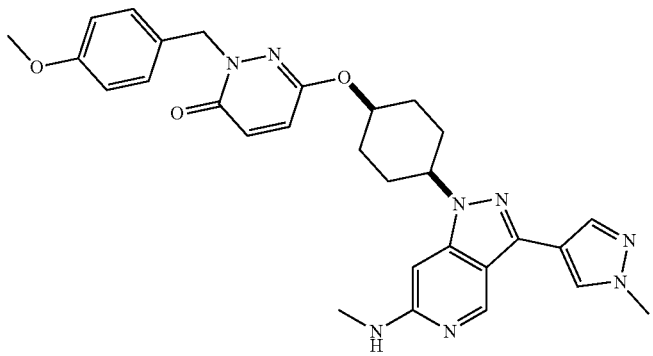 | C | B | D |
| 21 | 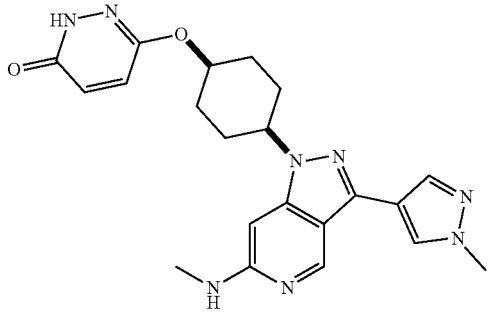 | B | B | D |
| 22 | 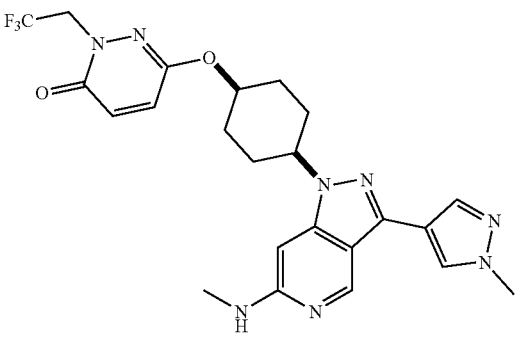 | B | B | C |
| 23 | 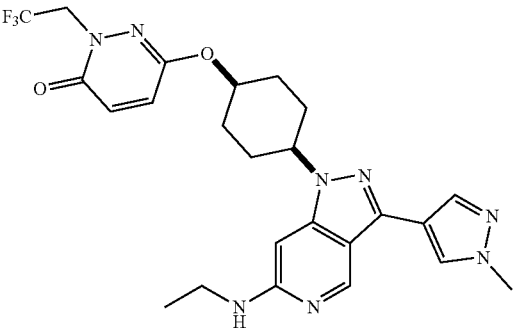 | B | B | C |

TABLE 1-continued
| Ex. | | AXL enzyme IC$_{50}$ | MER enzyme IC$_{50}$ | TYRO3 enzyme IC$_{50}$ |
|---|---|---|---|---|
| 24 | 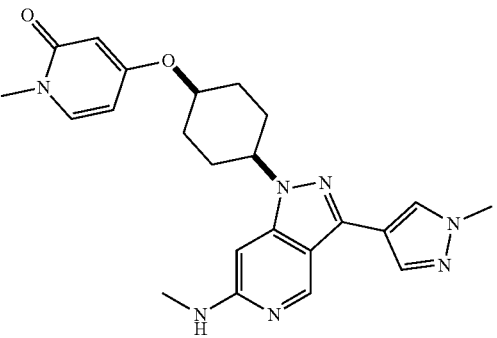 | B | B | A |
| 25 | 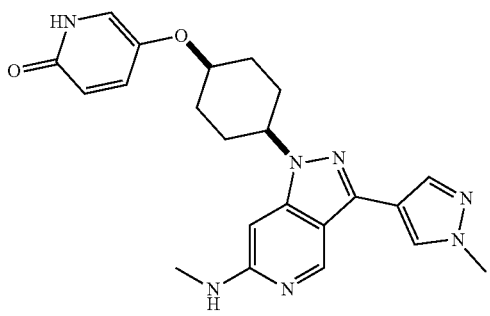 | B | A | B |
| 26 | 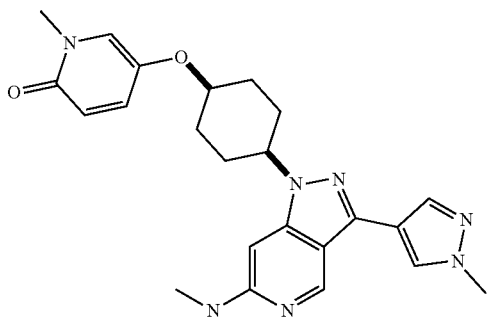 | B | B | C |
| 27 | 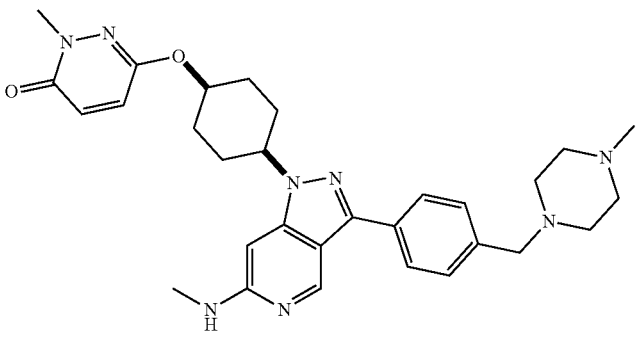 | A | A | C |

TABLE 1-continued
| Ex. | | AXL enzyme IC$_{50}$ | MER enzyme IC$_{50}$ | TYRO3 enzyme IC$_{50}$ |
|---|---|---|---|---|
| 28 | 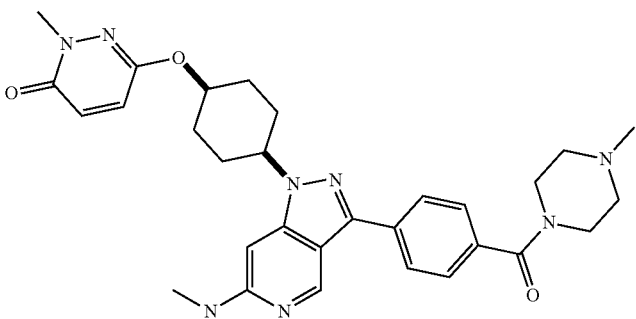 | B | B | C |
| 29 | 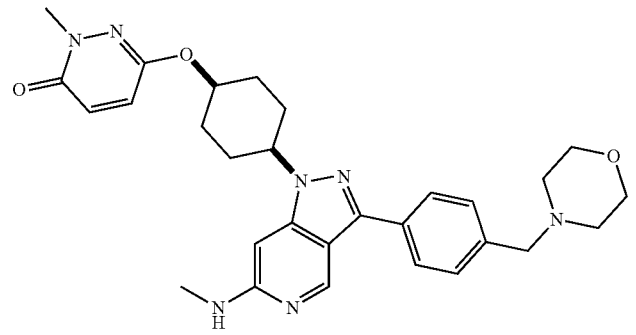 | B | B | C |
| 30 | 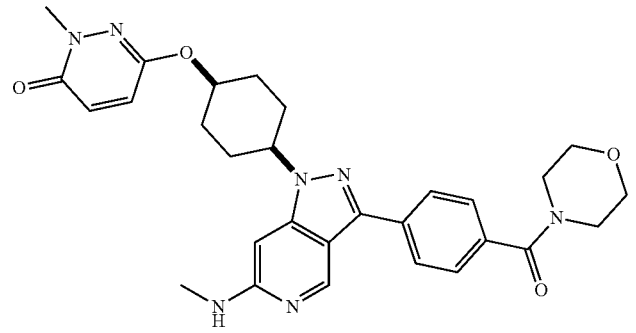 | B | B | C |
| 31 | 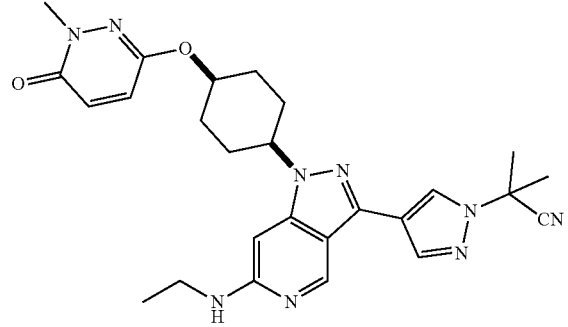 | C | B | C |

TABLE 1-continued

| Ex. | Structure | AXL enzyme IC$_{50}$ | MER enzyme IC$_{50}$ | TYRO3 enzyme IC$_{50}$ |
|---|---|---|---|---|
| 32 | | C | B | C |
| 33 | | C | C | C |
| 34 | | C | B | C |
| 35 | | C | B | C |

TABLE 1-continued

| Ex. | | AXL enzyme IC$_{50}$ | MER enzyme IC$_{50}$ | TYRO3 enzyme IC$_{50}$ |
|---|---|---|---|---|
| 36 | | C | B | C |
| 37 | | C | B | C |
| 38 | | B | B | C |
| 39 | | C | B | C |

TABLE 1-continued

| Ex. | | AXL enzyme IC$_{50}$ | MER enzyme IC$_{50}$ | TYRO3 enzyme IC$_{50}$ |
|---|---|---|---|---|
| 40 | | C | B | C |
| 41 | | C | B | C |
| 42 | | C | B | C |
| 43 | | C | B | C |

TABLE 1-continued

| Ex. | AXL enzyme IC$_{50}$ | MER enzyme IC$_{50}$ | TYRO3 enzyme IC$_{50}$ |
|---|---|---|---|
| 44 | C | B | C |
| 45 | B | B | C |
| 46 | B | B | C |
| 47 | B | B | C |

TABLE 1-continued

| Ex. | AXL enzyme IC$_{50}$ | MER enzyme IC$_{50}$ | TYRO3 enzyme IC$_{50}$ |
|---|---|---|---|
| 48 | B | B | C |
| 49 | B | B | C |
| 50 | C | B | C |
| 51 | C | C | D |

TABLE 1-continued

| Ex. | Structure | AXL enzyme IC$_{50}$ | MER enzyme IC$_{50}$ | TYRO3 enzyme IC$_{50}$ |
|---|---|---|---|---|
| 52 | | C | C | D |
| 53 | | A | A | C |
| 54 | | B | B | C |
| 55 | | B | B | C |

TABLE 1-continued

| Ex. | | AXL enzyme IC$_{50}$ | MER enzyme IC$_{50}$ | TYRO3 enzyme IC$_{50}$ |
|---|---|---|---|---|
| 56 | (structure) | B | B | C |
| 57 | (structure) | C | B | D |
| 58 | (structure) | B | B | C |
| 59 | (structure) | B | B | C |

TABLE 1-continued

| Ex. | | AXL enzyme IC$_{50}$ | MER enzyme IC$_{50}$ | TYRO3 enzyme IC$_{50}$ |
|---|---|---|---|---|
| 60 | [structure] | C | B | C |
| 61 | [structure] | C | B | C |
| 62 | [structure] | C | C | D |
| 63 | [structure] | B | B | C |

TABLE 1-continued

| Ex. | AXL enzyme IC$_{50}$ | MER enzyme IC$_{50}$ | TYRO3 enzyme IC$_{50}$ |
|---|---|---|---|
| 64 | B | B | C |
| 65 | C | B | B |
| 66 | C | B | A |
| 67 | C | B | B |

TABLE 1-continued

| Ex. | | AXL enzyme IC$_{50}$ | MER enzyme IC$_{50}$ | TYRO3 enzyme IC$_{50}$ |
|---|---|---|---|---|
| 68 | | C | C | B |
| 69 | | C | C | B |
| 70 | | C | B | C |
| 71 | | C | B | B |

TABLE 1-continued

| Ex. | Structure | AXL enzyme IC$_{50}$ | MER enzyme IC$_{50}$ | TYRO3 enzyme IC$_{50}$ |
|---|---|---|---|---|
| 72 | | C | B | B |
| 73 | | B | B | C |
| 74 | | C | C | D |
| 75 | | D | D | D |

TABLE 1-continued
| Ex. | | AXL enzyme IC$_{50}$ | MER enzyme IC$_{50}$ | TYRO3 enzyme IC$_{50}$ |
|---|---|---|---|---|
| 76 | 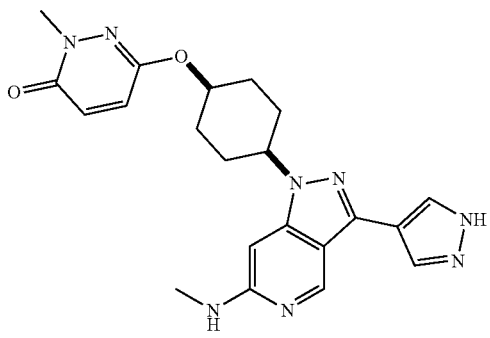 | B | B | C |
| 77 | 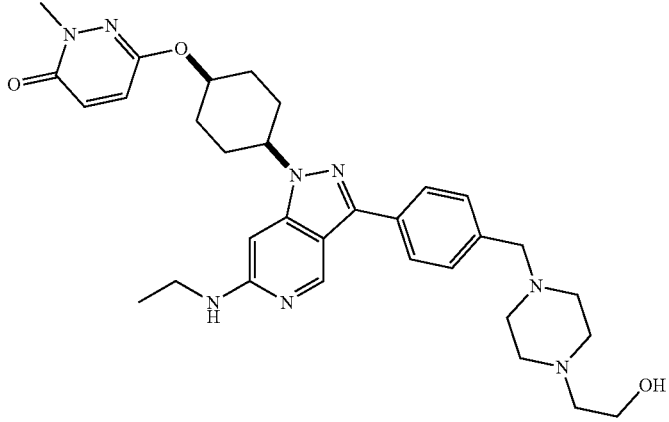 | B | B | C |
| 78 | 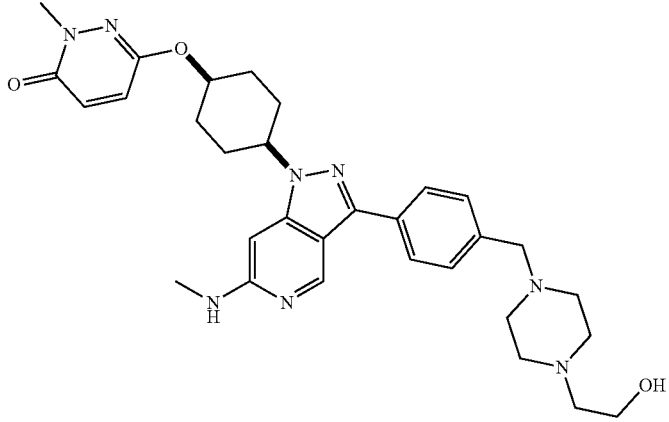 | A | A | C |

TABLE 1-continued
| Ex. | AXL enzyme IC$_{50}$ | MER enzyme IC$_{50}$ | TYRO3 enzyme IC$_{50}$ |
|---|---|---|---|
| 79 | A | B | C |
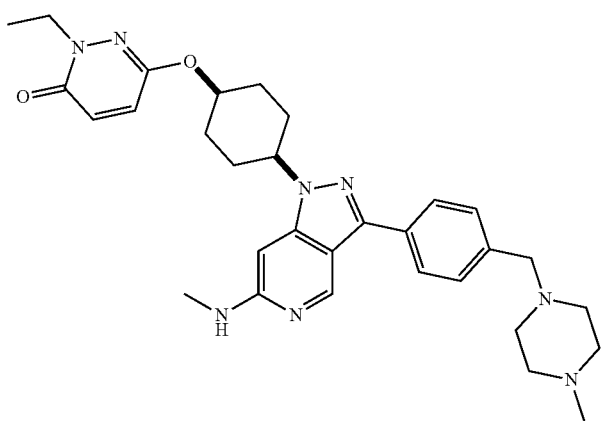
| | | | |
|---|---|---|---|
| 80 | B | B | B |
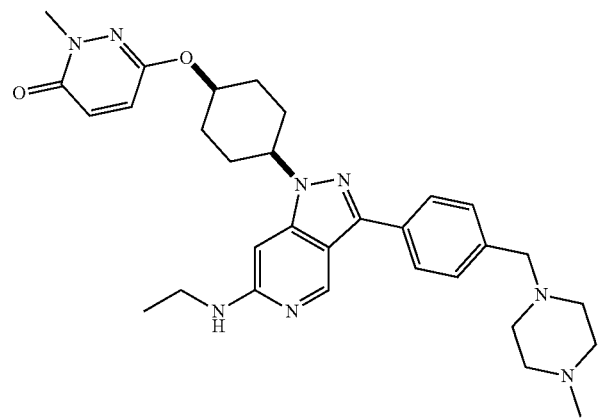
| | | | |
|---|---|---|---|
| 81 | D | D | D |
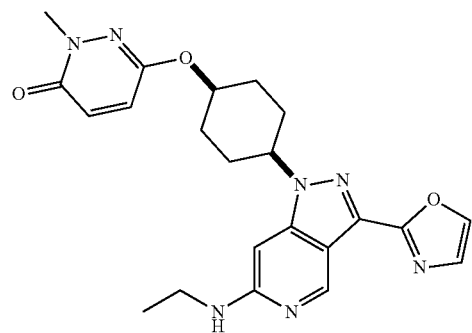

TABLE 1-continued
| Ex. | AXL enzyme IC$_{50}$ | MER enzyme IC$_{50}$ | TYRO3 enzyme IC$_{50}$ |
|---|---|---|---|
| 82 | B | A | B |
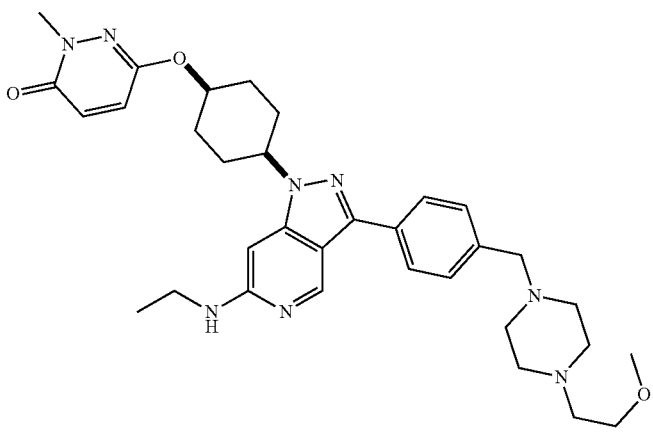
| | | | |
|---|---|---|---|
| 83 | B | A | B |
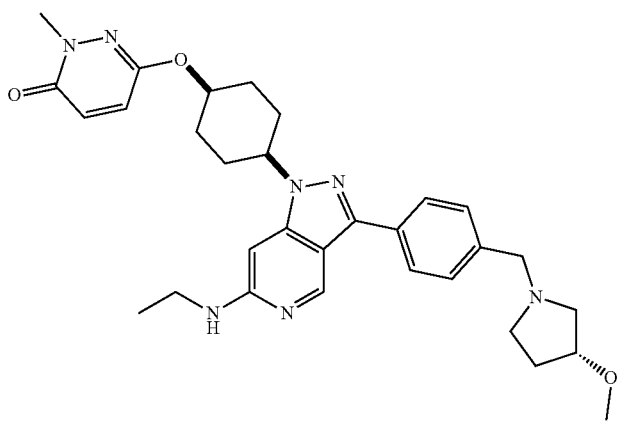
| | | | |
|---|---|---|---|
| 84 | B | B | C |
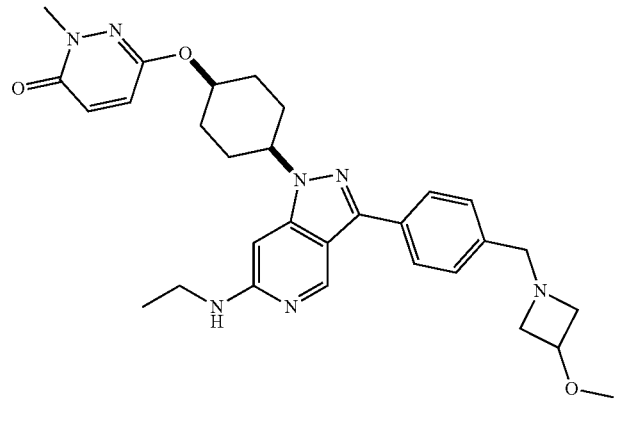

TABLE 1-continued

| Ex. | AXL enzyme IC$_{50}$ | MER enzyme IC$_{50}$ | TYRO3 enzyme IC$_{50}$ |
|---|---|---|---|
| 85 | B | B | C |
| 86 | B | B | B |
| 87 | B | B | C |

TABLE 1-continued
| Ex. | AXL enzyme IC$_{50}$ | MER enzyme IC$_{50}$ | TYRO3 enzyme IC$_{50}$ |
|---|---|---|---|
| 88 | B | B | C |
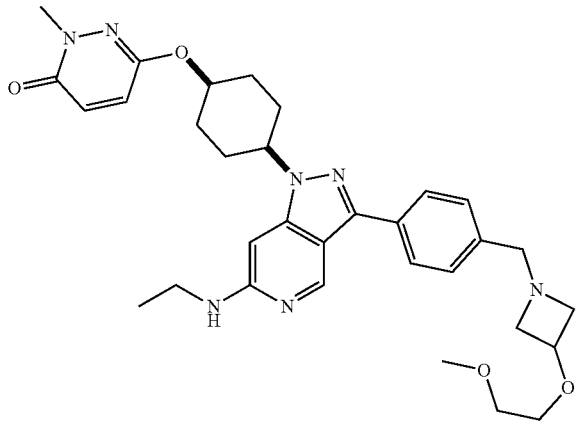
| | | | |
|---|---|---|---|
| 89 | B | B | C |
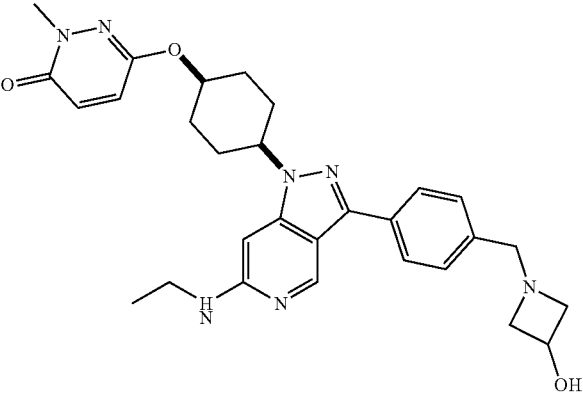
| | | | |
|---|---|---|---|
| 90 | B | A | B |
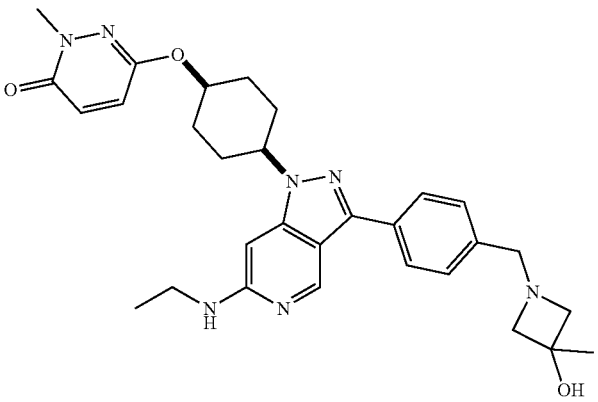

TABLE 1-continued
| Ex. | | AXL enzyme IC$_{50}$ | MER enzyme IC$_{50}$ | TYRO3 enzyme IC$_{50}$ |
|---|---|---|---|---|
| 91 | 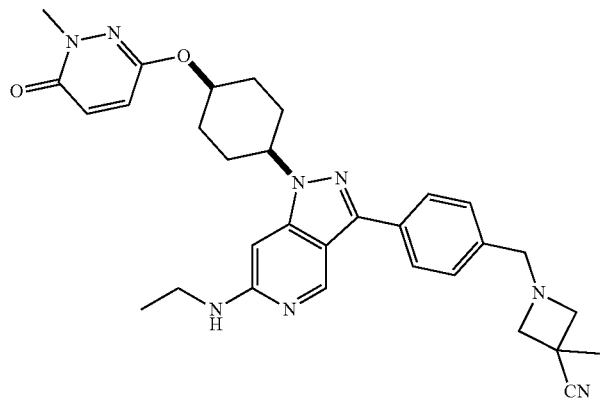 | B | B | C |
| 92 | 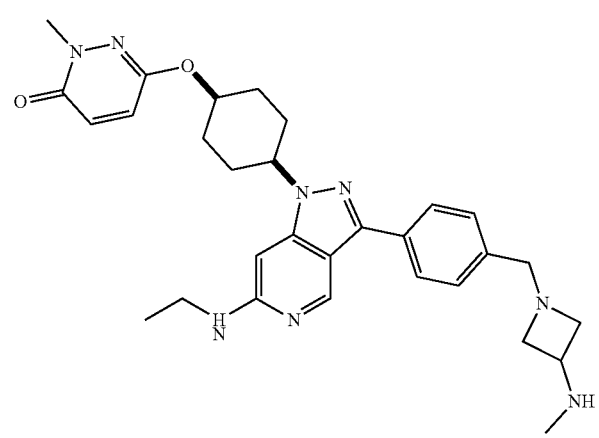 | B | B | B |
| 93 | 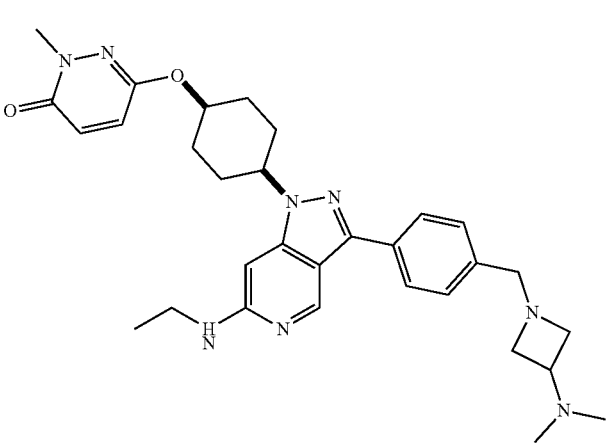 | B | B | B |

TABLE 1-continued

| Ex. | AXL enzyme IC$_{50}$ | MER enzyme IC$_{50}$ | TYRO3 enzyme IC$_{50}$ |
|---|---|---|---|
| 94 | B | B | B |
| 95 | B | A | B |
| 96 | B | A | B |

TABLE 1-continued
| Ex. | AXL enzyme IC$_{50}$ | MER enzyme IC$_{50}$ | TYRO3 enzyme IC$_{50}$ |
|---|---|---|---|
| 97 | B | B | C |
| 98 | B | A | B |
| 99 | B | B | C |
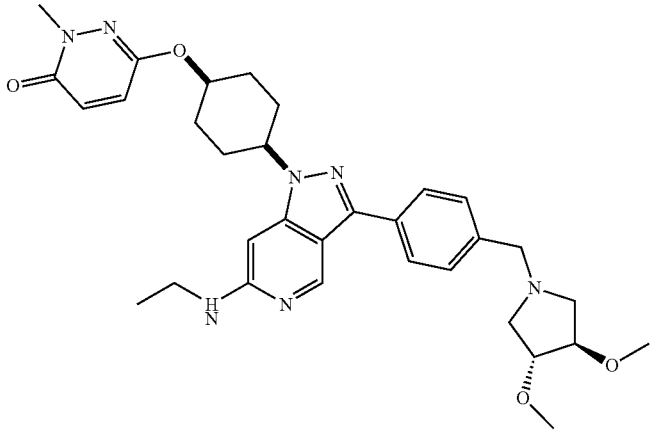
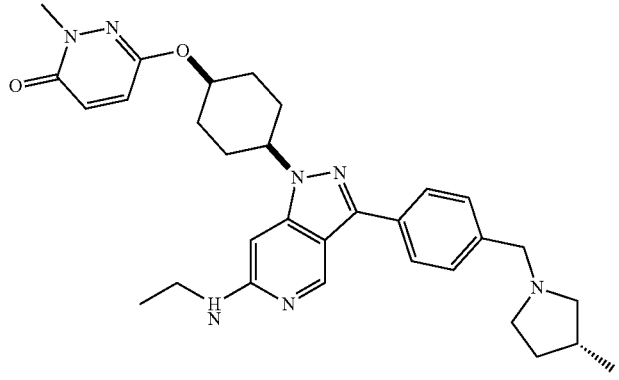
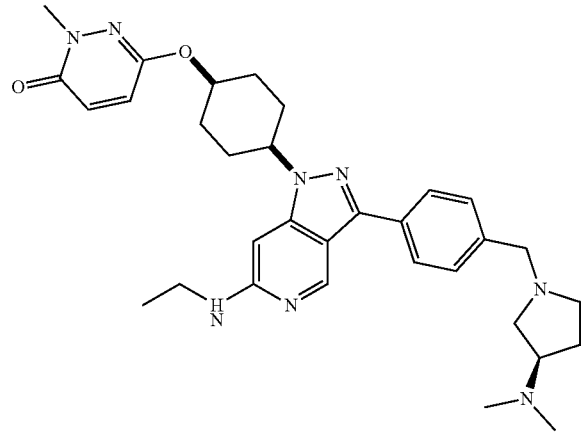

TABLE 1-continued

| Ex. | | AXL enzyme IC$_{50}$ | MER enzyme IC$_{50}$ | TYRO3 enzyme IC$_{50}$ |
|---|---|---|---|---|
| 100 | | C | C | C |
| 101 | | D | C | D |
| 102 | | B | B | C |
| 103 | | B | B | B |

TABLE 1-continued
| Ex. | | AXL enzyme IC$_{50}$ | MER enzyme IC$_{50}$ | TYRO3 enzyme IC$_{50}$ |
|---|---|---|---|---|
| 104 | 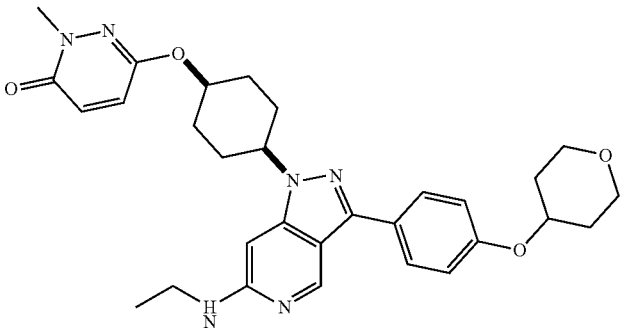 | C | B | C |
| 105 | 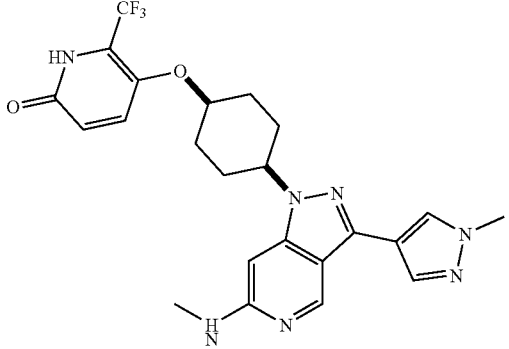 | A | A | A |
| 106 | 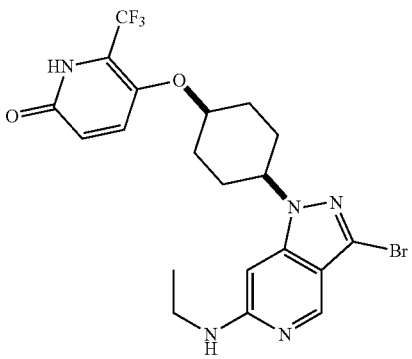 | B | A | B |
| 107 | 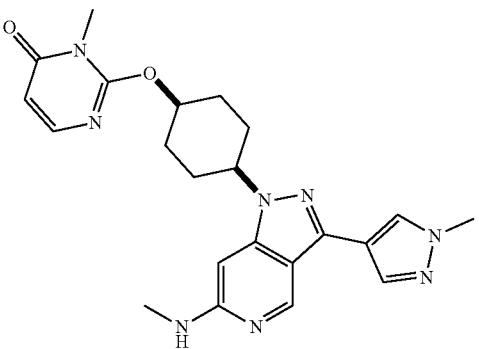 | B | B | C |

TABLE 1-continued

| Ex. | AXL enzyme IC$_{50}$ | MER enzyme IC$_{50}$ | TYRO3 enzyme IC$_{50}$ |
|---|---|---|---|
| 108 | B | B | D |
| 109 | D | C | D |
| 110 | B | A | B |
| 111 | A | A | B |

TABLE 1-continued

| Ex. | | AXL enzyme IC$_{50}$ | MER enzyme IC$_{50}$ | TYRO3 enzyme IC$_{50}$ |
|---|---|---|---|---|
| 112 | | B | B | C |
| 113 | | C | C | C |
| 114 | | B | B | D |
| 115 | | B | B | C |

TABLE 1-continued

| Ex. | | AXL enzyme IC$_{50}$ | MER enzyme IC$_{50}$ | TYRO3 enzyme IC$_{50}$ |
|---|---|---|---|---|
| 116 | | A | A | B |
| 117 | | B | B | C |
| 118 | | C | C | D |
| 119 | | C | C | D |
| 120 | | B | B | D |

TABLE 1-continued

| Ex. | | AXL enzyme IC$_{50}$ | MER enzyme IC$_{50}$ | TYRO3 enzyme IC$_{50}$ |
|---|---|---|---|---|
| 121 | | B | B | D |
| 122 | | A | A | B |
| 123 | | B | B | D |
| 124 | | B | B | B |

TABLE 1-continued

| Ex. | | AXL enzyme IC$_{50}$ | MER enzyme IC$_{50}$ | TYRO3 enzyme IC$_{50}$ |
|---|---|---|---|---|
| 125 | | A | A | B |
| 126 | | B | B | D |
| 127 | | B | B | D |
| 128 | | A | A | B |
| 129 | | B | B | C |

TABLE 1-continued

| Ex. | | AXL enzyme IC$_{50}$ | MER enzyme IC$_{50}$ | TYRO3 enzyme IC$_{50}$ |
|---|---|---|---|---|
| 130 | | B | B | D |
| 131 | | C | C | D |
| 132 | | B | B | C |
| 133 | | B | B | C |

TABLE 1-continued

| Ex. | Structure | AXL enzyme IC$_{50}$ | MER enzyme IC$_{50}$ | TYRO3 enzyme IC$_{50}$ |
|---|---|---|---|---|
| 134 | | B | B | C |
| 135 | | A | A | B |
| 136 | | B | B | C |
| 137 | | A | A | A |
| 138 | | B | B | D |

TABLE 1-continued

| Ex. | AXL enzyme IC$_{50}$ | MER enzyme IC$_{50}$ | TYRO3 enzyme IC$_{50}$ |
|---|---|---|---|
| 139 | B | B | C |
| 140 | A | A | A |
| 141 | B | B | D |
| 142 | B | A | C |

TABLE 1-continued

| Ex. | Structure | AXL enzyme IC$_{50}$ | MER enzyme IC$_{50}$ | TYRO3 enzyme IC$_{50}$ |
|---|---|---|---|---|
| 143 | | B | A | C |
| 144 | | B | B | C |
| 145 | | A | A | B |
| 146 | | A | A | B |
| 147 | | B | B | C |

TABLE 1-continued

| Ex. | AXL enzyme IC$_{50}$ | MER enzyme IC$_{50}$ | TYRO3 enzyme IC$_{50}$ |
|---|---|---|---|
| 148 | B | B | C |
| 149 | C | B | C |
| 150 | A | A | B |
| 151 | B | A | C |

TABLE 1-continued

| Ex. | | AXL enzyme IC$_{50}$ | MER enzyme IC$_{50}$ | TYRO3 enzyme IC$_{50}$ |
|---|---|---|---|---|
| 152 | | B | B | C |
| 153 | | B | A | C |
| 154 | | C | B | D |
| 155 | | A | B | C |

TABLE 1-continued

| Ex. | | AXL enzyme IC$_{50}$ | MER enzyme IC$_{50}$ | TYRO3 enzyme IC$_{50}$ |
|---|---|---|---|---|
| 156 | | B | B | C |
| 157 | | B | B | C |
| 158 | | B | B | C |
| 159 | | B | B | B |

TABLE 1-continued

| Ex. | | AXL enzyme IC$_{50}$ | MER enzyme IC$_{50}$ | TYRO3 enzyme IC$_{50}$ |
|---|---|---|---|---|
| 160 | | A | A | A |
| 161 | | B | B | C |
| 162 | | A | A | A |
| 163 | | A | A | A |
| 164 | | A | A | A |

TABLE 1-continued

| Ex. | | AXL enzyme IC$_{50}$ | MER enzyme IC$_{50}$ | TYRO3 enzyme IC$_{50}$ |
|---|---|---|---|---|
| 165 | | A | A | B |
| 166 | | B | B | C |
| 167 | | B | B | C |
| 168 | | B | B | B |

TABLE 1-continued

| Ex. | | AXL enzyme IC$_{50}$ | MER enzyme IC$_{50}$ | TYRO3 enzyme IC$_{50}$ |
|---|---|---|---|---|
| 169 | | B | B | C |
| 170 | | A | A | C |
| 171 | | A | A | A |
| 172 | | B | B | C |

TABLE 1-continued
| Ex. | | AXL enzyme IC$_{50}$ | MER enzyme IC$_{50}$ | TYRO3 enzyme IC$_{50}$ |
|---|---|---|---|---|
| 173 | 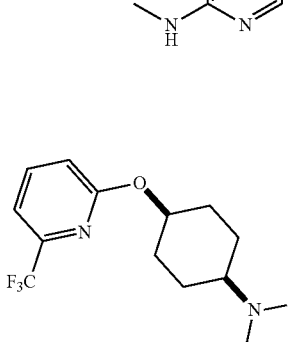 | A | A | B |
| 174 | 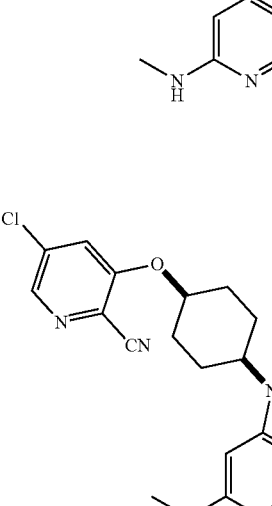 | B | B | D |
| 175 | 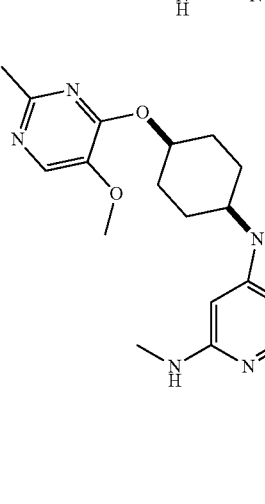 | A | A | B |
| 176 |  | B | B | D |

TABLE 1-continued

| Ex. | | AXL enzyme IC$_{50}$ | MER enzyme IC$_{50}$ | TYRO3 enzyme IC$_{50}$ |
|---|---|---|---|---|
| 177 | | B | B | C |
| 178 | | A | B | C |
| 179 | | B | B | B |
| 180 | | B | B | B |
| 181 | | B | A | B |

TABLE 1-continued

| Ex. | AXL enzyme IC$_{50}$ | MER enzyme IC$_{50}$ | TYRO3 enzyme IC$_{50}$ |
|---|---|---|---|
| 182 | B | B | B |
| 183 | A | A | A |
| 184 | A | A | A |
| 185 | B | A | B |

TABLE 1-continued

| Ex. | Structure | AXL enzyme IC$_{50}$ | MER enzyme IC$_{50}$ | TYRO3 enzyme IC$_{50}$ |
|---|---|---|---|---|
| 186 | | B | A | B |
| 187 | | C | B | C |
| 188 | | A | A | A |
| 189 | | B | A | B |
| 190 | | A | A | B |

TABLE 1-continued

| Ex. | AXL enzyme IC$_{50}$ | MER enzyme IC$_{50}$ | TYRO3 enzyme IC$_{50}$ |
|---|---|---|---|
| 191 | C | B | C |
| 192 | B | A | B |
| 193 | B | A | B |
| 194 | A | A | A |

TABLE 1-continued

| Ex. | | AXL enzyme IC$_{50}$ | MER enzyme IC$_{50}$ | TYRO3 enzyme IC$_{50}$ |
|---|---|---|---|---|
| 195 | | B | B | B |
| 196 | | B | B | C |
| 197 | | B | B | B |
| 198 | | A | A | B |

TABLE 1-continued

| Ex. | Structure | AXL enzyme IC$_{50}$ | MER enzyme IC$_{50}$ | TYRO3 enzyme IC$_{50}$ |
|---|---|---|---|---|
| 199 | | A | A | A |
| 200 | | B | A | B |
| 201 | | B | B | B |
| 202 | | A | A | B |

TABLE 1-continued

| Ex. | | AXL enzyme IC$_{50}$ | MER enzyme IC$_{50}$ | TYRO3 enzyme IC$_{50}$ |
|---|---|---|---|---|
| 203 | | B | B | C |
| 204 | | A | A | A |
| 205 | | A | A | A |
| 206 | | A | A | A |

TABLE 1-continued

| Ex. | | AXL enzyme IC$_{50}$ | MER enzyme IC$_{50}$ | TYRO3 enzyme IC$_{50}$ |
|---|---|---|---|---|
| 207 | [structure] | A | A | A |
| 208 | [structure] | A | A | A |
| 209 | [structure] | A | A | A |
| 210 | [structure] | A | A | A |
| 211 | [structure] | A | A | B |

TABLE 1-continued

| Ex. | | AXL enzyme IC$_{50}$ | MER enzyme IC$_{50}$ | TYRO3 enzyme IC$_{50}$ |
|---|---|---|---|---|
| 212 | | A | A | B |
| 213 | | A | A | B |
| 214 | | A | A | B |
| 215 | | A | A | B |

TABLE 1-continued

| Ex. | | AXL enzyme IC$_{50}$ | MER enzyme IC$_{50}$ | TYRO3 enzyme IC$_{50}$ |
|---|---|---|---|---|
| 216 | | A | A | A |
| 217 | | A | A | A |
| 218 | | A | A | A |
| 219 | | A | A | A |
| 220 | | B | B | C |

TABLE 1-continued
| Ex. | | AXL enzyme IC$_{50}$ | MER enzyme IC$_{50}$ | TYRO3 enzyme IC$_{50}$ |
|---|---|---|---|---|
| 221 | 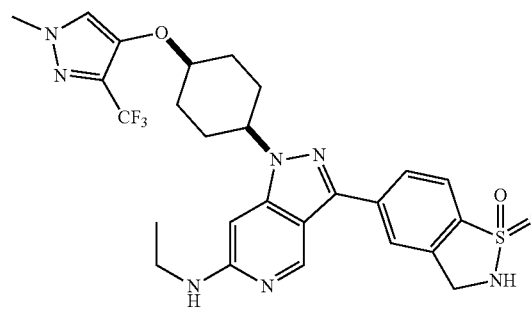 | A | A | A |
| 222 | 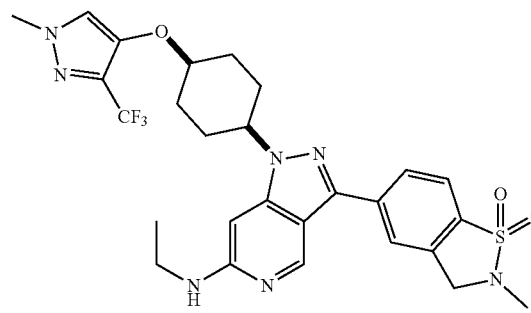 | A | A | A |
| 223 | 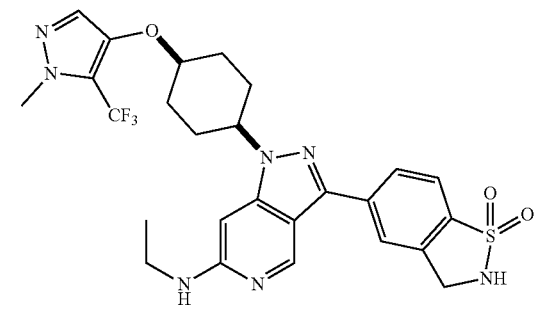 | B | B | C |
| 224 | 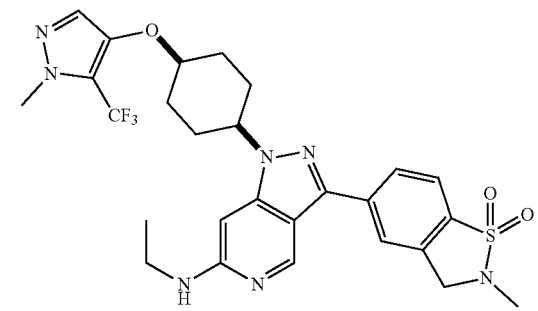 | D | C | D |

TABLE 1-continued
| Ex. | | AXL enzyme IC$_{50}$ | MER enzyme IC$_{50}$ | TYRO3 enzyme IC$_{50}$ |
|---|---|---|---|---|
| 225 | 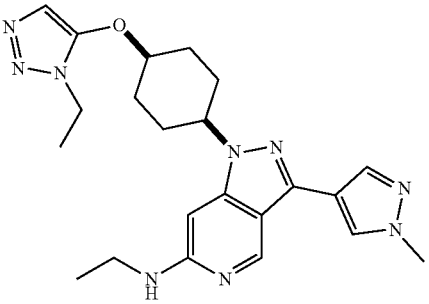 | B | A | C |
| 226 | 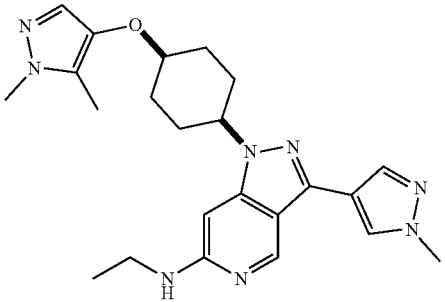 | C | C | D |
| 227 | 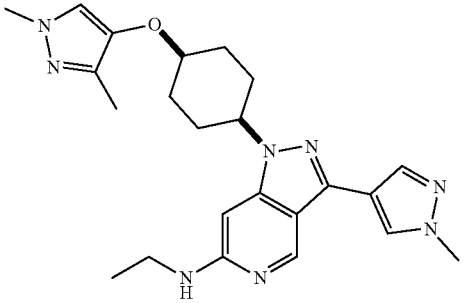 | B | B | B |
| 228 | 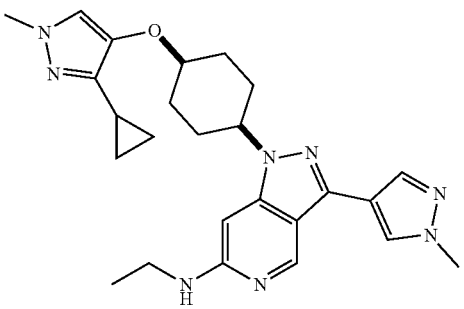 | B | B | B |
| 229 | 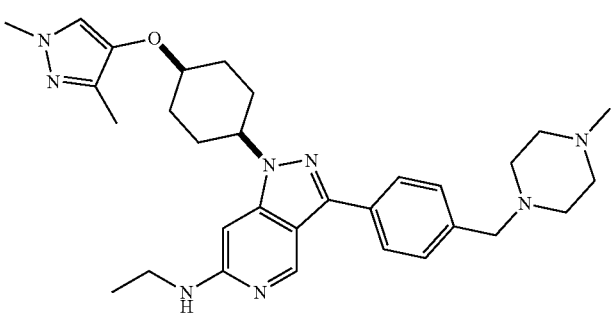 | B | A | B |

TABLE 1-continued
| Ex. | | AXL enzyme IC$_{50}$ | MER enzyme IC$_{50}$ | TYRO3 enzyme IC$_{50}$ |
|---|---|---|---|---|
| 230 | 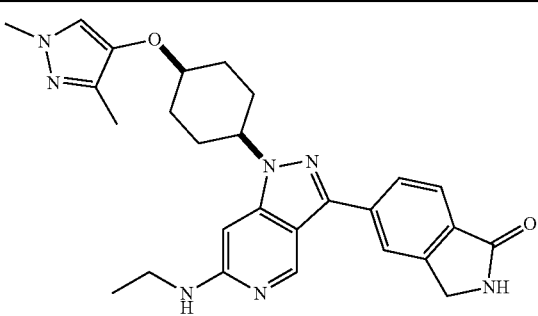 | B | A | B |
| 231 | 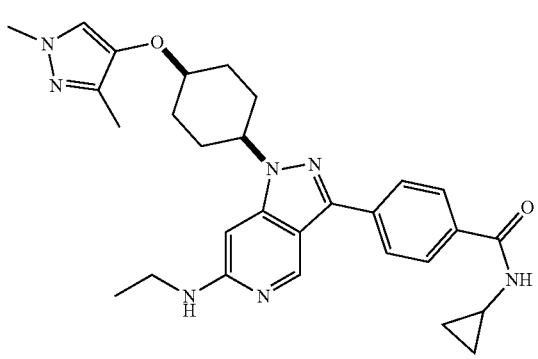 | B | A | B |
| 232 | 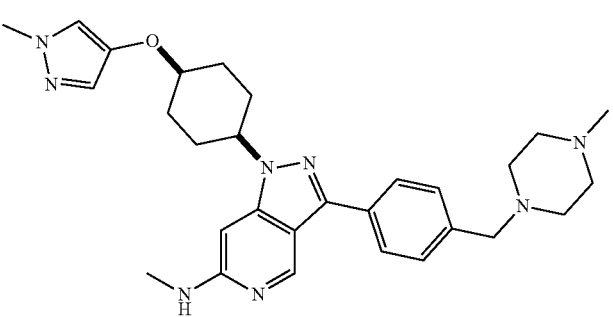 | A | A | C |
| 233 | 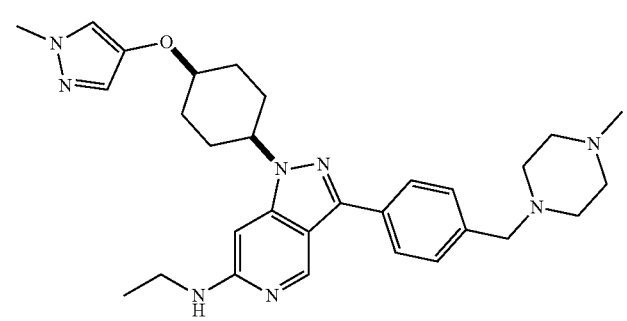 | B | A | B |

TABLE 1-continued

| Ex. | | AXL enzyme IC$_{50}$ | MER enzyme IC$_{50}$ | TYRO3 enzyme IC$_{50}$ |
|---|---|---|---|---|
| 234 | | A | A | B |
| 235 | | A | A | B |
| 236 | | A | A | B |
| 237 | | A | A | B |

TABLE 1-continued

| Ex. | | AXL enzyme IC$_{50}$ | MER enzyme IC$_{50}$ | TYRO3 enzyme IC$_{50}$ |
|---|---|---|---|---|
| 238 | | A | A | B |
| 239 | | A | A | A |
| 240 | | B | B | C |
| 241 | | B | A | B |

TABLE 1-continued
| Ex. | | AXL enzyme IC$_{50}$ | MER enzyme IC$_{50}$ | TYRO3 enzyme IC$_{50}$ |
|---|---|---|---|---|
| 242 | 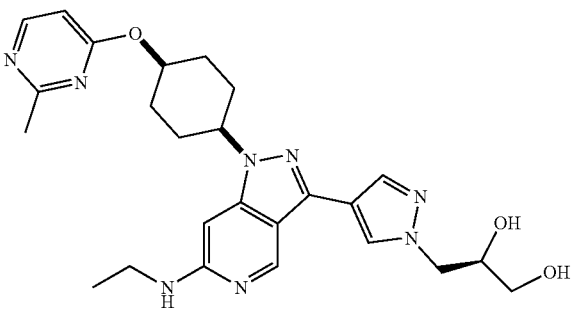 | C | B | C |
| 243 | 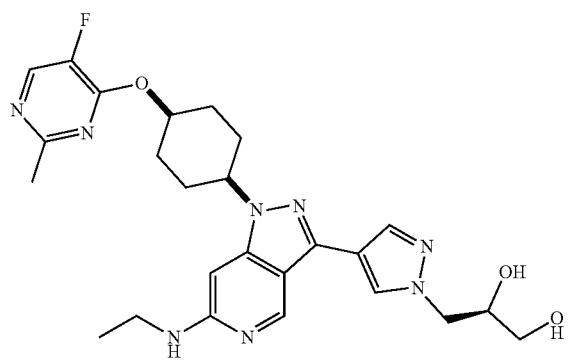 | B | B | C |
| 244 | 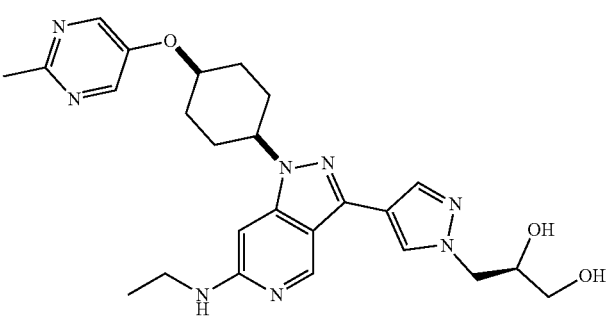 | C | B | C |
| 245 | 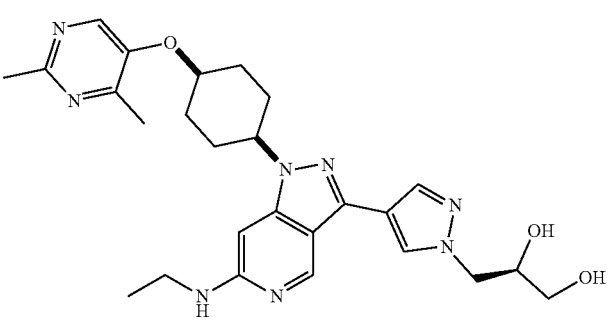 | C | B | C |

TABLE 1-continued

| Ex. | | AXL enzyme IC$_{50}$ | MER enzyme IC$_{50}$ | TYRO3 enzyme IC$_{50}$ |
|---|---|---|---|---|
| 246 | | A | A | B |
| 247 | | A | A | A |
| 248 | | A | A | A |
| 249 | | B | B | C |

TABLE 1-continued

| Ex. | | AXL enzyme IC$_{50}$ | MER enzyme IC$_{50}$ | TYRO3 enzyme IC$_{50}$ |
|---|---|---|---|---|
| 250 | | B | B | C |
| 251 | | B | B | C |
| 252 | | B | B | C |
| 253 | | B | B | C |

TABLE 1-continued

| Ex. | | AXL enzyme IC$_{50}$ | MER enzyme IC$_{50}$ | TYRO3 enzyme IC$_{50}$ |
|---|---|---|---|---|
| 254 | | B | B | C |
| 255 | | A | A | B |
| 256 | | A | A | B |
| 257 | | A | A | B |

TABLE 1-continued

| Ex. | | AXL enzyme IC$_{50}$ | MER enzyme IC$_{50}$ | TYRO3 enzyme IC$_{50}$ |
|---|---|---|---|---|
| 258 | | A | A | A |
| 259 | | A | A | B |
| 260 | | A | A | C |
| 261 | | A | A | B |

TABLE 1-continued

| Ex. | | AXL enzyme IC$_{50}$ | MER enzyme IC$_{50}$ | TYRO3 enzyme IC$_{50}$ |
|---|---|---|---|---|
| 262 | (structure) | A | A | B |
| 263 | (structure) | A | A | C |
| 264 | (structure) | A | A | B |
| 265 | (structure) | B | B | C |
| 266 | (structure) | A | A | B |

TABLE 1-continued

| Ex. | | AXL enzyme IC$_{50}$ | MER enzyme IC$_{50}$ | TYRO3 enzyme IC$_{50}$ |
|---|---|---|---|---|
| 267 | | B | B | C |
| 268 | | A | A | B |
| 269 | | B | A | C |
| 270 | | B | B | C |

TABLE 1-continued

| Ex. | AXL enzyme IC$_{50}$ | MER enzyme IC$_{50}$ | TYRO3 enzyme IC$_{50}$ |
|---|---|---|---|
| 271 | A | A | B |
| 272 | A | A | B |
| 273 | B | B | C |
| 274 | B | B | C |

TABLE 1-continued

| Ex. | | AXL enzyme IC$_{50}$ | MER enzyme IC$_{50}$ | TYRO3 enzyme IC$_{50}$ |
|---|---|---|---|---|
| 275 | | B | B | C |
| 276 | | C | B | D |
| 277 | | C | C | D |
| 278 | | B | B | C |

TABLE 1-continued

| Ex. | Structure | AXL enzyme IC$_{50}$ | MER enzyme IC$_{50}$ | TYRO3 enzyme IC$_{50}$ |
|---|---|---|---|---|
| 279 | | A | A | A |
| 280 | | A | A | A |
| 281 | | B | B | C |
| 282 | | B | B | C |
| 283 | | A | A | A |

TABLE 1-continued

| Ex. | | AXL enzyme IC$_{50}$ | MER enzyme IC$_{50}$ | TYRO3 enzyme IC$_{50}$ |
|---|---|---|---|---|
| 284 | | A | A | A |
| 285 | | A | A | A |
| 286 | | A | A | A |
| 287 | | A | A | A |
| 288 | | A | A | A |

TABLE 1-continued
| Ex. | | AXL enzyme IC$_{50}$ | MER enzyme IC$_{50}$ | TYRO3 enzyme IC$_{50}$ |
|---|---|---|---|---|
| 289 | 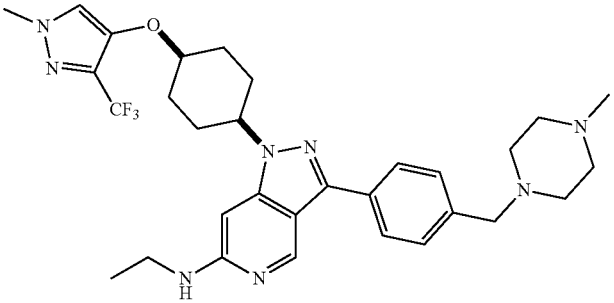 | A | A | A |
| 290 | 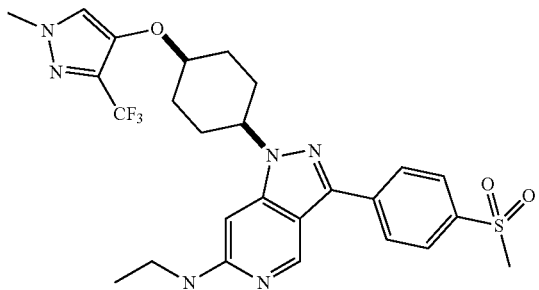 | A | A | A |
| 291 | 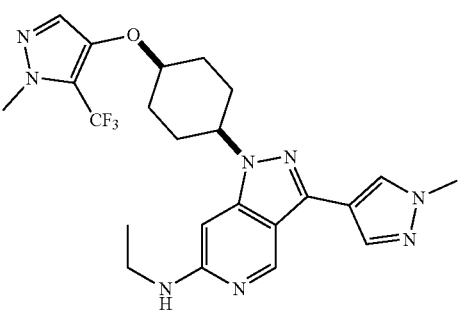 | B | A | B |
| 292 | 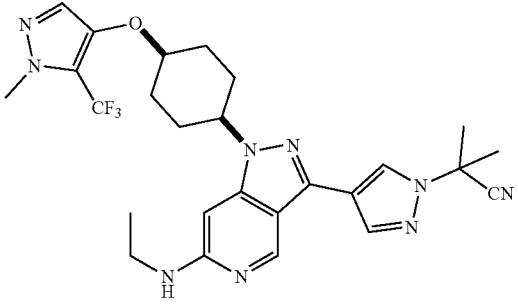 | B | B | C |
| 293 | 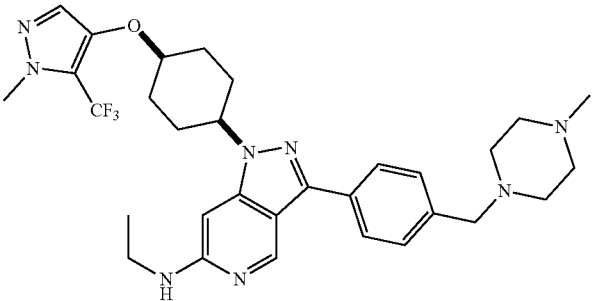 | A | A | B |

TABLE 1-continued

| Ex. | AXL enzyme IC$_{50}$ | MER enzyme IC$_{50}$ | TYRO3 enzyme IC$_{50}$ |
|---|---|---|---|
| 294 | B | B | C |
| 295 | B | B | C |
| 296 | B | B | C |
| 297 | A | A | B |

TABLE 1-continued

| Ex. | | AXL enzyme IC$_{50}$ | MER enzyme IC$_{50}$ | TYRO3 enzyme IC$_{50}$ |
|---|---|---|---|---|
| 298 | | A | A | B |
| 299 | | A | A | B |
| 300 | | A | A | B |
| 301 | | B | B | C |

TABLE 1-continued
| Ex. | | AXL enzyme IC$_{50}$ | MER enzyme IC$_{50}$ | TYRO3 enzyme IC$_{50}$ |
|---|---|---|---|---|
| 302 | 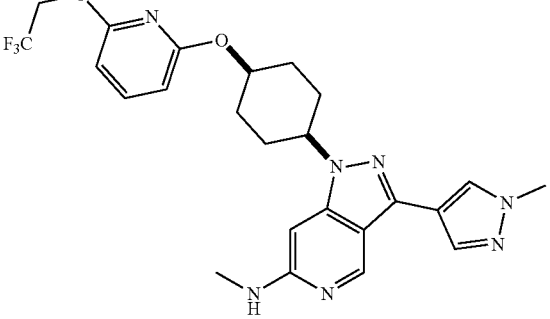 | C | C | D |
| 303 | 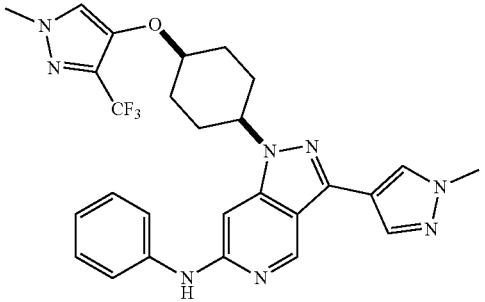 | C | B | A |
| 304 | 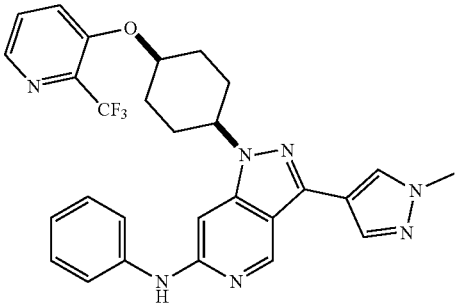 | C | B | A |
| 305 | 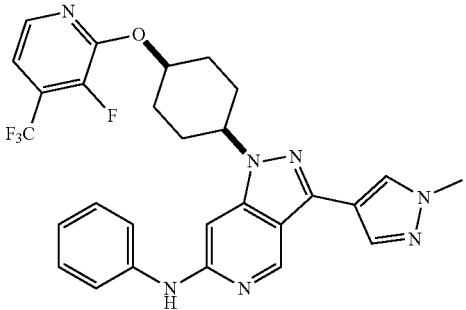 | C | C | B |

TABLE 1-continued

| Ex. | | AXL enzyme IC$_{50}$ | MER enzyme IC$_{50}$ | TYRO3 enzyme IC$_{50}$ |
|---|---|---|---|---|
| 306 | | D | C | B |
| 307 | | B | B | C |
| 308 | | A | A | C |
| 309 | | B | B | C |

TABLE 1-continued
| Ex. | | AXL enzyme IC$_{50}$ | MER enzyme IC$_{50}$ | TYRO3 enzyme IC$_{50}$ |
|---|---|---|---|---|
| 310 | 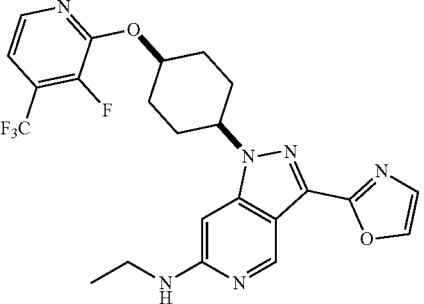 | B | B | C |
| 311 | 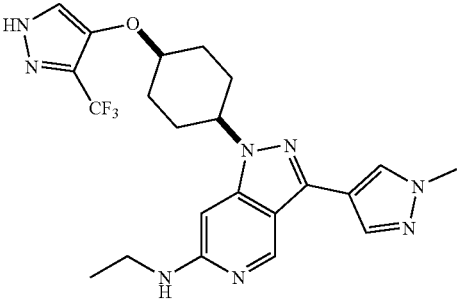 | A | A | A |
| 312 | 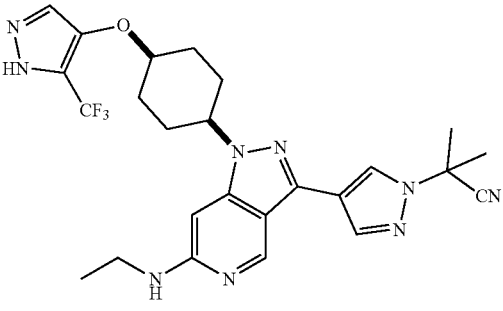 | A | A | A |
| 313 | 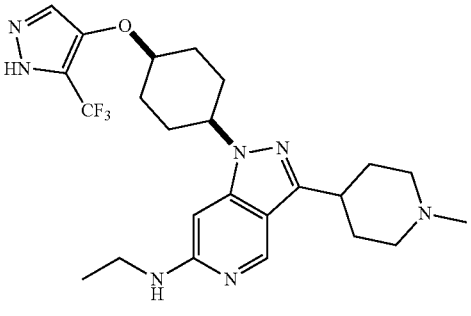 | A | A | A |
| 314 | 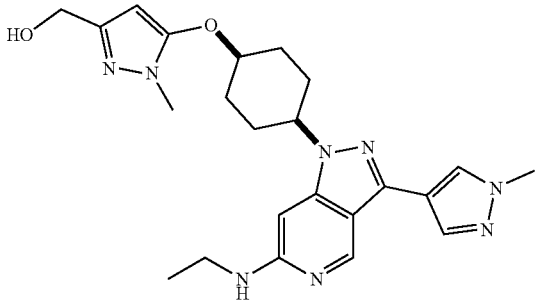 | B | B | C |

TABLE 1-continued

| Ex. | | AXL enzyme IC$_{50}$ | MER enzyme IC$_{50}$ | TYRO3 enzyme IC$_{50}$ |
|---|---|---|---|---|
| 315 | | B | B | C |
| 316 | | A | A | B |
| 317 | | A | A | C |
| 318 | | B | A | C |

TABLE 1-continued
| Ex. | | AXL enzyme IC$_{50}$ | MER enzyme IC$_{50}$ | TYRO3 enzyme IC$_{50}$ |
|---|---|---|---|---|
| 319 | 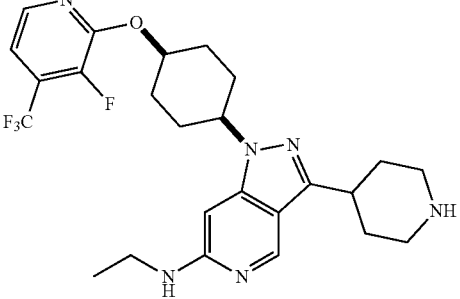 | A | A | A |
| 320 | 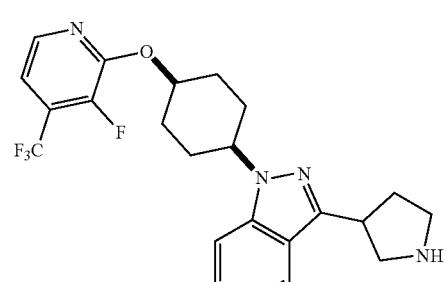 | A | A | B |
| 321 | 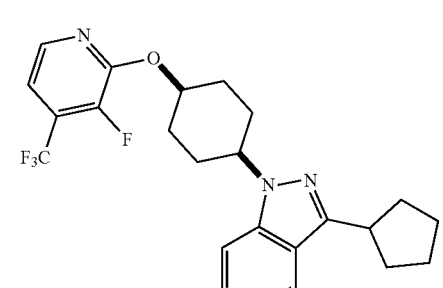 | B | B | D |
| 322 | 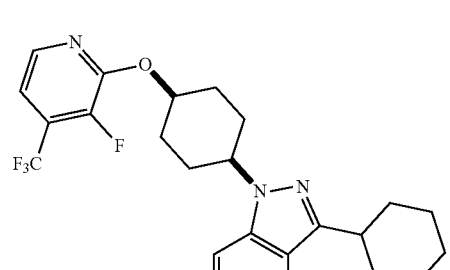 | C | B | D |

TABLE 1-continued
| Ex. | | AXL enzyme IC$_{50}$ | MER enzyme IC$_{50}$ | TYRO3 enzyme IC$_{50}$ |
|---|---|---|---|---|
| 323 | 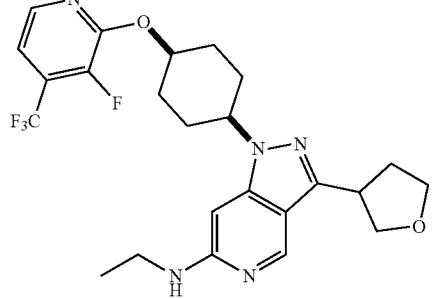 | A | A | B |
| 324 | 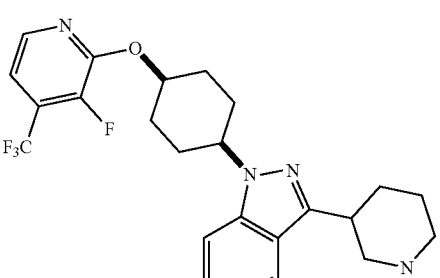 | A | A | B |
| 325 | 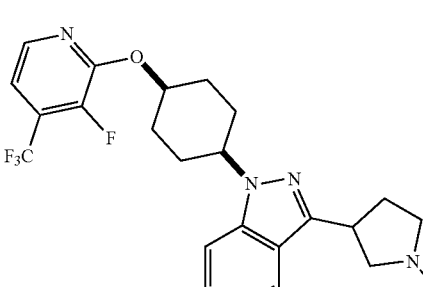 | A | A | B |
| 326 | 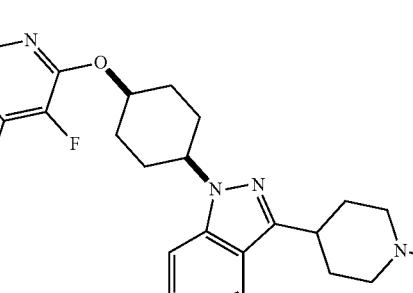 | A | A | B |

TABLE 1-continued

| Ex. | AXL enzyme IC$_{50}$ | MER enzyme IC$_{50}$ | TYRO3 enzyme IC$_{50}$ |
|---|---|---|---|
| 327 | A | A | B |
| 328 | A | A | A |
| 329 | A | A | B |
| 330 | A | A | B |

TABLE 1-continued

| Ex. | AXL enzyme IC$_{50}$ | MER enzyme IC$_{50}$ | TYRO3 enzyme IC$_{50}$ |
|---|---|---|---|
| 331 | A | A | A |
| 332 | A | A | B |
| 333 | A | A | A |
| 334 | A | A | A |

TABLE 1-continued

| Ex. | | AXL enzyme IC$_{50}$ | MER enzyme IC$_{50}$ | TYRO3 enzyme IC$_{50}$ |
|---|---|---|---|---|
| 335 | | A | A | B |
| 336 | | A | A | B |
| 337 | | B | B | C |
| 338 | | A | A | B |

TABLE 1-continued

| Ex. | | AXL enzyme IC$_{50}$ | MER enzyme IC$_{50}$ | TYRO3 enzyme IC$_{50}$ |
|---|---|---|---|---|
| 339 | | A | A | A |
| 340 | | B | B | C |
| 341 | | B | B | C |
| 342 | | A | A | B |

TABLE 1-continued
| Ex. | | AXL enzyme IC$_{50}$ | MER enzyme IC$_{50}$ | TYRO3 enzyme IC$_{50}$ |
|---|---|---|---|---|
| 343 | 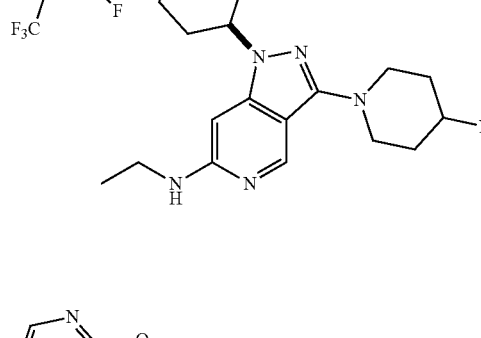 | A | A | A |
| 344 | 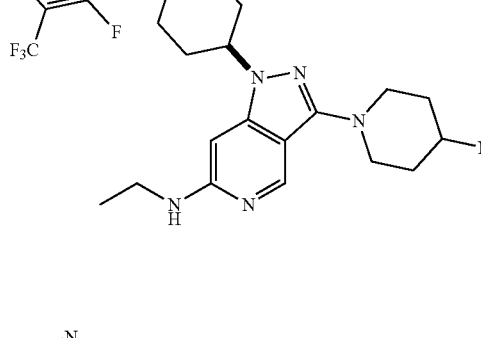 | A | A | B |
| 345 | 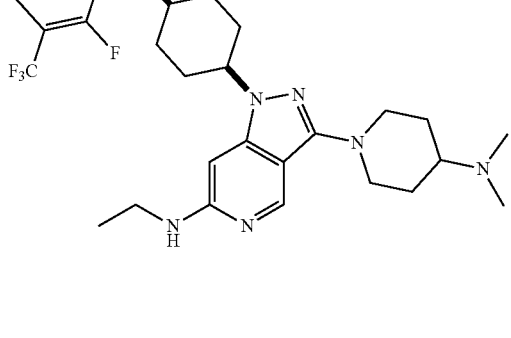 | A | A | B |
| 346 | 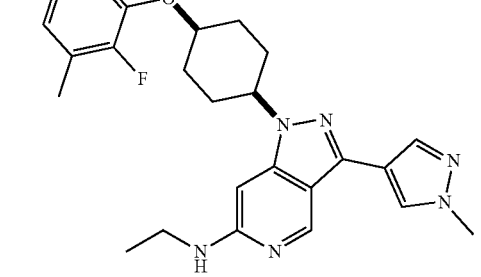 | A | A | B |

TABLE 1-continued

| Ex. | | AXL enzyme IC$_{50}$ | MER enzyme IC$_{50}$ | TYRO3 enzyme IC$_{50}$ |
|---|---|---|---|---|
| 347 | | A | A | B |
| 348 | | B | B | C |
| 349 | | A | A | C |
| 350 | | A | A | B |

TABLE 1-continued

| Ex. | Structure | AXL enzyme IC$_{50}$ | MER enzyme IC$_{50}$ | TYRO3 enzyme IC$_{50}$ |
|---|---|---|---|---|
| 351 | | A | A | A |
| 352 | | A | A | B |
| 353 | | A | A | B |
| 354 | | A | A | B |

TABLE 1-continued
| Ex. | | AXL enzyme IC$_{50}$ | MER enzyme IC$_{50}$ | TYRO3 enzyme IC$_{50}$ |
|---|---|---|---|---|
| 355 | 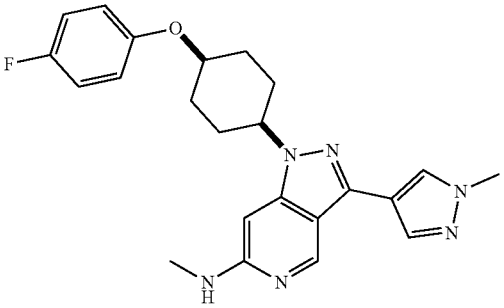 | A | A | B |
| 356 | 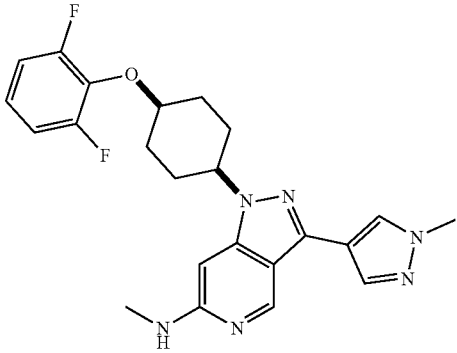 | B | A | C |
| 357 | 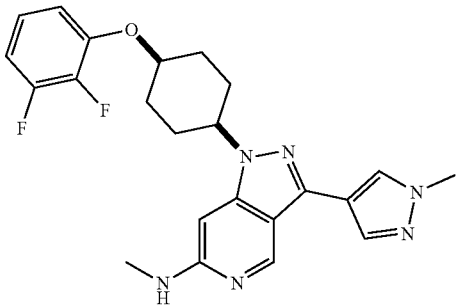 | A | A | B |
| 358 | 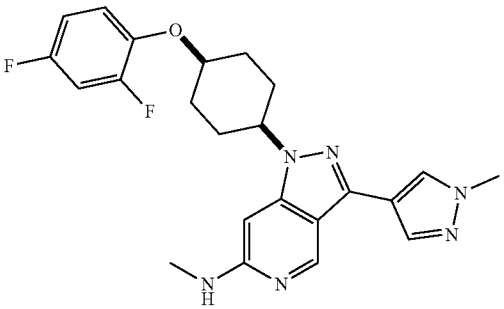 | A | A | B |

TABLE 1-continued

| Ex. | | AXL enzyme IC$_{50}$ | MER enzyme IC$_{50}$ | TYRO3 enzyme IC$_{50}$ |
|---|---|---|---|---|
| 359 | | B | B | C |
| 360 | | A | A | B |
| 361 | | A | A | C |
| 362 | | A | A | B |

TABLE 1-continued

| Ex. | Structure | AXL enzyme IC$_{50}$ | MER enzyme IC$_{50}$ | TYRO3 enzyme IC$_{50}$ |
|---|---|---|---|---|
| 363 | | A | A | B |
| 364 | | B | B | C |
| 365 | | B | B | C |
| 366 | | B | A | C |
| 367 | | B | B | C |

TABLE 1-continued

| Ex. | | AXL enzyme IC$_{50}$ | MER enzyme IC$_{50}$ | TYRO3 enzyme IC$_{50}$ |
|---|---|---|---|---|
| 368 | | B | B | C |
| 369 | | A | A | B |
| 370 | | A | B | C |
| 371 | | A | A | B |

TABLE 1-continued

| Ex. | | AXL enzyme IC$_{50}$ | MER enzyme IC$_{50}$ | TYRO3 enzyme IC$_{50}$ |
|---|---|---|---|---|
| 372 | | B | A | B |
| 373 | | B | B | C |
| 374 | | A | A | B |
| 375 | | A | A | B |
| 376 | | B | B | B |

TABLE 1-continued

| Ex. | | AXL enzyme IC$_{50}$ | MER enzyme IC$_{50}$ | TYRO3 enzyme IC$_{50}$ |
|---|---|---|---|---|
| 377 | | A | A | A |
| 378 | | A | A | B |
| 379 | | B | B | C |
| 380 | | B | B | C |

TABLE 1-continued

| Ex. | | AXL enzyme IC$_{50}$ | MER enzyme IC$_{50}$ | TYRO3 enzyme IC$_{50}$ |
|---|---|---|---|---|
| 381 | | B | B | C |
| 382 | | A | A | A |
| 383 | | B | B | C |
| 384 | | A | A | A |
| 385 | | B | B | B |

TABLE 1-continued

| Ex. | AXL enzyme IC$_{50}$ | MER enzyme IC$_{50}$ | TYRO3 enzyme IC$_{50}$ |
|---|---|---|---|
| 386 | B | B | C |
| 387 | B | B | C |
| 388 | C | B | C |
| 389 | B | B | C |

TABLE 1-continued
| Ex. | | AXL enzyme IC$_{50}$ | MER enzyme IC$_{50}$ | TYRO3 enzyme IC$_{50}$ |
|---|---|---|---|---|
| 390 | 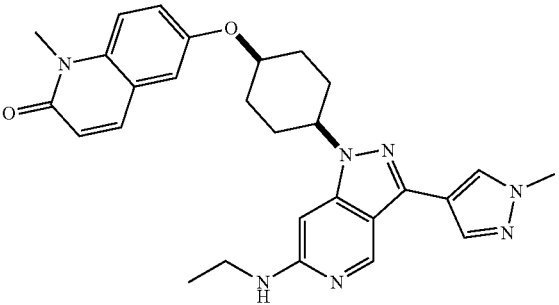 | B | B | C |
| 391 | 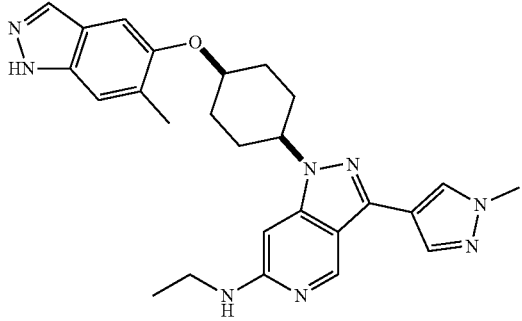 | C | B | C |
| 392 | 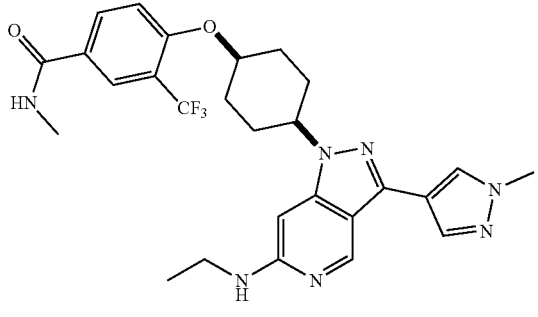 | B | A | B |
| 393 | 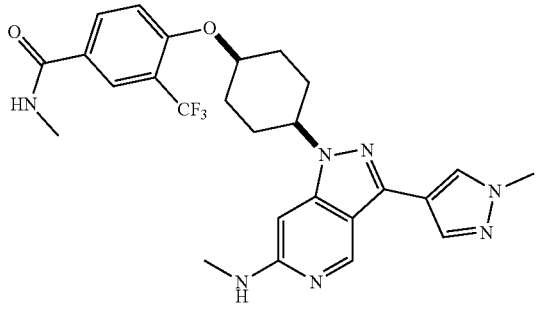 | A | A | B |

TABLE 1-continued
| Ex. | | AXL enzyme IC$_{50}$ | MER enzyme IC$_{50}$ | TYRO3 enzyme IC$_{50}$ |
|---|---|---|---|---|
| 394 | 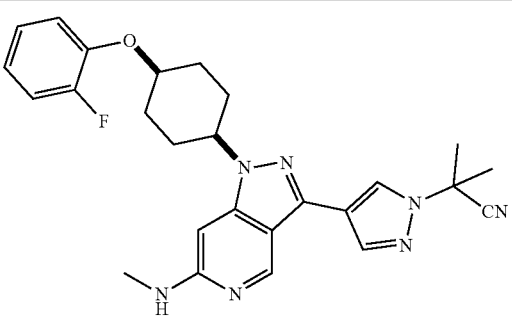 | A | A | B |
| 395 | 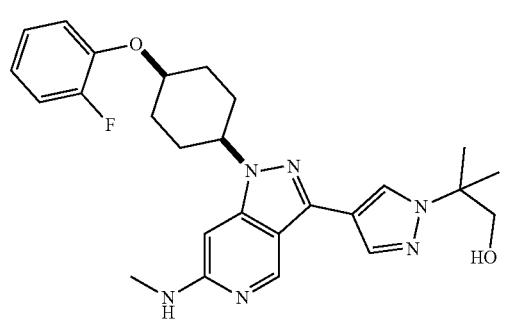 | A | A | B |
| 396 | 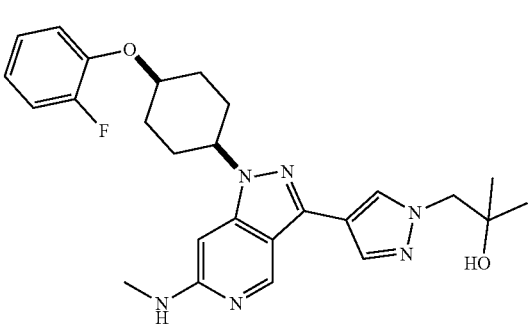 | A | A | B |
| 397 | 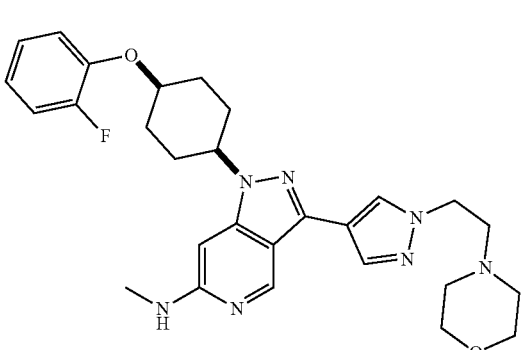 | A | A | B |

TABLE 1-continued

| Ex. | Structure | AXL enzyme IC$_{50}$ | MER enzyme IC$_{50}$ | TYRO3 enzyme IC$_{50}$ |
|---|---|---|---|---|
| 398 | | B | A | B |
| 399 | | A | A | B |
| 400 | | B | A | B |
| 401 | | B | A | B |

TABLE 1-continued
| Ex. | | AXL enzyme IC$_{50}$ | MER enzyme IC$_{50}$ | TYRO3 enzyme IC$_{50}$ |
|---|---|---|---|---|
| 402 | 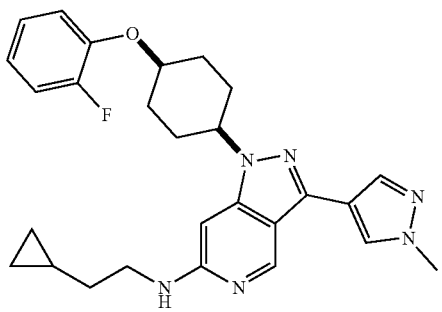 | D | C | B |
| 403 | 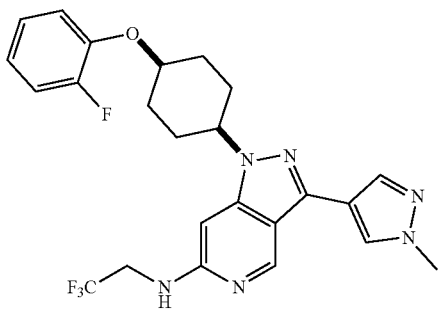 | C | B | B |
| 404 | 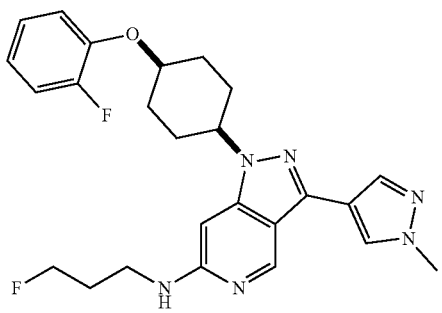 | C | B | B |
| 405 | 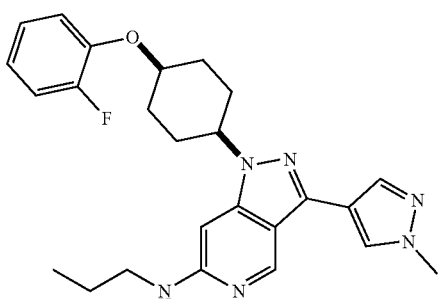 | B | B | A |
| 406 | 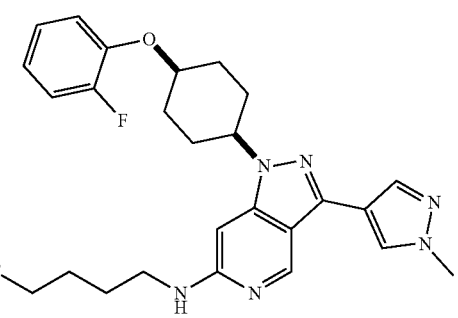 | C | C | B |

TABLE 1-continued

| Ex. | AXL enzyme IC$_{50}$ | MER enzyme IC$_{50}$ | TYRO3 enzyme IC$_{50}$ |
|---|---|---|---|
| 407 | C | C | C |
| 408 | A | A | B |
| 409 | A | A | B |
| 410 | A | A | B |

TABLE 1-continued

| Ex. | Structure | AXL enzyme IC$_{50}$ | MER enzyme IC$_{50}$ | TYRO3 enzyme IC$_{50}$ |
|---|---|---|---|---|
| 411 | | B | A | B |
| 412 | | B | A | B |
| 413 | | B | A | B |
| 414 | | A | A | B |
| 415 | | A | A | A |

TABLE 1-continued

| Ex. | | AXL enzyme IC$_{50}$ | MER enzyme IC$_{50}$ | TYRO3 enzyme IC$_{50}$ |
|---|---|---|---|---|
| 416 | | B | A | B |
| 417 | | B | B | B |
| 418 | | B | A | B |
| 419 | | A | A | B |

TABLE 1-continued

| Ex. | | AXL enzyme IC$_{50}$ | MER enzyme IC$_{50}$ | TYRO3 enzyme IC$_{50}$ |
|---|---|---|---|---|
| 420 | (structure) | A | A | B |
| 421 | (structure) | B | B | C |
| 422 | (structure) | A | A | B |
| 423 | (structure) | A | A | B |
| 424 | (structure) | B | B | C |

TABLE 1-continued

| Ex. | AXL enzyme IC$_{50}$ | MER enzyme IC$_{50}$ | TYRO3 enzyme IC$_{50}$ |
|---|---|---|---|
| 425 | B | A | B |
| 426 | B | A | B |
| 427 | A | A | B |
| 428 | A | A | B |

TABLE 1-continued

| Ex. | | AXL enzyme IC$_{50}$ | MER enzyme IC$_{50}$ | TYRO3 enzyme IC$_{50}$ |
|---|---|---|---|---|
| 429 | | A | A | A |
| 430 | | B | A | B |
| 431 | | A | A | B |
| 432 | | A | A | A |
| 433 | | A | A | A |

TABLE 1-continued

| Ex. | AXL enzyme IC$_{50}$ | MER enzyme IC$_{50}$ | TYRO3 enzyme IC$_{50}$ |
|---|---|---|---|
| 434 | A | A | A |
| 435 | B | B | B |
| 436 | A | A | B |
| 437 | A | A | B |

TABLE 1-continued
| Ex. | | AXL enzyme IC$_{50}$ | MER enzyme IC$_{50}$ | TYRO3 enzyme IC$_{50}$ |
|---|---|---|---|---|
| 438 | 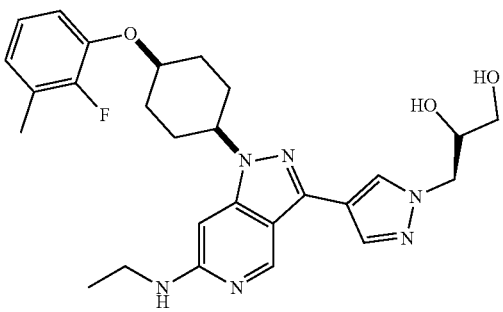 | B | A | B |
| 439 | 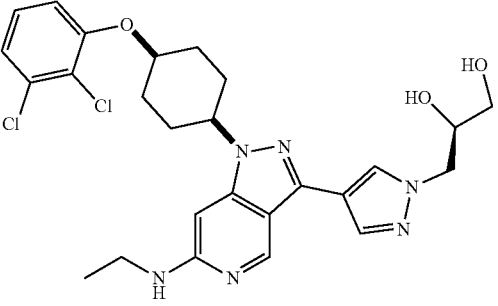 | A | A | B |
| 440 | 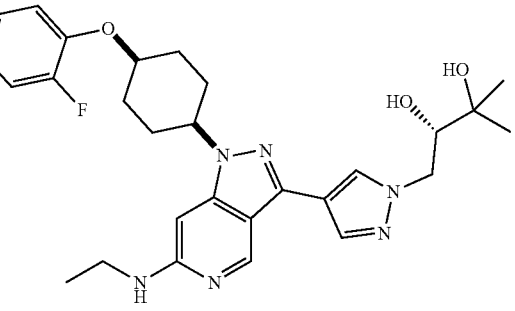 | A | A | B |
| 441 | 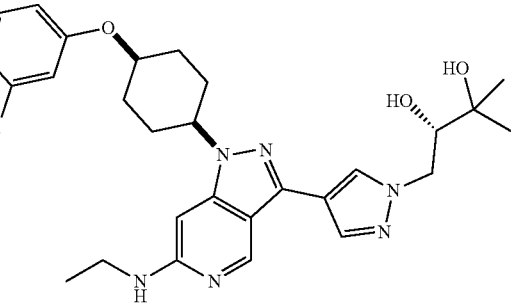 | A | A | B |
| 442 | 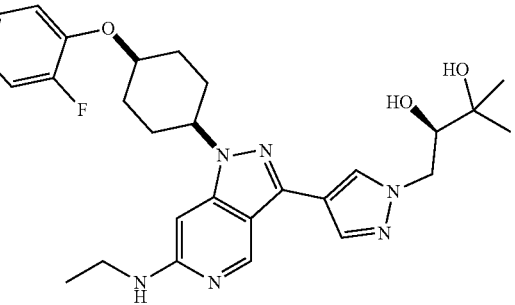 | A | A | B |

TABLE 1-continued
| Ex. | | AXL enzyme IC$_{50}$ | MER enzyme IC$_{50}$ | TYRO3 enzyme IC$_{50}$ |
|---|---|---|---|---|
| 443 | 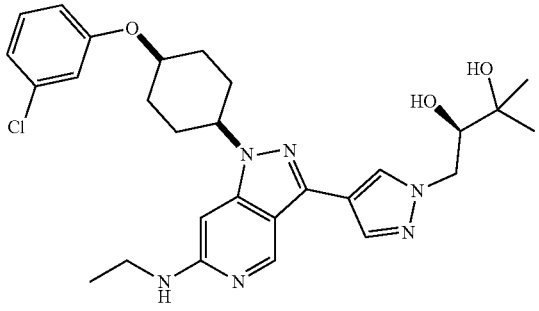 | B | A | B |
| 444 | 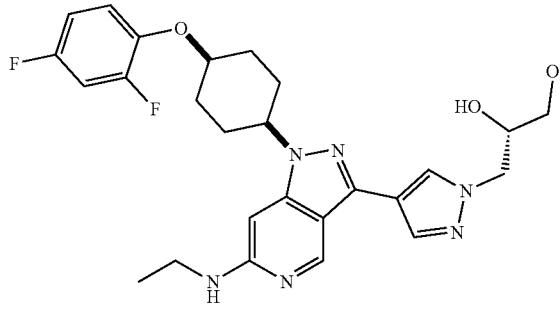 | A | A | B |
| 445 | 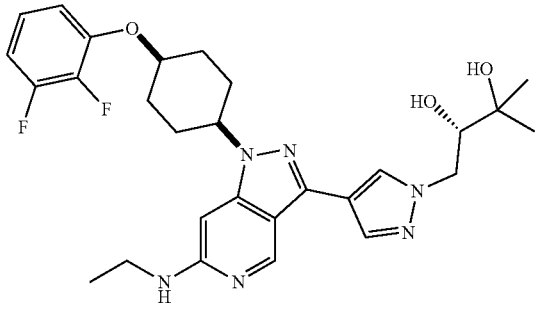 | A | A | A |
| 446 | 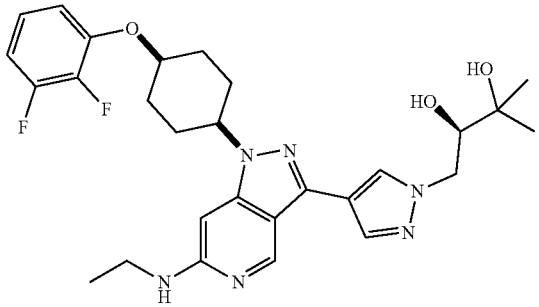 | A | A | A |

TABLE 1-continued

| Ex. | | AXL enzyme IC$_{50}$ | MER enzyme IC$_{50}$ | TYRO3 enzyme IC$_{50}$ |
|---|---|---|---|---|
| 447 | | A | A | B |
| 448 | | A | A | B |
| 449 | | B | B | C |
| 450 | | B | B | C |
| 451 | | B | B | C |

TABLE 1-continued

| Ex. | AXL enzyme IC$_{50}$ | MER enzyme IC$_{50}$ | TYRO3 enzyme IC$_{50}$ |
|---|---|---|---|
| 452 | B | B | C |
| 453 | B | B | C |
| 454 | B | B | D |
| 455 | B | B | D |

TABLE 1-continued

| Ex. | | AXL enzyme IC$_{50}$ | MER enzyme IC$_{50}$ | TYRO3 enzyme IC$_{50}$ |
|---|---|---|---|---|
| 456 | | B | B | C |
| 457 | | B | B | D |
| 458 | | B | B | D |
| 459 | | B | B | D |
| 460 | | A | B | B |

TABLE 1-continued
| Ex. | AXL enzyme IC$_{50}$ | MER enzyme IC$_{50}$ | TYRO3 enzyme IC$_{50}$ |
|---|---|---|---|
| 461 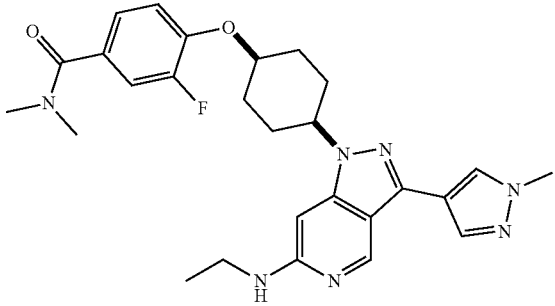 | C | B | C |
| 462 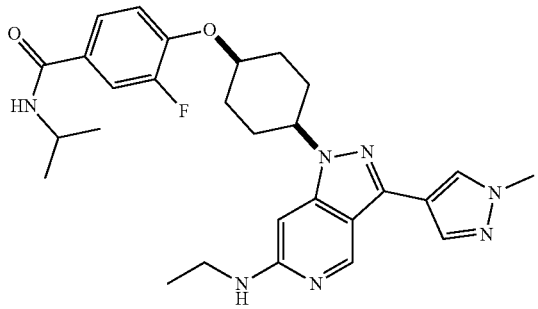 | B | B | C |
| 463 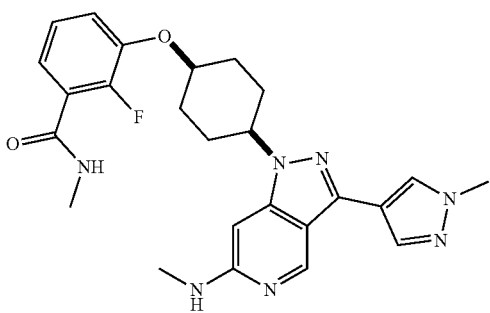 | B | B | B |
| 464 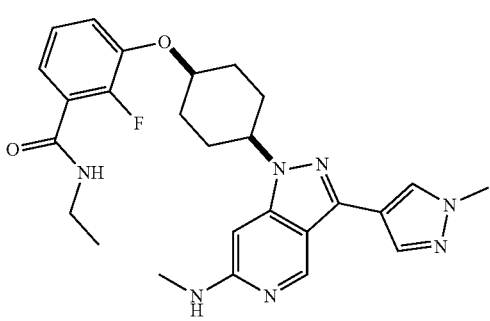 | B | B | C |

TABLE 1-continued

| Ex. | | AXL enzyme IC$_{50}$ | MER enzyme IC$_{50}$ | TYRO3 enzyme IC$_{50}$ |
|---|---|---|---|---|
| 465 | | B | B | C |
| 466 | | B | B | D |
| 467 | | B | B | C |
| 468 | | B | B | C |
| 469 | | C | B | C |

TABLE 1-continued

| Ex. | | AXL enzyme IC$_{50}$ | MER enzyme IC$_{50}$ | TYRO3 enzyme IC$_{50}$ |
|---|---|---|---|---|
| 470 | | A | A | B |
| 471A | | A | A | B |
| 471B | | A | A | B |
| 472 | | B | B | C |

TABLE 1-continued

| Ex. | | AXL enzyme IC$_{50}$ | MER enzyme IC$_{50}$ | TYRO3 enzyme IC$_{50}$ |
|---|---|---|---|---|
| 473 | | B | B | C |
| 474 | | C | C | C |
| 475 | | C | C | D |
| 476 | | C | C | D |

TABLE 1-continued
| Ex. | | AXL enzyme IC$_{50}$ | MER enzyme IC$_{50}$ | TYRO3 enzyme IC$_{50}$ |
|---|---|---|---|---|
| 477 | 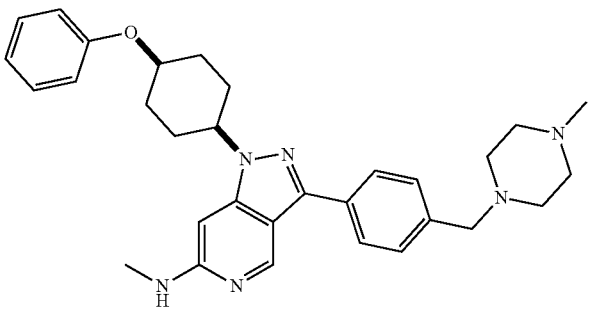 | A | A | B |
| 478 | 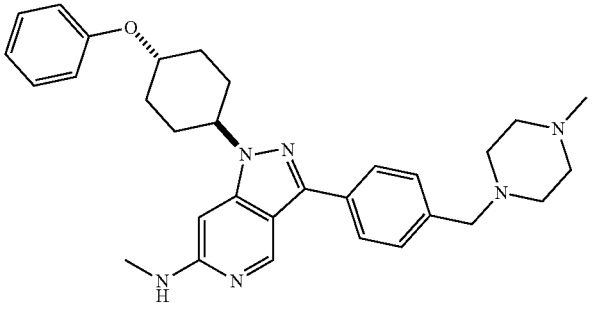 | B | B | C |
| 479 | 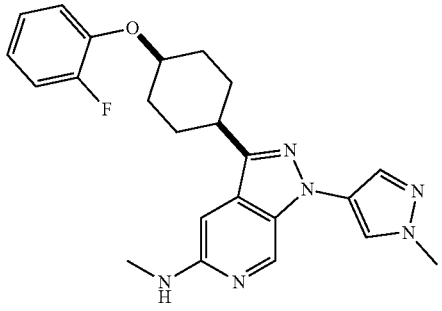 | A | A | B |
| 480 | 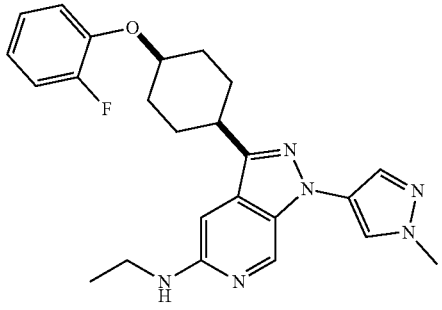 | B | B | B |
| 481 | 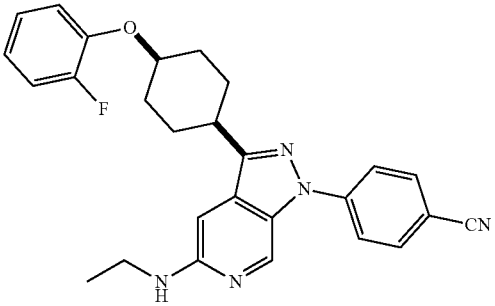 | C | B | C |

TABLE 1-continued

| Ex. | AXL enzyme IC$_{50}$ | MER enzyme IC$_{50}$ | TYRO3 enzyme IC$_{50}$ |
|---|---|---|---|
| 482 | B | A | B |
| 483 | B | B | C |
| 484 | C | B | C |
| 485 | B | B | B |

TABLE 1-continued
| Ex. | | AXL enzyme IC$_{50}$ | MER enzyme IC$_{50}$ | TYRO3 enzyme IC$_{50}$ |
|---|---|---|---|---|
| 486 | 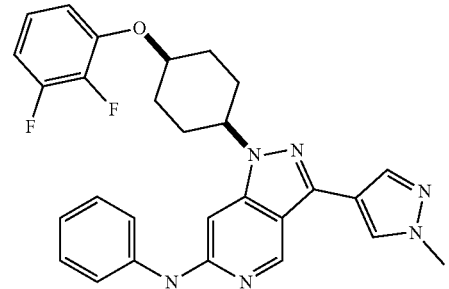 | D | C | B |
| 487 | 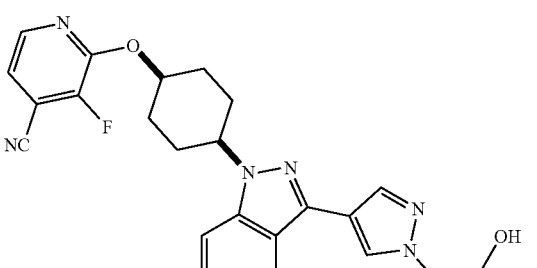 | A | A | A |
| 488 | 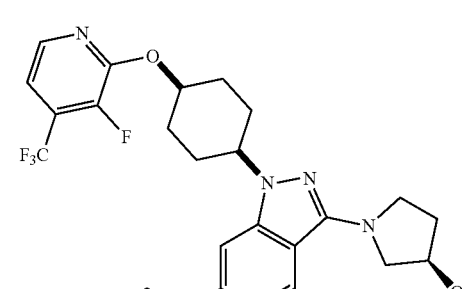 | A | A | B |
| 489 | 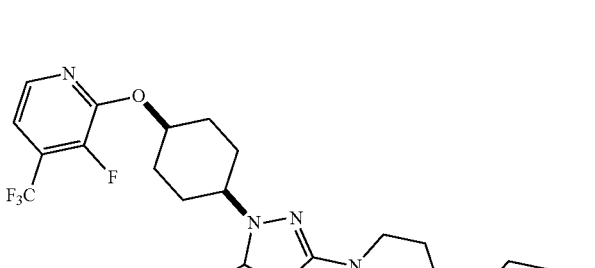 | A | A | B |

TABLE 1-continued
| Ex. | | AXL enzyme IC$_{50}$ | MER enzyme IC$_{50}$ | TYRO3 enzyme IC$_{50}$ |
|---|---|---|---|---|
| 490 | 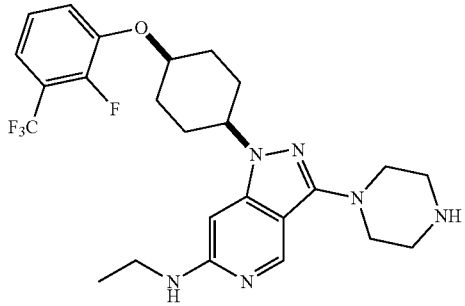 | A | A | A |
| 491 | 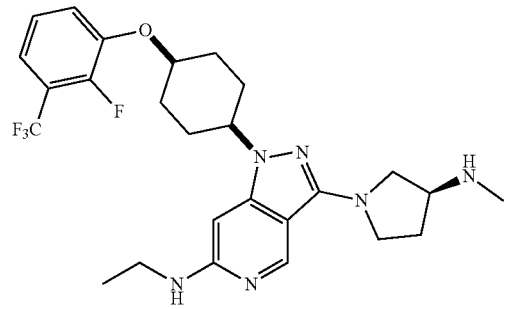 | A | A | B |
| 492 | 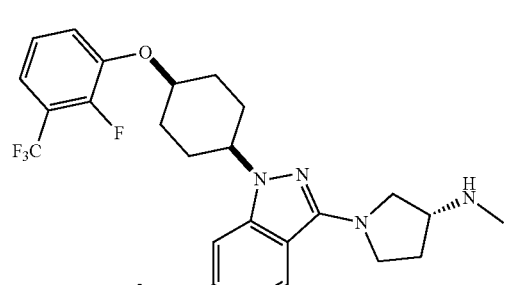 | A | A | B |
| 493 | 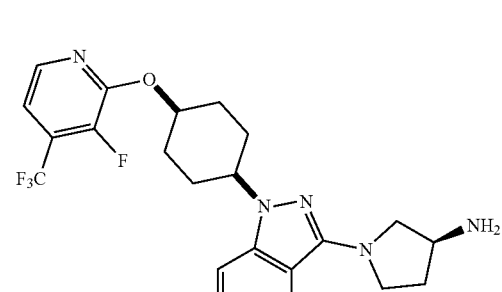 | A | A | B |

TABLE 1-continued
| Ex. | | AXL enzyme IC$_{50}$ | MER enzyme IC$_{50}$ | TYRO3 enzyme IC$_{50}$ |
|---|---|---|---|---|
| 494 | 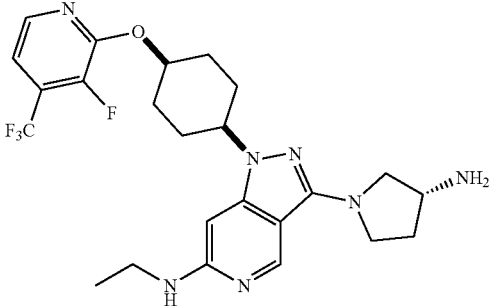 | A | A | B |
| 495 | 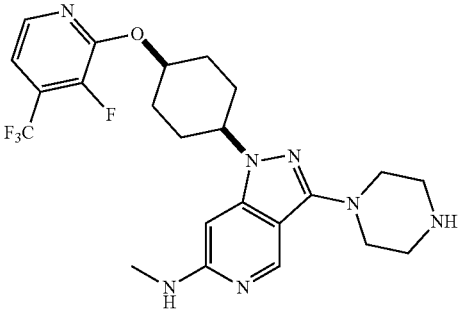 | A | A | A |
| 496 | 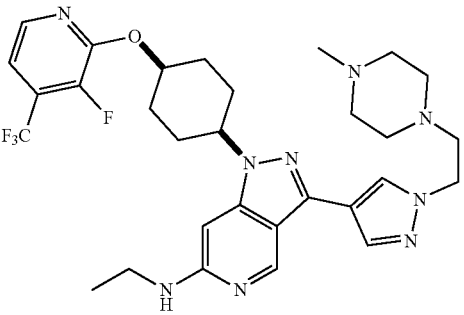 | A | A | A |
| 497 | 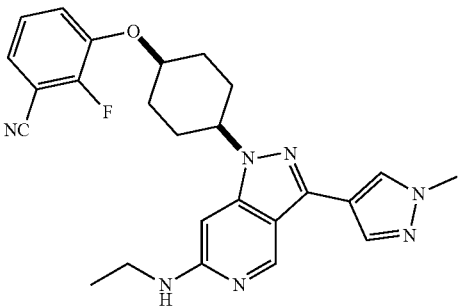 | A | A | A |

TABLE 1-continued
| Ex. | | AXL enzyme IC$_{50}$ | MER enzyme IC$_{50}$ | TYRO3 enzyme IC$_{50}$ |
|---|---|---|---|---|
| 498 | 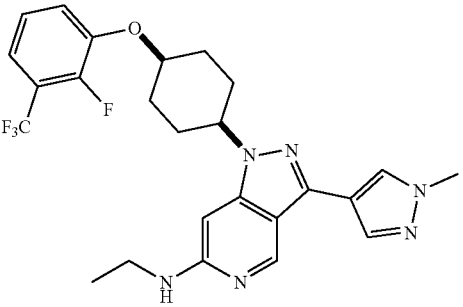 | A | A | B |
| 499 | 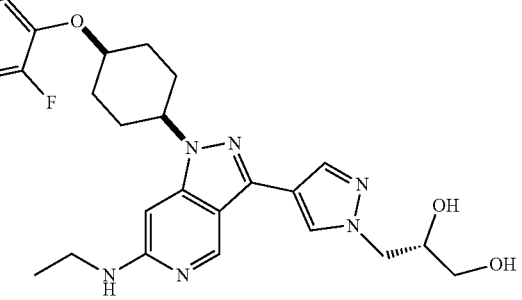 | A | A | B |
| 500 | 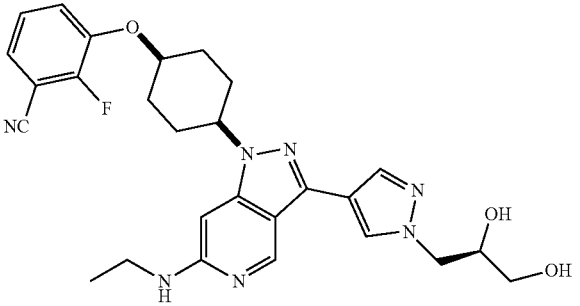 | A | A | A |
| 501 | 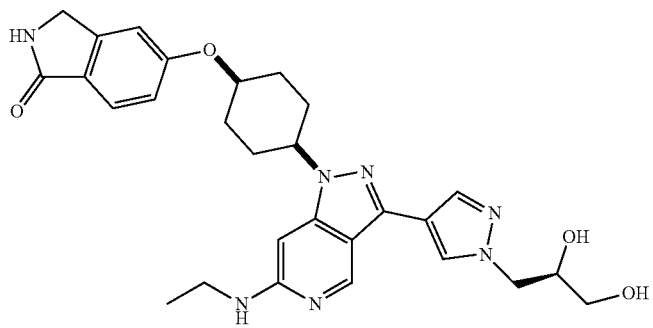 | A | A | B |

TABLE 1-continued
| Ex. | | AXL enzyme IC$_{50}$ | MER enzyme IC$_{50}$ | TYRO3 enzyme IC$_{50}$ |
|---|---|---|---|---|
| 502 | 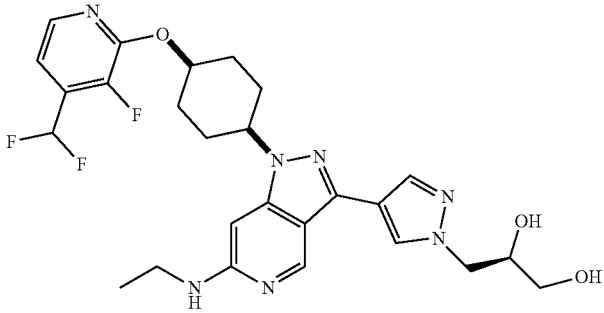 | A | A | B |
| 503 | 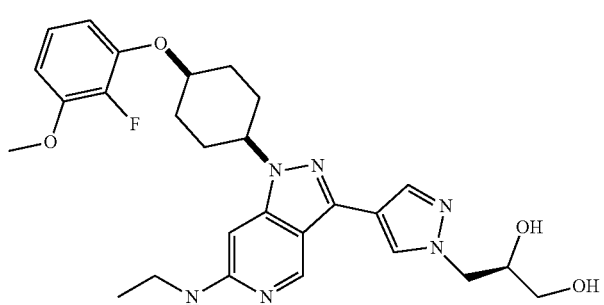 | A | A | B |
| 504 | 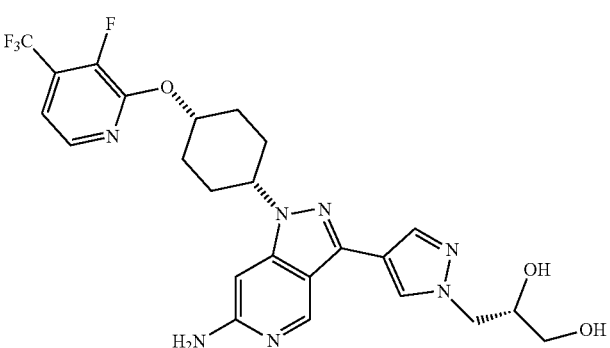 | B | B | D |
| 505 | 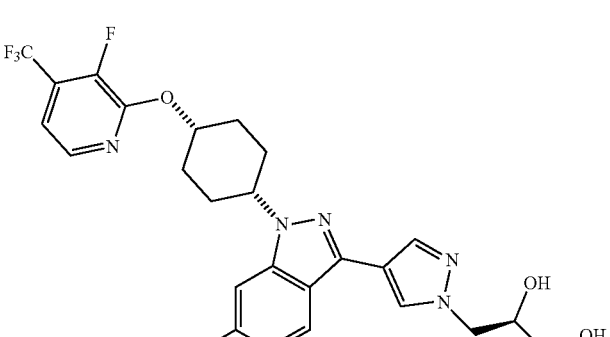 | B | C | D |

TABLE 1-continued

| Ex. | | AXL enzyme IC$_{50}$ | MER enzyme IC$_{50}$ | TYRO3 enzyme IC$_{50}$ |
|---|---|---|---|---|
| 506 | | A | A | A |
| 507 | | A | A | A |
| 508 | | A | A | B |
| 509 | | A | A | B |

TABLE 1-continued

| Ex. | | AXL enzyme IC$_{50}$ | MER enzyme IC$_{50}$ | TYRO3 enzyme IC$_{50}$ |
|---|---|---|---|---|
| 510 | (structure) | A | A | B |

Synthetic Examples

Synthesis of Synthetic Intermediates

Intermediate 1 cis-4-((tert-butyldimethylsilyl)oxy)cyclohexyl 4-methylbenzenesulfonate)

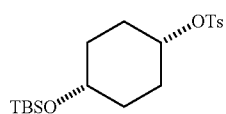

Step A: Cyclohexane-1,4-diol (1000 g, 8609 mmol) was dissolved in DMF (5000 mL) and cooled to 0° C. and treated with 1H-imidazole (146.5 g, 2152 mmol), followed by tert-butylchlorodimethylsilane (324.4 g, 2152 mmol) in portions, keeping the temperature below 5° C. The reaction mixture was warmed to room temperature overnight. The reaction mixture was partitioned between 9 L 80% brine and 4 L MTBE, washed with brine and concentrated to an oil and dried under high vacuum in 40° C. water bath to afford crude 4-((tert-butyldimethylsilyl)oxy)cyclohexan-1-ol (473 g, 2053 mmol, 95.38% yield) as an oil.

Step B: 4-((tert-butyldimethylsilyl)oxy)cyclohexan-1-ol (473 g, 2053 mmol) was dissolved in pyridine (4v) and cooled in ice bath. 4-Methylbenzenesulfonyl chloride (391 g, 2053 mmol) was added and allowed to warm to room temperature overnight. The reaction mixture was poured into water (15 v) and stirred for 60 min. The solids were filtered, washed with water, and dried under vacuum at 40° C. overnight to afford 750 g of crude material as an off-white solid.

Step C: Crude cis-trans 4-((tert-butyldimethylsilyl)oxy) cyclohexyl 4-methylbenzenesulfonate (1:1 mix of cis and trans) was suspended in hexanes (1 v) and warmed to reflux. The solution was allowed to fully cool to room temperature overnight. The resultant solids were filtered to afford an 8:1 mixture of cis-trans as a white solid. Two additional crystallizations with 1 volume of hexanes results in >99:1 purity for cis-4-((tert-butyldimethylsilyl)oxy)cyclohexyl 4-methylbenzenesulfonate.

Intermediate 2 trans-4-((tert-butyldimethylsilyl)oxy)cyclohexyl 4-methylbenzenesulfonate)

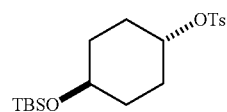 [SMILES: Cc1ccc(S(=O)(=O)O[C@H]2CC[C@H](O[Si](C)(C)C(C)(C)C)CC2)cc1]

The filtrate from the first crystallization from the preparation of Intermediate 1, Step C, was concentrated and purified over silica gel (0-8% EtOAc in hexane) to afford trans-4-((tert-butyldimethylsilyl)oxy)cyclohexyl 4-methylbenzenesulfonate). The trans isomer was the faster eluting isomer.

Intermediate 3

3-bromo-1-((1r,4r)-4-((tert-butyldimethylsilyl)oxy) cyclohexyl)-6-chloro-1H-pyrazolo[4,3-c]pyridine

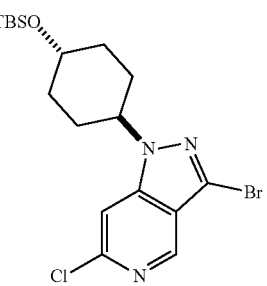

Step A: 6-chloro-1H-pyrazolo[4,3-c]pyridine (1.0 eq) was added to DMF (3v) and the solution was heated to 27° C. (internal temperature should not exceed 35° C.). NBS (1.2 eq) was dissolved in DMF (3v) and added to the reaction over 1.5 h while maintaining the internal temperature at 22-32° C. After 4 h the reaction was cooled to 0° C. and 10% sodium thiosulfate (1.5v) was added dropwise while keeping the internal temperature below 20° C. Water (11 v) was added slowly. The solids were filtered and washed with water (5v). The wet cake was suspended in DCM (3v) and slurried at 22° C. for 1 h. The solids were filtered and washed with DCM (2v). The solids were dried in a vacuum oven at 35° C. for 20 h. (1s,4s)-4-((tert-butyldimethylsilyl)oxy)cyclohexyl 4-methylbenzenesulfonate was isolated as a yellow solid (131 g, 87%).

Step B: (1s,4s)-4-((tert-butyldimethylsilyl)oxy)cyclohexyl 4-methylbenzenesulfonate (1 eq), 6-chloro-1H-pyrazolo[4,3-c]pyridine (2 eq) and $K_3PO_4$ (2.5 eq) were added to a round bottom flask equipped with a large magnetic stir bar. DMA (8 v) was then added and the reaction was heated to 85° C. After 20 h, the reaction was cooled to room temperature and filtered through Celite®. The inorganic solids were washed with EtOAc (10v). Water (10 v) was added and the layers were separated. The aqueous solution was extracted once with EtOAc (5v). The combined organic layers were washed with water (10 v) twice. The EtOAc solution was concentrated and the product was chromatographed with (0 to 5% EtOAc/heptane) to afford 3-bromo-1-((1r,4r)-4-((tert-butyldimethylsilyl)oxy)cyclohexyl)-6-chloro-1H-pyrazolo[4,3-c]pyridine (68%) as a white solid.

Using the procedure for the preparation of Intermediate 3, the following compound was also synthesized:

| Intermediate | Structure | Name |
|---|---|---|
| 4 | 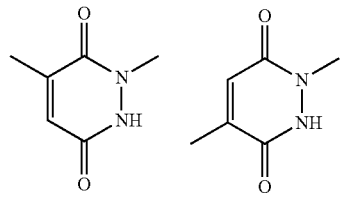 | 3-bromo-1-((1s,4s)-4-((tert-butyldimethylsilyl)oxy)cyclohexyl)-6-chloro-1H-pyrrolo[3,2-c]pyridine |

Intermediate 5

3-bromo-6-chloro-1-((2-(trimethylsilyl)ethoxy)methyl)-1H-pyrazolo[4,3-c]pyridine

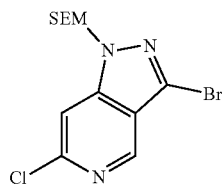 [SMILES: C[Si](C)(C)CCOCn1nc(Br)c2cnc(Cl)cc21]

3-Bromo-6-chloro-1H-pyrazolo[4,3-c]pyridine (1.0 g, 4.30 mmol) was dissolved in DMF (20 mL) and cooled in ice bath. Sodium hydride (0.189 g, 4.73 mmol) was added and the reaction stirred at room temperature for 5 min. (2-(chloromethoxy)ethyl)trimethylsilane (0.914 mL, 5.16 mmol) was added and the reaction was stirred overnight. The reaction mixture was partitioned between 50% brine and MTBE. The reaction mixture was extracted with 50% brine, dried over sodium sulfate, filtered and concentrated. Purified over silica gel (50 to 100% DCM in hexanes) to afford 3-bromo-6-chloro-1-((2-(trimethylsilyl)ethoxy)methyl)-1H-pyrazolo[4,3-c]pyridine (1.30 g, 3.58 mmol, 83.3% yield) as a slowly crystallizing colorless oil.

Intermediate 6

1,5-dimethyl-1,2-dihydropyridazine-3,6-dione and 1,4-dimethyl-1,2-dihydropyridazine-3,6-dione To a solution of methylhydrazine (0.427 mL, 8.11 mmol) in HOAc (10 mL) in a pressure vessel, 3-methylfuran-2,5-dione (0.806 mL, 8.92 mmol) was added. The reaction mixture was sealed and heated to 120° C. overnight. The reaction mixture was concentrated and purified over silica gel (0 to 10% MeOH in EtOAc) to afford each isomer. The first eluting material was 1,5-dimethyl-1,2-dihydropyridazine-3,6-dione (300 mg, 2.14 mmol, 26.4% yield) and the later eluting material was 1,4-dimethyl-1,2-dihydropyridazine-3,6-dione (400 mg, 2.85 mmol, 35.2% yield).

Using the procedure for the preparation of Intermediate 6, the following compounds were also synthesized:

| Intermediate | Structure | Name |
|---|---|---|
| 7 | | 1-methyl-5-(trifluoromethyl)-1,2-dihydropyridazine-3,6-dione and 1-methyl-4-(trifluoromethyl)-1,2-dihydropyridazine-3,6-dione |
| 8 | 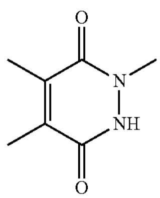 | 1,4,5-trimethyl-1,2-dihydropyridazine-3,6-dione |

Intermediate 9

1-benzyl-1,2-dihydropyridazine-3,6-dione

To a solution of 1 g of benzylhydrazine dihydrochloride (1.5 g, 7.7 mmol) in glacial AcOH (19 mL) was added 0.55 g maleic anhydride (0.83 g, 8.5 mmol) at room temperature. The reaction mixture was heated to 120° C. overnight. The reaction mixture was cooled to room temperature and added water (15 mL) and stirred for 10 minutes. The resultant solids were filtered and washed with water to afford 1-benzyl-1,2-dihydropyridazine-3,6-dione (1.0 g, 4.9 mmol, 64% yield) as a white powder.

Using the procedure in Intermediate 9, the following compounds were also synthesized:

| Intermediate | Structure | Name |
|---|---|---|
| 10 | 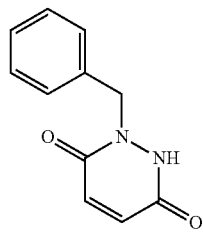 [SMILES: O=c1ccc(=O)n(Cc2ccccc2)[nH]1] | 1-isopropyl-1,2-dihydropyridazine-3,6-dione |
| 11 | 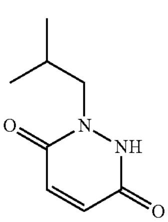 | 1-isobutyl-1,2-dihydropyridazine-3,6-dione |
| 12 | | 1-(4-methoxybenzyl)-1,2-dihydropyridazine-3,6-dione |

Intermediate 13

1-ethyl-1,2-dihydropyridazine-3,6-dione

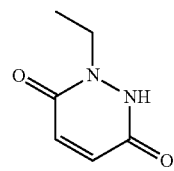

To a solution of ethylhydrazine oxalate (0.378 g, 2.52 mmol) in glacial AcOH (3.15 mL) was added 0.55 g of maleic anhydride (0.272 g, 2.77 mmol). The reaction mixture was heated to 120° C. overnight. The reaction mixture was cooled and water (30 mL) added, partitioned between 4:1 DCM:IPA (15 mL) and saturated NaHCO$_3$(50 mL). Extracted with 4:1 DCM:IPA (2×10 mL), dried over sodium sulfate, filtered and concentrated to afford 1-ethyl-1,2-dihydropyridazine-3,6-dione (0.129 g, 0.920 mmol, 36.6% yield) as a yellowish white powder Using the procedure for the preparation of Intermediate 13, the following compounds were also synthesized:

| Intermediate | Structure | Name |
|---|---|---|
| 14 | 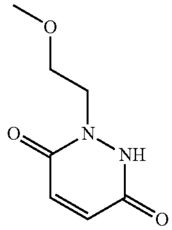 | 1-(2-methoxyethyl)-1,2-dihydropyridazine-3,6-dione |
| 15 | 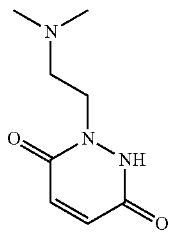 | 1-(2-(dimethylamino)ethyl)-1,2-dihydropyridazine-3,6-dione |
| 16 | 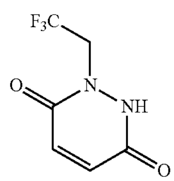 [SMILES: O=c1ccc(=O)n(CC(F)(F)F)[nH]1] | 1-(2,2,2-trifluoroethyl)-1,2-dihydropyridazine-3,6-dione |

Intermediate 17 tert-butyl (3-bromo-1-((2-(trimethylsilyl)ethoxy)methyl)-1H-pyrazolo[4,3-c]pyridin-6-yl)(ethyl)carbamate

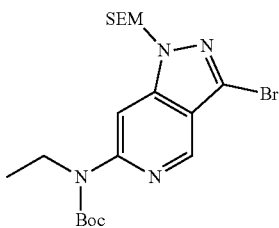 [SMILES: CCN(C(=O)OC(C)(C)C)c1cc2c(cn1)c(Br)nn2COCC[Si](C)(C)C]

Step A: 3-Bromo-6-chloro-1-((2-(trimethylsilyl)ethoxy)methyl)-1H-pyrazolo[4,3-c]pyridine (50.0 g, 138 mmol) was diluted with dry NMP (100 mL) and then purged with Argon for 15 mins in a large parr stainless steel pressure reactor equipped with a regulator. Ethylamine (219 mL, 70% in water, 2757 mmol) was added and then the reactor was sealed and heated to 125° C. for 16 h. The vessel was cooled in ice and then poured into water (1 L) and stirred for 1 h. Filtered and dried in a vacuum oven overnight. The solids were dissolved in EtOAc (500 mL) and washed with water (4×200 mL) and brine (200 mL), then dried over Na₂SO₄, filtered and concentrated to afford a 3-bromo-N-ethyl-1-((2-(trimethylsilyl)ethoxy)methyl)-1H-pyrazolo[4,3-c]pyridin-6-amine (50.8 g, 99% yield) as a tan solid.

Step B: A solution of 3-bromo-N-ethyl-1-((2-(trimethylsilyl)ethoxy)methyl)-1H-pyrazolo[4,3-c]pyridin-6-amine (50.8 g, 137 mmol) in DCE (557 mL) was treated with Boc2O (89.6 g, 410 mmol) and DMAP (836 mg, 6.84 mmol). The reaction mixture was heated to 50° C. overnight. The reaction mixture was concentrated, dissolved in DCM (1 L), washed with sat. NaHCO₃(2×400 mL), brine (200 mL), dried over Na₂SO₄, filtered and concentrated. The residue was purified over silica gel (5-10% EtOAc in hexanes) to afford tert-butyl (3-bromo-1-((2-(trimethylsilyl)ethoxy)methyl)-1H-pyrazolo[4,3-c]pyridin-6-yl)(ethyl)carbamate (54.5 g, 85% yield) as a syrup.

Using the procedure for the preparation of Intermediate 17, the following compound was also synthesized:

| Intermediate | Structure | Name |
|---|---|---|
| 18 | 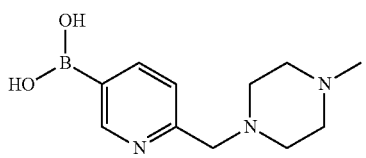 [SMILES: CN1CCN(Cc2ccc(B(O)O)cn2)CC1] | tert-butyl (3-bromo-1-((2-(trimethylsilyl)ethoxy)methyl)-1H-pyrazolo[4,3-c]pyridin-6-yl)(methyl)carbamate |

Intermediate 19

(6-((4-methylpiperazin-1-yl)methyl)pyridin-3-yl)boronic acid

To a mixture of 5-(4,4,5,5-Tetramethyl-1,3,2-dioxaborolan-2-yl)picolinaldehyde (0.300 g, 1.29 mmol) and HOAc (0.0884 mL, 1.54 mmol) in DCM (5 mL) was added a solution of 1-Methylpiperazine (0.143 mL, 1.29 mmol) in DCM (6 mL). To this mixture was added sodium triacetoxyborohydride (0.409 g, 1.93 mmol). After 45 mins, the reaction was diluted with 4:1 DCM:IPA (15 mL) and water (15 mL) and separated. Extracted with 4:1 DCM:IPA (2×15 mL), washed with brine (25 mL), dried over Na₂SO₄, filtered and concentrated to obtain crude (6-((4-methylpiperazin-1-yl)methyl)pyridin-3-yl)boronic acid (0.303 g, 1.29 mmol, 100% yield) as a yellow oil which was used in subsequent reactions without further purification.

Using the procedure described for the preparation of Intermediate 19, the following compound was also synthesized:

| Intermediate | Structure | Name |
|---|---|---|
| 20 | 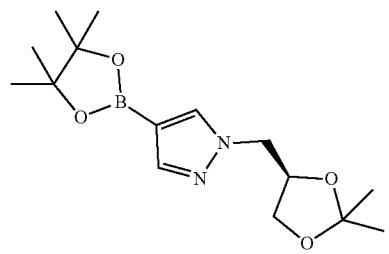 | 1-(2-((tert-butyldimethylsilyl)oxy)ethyl)-4-(4-(4,4,5,5-tetramethyl-1,3,2-dioxaborolan-2-yl)benzyl)piperazine |

Intermediate 21

(1r,4r)-4-((1-methyl-6-oxo-1,6-dihydropyridazin-3-yl)oxy)cyclohexyl 4-methylbenzenesulfonate

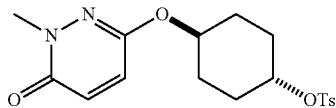 [SMILES: Cc1ccc(S(=O)(=O)O[C@H]2CC[C@H](Oc3ccc(=O)n(C)n3)CC2)cc1]

Step A: 6-hydroxy-2-methylpyridazin-3(2H)-one (1.0 g, 7.9 mmol) was dissolved in DMA (40 mL) and (1s,4s)-4-((tert-butyldimethylsilyl)oxy)cyclohexyl 4-methylbenzenesulfonate (6.1 g, 16 mmol) and cesium carbonate (5.2 g, 16 mmol) were added and heated to 85° C. overnight. The reaction mixture was diluted with water, extracted with EtOAc (×2), washed with brine, dried over sodium sulfate and concentrated. The residue was purified over silica gel (5-100% EtOAc in hexanes) to afford 6-(((1r,4r)-4-((tert-butyldimethylsilyl)oxy)cyclohexyl)oxy)-2-methylpyridazin-3(2H)-one (1.0 g, 37% yield) as a white solid.

Step B: 6-(((1r,4r)-4-((tert-butyldimethylsilyl)oxy)cyclohexyl)oxy)-2-methylpyridazin-3(2H)-one (1.0 g, 2.95 mmol) was diluted with THF (30 mL), and TBAF (8.9 mL, 8.9 mmol, 1M in TIF) was added and heated to 50° C. for 3 h. The reaction mixture was diluted with EtOAc, washed with 10% $K_2CO_3$ (×2), dried over sodium sulfate and concentrated to afford 6-(((1r,4r)-4-hydroxycyclohexyl)oxy)-2-methylpyridazin-3(2H)-one (272 mg, 41% yield).

Step C: 6-(((1r,4r)-4-hydroxycyclohexyl)oxy)-2-methylpyridazin-3(2H)-one (270 mg, 1.2 mmol) was dissolved in pyridine (12 mL) and TsCl (381 mg, 2.0 mmol) was added and stirred at room temperature overnight. The reaction mixture was diluted with water, extracted with EtOAc (×2), washed with 1N HCl, 10% $K_2CO_3$, dried over sodium sulfate, filtered and concentrated. The crude material was purified over silica gel (0-10% MeOH in DCM) to afford (1r,4r)-4-((1-methyl-6-oxo-1,6-dihydropyridazin-3-yl)oxy)cyclohexyl 4-methylbenzenesulfonate (268 mg, 59% yield).

Using the procedure for the preparation of Intermediate 21, the following compound was also synthesized:

| Intermediate | Structure | Name |
|---|---|---|
| 22 | 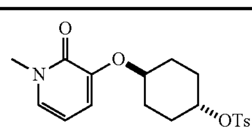 | (1r,4r)-4-((1-methyl-2-oxo-1,2-dihydropyridin-3-yl)oxy)cyclohexyl 4-methylbenzenesulfonate |

Intermediate 23

(R)-1-((2,2-dimethyl-1,3-dioxolan-4-yl)methyl)-4-(4,4,5,5-tetramethyl-1,3,2-dioxaborolan-2-yl)-1H-pyrazole Step A: A 3 neck, 2 liter round bottom flask equipped with an overhead stirrer, condenser with a nitrogen inlet, and a temperature probe was charged with 4-iodo-1H-pyrazole (20 g, 103 mmol) and dry DMA (400 mL). To this was added cesium carbonate (67 g, 206 mmol) and (S)-4-(chloromethyl)-2,2-dimethyl-1,3-dioxolane (31 g, 206 mmol). The mixture was heated to 100° C. overnight. The mixture was diluted with water (750 mL), extracted with MTBE (3×400 mL), washed with water (4×200 mL), brine (400 mL), dried over sodium sulfate, filtered and concentrated. The residue was purified over silica gel (0-40% EtOAc in hexanes) to afford (R)-1-((2,2-dimethyl-1,3-dioxolan-4-yl)methyl)-4-iodo-1H-pyrazole (29.7 g, 93% yield) as an oil.

Step B: (R)-1-((2,2-dimethyl-1,3-dioxolan-4-yl)methyl)-4-iodo-1H-pyrazole (29.7 g, 96.4 mmol) was charged with dry THF (450 mL) and 2-isopropoxy-4,4,5,5-tetramethyl-1,3,2-dioxaborolane (29.5 mL, 145 mmol). The reaction mixture was cooled to 0° C. and iPrMgCl.LiCl (111 mL, 145 mmol, 1.3 M in TIF) was then added via addition funnel over 5 minutes. The reaction mixture was stirred at 0° C. for 15 minutes then allowed to warm to room temperature. The reaction mixture was cooled to 0° C. and quenched carefully with saturated ammonium chloride solution (250 mL), diluted with water (250 mL), extracted with EtOAc (3×600 mL), and washed with brine (400 mL). The organic layer was dried over sodium sulfate and concentrated. The reside was purified over silica gel (10-50% EtOAc in hexanes) to afford (R)-1-((2,2-dimethyl-1,3-dioxolan-4-yl)methyl)-4-(4,4,5,5-tetramethyl-1,3,2-dioxaborolan-2-yl)-1H-pyrazole (28.3 g, 95% yield) as an oil.

Intermediate 24 tert-butyl (2,2,2-trifluoroethyl)carbamate

2,2,2-trifluoroethan-1-amine (397 μL, 5.05 mmol) was diluted with DCM (30 mL) followed by the addition of DIEA (882 μL, 5.05 mmol) and di-tert-butyl dicarbonate (1102 mg, 5.05 mmol). After stirring for 12 hours, the reaction was diluted with DCM and water. The layers were separated and the ethyl acetate was dried over MgSO4, filtered and concentrated. The material was purified on silica gel (10-30% ethyl acetate/hexanes) to afford tert-butyl (2,2,2-trifluoroethyl)carbamate (850 mg, 4.27 mmol, 84.5% yield).

Using the procedure for the preparation of Intermediate 24, the following compounds were also synthesized:

| Intermediate | Structure | Name |
| --- | --- | --- |
| 25 | 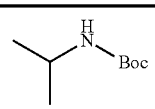 | tert-butyl isopropylcarbamate |
| 26 | 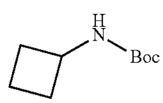 [SMILES: CC(C)(C)OC(=O)NC1CCC1] | tert-butyl cyclobutylcarbamate |
| 27 | 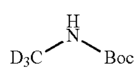 | tert-butyl (methyl-d3)carbamate |
| 28 | 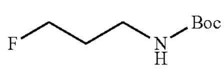 [SMILES: CC(C)(C)OC(=O)NCCCF] | tert-butyl (3-fluoropropyl)carbamate |
| 29 | 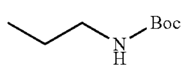 | tert-butyl propylcarbamate |
| 30 | 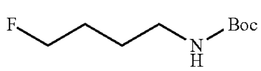 [SMILES: CC(C)(C)OC(=O)NCCCCF] | tert-butyl (4-fluorobutyl)carbamate |

Intermediate 31

3-fluoro-1-(4-(4,4,5,5-tetramethyl-1,3,2-dioxaborolan-2-yl)benzyl)azetidine

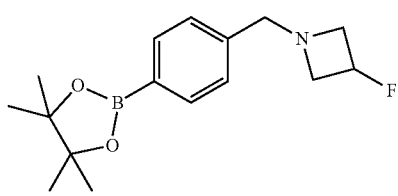 [SMILES: CC1(C)OB(c2ccc(CN3CC(F)C3)cc2)OC1(C)C]

2-(4-(bromomethyl)phenyl)-4,4,5,5-tetramethyl-1,3,2-dioxaborolane (250 mg, 0.84 mmol) was dissolved in acetonitrile (8 mL). 3-fluoroazetidine hydrochloride (103 mg, 0.93 mmol) and DIEA (0.37 mL, 2.1 mmol) were added and the reaction was heated to 65° C. overnight. The reaction mixture was concentrated and partitioned between EtOAc and 10% K2CO3, dried over sodium sulfate, filtered and concentrated to afford crude 3-fluoro-1-(4-(4,4,5,5-tetramethyl-1,3,2-dioxaborolan-2-yl)benzyl)azetidine (225 mg, 92% yield). Used without further purification.

Intermediate 32

6-methoxy-2-(trifluoromethyl)pyridin-3-ol

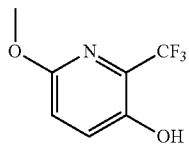

Step A: 3-iodo-6-methoxy-2-(trifluoromethyl)pyridine (700 mg, 2.31 mmol) was dissolved in THF (15 mL) and cooled to −78° C. Butyllithium (2.5 M, 1016 μL, 2.54 mmol) was added dropwise and allowed to stir for 5 min. Trimethyl borate (525 μL, 4.62 mmol) was added and the reaction allowed to warm to room temperature. The reaction mixture was quenched with 10% citric acid, extracted with EtOAc, dried over sodium sulfate, filtered and concentrated to afford crude (6-methoxy-2-(trifluoromethyl)pyridin-3-yl)boronic acid (400 mg, 1.81 mmol, 78.4% yield) taken on to next reaction.

Step B: (6-methoxy-2-(trifluoromethyl)pyridin-3-yl)boronic acid (400 mg, 1.81 mmol) was dissolved in THF (10 mL) and a premixed solution of hydrogen peroxide (222 μL, 2.17 mmol) and 1M sodium hydroxide (2173 μL, 2.17 mmol). The reaction mixture was stirred at room temperature for 2 h. Additional sodium hydroxide (200 μL) was added and stirred for another 2 h. The reaction mixture was partitioned between 1N HCl and EtOAc, washed with brine, dried over sodium sulfate, filtered and concentrated. The residue was purified over silica gel (20% EtOAc in hexanes) to afford 6-methoxy-2-(trifluoromethyl)pyridin-3-ol (290 mg, 1.50 mmol, 82.9% yield) as a white solid.

Intermediate 33

6-(benzyloxy)pyridin-2-ol

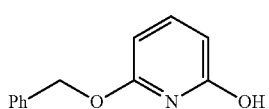

Step A: Phenylmethanol (1.798 mL, 17.38 mmol) was added to NaH (60% in mineral oil, 0.7994 g, 19.99 mmol) in THF (17.38 mL) and heated to 50° C. for 45 min. The reaction mixture was cooled to room temperature and 2,6-difluoropyridine (1.57 mL, 17.3 mmol) was added and stirred for 2 hours and then partitioned between EtOAc and water, washed with brine and dried over Na2SO4, filtered and concentrated to afford 2-(benzyloxy)-6-fluoropyridine (2.65 g, 13.04 mmol, 75.04% yield).

Step B: (2,4-dimethoxyphenyl)methanol (1.545 mL, 10.63 mmol) was added to NaH (0.4605 g, 11.51 mmol) in THF (44.2 mL) and heated to 50° C. for 30 min. The reaction mixture was cooled to room temperature and 2-(benzyloxy)-6-fluoropyridine (1.80 g, 8.858 mmol) in THF (2 mL) was added slowly and heated to 65° C. overnight. The reaction mixture was partitioned between EtOAc and water, washed with brine, dried over sodium sulfate, filtered and concentrated. The residue was purified over silica gel (1-8% EtOAc in hexanes) to afford 2-(benzyloxy)-6-((2,4-dimethoxybenzyl)oxy)pyridine (2.428 g, 6.909 mmol, 78.01% yield).

Step C: TFA (1.06 mL, 13.8 mmol) was added to 2-(benzyloxy)-6-((2,4-dimethoxybenzyl)oxy)pyridine (2.428 g, 6.909 mmol) in DCM (17.2 mL) at room temp. The reaction mixture was stirred for 30 min and then concentrated. The residue was diluted with DCM and MP carbonate resin was added and the mixture was stirred for 30 min, then filtered and concentrated. The residue was purified over silica gel (10-90% EtOAc in hexanes) to afford 6-(benzyloxy)pyridin-2-ol (1.34 g, 6.659 mmol, 96.38% yield).

Intermediate 34

(1s,4s)-4-(pyridin-2-yloxy)cyclohexyl 4-methylbenzenesulfonate

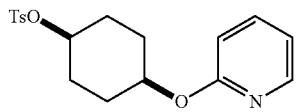

Step A: (1r,4r)-cyclohexane-1,4-diol (500 mg, 4.304 mmol), pyridin-2-ol (272.9 mg, 2.870 mmol) and triphenylphosphine (752.7 mg, 2.870 mmol) were dissolved in THF (10 mL). DIAD (565.0 µL, 2.870 mmol) was added dropwise and stirred overnight. The reaction mixture was partitioned between 50% brine and EtOAc, dried over sodium sulfate, filtered and concentrated. The residue was purified over silica gel (30 to 80% EtOAc in hexanes) to afford (1s,4s)-4-(pyridin-2-yloxy)cyclohexan-1-ol (113 mg, 0.5847 mmol, 20.38% yield).

Step B: (1s,4s)-4-(pyridin-2-yloxy)cyclohexan-1-ol (110 mg, 0.569 mmol) was dissolved in pyridine (3 mL) and 4-methylbenzenesulfonyl chloride (130 mg, 0.683 mmol) was added and the reaction was stirred overnight. The reaction mixture was concentrated, partitioned between water and EtOAc, dried over sodium sulfate, filtered and concentrated. The residue was purified over silica gel (20 to 80% EtOAc in hexanes) to afford (1s,4s)-4-(pyridin-2-yloxy)cyclohexyl 4-methylbenzenesulfonate (75 mg, 0.216 mmol, 37.9% yield) as a white solid.

Using the procedure for the preparation of Intermediate 34, the following compounds were also synthesized:

| Intermediate | Structure | Name |
|---|---|---|
| 35 | TsO""⟨cyclohexyl⟩—O—pyridine | (1r,4r)-4-(pyridin-2-yloxy)cyclohexyl 4-methylbenzenesulfonate |
| 36 | TsO""⟨cyclohexyl⟩—O—phenyl | (1r,4r)-4-phenoxycyclohexyl 4-methylbenzenesulfonate |
| 37 | TsO⟨cyclohexyl⟩—O—phenyl | (1s,4s)-4-phenoxycyclohexyl 4-methylbenzenesulfonate |
| 38 | TsO""⟨cyclohexyl⟩—O—(2-F-phenyl) | (1r,4r)-4-(2-fluorophenoxy)cyclohexyl 4-methylbenzenesulfonate |
| 39 | TsO⟨cyclohexyl⟩—O—(2-F-phenyl) | (1s,4s)-4-(2-fluorophenoxy)cyclohexyl 4-methylbenzenesulfonate |
| 40 | TsO⟨cyclohexyl⟩—O—(3-F-phenyl) | (1s,4s)-4-(3-fluorophenoxy)cyclohexyl 4-methylbenzenesulfonate |
| 41 | TsO⟨cyclohexyl⟩—O—(4-F-phenyl) | (1s,4s)-4-(4-fluorophenoxy)cyclohexyl 4-methylbenzenesulfonate |

Intermediate 42 tert-butyl methyl(3-(4-(4-methylpiperazine-1-carbonyl)phenyl)-1H-pyrazolo[4,3-c]pyridin-6-yl)carbamate

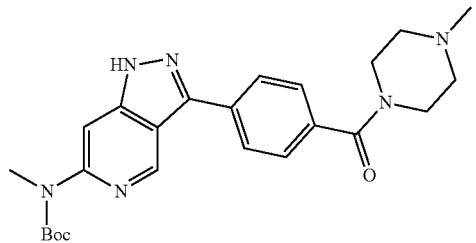

Step A: 3-bromo-N-methyl-1-((2-(trimethylsilyl)ethoxy)methyl)-1H-pyrazolo[4,3-c]pyridin-6-amine (2.35 g, 6.58 mmol) was dissolved in dioxane (40 mL) and (4-methylpiperazin-1-yl)(4-(4,4,5,5-tetramethyl-1,3,2-dioxaborolan-2-yl)phenyl)methanone (2.39 g, 7.23 mmol) and $Na_2CO_3$ (6.58 mL, 13.2 mmol) was added. Nitrogen was bubbled through the mixture for 5 min. $Pd(PPh_3)_4$ (0.380 g, 0.329 mmol) was added and the reaction was heated to 95° C. overnight. The reaction mixture was decanted, rinsed with EtOAc, concentrated and purified over silica gel (2 to 20% MeOH in DCM with 0.2% NH3) to afford (4-(6-(methylamino)-1-((2-(trimethylsilyl)ethoxy)methyl)-1H-pyrazolo[4,3-c]pyridin-3-yl)phenyl)(4-methylpiperazin-1-yl)methanone (2.25 g, 4.68 mmol, 71.2% yield) as a foam.

Step B: (4-(6-(methylamino)-1-((2-(trimethylsilyl)ethoxy)methyl)-1H-pyrazolo[4,3-c]pyridin-3-yl)phenyl)(4-methylpiperazin-1-yl)methanone (2.25 g, 4.68 mmol) was dissolved in DCM (40 mL) and di-tert-butyl dicarbonate (3.06 g, 14.0 mmol) was added, followed by N,N-dimethylpyridin-4-amine (0.0286 g, 0.234 mmol). The reaction mixture was heated to reflux overnight. The reaction mixture was partitioned between water and DCM, dried over sodium sulfate, filtered and concentrated. The residue was purified over silica gel (1 to 15% MeOH in DCM, with 0.2% $NH_3$) to afford tert-butyl methyl(3-(4-(4-methylpiperazine-1-carbonyl)phenyl)-1-((2-(trimethylsilyl)ethoxy)methyl)-1H-pyrazolo[4,3-c]pyridin-6-yl)carbamate (2.55 g, 4.39 mmol, 93.8% yield) as a white foam.

Step C: tert-butyl methyl(3-(4-(4-methylpiperazine-1-carbonyl)phenyl)-1-((2-(trimethylsilyl)ethoxy)methyl)-1H-pyrazolo[4,3-c]pyridin-6-yl)carbamate (2.55 g, 4.39 mmol) was dissolved in 1M TBAF in THF (8.78 mL, 8.78 mmol) and heated to reflux overnight. The reaction mixture was partitioned between 0.1 N NaOH and EtOAc, washed with water, dried over sodium sulfate, filtered and concentrated to afford tert-butyl methyl(3-(4-(4-methylpiperazine-1-carbonyl)phenyl)-1H-pyrazolo[4,3-c]pyridin-6-yl)carbamate.

Using the procedure for the preparation of Intermediate 42, the following compounds were also synthesized:

| Intermediate | Structure | Name |
|---|---|---|
| 43 | 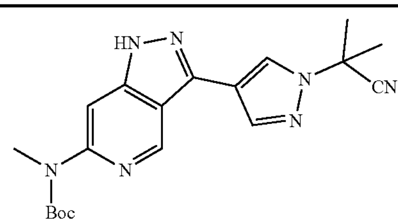 | tert-butyl (3-(1-(2-cyanopropan-2-yl)-1H-pyrazol-4-yl)-1H-pyrazolo[4,3-c]pyridin-6-yl)(methyl)carbamate |
| 44 | 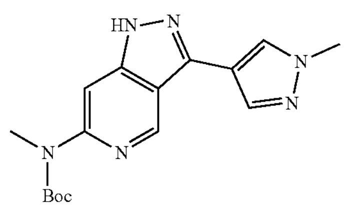 | tert-butyl methyl(3-(1-methyl-1H-pyrazol-4-yl)-1H-pyrazolo[4,3-c]pyridin-6-yl)carbamate |
| 45 | 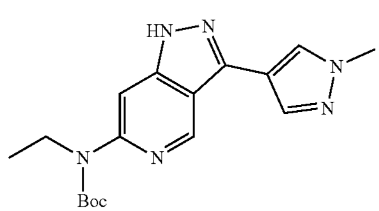 [SMILES: CCN(C(=O)OC(C)(C)C)c1cc2[nH]nc(-c3cnn(C)c3)c2cn1] | tert-butyl ethyl(3-(1-methyl-1H-pyrazol-4-yl)-1H-pyrazolo[4,3-c]pyridin-6-yl)carbamate |
| 46 | 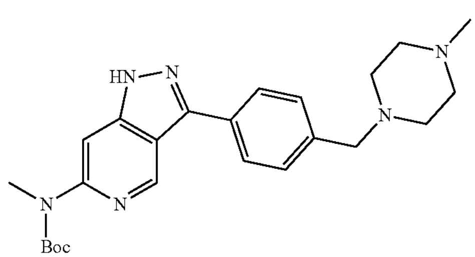 | tert-butylmethyl(3-(4-((4-methylpiperazin-1-yl)methyl)phenyl)-1H-pyrazolo[4,3-c]pyridin-6-yl)carbamate |

Intermediate 47 tert-butyl (1-((1s,4s)-4-hydroxycyclohexyl)-3-(1-methyl-1H-pyrazol-4-yl)-1H-pyrazolo[4,3-c]pyridin-6-yl)(methyl)carbamate

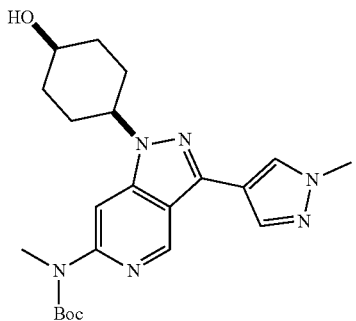

Step A: To a solution of tert-butyl methyl(3-(1-methyl-1H-pyrazol-4-yl)-1H-pyrazolo[4,3-c]pyridin-6-yl)carbamate (0.103 g, 0.314 mmol) in DMF (3.1 mL) was added Cs$_2$CO$_3$ (0.153 g, 0.470 mmol) and (1r,4r)-4-((tert-butyldimethylsilyl)oxy)cyclohexyl 4-methylbenzenesulfonate (0.181 g, 0.470 mmol). The reaction mixture was placed under Ar and heated to 85° C. for 48 hours. Partitioned between EtOAc (15 mL) and water (15 mL), separated and extracted with EtOAc (2×10 mL), washed with water (15 mL), brine (15 mL), dried with Na2SO4, filtered and concentrated. The residue was purified over silica gel (10-95% EtOAc in hexanes) to afford tert-butyl (1-((1s,4s)-4-((tert-butyldimethylsilyl)oxy)cyclohexyl)-3-(1-methyl-1H-pyrazol-4-yl)-1H-pyrazolo[4,3-c]pyridin-6-yl)(methyl)carbamate (0.115 g, 0.213 mmol, 67.8% yield) as a white solid.

Step B: tert-butyl (1-((1s,4s)-4-((tert-butyldimethylsilyl)oxy)cyclohexyl)-3-(1-methyl-1H-pyrazol-4-yl)-1H-pyrazolo[4,3-c]pyridin-6-yl)(methyl)carbamate (0.587 g, 1.09 mmol) was diluted with THF (5.4 mL), followed by the addition of 1M TBAF in THF (2.17 mL, 2.17 mmol) and heated to 70° C. overnight and then concentrated. The residue was purified over silica gel (1.0-9.5% MeOH in DCM) to afford tert-butyl (1-((1s,4s)-4-hydroxycyclohexyl)-3-(1-methyl-1H-pyrazol-4-yl)-1H-pyrazolo[4,3-c]pyridin-6-yl)(methyl)carbamate (0.490 g, 1.15 mmol, 106% yield).

Using the procedure for the preparation of Intermediate 47, the following compounds were also synthesized:

| Intermediate | Structure | Name |
|---|---|---|
| 48 | 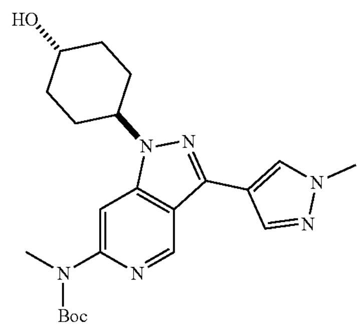 | tert-butyl (1-((1r,4r)-4-hydroxycyclohexyl)-3-(1-methyl-1H-pyrazol-4-yl)-1H-pyrazolo[4,3-c]pyridin-6-yl)(methyl)carbamate |
| 49 | 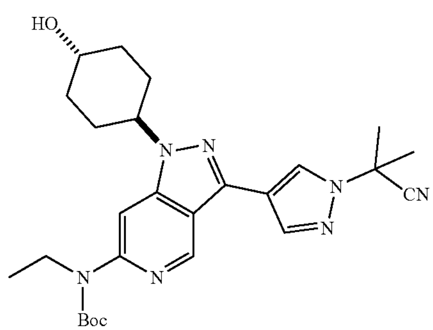 | tert-butyl (3-(1-(2-cyanopropan-2-yl)-1H-pyrazol-4-yl)-1-((1r,4r)-4-hydroxycyclohexyl)-1H-pyrazolo[4,3-c]pyridin-6-yl)(ethyl)carbamate |
| 50 | 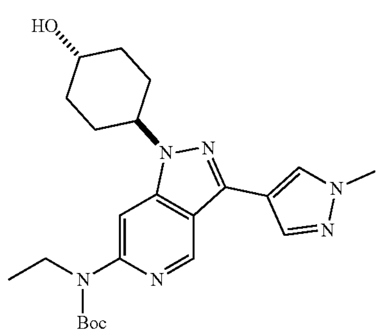 | tert-butyl ethyl(1-((1r,4r)-4-hydroxycyclohexyl)-3-(1-methyl-1H-pyrazol-4-yl)-1H-pyrazolo[4,3-c]pyridin-6-yl)carbamate |

Intermediate 51

2-(4-(1-((1r,4r)-4-hydroxycyclohexyl)-6-(methylamino)-1H-pyrazolo[4,3-c]pyridin-3-yl)-1H-pyrazol-1-yl)-2-methylpropanenitrile

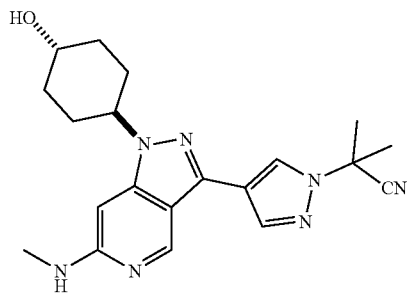

Step C: 2-(4-(1-((1r,4r)-4-((tert-butyldimethylsilyl)oxy)cyclohexyl)-6-(methylamino)-1H-pyrazolo[4,3-c]pyridin-3-yl)-1H-pyrazol-1-yl)-2-methylpropanenitrile (2.6396 g, 5.35 mmol) was dissolved in DCM (30 mL) and treated with 4N HCl/dioxane (30 mL) and stirred for 1 h. The reaction mixture was concentrated, triturated with EtOAc and dried to afford a yellow solid. The solid was partitioned between 1N NaOH (100 mL) and 10% MeOH/DCM (100 mL), extracted with 10% MeOH/DCM (2×50 mL) and the combined organic phases were washed with brine (30 mL), dried over $Na_2SO_4$, filtered and concentrated. The residue was purified over silica gel (20-50% gradient of 20% MeOH/DCM in DCM) to afford 2-(4-(1-((1r,4r)-4-hydroxycyclohexyl)-6-(methylamino)-1H-pyrazolo[4,3-c]pyridin-3-yl)-1H-pyrazol-1-yl)-2-methylpropanenitrile (1.75 g, 84% yield).

Using the procedure for the preparation of Intermediate 51, the following compounds were also synthesized:

| Intermediate | Structure | Name |
|---|---|---|
| 52 | 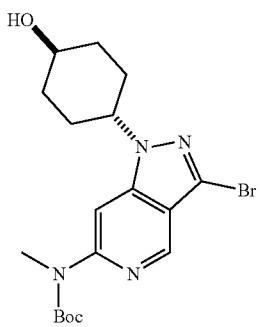 | 2-(4-(6-(ethylamino)-1-((1r,4r)-4-hydroxycyclohexyl)-1H-pyrazolo[4,3-c]pyridin-3-yl)-1H-pyrazol-1-yl)-2-methylpropanenitrile |

Step A: 3-bromo-1-((1r,4r)-4-((tert-butyldimethylsilyl)oxy)cyclohexyl)-6-chloro-1H-pyrazolo[4,3-c]pyridine (1.37 g, 3.08 mmol) in anhydrous DMA (8 mL) and 40% methanamine in water (8.06 mL, 67.4 mmol) was heated at high power in the microwave at 150° C. for 8 h. Water (100 mL) was added to the mixture and stirred. The resultant solid was filtered and dried in vacuo to afford 3-bromo-1-((1r,4r)-4-((tert-butyldimethylsilyl)oxy)cyclohexyl)-N-methyl-1H-pyrazolo[4,3-c]pyridin-6-amine (1.78 g, 132% yield).

Step B: A pressure tube equipped with a stir bar was charged with 3-bromo-1-((1r,4r)-4-((tert-butyldimethylsilyl)oxy)cyclohexyl)-N-methyl-1H-pyrazolo[4,3-c]pyridin-6-amine (2.4831 g, 5.65 mmol) and 2-methyl-2-(4-(4,4,5,5-tetramethyl-1,3,2-dioxaborolan-2-yl)-1H-pyrazol-1-yl)propanenitrile (2.95 g, 11.3 mmol) in dioxane (30 mL) and aq. 2N $K_2CO_3$ (8.48 mL, 16.95 mmol) and Pd(Ph$_3$P)$_4$ (653 mg, 0.565 mmol) were added. The sealed tube was heated to 100° C. overnight. The mixture was diluted with water (150 mL), extracted with EtOAc (3×50 mL), washed with brine (150 mL), dried over sodium sulfate, filtered and concentrated. The residue was purified over silica gel (30-100% EtOAc/hexanes) to afford 2-(4-(1-((1r,4r)-4-((tert-butyldimethylsilyl)oxy)cyclohexyl)-6-(methylamino)-1H-pyrazolo[4,3-c]pyridin-3-yl)-1H-pyrazol-1-yl)-2-methylpropanenitrile (2.63 g, 94% yield).

Intermediate 53 tert-butyl (3-bromo-1-((1r,4r)-4-hydroxycyclohexyl)-1H-pyrazolo[4,3-c]pyridin-6-yl)(methyl)carbamate Step A: To a solution of tert-butyl (3-bromo-1-((2-(trimethylsilyl)ethoxy)methyl)-1H-pyrazolo[4,3-c]pyridin-6-yl)(methyl)carbamate (6.87 g, 15.0 mmol) in THF (100 mL) was added TBAF (45.1 mL, 1M, 45.1 mmol) and heated to reflux overnight. The mixture was partitioned between water (200 mL) and EtOAc (100 mL) and the aqueous layer was extracted with EtOAc (2×100 mL). The combined organic phases were washed with brine (100 mL), dried over Na₂SO₄, filtered and concentrated. The residue was purified over silica gel (10:50% EtOAc/hexanes) to afford tert-butyl (3-bromo-1H-pyrazolo[4,3-c]pyridin-6-yl)(methyl)carbamate (2.39 g, 48.6% yield).

Step B: A solution of tert-butyl (3-bromo-1H-pyrazolo[4,3-c]pyridin-6-yl)(methyl)carbamate (2.0 g, 6.11 mmol) in DMA (20 mL) was treated with Cs₂CO₃ (3.98 g, 12.2 mmol) followed by (1s,4s)-4-((tert-butyldimethylsilyl)oxy)cyclohexyl 4-methylbenzenesulfonate (4.7 g, 12.2 mmol). The mixture was stirred at 100° C. overnight. The cooled mixture was partitioned between water (100 mL) and EtOAc (100 mL) and the aqueous layer was extracted with EtOAc (2×50 mL). The combined organic phases were washed with water (4×50 mL) and brine (50 mL) then dried over Na2SO4, filtered and concentrated. The residue was purified over silica gel (5-30% EtOAc/hexanes) to afford tert-butyl (3-bromo-1-((1r,4r)-4-((tert-butyldimethylsilyl)oxy)cyclohexyl)-1H-pyrazolo[4,3-c]pyridin-6-yl)(methyl)carbamate (1.78 g, 54% yield).

Step C: A solution of tert-butyl (3-bromo-1-((1r,4r)-4-((tert-butyldimethylsilyl)oxy)cyclohexyl)-1H-pyrazolo[4,3-c]pyridin-6-yl)(methyl)carbamate (641 mg, 1.19 mmol) in THF (15 mL) was cooled to 0° C. and treated with TBAF (3.56 mL, 1.0 M, 3.56 mmol). The mixture was allowed to warm slowly to room temperature overnight. The mixture was partitioned between water (30 mL) and EtOAc (30 mL) and the aqueous layer was extracted with EtOAc (2×20 mL). The combined organic phases were washed with brine (20 mL), dried over Na₂SO₄, filtered and concentrated. The residue was purified over silica gel (20-80% EtOAc/hexanes) to afford tert-butyl (3-bromo-1-((1r,4r)-4-hydroxycyclohexyl)-1H-pyrazolo[4,3-c]pyridin-6-yl)(methyl)carbamate (516 mg, 102% yield).

Using the procedure for the preparation of Intermediate 53, the following compound was also synthesized:

| Intermediate | Structure | Name |
|---|---|---|
| 54 | 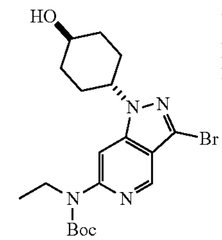 | tert-butyl (3-bromo-1-((1r,4r)-4-hydroxycyclohexyl)-1H-pyrazolo[4,3-c]pyridin-6-yl)(ethyl)carbamate |

Intermediate 55

1-methyl-3-(trifluoromethyl)-1H-pyrazol-4-ol

To a solution of 1-Methyl-3-trifluoromethylpyrazole-4-boronic acid (5.0 g, 18.1 mmol) in THF (92 mL) was added a pre-mixed solution of 2M NaOH (10.8 mL, 21.7 mmol) and 30% H2O2 (2.22 mL, 21.7 mmol). The resulting suspension was stirred for 3 h, then concentrated to ¼ volume and diluted with water (150 mL) and DCM (100 mL). The pH was adjusted to 4-5 using 10% citric acid, extracted using DCM (5×60 mL), the organic washes were combined and dried over sodium sulfate, and concentrated. The residue was purified over silica gel (0-50% EtOAc/hexanes) to afford 1-methyl-3-(trifluoromethyl)-1H-pyrazol-4-ol (3.08 g, 102% yield).

Using the procedure for the preparation of Intermediate 55, the following compounds were also synthesized:

| Intermediate | Structure | Name |
|---|---|---|
| 56 | 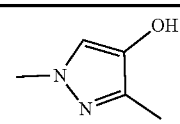 | 1,3-dimethyl-1H-pyrazol-4-ol |
| 57 | 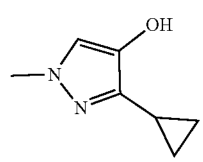 | 3-cyclopropyl-1-methyl-1H-pyrazol-4-ol |
| 58 | 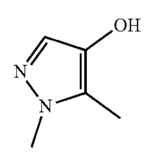 | 1,5-dimethyl-1H-pyrazol-4-ol |
| 59 | | 3-(trifluoromethyl)-1-((2-(trimethylsilyl)ethoxy)methyl)-1H-pyrazol-4-ol and 5-(trifluoromethyl)-1-((2-(trimethylsilyl)ethoxy)methyl)-1H-pyrazol-4-ol |

| Intermediate | Structure | Name |
|---|---|---|
| 60 | 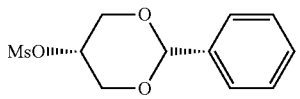 | 4-methyl-1H-indazol-5-ol |

Intermediate 61

(cis)-2-phenyl-1,3-dioxan-5-yl methane sulfonate cis-1,3-O-Benzylideneglycerol (7.0 g, 38.8 mmol) was dissolved in DCM (150 mL) and cooled in ice bath. triethylamine (8.12 mL, 58.3 mmol) was added, followed by methanesulfonyl chloride (3.63 mL, 46.6 mmol) and ice bath removed. After 30 min, the reaction was partitioned between dilute HCl and DCM, washed with bicarb and brine, dried over sodium sulfate, filtered and concentrated to afford (cis)-2-phenyl-1,3-dioxan-5-yl methanesulfonate (10 g, 38.7 mmol, 99.7% yield) as a white solid.

Intermediate 62

(1r,4r)-4-((1-ethyl-1H-1,2,3-triazol-5-yl)oxy)cyclohexyl 4-methylbenzenesulfonate Step A: To a solution of TMSCHN2 (59.93 mL, 119.9 mmol)(2M in Hexanes) in Et2O (300 mL) cooled in a −78° C. bath, was added n-BuLi (47.95 mL, 119.9 mmol) and the reaction was stirred for 20 min in the −78° C. bath. A solution of isocyanatoethane (7.10 g, 99.89 mmol) in 100 ml Et2O was added dropwise over 20 minutes and the reaction stirred 90 min in the −78° C. bath and then allowed to warm to room temperature and stirred 4 h. The reaction mixture was quenched with 150 mL water and the aqueous layer separated. The organic layer was extracted with water 150 mL and the combined aqueous layers were acidified with 2 N HCl. The resulting solids were extracted with 200 mL×18 (DCM/20% IPA), and concentrated to a residue to give crude 1-ethyl-1H-1,2,3-triazol-5-ol (10.33 g, 91.42% yield) as light yellow solids that were used directly in the next reaction without further purification.

Step B: 1-ethyl-1H-1,2,3-triazol-5-ol (428 mg, 3.78 mmol) and (1s,4s)-4-((tert-butyldimethylsilyl)oxy)cyclohexyl 4-methylbenzenesulfonate (2.18 g, 5.68 mmol) were dissolved in acetonitrile (15 mL) and Cs2CO3 (2.47 g, 7.57 mmol) was added and the reaction was heated to 80° C. overnight. The reaction mixture was filtered through GF/F filter paper and the filtrate was concentrated. The resulting crude material was partitioned between water and EtOAc, extracted with EtOAc, dried over sodium sulfate, filtered and concentrated. The residue was purified over silica gel (5-85% EtOAc in hexanes) to afford 5-(((1r,4r)-4-((tert-butyldimethylsilyl)oxy)cyclohexyl)oxy)-1-ethyl-1H-1,2,3-triazole (562 mg, 45% yield).

Step C: 5-(((1r,4r)-4-((tert-butyldimethylsilyl)oxy)cyclohexyl)oxy)-1-ethyl-1H-1,2,3-triazole (0.56 g, 1.72 mmol) was dissolved in THF (9 mL) and TBAF (9 mL, 9 mmol, 1M in THF) was added and heated to 50° C. overnight. The reaction mixture was partitioned between 10% K2CO3 and EtOAc, washed with brine, dried over sodium sulfate, filtered and concentrated to afford (1r,4r)-4-((1-ethyl-1H-1,2,3-triazol-5-yl)oxy)cyclohexan-1-ol (180 mg, 49.5% yield).

Step D: (1r,4r)-4-((1-ethyl-1H-1,2,3-triazol-5-yl)oxy)cyclohexan-1-ol (0.18 g, 0.852 mmol) was dissolved in pyridine (9 mL) and TsCl (0.195 g, 1.02 mmol) was added, followed by a catalytic amount of DMAP and stirred overnight. The reaction mixture was partitioned between water and EtOAc, extracted with EtOAc, washed with 1M HCl, 10% K2CO3, dried over sodium sulfate, filtered and concentrated. The residue was purified over silica gel (0-90% EtOAc in DCM) to afford (1r,4r)-4-((1-ethyl-1H-1,2,3-triazol-5-yl)oxy)cyclohexyl 4-methylbenzenesulfonate (60 mg, 19% yield).

Using the procedure for the preparation of Intermediate 62, the following compounds were also synthesized:

| Intermediate | Structure | Name |
|---|---|---|
| 63 | 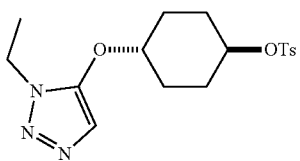 [SMILES: CCn1nncc1O[C@H]1CC[C@H](OS(=O)(=O)c2ccc(C)cc2)CC1] | (1r,4r)-4-((1,3-dimethyl-1H-pyrazol-4-yl)oxy)cyclohexyl 4-methylbenzenesulfonate |

-continued

| Intermediate | Structure | Name |
|---|---|---|
| 64 | 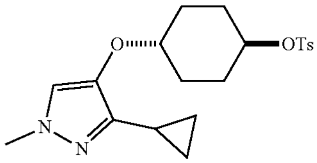 [SMILES: Cc1ccc(S(=O)(=O)O[C@H]2CC[C@H](Oc3cn(C)nc3C3CC3)CC2)cc1] | (1r,4r)-4-((3-cyclopropyl-1-methyl-1H-pyrazol-4-yl)oxy)cyclohexyl 4-methylbenzenesulfonate |
| 65 | 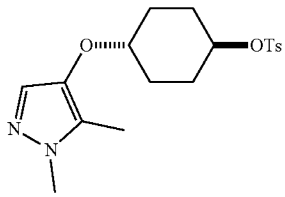 [SMILES: Cc1ccc(S(=O)(=O)O[C@H]2CC[C@H](Oc3cnn(C)c3C)CC2)cc1] | (1r,4r)-4-((1,5-dimethyl-1H-pyrazol-4-yl)oxy)cyclohexyl 4-methylbenzenesulfonate |
| 66 | 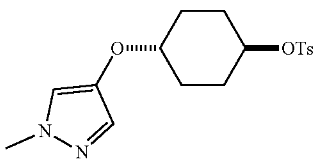 [SMILES: Cc1ccc(S(=O)(=O)O[C@H]2CC[C@H](Oc3cnn(C)c3)CC2)cc1] | (1r,4r)-4-((1-methyl-1H-pyrazol-4-yl)oxy)cyclohexyl 4-methylbenzenesulfonate |
| 67 | 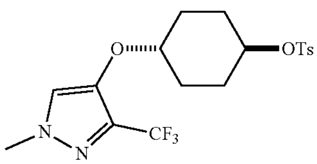 [SMILES: Cc1ccc(S(=O)(=O)O[C@H]2CC[C@H](Oc3cn(C)nc3C(F)(F)F)CC2)cc1] | (1r,4r)-4-((1-methyl-3-(trifluoromethyl)-1H-pyrazol-4-yl)oxy)cyclohexyl 4-methylbenzenesulfonate |

Intermediate 68

(R)-1-((2,2-dimethyl-1,3-dioxolan-4-yl)methyl)-4-(4,4,5,5-tetramethyl-1,3,2-dioxaborolan-2-yl)-1H-pyrazole

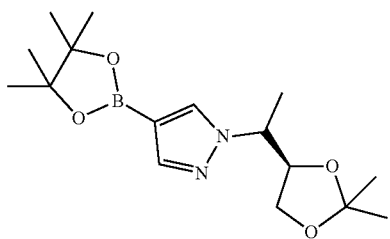

Step A: A 3 neck, 2 liter round bottom flask equipped with an overhead stirrer, condenser with a nitrogen inlet, and a temperature probe was charged with 4-iodo-1H-pyrazole (20 g, 103 mmol) and dry DMA (400 mL). To this was added cesium carbonate (67 g, 206 mmol) and (S)-4-(chloromethyl)-2,2-dimethyl-1,3-dioxolane (31 g, 206 mmol). The mixture was heated to 100° C. overnight. The mixture was diluted with water (750 mL), extracted with MTBE (3×400 mL), washed with water (4×200 mL), brine (400 mL), dried over sodium sulfate, filtered and concentrated. The residue was purified over silica gel (0-40% EtOAc in hexanes) to afford (R)-1-((2,2-dimethyl-1,3-dioxolan-4-yl)methyl)-4-iodo-1H-pyrazole (29.7 g, 93% yield) as an oil.

Step B: (R)-1-((2,2-dimethyl-1,3-dioxolan-4-yl)methyl)-4-iodo-1H-pyrazole (29.7 g, 96.4 mmol) was charged with dry THF (450 mL) and 2-isopropoxy-4,4,5,5-tetramethyl-1,3,2-dioxaborolane (29.5 mL, 145 mmol). The reaction mixture was cooled to 0° C. and iPrMgCl.LiCl (111 mL, 145 mmol, 1.3 M in THF) was then added via addition funnel over 5 minutes. The reaction mixture was stirred at 0° C. for 15 minutes then allowed to warm to room temperature. The reaction mixture was cooled to 0° C. and quenched carefully with saturated ammonium chloride solution (250 mL), diluted with water (250 mL), extracted with EtOAc (3×600 mL), and washed with brine (400 mL). The organic layer was dried over sodium sulfate and concentrated. The reside was purified over silica gel (10-50% EtOAc in hexanes) to afford (R)-1-((2,2-dimethyl-1,3-dioxolan-4-yl)methyl)-4-(4,4,5,5-tetramethyl-1,3,2-dioxaborolan-2-yl)-1H-pyrazole (28.3 g, 95% yield) as an oil.

Using the procedure for the preparation of Intermediate 68, the following compounds were also synthesized:

| Intermediate | Structure | Name |
| --- | --- | --- |
| 69 | 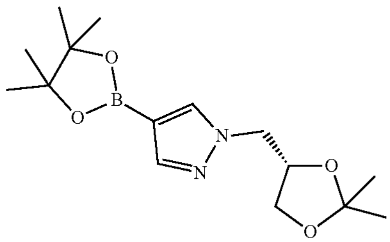 | (S)-1-((2,2-dimethyl-1,3-dioxolan-4-yl)methyl)-4-(4,4,5,5-tetramethyl-1,3,2-dioxaborolan-2-yl)-1H-pyrazole |
| 70 | 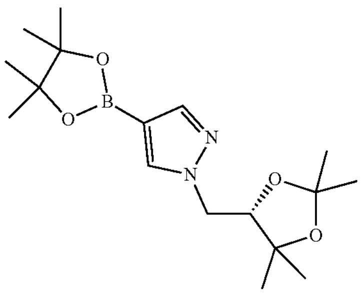 | (S)-4-(4,4,5,5-tetramethyl-1,3,2-dioxaborolan-2-yl)-1-((2,2,5,5-tetramethyl-1,3-dioxolan-4-yl)methyl)-1H-pyrazole |
| 71 | 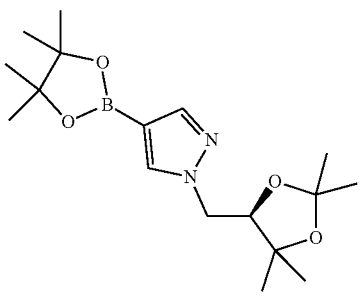 | (R)-4-(4,4,5,5-tetramethyl-1,3,2-dioxaborolan-2-yl)-1-((2,2,5,5-tetramethyl-1,3-dioxolan-4-yl)methyl)-1H-pyrazole |
| 72 | 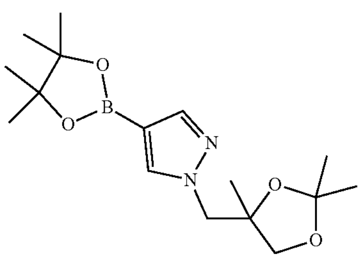 | 4-(4,4,5,5-tetramethyl-1,3,2-dioxaborolan-2-yl)-1-((2,2,4-trimethyl-1,3-dioxolan-4-yl)methyl)-1H-pyrazole |
| 73 | 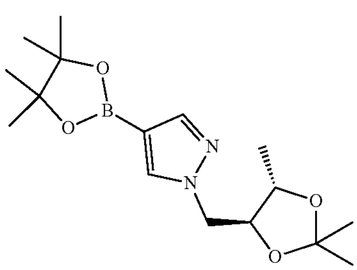 | 4-(4,4,5,5-tetramethyl-1,3,2-dioxaborolan-2-yl)-1-(((4S,5S)-2,2,5-trimethyl-1,3-dioxolan-4-yl)methyl)-1H-pyrazole |
| 74 | 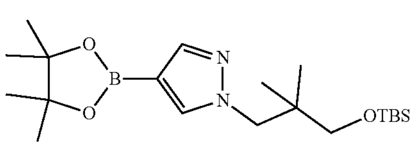 [SMILES: CC(C)(CO[Si](C)(C)C(C)(C)C)Cn1cc(B2OC(C)(C)C(C)(C)O2)cn1] | 1-(3-((tert-butyldimethylsilyl)oxy)-2,2-dimethylpropyl)-4-(4,4,5,5-tetramethyl-1,3,2-dioxaborolan-2-yl)-1H-pyrazole |

| Intermediate | Structure | Name |
|---|---|---|
| 75 | 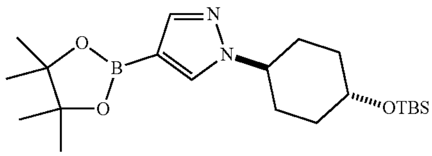 | 1-((1r,4r)-4-((tert-butyldimethylsilyl)oxy)cyclohexyl)-4-(4,4,5,5-tetramethyl-1,3,2-dioxaborolan-2-yl)-1H-pyrazole |

Intermediate 76

3-fluoro-4-iodopyridin-2(1H)-one

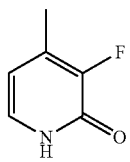

To a solution of 2,3-Difluoro-4-iodopyridine (0.250 g, 1.04 mmol) in a mixture of water (1.04 mL, 1.04 mmol) and dioxane (0.10 mL) was added powdered KOH (0.116 g, 2.07 mmol) and heated to 100° C. overnight. The mixture was cooled to room temperature, at which time a white solid crashed out. Water (15 mL) and 3 mL glacial acetic acid were added and the reaction mixture was stirred for 30 min. The aqueous layer was extracted with 4:1 DCM:IPA (3×10 mL), dried over $Na_2SO_4$, filtered and concentrated to afford 3-fluoro-4-iodopyridin-2(1H)-one (0.162 g, 0.678 mmol, 65.3% yield) as a white solid.

Intermediate 77

(S)-tert-butyl 2,2-dimethyl-4-((4-(4,4,5,5-tetramethyl-1,3,2-dioxaborolan-2-yl)-1H-pyrazol-1-yl)methyl)oxazolidine-3-carboxylate

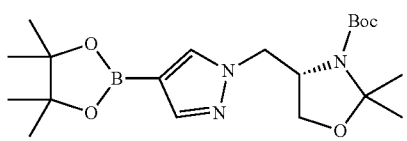

In 2 mL of DMF were combined 4-(4,4,5,5-tetramethyl-1,3-dioxolan-2-yl)-1H-pyrazole (0.250 g, 1.27 mmol) and cesium carbonate (0.540 g, 1.66 mmol) and heated to 70° C. for 30 min before (R)-tert-butyl 2,2-dimethyl-4-((tosyloxy)-methyl)oxazolidine-3-carboxylate (0.596 g, 1.55 mmol) was added and the reaction was sealed and heated to 70° C. overnight. The reaction mixture was diluted with 20 mL of MTBE and washed with water (10 mL), saturated $NH_4Cl$ (10 mL), water (10 mL), and brine (10 mL), dried over $MgSO_4$, filtered, and concentrated. The residue was purified over silica gel (20% EtOAc in hexanes) to afford (S)-tert-butyl 2,2-dimethyl-4-((4-(4,4,5,5-tetramethyl-1,3,2-dioxaborolan-2-yl)-1H-pyrazol-1-yl)methyl)oxazolidine-3-carboxylate (0.166 g, 0.408 mmol, 31.6% yield).

Using the procedure for the preparation of Intermediate 77, the following compound was also synthesized:

| Intermediate | Structure | Name |
|---|---|---|
| 78 | 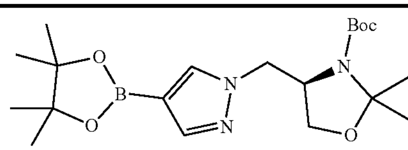 | tert-butyl (R)-2,2-dimethyl-4-((4-(4,4,5,5-tetramethyl-1,3,2-dioxaborolan-2-yl)-1H-pyrazol-1-yl)methyl)oxazolidine-3-carboxylate |

Intermediate 79

4-hydroxy-N-methyl-3-(trifluoromethyl)benzamide

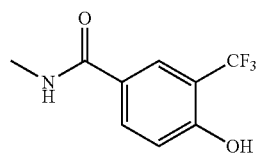

4-hydroxy-3-(trifluoromethyl)benzoic acid (100 mg, 0.485 mmol), HATU (203 mg, 0.534 mmol) and methylamine hydrochloride (39.3 mg, 0.582 mmol) were diluted with DMF (3 mL) followed by the addition of DIEA (254 µL, 1.46 mmol). After stirring for 12 hours, the reaction was diluted with ethyl acetate and water. The layers were separated and the ethyl acetate was dried over $MgSO_4$, filtered and concentrated to afford 4-hydroxy-N—methyl-3-(trifluoromethyl)benzamide (100 mg, 0.456 mmol, 94.0% yield).

Intermediate 80 tert-butyl 5-hydroxy-1-oxoisoindoline-2-carboxylate

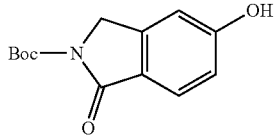 [SMILES: CC(C)(C)OC(=O)N1Cc2cc(O)ccc2C1=O]

5-Hydroxyisoindolin-1-one (0.100 g, 0.670 mmol) was diluted with dichloroethane (3.3 mL) followed by the addition of di-tert-butyl dicarbonate (0.467 mL, 2.01 mmol) and DMAP (0.00819 g, 0.0670 mmol). The reaction was heated to 60° C. and stirred for 30 min, then cooled to RT. EtOAc (15 mL) and water (15 mL) were added to the cooled mixture and the organic layer was separated, washed with brine (2×15 mL), dried with $Na_2SO_4$, filtered and concentrated to obtain crude tert-butyl 5-hydroxy-1-oxoisoindoline-2-carboxylate (0.152 g, 0.610 mmol, 90.9% yield) as a white solid.

Intermediate 81

4-(difluoromethyl)-3-fluoropyridin-2(1H)-one

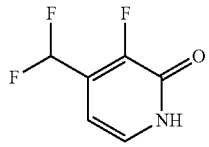

To a solution of alpha,alpha,2,3-Tetrafluoro-4-picoline (0.100 ml, 0.606 mmol) in a mixture of water (1.3 ml) and dioxane (0.15 ml) was added powdered KOH (0.0680 g, 1.21 mmol). The temperature was increased to 100° C. and the reaction mixture was stirred overnight. The mixture was cooled to room temperature, at which time a white solid crashed out. Water (15 mL) and 3 mL glacial acetic acid were added, and the mixture was stirred for 30 min. The mixture was extracted with 4:1 DCM:IPA (3×10 mL) and combined organic layers were dried over $Na_2SO_4$, filtered and concentrated to obtain 4-(difluoromethyl)-3-fluoropyridin-2(1H)-one (0.074 g, 0.454 mmol, 74.9% yield) as a white solid.

Preparation of Synthetic Examples

Example 1

2-methyl-6-(((1s,4s)-4-(3-(1-methyl-1H-pyrazol-4-yl)-6-(methylamino)-1H-pyrazolo[4,3-c]pyridin-1-yl)cyclohexyl)oxy)pyridazin-3(2H)-one

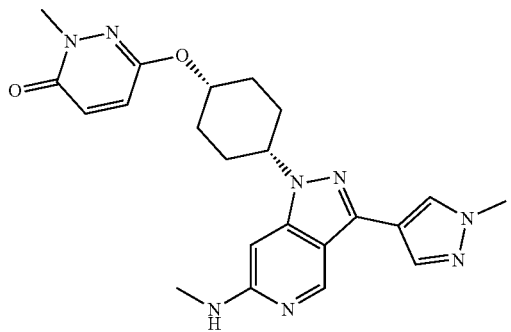 [SMILES: CNc1cc2c(cn1)c(-c1cnn(C)c1)nn2[C@H]1CC[C@@H](Oc2ccc(=O)n(C)n2)CC1]

Step A: tert-butyl (3-bromo-1-((2-(trimethylsilyl)ethoxy)methyl)-1H-pyrazolo[4,3-c]pyridin-6-yl)(methyl)carbamate (56 g, 122 mmol) was diluted with THF (150 mL) and ethane-1,2-diamine (82 mL, 1224 mmol) followed by the addition of 1M TBAF in THF (367 mL, 367 mmol). The reaction mixture was heated to 50° C. and stirred for 12 h. The reaction mixture was poured into cool water, extracted with ethyl acetate, dried over $MgSO_4$, filtered and concentrated. The residue was purified over silica gel (50-100% ethyl acetate/hexanes) to afford tert-butyl (3-bromo-1H-pyrazolo[4,3-c]pyridin-6-yl)(methyl)carbamate (26 g, 79 mmol, 65% yield).

Step B: (1s,4s)-4-((tert-butyldimethylsilyl)oxy)cyclohexyl 4-methylbenzenesulfonate (61 g, 159 mmol), tert-butyl (3-bromo-1H-pyrazolo[4,3-c]pyridin-6-yl)(methyl)carbamate (26 g, 79 mmol) and Cs2CO3 (52 g, 159 mmol) were diluted with DMA (318 mL). The reaction mixture was placed under nitrogen and heated to 100° C. After stirring for 12 hours, the reaction was allowed to cool, diluted with ethyl acetate and water. The layers were separated and dried over $MgSO_4$, filtered and concentrated. The residue was purified over silica gel (10% ethyl acetate/hexanes) to afford tert-butyl (3-bromo-1-((1r,4r)-4-((tert-butyldimethylsilyl)oxy)cyclohexyl)-1H-pyrazolo[4,3-c]pyridin-6-yl)(methyl)carbamate (26 g, 48 mmol, 61% yield).

Step C: tert-butyl (3-bromo-1-((1r,4r)-4-((tert-butyldimethylsilyl)oxy)cyclohexyl)-1H-pyrazolo[4,3-c]pyridin-6-yl)(methyl)carbamate (25.6 g, 47.4 mmol) was diluted with THF (200 mL) followed by the addition of 1M TBAF in THF (94.9 mL, 94.9 mmol). The reaction mixture was placed under nitrogen, heated to 50° C. and stirred for 12 hours. The reaction mixture was poured into water and extracted with ethyl acetate, dried over MgSO4, filtered and concentrated. The residue was taken up in 10% ethyl acetate/heptanes, stirred for 30 minutes, filtered and rinsed with heptanes to afford tert-butyl (3-bromo-1-((1r,4r)-4-hydroxycyclohexyl)-1H-pyrazolo[4,3-c]pyridin-6-yl)(methyl)carbamate (15 g, 35.3 mmol, 74.3% yield) as a white solid.

Step D: A mixture of tert-butyl (3-bromo-1-((1r,4r)-4-hydroxycyclohexyl)-1H-pyrazolo[4,3-c]pyridin-6-yl)(methyl)carbamate (16.6 g, 39.0 mmol), 1-methyl-4-(4,4,5,5-tetramethyl-1,3,2-dioxaborolan-2-yl)-1H-pyrazole (10.6 g, 50.7 mmol), $Pd(PPh_3)_4$ (2.26 g, 1.95 mmol) and $Na_2CO_3$ (41.0 mL, 82.0 mmol) in dioxane (195 mL) was heated to 90° C. overnight. The reaction mixture was partitioned between DCM and water, extracted (×2) with DCM, washed with brine, dried over sodium sulfate, filtered and concentrated. The residue was purified over silica gel (1-10% MeOH in EtOAc) to afford tert-butyl (1-((1r,4r)-4-hydroxycyclohexyl)-3-(1-methyl-1H-pyrazol-4-yl)-1H-pyrazolo[4,3-c]pyridin-6-yl)(methyl)carbamate (15.1 g, 35.4 mmol, 90.7% yield).

Step E: DIAD (7.675 mL, 38.94 mmol) was added to $Ph_3P$ (10.21 g, 38.94 mmol), tert-butyl (1-((1r,4r)-4-hydroxycyclohexyl)-3-(1-methyl-1H-pyrazol-4-yl)-1H-pyrazolo[4,3-c]pyridin-6-yl)(methyl)carbamate (15.1 g, 35.40 mmol) and 6-hydroxy-2-methylpyridazin-3(2H)-one (5.804 g, 46.02 mmol) in THF (177.0 mL, 35.40 mmol) at 0° C. The reaction mixture was stirred at room temperature overnight. The reaction mixture was partitioned between DCM and water, washed with water, brine and dried with $Na_2SO_4$, filtered and concentrated. The residue was purified over silica gel (1-10% MeOH in EtOAc) to tert-butyl methyl(3-(1-methyl-1H-pyrazol-4-yl)-1-((1s,4s)-4-((1-methyl-6-oxo-1,6-dihydropyridazin-3-yl)oxy)cyclohexyl)-1H-pyrazolo[4,3-c]pyridin-6-yl)carbamate (16.8 g, 31.42 mmol, 88.76% yield).

Step F: TFA (145.3 mL, 1885 mmol) was added to tert-butyl methyl(3-(1-methyl-1H-pyrazol-4-yl)-1-((1s,4s)-4-((1-methyl-6-oxo-1,6-dihydropyridazin-3-yl)oxy)cyclohexyl)-1H-pyrazolo[4,3-c]pyridin-6-yl)carbamate (16.8 g, 31.42 mmol) in DCM (104.7 mL). The reaction mixture was stirred for 3 hours at room temperature. The reaction mixture was concentrated and partitioned between aqueous $Na_2CO_3$ and DCM, washed with brine, dried with $Na_2SO_4$, filtered and concentrated. The desired product was crystallized from EtOH to afford 2-methyl-6-(((1s,4s)-4-(3-(1-methyl-1H-pyrazol-4-yl)-6-(methylamino)-1H-pyrazolo[4,3-c]pyridin-1-yl)cyclohexyl)oxy)pyridazin-3(2H)-one (9.406 g, 21.65 mmol, 68.89% yield). Mass spectrum (apci) m/z=453.2 (M+H). 1H NMR (CDCl$_3$) δ 8.67 (d, J=0.8 Hz, 1H), 7.97 (s, 1H), 7.84 (s, 1H), 6.99 (d, J=9.8 Hz, 1H), 6.91 (d, J=9.8 Hz, 1H), 6.01 (s, 1H), 5.07 (m, 1H), 4.76 (q, J=5.1 Hz, 1H), 4.31 (tt, J=11.5, 3.7 Hz, 1H), 3.97 (s, 3H), 3.64 (s, 3H), 2.95 (d, J=5.3 Hz, 3H), 2.49-2.27 (m, 4H), 1.95-1.87 (m, 2H), 1.82-1.71 (m, 2H).

Using the procedure described for the preparation of Example 1, the following compounds were also synthesized:

| Example | Structure | Name | Data |
|---|---|---|---|
| 2 | 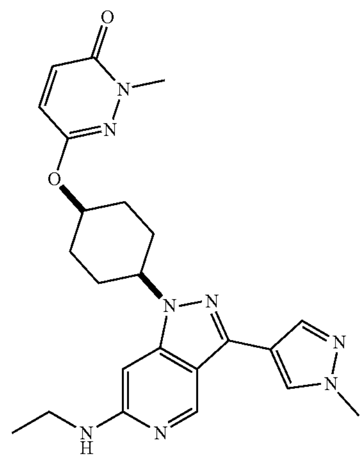 | 6-(((1s,4s)-4-(6-(ethylamino)-3-(1-methyl-1H-pyrazol-4-yl)-1H-pyrazolo[4,3-c]pyridin-1-yl)cyclohexyl)oxy)-2-methylpyridazin-3(2H)-one | Mass spectrum (apci) m/z = 449.2 |
| 3 | 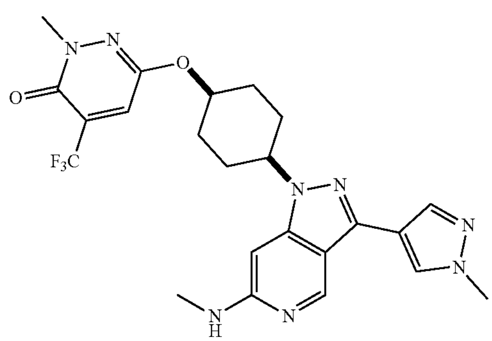 | 2-methyl-6-(((1s,4s)-4-(3-(1-methyl-1H-pyrazol-4-yl)-6-(methylamino)-1H-pyrazolo[4,3-c]pyridin-1-yl)cyclohexyl)oxy)-4-(trifluoromethyl)pyridazin-3(2H)-one | Mass spectrum (apci) m/z = 503.2 |
| 4 | 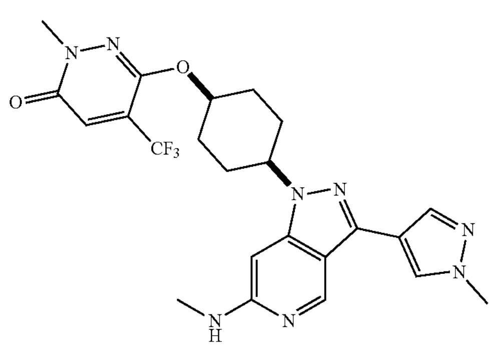 | 2-methyl-6-(((1s,4s)-4-(3-(1-methyl-1H-pyrazol-4-yl)-6-(methylamino)-1H-pyrazolo[4,3-c]pyridin-1-yl)cyclohexyl)oxy)-5-(trifluoromethyl)pyridazin-3(2H)-one | Mass spectrum (apci) m/z = 503.2 |

| Example | Structure | Name | Data |
|---|---|---|---|
| 5 | 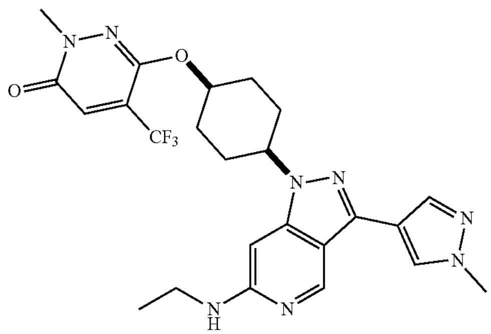 | 6-(((1s,4s)-4-(6-(ethylamino)-3-(1-methyl-1H-pyrazol-4-yl)-1H-pyrazolo[4,3-c]pyridin-1-yl)cyclohexyl)oxy)-2-methyl-5-(trifluoromethyl)pyridazin-3(2H)-one | Mass spectrum (apci) m/z = 517.2 |
| 6 | 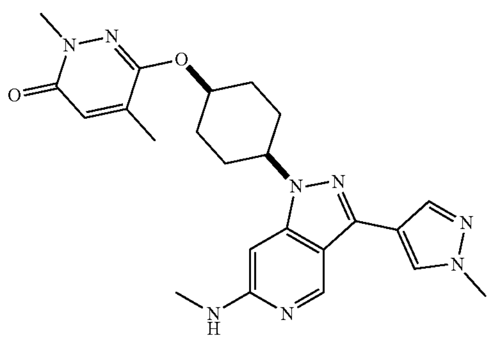 | 2,5-dimethyl-6-(((1s,4s)-4-(3-(1-methyl-1H-pyrazol-4-yl)-6-(methylamino)-1H-pyrazolo[4,3-c]pyridin-1-yl)cyclohexyl)oxy)pyridazin-3(2H)-one | Mass spectrum (apci) m/z = 449.2 |
| 7 | 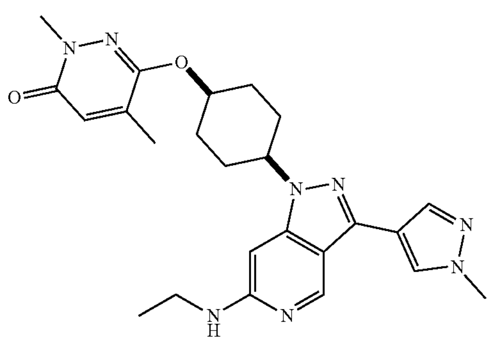 | 6-(((1s,4s)-4-(6-(ethylamino)-3-(1-methyl-1H-pyrazol-4-yl)-1H-pyrazolo[4,3-c]pyridin-1-yl)cyclohexyl)oxy)-2,5-dimethylpyridazin-3(2H)-one | Mass spectrum (apci) m/z = 463.2 |
| 8 | 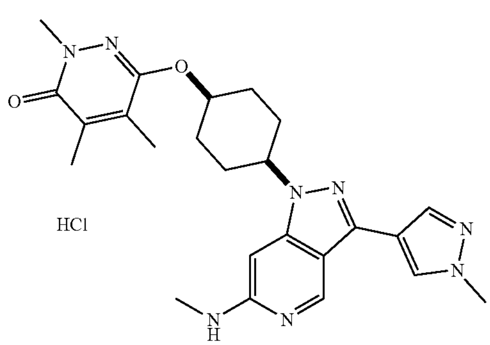 | 2,4,5-trimethyl-6-(((1s,4s)-4-(3-(1-methyl-1H-pyrazol-4-yl)-6-(methylamino)-1H-pyrazolo[4,3-c]pyridin-1-yl)cyclohexyl)oxy)pyridazin-3(2H)-one hydrochloride | Mass spectrum (apci) m/z = 463.3 |

| Example | Structure | Name | Data |
|---|---|---|---|
| 9 | 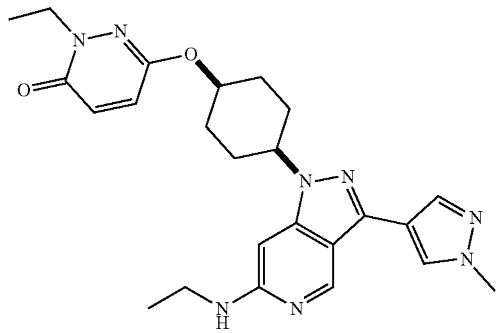 | 2-ethyl-6-(((1s,4s)-4-(6-(ethylamino)-3-(1-methyl-1H-pyrazol-4-yl)-1H-pyrazolo[4,3-c]pyridin-1-yl)cyclohexyl)oxy)pyridazin-3(2H)-one | Mass spectrum (apci) m/z = 463.2 |
| 10 | 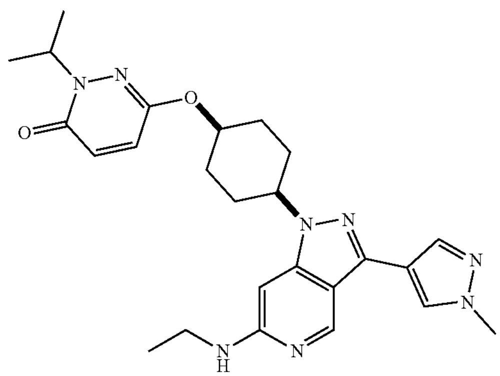 | 6-(((1s,4s)-4-(6-(ethylamino)-3-(1-methyl-1H-pyrazol-4-yl)-1H-pyrazolo[4,3-c]pyridin-1-yl)cyclohexyl)oxy)-2-isopropylpyridazin-3(2H)-one | Mass spectrum (apci) m/z = 477.2 |
| 11 | 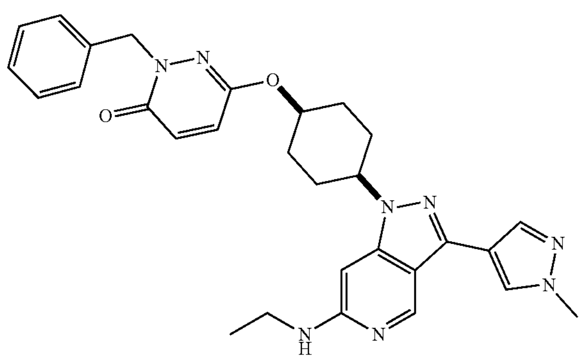 | 2-benzyl-6-(((1s,4s)-4-(6-(ethylamino)-3-(1-methyl-1H-pyrazol-4-yl)-1H-pyrazolo[4,3-c]pyridin-1-yl)cyclohexyl)oxy)pyridazin-3(2H)-one | Mass spectrum (apci) m/z = 525.2 |
| 12 | 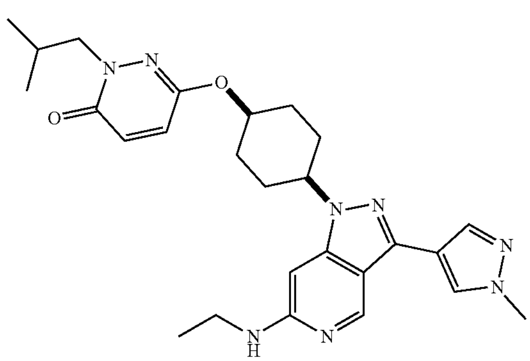 | 6-(((1s,4s)-4-(6-(ethylamino)-3-(1-methyl-1H-pyrazol-4-yl)-1H-pyrazolo[4,3-c]pyridin-1-yl)cyclohexyl)oxy)-2-isobutylpyridazin-3(2H)-one | Mass spectrum (apci) m/z = 491.3 |

| Example | Structure | Name | Data |
|---|---|---|---|
| 13 | 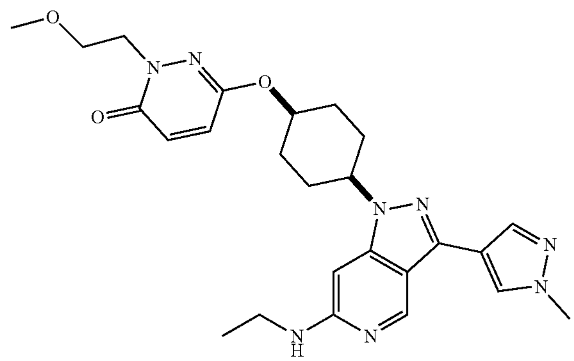 | 6-(((1s,4s)-4-(6-(ethylamino)-3-(1-methyl-1H-pyrazol-4-yl)-1H-pyrazolo[4,3-c]pyridin-1-yl)cyclohexyl)oxy)-2-(2-methoxyethyl)pyridazin-3(2H)-one | Mass spectrum (apci) m/z = 493.2 |
| 14 | 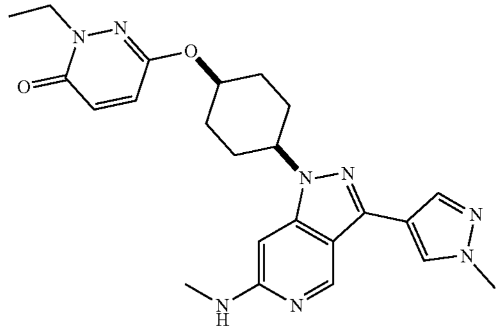 | 2-ethyl-6-(((1s,4s)-4-(3-(1-methyl-1H-pyrazol-4-yl)-6-(methylamino)-1H-pyrazolo[4,3-c]pyridin-1-yl)cyclohexyl)oxy)pyridazin-3(2H)-one | Mass spectrum (apci) m/z = 449.2 |
| 15 | 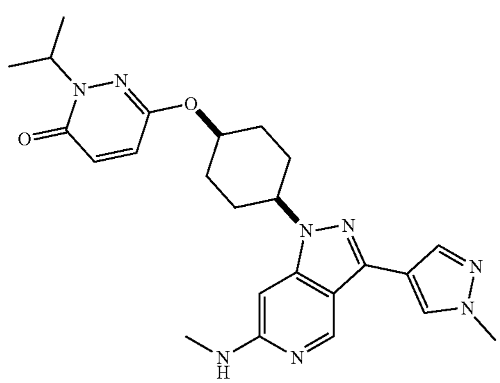 | 2-isopropyl-6-(((1s,4s)-4-(3-(1-methyl-1H-pyrazol-4-yl)-6-(methylamino)-1H-pyrazolo[4,3-c]pyridin-1-yl)cyclohexyl)oxy)pyridazin-3(2H)-one | Mass spectrum (apci) m/z = 463.2 |
| 16 | 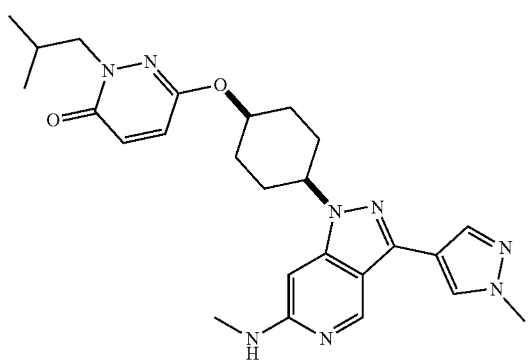 | 2-isobutyl-6-(((1s,4s)-4-(3-(1-methyl-1H-pyrazol-4-yl)-6-(methylamino)-1H-pyrazolo[4,3-c]pyridin-1-yl)cyclohexyl)oxy)pyridazin-3(2H)-one | Mass spectrum (apci) m/z = 477.2 |

-continued

| Example | Structure | Name | Data |
|---|---|---|---|
| 17 | 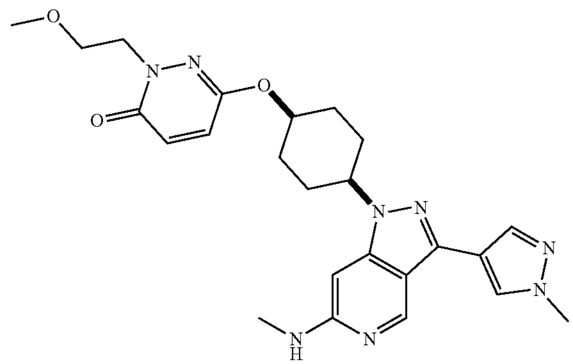 | 2-(2-methoxyethyl)-6-(((1s,4s)-4-(3-(1-methyl-1H-pyrazol-4-yl)-6-(methylamino)-1H-pyrazolo[4,3-c]pyridin-1-yl)cyclohexyl)oxy)pyridazin-3(2H)-one | Mass spectrum (apci) m/z = 479.2 |
| 18 | 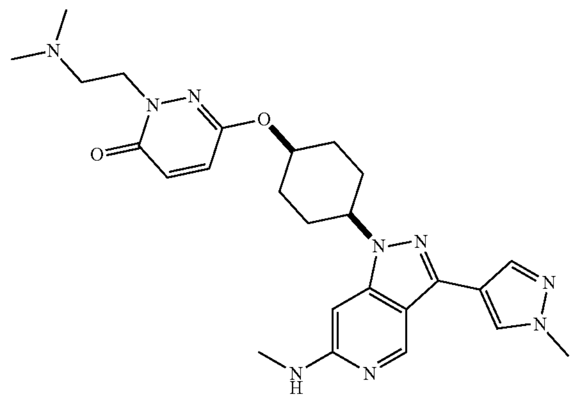 | 2-(2-(dimethylamino)ethyl)-6-(((1s,4s)-4-(3-(1-methyl-1H-pyrazol-4-yl)-6-(methylamino)-1H-pyrazolo[4,3-c]pyridin-1-yl)cyclohexyl)oxy)pyridazin-3(2H)-one | Mass spectrum (apci) m/z = 492.3 |
| 19 | 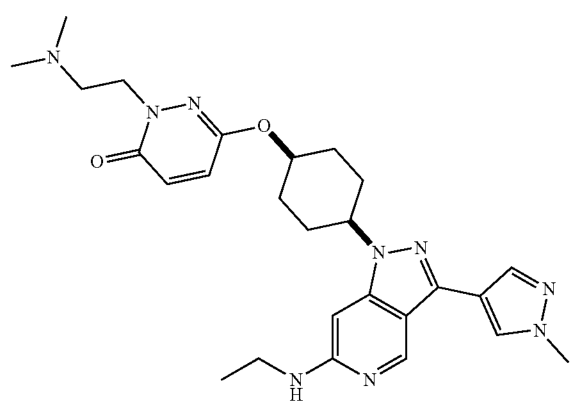 | 2-(2-(dimethylamino)ethyl)-6-(((1s,4s)-4-(6-(ethylamino)-3-(1-methyl-1H-pyrazol-4-yl)-1H-pyrazolo[4,3-c]pyridin-1-yl)cyclohexyl)oxy)pyridazin-3(2H)-one | Mass spectrum (apci) m/z = 506.3 |
| 20 | 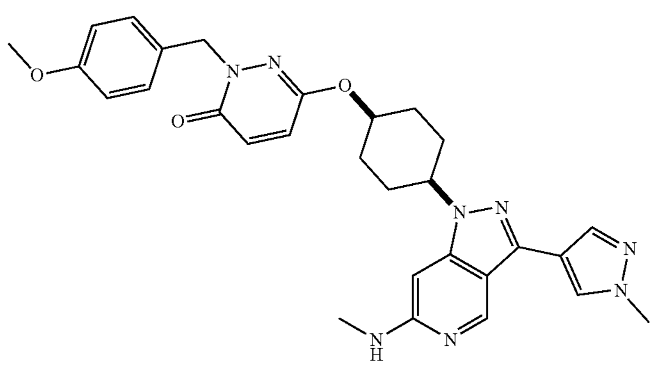 | 2-(4-methoxybenzyl)-6-(((1s,4s)-4-(3-(1-methyl-1H-pyrazol-4-yl)-6-(methylamino)-1H-pyrazolo[4,3-c]pyridin-1-yl)cyclohexyl)oxy)pyridazin-3(2H)-one | Mass spectrum (apci) m/z = 541.2 |

-continued

| Example | Structure | Name | Data |
|---|---|---|---|
| 21 | 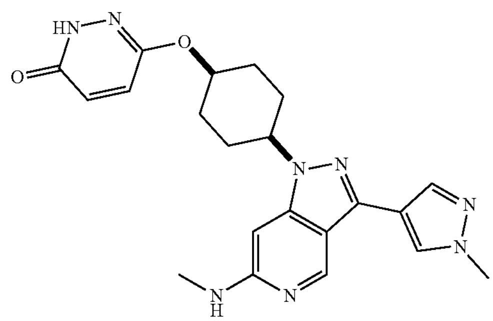 | 6-(((1s,4s)-4-(3-(1-methyl-1H-pyrazol-4-yl)-6-(methylamino)-1H-pyrazolo[4,3-c]pyridin-1-yl)cyclohexyl)oxy)pyridazin-3(2H)-one | Mass spectrum (apci) m/z = 421.2 |
| 22 | 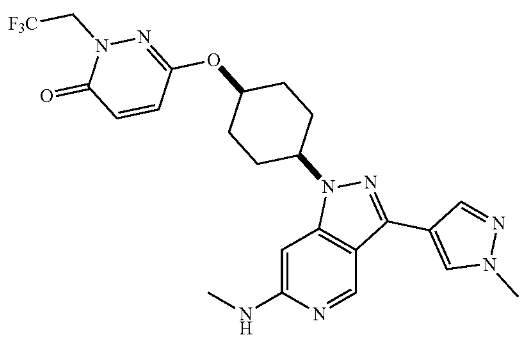 | 6-(((1s,4s)-4-(3-(1-methyl-1H-pyrazol-4-yl)-6-(methylamino)-1H-pyrazolo[4,3-c]pyridin-1-yl)cyclohexyl)oxy)-2-(2,2,2-trifluoroethyl)pyridazin-3(2H)-one | Mass spectrum (apci) m/z = 503.2 |
| 23 | 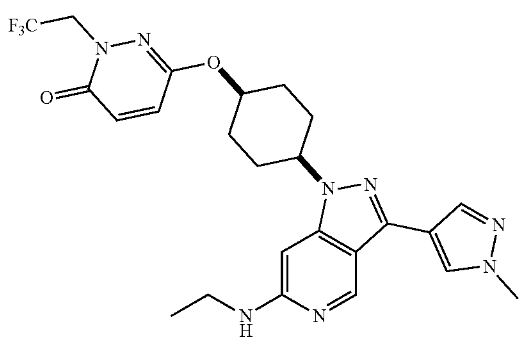 | 6-(((1s,4s)-4-(6-(ethylamino)-3-(1-methyl-1H-pyrazol-4-yl)-1H-pyrazolo[4,3-c]pyridin-1-yl)cyclohexyl)oxy)-2-(2,2,2-trifluoroethyl)pyridazin-3(2H)-one | Mass spectrum (apci) m/z = 517.2 |
| 24 | 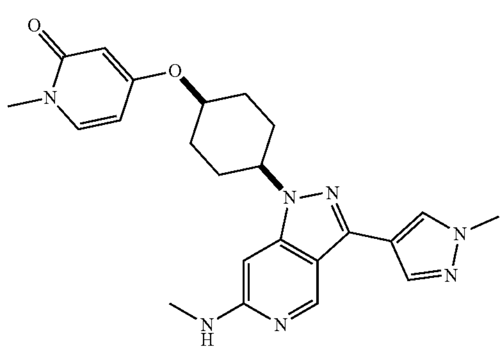 | 1-methyl-4-(((1s,4s)-4-(3-(1-methyl-1H-pyrazol-4-yl)-6-(methylamino)-1H-pyrazolo[4,3-c]pyridin-1-yl)cyclohexyl)oxy)pyridin-2(1H)-one | Mass spectrum (apci) m/z = 434.2 |

Example 25

5-(((1s,4s)-4-(3-(1-methyl-1H-pyrazol-4-yl)-6-(methylamino)-1H-pyrazolo[4,3-c]pyridin-1-yl)cyclohexyl)oxy)pyridin-2(1H)-one

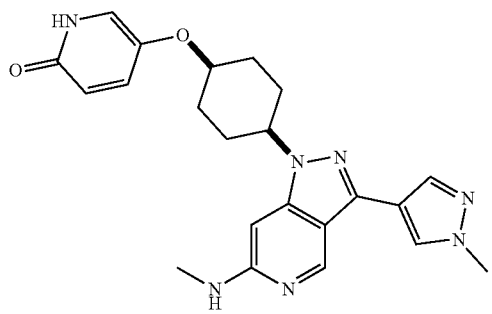

Step A: DIAD (0.01213 mL, 0.06154 mmol) was added to Ph₃P (0.01614 g, 0.06154 mmol) in THF (0.5861 mL, 0.05861 mmol). To this was added tert-butyl (1-((1r,4r)-4-hydroxycyclohexyl)-3-(1-methyl-1H-pyrazol-4-yl)-1H-pyrazolo[4,3-c]pyridin-6-yl)(methyl)carbamate (Example 1, Step D, 0.025 g, 0.05861 mmol) followed by 6-(benzyloxy)pyridin-3-ol (0.01533 g, 0.07620 mmol). The mixture was stirred at 60° C. overnight. The reaction mixture was partitioned between DCM and water, washed with brine and dried over sodium sulfate, filtered and concentrated to afford crude tert-butyl methyl(3-(1-methyl-1H-pyrazol-4-yl)-1-((1s,4s)-4-((6-oxo-1,6-dihydropyridin-3-yl)oxy)cyclohexyl)-1H-pyrazolo[4,3-c]pyridin-6-yl)carbamate.

Step B: Crude tert-butyl methyl(3-(1-methyl-1H-pyrazol-4-yl)-1-((1s,4s)-4-((6-oxo-1,6-dihydropyridin-3-yl)oxy)cyclohexyl)-1H-pyrazolo[4,3-c]pyridin-6-yl)carbamate was dissolved in TFA:DCM (2:1) and stirred for 1 hour. The reaction mixture was concentrated and purified on preparative HPLC (water:ACN 5-95% with 1% TFA). The resultant residue was partitioned between DCM and aqueous NaHCO₃, dried over sodium sulfate, filtered and concentrated to 1-((1s,4s)-4-((6-(benzyloxy)pyridin-3-yl)oxy)cyclohexyl)-N-methyl-3-(1-methyl-1H-pyrazol-4-yl)-1H-pyrazolo[4,3-c]pyridin-6-amine (0.014 g, 0.02747 mmol, 46.87% yield).

Step C: 1-((1s,4s)-4-((6-(benzyloxy)pyridin-3-yl)oxy)cyclohexyl)-N-methyl-3-(1-methyl-1H-pyrazol-4-yl)-1H-pyrazolo[4,3-c]pyridin-6-amine (0.012 g, 0.024 mmol) was stirred in MeOH (2 mL) with 10% Pd/C and a H2 balloon for 1 hour. The reaction mixture was filtered and concentrated to afford 5-(((1s,4s)-4-(3-(1-methyl-1H-pyrazol-4-yl)-6-(methylamino)-1H-pyrazolo[4,3-c]pyridin-1-yl)cyclohexyl)oxy)pyridin-2(1H)-one (0.0078 g, 0.019 mmol, 790% yield). Mass spectrum (apci) m/z=420.2 (M+H). 1H NMR (CDCl₃) δ 8.69 (d, J=0.8 Hz, 1H), 7.98 (s, 1H), 7.89 (s, 1H), 7.41 (dd, J=9.8, 3.1 Hz, 1H), 7.08 (d, J=3.1 Hz, 1H), 6.59 (d, J=9.8 Hz, 1H), 6.03 (s, 1H), 5.20 (br s, 1H), 4.35-4.25 (m, 2H), 4.00 (s, 3H), 2.97 (s, 3H), 2.48 (qd, J=13.5, 3.5 Hz, 2H), 2.29-2.21 (m, 2H), 1.94-1.85 (m, 2H), 1.80-1.70 (m, 2H).

Example 26

1-methyl-5-(((1s,4s)-4-(3-(1-methyl-1H-pyrazol-4-yl)-6-(methylamino)-1H-pyrazolo[4,3-c]pyridin-1-yl)cyclohexyl)oxy)pyridin-2(1H)-one

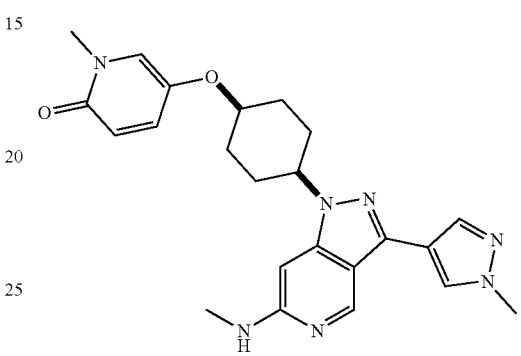

Step A: tert-butyl (1-((1s,4s)-4-((6-(benzyloxy)pyridin-3-yl)oxy)cyclohexyl)-3-(1-methyl-1H-pyrazol-4-yl)-1H-pyrazolo[4,3-c]pyridin-6-yl)(methyl)carbamate (Example 24, Step A, 0.078 g, 0.13 mmol) was stirred in MeOH (2 mL) with Pd/C and a H2 balloon. After 1 hour, the mixture was filtered, concentrated and purified over silica gel (1-10% MeOH in DCM) to afford tert-butyl methyl(3-(1-methyl-1H-pyrazol-4-yl)-1-((1s,4s)-4-((6-oxo-1,6-dihydropyridin-3-yl)oxy)cyclohexyl)-1H-pyrazolo[4,3-c]pyridin-6-yl)carbamate (0.011 g, 0.021 mmol, 17% yield).

Step B: NaH (0.000931 g, 0.0233 mmol) was added to tert-butyl methyl(3-(1-methyl-1H-pyrazol-4-yl)-1-((1s,4s)-4-((6-oxo-1,6-dihydropyridin-3-yl)oxy)cyclohexyl)-1H-pyrazolo[4,3-c]pyridin-6-yl)carbamate (0.011 g, 0.0212 mmol) in THF (0.212 mL). Iodomethane (0.00138 mL, 0.0222 mmol) was added and heated to 50° C. overnight. Additional NaH (0.000931 g, 0.0233 mmol) and iodomethane (0.00138 mL, 0.0222 mmol) were added and stirred at 50° C. for 1 hour. The reaction mixture was concentrated and dissolved in DCM (1 mL) and TFA (1 mL) and stirred for 1 hour. The reaction mixture was concentrated and purified on C18 column (5-95% ACN in water 1% TFA). The residue was partitioned between DCM and aqueous NaHCO₃, dried filtered and concentrated to afford 1-methyl-5-(((1s,4s)-4-(3-(1-methyl-1H-pyrazol-4-yl)-6-(methylamino)-1H-pyrazolo[4,3-c]pyridin-1-yl)cyclohexyl)oxy)pyridin-2(1H)-one (0.0027 g, 0.00623 mmol, 29.4% yield). Mass spectrum (apci) m/z=434.2 (M+H). 1H NMR (CDCl₃) δ 8.67 (s, 1H), 7.99 (s, 1H), 7.87 (s, 1H), 7.30 (dd, J=9.8, 3.1 Hz, 1H), 7.02 (d, J=3.1 Hz, 1H), 6.58 (d, J=9.8 Hz, 1H), 6.04 (s, 1H), 4.35-4.23 (m, 2H), 4.00 (s, 3H), 3.33 (s, 3H), 2.97 (s, 3H), 2.55-2.43 (m, 2H), 2.28-2.20 (m, 2H), 1.95-1.87 (m, 2H), 1.80-1.70 (m, 2H).

Example 27

2-methyl-6-(((1s,4s)-4-(6-(methylamino)-3-(4-((4-methylpiperazin-1-yl)methyl)phenyl)-1H-pyrazolo[4,3-c]pyridin-1-yl)cyclohexyl)oxy)pyridazin-3(2H)-one

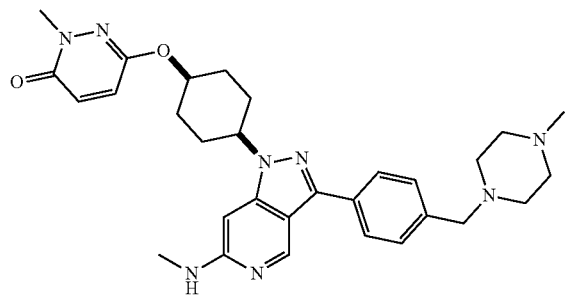

Step A: tert-butyl (3-bromo-1-((1r,4r)-4-hydroxycyclohexyl)-1H-pyrazolo[4,3-c]pyridin-6-yl)(methyl)carbamate (Example 1, Step C, 2.13 g, 5.01 mmol), PPh₃ (1.44 g, 5.51 mmol) and 3-Hydroxy-1-methylpyridazin-6(1H)-one (0.821 g, 6.51 mmol) were diluted with THF (30 mL), placed under nitrogen and cooled to 0° C. DIAD (1.07 mL, 5.51 mmol) was added slowly and the reaction was left to stir for 12 hours warming to room temperature. The reaction mixture was partitioned between ethyl acetate and water, dried over magnesium sulfate, filtered and concentrated. The residue was purified over silica gel (20-80% ethyl acetate in hexanes) to afford tert-butyl (3-bromo-1-((1s,4s)-4-((1-methyl-6-oxo-1,6-dihydropyridazin-3-yl)oxy)cyclohexyl)-1H-pyrazolo[4,3-c]pyridin-6-yl)(methyl)carbamate (1.8 g, 3.37 mmol, 67.4% yield).

Step B: tert-butyl (3-bromo-1-((1s,4s)-4-((1-methyl-6-oxo-1,6-dihydropyridazin-3-yl)oxy)cyclohexyl)-1H-pyrazolo[4,3-c]pyridin-6-yl)(methyl)carbamate (0.025 g, 0.0469 mmol), 1-Methyl-4-[4-(4,4,5,5-tetramethyl-1,3,2-dioxaborolan-2-yl)benzyl]piperazine (0.0296 g, 0.0937 mmol), Pd(PPh₃)₄ (0.00271 g, 0.00234 mmol) and 2M Na₂CO₃ (0.0492 mL, 0.0984 mmol) in dioxane (0.469 mL) was heated to 90° C. for 17 h. The reaction mixture was partitioned between water and EtOAc, dried, filtered and concentrated. The crude material was used in the next reaction without further purification.

Step C: The crude material from the last reaction was diluted with dichloromethane (2 mL) and then treated with TFA (5 mL). After 1 h, the reaction mixture was concentrated in vacuo and the resultant oil was resuspended in 1 mL of a solution of 60:40 ACN:water with 2% TFA modifier. The product was purified by C18 HPLC (5-50% ACN in water with 0.2% TFA modifier). The product fractions were partitioned between DCM and aqueous NaHCO₃(15 mL), extracted with DCM (2×15 mL), washed with brine, dried over sodium sulfate, filtered and concentrated to afford 2-methyl-6-(((1s,4s)-4-(6-(methylamino)-3-(4-((4-methylpiperazin-1-yl)methyl)phenyl)-1H-pyrazolo[4,3-c]pyridin-1-yl)cyclohexyl)oxy)pyridazin-3(2H)-one (0.0122 g, 0.0225 mmol, 48.0% yield) as a solid. Mass spectrum (apci) m/z=543.3 (M+H). ¹H NMR (CDCl₃) δ 8.83 (d, J=0.8 Hz, 1H), 7.88 (m, 2H), 7.45 (m, 2H), 7.01 (d, J=9.6 Hz, 1H), 6.93 (d, J=9.6 Hz, 1H), 6.06 (s, 1H), 5.30 (s, 1H), 5.10 (m, 1H), 4.78 (m, 1H), 4.36 (tt, J=11.3, 4.1 Hz, 1H), 3.66 (s, 3H), 3.57 (s, 2H), 2.98 (d, J=5.3 Hz, 3H), 2.60-2.28 (m, 14H), 2.00-1.91 (m, 2H), 1.85-1.75 (m, 2H).

Using the procedure described for the preparation of Example 27, the following compounds were also synthesized:

| Example | Structure | Name | Data |
|---|---|---|---|
| 28 | 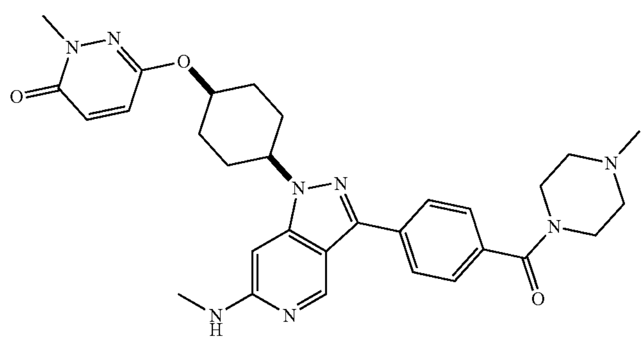 | 2-methyl-6-(((1s,4s)-4-(6-(methylamino)-3-(4-(4-methylpiperazine-1-carbonyl)phenyl)-1H-pyrazolo[4,3-c]pyridin-1-yl)cyclohexyl)oxy)pyridazin-3(2H)-one | Mass spectrum (apci) m/z = 557.3 |
| 29 | 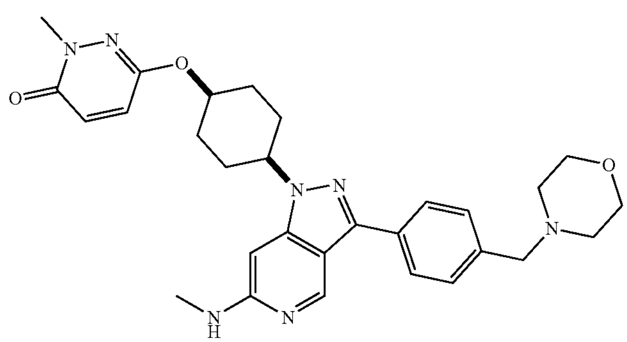 | 2-methyl-6-(((1s,4s)-4-(6-(methylamino)-3-(4-(morpholinomethyl)phenyl)-1H-pyrazolo[4,3-c]pyridin-1-yl)cyclohexyl)oxy)pyridazin-3(2H)-one | Mass spectrum (apci) m/z = 530.2 |

-continued

| Example | Structure | Name | Data |
|---|---|---|---|
| 30 | 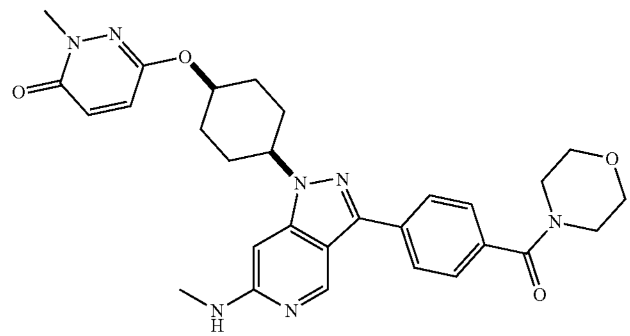 | 2-methyl-6-(((1s,4s)-4-(6-(methylamino)-3-(4-(morpholine-4-carbonyl)phenyl)-1H-pyrazolo[4,3-c]pyridin-1-yl)cyclohexyl)oxy)pyridazin-3(2H)-one | Mass spectrum (apci) m/z = 544.3 |
| 31 | 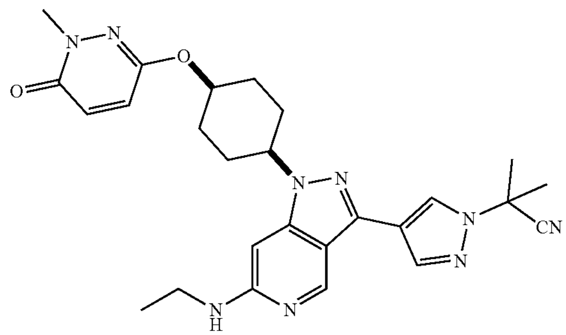 | 2-(4-(6-(ethylamino)-1-((1s,4s)-4-((1-methyl-6-oxo-1,6-dihydropyridazin-3-yl)oxy)cyclohexyl)-1H-pyrazolo[4,3-c]pyridin-3-yl)-1H-pyrazol-1-yl)-2-methylpropanenitrile | Mass spectrum (apci) m/z = 502.2 |
| 32 | 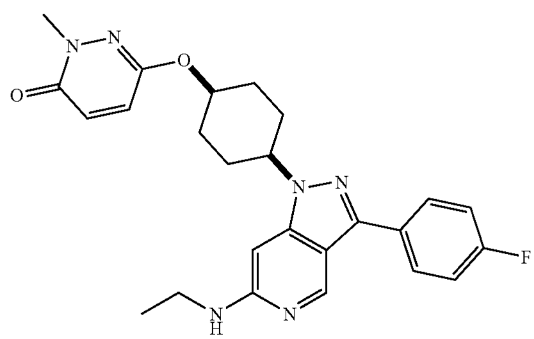 | 6-(((1s,4s)-4-(6-(ethylamino)-3-(4-fluorophenyl)-1H-pyrazolo[4,3-c]pyridin-1-yl)cyclohexyl)oxy)-2-methylpyridazin-3(2H)-one | Mass spectrum (apci) m/z = 463.2 |
| 33 | 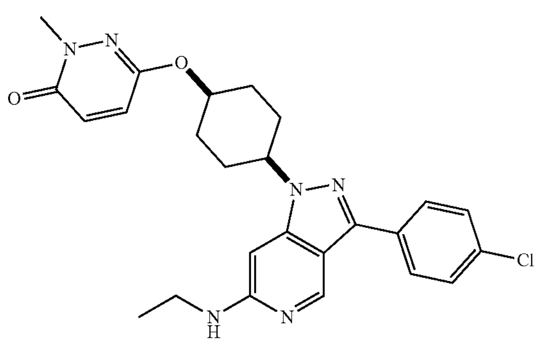 | 6-(((1s,4s)-4-(3-(4-chlorophenyl)-6-(ethylamino)-1H-pyrazolo[4,3-c]pyridin-1-yl)cyclohexyl)oxy)-2-methylpyridazin-3(2H)-one | Mass spectrum (apci) m/z = 479.1 |

| Example | Structure | Name | Data |
|---|---|---|---|
| 34 | 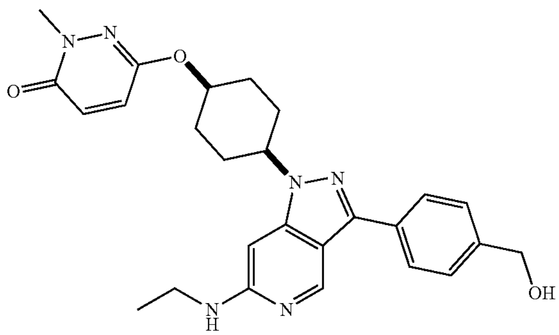 | 6-(((1s,4s)-4-(6-(ethylamino)-3-(4-(hydroxymethyl)phenyl)-1H-pyrazolo[4,3-c]pyridin-1-yl)cyclohexyl)oxy)-2-methylpyridazin-3(2H)-one | Mass spectrum (apci) m/z = 475.2 |
| 35 | 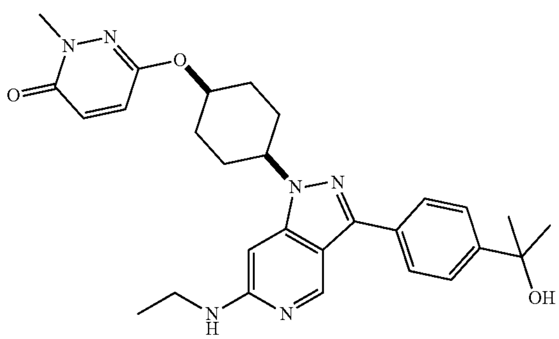 | 6-(((1s,4s)-4-(6-(ethylamino)-3-(4-(2-hydroxypropan-2-yl)phenyl)-1H-pyrazolo[4,3-c]pyridin-1-yl)cyclohexyl)oxy)-2-methylpyridazin-3(2H)-one | Mass spectrum (apci) m/z = 503.2 |
| 36 | 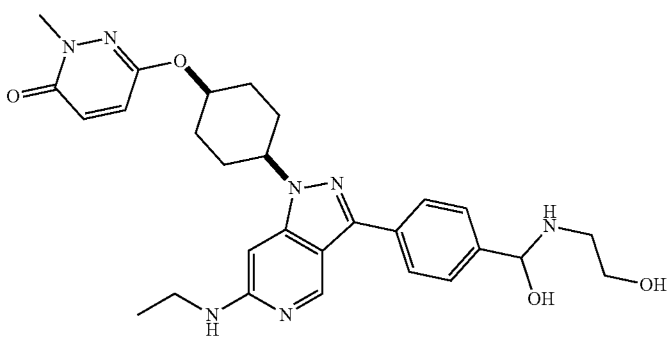 | 4-(6-(ethylamino)-1-((1s,4s)-4-((1-methyl-6-oxo-1,6-dihydropyridazin-3-yl)oxy)cyclohexyl)-1H-pyrazolo[4,3-c]pyridin-3-yl)-N-(2-hydroxyethyl)benzamide | Mass spectrum (apci) m/z = 532.2 |
| 37 | 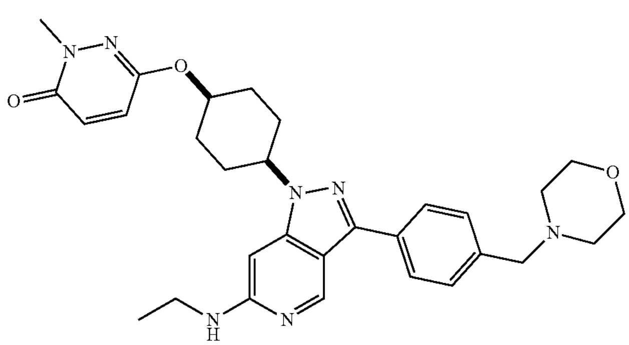 | 6-(((1s,4s)-4-(6-(ethylamino)-3-(4-(morpholinomethyl)phenyl)-1H-pyrazolo[4,3-c]pyridin-1-yl)cyclohexyl)oxy)-2-methylpyridazin-3(2H)-one | Mass spectrum (apci) m/z = 544.3 |

| Example | Structure | Name | Data |
|---|---|---|---|
| 38 | 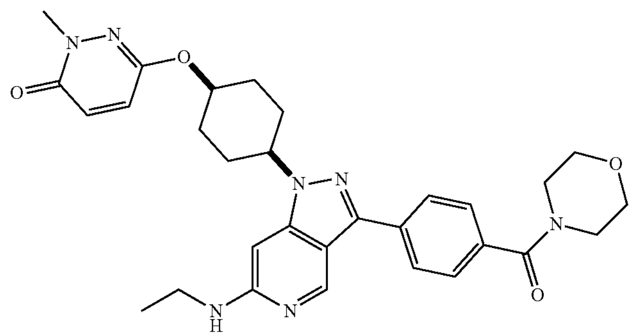 | 6-(((1s,4s)-4-(6-(ethylamino)-3-(4-(morpholine-4-carbonyl)phenyl)-1H-pyrazolo[4,3-c]pyridin-1-yl)cyclohexyl)oxy)-2-methylpyridazin-3(2H)-one | Mass spectrum (apci) m/z = 558.3 |
| 39 | 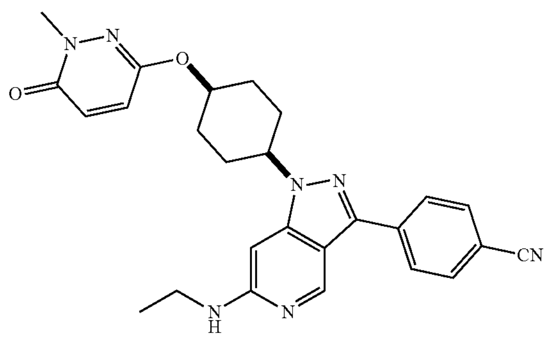 | 4-(6-(ethylamino)-1-((1s,4s)-4-((1-methyl-6-oxo-1,6-dihydropyridazin-3-yl)oxy)cyclohexyl)-1H-pyrazolo[4,3-c]pyridin-3-yl)benzonitrile | Mass spectrum (apci) m/z = 470.2 |
| 40 | 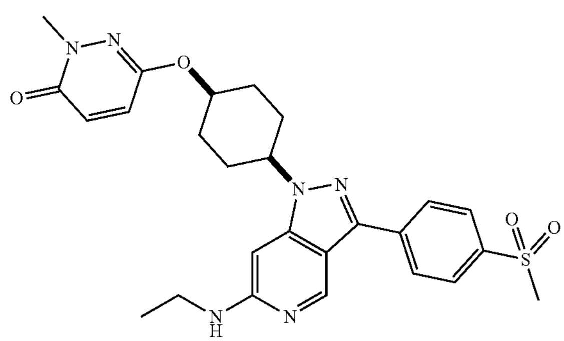 | 6-(((1s,4s)-4-(6-(ethylamino)-3-(4-(methylsulfonyl)phenyl)-1H-pyrazolo[4,3-c]pyridin-1-yl)cyclohexyl)oxy)-2-methylpyridazin-3(2H)-one | Mass spectrum (apci) m/z = 523.2 |
| 41 | 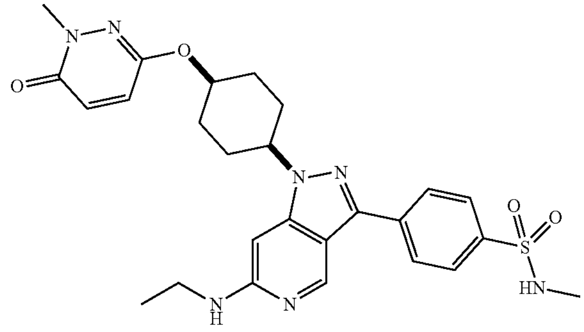 | 4-(6-(ethylamino)-1-((1s,4s)-4-((1-methyl-6-oxo-1,6-dihydropyridazin-3-yl)oxy)cyclohexyl)-1H-pyrazolo[4,3-c]pyridin-3-yl)-N-methylbenzenesulfonamide | Mass spectrum (apci) m/z = 538.2 |

-continued

| Example | Structure | Name | Data |
|---------|-----------|------|------|
| 42 | 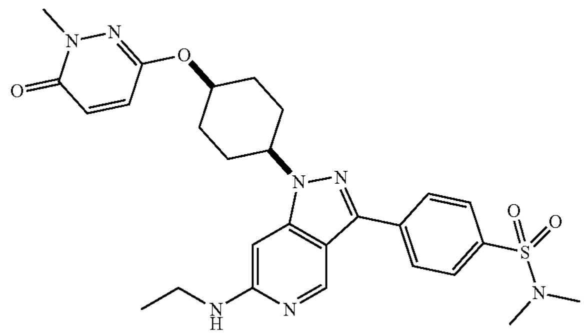 | 4-(6-(ethylamino)-1-((1s,4s)-4-((1-methyl-6-oxo-1,6-dihydropyridazin-3-yl)oxy)cyclohexyl)-1H-pyrazolo[4,3-c]pyridin-3-yl)-N,N-dimethylbenzenesulfonamide | Mass spectrum (apci) m/z = 552.2 |
| 43 | 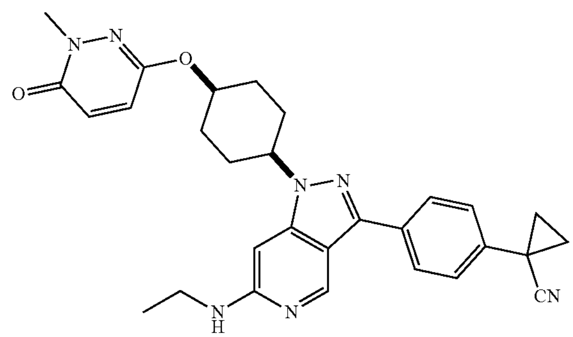 | 1-(4-(6-(ethylamino)-1-((1s,4s)-4-((1-methyl-6-oxo-1,6-dihydropyridazin-3-yl)oxy)cyclohexyl)-1H-pyrazolo[4,3-c]pyridin-3-yl)phenyl)cyclopropane-1-carbonitrile | Mass spectrum (apci) m/z = 510.2 |
| 44 | 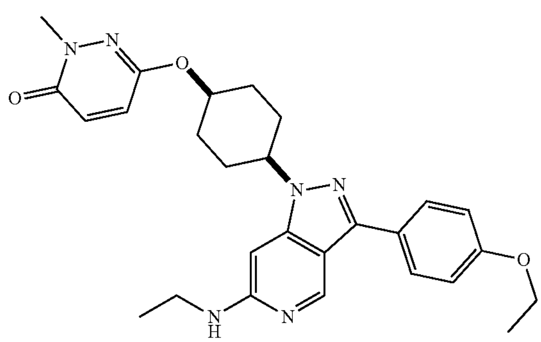 | 6-(((1s,4s)-4-(3-(4-ethoxyphenyl)-6-(ethylamino)-1H-pyrazolo[4,3-c]pyridin-1-yl)cyclohexyl)oxy)-2-methylpyridazin-3(2H)-one | Mass spectrum (apci) m/z = 489.2 |
| 45 | 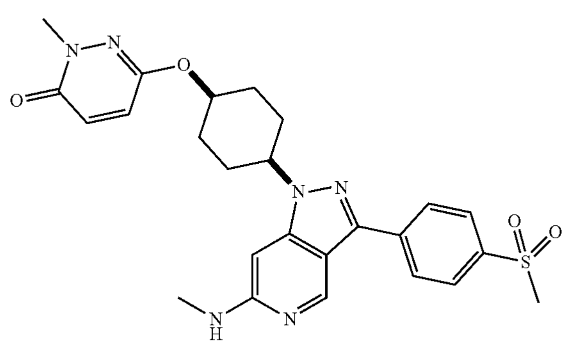 | 2-methyl-6-(((1s,4s)-4-(6-(methylamino)-3-(4-(methylsulfonyl)phenyl)-1H-pyrazolo[4,3-c]pyridin-1-yl)cyclohexyl)oxy)pyridazin-3(2H)-one | Mass spectrum (apci) m/z = 509.2 |

-continued

| Example | Structure | Name | Data |
|---|---|---|---|
| 46 | 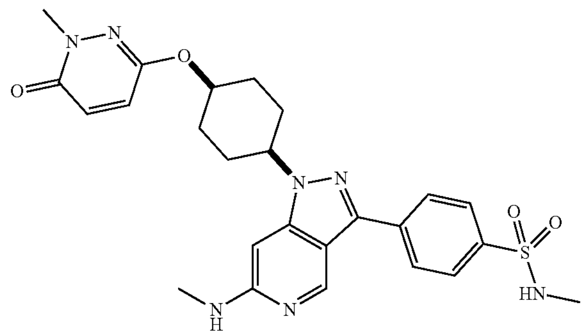 | N-methyl-4-(1-((1s,4s)-4-((1-methyl-6-oxo-1,6-dihydropyridazin-3-yl)oxy)cyclohexyl)-6-(methylamino)-1H-pyrazolo[4,3-c]pyridin-3-yl)benzenesulfonamide | Mass spectrum (apci) m/z = 524.1 |
| 47 | 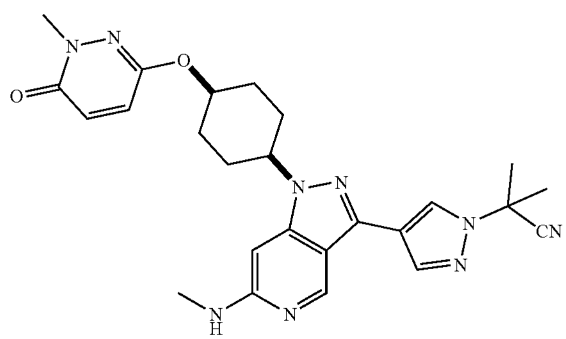 | 2-methyl-2-(4-(1-((1s,4s)-4-((1-methyl-6-oxo-1,6-dihydropyridazin-3-yl)oxy)cyclohexyl)-6-(methylamino)-1H-pyrazolo[4,3-c]pyridin-3-yl)-1H-pyrazol-1-yl)propanenitrile | Mass spectrum (apci) m/z = 488.2 |
| 48 | 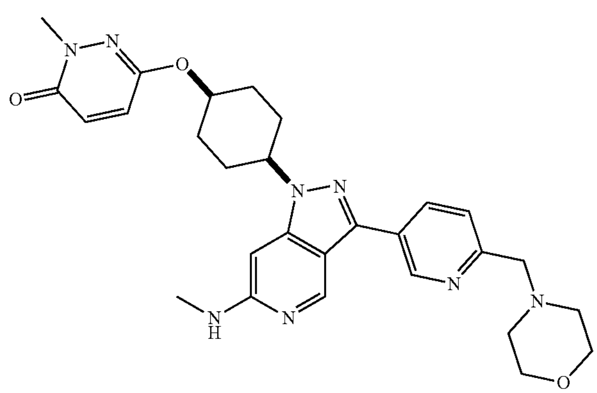 | 2-methyl-6-(((1s,4s)-4-(6-(methylamino)-3-(6-(morpholinomethyl)pyridin-3-yl)-1H-pyrazolo[4,3-c]pyridin-1-yl)cyclohexyl)oxy)pyridazin-3(2H)-one | Mass spectrum (apci) m/z = 531.3 |
| 49 | 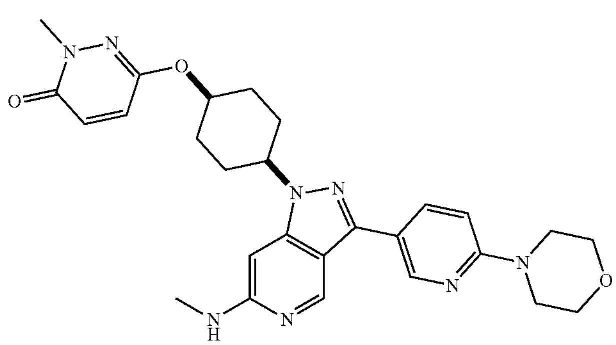 | 2-methyl-6-(((1s,4s)-4-(6-(methylamino)-3-(6-morpholinopyridin-3-yl)-1H-pyrazolo[4,3-c]pyridin-1-yl)cyclohexyl)oxy)pyridazin-3(2H)-one | Mass spectrum (apci) m/z = 517.3 |

-continued

| Example | Structure | Name | Data |
|---|---|---|---|
| 50 | 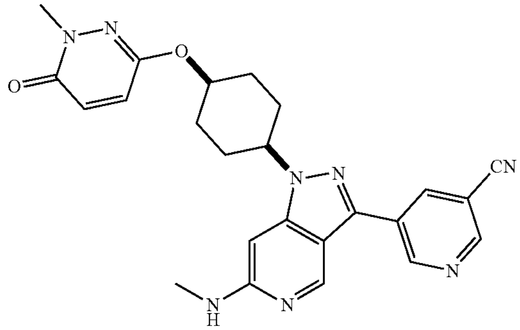 | 5-(1-((1s,4s)-4-((1-methyl-6-oxo-1,6-dihydropyridazin-3-yl)oxy)cyclohexyl)-6-(methylamino)-1H-pyrazolo[4,3-c]pyridin-3-yl)nicotinonitrile | Mass spectrum (apci) m/z = 457.2 |
| 51 | 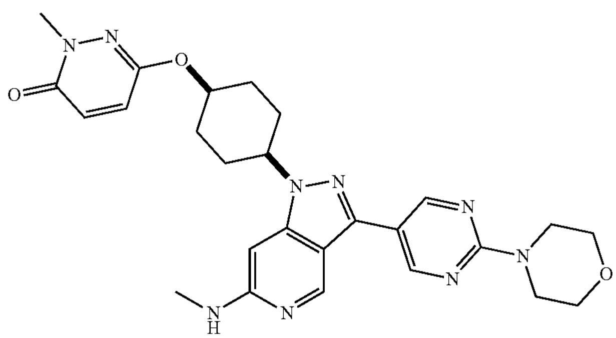 | 2-methyl-6-(((1s,4s)-4-(6-(methylamino)-3-(2-morpholinopyrimidin-5-yl)-1H-pyrazolo[4,3-c]pyridin-1-yl)cyclohexyl)oxy)pyridazin-3(2H)-one | Mass spectrum (apci) m/z = 518.2 |
| 52 | 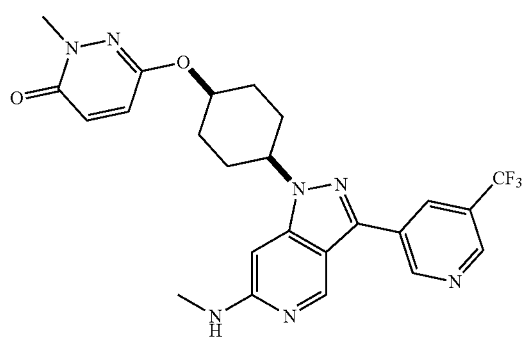 | 2-methyl-6-(((1s,4s)-4-(6-(methylamino)-3-(5-(trifluoromethyl)pyridin-3-yl)-1H-pyrazolo[4,3-c]pyridin-1-yl)cyclohexyl)oxy)pyridazin-3(2H)-one | Mass spectrum (apci) m/z = 500.2 |
| 53 | 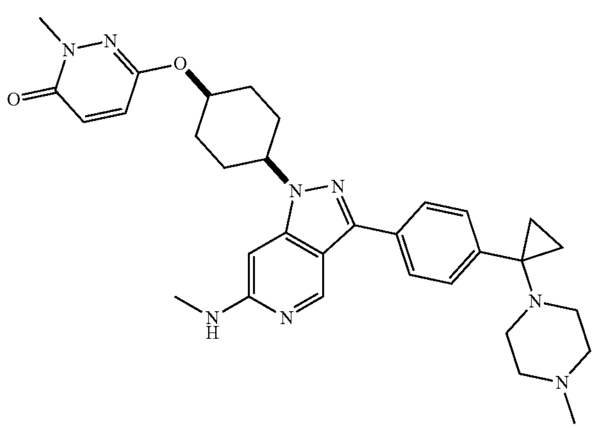 | 2-methyl-6-(((1s,4s)-4-(6-(methylamino)-3-(4-(1-(4-methylpiperazin-1-yl)cyclopropyl)phenyl)-1H-pyrazolo[4,3-c]pyridin-1-yl)cyclohexyl)oxy)pyridazin-3(2H)-one | Mass spectrum (apci) m/z = 569.3 |

-continued

| Example | Structure | Name | Data |
|---|---|---|---|
| 54 | 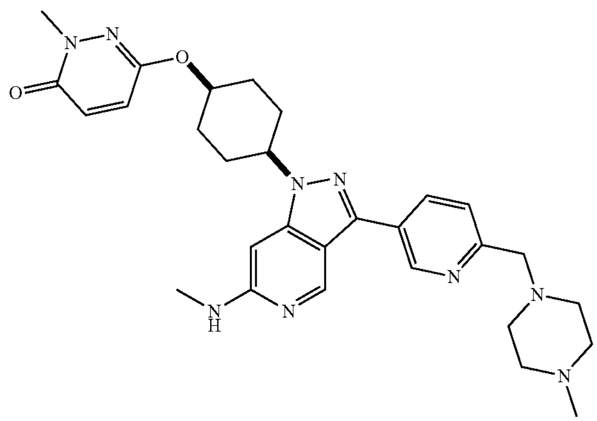 | 2-methyl-6-(((1s,4s)-4-(6-(methylamino)-3-(6-((4-methylpiperazin-1-yl)methyl)pyridin-3-yl)-1H-pyrazolo[4,3-c]pyridin-1-yl)cyclohexyl)oxy)pyridazin-3(2H)-one | Mass spectrum (apci) m/z = 544.3 |
| 55 | 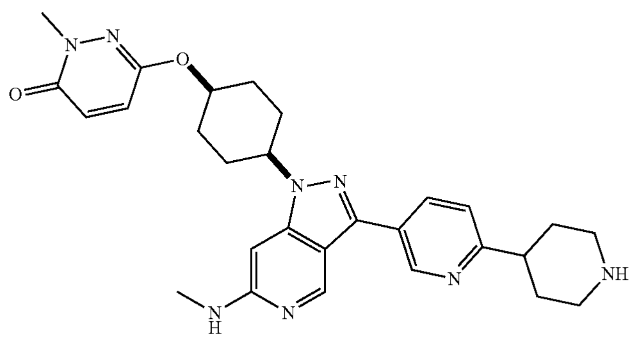 | 2-methyl-6-(((1s,4s)-4-(6-(methylamino)-3-(6-(piperidin-4-yl)pyridin-3-yl)-1H-pyrazolo[4,3-c]pyridin-1-yl)cyclohexyl)oxy)pyridazin-3(2H)-one | Mass spectrum (apci) m/z = 515.2 |
| 56 | 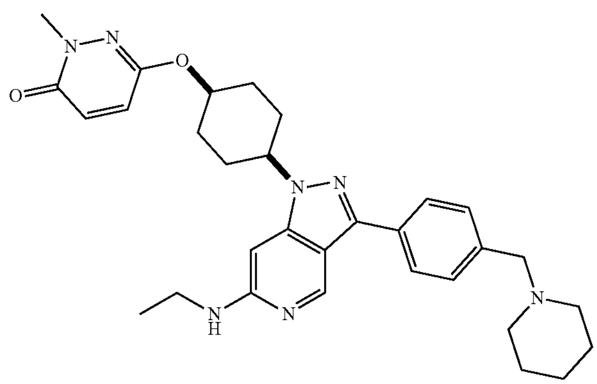 | 6-(((1s,4s)-4-(6-(ethylamino)-3-(4-(piperidin-1-ylmethyl)phenyl)-1H-pyrazolo[4,3-c]pyridin-1-yl)cyclohexyl)oxy)-2-methylpyridazin-3(2H)-one | Mass spectrum (apci) m/z = 542.2 |
| 57 | 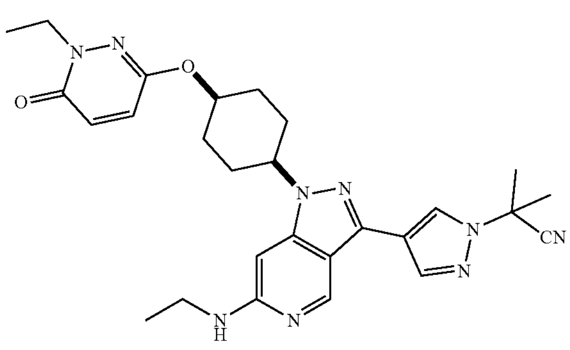 | 2-(4-(1-((1s,4s)-4-((1-ethyl-6-oxo-1,6-dihydropyridazin-3-yl)oxy)cyclohexyl)-6-(ethylamino)-1H-pyrazolo[4,3-c]pyridin-3-yl)-1H-pyrazol-1-yl)-2-methylpropanenitrile | Mass spectrum (apci) m/z = 516.3 |

-continued

| Example | Structure | Name | Data |
|---|---|---|---|
| 58 | 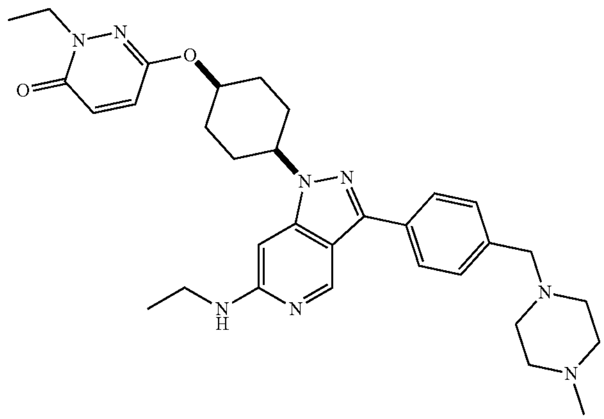 | 2-ethyl-6-(((1s,4s)-4-(6-(ethylamino)-3-(4-((4-methylpiperazin-1-yl)methyl)phenyl)-1H-pyrazolo[4,3-c]pyridin-1-yl)cyclohexyl)oxy)pyridazin-3(2H)-one | Mass spectrum (apci) m/z = 571.3 |
| 59 | 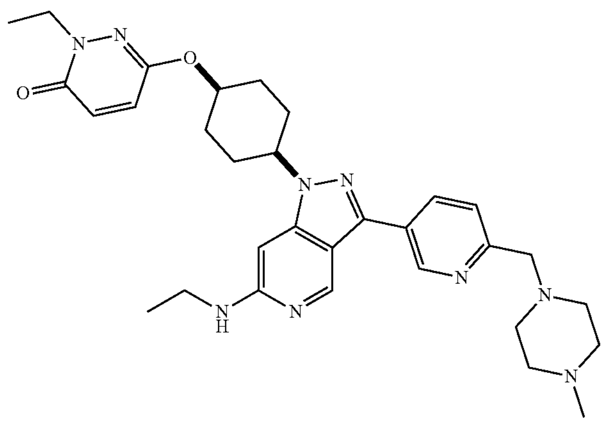 | 2-ethyl-6-(((1s,4s)-4-(6-(ethylamino)-3-(6-((4-methylpiperazin-1-yl)methyl)pyridin-3-yl)-1H-pyrazolo[4,3-c]pyridin-1-yl)cyclohexyl)oxy)pyridazin-3(2H)-one | Mass spectrum (apci) m/z = 572.3 |
| 60 | 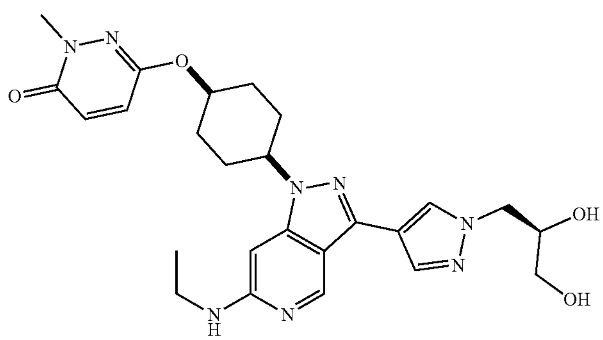 | 6-(((1S,4s)-4-(3-(1-((R)-2,3-dihydroxypropyl)-1H-pyrazol-4-yl)-6-(ethylamino)-1H-pyrazolo[4,3-c]pyridin-1-yl)cyclohexyl)oxy)-2-methylpyridazin-3(2H)-one | Mass spectrum (apci) m/z = 509.2 |
| 61 | 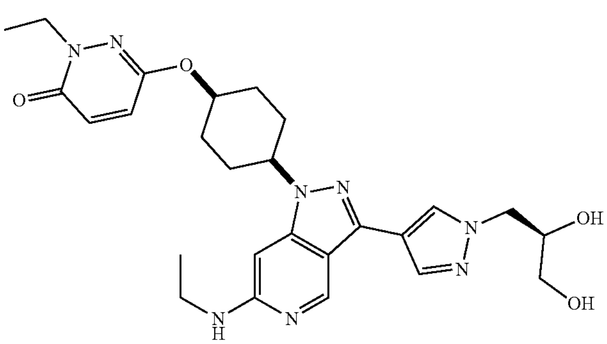 | 6-(((1S,4s)-4-(3-(1-((R)-2,3-dihydroxypropyl)-1H-pyrazol-4-yl)-6-(ethylamino)-1H-pyrazolo[4,3-c]pyridin-1-yl)cyclohexyl)oxy)-2-ethylpyridazin-3(2H)-one | Mass spectrum (apci) m/z = 523.3 |

-continued

| Example | Structure | Name | Data |
|---|---|---|---|
| 62 | 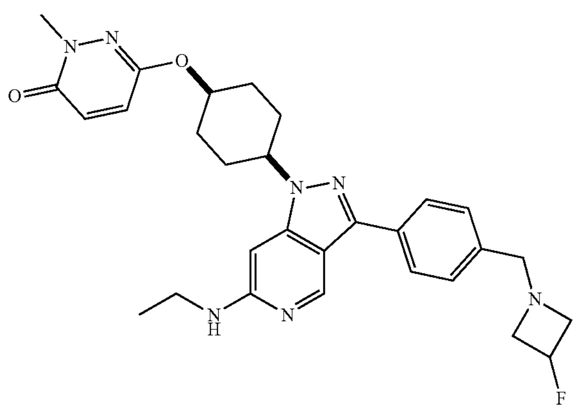 | 6-(((1s,4s)-4-(6-(ethylamino)-3-(4-((3-fluoroazetidin-1-yl)methyl)phenyl)-1H-pyrazolo[4,3-c]pyridin-1-yl)cyclohexyl)oxy)-2-methylpyridazin-3(2H)-one | Mass spectrum (apci) m/z = 532.2 |
| 63 | 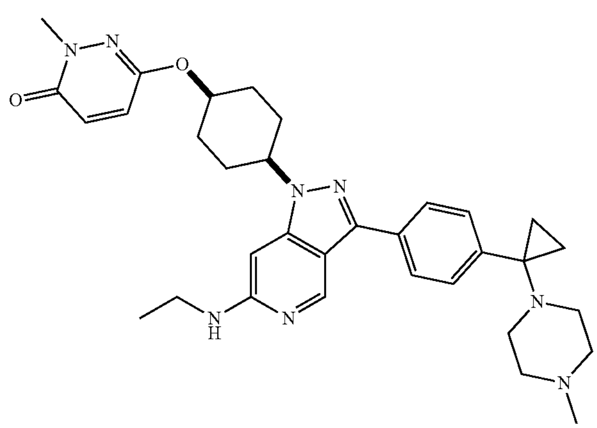 | 6-(((1s,4s)-4-(6-(ethylamino)-3-(4-(1-(4-methylpiperazin-1-yl)cyclopropyl)phenyl)-1H-pyrazolo[4,3-c]pyridin-1-yl)cyclohexyl)oxy)-2-methylpyridazin-3(2H)-one | Mass spectrum (apci) m/z = 583.3 |

Example 64

2-methyl-6-(((1s,4s)-4-(3-(1-methyl-1H-pyrazol-4-yl)-6-(methylamino)-1H-pyrrolo[3,2-c]pyridin-1-yl)cyclohexyl)oxy)pyridazin-3(2H)-one

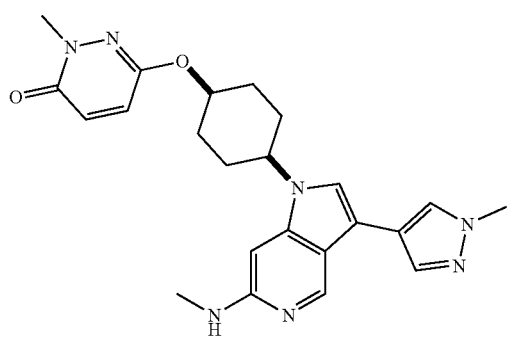

Step A: 3-bromo-6-chloro-1H-pyrrolo[3,2-c]pyridine (80 mg, 0.35 mmol) was dissolved in DMA (3.5 mL). (1r,4r)-4-((1-methyl-6-oxo-1,6-dihydropyridazin-3-yl)oxy)cyclohexyl 4-methylbenzenesulfonate (260 mg, 0.69 mmol) and Cs$_2$CO$_3$ (230 mg, 0.69 mmol) were added and the reaction was heated to 100° C. overnight. The reaction mixture was partitioned between EtOAc and 50% brine, washed with brine, dried over sodium sulfate, filtered and concentrated. The residue was purified by preparative TLC plates (2% MeOH in DCM) to afford 6-(((1s,4s)-4-(3-bromo-6-chloro-1H-pyrrolo[3,2-c]pyridin-1-yl)cyclohexyl)oxy)-2-methylpyridazin-3(2H)-one (0.088 g, 58% yield).

Step B: A heavy walled pressure tube was charged with 6-(((1s,4s)-4-(3-bromo-6-chloro-1H-pyrrolo[3,2-c]pyridin-1-yl)cyclohexyl)oxy)-2-methylpyridazin-3(2H)-one (0.088 g, 0.20 mmol), 1-methyl-4-(4,4,5,5-tetramethyl-1,3,2-dioxaborolan-2-yl)-1H-pyrazole (0.046 g, 0.22 mmol), 2M K$_2$CO$_3$ (0.30 mL, 0.60 mmol), and Pd(PPh$_3$)$_4$ (0.023 g, 0.020 mmol). The mixture was purged with argon for 5 minutes, tube sealed and warmed to 100° C. overnight. The reaction mixture was partitioned between water/EtOAc, extracted with EtOAc, dried over sodium sulfate and concentrated. Purified over silica gel (0-10% MeOH in DCM) to afford 6-(((1s,4s)-4-(6-chloro-3-(1-methyl-1H-pyrazol-4-yl)-1H-pyrrolo[3,2-c]pyridin-1-yl)cyclohexyl)oxy)-2-methylpyridazin-3(2H)-one (0.029 g, 33% yield).

Step C: A microwave reaction tube equipped with a stir bar was charged with 6-(((1s,4s)-4-(6-chloro-3-(1-methyl-1H-pyrazol-4-yl)-1H-pyrrolo[3,2-c]pyridin-1-yl)cyclohexyl)oxy)-2-methylpyridazin-3(2H)-one (0.029 g, 0.066 mmol), tert-butyl methylcarbamate (0.035 g, 0.26 mmol), dioxane (0.5 mL), dicyclohexyl(2',6'-diisopropoxy-[1,1'-biphenyl]-2-yl)phosphane (0.012 g, 0.026 mmol), sodium t-butoxide (0.013 g, 0.13 mmol) and Pd2dba3 (0.012 g, 0.013 mmol) under a nitrogen atmosphere. The tube was sealed and warmed to 100° C. overnight, partitioned between water/EtOAc, extracted with EtOAc, dried over sodium sulfate and concentrated. The crude material was taken forward without further purification.

Step D: Crude tert-butyl methyl(3-(1-methyl-1H-pyrazol-4-yl)-1-((1s,4s)-4-((1-methyl-6-oxo-1,6-dihydropyridazin-3-yl)oxy)cyclohexyl)-1H-pyrrolo[3,2-c]pyridin-6-yl)carbamate was dissolved in DCM (1 mL) and TFA (1 mL) was added and stirred at room temperature for 1.5 h. The reaction mixture was concentrated and purified over C18 column (5 to 95% ACN in water with 0.1% TFA as buffer) to afford 2-methyl-6-(((1s,4s)-4-(3-(1-methyl-1H-pyrazol-4-yl)-6-(methylamino)-1H-pyrrolo[3,2-c]pyridin-1-yl)cyclohexyl)oxy)pyridazin-3(2H)-one (8 mg, 18% yield). Mass spectrum (apci) m/z=434.2 (M+H). $^1$H NMR (CD3OD) δ 8.44 (s, 1H), 8.01 (s, 1H), 7.84 (s, 1H), 7.77 (s, 1H), 7.26 (d, J=9.6 Hz, 1H), 7.00 (d, J=9.8 Hz, 1H), 6.86 (s, 1H), 5.16 (s, 1H), 4.52 (m, 1H), 3.96 (s, 3H), 3.66 (s, 3H), 3.04 (s, 3H), 2.39-2.15 (m, 4H), 1.99-1.86 (m, 4H).

Example 65

2-methyl-6-(((1s,4s)-4-(3-(1-methyl-1H-pyrazol-4-yl)-6-(phenylamino)-1H-pyrazolo[4,3-c]pyridin-1-yl)cyclohexyl)oxy)pyridazin-3(2H)-one

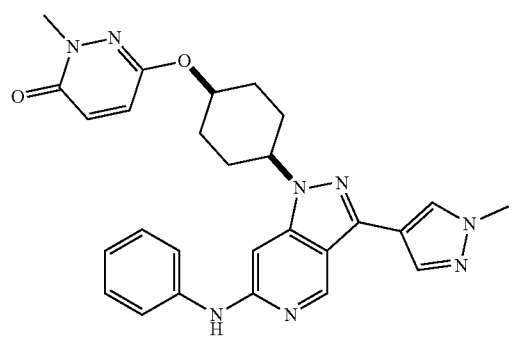

Step A: 3-bromo-1-((1r,4r)-4-((tert-butyldimethylsilyl)oxy)cyclohexyl)-6-chloro-1H-pyrazolo[4,3-c]pyridine (4.05 g, 9.10 mmol) was diluted with THF (50 mL) followed by the addition of 1M TBAF in THF (18.2 mL, 18.2 mmol). The reaction mixture was placed under nitrogen and heated to 50° C. for 12 h. The reaction mixture was partitioned between EtOAc and water, dried over MgSO4, filtered and concentrated. The residue was triturated with 1:1 hexane/ethyl acetate to afford (1r,4r)-4-(3-bromo-6-chloro-1H-pyrazolo[4,3-c]pyridin-1-yl)cyclohexan-1-ol (2.5 g, 7.56 mmol, 83.1% yield).

Step B: (1r,4r)-4-(3-bromo-6-chloro-1H-pyrazolo[4,3-c]pyridin-1-yl)cyclohexan-1-ol (1.5 g, 4.5 mmol), 3-Hydroxy-1-methylpyridazin-6(1H)-one (0.74 g, 5.9 mmol) and PPh3 (1.3 g, 5.0 mmol) were diluted with THF (30 mL) followed by the addition of DIAD (0.97 mL, 5.0 mmol). After stirring for 12 hours, the reaction was partitioned between ethyl acetate and water, dried over MgSO4, filtered and concentrated. The residue was purified over silica gel (15-70% ethyl acetate/hexanes) to afford 6-(((1s,4s)-4-(3-bromo-6-chloro-1H-pyrazolo[4,3-c]pyridin-1-yl)cyclohexyl)oxy)-2-methylpyridazin-3(2H)-one (2.0 g, 4.6 mmol, 100% yield).

Step C: 6-(((1s,4s)-4-(3-bromo-6-chloro-1H-pyrazolo[4,3-c]pyridin-1-yl)cyclohexyl)oxy)-2-methylpyridazin-3(2H)-one (2.0 g, 4.6 mmol), 1-methyl-4-(4,4,5,5-tetramethyl-1,3,2-dioxaborolan-2-yl)-1H-pyrazole (1.0 g, 5.0 mmol) and Pd(PPh3)4 (0.26 g, 0.23 mmol) were diluted with dioxane (40 mL) followed by the addition of 2M Na2CO3 (6.8 mL, 14 mmol). The reaction mixture was placed under nitrogen and heated to 90° C. for 12 h. The reaction mixture was partitioned between ethyl acetate and water, dried over MgSO4, filtered and concentrated. The residue was purified over silica gel (30-80% ethyl acetate in hexanes) to afford 6-(((1s,4s)-4-(6-chloro-3-(1-methyl-1H-pyrazol-4-yl)-1H-pyrazolo[4,3-c]pyridin-1-yl)cyclohexyl)oxy)-2-methylpyridazin-3(2H)-one (1.3 g, 3.0 mmol, 65% yield).

Step D: 6-(((1s,4s)-4-(6-chloro-3-(1-methyl-1H-pyrazol-4-yl)-1H-pyrazolo[4,3-c]pyridin-1-yl)cyclohexyl)oxy)-2-methylpyridazin-3(2H)-one (35 mg, 0.080 mmol), 2-(Dicyclohexylphosphino)-2',4',6'-tri-1-propyl-1,1'-biphenyl (30 mg, 0.064 mmol), sodium tert-butoxide (23 mg, 0.24 mmol) and Pd2(dba)3 (29 mg, 0.032 mmol) were diluted with dioxane (500 μL) followed by the addition of aniline (74 mg, 0.80 mmol). The reaction mixture was purged with argon, sealed and heated to 100° C. for 12 h. The reaction mixture was partitioned between ethyl acetate and water, dried over MgSO4, filtered and concentrated. The residue was purified over C-18 column (5-95% ACN/water with 0.1% TFA). The pure fractions were partitioned between ethyl acetate and saturated sodium bicarbonate, dried over MgSO4, filtered and concentrated to afford 2-methyl-6-(((1s,4s)-4-(3-(1-methyl-1H-pyrazol-4-yl)-6-(phenylamino)-1H-pyrazolo[4,3-c]pyridin-1-yl)cyclohexyl)oxy)pyridazin-3(2H)-one (15 mg, 0.030 mmol, 38% yield). Mass spectrum (apci) m/z=497.2 (M+H). $^1$H NMR (CDCl3) δ 8.80 (s, 1H), 8.00 (s, 1H), 7.89 (s, 1H), 7.40 (m, 2H), 7.34 (m, 2H), 7.12 (m, 1H), 6.89 (d, J=9.8 Hz, 1H), 6.85 (d, J=9.8 Hz, 1H), 6.79 (d, J=0.8 Hz, 1H), 5.06 (m, 1H), 4.31 (tt, J=11.9, 3.9 Hz, 1H), 4.01 (s, 3H), 3.64 (s, 3H), 2.47-2.35 (m, 2H), 2.34-2.26 (m, 2H), 1.93-1.85 (m, 2H), 1.79-1.68 (in, 2H).

Using the procedure described for the preparation of Example 65, the following compounds were also synthesized:

| Example | Structure | Name | Data |
|---------|-----------|------|------|
| 66 | 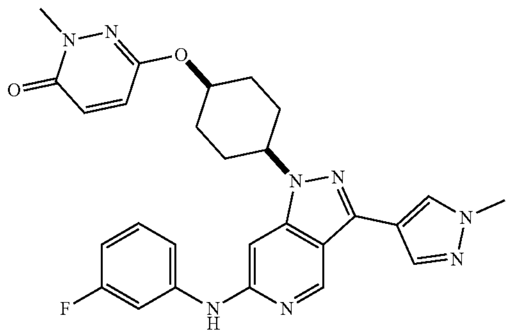 | 6-(((1s,4s)-4-(6-((3-fluorophenyl)amino)-3-(1-methyl-1H-pyrazol-4-yl)-1H-pyrazolo[4,3-c]pyridin-1-yl)cyclohexyl)oxy)-2-methylpyridazin-3(2H)-one | Mass spectrum (apci) m/z = 515.2 |
| 67 | 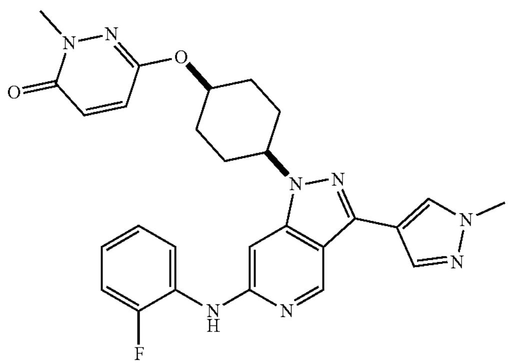 | 6-(((1s,4s)-4-(6-((2-fluorophenyl)amino)-3-(1-methyl-1H-pyrazol-4-yl)-1H-pyrazolo[4,3-c]pyridin-1-yl)cyclohexyl)oxy)-2-methylpyridazin-3(2H)-one | Mass spectrum (apci) m/z = 515.2 |
| 68 | 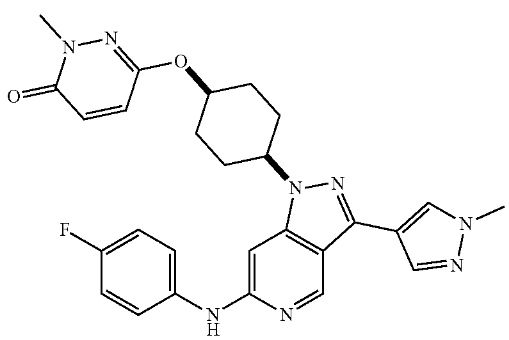 | 6-(((1s,4s)-4-(6-((4-fluorophenyl)amino)-3-(1-methyl-1H-pyrazol-4-yl)-1H-pyrazolo[4,3-c]pyridin-1-yl)cyclohexyl)oxy)-2-methylpyridazin-3(2H)-one | Mass spectrum (apci) m/z = 515.2 |
| 69 | 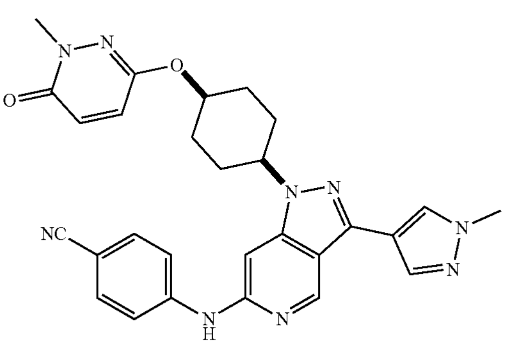 | 4-((3-(1-methyl-1H-pyrazol-4-yl)-1-((1s,4s)-4-((1-methyl-6-oxo-1,6-dihydropyridazin-3-yl)oxy)cyclohexyl)-1H-pyrazolo[4,3-c]pyridin-6-yl)amino)benzonitrile | Mass spectrum (apci) m/z = 522.2 |

Example 70

2-methyl-6-(((1s,4s)-4-(3-(1-methyl-1H-pyrazol-4-yl)-6-((2,2,2-trifluoroethyl)amino)-1H-pyrazolo[4,3-c]pyridin-1-yl)cyclohexyl)oxy)pyridazin-3(2H)-one

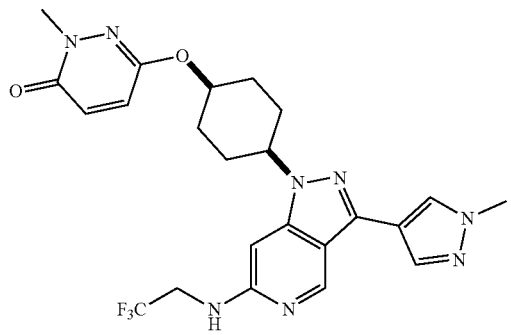

Step A: 6-(((1s,4s)-4-(6-chloro-3-(1-methyl-1H-pyrazol-4-yl)-1H-pyrazolo[4,3-c]pyridin-1-yl)cyclohexyl)oxy)-2-methylpyridazin-3(2H)-one (35 mg, 0.080 mmol), 2-(Dicyclohexylphosphino)-2',4',6'-tri-1-propyl-1,1'-biphenyl (30 mg, 0.064 mmol), sodium tert-butoxide (23 mg, 0.24 mmol) and Pd2(dba)3 (29 mg, 0.032 mmol) were diluted with dioxane (600 µL) followed by the addition of tert-butyl (2,2,2-trifluoroethyl)carbamate (158 mg, 0.80 mmol). The reaction mixture was purged with argon, sealed and heated to 100° C. for 12 h. The reaction mixture was partitioned between ethyl acetate and water, dried over MgSO4, filtered and concentrated to afford tert-butyl (3-(1-methyl-1H-pyrazol-4-yl)-1-((1s,4s)-4-((1-methyl-6-oxo-1,6-dihydropyridazin-3-yl)oxy)cyclohexyl)-1H-pyrazolo[4,3-c]pyridin-6-yl)(2,2,2-trifluoroethyl)carbamate (45 mg, 0.075 mmol, 94% yield) which was taken forward crude.

Step B: tert-butyl (3-(1-methyl-1H-pyrazol-4-yl)-1-((1s,4s)-4-((1-methyl-6-oxo-1,6-dihydropyridazin-3-yl)oxy)cyclohexyl)-1H-pyrazolo[4,3-c]pyridin-6-yl)(2,2,2-trifluoroethyl)carbamate (25 mg, 0.041 mmol) was diluted with DCM (1 mL) followed by the addition of TFA (1 mL). After stirring for 3 hours, the reaction was concentrated. The material was purified on C-18 silica gel (5-95% ACN/water (0.1% TFA)). The pure fractions were partitioned between ethyl acetate and saturated sodium bicarbonate, dried over MgSO4, filtered and concentrated to afford 2-methyl-6-(((1s,4s)-4-(3-(1-methyl-1H-pyrazol-4-yl)-6-((2,2,2-trifluoroethyl)amino)-1H-pyrazolo[4,3-c]pyridin-1-yl)cyclohexyl)oxy)pyridazin-3(2H)-one (17 mg, 0.034 mmol, 82% yield). Mass spectrum (apci) m/z=503.2 (M+H). $^1$H NMR (CDCl3) δ 8.75 (d, J=0.8 Hz, 1H), 7.99 (s, 1H), 7.87 (s, 1H), 7.02 (d, J=9.8 Hz, 1H), 6.93 (d, J=9.6 Hz, 1H), 6.28 (d, J=0.8 Hz, 1H), 5.09 (m, 1H), 4.81 (br s, 1H), 4.30 (tt, J=11.2, 4.1 Hz, 1H), 4.16-4.05 (m, 2H), 4.00 (s, 3H), 3.66 (s, 3H), 2.50-2.29 (m, 4H), 1.96-1.88 (m, 2H), 1.83-1.72 (m, 2H).

Using the procedure described for the preparation of Example 70, the following compounds were also synthesized:

| Example | Structure | Name | Data |
|---|---|---|---|
| 71 | 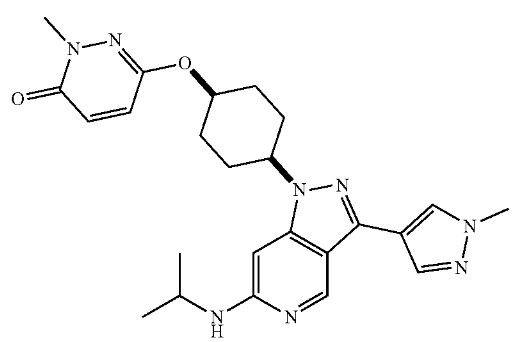 | 6-(((1s,4s)-4-(6-(isopropylamino)-3-(1-methyl-1H-pyrazol-4-yl)-1H-pyrazolo[4,3-c]pyridin-1-yl)cyclohexyl)oxy)-2-methylpyridazin-3(2H)-one | Mass spectrum (apci) m/z = 463.2 |
| 72 | 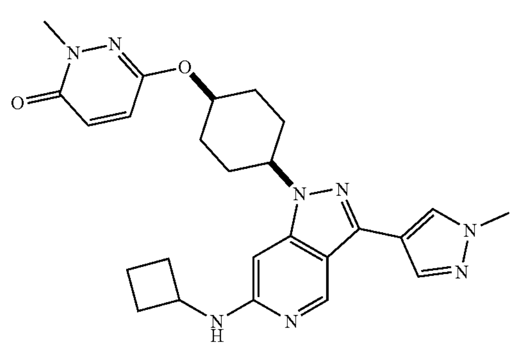 | 6-(((1s,4s)-4-(6-(cyclobutylamino)-3-(1-methyl-1H-pyrazol-4-yl)-1H-pyrazolo[4,3-c]pyridin-1-yl)cyclohexyl)oxy)-2-methylpyridazin-3(2H)-one | Mass spectrum (apci) m/z = 475.2 |

| Example | Structure | Name | Data |
|---|---|---|---|
| 73 | 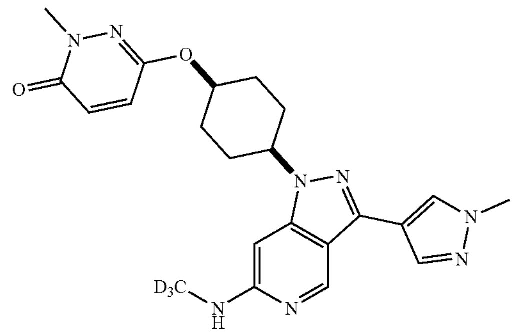 | 2-methyl-6-(((1s,4s)-4-(3-(1-methyl-1H-pyrazol-4-yl)-6-((methyl-d3)amino)-1H-pyrazolo[4,3-c]pyridin-1-yl)cyclohexyl)oxy)pyridazin-3(2H)-one | Mass spectrum (apci) m/z = 438.2 |

Example 74

2-methyl-6-(((1s,4s)-4-(3-(1-methyl-1H-pyrazol-3-yl)-6-(methylamino)-1H-pyrrolo[3,2-c]pyridin-1-yl)cyclohexyl)oxy)pyridazin-3(2H)-one

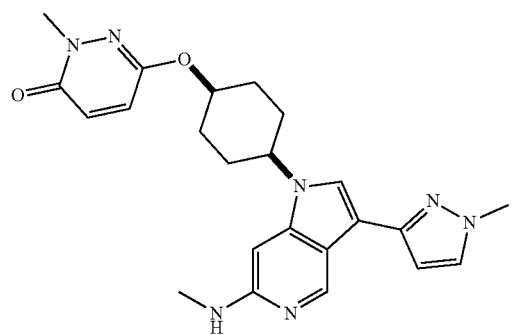

Step A: 3-bromo-1-((1r,4r)-4-((tert-butyldimethylsilyl)oxy)cyclohexyl)-6-chloro-1H-pyrrolo[3,2-c]pyridine (253 mg, 0.57 mmol) was dissolved in dioxane (6 mL). 1-methyl-3-(4,4,5,5-tetramethyl-1,3,2-dioxaborolan-2-yl)-1H-pyrazole (130 mg, 0.63 mmol), 2M $K_2CO_3$ (0.86 mL, 1.71 mmol) and $Pd(PPh_3)_4$ were added and heated to 100° C. overnight under nitrogen. The reaction mixture was partitioned between water and EtOAc, dried over sodium sulfate, filtered and concentrated. The residue was purified over silica gel (0-50% EtOAc in DCM) to afford 1-((1r,4r)-4-((tert-butyldimethylsilyl)oxy)cyclohexyl)-6-chloro-3-(1-methyl-1H-pyrazol-3-yl)-1H-pyrrolo[3,2-c]pyridine (65 mg, 25% yield).

Step B: tert-butyl (1-((1r,4r)-4-hydroxycyclohexyl)-3-(1-methyl-1H-pyrazol-3-yl)-1H-pyrrolo[3,2-c]pyridin-6-yl)(methyl)carbamate (0.011 g, 0.0258 mmol) was dissolved in THF (0.3 mL). 6-hydroxy-2-methylpyridazin-3(2H)-one (0.010 g, 0.078 mmol), triphenylphosphine (0.0203 g, 0.078 mmol), and DIAD (0.016 g, 0.078 mmol) were added and stirred overnight. The reaction mixture was partitioned between EtOAc/water, washed with 10% $K_2CO_3$, dried over sodium sulfate and concentrated. The residue was dissolved in DCM/4M-HCl-dioxane, stirred for 1 h and concentrated. The residue was purified by C18 HPLC (5 to 95% ACN in water with 0.1% TFA). The product fractions were concentrated under reduced pressure to afford 2-methyl-6-(((1s,4s)-4-(3-(1-methyl-1H-pyrazol-3-yl)-6-(methylamino)-1H-pyrrolo[3,2-c]pyridin-1-yl)cyclohexyl)oxy)pyridazin-3(2H)-one bis(2,2,2-trifluoroacetate) (2.6 mg, 15% yield). Mass spectrum (apci) m/z=434.2 (M+H). $^1$H NMR (CD3OD) δ 8.76 (s, 1H), 7.92 (s, 1H), 7.61 (s, 1H), 7.27 (d, J=9.6 Hz, 1H), 7.00 (d, J=9.6 Hz, 1H), 6.86 (s, 1H), 6.62 (s, 1H), 5.15 (m, 1H), 4.52 (m, 1H), 3.95 (s, 3H), 3.66 (s, 3H), 3.04 (s, 3H), 2.40-2.17 (m, 4H), 1.99-1.85 (m, 4H).

Example 75

6-(((1s,4s)-4-(6-amino-3-(1-methyl-1H-pyrazol-4-yl)-1H-pyrazolo[4,3-c]pyridin-1-yl)cyclohexyl)oxy)-2-methylpyridazin-3(2H)-one

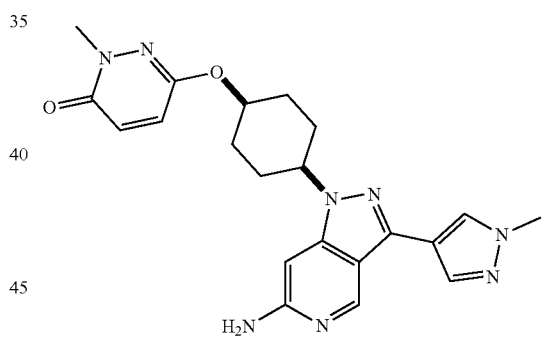

Step A: 6-(((1s,4s)-4-(6-chloro-3-(1-methyl-1H-pyrazol-4-yl)-1H-pyrazolo[4,3-c]pyridin-1-yl)cyclohexyl)oxy)-2-methylpyridazin-3(2H)-one (35 mg, 0.080 mmol), 2-(Dicyclohexylphosphino)-2',4',6'-tri-1-propyl-1,1'-biphenyl (30 mg, 0.064 mmol), sodium tert-butoxide (23 mg, 0.24 mmol) and $Pd_2(dba)_3$ (29 mg, 0.032 mmol) were diluted with dioxane (600 μL) followed by the addition of diphenylmethanimine (58 mg, 0.32 mmol). The reaction mixture was purged with argon, sealed and heated to 100° C. for 12 h. The reaction mixture was partitioned between EtOAc and water, dried over $MgSO_4$, filtered and concentrated to afford crude 6-(((1s,4s)-4-(6-((diphenylmethylene)amino)-3-(1-methyl-1H-pyrazol-4-yl)-1H-pyrazolo[4,3-c]pyridin-1-yl)cyclohexyl)oxy)-2-methylpyridazin-3(2H)-one (40 mg, 0.068 mmol, 86% yield) which was taken forward without further purification.

Step B: 6-(((1s,4s)-4-(6-((diphenylmethylene)amino)-3-(1-methyl-1H-pyrazol-4-yl)-1H-pyrazolo[4,3-c]pyridin-1-yl)cyclohexyl)oxy)-2-methylpyridazin-3(2H)-one (25 mg, 0.043 mmol) was diluted with dioxane (500 μL) followed by the addition of 2N HCl (200 μL). After stirring for 3 hours, the reaction was partitioned between ethyl acetate and saturated sodium bicarbonate, dried over MgSO$_4$, filtered and concentrated. The residue was purified over C-18 silica gel (5-95% ACN/water (0.1% TFA)). The pure fractions were partitioned between ethyl acetate and saturated sodium bicarbonate, dried over MgSO$_4$, filtered and concentrated to afford 6-(((1s,4s)-4-(6-amino-3-(1-methyl-1H-pyrazol-4-yl)-1H-pyrazolo[4,3-c]pyridin-1-yl)cyclohexyl)oxy)-2-methylpyridazin-3(2H)-one (5 mg, 0.012 mmol, 28% yield). Mass spectrum (apci) m/z=421.2 (M+H). $^1$H NMR (CDCl$_3$) δ 8.67 (d, J=1.0 Hz, 1H), 7.98 (d, J=0.6 Hz, 1H), 7.87 (s, 1H), 7.02 (d, J=0.8 Hz, 1H), 6.94 (d, J=9.8 Hz, 1H), 6.34 (d, J=0.8 Hz, 1H), 5.09 (m, 1H), 4.95 (br s, 2H), 4.27 (tt, J=11.7, 3.7 Hz, 1H), 4.00 (s, 3H), 3.66 (s, 3H), 2.50-2.29 (m, 4H), 1.95-1.87 (m, 2H), 1.81-1.70 (m, 2H).

Example 76

2-methyl-6-(((1s,4s)-4-(6-(methylamino)-3-(1H-pyrazol-4-yl)-1H-pyrazolo[4,3-c]pyridin-1-yl)cyclohexyl)oxy)pyridazin-3(2H)-one

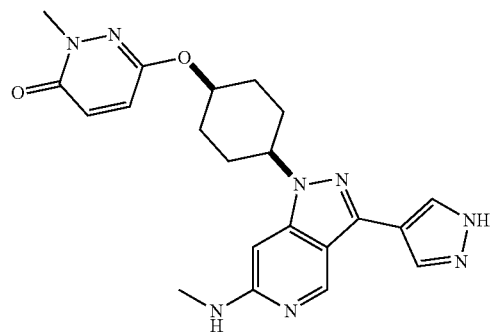

Step A: tert-butyl (3-bromo-1-((1s,4s)-4-((1-methyl-6-oxo-1,6-dihydropyridazin-3-yl)oxy)cyclohexyl)-1H-pyrazolo[4,3-c]pyridin-6-yl)(methyl)carbamate (50 mg, 0.094 mmol), Pyrazole-4-boronic acid pinacol ester (27 mg, 0.14 mmol) and Pd(PPh$_3$)$_4$ (11 mg, 0.0094 mmol) were diluted with dioxane (350 μL) followed by the addition of 2M Na$_2$CO$_3$ (141 μL, 0.28 mmol). The reaction mixture was purged with argon, sealed and heated to 90° C. for 12 h. The reaction mixture was partitioned between EtOAc and water, dried over MgSO$_4$, filtered and concentrated to afford tert-butyl methyl(1-((1s,4s)-4-((1-methyl-6-oxo-1,6-dihydropyridazin-3-yl)oxy)cyclohexyl)-3-(1H-pyrazol-4-yl)-1H-pyrazolo[4,3-c]pyridin-6-yl)carbamate (48 mg, 0.092 mmol, 98% yield).

Step B: tert-butyl methyl(1-((1s,4s)-4-((1-methyl-6-oxo-1,6-dihydropyridazin-3-yl)oxy)cyclohexyl)-3-(1H-pyrazol-4-yl)-1H-pyrazolo[4,3-c]pyridin-6-yl)carbamate (48 mg, 0.092 mmol) was diluted with DCM (1 mL) and TFA (1 mL) for 3 h and concentrated. The residue was purified over C-18 silica gel (5-95% ACN/water (0.1% TFA)). The pure fractions were partitioned between ethyl acetate and saturated sodium bicarbonate, dried over MgSO$_4$, filtered and concentrated to afford 2-methyl-6-(((1s,4s)-4-(6-(methylamino)-3-(1H-pyrazol-4-yl)-1H-pyrazolo[4,3-c]pyridin-1-yl)cyclohexyl)oxy)pyridazin-3(2H)-one (9.1 mg, 0.022 mmol, 23% yield). Mass spectrum (apci) m/z=421.2 (M+H). $^1$H NMR (CDCl$_3$) δ 8.66 (s, 1H), 8.09 (s, 2H), 7.11 (d, J=9.6 Hz, 1H), 6.96 (d, J=9.7 Hz, 1H), 6.07 (s, 1H), 5.13 (m, 1H), 4.36 (tt, J=11.7, 4.3 Hz, 1H), 3.68 (s, 3H), 2.96 (s, 3H), 2.51-2.31 (m, 4H), 1.98-1.90 (m, 2H), 1.87-1.76 (i, 2H).

Using the procedure described for the preparation of Example 76, the following compounds were also synthesized:

| Example | Structure | Name | Data |
| --- | --- | --- | --- |
| 77 | 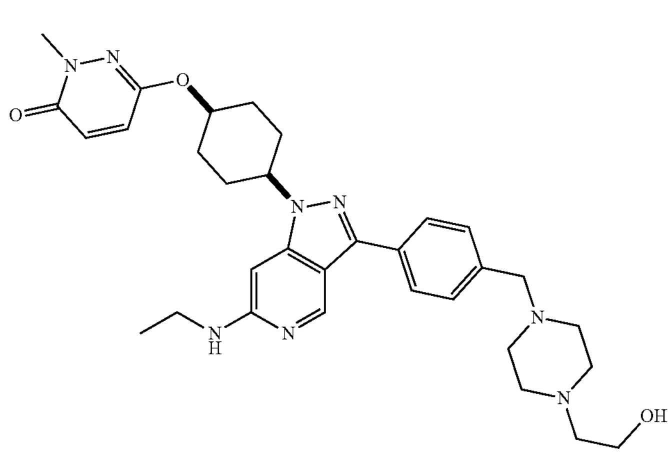 | 6-(((1s,4s)-4-(6-(ethylamino)-3-(4-((4-(2-hydroxyethyl)piperazin-1-yl)methyl)phenyl)-1H-pyrazolo[4,3-c]pyridin-1-yl)cyclohexyl)oxy)-2-methylpyridazin-3(2H)-one | Mass spectrum (apci) m/z = 587.3 |

| Example | Structure | Name | Data |
|---|---|---|---|
| 78 | 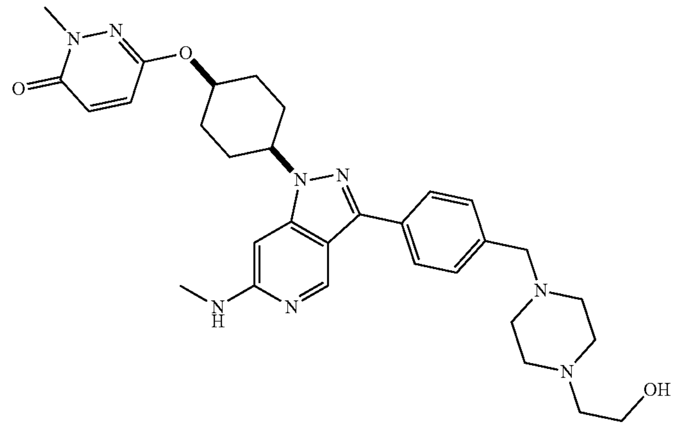 | 6-(((1s,4s)-4-(3-(4-((4-(2-hydroxyethyl)piperazin-1-yl)methyl)phenyl)-6-(methylamino)-1H-pyrazolo[4,3-c]pyridin-1-yl)cyclohexyl)oxy)-2-methylpyridazin-3(2H)-one | Mass spectrum (apci) m/z = 573.3 |

Example 79

2-ethyl-6-(((1s,4s)-4-(6-(methylamino)-3-(4-((4-methylpiperazin-1-yl)methyl)phenyl)-1H-pyrazolo[4,3-c]pyridin-1-yl)cyclohexyl)oxy)pyridazin-3(2H)-one

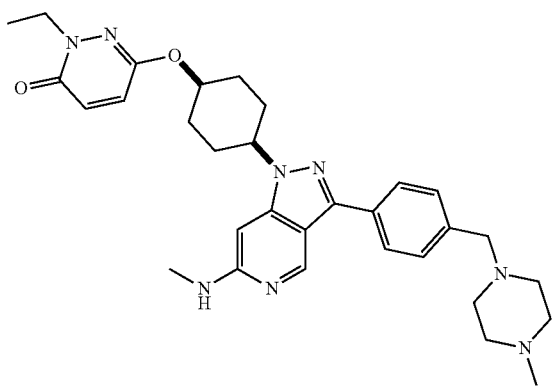

Step A: A mixture of tert-butyl (3-bromo-1-((1r,4r)-4-((tert-butyldimethylsilyl)oxy)cyclohexyl)-1H-pyrazolo[4,3-c]pyridin-6-yl)(methyl)carbamate (Example 1 step B, 0.508 g, 0.941 mmol), 1-Methyl-4-[4-(4,4,5,5-tetramethyl-1,3,2-dioxaborolan-2-yl)benzyl]piperazine (0.447 g, 1.41 mmol), Pd(PPh$_3$)$_4$ (0.0544 g, 0.0471 mmol) and 2M Na$_2$CO$_3$ (0.989 mL, 1.98 mmol) in dioxane (9.41 mL, 0.941 mmol) was heated to 90° C. overnight. The reaction mixture was partitioned between EtOAc and water, washed with brine, dried over Na$_2$SO$_4$, filtered and concentrated. The residue was purified over silica gel (1-10% MeOH in DCM with 1% NH$_{40}$H modifier) to afford tert-butyl (1-((1r,4r)-4-((tert-butyldimethylsilyl)oxy)cyclohexyl)-3-(4-((4-methylpiperazin-1-yl)methyl)phenyl)-1H-pyrazolo[4,3-c]pyridin-6-yl)(methyl)carbamate (0.670 g, 1.03 mmol, 110% yield) as a white solid.

Step B: tert-Butyl (1-((1r,4r)-4-((tert-butyldimethylsilyl)oxy)cyclohexyl)-3-(4-((4-methylpiperazin-1-yl)methyl)phenyl)-1H-pyrazolo[4,3-c]pyridin-6-yl)(methyl)carbamate (0.670 g, 1.03 mmol) was diluted with THF (5.1 mL), followed by the addition of 1M TBAF in THF (2.06 mL, 2.06 mmol) and heated to 70° C. overnight. The reaction mixture was partitioned between EtOAc and water, washed with water (3×25 mL), brine (25 mL), dried over Na$_2$SO$_4$, filtered and concentrated to afford tert-butyl (1-((1r,4r)-4-hydroxycyclohexyl)-3-(4-((4-methylpiperazin-1-yl)methyl)phenyl)-1H-pyrazolo[4,3-c]pyridin-6-yl)(methyl)carbamate (0.492 g, 0.920 mmol, 89.1% yield).

Step C: To a solution of Ph$_3$P (0.02453 g, 0.09351 mmol), tert-butyl (1-((1r,4r)-4-hydroxycyclohexyl)-3-(4-((4-methylpiperazin-1-yl)methyl)phenyl)-1H-pyrazolo[4,3-c]pyridin-6-yl)(methyl)carbamate (0.025 g, 0.04675 mmol) and 2-ethyl-6-hydroxypyridazin-3(2H)-one (0.01310 g, 0.09351 mmol) in THF (0.4675 mL) was added DIAD (0.01843 mL, 0.09351 mmol). After 1 h, the reaction was partitioned between EtOAc and water, washed with water (2×25 mL), brine (2×25 mL), dried over Na$_2$SO$_4$, filtered and concentrated. The residue was resuspended in 1 mL of a solution of 60:40 ACN:water with 2% TFA modifier and purified by C-18 HPLC (5-60% ACN in water with 0.2% TFA modifier). To the combined product fractions was added TFA (2 mL). After 4 h, the reaction was concentrated and partitioned between DCM and aqueous NaHCO$_3$, extracted with DCM (2×15 mL), washed with brine (2×15 mL), dried over Na$_2$SO$_4$, filtered and concentrated to afford 2-ethyl-6-(((1s,4s)-4-(6-(methylamino)-3-(4-((4-methylpiperazin-1-yl)methyl)phenyl)-1H-pyrazolo[4,3-c]pyridin-1-yl)cyclohexyl)oxy)pyridazin-3(2H)-one (0.0075 g, 0.01347 mmol, 28.81% yield) as a white solid. Mass spectrum (apci) m/z=557.3 (M+H). $^1$H NMR (CDCl$_3$) δ 8.83 (s, 1H), 7.88 (m, 2H), 7.45 (m, 2H), 6.99 (d, J=9.6 Hz, 1H), 6.92 (d, J=9.6 Hz, 1H), 6.07 (s, 1H), 5.11 (m, 1H), 4.78 (q, J=5.3 Hz, 1H), 4.37 (tt, J=11.3, 4.1 Hz, 1H), 4.08 (q, J=7.2 Hz, 2H), 3.57 (s, 2H), 2.98 (J=5.3 Hz, 3H), 2.60-2.42 (m, 8H), 2.39-2.31 (m, 2H), 2.30 (s, 3H), 2.00-1.92 (m, 2H), 1.86-1.75 (m, 2H), 1.35 (t, J=7.2 Hz, 3H).

Using the procedure described for the preparation of Example 79, the following compound was also synthesized:

| Example | Structure | Name | Data |
|---|---|---|---|
| 80 | 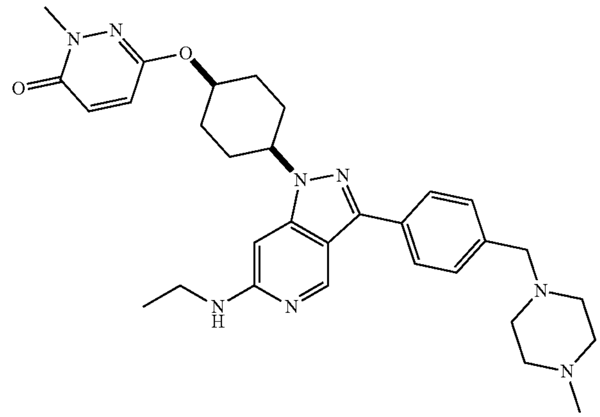 | 6-(((1s,4s)-4-(6-(ethylamino)-3-(4-((4-methylpiperazin-1-yl)methyl)phenyl)-1H-pyrazolo[4,3-c]pyridin-1-yl)cyclohexyl)oxy)-2-methylpyridazin-3(2H)-one | Mass spectrum (apci) m/z = 557.3 |

Example 81

6-(((1s,4s)-4-(6-(ethylamino)-3-(oxazol-2-yl)-1H-pyrazolo[4,3-c]pyridin-1-yl)cyclohexyl)oxy)-2-methylpyridazin-3(2H)-one bis(2,2,2-trifluoroacetate)

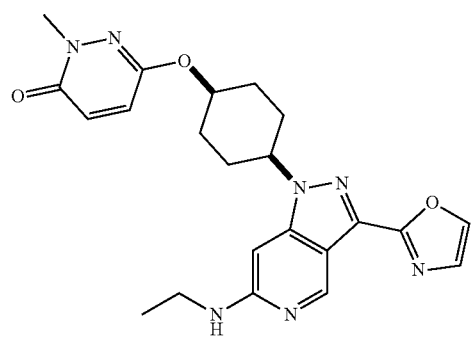

Step A: tert-butyl (3-bromo-1-((1r,4r)-4-((tert-butyldimethylsilyl)oxy)cyclohexyl)-1H-pyrazolo[4,3-c]pyridin-6-yl)(ethyl)carbamate (250 mg, 0.45 mmol) was dissolved in toluene (5 mL). 2-(tributylstannyl)oxazole (323 mg, 0.90 mmol), copper(I)iodide (8.6 mg, 0.045 mmol) and Pd(PPh₃)₄ were added and heated to 100° C. under nitrogen overnight. The reaction mixture was partitioned between EtOAc and water, washed with 10% K₂CO₃, dried over sodium sulfate, filtered and concentrated. The residue was purified over silica gel (10-75% EtOAc in hexanes) to afford tert-butyl (1-((1r,4r)-4-((tert-butyldimethylsilyl)oxy)cyclohexyl)-3-(oxazol-2-yl)-1H-pyrazolo[4,3-c]pyridin-6-yl)(ethyl)carbamate (160 mg, 65% yield).

Step B: tert-butyl (1-((1r,4r)-4-((tert-butyldimethylsilyl)oxy)cyclohexyl)-3-(oxazol-2-yl)-1H-pyrazolo[4,3-c]pyridin-6-yl)(ethyl)carbamate (160 mg, 0.30 mmol) was dissolved in THF (2 mL) and 1M TBAF in THF (1.5 mL, 1.5 mmol) was added and the reaction was heated to 50° C. for 2.5 h. The reaction mixture was partitioned between EtOAc and water, washed with 10% K₂CO₃ (×2), dried over sodium sulfate, filtered and concentrated to afford tert-butyl ethyl (1-((1r,4r)-4-hydroxycyclohexyl)-3-(oxazol-2-yl)-1H-pyrazolo[4,3-c]pyridin-6-yl)carbamate (130 mg, 103% yield).

Step C: tert-butyl ethyl(1-((1r,4r)-4-hydroxycyclohexyl)-3-(oxazol-2-yl)-1H-pyrazolo[4,3-c]pyridin-6-yl)carbamate (30 mg, 0.07 mmol) was dissolved in THF (0.5 mL). 6-hydroxy-2-methylpyridazin-3(2H)-one (26 mg, 0.21 mmol) and PPh₃ (55 mg, 0.21 mmol) were added, followed by DIAD (0.041 mL, 0.21 mmol). The reaction mixture was stirred overnight and then concentrated. The residue was dissolved in DCM (1 mL) and 4N HCl in dioxane (1 mL) was added and stirred for 2 h. The reaction mixture was concentrated and the residue purified on C-18 silica column (5 to 95% ACN in water with 0.1% TFA) to afford N-ethyl-1-((1s,4s)-4-((3-fluoro-4-(trifluoromethyl)pyridin-2-yl)oxy)cyclohexyl)-3-(oxazol-2-yl)-1H-pyrazolo[4,3-c]pyridin-6-amine bis(2,2,2-trifluoroacetate) (17.2 mg, 20% yield). Mass spectrum (apci) m/z=436.2 (M+H). ¹H NMR (CD3OD) δ 9.05 (s, 1H), 8.15 (s, 1H), 7.47 (s, 1H), 7.28 (d, J=9.6 Hz, 1H), 7.00 (d, J=9.6 Hz, 1H), 6.97 (s, 1H), 5.16 (m, 1H), 4.75 (m, 1H), 3.65 (s, 3H), 3.45 (q, J=7.2 Hz, 2H), 2.50-2.31 (m, 4H), 1.99-1.86 (m, 4H), 1.38 (t, J=7.2 Hz, 3H).

Example 82

6-(((1s,4s)-4-(6-(ethylamino)-3-(4-((4-(2-methoxyethyl)piperazin-1-yl)methyl)phenyl)-1H-pyrazolo[4,3-c]pyridin-1-yl)cyclohexyl)oxy)-2-methylpyridazin-3(2H)-one

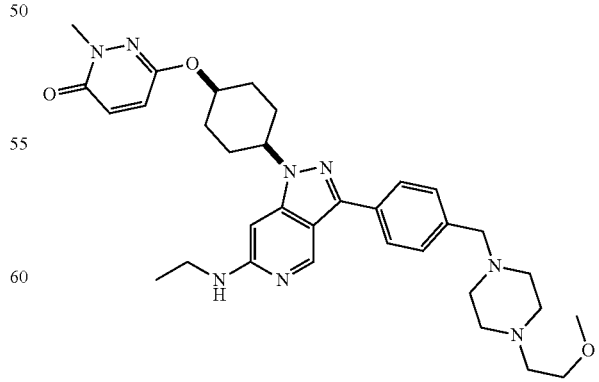

Step A: To a solution of tert-butyl (3-bromo-1-((1s,4s)-4-((1-methyl-6-oxo-1,6-dihydropyridazin-3-yl)oxy)cyclohexyl)-1H-pyrazolo[4,3-c]pyridin-6-yl)(ethyl)carbamate (0.100 g, 0.183 mmol), Pd(Ph₃P)₄ (0.0211 g, 0.0183 mmol) and 4-formylphenylboronic acid pinacol ester (0.0848 g, 0.365 mmol) in 1,4-dioxane (1.83 mL, 0.183 mmol) was added 2M Na₂CO₃ (0.192 mL, 0.384 mmol) and heated to 90° C. for 1 h. The reaction mixture was partitioned between EtOAc and water, washed with brine (2×25 mL), dried over Na₂SO₄, filtered and concentrated. The residue was purified over silica gel (10-100% EtOAc in hexanes) to afford tert-butyl ethyl(3-(4-formylphenyl)-1-((1s,4s)-4-((1-methyl-6-oxo-1,6-dihydropyridazin-3-yl)oxy)cyclohexyl)-1H-pyrazolo[4,3-c]pyridin-6-yl)carbamate (0.110 g, 0.192 mmol, 105% yield) as a white solid.

Step B: To a mixture of tert-butyl ethyl(3-(4-formylphenyl)-1-((1s,4s)-4-((1-methyl-6-oxo-1,6-dihydropyridazin-3-yl)oxy)cyclohexyl)-1H-pyrazolo[4,3-c]pyridin-6-yl)carbamate (0.020 g, 0.0349 mmol) and 1-(2-methoxyethyl) piperazine (0.0104 mL, 0.0698 mmol) in DCM (0.466 mL, 0.0349 mmol) was added sodium triacetoxyborohydride (0.0111 g, 0.0524 mmol) and stirred for 1.5 h. Dichloromethane (2 mL) was added and then TFA (5 mL) was added at room temperature. After 1 hour, the reaction mixture was concentrated and the resultant oil was resuspended in 1 mL of a solution of 60:40 ACN:water with 2% TFA modifier, purified by C-18 HPLC (5-60% ACN in water with 0.2% TFA modifier). The product fractions were partitioned between DCM and aqueous NaHCO₃ (15 mL), extracted with DCM (2×15 mL), washed with brine (15 mL), dried over Na₂SO₄, filtered and concentrated to afford 6-(((1s,4s)-4-(6-(ethylamino)-3-(4-((4-(2-methoxyethyl) piperazin-1-yl)methyl)phenyl)-1H-pyrazolo[4,3-c]pyridin-1-yl)cyclohexyl)oxy)-2-methylpyridazin-3(2H)-one (0.0086 g, 0.0143 mmol, 41.0% yield) as a solid. Mass spectrum (apci) m/z=601.2 (M+H). ¹H NMR (CD3OD) δ 8.81 (s, 1H), 7.88 (m, 2H), 7.44 (m, 2H), 7.01 (d, J=9.6 Hz, 1H), 6.93 (d, J=9.8 Hz, 1H). 6.07 (s, 1H), 5.10 (m, 1H), 4.34 (tt, J=11.3, 3.7 Hz, 1H), 3.66 (s, 3H), 3.65-3.51 (m, 4H), 3.35 (s, 3H), 3.30 (m, 2H), 2.80-2.55 (m, 8H), 2.55-2.40 (m, 2H), 2.38-2.30 (m, 2H), 1.99-1.92 (m, 2H), 1.85-1.75 (m, 2H), 1.36 (t, J=7.0 Hz, 3H).

Using the procedure described for the preparation of Example 82, the following compounds were also synthesized:

| Example | Structure | Name | Data |
|---|---|---|---|
| 83 | 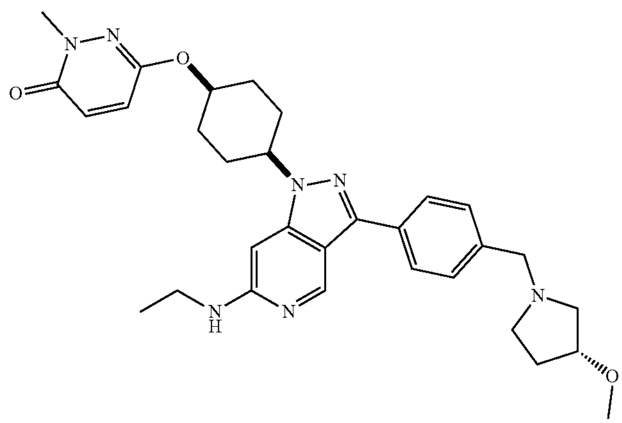 | 6-(((1S,4s)-4-(6-(ethylamino)-3-(4-(((R)-3-methoxypyrrolidin-1-yl)methyl)phenyl)-1H-pyrazolo[4,3-c]pyridin-1-yl)cyclohexyl)oxy)-2-methylpyridazin-3(2H)-one | Mass spectrum (apci) m/z = 558.3 |
| 84 | 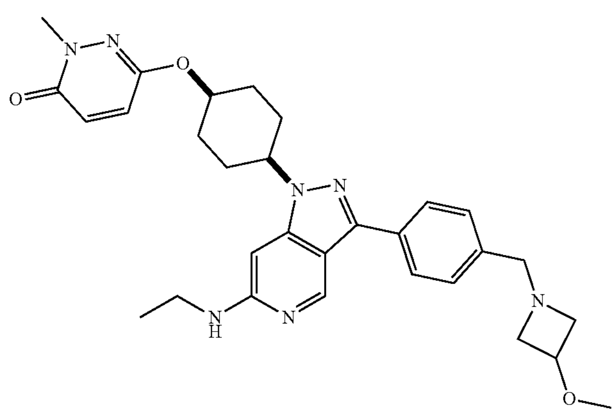 | 6-(((1s,4s)-4-(6-(ethylamino)-3-(4-((3-methoxyazetidin-1-yl)methyl)phenyl)-1H-pyrazolo[4,3-c]pyridin-1-yl)cyclohexyl)oxy)-2-methylpyridazin-3(2H)-one | Mass spectrum (apci) m/z = 544.3 |

| Example | Structure | Name | Data |
|---|---|---|---|
| 85 | 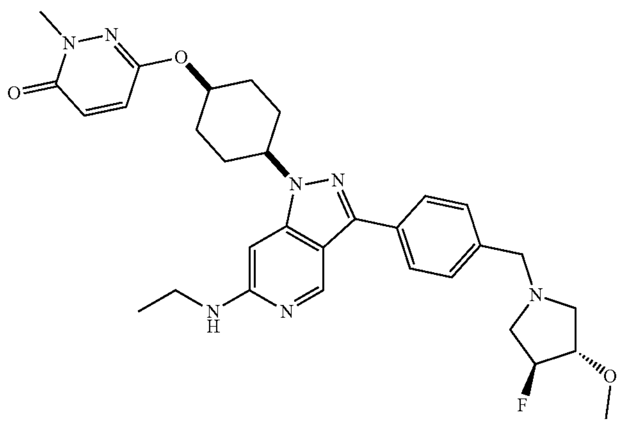 | 6-(((1R,4s)-4-(6-(ethylamino)-3-(4-(((3S,4S)-3-fluoro-4-methoxypyrrolidin-1-yl)methyl)phenyl)-1H-pyrazolo[4,3-c]pyridin-1-yl)cyclohexyl)oxy)-2-methylpyridazin-3(2H)-one | Mass spectrum (apci) m/z = 576.3 |
| 86 | 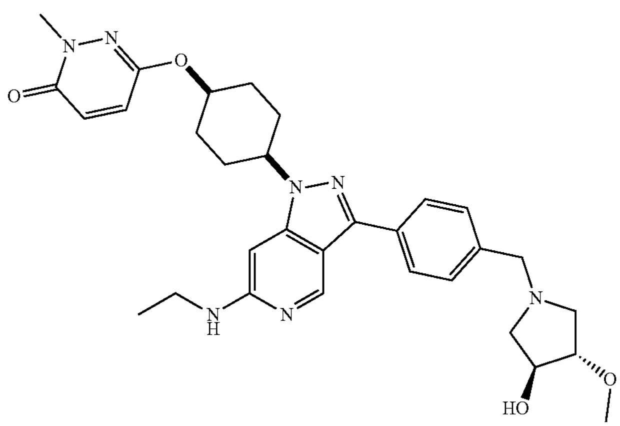 | 6-(((1R,4s)-4-(6-(ethylamino)-3-(4-(((3S,4S)-3-hydroxy-4-methoxypyrrolidin-1-yl)methyl)phenyl)-1H-pyrazolo[4,3-c]pyridin-1-yl)cyclohexyl)oxy)-2-melhylpyridazin-3(2H)-one | Mass spectrum (apci) m/z = 574.3 |
| 87 | 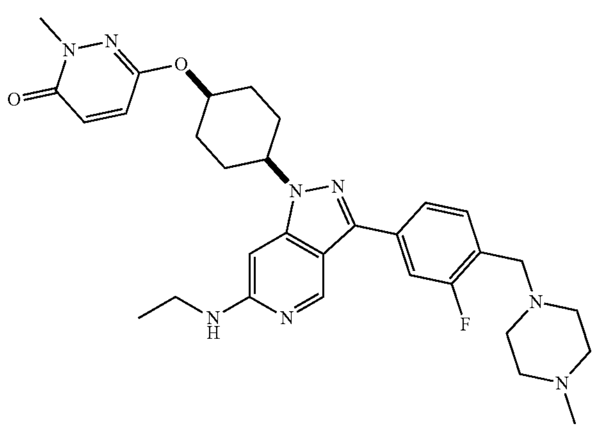 | tert-butyl ethyl(3-(3-fluoro-4-formylphenyl)-1-((1s,4s)-4-((1-methyl-6-oxo-1,6-dihydropyridazin-3-yl)oxy)cyclohexyl)-1H-pyrazolo[4,3-c]pyridin-6-yl)carbamate | Mass spectrum (apci) m/z = 591.2 |

-continued

| Example | Structure | Name | Data |
|---|---|---|---|
| 88 | 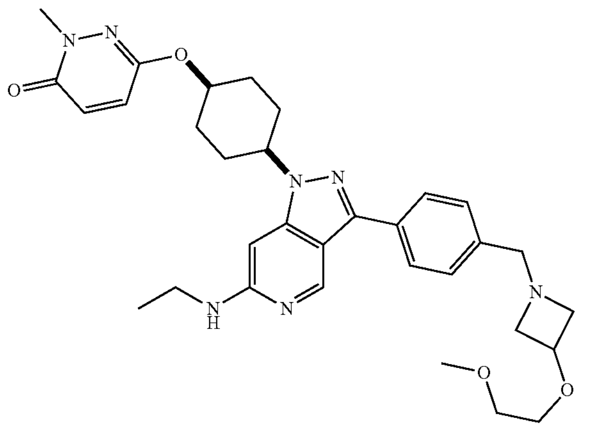 | 6-(((1s,4s)-4-(6-(ethylamino)-3-(4-((3-(2-methoxyethoxy)azetidin-1-yl)methyl)phenyl)-1H-pyrazolo[4,3-c]pyridin-1-yl)cyclohexyl)oxy)-2-methylpyridazin-3(2H)-one | Mass spectrum (apci) m/z = 588.3 |
| 89 | 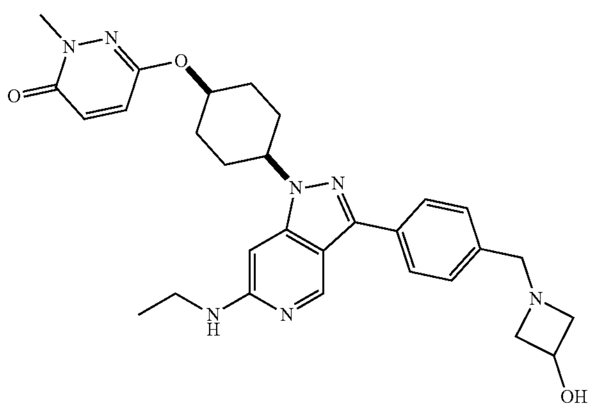 | 6-(((1s,4s)-4-(6-(ethylamino)-3-(4-((3-hydroxyazetidin-1-yl)methyl)phenyl)-1H-pyrazolo[4,3-c]pyridin-1-yl)cyclohexyl)oxy)-2-methylpyridazin-3(2H)-one | Mass spectrum (apci) m/z = 530.3 |
| 90 | 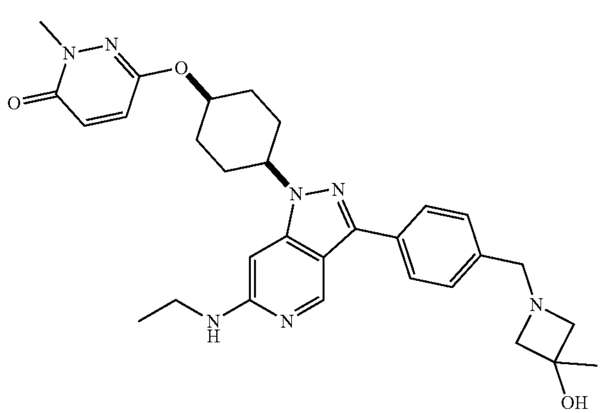 | 6-(((1s,4s)-4-(6-(ethylamino)-3-(4-((3-hydroxy-3-methylazetidin-1-yl)methyl)phenyl)-1H-pyrazolo[4,3-c]pyridin-1-yl)cyclohexyl)oxy)-2-methylpyridazin-3(2H)-one | Mass spectrum (apci) m/z = 544.2 |

-continued

| Example | Structure | Name | Data |
|---|---|---|---|
| 91 | 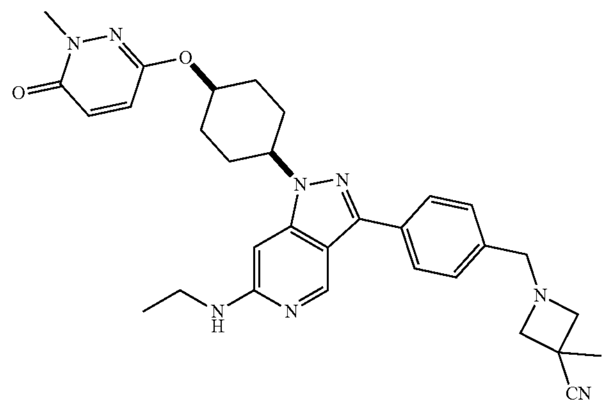 | 1-(4-(6-(ethylamino)-1-((1s,4s)-4-((1-methyl-6-oxo-1,6-dihydropyridazin-3-yl)oxy)cyclohexyl)-1H-pyrazolo[4,3-c]pyridin-3-yl)benzyl)-3-methylazetidine-3-carbonitrile | Mass spectrum (apci) m/z = 553.3 |
| 92 | 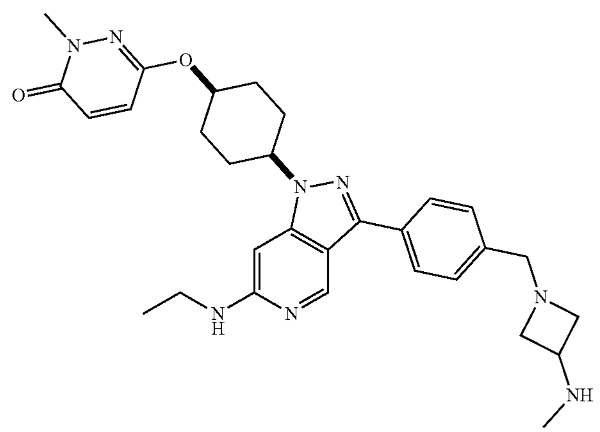 | 6-(((1s,4s)-4-(6-(ethylamino)-3-(4-((3-(methylamino)azetidin-1-yl)methyl)phenyl)-1H-pyrazolo[4,3-c]pyridin-1-yl)cyclohexyl)oxy)-2-methylpyridazin-3(2H)-one | Mass spectrum (apci) m/z = 543.3 |
| 93 | 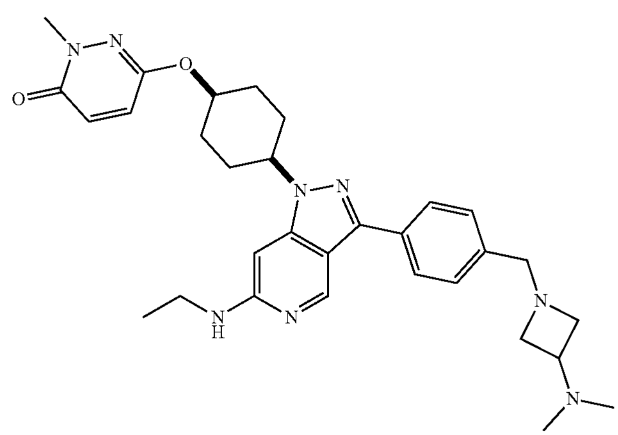 | 6-(((1s,4s)-4-(3-(4-((3-(dimethylamino)azetidin-1-yl)methyl)phenyl)-6-(ethylamino)-1H-pyrazolo[4,3-c]pyridin-1-yl)cyclohexyl)oxy)-2-methylpyridazin-3(2H)-one | Mass spectrum (apci) m/z = 557.3 |

-continued

| Example | Structure | Name | Data |
|---|---|---|---|
| 94 | 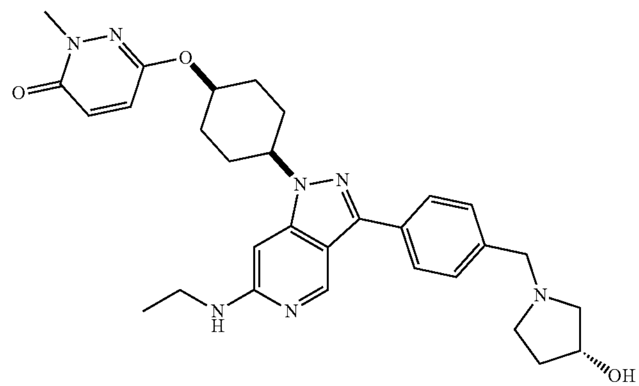 | 6-(((1S,4s)-4-(6-(ethylamino)-3-(4-(((R)-3-hydroxypyrrolidin-1-yl)methyl)phenyl)-1H-pyrazolo[4,3-c]pyridin-1-yl)cyclohexyl)oxy)-2-methylpyridazin-3(2H)-one | Mass spectrum (apci) m/z = 544.3 |
| 95 | 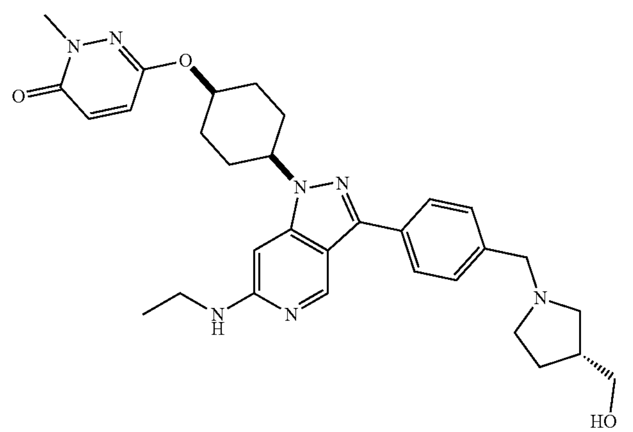 | 6-(((1S,4s)-4-(6-(ethylamino)-3-(4-(((R)-3-(hydroxymethyl)pyrrolidin-1-yl)methyl)phenyl)-1H-pyrazolo[4,3-c]pyridin-1-yl)cyclohexyl)oxy)-2-methylpyridazin-3(2H)-one | Mass spectrum (apci) m/z = 558.3 |
| 96 | 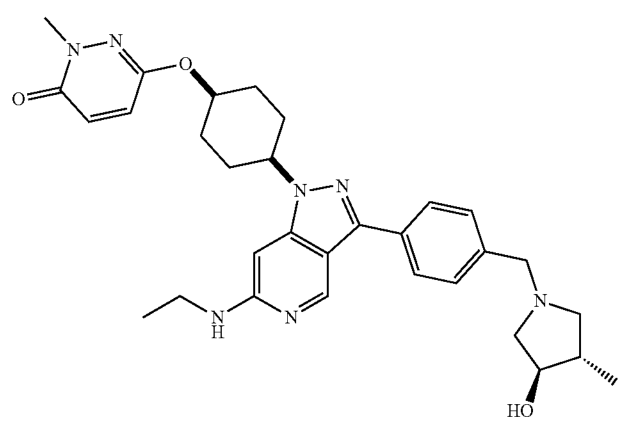 | 6-(((1S,4s)-4-(6-(ethylamino)-3-(4-(((3R,4S)-3-hydroxy-4-methylpyrrolidin-1-yl)methyl)phenyl)-1H-pyrazolo[4,3-c]pyridin-1-yl)cyclohexyl)oxy)-2-methylpyridazin-3(2H)-one | Mass spectrum (apci) m/z = 558.3 |

-continued

| Example | Structure | Name | Data |
|---|---|---|---|
| 97 | 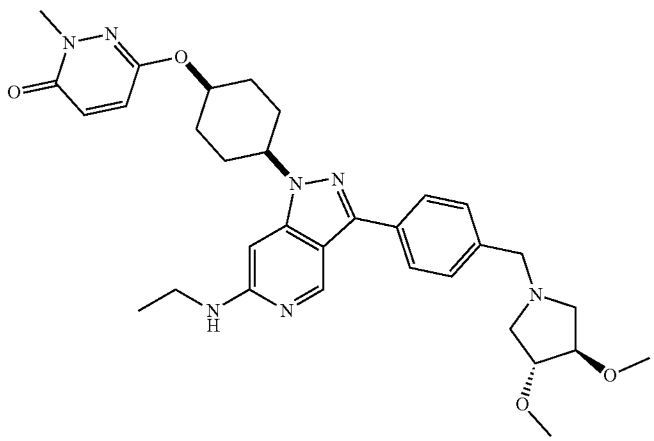 | 6-(((1S,4s)-4-(3-(4-(((3R,4R)-3,4-dimethoxypyrrolidin-1-yl)methyl)phenyl)-6-(ethylamino)-1H-pyrazolo[4,3-c]pyridin-1-yl)cyclohexyl)oxy)-2-methylpyridazin-3(2H)-one | Mass spectrum (apci) m/z = 588.3 |
| 98 | 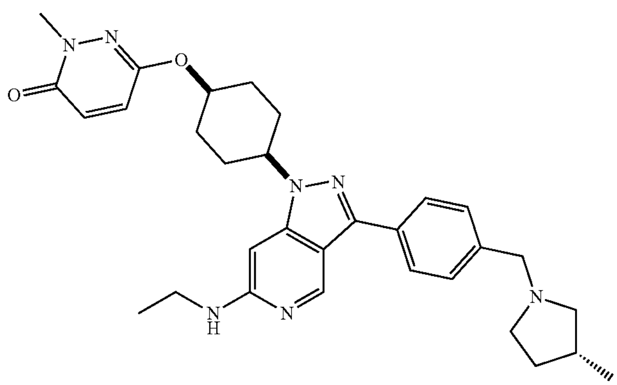 | 6-(((1S,4s)-4-(6-(ethylamino)-3-(4-(((R)-3-methylpyrrolidin-1-yl)methyl)phenyl)-1H-pyrazolo[4,3-c]pyridin-1-yl)cyclohexyl)oxy)-2-methylpyridazin-3(2H)-one | Mass spectrum (apci) m/z = 544.2 |
| 99 | 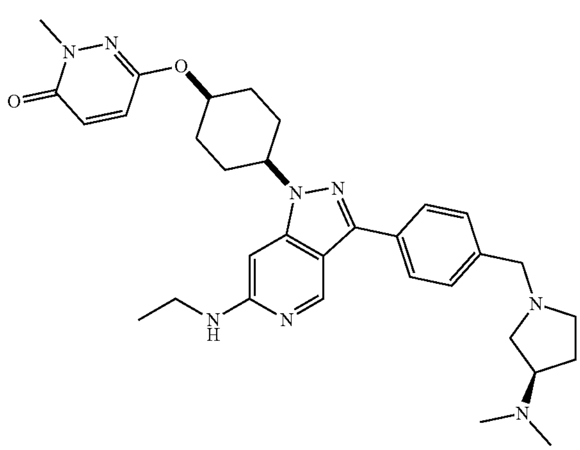 | 6-(((1S,4s)-4-(3-(4-(((R)-3-(dimethylamino)pyrrolidin-1-yl)methyl)phenyl)-6-(ethylamino)-1H-pyrazolo[4,3-c]pyridin-1-yl)cyclohexyl)oxy)-2-melhylpyridazin-3(2H)-one | Mass spectrum (apci) m/z = 571.3 |

Example 100

6-(((1s,4s)-4-(6-(ethylamino)-3-(1-((tetrahydro-2H-pyran-4-yl)methyl)-1H-pyrazol-3-yl)-1H-pyrazolo[4,3-c]pyridin-1-yl)cyclohexyl)oxy)-2-methylpyridazin-3(2H)-one

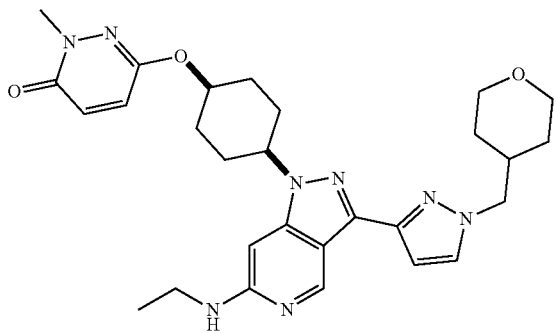

Step A: To a solution of tert-butyl (3-bromo-1-((1s,4s)-4-((1-methyl-6-oxo-1,6-dihydropyridazin-3-yl)oxy)cyclohexyl)-1H-pyrazolo[4,3-c]pyridin-6-yl)(ethyl)carbamate (0.100 g, 0.183 mmol), Pd(PPh$_3$)$_4$ (0.0211 g, 0.0183 mmol) and 3-(4,4,5,5-tetramethyl-1,3,2-dioxaborolan-2-yl)-1H-pyrazole (0.0709 g, 0.365 mmol) in 1,4-dioxane (1.8 mL) was added 2M Na$_2$CO$_3$ (0.192 mL, 0.384 mmol). This mixture was heated to 90° C. under nitrogen. After 24 h, 0.1 eq of Pd(PPh$_3$)$_4$ and 2 eq of boronic ester were added heated overnight again. The reaction mixture was partitioned between EtOAc and water, washed with brine (2×25 mL), dried over Na$_2$SO$_4$, filtered and concentrated. The residue was purified over silica gel (10-100% EtOAc in hexanes) to afford tert-butyl ethyl(1-((1s,4s)-4-((1-methyl-6-oxo-1,6-dihydropyridazin-3-yl)oxy)cyclohexyl)-3-(1H-pyrazol-3-yl)-1H-pyrazolo[4,3-c]pyridin-6-yl)carbamate (0.091 g, 0.170 mmol, 93.2% yield) as a white solid.

Step B: To a mixture of tert-butyl ethyl(1-((1s,4s)-4-((1-methyl-6-oxo-1,6-dihydropyridazin-3-yl)oxy)cyclohexyl)-3-(1H-pyrazol-3-yl)-1H-pyrazolo[4,3-c]pyridin-6-yl)carbamate (0.022 g, 0.041 mmol) and 4-(Bromomethyl)tetrahydropyran (0.015 g, 0.082 mmol) in DMA (0.4 mL) was added Cs$_2$CO$_3$ (0.028 g, 0.086 mmol) and the reaction was heated to 100° C. After 3 h, the reaction was cooled to room temperature and DCM (2 mL) was added and then TFA (5 mL) added. After 1 hr, the reaction mixture was concentrated and the resultant oil was resuspended in 1 mL of a solution of 60:40 ACN:water with 2% TFA modifier. The product was purified by C-18 HPLC (5-60% ACN in water with 0.2% TFA modifier). The product fractions were partitioned between aqueous NaHCO$_3$ and DCM, extracted with DCM (2×15 mL), washed with brine (15 mL), dried over Na$_2$SO$_4$, filtered and concentrated to afford 6-(((1s,4s)-4-(6-(ethylamino)-3-(1-((tetrahydro-2H-pyran-4-yl)methyl)-1H-pyrazol-3-yl)-1H-pyrazolo[4,3-c]pyridin-1-yl)cyclohexyl)oxy)-2-methylpyridazin-3(2H)-one (0.0087 g, 0.015 mmol, 37% yield) as a solid. Mass spectrum (apci) m/z=533.2 (M+H). $^1$H NMR (CDCl$_3$) δ 9.08 (s, 1H), 7.42 (d, J=2.2 Hz, 1H), 7.02 (d, J=9.8 Hz, 1H), 6.94 (d, J=9.8 Hz, 1H), 6.78 (d, J=2.4 Hz, 1H), 6.08 (s, 1H), 5.10 (m, 1H), 4.32 (tt, J=11.5, 3.9 Hz, 1H), 4.07 (d, J=7.2 Hz, 2H), 3.97 (m, 2H), 3.66 (s, 3H), 3.43-3.26 (m, 4H), 2.53-2.40 (m, 2H), 2.38-2.20 (m, 3H), 1.97-1.89 (m, 2H), 1.84-1.73 (m, 2H), 1.59-1.51 (m, 2H), 1.45-1.33 (i, 5H).

Using the procedure described for the preparation of Example 100, the following compounds were also synthesized:

| Example | Structure | Name | Data |
|---|---|---|---|
| 101 | 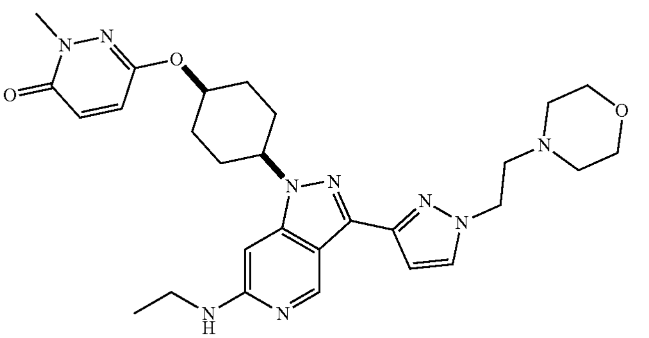 | 6-(((1s,4s)-4-(6-(ethylamino)-3-(1-(2-morpholinoethyl)-1H-pyrazol-3-yl)-1H-pyrazolo[4,3-c]pyridin-1-yl)cyclohexyl)oxy)-2-methylpyridazin-3(2H)-one | Mass spectrum (apci) m/z = 548.3 |
| 102 | 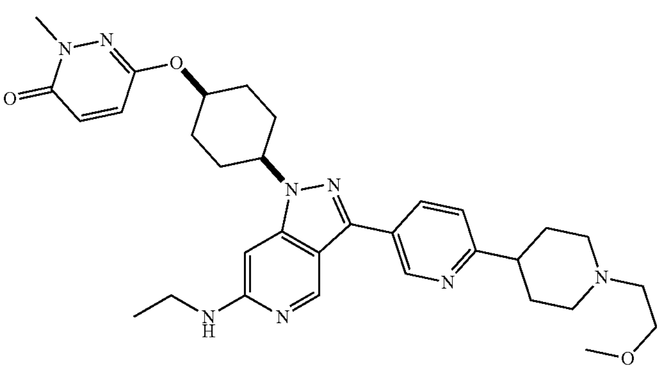 | 6-(((1s,4s)-4-(3-(6-(1-(2-methoxyethyl)piperidin-4-yl)pyridin-3-yl)-6-(methylamino)-1H-pyrazolo[4,3-c]pyridin-1-yl)cyclohexyl)oxy)-2-methylpyridazin-3(2H)-one | Mass spectrum (apci) m/z = 573.3 |

Example 103

6-(((1s,4s)-4-(6-(ethylamino)-3-(4-((1-methylpiperidin-4-yl)oxy)phenyl)-1H-pyrazolo[4,3-c]pyridin-1-yl)cyclohexyl)oxy)-2-methylpyridazin-3(2H)-one

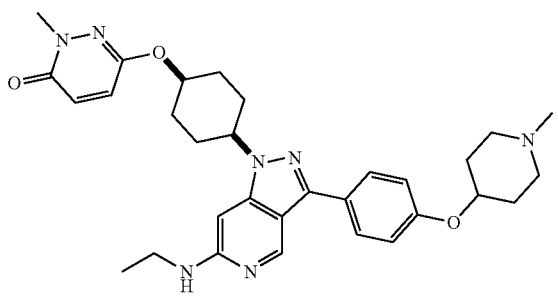

with 2% TFA modifier. The product was purified by C-18 HPLC (5-60% ACN in water with 0.2% TFA modifier). The product fractions were partitioned between DCM and aqueous NaHCO$_3$, extracted with DCM (2×15 mL), washed with brine (15 mL), dried over Na$_2$SO$_4$, filtered and concentrated to afford 6-(((1s,4s)-4-(6-(ethylamino)-3-(4-((1-methylpiperidin-4-yl)oxy)phenyl)-1H-pyrazolo[4,3-c]pyridin-1-yl)cyclohexyl)oxy)-2-methylpyridazin-3(2H)-one (0.0083 g, 0.01488 mmol, 33.38% yield) as a white solid. Mass spectrum (apci) m/z=558.3 (M+H). $^1$H NMR (CDCl$_3$) δ 8.79 (d, J=1.0 Hz, 1H), 7.85 (m, 2H), 7.05-6.99 (m, 3H), 6.94 (d, J=9.8 Hz, 1H), 6.06 (s, 1H), 5.09 (m, 1H), 4.69 (br s, 1H), 4.45 (br s, 1H), 4.33 (tt, J=11.4, 3.7 Hz, 1H), 3.66 (s, 3H), 3.30 (m, 2H), 2.80 (m, 2H), 2.54-2.30 (m, 8H), 2.10 (m, 2H), 2.00-1.90 (m, 4H), 1.85-1.74 (m, 2H), 1.35 (t, J=7.2 Hz, 3H).

Using the procedure described for the preparation of Example 103, the following compound was also synthesized:

| Example | Structure | Name | Data |
|---|---|---|---|
| 104 | 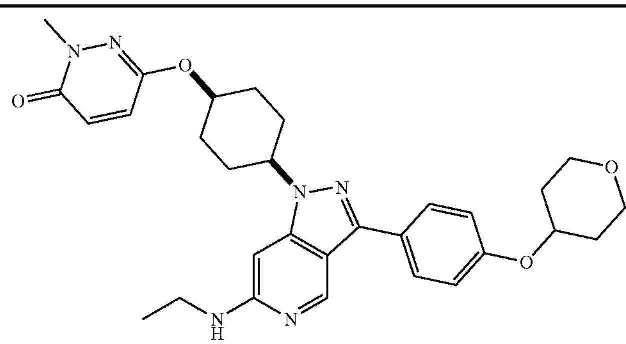 | 6-(((1s,4s)-4-(6-(ethylamino)-3-(4-((tetrahydro-2H-pyran-4-yl)oxy)phenyl)-1H-pyrazolo[4,3-c]pyridin-1-yl)cyclohexyl)oxy)-2-methylpyridazin-3(2H)-one | Mass spectrum (apci) m/z = 545.3 |

Step A: A mixture of tert-butyl (3-bromo-1-((1s,4s)-4-((1-methyl-6-oxo-1,6-dihydropyridazin-3-yl)oxy)cyclohexyl)-1H-pyrazolo[4,3-c]pyridin-6-yl)(ethyl)carbamate (0.100 g, 0.183 mmol), 4-(4,4,5,5-tetramethyl-1,3,2-dioxaborolan-2-yl)phenol (80 mg, 0.36 mmol), Pd(PPh$_3$)$_4$ (0.0106 g, 0.00913 mmol) and 2M Na$_2$CO$_3$ (0.192 mL, 0.384 mmol) in dioxane (1.8 mL) was heated to 90° C. for 2 hrs under nitrogen. The reaction mixture was partitioned between EtOAc and water, washed with water, brine, dried over sodium sulfate, filtered and concentrated. The residue was purified over silica gel (10-100% EtOAc in hexanes) to afford tert-butyl ethyl(3-(4-hydroxyphenyl)-1-((1s,4s)-4-((1-methyl-6-oxo-1,6-dihydropyridazin-3-yl)oxy)cyclohexyl)-1H-pyrazolo[4,3-c]pyridin-6-yl)carbamate (0.105 g, 0.187 mmol, 103% yield) as a white solid.

Step B: To a solution of Ph$_3$P (0.02339 g, 0.08918 mmol), tert-butyl ethyl(3-(4-hydroxyphenyl)-1-((1s,4s)-4-((1-methyl-6-oxo-1,6-dihydropyridazin-3-yl)oxy)cyclohexyl)-1H-pyrazolo[4,3-c]pyridin-6-yl)carbamate (0.025 g, 0.04459 mmol) and N-Methyl-4-piperidinol (0.01572 mL, 0.1338 mmol) in THF (0.45 mL) was added DIAD (0.01758 mL, 0.08918 mmol) at room temperature. After 16 h, the reaction was diluted with dichloromethane (2 mL) and then TFA (5 mL) was added and stirred at room temperature. After 1 hr, the reaction was concentrated and the resultant oil was resuspended in 1 mL of a solution of 60:40 ACN:water

Example 105

5-(((1s,4s)-4-(3-(1-methyl-1H-pyrazol-4-yl)-6-(methylamino)-1H-pyrazolo[4,3-c]pyridin-1-yl)cyclohexyl)oxy)-6-(trifluoromethyl)pyridin-2(1H)-one

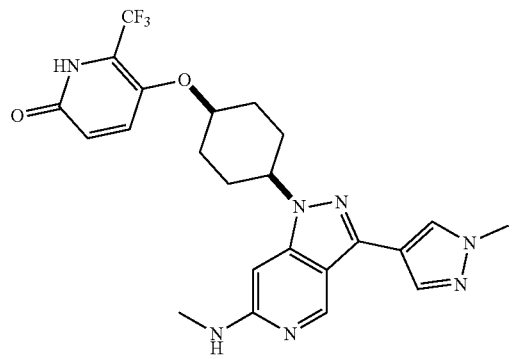

Step A: A solution of triphenylphosphane (46.12 mg, 0.1758 mmol) in THF (1 mL) was cooled in ice bath. DIAD (34.66 µL, 0.1758 mmol) was added and stirred for 15 min. tert-butyl (1-((1r,4r)-4-hydroxycyclohexyl)-3-(1-methyl-1H-pyrazol-4-yl)-1H-pyrazolo[4,3-c]pyridin-6-yl)(methyl)carbamate (50 mg, 0.1172 mmol) was added. 6-methoxy-2-

(trifluoromethyl)pyridin-3-ol (45.28 mg, 0.2345 mmol) was dissolved in THF (0.5 mL) and added dropwise. After the addition was complete, the reaction was stirred in ice for 5 min and the allowed to warm to RT overnight. Additional triphenylphosphane (46.12 mg, 0.1758 mmol) and DIAD (34.66 µL, 0.1758 mmol) were added and stirred at room temperature for 4 h. The reaction mixture was concentrated and purified over silica gel (40 to 100% EtOAc in hexanes) to afford crude tert-butyl (1-((1s,4s)-4-((6-methoxy-2-(trifluoromethyl)pyridin-3-yl)oxy)cyclohexyl)-3-(1-methyl-1H-pyrazol-4-yl)-1H-pyrazolo[4,3-c]pyridin-6-yl)(methyl)carbamate (143 mg, 0.2377 mmol, 202.8% yield).

Step B: tert-butyl (1-((1s,4s)-4-((6-methoxy-2-(trifluoromethyl)pyridin-3-yl)oxy)cyclohexyl)-3-(1-methyl-1H-pyrazol-4-yl)-1H-pyrazolo[4,3-c]pyridin-6-yl)(methyl)carbamate (70 mg, 0.12 mmol) was dissolved in DCM (2 mL) and TFA (2 mL) was added and stirred at room temperature for 2 h. The reaction mixture was concentrated, diluted with DCM and concentrated (×2), partitioned between DCM and aqueous NaHCO$_3$, dried over sodium sulfate, filtered and concentrated. The reside was purified over silica gel (0 to 20% MeOH in EtOAc) to afford 1-((1s,4s)-4-((6-methoxy-2-(trifluoromethyl)pyridin-3-yl)oxy)cyclohexyl)-N-methyl-3-(1-methyl-1H-pyrazol-4-yl)-1H-pyrazolo[4,3-c]pyridin-6-amine (40 mg, 0.080 mmol, 69% yield) as a white solid.

Step C: 1-((1s,4s)-4-((6-methoxy-2-(trifluoromethyl)pyridin-3-yl)oxy)cyclohexyl)-N-methyl-3-(1-methyl-1H-pyrazol-4-yl)-1H-pyrazolo[4,3-c]pyridin-6-amine (39 mg, 0.0778 mmol) was suspended in ACN (1 mL) and concentrated HBr (2 mL) added and heated to 60° C. for 24 h and then at 70° C. for another 24 h. The reaction mixture was cooled to room temperature, quenched with solid K$_2$CO$_3$, extracted with 10% MeOH in EtOAc, dried over sodium sulfate, filtered and concentrated. The residue was purified over silica gel (0 10% MeOH in DCM) to afford 5-(((1s,4s)-4-(3-(1-methyl-1H-pyrazol-4-yl)-6-(methylamino)-1H-pyrazolo[4,3-c]pyridin-1-yl)cyclohexyl)oxy)-6-(trifluoromethyl)pyridin-2-ol (18 mg, 0.0369 mmol, 47.5% yield) as a tan solid. Mass spectrum (apci) m/z=488.2 (M+H). $^1$H NMR (CDCl$_3$) δ 8.82 (s, 1H), 7.99 (s, 1H), 7.88 (s, 1H), 7.47 (d, J=9.2 Hz, 1H), 6.94 (d, J=9.0 Hz, 1H), 6.87 (br s, 1H), 6.28 (s, 1H), 4.71 (m, 1H), 4.55 (tt, J=12.5, 3.3 Hz, 1H), 4.00 (s, 3H), 3.07 (s, 3H), 2.66 (m, 2H), 2.31 (m, 2H), 1.99 (m, 2H), 1.84 (m, 2H).

Using the procedure described for the preparation of Example 105 (Steps A and C), the following compound was also synthesized:

Example 107

3-methyl-2-(((1s,4s)-4-(3-(1-methyl-1H-pyrazol-4-yl)-6-(methylamino)-1H-pyrazolo[4,3-c]pyridin-1-yl)cyclohexyl)oxy)pyrimidin-4(3H)-one

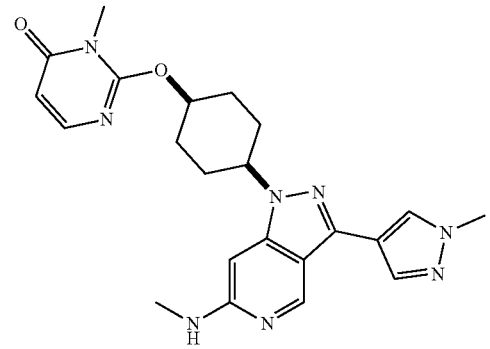

Step A: A mixture of tert-butyl (1-(4-hydroxycyclohexyl)-3-(1-methyl-1H-pyrazol-4-yl)-1H-pyrazolo[4,3-c]pyridin-6-yl)(methyl)carbamate (0.100 g, 0.234 mmol), 4-(benzyloxy)-2-chloropyrimidine (0.0673 g, 0.305 mmol) and NaH (0.0141 g, 0.352 mmol) in DMF (1.17 mL, 0.234 mmol) was heated to 90° C. overnight. The reaction mixture was worked up with EtOAc and water. The combined organic layers were washed with water and brine and dried over Na$_2$SO$_4$. The organic layer was filtered and concentrated down. The mixture was purified on a column using EtOAc: Hexane to give tert-butyl (1-(4-((4-(benzyloxy)pyrimidin-2-yl)oxy)cyclohexyl)-3-(1-methyl-1H-pyrazol-4-yl)-1H-pyrazolo[4,3-c]pyridin-6-yl)(methyl)carbamate (0.047 g, 0.0770 mmol, 32.8% yield).

Step B: To a stirred solution of tert-butyl (1-(4-((4-(benzyloxy)pyrimidin-2-yl)oxy)cyclohexyl)-3-(1-methyl-1H-pyrazol-4-yl)-1H-pyrazolo[4,3-c]pyridin-6-yl)(methyl) carbamate (47 mg, 0.077 mmol) in 1 mL of 95% ethanol at room temperature was added 5% Pd—C (41 mg, 0.019 mmol) neat as a solid. The reaction mixture was stirred under a balloon of hydrogen for 1 h. The reaction mixture was filtered through GF/F filter paper with ethanol and the filtrate concentrated to a crude oil and purified over silica gel (0-10% MeOH in DCM) to afford two major peaks. The

| Example | Structure | Name | Data |
|---|---|---|---|
| 106 |  | 5-(((1s,4s)-4-(3-bromo-6-(ethylamino)-1H-pyrazolo[4,3-c]pyridin-1-yl)cyclohexyl)oxy)-6-(trifluoromethyl)pyridin-2(1H)-one | Mass spectrum (apci) m/z = 500.1 and 502.1 | faster eluting material was tert-butyl methyl(3-(1-methyl-1H-pyrazol-4-yl)-1-((1s,4s)-4-((6-oxo-1,6-dihydropyrimidin-2-yl)oxy)cyclohexyl)-1H-pyrazolo[4,3-c]pyridin-6-yl)carbamate (26 mg, 65% yield).

Step C: To a stirred solution of tert-butyl methyl(3-(1-methyl-1H-pyrazol-4-yl)-1-((1s,4s)-4-((6-oxo-1,6-dihydropyrimidin-2-yl)oxy)cyclohexyl)-1H-pyrazolo[4,3-c]pyridin-6-yl)carbamate (26 mg, 0.04994 mmol) in 500 µL of THF in a capped reaction vial at room temperature was added NaH (2.397 mg, 0.05993 mmol) neat as a solid. After 15 minutes, methyl para-toluenesulfonate (9.044 µL, 0.05993 mmol) was added neat by syringe. The reaction mixture was capped, heated to 50° C. and stirred overnight. The reaction mixture was quenched with 1 mL of water and partitioned between ethyl acetate (15 mL) and water (15 mL), washed with brine, dried over MgSO$_4$, filtered and concentrated, to afford crude tert-butyl methyl(3-(1-methyl-1H-pyrazol-4-yl)-1-((1s,4s)-4-((1-methyl-6-oxo-1,6-dihydropyrimidin-2-yl)oxy)cyclohexyl)-1H-pyrazolo[4,3-c]pyridin-6-yl)carbamate (26 mg, 97% yield), which was taken forward without further purification.

Step D: To a stirred solution of tert-butyl methyl(3-(1-methyl-1H-pyrazol-4-yl)-1-((1s,4s)-4-((1-methyl-6-oxo-1,6-dihydropyrimidin-2-yl)oxy)cyclohexyl)-1H-pyrazolo[4,3-c]pyridin-6-yl)carbamate (26 mg, 0.0486 mmol) in 500 µL of dichloromethane at room temperature was added TFA (375 µL, 4.86 mmol). After stirring for 2 hours, the reaction was concentrated. The crude residue was purified by reverse phase HPLC using an acetonitrile/water/0.02% TFA gradient (5% to 95% acetonitrile). The product was partitioned between DCM and aqueous NaHCO$_3$, extracted 2×15 mL with dichloromethane, dried over MgSO$_4$, filtered and concentrated to afford 3-methyl-2-(((1s,4s)-4-(3-(1-methyl-1H-pyrazol-4-yl)-6-(methylamino)-1H-pyrazolo[4,3-c]pyridin-1-yl)cyclohexyl)oxy)pyrimidin-4(3H)-one (4.0 mg, 18% yield). Mass spectrum (apci) m/z=435.2 (M+H). $^1$H NMR (CDCl$_3$) δ 8.70 (s, 1H), 7.97 (s, 1H), 7.84 (s, 1H), 7.65 (d, J=6.5 Hz, 1H), 6.14 (d, J=6.5 Hz, 1H), 6.02 (s, 1H), 5.45 (m, 1H), 4.85 (br s, 1H), 4.36 (tt, J=11.2, 3.9 Hz, 1H), 4.00 (s, 3H), 3.57 (s, 3H), 2.96 (d, J=4.3 Hz, 3H), 2.51-2.29 (m, 4H), 2.03-1.95 (m, 2H), 1.92-1.81 (m, 2H).

Using the procedure described for the preparation of Example 107 and using the later eluting isomer from Step B, the following compound was also synthesized:

Example 109

3-(((1s,4s)-4-(6-(ethylamino)-3-(1-methyl-1H-pyrazol-4-yl)-1H-pyrazolo[4,3-c]pyridin-1-yl)cyclohexyl)oxy)-1-methylpyridin-2(1H)-one

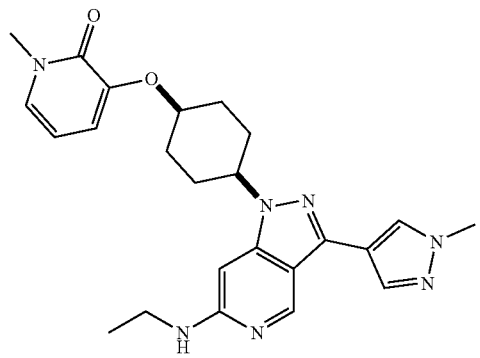

Step A: To a stirred solution of tert-butyl ethyl(3-(1-methyl-1H-pyrazol-4-yl)-1H-pyrazolo[4,3-c]pyridin-6-yl)carbamate (40 mg, 0.11 mmol) in 550 µL of DMF at room temperature in a capped reaction vial was added (1r,4r)-4-((1-methyl-2-oxo-1,2-dihydropyridin-3-yl)oxy)cyclohexyl 4-methylbenzenesulfonate (44.0 mg, 0.11 mmol) neat as a solid followed by Cs$_2$CO$_3$ (76.1 mg, 0.233 mmol) neat as a solid. The reaction mixture was capped and heated to 100° C. overnight. The reaction mixture was cooled to room temperature and partitioned between ethyl acetate (15 mL) and water (15 mL), washed 3×15 mL with water and 1×15 mL with brine, dried over MgSO$_4$, filtered and concentrated. The crude product was purified over silica gel (30% to 75% ethyl acetate in hexanes) to afford tert-butyl ethyl(3-(1-methyl-1H-pyrazol-4-yl)-1-((1s,4s)-4-((1-methyl-2-oxo-1,2-dihydropyridin-3-yl)oxy)cyclohexyl)-1H-pyrazolo[4,3-c]pyridin-6-yl)carbamate (20 mg, 31% yield).

Step B: To a stirred solution of tert-butyl ethyl(3-(1-methyl-1H-pyrazol-4-yl)-1-((1s,4s)-4-((1-methyl-2-oxo-1,2-dihydropyridin-3-yl)oxy)cyclohexyl)-1H-pyrazolo[4,3-c]pyridin-6-yl)carbamate (20 mg, 0.036 mmol) in 700 µL of dichloromethane at room temperature was added TFA (703 µL, 9.13 mmol). After stirring for 2 hours, the reaction was concentrated. The crude residue was purified by reverse phase HPLC using an acetonitrile/water/0.02% TFA gradi-

| Example | Structure | Name | Data |
| --- | --- | --- | --- |
| 108 | | 3-methyl-2-(((1r,4r)-4-(3-(1-methyl-1H-pyrazol-4-yl)-6-(methylamino)-1H-pyrazolo[4,3-c]pyridin-1-yl)cyclohexyl)oxy)pyrimidin-4(3H)-one | Mass spectrum (apci) m/z = 435.2 | ent (5% to 95% acetonitrile). Fractions containing the desired product were partitioned between DCM and aqueous NaHCO₃, extracted 2×15 mL with dichloromethane, dried over MgSO₄, filtered and concentrated to afford 3-(((1s,4s)-4-(6-(ethylamino)-3-(1-methyl-1H-pyrazol-4-yl)-1H-pyrazolo[4,3-c]pyridin-1-yl)cyclohexyl)oxy)-1-methylpyridin-2(1H)-one (8.5 mg, 49% yield). Mass spectrum (apci) m/z=448.2 (M+H). ¹H NMR (CDCl₃) δ 8.71 (s, 1H0, 7.99 (s, 1H), 7.88 (s, 1H), 6.98 (d, J=6.8 Hz, 1H), 6.83 (d, J=7.4 Hz, 1H), 6.52 (s, 1H), 6.10 (t, J=7.2 Hz, 1H), 4.98 (br s, 1H), 4.73 (m, 1H), 4.40 (tt, J=11.3, 4.3 Hz, 1H), 3.99 (s, 3H), 3.60 (s, 3H), 3.40 (m, 2H), 2.71-2.59 (m, 2H), 2.34-2.25 (m, 2H), 1.92-1.84 (m, 2H), 1.76-1.66 (m, 2H), 1.34 (t, J=7.2 Hz, 3H).

Example 110

1-methyl-6-(((1s,4s)-4-(3-(1-methyl-1H-pyrazol-4-yl)-6-(methylamino)-1H-pyrazolo[4,3-c]pyridin-1-yl)cyclohexyl)oxy)pyridin-2(1H)-one

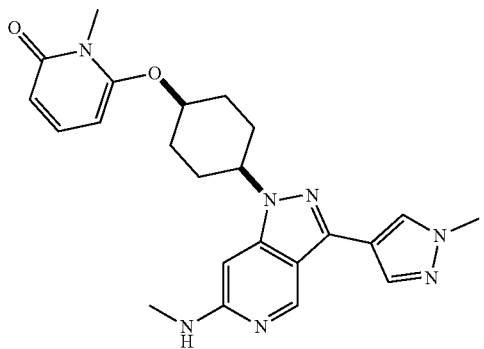

Step A: DIAD (0.0363 mL, 0.1846 mmol) was added to Ph₃P (0.0484 g, 0.1846 mmol), tert-butyl (1-((1r,4r)-4-hydroxycyclohexyl)-3-(1-methyl-1H-pyrazol-4-yl)-1H-pyrazolo[4,3-c]pyridin-6-yl)(methyl)carbamate (0.075 g, 0.1758 mmol) and 6-(benzyloxy)pyridin-2-ol (0.0460 g, 0.228 mmol) in THF (1.75 mL) and heated to 60° C. overnight. The mixture was concentrated and purified over silica gel (1-10% MeOH in DCM) to afford tert-butyl (1-((1s,4s)-4-((6-(benzyloxy)pyridin-2-yl)oxy)cyclohexyl)-3-(1-methyl-1H-pyrazol-4-yl)-1H-pyrazolo[4,3-c]pyridin-6-yl)(methyl)carbamate (0.080 g, 0.1312 mmol, 74.62% yield).

Step B: tert-butyl (1-((1s,4s)-4-((6-(benzyloxy)pyridin-2-yl)oxy)cyclohexyl)-3-(1-methyl-1H-pyrazol-4-yl)-1H-pyrazolo[4,3-c]pyridin-6-yl)(methyl)carbamate (0.200 g, 0.328 mmol) and 10% Pd/C (0.0349 g, 0.328 mmol) was stirred in MeOH (5 mL) under H2 balloon at room temperature overnight. The reaction mixture was filtered and concentrated. The residue was purified over silica gel (1-14% MeOH in DCM) to afford tert-butyl methyl(3-(1-methyl-1H-pyrazol-4-yl)-1-((1s,4s)-4-((6-oxo-1,6-dihydropyridin-2-yl)oxy)cyclohexyl)-1H-pyrazolo[4,3-c]pyridin-6-yl)carbamate (0.070 g, 0.135 mmol, 41.1% yield).

Step C: NaH (60% in mineral oil, 0.0063 g, 0.158 mmol) was added to tert-butyl methyl(3-(1-methyl-1H-pyrazol-4-yl)-1-((1s,4s)-4-((6-oxo-1,6-dihydropyridin-2-yl)oxy)cyclohexyl)-1H-pyrazolo[4,3-c]pyridin-6-yl)carbamate (0.055 g, 0.105 mmol) in THF (1.0 mL). Methyl 4-methylbenzenesulfonate (0.023 mL, 0.158 mmol) was then added and heated to 50° C. overnight. The reaction mixture was concentrated and diluted with DCM (1 mL) and TFA (1 mL) added and stirred for 1 h. The reaction mixture was concentrated and purified on C18 HPLC (water:ACN 5-95% with 1% TFA). The slower eluting product was collected and partitioned between DCM and aqueous NaHCO₃, dried over sodium sulfate, filtered and concentrated to afford 1-methyl-6-(((1s,4s)-4-(3-(1-methyl-1H-pyrazol-4-yl)-6-(methylamino)-1H-pyrazolo[4,3-c]pyridin-1-yl)cyclohexyl)oxy)pyridin-2(1H)-one (0.027 g, 0.06228 mmol, 58.84% yield). Mass spectrum (apci) m/z=434.2 (M+H). ¹H NMR (CDCl₃) δ 8.69 (s, 1H), 7.96 (s, 1H), 7.84 (s, 1H), 7.29 (dd, J=9.0, 7.8 Hz, 1H), 6.21 (dd, J=9.0, 1.0 Hz, 1H), 6.02 (s, 1H), 5.57 (d, J=7.8 Hz, 1H), 5.15 (br s, 1H), 4.73 (m, 1H), 4.36 (tt, J=11.7, 4.1 Hz, 1H), 4.00 (s, 3H), 3.65 (s, 3H), 2.96 (s, 3H), 2.54-2.34 (m, 4H), 2.02-1.94 (m, 2H), 1.91-1.80 (m, 2H).

Using the procedure described for the preparation of Example 110, the following compound was also synthesized:

| Example | Structure | Name | Data |
| --- | --- | --- | --- |
| 111 | 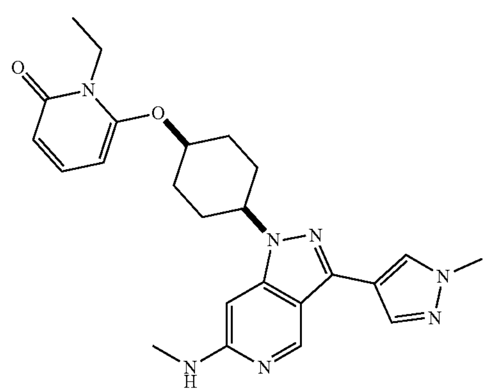 | 1-ethyl-6-(((1s,4s)-4-(3-(1-methyl-1H-pyrazol-4-yl)-6-(methylamino)-1H-pyrazolo[4,3-c]pyridin-1-yl)cyclohexyl)oxy)pyridin-2(1H)-one | Mass spectrum (apci) m/z = 448.2 |

Example 112

N-(4-(6-(ethylamino)-1-((1s,4s)-4-((1-methyl-6-oxo-1,6-dihydropyridazin-3-yl)oxy)cyclohexyl)-1H-pyrazolo[4,3-c]pyridin-3-yl)benzyl)acetamide

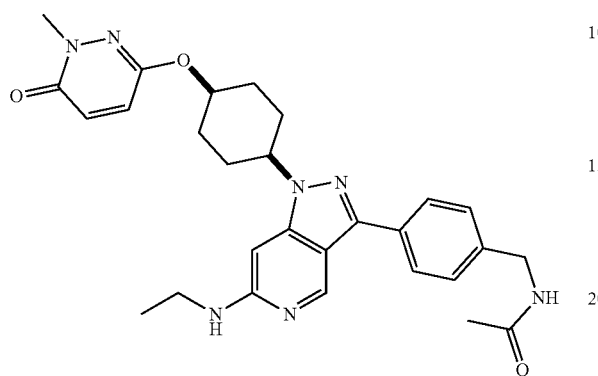

Step A: tert-butyl (3-bromo-1-((1s,4s)-4-((1-methyl-6-oxo-1,6-dihydropyridazin-3-yl)oxy)cyclohexyl)-1H-pyrazolo[4,3-c]pyridin-6-yl)(ethyl)carbamate (0.100 g, 0.183 mmol), (4-(aminomethyl)phenyl)boronic acid (0.0552 g, 0.365 mmol), Pd(PPh$_3$)$_4$ (0.0106 g, 0.00913 mmol) and 2M Na$_2$CO$_3$ (0.192 mL, 0.384 mmol) were added to dioxane (1.8 mL) and heated to 90° C. for 16 hrs. The reaction mixture was partitioned between EtOAc and water, washed with water (×2) and brine, dried over Na$_2$SO$_4$, filtered and concentrated. The crude oil was purified over silica gel (1-20% MeOH in DCM) to afford tert-butyl (3-(4-(aminomethyl)phenyl)-1-((1s,4s)-4-((1-methyl-6-oxo-1,6-dihydropyridazin-3-yl)oxy)cyclohexyl)-1H-pyrazolo[4,3-c]pyridin-6-yl)(ethyl)carbamate (0.068 g, 0.119 mmol, 64.9% yield) as a white solid.

Step B: To a mixture of tert-butyl (3-(4-(aminomethyl)phenyl)-1-((1s,4s)-4-((1-methyl-6-oxo-1,6-dihydropyridazin-3-yl)oxy)cyclohexyl)-1H-pyrazolo[4,3-c]pyridin-6-yl)(ethyl)carbamate (0.020 g, 0.035 mmol) and DIEA (0.018 mL, 1.0 mmol) in THF (0.5 mL) was added acetyl chloride (0.070 mL, 0.070 mmol) and stirred for 1 h. Dichloromethane (2 mL) was added and then TFA (5 mL). After 1 h, the reaction was concentrated and the resultant oil was resuspended in 1 mL of a solution of 60:40 ACN:water with 2% TFA modifier and purified by C18 HPLC (5-60% ACN in water with 0.2% TFA modifier). The product fractions were partitioned between DCM and aqueous NaHCO$_3$, extracted with DCM (×2), washed with brine, dried over Na$_2$SO$_4$, filtered and concentrated to afford N-(4-(6-(ethylamino)-1-((1s,4s)-4-((1-methyl-6-oxo-1,6-dihydropyridazin-3-yl)oxy)cyclohexyl)-1H-pyrazolo[4,3-c]pyridin-3-yl)benzyl)acetamide (0.012 g, 0.023 mmol, 67% yield). Mass spectrum (apci) m/z=516.2 (M+H). $^1$H NMR (CDCl$_3$) δ 8.79 (s, 1H), 7.90 (m, 2H), 7.41 (m, 2H), 7.01 (d, J=9.6 Hz, 1H), 6.93 (d, J=9.8 Hz, 1H), 6.08 (s, 1H), 5.75 (m, 1H), 5.10 (m, 1H), 4.50 (d, J=5.9 Hz, 2H), 4.35 (tt, J=11.1, 3.9 Hz, 1H), 3.66 (s, 3H), 3.30 (m, 2H), 2.54-2.41 (m, 2H), 2.39-2.30 (m, 2H), 2.06 (s, 3H), 1.99-1.91 (m, 2H), 1.85-1.75 (m, 2H), 1.36 (t, J=7.2 Hz, 3H).

Example 113

6-(((1s,4s)-4-(6-(ethylamino)-3-(1-methylpiperidin-4-yl)-1H-pyrazolo[4,3-c]pyridin-1-yl)cyclohexyl)oxy)-2-methylpyridazin-3(2H)-one

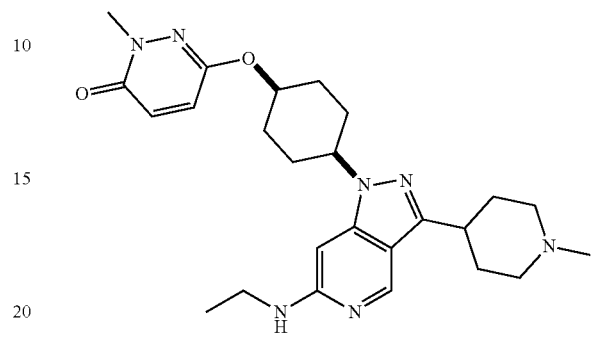

Step A: tert-butyl (3-bromo-1-((1s,4s)-4-((1-methyl-6-oxo-1,6-dihydropyridazin-3-yl)oxy)cyclohexyl)-1H-pyrazolo[4,3-c]pyridin-6-yl)(ethyl)carbamate (50 mg, 0.0913 mmol), 1-methyl-4-(4,4,5,5-tetramethyl-1,3,2-dioxaborolan-2-yl)-1,2,3,6-tetrahydropyridine (41 mg, 0.183 mmol) and Pd(PPh$_3$)$_4$ (11 mg, 0.00913 mmol) were combined in dioxane (2 mL) and treated with 2M K$_2$CO$_3$ (137 µL, 0.274 mmol). The mixture was heated to 100° C. in a sealed tube under nitrogen overnight. The reaction mixture was partitioned between water and EtOAc, extracted with EtOAc (2×), washed with brine, dried over Na$_2$SO$_4$, filtered and concentrated. The residue was purified over silica gel (0-20% MeOH in DCM) to afford tert-butyl ethyl(3-(1-methyl-1,2,3,6-tetrahydropyridin-4-yl)-1-((1s,4s)-4-((1-methyl-6-oxo-1,6-dihydropyridazin-3-yl)oxy)cyclohexyl)-1H-pyrazolo[4,3-c]pyridin-6-yl)carbamate (33.4 mg, 65% yield).

Step B: A solution of tert-butyl ethyl(3-(1-methyl-1,2,3,6-tetrahydropyridin-4-yl)-1-((1s,4s)-4-((1-methyl-6-oxo-1,6-dihydropyridazin-3-yl)oxy)cyclohexyl)-1H-pyrazolo[4,3-c]pyridin-6-yl)carbamate (33.4 mg, 0.0593 mmol) in MeOH (2 mL) was treated with 10% Pd/C (wet, Degussa type, 10 mg) and hydrogenated under a balloon atmosphere overnight. Additional 10% Pd/C (wet, Degussa type, 15 mg) was added to solution and a fresh hydrogen balloon added and stirred overnight again. The reaction mixture was filtered through GF paper and concentrated to afford a black foam which was used directly without purification.

Step C: tert-butyl ethyl(1-((1s,4s)-4-((1-methyl-6-oxo-1,6-dihydropyridazin-3-yl)oxy)cyclohexyl)-3-(1-methylpiperidin-4-yl)-1H-pyrazolo[4,3-c]pyridin-6-yl)carbamate (29.7 mg, 0.0525 mmol) was dissolved in MeOH (2 mL) and treated with 4N HCl/dioxane (2 mL) and stirred for 45 minutes. The reaction mixture was concentrated and purified on C18 HPLC (5 to 95% ACN in water with 0.1% TFA buffer). The fractions containing the desired product were partitioned between DCM and 2N NaOH, extracted with DCM (×3), dried over sodium sulfate, filtered and concentrated to afford 6-(((1s,4s)-4-(6-(ethylamino)-3-(1-methylpiperidin-4-yl)-1H-pyrazolo[4,3-c]pyridin-1-yl)cyclohexyl)oxy)-2-methylpyridazin-3(2H)-one (8.2 mg, 33% yield). Mass spectrum (apci) m/z=466.3 (M+H). $^1$H NMR (CDCl$_3$) δ 8.64 (d, J=1.0 Hz, 1H), 7.00 (d, J=9.8 Hz, 1H), 6.92 (d, J=9.8 Hz, 1H), 5.99 (d, J=0.8 Hz, 1H), 5.06 (m, 1H), 4.61 (m, 1H), 4.24 (tt, J=11.5, 3.7 Hz, 1H), 3.65 (s, 3H), 3.25 (m, 2H), 3.02-2.92 (m, 3H), 2.42-2.25 (m, 7H), 2.15-1.96 (m, 5H), 1.90-1.70 (m, 4H), 1.32 (t, J=7.2 Hz, 3H).

Example 114

1-methyl-6-(((1s,4s)-4-(3-(1-methyl-1H-pyrazol-4-yl)-6-(methylamino)-1H-pyrazolo[4,3-c]pyridin-1-yl)cyclohexyl)oxy)pyridazin-4(1H)-one

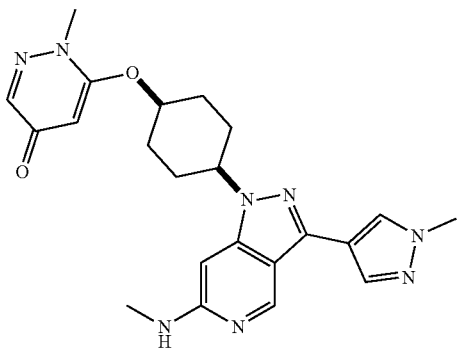

Step A: 60% NaH (0.0047 g, 0.12 mmol) was added to a mixture of tert-butyl (1-((1s,4s)-4-hydroxycyclohexyl)-3-(1-methyl-1H-pyrazol-4-yl)-1H-pyrazolo[4,3-c]pyridin-6-yl)(methyl)carbamate (0.042 g, 0.098 mmol) and 5-(benzyloxy)-3-chloropyridazine (0.065 g, 0.30 mmol) in DMSO (1.0 mL) and heated to 90° C. overnight. The reaction mixture was partitioned between water and EtOAc, washed with brine, dried over $Na_2SO_4$, filtered and concentrated. The residue was purified over silica gel (10-90% EtOAc in hexanes) to afford tert-butyl (1-((1s,4s)-4-((5-(benzyloxy)pyridazin-3-yl)oxy)cyclohexyl)-3-(1-methyl-1H-pyrazol-4-yl)-1H-pyrazolo[4,3-c]pyridin-6-yl)(methyl)carbamate (0.050 g, 0.082 mmol, 83% yield).

Step B: tert-butyl (1-((1s,4s)-4-((5-(benzyloxy)pyridazin-3-yl)oxy)cyclohexyl)-3-(1-methyl-1H-pyrazol-4-yl)-1H-pyrazolo[4,3-c]pyridin-6-yl)(methyl)carbamate (0.050 g, 0.082 mmol) and 10% Pd/C (0.0087 g) were stirred in MeOH (2 mL) under H2 balloon at room temperature overnight. The reaction mixture was filtered and concentrated to afford tert-butyl (1-((1s,4s)-4-((5-hydroxypyridazin-3-yl)oxy)cyclohexyl)-3-(1-methyl-1H-pyrazol-4-yl)-1H-pyrazolo[4,3-c]pyridin-6-yl)(methyl)carbamate (0.043 g, 0.083 mmol, 101% yield).

Step C: NaH (0.004955 g, 0.1239 mmol) was added to tert-butyl methyl(3-(1-methyl-1H-pyrazol-4-yl)-1-((1s,4s)-4-((5-oxo-2,5-dihydropyridazin-3-yl)oxy)cyclohexyl)-1H-pyrazolo[4,3-c]pyridin-6-yl)carbamate (0.043 g, 0.08260 mmol) in THF (0.8 mL). Methyl 4-methylbenzenesulfonate (0.03739 mL, 0.2478 mmol) was then added and heated to 50° C. overnight. The reaction was concentrated and dissolved in DCM (1 mL) and TFA (1 mL) and stirred for 1 hour. The mixture was concentrated and purified on preparative HPLC (water:ACN 5-95% with 1% TFA). The product containing fractions were partitioned between DCM and aqueous $NaHCO_3$, washed with brine, dried over $Na_2SO_4$, filtered and concentrated to 1-methyl-6-(((1s,4s)-4-(3-(1-methyl-1H-pyrazol-4-yl)-6-(methylamino)-1H-pyrazolo[4,3-c]pyridin-1-yl)cyclohexyl)oxy)pyridazin-4(1H)-one (0.0041 g, 0.009436 mmol, 11.42% yield). Mass spectrum (apci) m/z=435.2 (M+H). $^1$H NMR (CDCl$_3$) δ 8.69 (s, 1H), 7.98 (s, 1H), 7.87 (s, 1H), 7.65 (d, J=2.8 Hz, 1H), 6.17 (d, J=2.9 Hz, 1H), 6.01 (s, 1H), 4.86 (br s, 1H), 4.58 (m, 1H), 4.33 (tt, J=11.3, 3.7 Hz, 1H), 4.00 (s, 3H), 3.73 (s, 3H), 2.97 (d, J=3.7 Hz, 3H), 2.51-2.27 (m, 4H), 1.98-1.79 (m, 2H).

Example 115

(4-(6-(methylamino)-1-((1r,4r)-4-(pyridin-2-yloxy)cyclohexyl)-1H-pyrazolo[4,3-c]pyridin-3-yl)phenyl)(4-methylpiperazin-1-yl)methanone

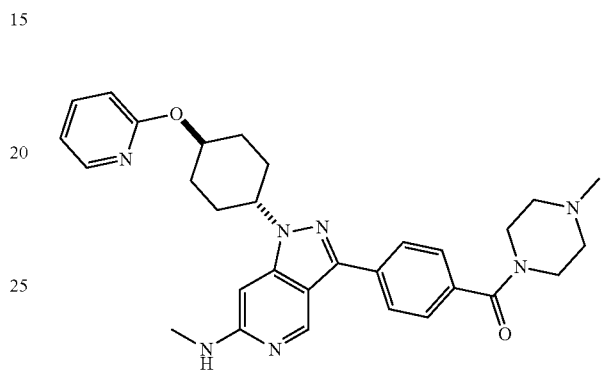

Step A: tert-butyl methyl(3-(4-(4-methylpiperazine-1-carbonyl)phenyl)-1H-pyrazolo[4,3-c]pyridin-6-yl)carbamate (50 mg, 0.11 mmol) was dissolved in DMA (0.5 mL). $Cs_2CO_3$ (72 mg, 0.22 mmol) was added, followed by (1s,4s)-4-(pyridin-2-yloxy)cyclohexyl 4-methylbenzenesulfonate (50 mg, 0.14 mmol) and the reaction was heated to 100° C. overnight. The reaction mixture was diluted with water, extracted with MTBE, dried over sodium sulfate, filtered and concentrated. The residue was purified over silica gel (1-15% MeOH in DCM with $NH_3$) to afford tert-butyl methyl(3-(4-(4-methylpiperazine-1-carbonyl)phenyl)-1-((1r,4r)-4-(pyridin-2-yloxy)cyclohexyl)-1H-pyrazolo[4,3-c]pyridin-6-yl)carbamate (37 mg, 0.059 mmol, 53% yield).

Step B: tert-butyl methyl(3-(4-(4-methylpiperazine-1-carbonyl)phenyl)-1-((1r,4r)-4-(pyridin-2-yloxy)cyclohexyl)-1H-pyrazolo[4,3-c]pyridin-6-yl)carbamate (37 mg, 0.0591 mmol) was dissolved in DCM (1 mL) and TFA (0.5 mL) was added and stirred at room temperature for 1 h and then 20 min at 30° C. The reaction mixture was concentrated and partitioned between 1M $Na_2CO_3$ and DCM, dried over sodium sulfate, filtered and concentrated. The residue was purified over silica gel (4 to 20% MeOH in DCM with 0.2% $NH_3$) to afford (4-(6-(methylamino)-1-((1r,4r)-4-(pyridin-2-yloxy)cyclohexyl)-1H-pyrazolo[4,3-c]pyridin-3-yl)phenyl)(4-methylpiperazin-1-yl)methanone (23.3 mg, 0.0443 mmol, 75.0% yield) as a white solid. Mass spectrum (apci) m/z=526.2 (M+H). $^1$H NMR (CDCl$_3$) δ 8.84 (s, 1H), 8.16 (m, 1H), 7.98 (m, 2H), 7.60-7.51 (m, 3H), 6.85 (m, 1H), 6.72 (m, 1H), 6.03 (s, 1H), 5.21 (m, 1H), 4.81 (m, 1H), 4.38 (m, 1H), 3.83 (br s, 2H), 3.52 (br s, 2H), 3.00 (d, J=5.1 Hz, 3H), 2.55-2.31 (m, 10H), 2.17 (m, 2H), 1.72 (m, 2H).

Using the procedure described for the preparation of Example 115, the following compounds were also synthesized:

| Example | Structure | Name | Data |
|---|---|---|---|
| 116 | 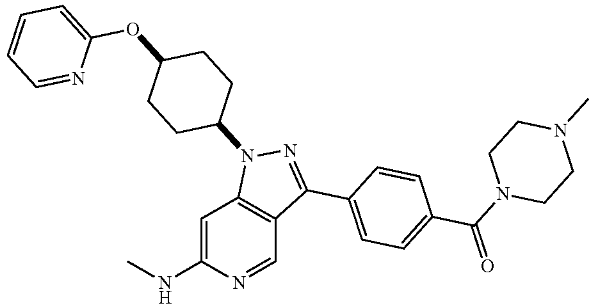 | (4-(6-(methylamino)-1-((1s,4s)-4-(pyridin-2-yloxy)cyclohexyl)-1H-pyrazolo[4,3-c]pyridin-3-yl)phenyl)(4-methylpiperazin-1-yl)methanone | Mass spectrum (apci) m/z = 526.2 |
| 117 | 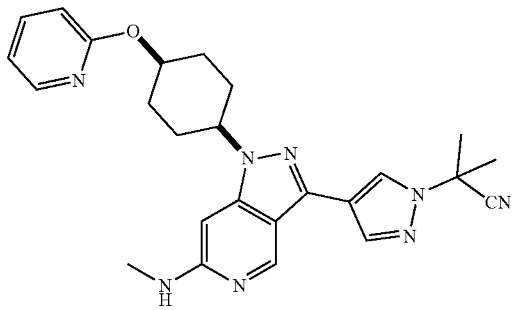 | 2-methyl-2-(4-(6-(niethylamino)-1-((1s,4s)-4-(pyridin-2-yloxy)cyclohexyl)-1H-pyrazolo[4,3-c]pyridin-3-yl)-1H-pyrazol-1-yl)propanenitrile | Mass spectrum (apci) m/z = 457.2 |
| 118 | 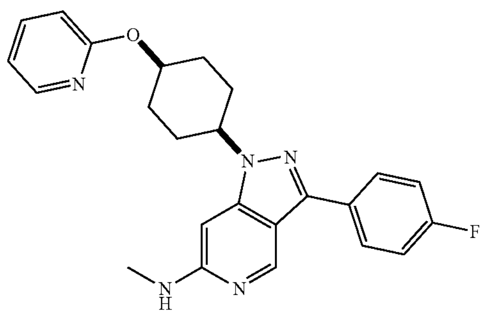 | 3-(4-fluorophenyl)-N-methyl-1-((1s,4s)-4-(pyridin-2-yloxy)cyclohexyl)-1H-pyrazolo[4,3-c]pyridin-6-amine | Mass spectrum (apci) m/z = 418.1 |

Example 119

N-methyl-3-(1-methyl-1H-pyrazol-4-yl)-1-((1r,4r)-4-(pyridazin-3-yloxy)cyclohexyl)-1H-pyrazolo[4,3-c]pyridin-6-amine

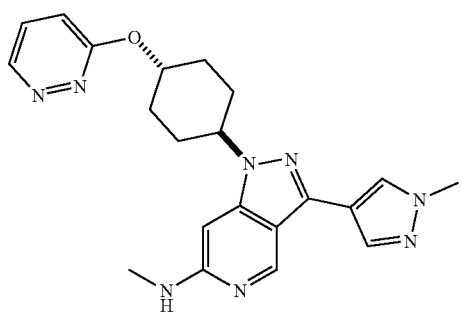

To a solution of tert-butyl (1-((1r,4r)-4-hydroxycyclohexyl)-3-(1-methyl-1H-pyrazol-4-yl)-1H-pyrazolo[4,3-c]pyridin-6-yl)(methyl)carbamate (0.0207 g, 0.0485 mmol) in N,N-dimethylformamide (0.48 mL) was added sodium hydride (0.00140 g, 0.0582 mmol). After 5 mins, 3-chloropyridazine (0.0111 g, 0.0971 mmol) was added and heated to 95° C. overnight. The reaction mixture was partitioned between ethyl acetate (10 mL) and water (10 mL), extracted with ethyl acetate (2×5 mL), washed with water (5 mL) and brine (5 mL), dried over $Na_2SO_4$, filtered and concentrated. The crude oil was resuspended in dichloromethane (5 mL) and TFA (5 mL) was added. After 1 hour, the reaction mixture was concentrated in vacuo and the resultant oil was resuspended in 1 mL of a solution of 60:40 ACN:water with 2% TFA modifier. The product was purified by HPLC (5-95% ACN in water with 0.2% TFA modifier). The product containing fractions were partitioned between DCM and aqueous $NaHCO_3$, dried over sodium sulfate, filtered and concentrated to obtain N-methyl-3-(1-methyl-1H-pyrazol-4-yl)-1-((1r,4r)-4-(pyridazin-3-yloxy)cyclohexyl)-1H-pyrazolo[4,3-c]pyridin-6-amine (0.0105 g, 0.0260 mmol, 53.5% yield) as a white solid. Mass spectrum (apci) m/z=405.2 (M+H). $^1$H NMR ($CDCl_3$) δ 8.83 (m, 1H), 8.69 9 (s, 1H), 7.98 (s, 1H), 7.87 (s, 1H), 7.37 (dd, J=9.0, 4.5 Hz, 1H), 6.95 (dd, J=9.0, 1.2 Hz, 1H), 6.04 (s, 1H), 5.49 (tt, J=11.0, 4.3 Hz, 1H), 4.87 (br s, 1H), 4.35 (tt, J=11.7, 4.1 Hz, 1H), 4.00 (s, 3H), 2.98 (d, J=5.1 Hz, 3H), 2.51 (m, 2H), 2.35 (m, 2H), 2.15 (m, 2H), 1.75 (m, 2H).

Using the procedure described for the preparation of Example 119, the following compounds were also synthesized:

| Example | Structure | Name | Data |
|---|---|---|---|
| 120 | 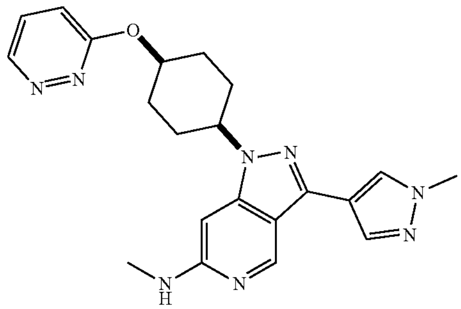 | N-methyl-3-(1-methyl-1H-pyrazol-4-yl)-1-((1s,4s)-4-(pyridazin-3-yloxy)cyclohexyl)-1H-pyrazolo[4,3-c]pyridin-6-amine | Mass spectrum (apci) m/z = 405.2 |
| 121 | 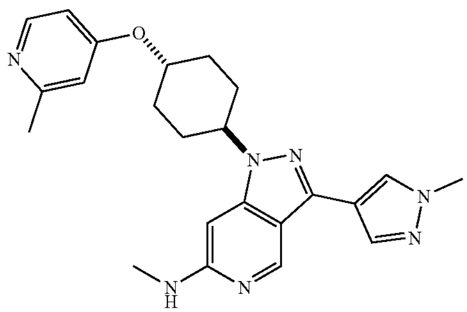 | N-methyl-3-(1-methyl-1H-pyrazol-4-yl)-1-((1r,4r)-4-((2-methylpyridin-4-yl)oxy)cyclohexyl)-1H-pyrazolo[4,3-c]pyridin-6-amine | Mass spectrum (apci) m/z = 418.3 |
| 122 | 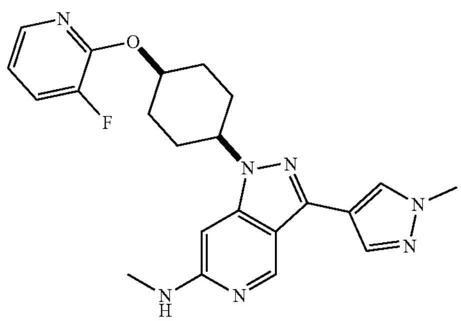 | 1-((1s,4s)-4-((3-fluoropyridin-2-yl)oxy)cyclohexyl)-N-methyl-3-(1-methyl-1H-pyrazol-4-yl)-1H-pyrazolo[4,3-c]pyridin-6-amine | Mass spectrum (apci) m/z = 422.2 |
| 123 | 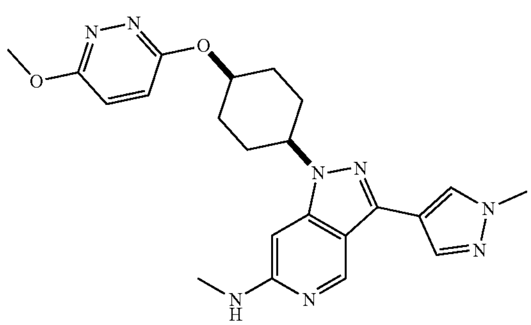 | 1-((1s,4s)-4-((6-methoxypyridazin-3-yl)oxy)cyclohexyl)-N-methyl-3-(1-methyl-1H-pyrazol-4-yl)-1H-pyrazolo[4,3-c]pyridin-6-amine | Mass spectrum (apci) m/z = 435.2 |
| 124 | 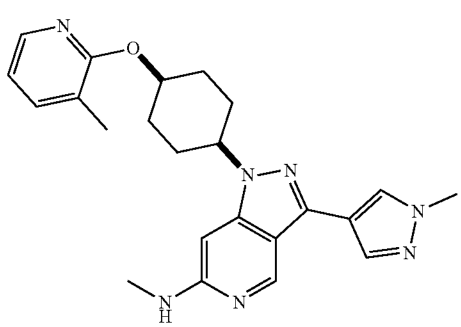 | N-methyl-3-(1-methyl-1H-pyrazol-4-yl)-1-((1s,4s)-4-((3-methylpyridin-2-yl)oxy)cyclohexyl)-1H-pyrazolo[4,3-c]pyridin-6-amine | Mass spectrum (apci) m/z = 418.2 |

| Example | Structure | Name | Data |
|---|---|---|---|
| 125 | 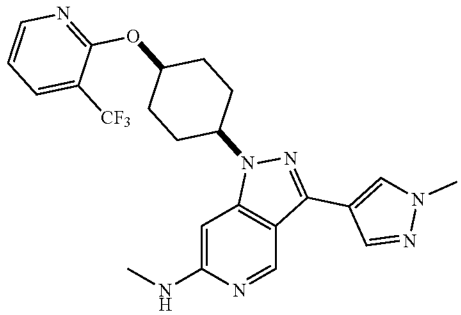 | N-methyl-3-(1-methyl-1H-pyrazol-4-yl)-1-((1s,4s)-4-((3-(trifluoromethyl)pyridin-2-yl)oxy)cyclohexyl)-1H-pyrazolo[4,3-c]pyridin-6-amine | Mass spectrum (apci) m/z = 472.2 |
| 126 | 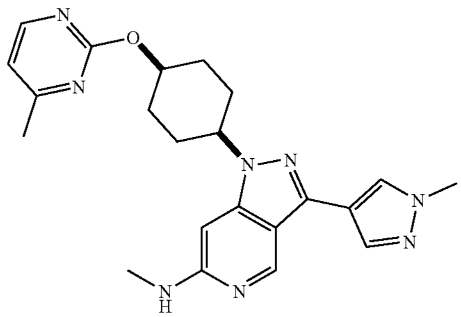 | N-methyl-3-(1-methyl-1H-pyrazol-4-yl)-1-((1s,4s)-4-((4-methylpyrimidin-2-yl)oxy)cyclohexyl)-1H-pyrazolo[4,3-c]pyridin-6-amine | Mass spectrum (apci) m/z = 419.2 |
| 127 | 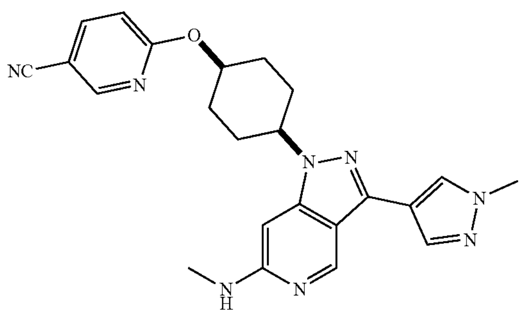 | 6-(((1s,4s)-4-(3-(1-methyl-1H-pyrazol-4-yl)-6-(methylamino)-1H-pyrazolo[4,3-c]pyridin-1-yl)cyclohexyl)oxy)nicotinonitrile | Mass spectrum (apci) m/z = 429.2 |

Example 128

N-methyl-3-(1-methyl-1H-pyrazol-4-yl)-1-((1s,4s)-4-(pyridin-3-yloxy)cyclohexyl)-1H-pyrazolo[4,3-c]pyridin-6-amine

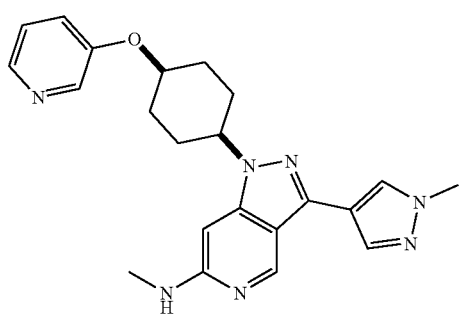

DIAD (0.01213 mL, 0.06154 mmol) was added to Ph₃P (0.01614 g, 0.06154 mmol) in THF (0.58 mL). To this was added tert-butyl (1-(((1r,4r)-4-hydroxycyclohexyl)-3-(1-methyl-1H-pyrazol-4-yl)-1H-pyrazolo[4,3-c]pyridin-6-yl) (methyl)carbamate (0.025 g, 0.05861 mmol) followed by pyridin-3-ol (0.007246 g, 0.07620 mmol) and heated to 60° C. overnight. The reaction mixture was partitioned between DCM and water, washed with brine, dried over sodium sulfate, filtered and concentrated. The residue was dissolved in TFA:DCM (2:1) and stirred for 1 h and concentrated. The residue was purified on preparative HPLC (water:ACN 5-95% with 1% TFA). The product containing fractions were partitioned between DCM and saturated NaHCO₃, dried over sodium sulfate, filtered and concentrated to afford N-methyl-3-(1-methyl-1H-pyrazol-4-yl)-1-((1s,4s)-4-(pyridin-3-yloxy)cyclohexyl)-1H-pyrazolo[4,3-c]pyridin-6-amine (0.0051 g, 0.01264 mmol, 21.56% yield). Mass spectrum (apci) m/z=404.2 (M+H). ¹H NMR (CDCl₃) δ 8.69 (d, J=1.0 Hz, 1H), 8.41 (d, J=2.7 Hz, 1H), 8.24 (dd, J=4.5, 1.4 Hz, 1H), 7.99 (s, 1H), 7.88 (s, 1H), 7.29 (ddd, J=8.4, 2.7, 1.6 Hz, 1H), 7.24 (dd, J=8.4, 3.7 Hz, 1H), 6.07 (s, 1H), 4.90 (br s, 1H), 4.68 (m, 1H), 4.36 (tt, J=11.5, 3.9 Hz, 1H), 4.00 (s, 3H), 2.98 (d, J=3.9 Hz, 3H), 2.55 (m, 2H), 2.32 (m, 2H), 1.92 (m, 2H), 1.82 (in, 2H).

Using the procedure described for the preparation of Example 128, the following compounds were also synthesized:

| Example | Structure | Name | Data |
|---|---|---|---|
| 129 | 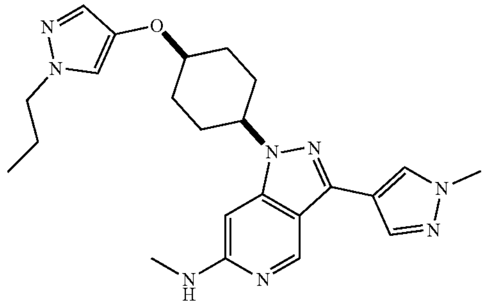 | N-methyl-3-(1-methyl-1H-pyrazol-4-yl)-1-((1s,4s)-4-((1-propyl-1H-pyrazol-4-yl)oxy)cyclohexyl)-1H-pyrazolo[4,3-c]pyridin-6-amine | Mass spectrum (apci) m/z = 435.3 |
| 130 | 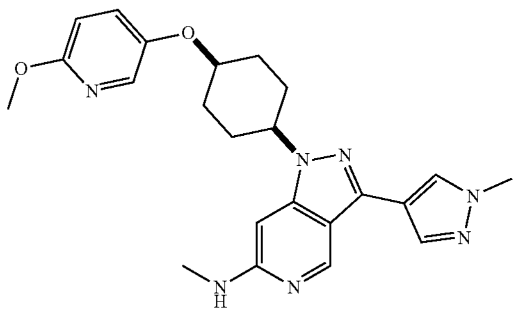 | 1-((1s,4s)-4-((6-methoxypyridin-3-yl)oxy)cyclohexyl)-N-methyl-3-(1-methyl-1H-pyrazol-4-yl)-1H-pyrazolo[4,3-c]pyridin-6-amine | Mass spectrum (apci) m/z = 434.3 |
| 131 | 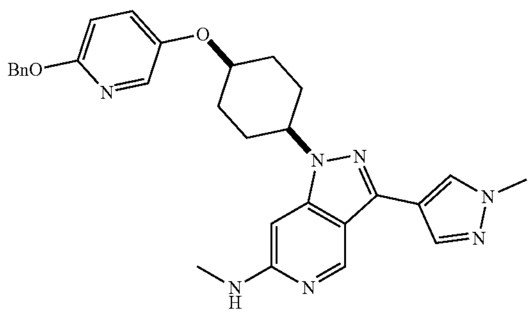 | 1-((1s,4s)-4-((6-(benzyloxy)pyridin-3-yl)oxy)cyclohexyl)-N-methyl-3-(1-methyl-1H-pyrazol-4-yl)-1H-pyrazolo[4,3-c]pyrdin-6-amine | Mass spectrum (apci) m/z = 510.3 |
| 132 | 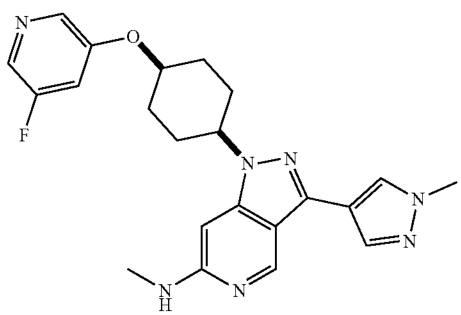 | 1-((1s,4s)-4-((5-fluoropyridin-3-yl)oxy)cyclohexyl)-N-methyl-3-(1-methyl-1H-pyrazol-4-yl)-1H-pyrazolo[4,3-c]pyridin-6-amine | Mass spectrum (apci) m/z = 422.2 |
| 133 | 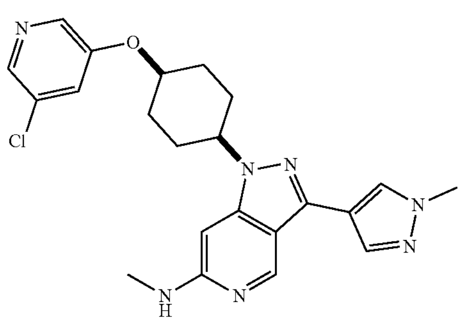 | 1-((1s,4s)-4-((5-chloropyridin-3-yl)oxy)cyclohexyl)-N-methyl-3-(1-methyl-1H-pyrazol-4-yl)-1H-pyrazolo[4,3-c]pyridin-6-amine | Mass spectrum (apci) m/z = 438.2 |

-continued

| Example | Structure | Name | Data |
|---|---|---|---|
| 134 | 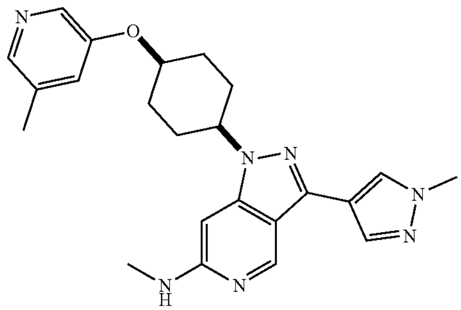 | N-methyl-3-(1-methyl-1H-pyrazol-4-yl)-1-((1s,4s)-4-((5-methylpyridin-3-yl)oxy)cyclohexyl)-1H-pyrazolo[4,3-c]pyridin-6-amine | Mass spectrum (apci) m/z = 418.2 |
| 135 | 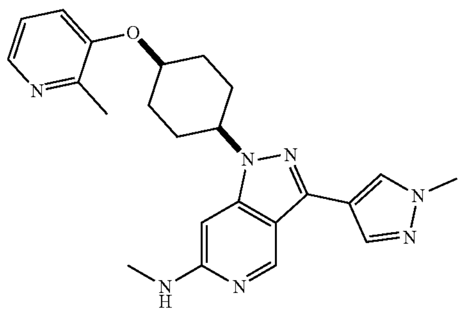 | N-methyl-3-(1-methyl-1H-pyrazol-4-yl)-1-((1s,4s)-4-((2-methylpyridin-3-yl)oxy)cyclohexyl)-1H-pyrazolo[4,3-c]pyridin-6-amine | Mass spectrum (apci) m/z = 418.2 |
| 136 | 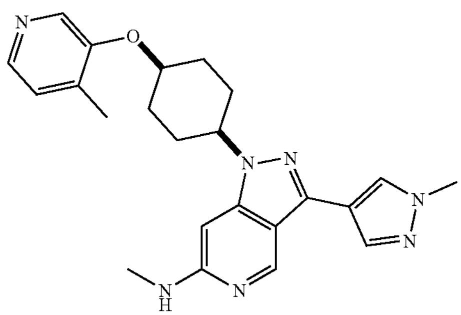 | N-methyl-3-(1-methyl-1H-pyrazol-4-yl)-1-((1s,4s)-4-((4-methylpyridin-3-yl)oxy)cyclohexyl)-1H-pyrazolo[4,3-c]pyridin-6-amine | Mass spectrum (apci) m/z = 418.2 |
| 137 | 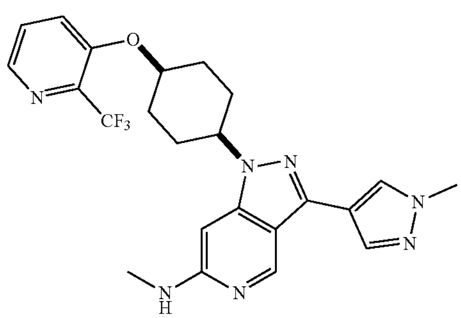 | N-methyl-3-(1-methyl-1H-pyrazol-4-yl)-1-((1s,4s)-4-((2-(trifluoromethyl)pyridin-3-yl)oxy)cyclohexyl)-1H-pyrazolo[4,3-c]pyridin-6-amine | Mass spectrum (apci) m/z = 472.2 |
| 138 | 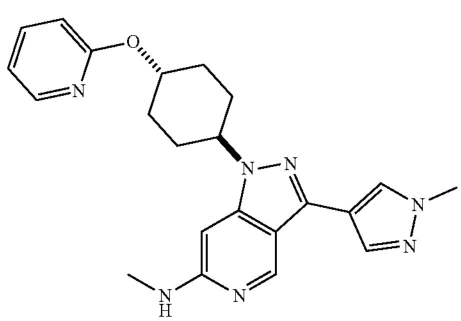 | N-methyl-3-(1-methyl-1H-pyrazol-4-yl)-1-((1r,4r)-4-(pyridin-2-yloxy)cyclohexyl)-1H-pyrazolo[4,3-c]pyridin-6-amine | Mass spectrum (apci) m/z = 404.2 |

-continued

| Example | Structure | Name | Data |
|---|---|---|---|
| 139 | 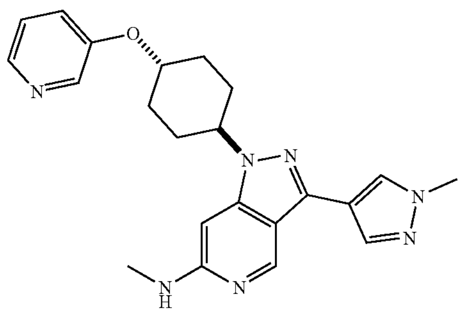 | N-methyl-3-(1-methyl-1H-pyrazol-4-yl)-1-((1r,4r)-4-(pyridin-3-yloxy)cyclohexyl)-1H-pyrazolo[4,3-c]pyridin-6-amine | Mass spectrum (apci) m/z = 404.2 |
| 140 | 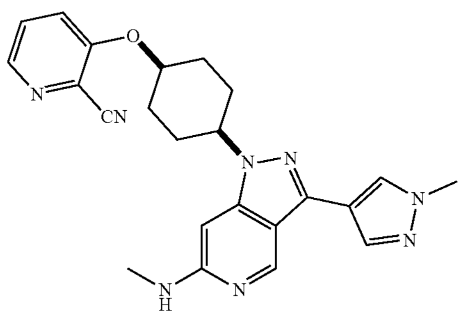 | 3-(((1s,4s)-4-(3-(1-methyl-1H-pyrazol-4-yl)-6-(methylamino)-1H-pyrazolo[4,3-c]pyridin-1-yl)cyclohexyl)oxy)picolinonitrile | Mass spectrum (apci) m/z = 429.2 |
| 141 | 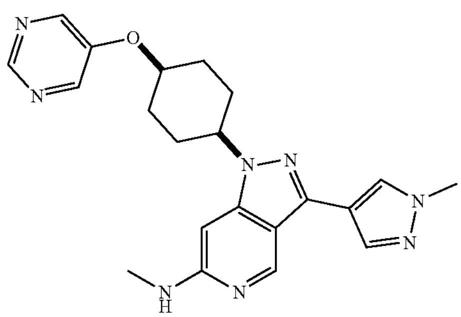 | N-methyl-3-(1-methyl-1H-pyrazol-4-yl)-1-((1s,4s)-4-(pyrimidin-5-yloxy)cyclohexyl)-1H-pyrazolo[4,3-c]pyridin-6-amine | Mass spectrum (apci) m/z = 405.2 |
| 142 | 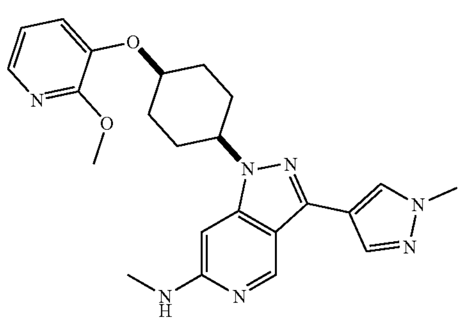 | 1-((1s,4s)-4-((2-methoxypyridin-3-yl)oxy)cyclohexyl)-N-methyl-3-(1-methyl-1H-pyrazol-4-yl)-1H-pyrazolo[4,3-c]pyridin-6-amine | Mass spectrum (apci) m/z = 434.3 |
| 143 | 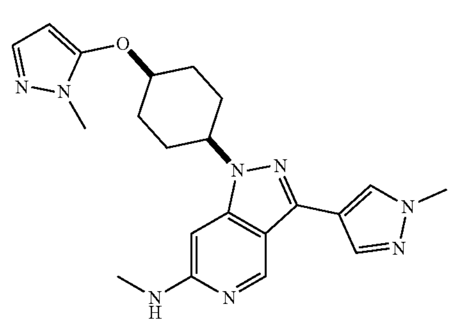 | N-methyl-3-(1-methyl-1H-pyrazol-4-yl)-1-((1s,4s)-4-((1-methyl-1H-pyrazol-5-yl)oxy)cyclohexyl)-1H-pyrazolo[4,3-c]pyridin-6-amine | Mass spectrum (apci) m/z = 407.3 |

-continued

| Example | Structure | Name | Data |
|---|---|---|---|
| 144 | 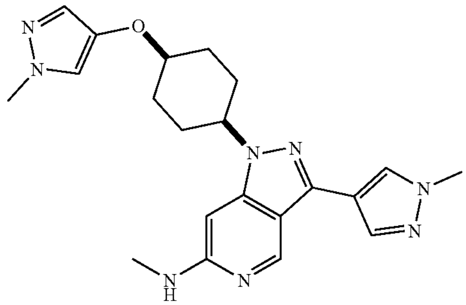 | N-methyl-3-(1-methyl-1H-pyrazol-4-yl)-1-((1s,4s)-4-((1-methyl-1H-pyrazol-4-yl)oxy)cyclohexyl)-1H-pyrazolo[4,3-c]pyridin-6-amine | Mass spectrum (apci) m/z = 407.3 |
| 145 | 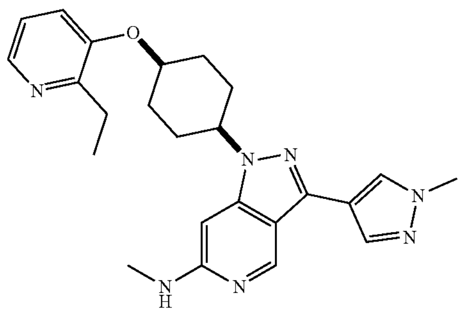 | 1-((1s,4s)-4-((2-ethylpyridin-3-yl)oxy)cyclohexyl)-N-methyl-3-(1-methyl-1H-pyrazol-4-yl)-1H-pyrazolo[4,3-c]pyridin-6-amine | Mass spectrum (apci) m/z = 432.2 |
| 146 | 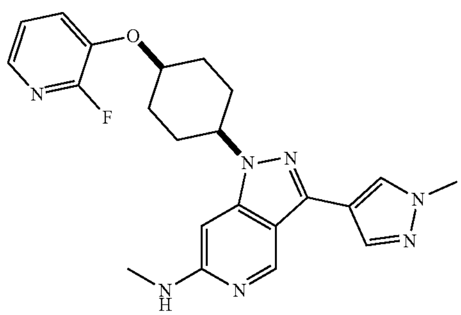 | 1-((1s,4s)-4-((2-fluoropyridin-3-yl)oxy)cyclohexyl)-N-methyl-3-(1-methyl-1H-pyrazol-4-yl)-1H-pyrazolo[4,3-c]pyridin-6-amine | Mass spectrum (apci) m/z = 422.2 |
| 147 | 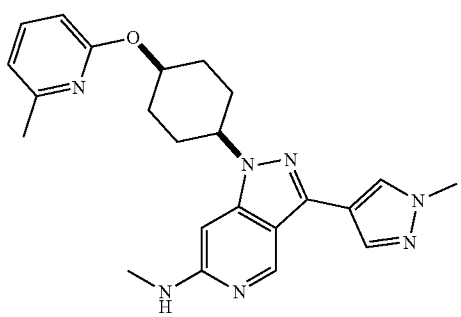 | N-methyl-3-(1-methyl-1H-pyrazol-4-yl)-1-((1s,4s)-4-((6-methylpyridin-2-yl)oxy)cyclohexyl)-1H-pyrazolo[4,3-c]pyridin-6-amine | Mass spectrum (apci) m/z = 418.2 |
| 148 | 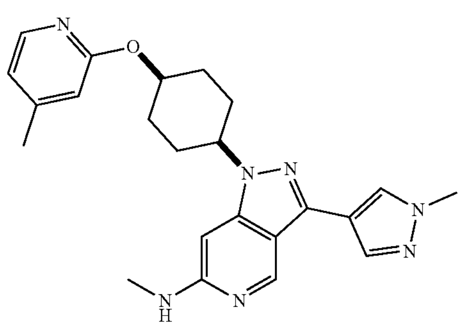 | N-methyl-3-(1-methyl-1H-pyrazol-4-yl)-1-((1s,4s)-4-((4-methylpyridin-2-yl)oxy)cyclohexyl)-1H-pyrazolo[4,3-c]pyridin-6-amine | Mass spectrum (apci) m/z = 418.2 |

-continued

| Example | Structure | Name | Data |
|---|---|---|---|
| 149 | 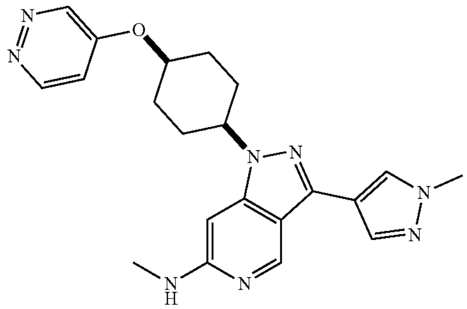 | N-methyl-3-(1-methyl-1H-pyrazol-4-yl)-1-((1s,4s)-4-(pyridazin-4-yloxy)cyclohexyl)-1H-pyrazolo[4,3-c]pyridin-6-amine | Mass spectrum (apci) m/z = 405.2 |
| 150 | 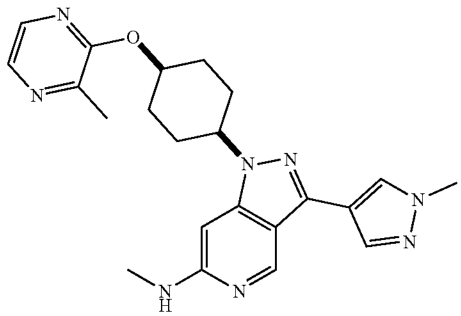 | N-methyl-3-(1-methyl-1H-pyrazol-4-yl)-1-((1s,4s)-4-((3-methylpyrazin-2-yl)oxy)cyclohexyl)-1H-pyrazolo[4,3-c]pyridin-6-amine | Mass spectrum (apci) m/z = 419.2 |
| 151 | 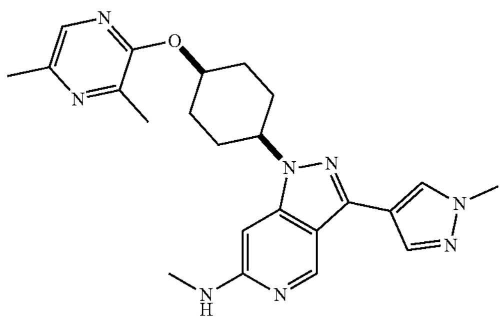 | 1-((1s,4s)-4-((2,6-dimethylpyridin-3-yl)oxy)cyclohexyl)-N-methyl-3-(1-methyl-1H-pyrazol-4-yl)-1H-pyrazolo[4,3-c]pyridin-6-amine | Mass spectrum (apci) m/z = 432.2 |
| 152 | 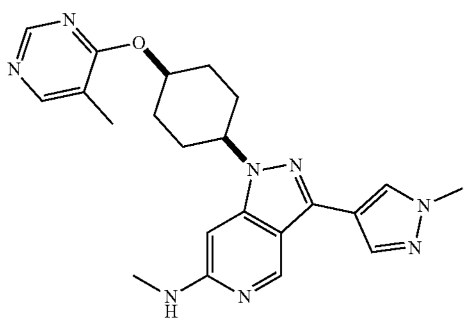 | N-methyl-3-(1-methyl-1H-pyrazol-4-yl)-1-((1s,4s)-4-((5-methylpyrimidin-4-yl)oxy)cyclohexyl)-1H-pyrazolo[4,3-c]pyridin-6-amine | Mass spectrum (apci) m/z = 419.2 |
| 153 | 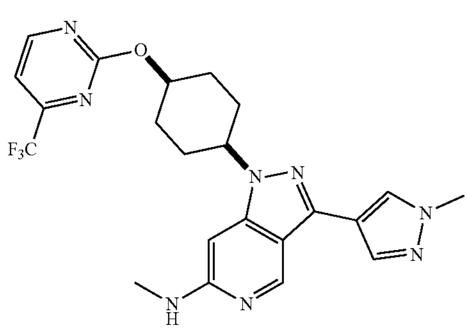 | N-methyl-3-(1-methyl-1H-pyrazol-4-yl)-1-((1s,4s)-4-((4-(trifluoromethyl)pyrimidin-2-yl)oxy)cyclohexyl)-1H-pyrazolo[4,3-c]pyridin-6-amine | Mass spectrum (apci) m/z = 473.2 |

-continued

| Example | Structure | Name | Data |
|---|---|---|---|
| 154 | 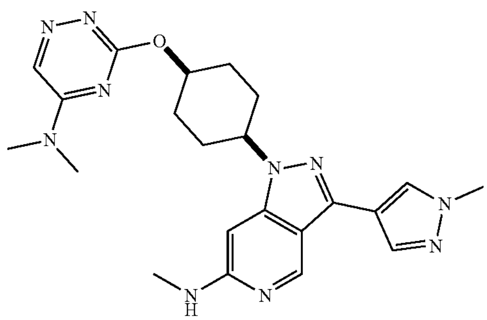 | 1-((1s,4s)-4-((5-(dimethylamino)pyridazin-3-yl)oxy)cyclohexyl)-N-methyl-3-(1-methyl-1H-pyrazol-4-yl)-1H-pyrazolo[4,3-c]pyridin-6-amine | Mass spectrum (apci) m/z = 448.2 |
| 155 | 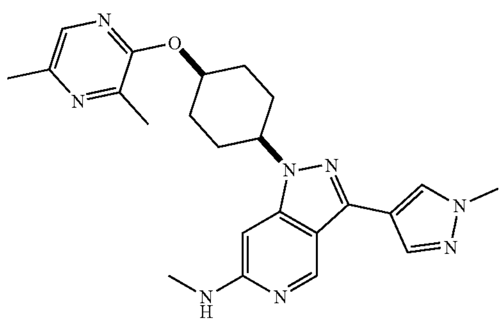 | 1-((1s,4s)-4-((3,5-dimethylpyrazin-2-yl)oxy)cyclohexyl)-N-methyl-3-(1-methyl-1H-pyrazol-4-yl)-1H-pyrazolo[4,3-c]pyridin-6-amine | Mass spectrum (apci) m/z = 433.2 |
| 156 | 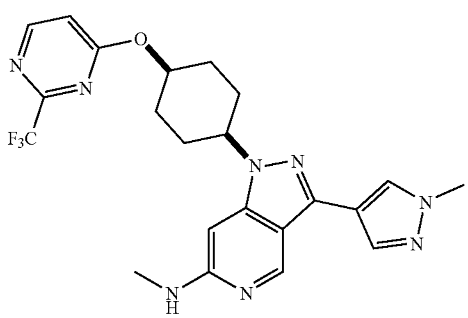 | N-methyl-3-(1-methyl-1H-pyrazol-4-yl)-1-((1s,4s)-4-((2-(trifluoromethyl)pyrimidin-4-yl)oxy)cyclohexyl)-1H-pyrazolo[4,3-c]pyridin-6-amine | Mass spectrum (apci) m/z = 473.2 |
| 157 | 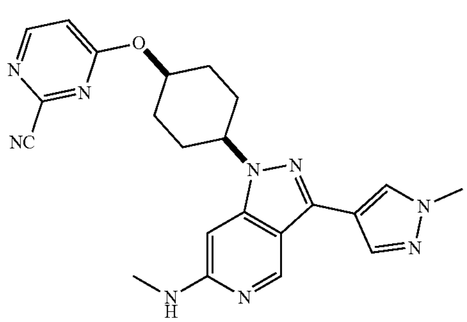 | 4-(((1s,4s)-4-(3-(1-methyl-1H-pyrazol-4-yl)-6-(methylamino)-1H-pyrazolo[4,3-c]pyridin-1-yl)cyclohexyl)oxy)pyrimidine-2-carbonitrile | Mass spectrum (apci) m/z = 430.2 |

-continued

| Example | Structure | Name | Data |
|---|---|---|---|
| 158 | 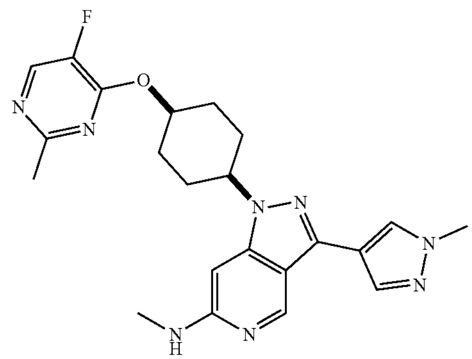 | 1-((1s,4s)-4-((5-fluoro-2-methylpyrimidin-4-yl)oxy)cyclohexyl)-N-methyl-3-(1-methyl-1H-pyrazol-4-yl)-1H-pyrazolo[4,3-c]pyridin-6-amine | Mass spectrum (apci) m/z = 437.2 |
| 159 | 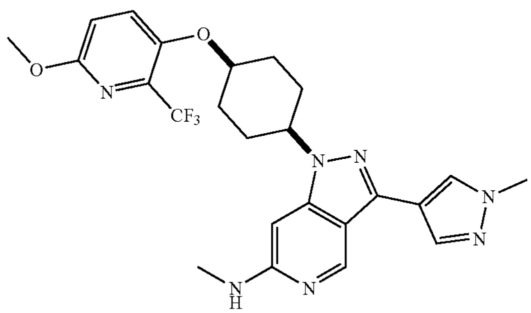 | 1-((1s,4s)-4-((6-methoxy-2-(trifluoromethyl)pyridin-3-yl)oxy)cyclohexyl)-N-methyl-3-(1-methyl-1H-pyrazol-4-yl)-1H-pyrazolo[4,3-c]pyridin-6-amine | Mass spectrum (apci) m/z = 502.2 |
| 160 | 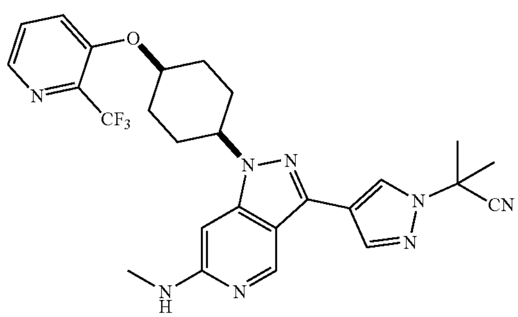 | 2-methyl-2-(4-(6-(methylamino)-1-((1s,4s)-4-((2-(trifluoromethyl)pyridin-3-yl)oxy)cyclohexyl)-1H-pyrazolo[4,3-c]pyridin-3-yl)-1H-pyrazol-1-yl)propanenitrile | Mass spectrum (apci) m/z = 525.2 |
| 161 | 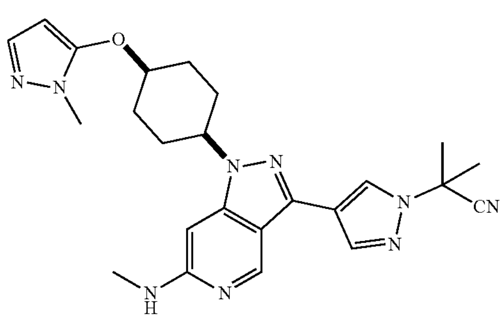 | 2-methyl-2-(4-(1-((1s,4s)-4-((1-methyl-1H-pyrazol-5-yl)oxy)cyclohexyl)-6-(methylamino)-1H-pyrazolo[4,3-c]pyridin-3-yl)-1H-pyrazol-1-yl)propanenitrile | Mass spectrum (apci) m/z = 460.2 |

| Example | Structure | Name | Data |
|---|---|---|---|
| 162 | 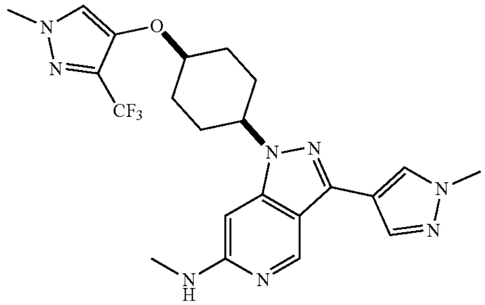 | N-methyl-3-(1-methyl-1H-pyrazol-4-yl)-1-((1s,4s)-4-((1-methyl-3-(trifluoromethyl)-1H-pyrazol-4-yl)oxy)cyclohexyl)-1H-pyrazolo[4,3-c]pyridin-6-amine | Mass spectrum (apci) m/z = 475.3 |
| 163 | 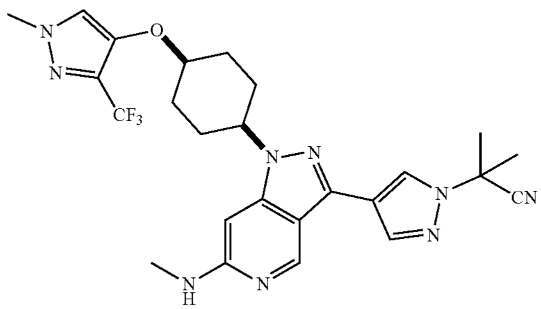 | 2-methyl-2-(4-(1-((1s,4s)-4-((1-methyl-3-(trifluoromethyl)-1H-pyrazol-4-yl)oxy)cyclohexyl)-6-(methylamino)-1H-pyrazolo[4,3-c]pyridin-3-yl)-1H-pyrazol-1-yl)propanenitrile | Mass spectrum (apci) m/z = 528.3 |
| 164 | 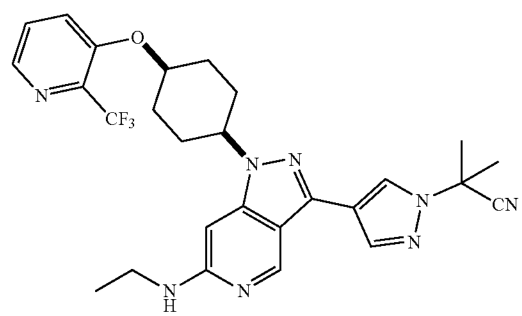 | 2-(4-(6-(ethylamino)-1-((1s,4s)-4-((2-(trifluoromethyl)pyridin-3-yl)oxy)cyclohexyl)-1H-pyrazolo[4,3-c]pyridin-3-yl)-1H-pyrazol-1-yl)-2-methylpropanenitrile | Mass spectrum (apci) m/z = 539.3 |

Example 165

1-((1s,4s)-4-((2-isopropylpyridin-3-yl)oxy)cyclohexyl)-N-methyl(1-methyl-1H-pyrazol-4-yl)-1H-pyrazolo[4,3-c]pyri din-6-amine

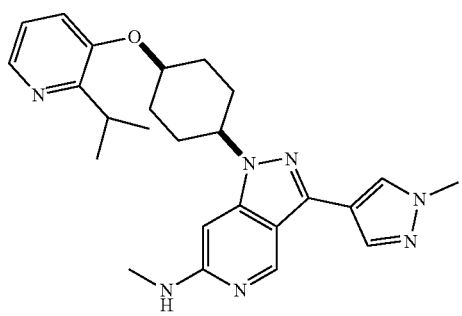

DIAD (0.009704 mL, 0.04924 mmol) was added to a solution of Ph₃P (0.01291 g, 0.04924 mmol), tert-butyl (1-((1r,4r)-4-hydroxycyclohexyl)-3-(1-methyl-1H-pyrazol-4-yl)-1H-pyrazolo[4,3-c]pyridin-6-yl)(methyl)carbamate (0.020 g, 0.04689 mmol) and 2-isopropylpyridin-3-ol (0.008362 g, 0.06096 mmol) in THF (0.46 mL) and heated to 60° C. overnight. The reaction mixture was concentrated and dissolved in TFA:DCM (2:1) and stirred for 1 hour. This reaction was concentrated and purified on preparative HPLC (water:ACN 5-95% with 1% TFA). The product containing fractions were partitioned between DCM and saturated NaHCO₃, washed with brine, dried over sodium sulfate, filtered and concentrated to afford 1-((1s,4s)-4-((2-isopropylpyridin-3-yl)oxy)cyclohexyl)-N-methyl-3-(1-methyl-1H-pyrazol-4-yl)-1H-pyrazolo[4,3-c]pyridin-6-amine (0.0085 g, 0.01908 mmol, 40.68% yield). Mass spectrum (apci) m/z=446.3 (M+H). ¹H NMR (CDCl₃) δ 8.70 (s, 1H), 8.17 (dd, J=4.7, 1.4 Hz, 1H), 7.99 (s, 1H), 7.84 (s, 1H), 7.13 (dd, J=8.2, 1.4 Hz, 1H), 7.07 (dd, J=8.2, 4.5 Hz, 1H), 6.06 (s, 1H), 4.79 (m, 1H), 4.66 (m, 1H), 4.37 (tt, J=11.7, 3.9 Hz, 1H), 4.00 (s, 3H), 3.70 (m, 1H), 2.97 (d, J=5.1 Hz, 1H), 2.57 (m, 2H), 2.32 (m, 2H), 1.93 (m, 2H), 1.82 (m, 2H), 1.38 (d, J=6.8 Hz, 6H).

Using the procedure described for the preparation of Example 165, the following compounds were also synthesized:

| Example | Structure | Name | Data |
|---|---|---|---|
| 166 | 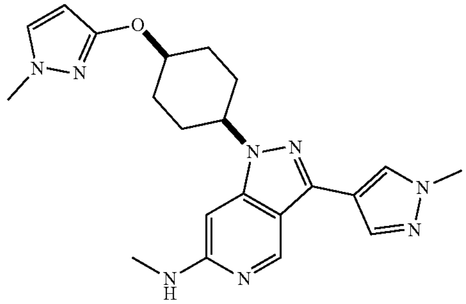 | N-methyl-1-((1s,4s)-4-((1-methyl-1H-pyrazol-3-yl)oxy)cyclohexyl)-3-(1-methyl-1H-pyrazol-4-yl)-1H-pyrazolo[4,3-c]pyridin-6-amine | Mass spectrum (apci) m/z = 407.3 |
| 167 | 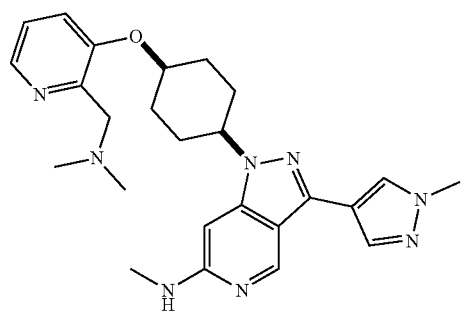 | 1-((1s,4s)-4-((2-((dimethylamino)methyl)pyridin-3-yl)oxy)cyclohexyl)-N-methyl-3-(1-methyl-1H-pyrazol-4-yl)-1H-pyrazolo[4,3-c]pyridin-6-amine | Mass spectrum (apci) m/z = 461.3 |
| 168 | 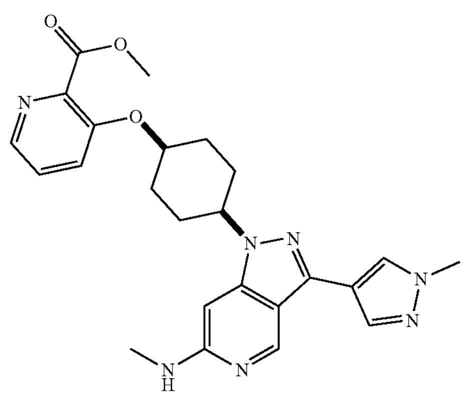 | methyl 3-(((1s,4s)-4-(3-(1-methyl-1H-pyrazol-4-yl)-6-(methylamino)-1H-pyrazolo[4,3-c]pyridin-1-yl)cyclohexyl)oxy)picolinate | Mass spectrum (apci) m/z = 462.2 |
| 169 | 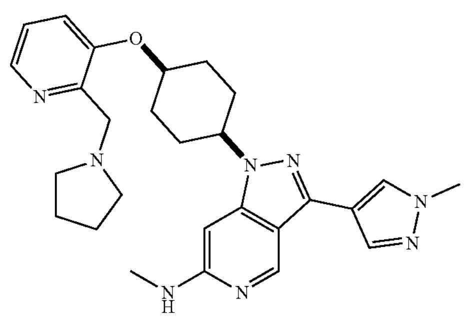 | N-methyl-3-(1-methyl-1H-pyrazol-4-yl)-1-((1s,4s)-4-((2-(pyrrolidin-1-ylmethyl)pyridin-3-yl)oxy)cyclohexyl)-1H-pyrazolo[4,3-c]pyridin-6-amine | Mass spectrum (apci) m/z = 487.2 |

-continued

| Example | Structure | Name | Data |
|---|---|---|---|
| 170 | 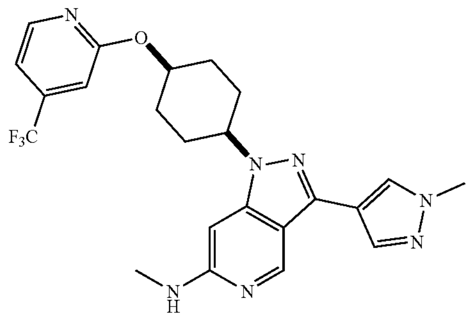 | N-methyl-3-(1-methyl-1H-pyrazol-4-yl)-1-((1s,4s)-4-((4-(trifluoromethyl)pyridin-2-yl)oxy)cyclohexyl)-1H-pyrazolo[4,3-c]pyridin-6-amine | Mass spectrum (apci) m/z = 472.2 |
| 171 | 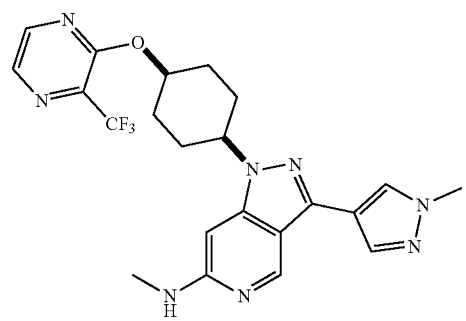 | N-methyl-3-(1-methyl-1H-pyrazol-4-yl)-1-((1s,4s)-4-((3-(trifluoromethyl)pyrazin-2-yl)oxy)cyclohexyl)-1H-pyrazolo[4,3-c]pyridin-6-amine | Mass spectrum (apci) m/z = 473.2 |
| 172 | 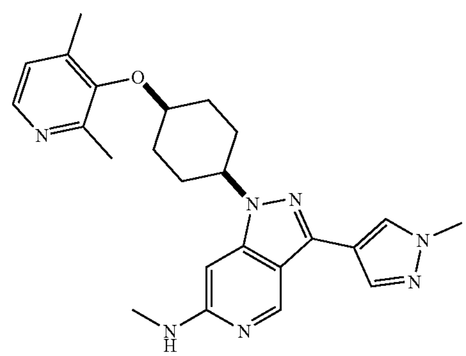 | 1-((1s,4s)-4-((2,4-dimethylpyridin-3-yl)oxy)cyclohexyl)-N-methyl-3-(1-methyl-1H-pyrazol-4-yl)-1H-pyrazolo[4,3-c]pyridin-6-amine | Mass spectrum (apci) m/z = 432.2 |
| 173 | 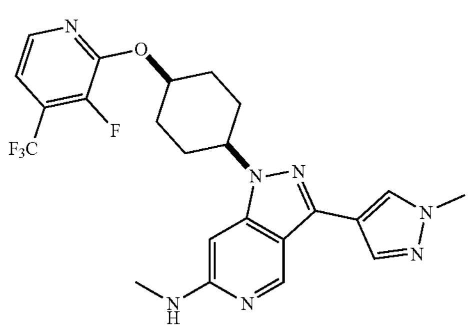 | 1-((1s,4s)-4-((3-fluoro-4-(trifluoromethyl)pyridin-2-yl)oxy)cyclohexyl)-N-methyl-3-(1-methyl-1H-pyrazol-4-yl)-1H-pyrazolo[4,3-c]pyridin-6-amine | Mass spectrum (apci) m/z = 490.1 |

-continued

| Example | Name | Data |
|---|---|---|
| 174 | N-methyl-3-(1-methyl-1H-pyrazol-4-yl)-1-((1s,4s)-4-((6-(trifluoromethyl)pyridin-2-yl)oxy)cyclohexyl)-1H-pyrazolo[4,3-c]pyridin-6-amine | Mass spectrum (apci) m/z = 472.2 |
| 175 | 5-chloro-3-(((1s,4s)-4-(3-(1-methyl-1H-pyrazol-4-yl)-6-(methylamino)-1H-pyrazolo[4,3-c]pyridin-1-yl)cyclohexyl)oxy)picolinonitrile | Mass spectrum (apci) m/z = 463.1 |
| 176 | 1-((1s,4s)-4-((5-methoxy-2-methylpyrimidin-4-yl)oxy)cyclohexyl)-N-methyl-3-(1-methyl-1H-pyrazol-4-yl)-1H-pyrazolo[4,3-c]pyridin-6-amine | Mass spectrum (apci) m/z = 449.2 |
| 177 | N-methyl-3-(1-methyl-1H-pyrazol-4-yl)-1-((1s,4s)-4-((6-(trifluoromethyl)pyridin-3-yl)oxy)cyclohexyl)-1H-pyrazolo[4,3-c]pyridin-6-amine | Mass spectrum (apci) m/z = 472.2 |

-continued

| Example | Name | Data |
|---|---|---|
| 178 | N-methyl-3-(1-methyl-1H-pyrazol-4-yl)-1-((1s,4s)-4-(pyridin-2-yloxy)cyclohexyl)-1H-pyrazolo[4,3-c]pyridin-6-amine | Mass spectrum (apci) m/z = 404.2 |
| 179 | 2-(4-(1-((1s,4s)-4-((2-cyclopropylpyridin-3-yl)oxy)cyclohexyl)-6-(ethylamino)-1H-pyrazolo[4,3-c]pyridin-3-yl)-1H-pyrazol-1-yl)-2-methylpropanenitrile | Mass spectrum (apci) m/z = 511.3 |
| 180 | 2-(4-(6-(ethylamino)-1-((1s,4s)-4-((2-isopropylpyridin-3-yl)oxy)cyclohexyl)-1H-pyrazolo[4,3-c]pyridin-3-yl)-1H-pyrazol-1-yl)-2-methylpropanenitrile | Mass spectrum (apci) m/z = 513.3 |
| 181 | 2-(4-(6-(ethylamino)-1-((1s,4s)-4-((3-methylpyrazin-2-yl)oxy)cyclohexyl)-1H-pyrazolo[4,3-c]pyridin-3-yl)-1H-pyrazol-1-yl)-2-methylpropanenitrile | Mass spectrum (apci) m/z = 486.3 |
| 182 | 2-(4-(6-(ethylamino)-1-((1s,4s)-4-((3-ethylpyrazin-2-yl)oxy)cyclohexyl)-1H-pyrazolo[4,3-c]pyridin-3-yl)-1H-pyrazol-1-yl)-2-methylpropanenitrile | Mass spectrum (apci) m/z = 500.3 |

-continued

| Example | Structure | Name | Data |
|---|---|---|---|
| 183 | 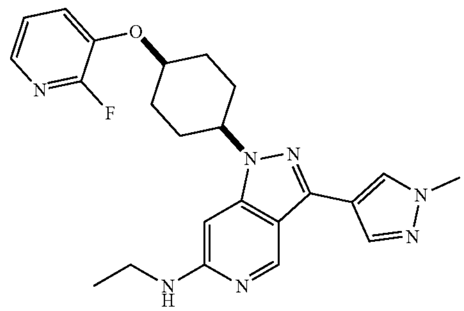 | N-ethyl-1-((1s,4s)-4-((2-fluoropyridin-3-yl)oxy)cyclohexyl)-3-(1-methyl-1H-pyrazol-4-yl)-1H-pyrazolo[4,3-c]pyridin-6-amine | Mass spectrum (apci) m/z = 436.2 |
| 184 | 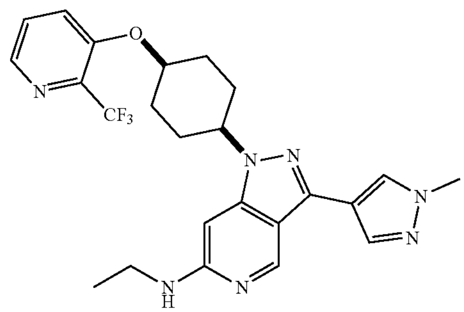 | N-ethyl-3-(1-methyl-1H-pyrazol-4-yl)-1-((1s,4s)-4-((2-(trifluoromethyl)pyridin-3-yl)oxy)cyclohexyl)-1H-pyrazolo[4,3-c]pyridin-6-amine | Mass spectrum (apci) m/z = 486.3 |
| 185 | 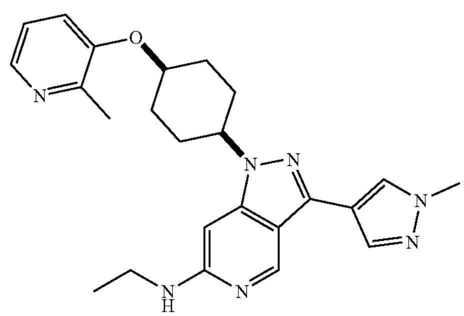 | N-ethyl-3-(1-methyl-1H-pyrazol-4-yl)-1-((1s,4s)-4-((2-methylpyridin-3-yl)oxy)cyclohexyl)-1H-pyrazolo[4,3-c]pyridin-6-amine | Mass spectrum (apci) m/z = 432.2 |
| 186 | 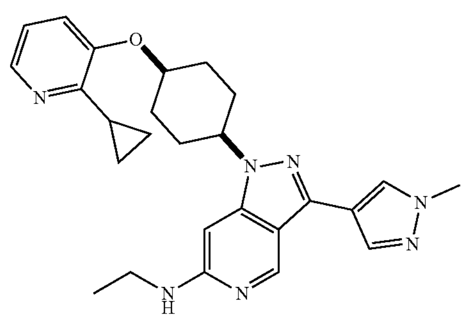 | 1-((1s,4s)-4-((2-cyclopropylpyridin-3-yl)oxy)cyclohexyl)-N-ethyl-3-(1-methyl-1H-pyrazol-4-yl)-1H-pyrazolo[4,3-c]pyridin-6-amine | Mass spectrum (apci) m/z = 458.2 |
| 187 | 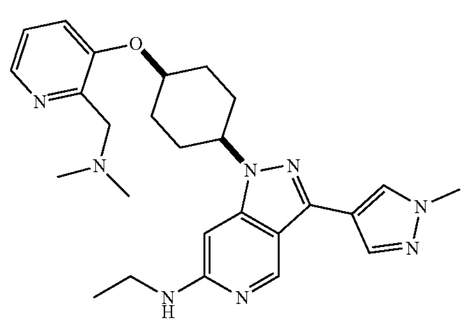 | 1-((1s,4s)-4-((2-((dimethylamino)methyl)pyridin-3-yl)oxy)cyclohexyl)-N-ethyl-3-(1-methyl-1H-pyrazol-4-yl)-1H-pyrazolo[4,3-c]pyridin-6-amine | Mass spectrum (apci) m/z = 475.3 |

-continued

| Example | Structure | Name | Data |
|---|---|---|---|
| 188 | 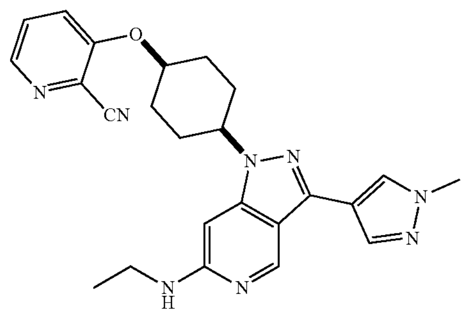 | 3-(((1s,4s)-4-(6-(ethylamino)-3-(1-methyl-1H-pyrazol-4-yl)-1H-pyrazolo[4,3-c]pyridin-1-yl)cyclohexyl)oxy)picolinonitrile | Mass spectrum (apci) m/z = 443.2 |
| 189 | 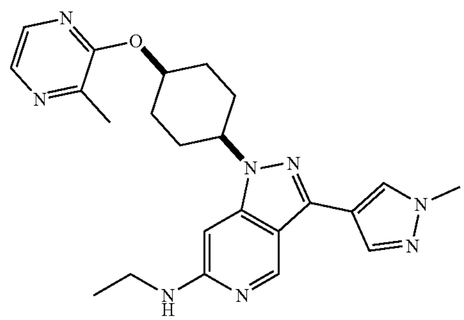 | N-ethyl-3-(1-methyl-1H-pyrazol-4-yl)-1-((1s,4s)-4-((3-methylpyrazin-2-yl)oxy)cyclohexyl)-1H-pyrazolo[4,3-c]pyridin-6-amine | Mass spectrum (apci) m/z = 433.2 |
| 190 | 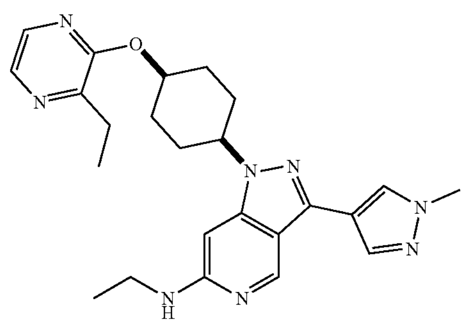 | N-ethyl-1-((1s,4s)-4-((3-ethyl pyrazin-2-yl)oxy)cyclohexyl)-3-(1-methyl-1H-pyrazol-4-yl)-1H-pyrazolo[4,3-c]pyridin-6-amine | Mass spectrum (apci) m/z = 447.2 |
| 191 | 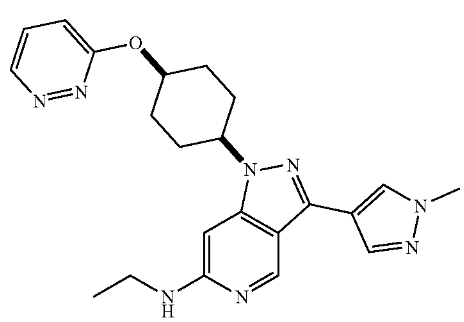 | N-ethyl-3-(1-methyl-1H-pyrazol-4-yl)-1-((1s,4s)-4-(pyridazin-3-yloxy)cyclohexyl)-1H-pyrazolo[4,3-c]pyridin-6-amine | Mass spectrum (apci) m/z = 419.2 |
| 192 | 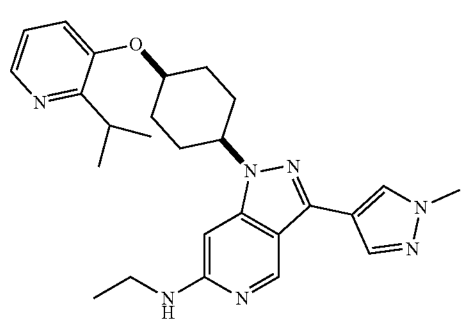 | N-ethyl-1-((1s,4s)-4-((2-isopropylpyridin-3-yl)oxy)cyclohexyl)-3-(1-methyl-1H-pyrazol-4-yl)-1H-pyrazolo[4,3-c]pyridin-6-amine | Mass spectrum (apci) m/z = 460.2 |

-continued

| Example | Structure | Name | Data |
|---------|-----------|------|------|
| 193 | 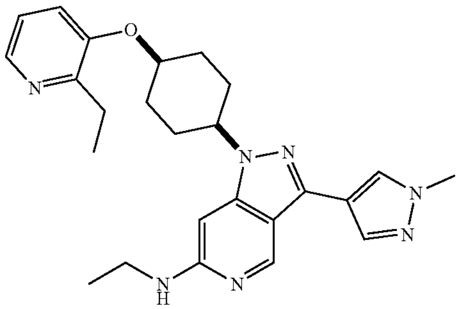 | N-ethyl-1-((1s,4s)-4-((2-ethylpyridin-3-yl)oxy)cyclohexyl)-3-(1-methyl-1H-pyrazol-4-yl)-1H-pyrazolo[4,3-c]pyridin-6-amine | Mass spectrum (apci) m/z = 446.2 |
| 194 | 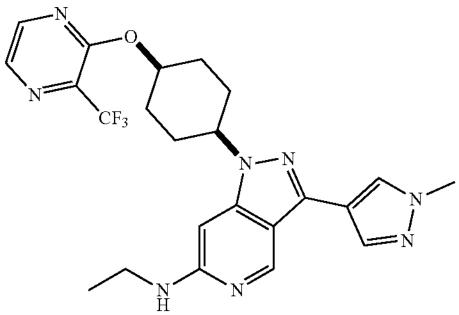 | N-ethyl-3-(1-methyl-1H-pyrazol-4-yl)-1-((1s,4s)-4-((3-(trifluoromethyl)pyrazin-2-yl)oxy)cyclohexyl)-1H-pyrazolo[4,3-c]pyridin-6-amine | Mass spectrum (apci) m/z = 487.2 |
| 195 | 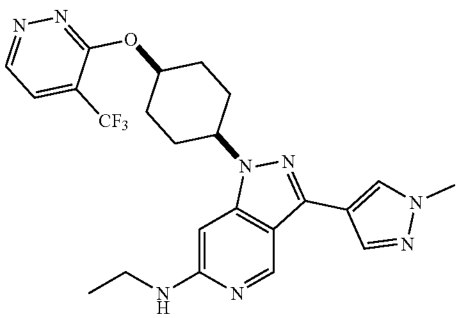 | N-ethyl-3-(1-methyl-1H-pyrazol-4-yl)-1-((1s,4s)-4-((4-(trifluoromethyl)pyridazin-3-yl)oxy)cyclohexyl)-1H-pyrazolo[4,3-c]pyridin-6-amine | Mass spectrum (apci) m/z = 487.2 |
| 196 | 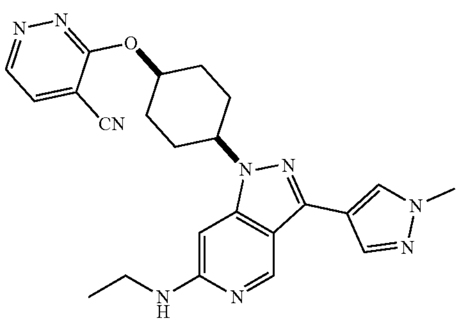 | 3-(((1s,4s)-4-(6-(ethylamino)-3-(1-methyl-1H-pyrazol-4-yl)-1H-pyrazolo[4,3-c]pyridin-1-yl)cyclohexyl)oxy)pyridazine-4-carbonitrile | Mass spectrum (apci) m/z = 444.2 |
| 197 | 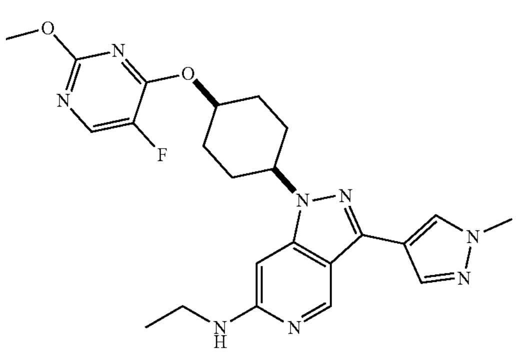 | N-ethyl-1-((1s,4s)-4-((5-fluoro-2-methoxypyrimidin-4-yl)oxy)cyclohexyl)-3-(1-methyl-1H-pyrazol-4-yl)-1H-pyrazolo[4,3-c]pyridin-6-amine | Mass spectrum (apci) m/z = 467.2 |

-continued

| Example | Structure | Name | Data |
|---|---|---|---|
| 198 | 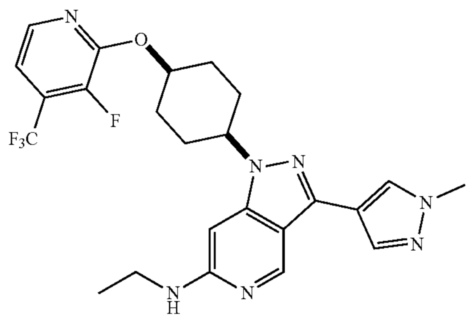 | N-ethyl-1-((1s,4s)-4-((3-fluoro-4-(trifluoromethyl)pyridin-2-yl)oxy)cyclohexyl)-3-(1-methyl-1H-pyrazol-4-yl)-1H-pyrazolo[4,3-c]pyridin-6-amine | Mass spectrum (apci) m/z = 504.2 |
| 199 | 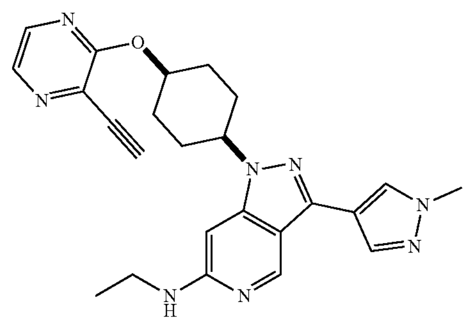 | N-ethyl-1-((1s,4s)-4-((2-ethynylpyridin-3-yl)oxy)cyclohexyl)-3-(1-methyl-1H-pyrazol-4-yl)-1H-pyrazolo[4,3-c]pyridin-6-amine | Mass spectrum (apci) m/z = 442.2 |
| 200 | 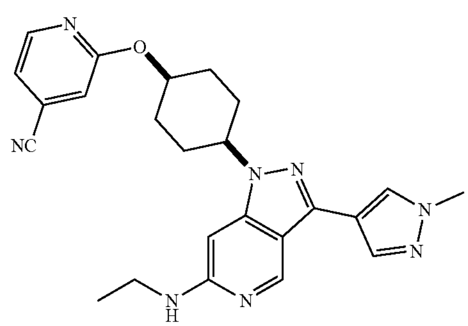 | 2-(((1s,4s)-4-(6-(ethylamino)-3-(1-methyl-1H-pyrazol-4-yl)-1H-pyrazolo[4,3-c]pyridin-1-yl)cyclohexyl)oxy)isonicotinonitrile | Mass spectrum (apci) m/z = 443.2 |
| 201 | 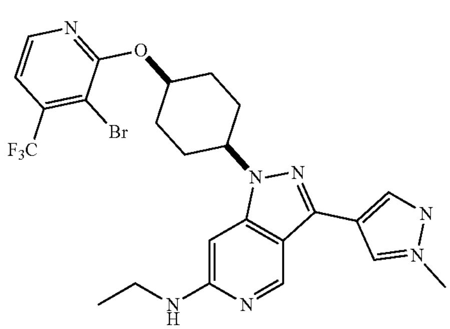 | 1-((1s,4s)-4-((3-bromo-4-(trifluoromethyl)pyridin-2-yl)oxy)cyclohexyl)-N-ethyl-3-(1-methyl-1H-pyrazol-4-yl)-1H-pyrazolo[4,3-c]pyridin-6-amine | Mass spectrum (apci) m/z = 564.1 nad 566.1 |

Example 202

2-methyl-2-(4-(6-(methylamino)-1-((1s,4s)-4-((2-methylpyridin-3-yl)oxy)cyclohexyl)-1H-pyrazolo[4,3-c]pyridin-3-yl)-1H-pyrazol-1-yl)propanenitrile

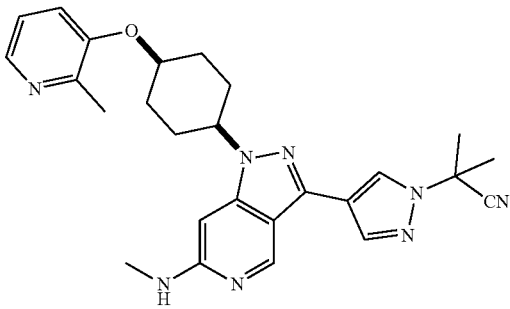

2-(4-(1-(((1r,4r)-4-hydroxycyclohexyl)-6-(methylamino)-1H-pyrazolo[4,3-c]pyridin-3-yl)-1H-pyrazol-1-yl)-2-methylpropanenitrile (20 mg, 0.053 mmol), 2-Methyl-3-pyridinol (7.5 mg, 0.069 mmol) and PPh$_3$ (14 mg, 0.053 mmol) were diluted with THF (400 µL) followed by the addition of DIAD (10 µL, 0.053 mmol). After stirring for 12 hours, the reaction was diluted with ethyl acetate and water. The layers were separated and the ethyl acetate was dried over MgSO$_4$, filtered and concentrated. The material was purified on c-18 silica gel (5-95% ACN in water with 0.1% TFA). The purified material was partitioned between ethyl acetate and saturated sodium carbonate, dried over MgSO$_4$, filtered and concentrated to afford 2-methyl-2-(4-(6-(methylamino)-1-((1s,4s)-4-((2-methylpyridin-3-yl)oxy)cyclohexyl)-1H-pyrazolo[4,3-c]pyridin-3-yl)-1H-pyrazol-1-yl)propanenitrile (5 mg, 0.011 mmol, 20% yield). Mass spectrum (apci) m/z=471.3 (M+H). $^1$H NMR (CDCl$_3$) δ 8.67 (s, 1H), 8.11 (dd, J=4.7, 1.6 Hz, 1H), 8.09 (s, 1H), 7.14 (dd, J=8.2, 1.6 Hz, 1H), 7.10 (dd, J=8.2, 4.5 Hz, 1H), 6.07 (s, 1H), 4.68 (m, 1H), 4.39 (tt, J=11.7, 3.9 Hz, 1H), 2.96 (s, 3H), 2.66 (s, 3H), 2.56 (m, 2H), 2.31 (m, 2H), 2.08 (s, 6H), 1.93 (m, 2H), 1.82 (m, 2H).

Using the procedure described for the preparation of Example 202, the following compounds were also synthesized:

Example 204

(S)-3-(4-(6-(methylamino)-1-((1s,4R)-4-((2-(trifluoromethyl)pyridin-3-yl)oxy)cyclohexyl)-1H-pyrazolo[4,3-c]pyridin-3-yl)-1H-pyrazol-1-yl)propane-1,2-diol hydrochloride

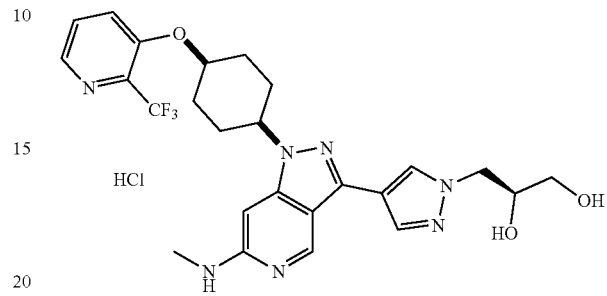

Step A: To a solution of tert-butyl (3-bromo-1-((1r,4r)-4-hydroxycyclohexyl)-1H-pyrazolo[4,3-c]pyridin-6-yl)(methyl)carbamate (505 mg, 1.19 mmol) in THF (10 mL) was added 2-(trifluromethyl)pyridin-3-ol (581 mg, 3.56 mmol) followed by triphenylphosphine (934 mg, 3.56 mmol) and DIAD (702 µL, 3.56 mmol). The mixture was warmed to 60° C. for 2 h. The mixture was partitioned between water (50 mL) and EtOAc (50 mL) and the aqueous layer was extracted with EtOAc (2×30 mL). The combined organic phases were washed with brine (20 mL), dried over Na$_2$SO$_4$, filtered and concentrated. The residue was purified over silica gel (5-50% EtOAc in hexanes) to afford tert-butyl (3-bromo-1-((1s,4s)-4-((2-(trifluoromethyl)pyridin-3-yl)oxy)cyclohexyl)-1H-pyrazolo[4,3-c]pyridin-6-yl)(methyl)carbamate (502 mg, 74% yield).

Step B: tert-butyl (3-bromo-1-((1s,4s)-4-((2-(trifluoromethyl)pyridin-3-yl)oxy)cyclohexyl)-1H-pyrazolo[4,3-c]pyridin-6-yl)(methyl)carbamate (400 mg, 0.70 mmol), tert-butyl 4-(4,4,5,5-tetramethyl-1,3,2-dioxaborolan-2-yl)-1H-pyrazole-1-carboxylate (619 mg, 2.10 mmol) and Pd(PPh$_3$)$_4$ (81 mg, 0.07 mmol) were combined in dioxanes (10 mL) and treated with K$_2$CO$_3$ (1.05 mL, 2N, 2.10 mmol) and heated to 100° C. in a sealed tube overnight. 50 mg of the boronate and 40 mg of Pd(PPh$_3$)$_4$ were added and the mixture heated overnight. The cooled mixture was partitioned between water (30 mL) and EtOAc (30 mL) and the aqueous layer was extracted with EtOAc (2×20 mL). The combined

| Example | Structure | Name | Data |
|---|---|---|---|
| 203 | | 2-(4-(1-((1s,4s)-4-((2,5-dimethylpyridin-3-yl)oxy)cyclohexyl)-6-(methylamino)-1H-pyrazolo[4,3-c]pyridin-3-yl)-1H-pyrazol-1-yl)-2-methylpropanenitrile | Mass spectrum (apci) m/z = 485.3 | organic phases were washed with brine (20 mL), dried over Na₂SO₄, filtered and concentrated. The residue was purified over silica gel (0-60% gradient of 20% MeOH/DCM in DCM) to afford tert-butyl (3-(1H-pyrazol-4-yl)-1-((1s,4s)-4-((2-(trifluoromethyl)pyridin-3-yl)oxy)cyclohexyl)-1H-pyrazolo[4,3-c]pyridin-6-yl)(methyl)carbamate (192 mg, 49% yield).

Step C: A solution of tert-butyl (3-(1H-pyrazol-4-yl)-1-((1s,4s)-4-((2-(trifluoromethyl)pyridin-3-yl)oxy)cyclohexyl)-1H-pyrazolo[4,3-c]pyridin-6-yl)(methyl)carbamate (185 mg, 0.33 mmol) in anhydrous DMA (5 mL) was treated with Cs₂CO₃ (216 mg, 0.66 mmol) followed by (R)-4-(chloromethyl)-2,2-dimethyl-1,3-dioxolane (100 mg, 0.66 mmol) and heated to 100° C. in a sealed tube overnight. The reaction mixture was treated with additional 100 mg of the chloride and 200 mg of Cs₂CO₃ and stirred overnight at 120° C. The cooled mixture was partitioned between water (10 mL) and EtOAc (10 mL) and the aqueous layer was extracted with EtOAc (2×10 mL). The combined organic phases were washed with water (4×10 mL) and brine (10 mL), dried over Na₂SO₄, filtered and concentrated. The residue was purified over silica gel (20-100% EtOAc in hexanes) to afford tert-butyl (3-(1-(((S)-2,2-dimethyl-1,3-dioxolan-4-yl)methyl)-1H-pyrazol-4-yl)-1-((1s,4R)-4-((2-(trifluoromethyl)pyridin-3-yl)oxy)cyclohexyl)-1H-pyrazolo[4,3-c]pyridin-6-yl)(methyl)carbamate (67 mg, 30.1% yield).

Step D: To a solution of tert-butyl (3-(1-(((S)-2,2-dimethyl-1,3-dioxolan-4-yl)methyl)-1H-pyrazol-4-yl)-1-((1s,4R)-4-((2-(trifluoromethyl)pyridin-3-yl)oxy)cyclohexyl)-1H-pyrazolo[4,3-c]pyridin-6-yl)(methyl)carbamate (67 mg, 0.10 mmol) in MeOH (5 mL) was added concentrated HCl (3 drops). The mixture was stirred at reflux for 2 h. The cooled mixture was concentrated. The residue was triturated with EtOAc, filtered and dried to afford (S)-3-(4-(6-(methylamino)-1-((1s,4R)-4-((2-(trifluoromethyl)pyridin-3-yl)oxy)cyclohexyl)-1H-pyrazolo[4,3-c]pyridin-3-yl)-1H-pyrazol-1-yl)propane-1,2-diol hydrochloride (53.5 mg, 94% yield) as a yellow solid. Mass spectrum (apci) m/z=532.2 (M+H). ¹H NMR (CD3OD) δ 8.91 (d, J=0.6 Hz, 1H), 8.36 (s, 1H), 8.20 (dd, J=4.5, 0.8 Hz, 1H), 8.12 (s, 1H), 7.78 (d, J=8.4 Hz, 1H), 7.63 (dd, J=8.6, 4.7 Hz, 1H), 6.83 (s, 1H), 4.97 (m, 1H), 4.69 (tt, J=11.5, 3.7 Hz, 1H), 4.42 (dd, J=14.1, 4.1 Hz, 1H), 4.25 (dd, J=14.1, 7.6 Hz, 1H), 4.06 (m, 1H), 3.56 (d, J=5.3 Hz, 2H), 3.05 (s, 3H), 2.52 (m, 2H), 2.30 (m, 2H), 1.98 (m, 2H), 1.90 (m, 2H).

Using the procedure described for the preparation of Example 204, the following compounds were also synthesized:

| Example | Structure | Name | Data |
|---|---|---|---|
| 205 | 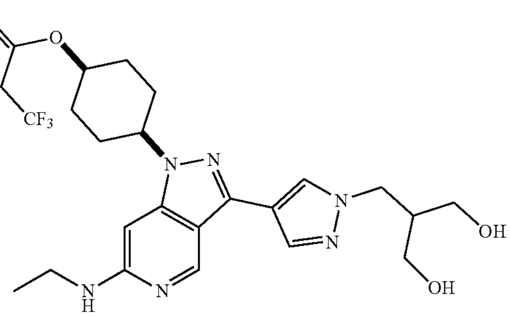 | 2-((4-(6-(ethylamino)-1-((1s,4s)-4-((2-(trifluoromethyl)pyridin-3-yl)oxy)cyclohexyl)-1H-pyrazolo[4,3-c]pyridin-3-yl)-1H-pyrazol-1-yl)methyl)propane-1,3-diol | Mass spectrum (apci) m/z = 560.2 |
| 206 | 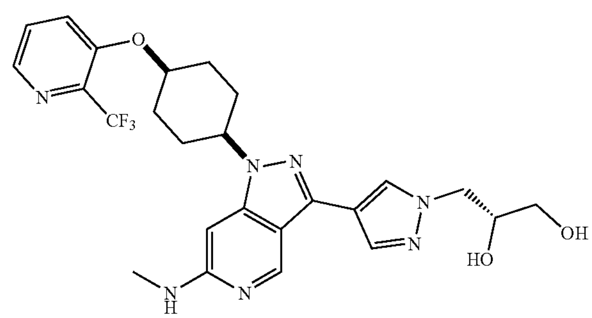 | ®-3-(4-(6-(methylamino)-1-((1s,4s)-4-((2-(trifluoromethyl)pyridin-3-yl)oxy)cyclohexyl)-1H-pyrazolo[4,3-c]pyridin-3-yl)-1H-pyrazol-1-yl)propane-1,2-diol | Mass spectrum (apci) m/z = 532.2 |
| 207 | 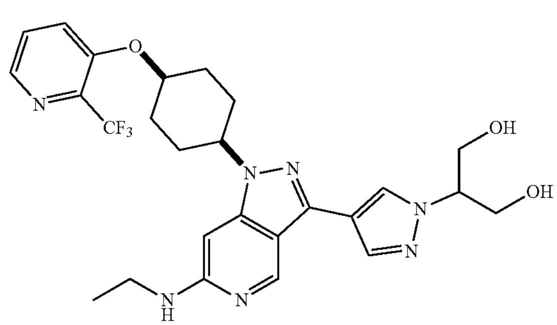 | 2-(4-(6-(ethylamino)-1-((1s,4s)-4-((2-(trifluoromethyl)pyridin-3-yl)oxy)cyclohexyl)-1H-pyrazolo[4,3-c]pyridin-3-yl)-1H-pyrazol-1-yl)propane-1,3-diol | Mass spectrum (apci) m/z = 546.2 |

-continued

| Example | Structure | Name | Data |
|---|---|---|---|
| 208 | 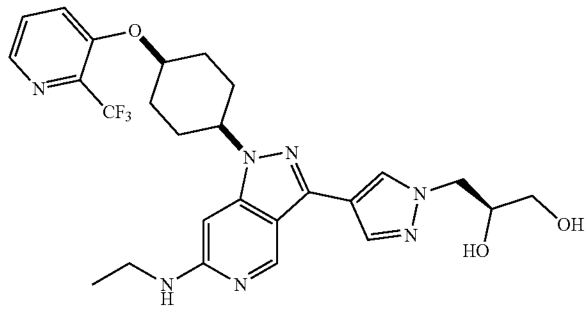 | (S)-3-(4-(6-(ethylamino)-1-((1s,4R)-4-((2-(trifluoromethyl)pyridin-3-yl)oxy)cyclohexyl)-1H-pyrazolo[4,3-c]pyridin-3-yl)-1H-pyrazol-1-yl)propane-1,2-diol | Mass spectrum (apci) m/z = 546.3 |
| 209 | 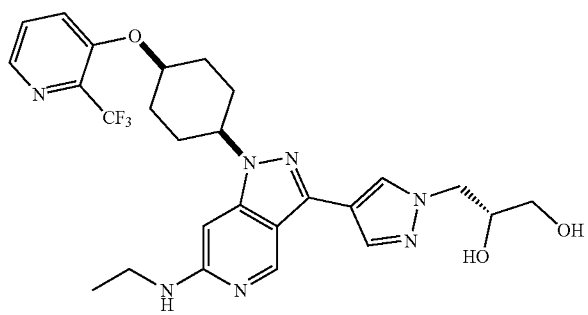 | ®-3-(4-(6-(ethylamino)-1-((1s,4R)-4-((2-(trifluoromethyl)pyridin-3-yl)oxy)cyclohexyl)-1H-pyrazolo[4,3-c]pyridin-3-yl)-1H-pyrazol-1-yl)propane-1,2-diol | Mass spectrum (apci) m/z = 546.3 |

Example 210

2-(4-(6-(methyl amino)-1-((1 s,4s)-4-((2-(trifluoromethyl)pyridin-3-yl)oxy)cyclohexyl)-1H-pyrazolo[4,3-c]pyridin-3-yl)-1H-pyrazol-1-yl)propane-1,3-diol

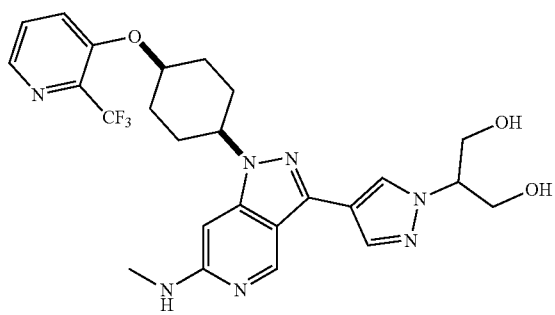

Step A: tert-butyl (3-bromo-1-((1r,4r)-4-((tert-butyldimethylsilyl)oxy)cyclohexyl)-1H-pyrazolo[4,3-c]pyridin-6-yl)(methyl)carbamate (520 mg, 0.964 mmol), tert-butyl 4-(4,4,5,5-tetramethyl-1,3,2-dioxaborolan-2-yl)-1H-pyrazole-1-carboxylate (567 mg, 1.93 mmol) and Pd(PPh$_3$)$_4$ (111 mg, 0.10 mmol) were combined in dioxanes (10 mL) and treated with K$_2$CO$_3$ (1.45 mL, 2N, 2.89 mmol) and heated to 100° C. in a sealed tube overnight. Additional 100 mg of the boronate and 50 mg of Pd(PPh$_3$)$_4$ were added and the mixture heated overnight. The cooled mixture was partitioned between water (30 mL) and EtOAc (30 mL) and the aqueous layer was extracted with EtOAc (2×20 mL). The combined organic phases were washed with brine (20 mL), dried over Na$_2$SO$_4$, filtered and concentrated. The residue was purified over silica gel (20-100% EtOAc/hexanes) to afford tert-butyl (1-((1r,4r)-4-((tert-butyldimethylsilyl)oxy)cyclohexyl)-3-(1H-pyrazol-4-yl)-1H-pyrazolo[4,3-c]pyridin-6-yl)(methyl)carbamate (584 mg, 115% yield).

Step B: A solution of tert-butyl (1-((1r,4r)-4-((tert-butyldimethylsilyl)oxy)cyclohexyl)-3-(1H-pyrazol-4-yl)-1H-pyrazolo[4,3-c]pyridin-6-yl)(methyl)carbamate (120 mg, 0.23 mmol) in DMA (3 mL) was treated with Cs2CO3 (148 mg, 0.46 mmol) followed by (2s,5s)-2-phenyl-1,3-dioxan-5-yl methanesulfonate (88 mg, 0.34 mmol) and heated to 100° C. overnight. Additional 50 mg of (2s,5s)-2-phenyl-1,3-dioxan-5-yl methanesulfonate was added and reaction continued over the weekend. The cooled mixture was partitioned between water (10 mL) and EtOAc (10 mL) and the aqueous layer was extracted with EtOAc (2×10 mL). The combined organic phases were washed with water (4×10 mL) and brine (10 mL) then dried over Na$_2$SO$_4$, filtered and concentrated. The residue was purified over silica gel (5-50% EtOAc/hexanes) to afford tert-butyl (1-((1r,4R)-4-((tert-butyldimethylsilyl)oxy)cyclohexyl)-3-(1-((2R,5r)-2-phenyl-1,3-dioxan-5-yl)-1H-pyrazol-4-yl)-1H-pyrazolo[4,3-c]pyridin-6-yl)(methyl)carbamate (40 mg, 25.5% yield).

Step C: To a solution of tert-butyl (1-((1r,4R)-4-((tert-butyldimethylsilyl)oxy)cyclohexyl)-3-(1-((2R,5r)-2-phenyl-1,3-dioxan-5-yl)-1H-pyrazol-4-yl)-1H-pyrazolo[4,3-c]pyridin-6-yl)(methyl)carbamate (40 mg, 0.058 mmol) in THF (2 mL) was added TBAF (290 μL, 1.0 M, 0.29 mmol) and stirred for 2 h. The mixture was partitioned between saturated NaHCO$_3$(10 mL) and EtOAc (10 mL) and the aqueous layer was extracted with EtOAc (2×10 mL). The combined organic phases were washed with brine (10 mL), dried over Na2SO4, filtered and concentrated to afford tert-butyl (1-((1r,4R)-4-hydroxycyclohexyl)-3-(1-((2R,5r)-2-phenyl-1,3-dioxan-5-yl)-1H-pyrazol-4-yl)-1H-pyrazolo[4,3-c]pyridin-6-yl)(methyl)carbamate (35 mg, 105% yield).

Step D: To a solution of tert-butyl (1-((1r,4R)-4-hydroxycyclohexyl)-3-(1-((2R,5r)-2-phenyl-1,3-dioxan-5-yl)-1H-pyrazol-4-yl)-1H-pyrazolo[4,3-c]pyridin-6-yl)(methyl)carbamate (33 mg, 0.06 mmol) and 2-(trifluoromethyl)pyridin-3-ol (28 mg, 0.17 mmol) in THF (2 mL) was added PPh3 (45 mg, 0.17 mmol) followed by DIAD (34 μL, 0.17 mmol) and heated to 60° C. for 2 h. The cooled mixture was partitioned between water (10 mL) and EtOAc (10 mL) and the aqueous layer was extracted with EtOAc (2×10 mL). The combined organic phases were washed with brine (10 mL), dried over Na$_2$SO$_4$, filtered and concentrated. The residue was purified over silica gel (20-100% EtOAc/hexanes) to afford tert-butyl methyl(3-(1-((2R,5r)-2-phenyl-1,3-dioxan-5-yl)-1H-pyrazol-4-yl)-1-((1s,4S)-4-((2-(trifluoromethyl)pyridin-3-yl)oxy)cyclohexyl)-1H-pyrazolo[4,3-c]pyridin-6-yl)carbamate (18 mg, 43.5% yield).

Step E: To a solution of tert-butyl methyl(3-(1-((2R,5r)-2-phenyl-1,3-dioxan-5-yl)-1H-pyrazol-4-yl)-1-((1s,4S)-4-((2-(trifluoromethyl)pyridin-3-yl)oxy)cyclohexyl)-1H-pyrazolo[4,3-c]pyridin-6-yl)carbamate (18 mg, 0.03 mmol) in MeOH (2 mL) was added concentrated HCl (3 drops). The mixture was stirred at reflux for 2 h. The cooled mixture was concentrated. The residue was purified on preparative HPLC (0-95% ACN/water/0.1% TFA over 20 min). Product containing fractions were combined, concentrated to ½ volume then partitioned between 1N NaOH/10% MeOH/DCM, dried over sodium sulfate, filtered and concentrated to afford 2-(4-(6-(methylamino)-1-((1s,4S)-4-((2-(trifluoromethyl)pyridin-3-yl)oxy)cyclohexyl)-1H-pyrazolo[4,3-c]pyridin-3-yl)-1H-pyrazol-1-yl)propane-1,3-diol (8 mg, 60% yield). Mass spectrum (apci) m/z=532.3 (M+H). $^1$H NMR (CDCl$_3$) δ 8.67 (s, 1H), 8.27 (dd, J=4.3, 1.0 Hz, 1H), 8.06 (s, 1H), 8.04 (s, 1H), 7.46 (dd, J=8.4, 4.5 Hz, 1H), 7.41 (d, J=8.4 Hz, 1H), 6.13 (s, 1H), 4.90 (br s, 1H), 4.79 (m, 1H), 4.48-4.37 (m, 2H), 4.16 (d, J=4.9 Hz, 4H), 2.97 (s, 3H), 2.60 (m, 2H), 2.32 (m, 2H), 1.94 (m, 2H), 1.85 (m, 2H).

Example 211

N-methyl-1-((1s,4s)-4-((3-methylpyrazin-2-yl)oxy)cyclohexyl)-3-(1-(2-(methylsulfonyl)ethyl)-1H-pyrazol-4-yl)-1H-pyrazolo[4,3-c]pyridin-6-amine

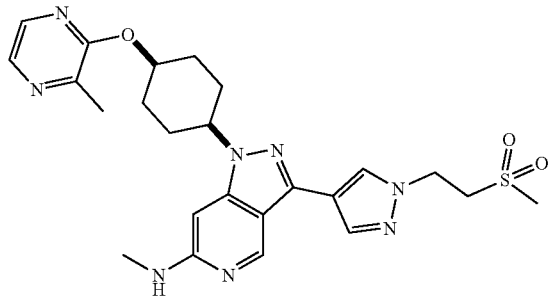

Step A: To a solution of Ph$_3$P (0.1573 g, 0.5999 mmol) and DIAD (0.1182 mL, 0.5999 mmol) in THF (5.713 mL) was added tert-butyl (3-bromo-1-((1r,4r)-4-hydroxycyclohexyl)-1H-pyrazolo[4,3-c]pyridin-6-yl)(methyl)carbamate (0.243 g, 0.5713 mmol) and 2-hydroxy-3-methylpyrazine (0.09437 g, 0.8570 mmol) and stirred overnight. One equivalent each of DIAD, Ph$_3$P and 2-hydroxy-3-methylpyrazine were mixed in 0.5 mL THF and the THF mixture was added to the reaction, which was then stirred for 1 h. The reaction mixture was partitioned between ethyl acetate (25 mL) and water (25 mL), extracted with ethyl acetate (2×10 mL), washed with water (2×10 mL) and brine (10 mL), dried over Na$_2$SO$_4$, filtered and concentrated. The residue was purified over silica gel (5-60% EtOAc in hexanes) to afford tert-butyl (3-bromo-1-((1s,4s)-4-((3-methylpyrazin-2-yl)oxy)cyclohexyl)-1H-pyrazolo[4,3-c]pyridin-6-yl)(methyl)carbamate (0.319 g, 0.6165 mmol, 107.9% yield).

Step B: tert-butyl (3-bromo-1-((1s,4s)-4-((3-methylpyrazin-2-yl)oxy)cyclohexyl)-1H-pyrazolo[4,3-c]pyridin-6-yl)(methyl)carbamate (0.020 g, 0.039 mmol), 1-(2-(methylsulfonyl)ethyl)-4-(4,4,5,5-tetramethyl-1,3,2-dioxaborolan-2-yl)-1H-pyrazole (14 mg, 0.046 mmol) and Pd(PPh$_3$)$_4$ (0.0022 g, 0.0019 mmol) were diluted with 1,4-dioxane (0.39 mL). 2M Na$_2$CO$_3$ (0.068 mL, 0.14 mmol) was added and the reaction mixture was heated to 85° C. for 6 h. The reaction mixture was cooled and diluted with DCM (2 mL) and filtered. The filtrate was diluted with DCM (3 mL) and TFA (5 mL) was added. After 1 h the reaction was concentrated. The resultant oil was resuspended in 1 mL of a solution of 60:40 ACN:water with 2% TFA modifier and purified by HPLC (5-70% ACN in water with 0.2% TFA modifier). The product fractions were free-based with saturated NaHCO$_3$(15 mL) and the organics were extracted from the water phase with DCM (2×15 mL). The pooled organic layer was washed with brine (15 mL), dried over Na$_2$SO$_4$, filtered and concentrated in vacuo to obtain N-methyl-1-((1s,4s)-4-((3-methylpyrazin-2-yl)oxy)cyclohexyl)-3-(1-(2-(methylsulfonyl)ethyl)-1H-pyrazol-4-yl)-1H-pyrazolo[4,3-c]pyridin-6-amine (0.013 g, 0.025 mmol, 66% yield) as a white solid. Mass spectrum (apci) m/z=511.2 (M+H). $^1$H NMR (CDCl$_3$) δ 8.69 (d, J=1.0 Hz, 1H), 8.08 (s, 1H), 8.02 (s, 1H), 8.00 (d, J=2.9 Hz, 1H), 7.92 (dd, J=2.9, 0.5 Hz, 1H), 6.07 (d, J=0.8 Hz, 1H). 5.43 (m, 1H), 4.80 (m, 1H), 4.71 (m, 2H), 4.39 (m, 1H), 3.71 (m, 2H), 2.97 (d, J=5.3 Hz, 3H), 2.62 (s, 3H), 2.58 (s, 3H), 2.52 (m, 2H), 2.33 (m, 2H), 1.95 (m, 2H), 1.85 (m, 2H).

Using the procedure described for the preparation of Example 211, the following compounds were also synthesized:

| Example | Structure | Name | Data |
|---|---|---|---|
| 212 | 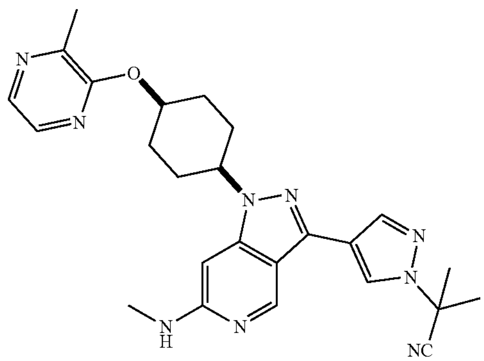 | 2-methyl-2-(4-(6-(methylamino)-1-((1s,4s)-4-((3-methylpyrazin-2-yl)oxy)cyclohexyl)-1H-pyrazolo[4,3-c]pyridin-3-yl)-1H-pyrazol-1-yl)propanenitrile | Mass spectrum (apci) m/z = 472.3 |
| 213 | 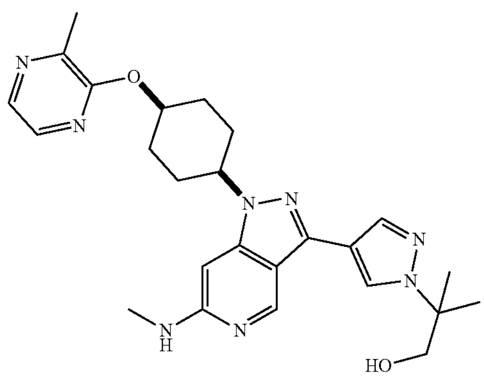 | 2-methyl-2-(4-(6-(methylamino)-1-((1s,4s)-4-((3-methylpyrazin-2-yl)oxy)cyclohexyl)-1H-pyrazolo[4,3-c]pyridin-3-yl)-1H-pyrazol-1-yl)propan-1-ol | Mass spectrum (apci) m/z = 477.3 |
| 214 | 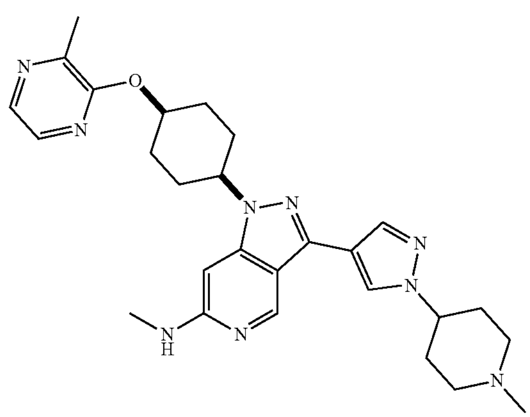 | N-methyl-3-(1-(1-methylpiperidin-4-yl)-1H-pyrazol-4-yl)-1-((1s,4s)-4-((3-methylpyrazin-2-yl)oxy)cyclohexyl)-1H-pyrazolo[4,3-c]pyridin-6-amine | Mass spectrum (apci) m/z = 502.2 |
| 215 | 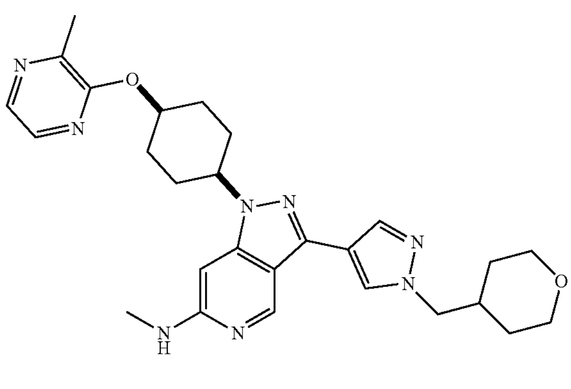 | N-methyl-1-((1s,4s)-4-((3-methylpyrazin-2-yl)oxy)cyclohexyl)-3-(1-((tetrahydro-2H-pyran-4-yl)methyl)-1H-pyrazol-4-yl)-1H-pyrazolo[4,3-c]pyridin-6-amine | Mass spectrum (apci) m/z = 503.3 |

| Example | Structure | Name | Data |
|---|---|---|---|
| 216 | 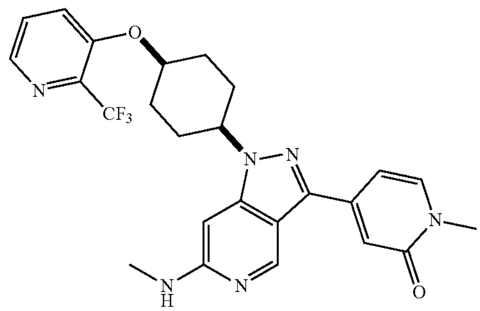 | 1-methyl-4-(6-(methylamino)-1-((1s,4s)-4-((2-(trifluoromethyl)pyridin-3-yl)oxy)cyclohexyl)-1H-pyrazolo[4,3-c]pyridin-3-yl)pyridin-2(1H)-one | Mass spectrum (apci) m/z = 499.2 |
| 217 | 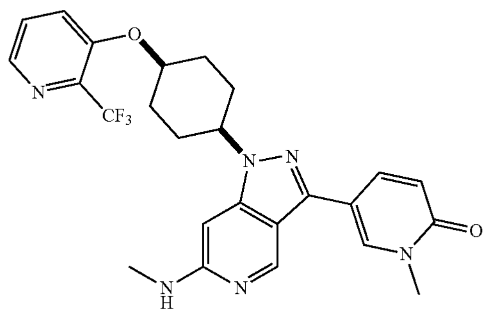 | 1-methyl-5-(6-(methylamino)-1-((1s,4s)-4-((2-(trifluoromethyl)pyridin-3-yl)oxy)cyclohexyl)-1H-pyrazolo[4,3-c]pyridin-3-yl)pyridin-2(1H)-one | Mass spectrum (apci) m/z = 499.2 |
| 218 | 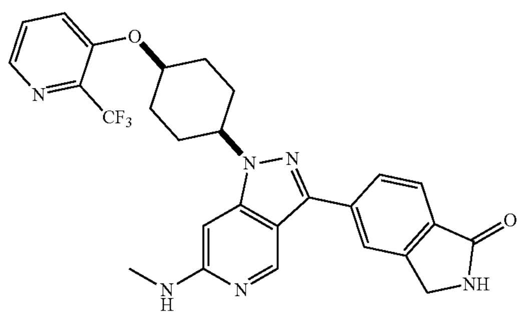 | 5-(6-(methylamino)-1-((1s,4s)-4-((2-(trifluoromethyl)pyridin-3-yl)oxy)cyclohexyl)-1H-pyrazolo[4,3-c]pyridin-3-yl)isoindolin-1-one | Mass spectrum (apci) m/z = 523.2 |
| 219 | 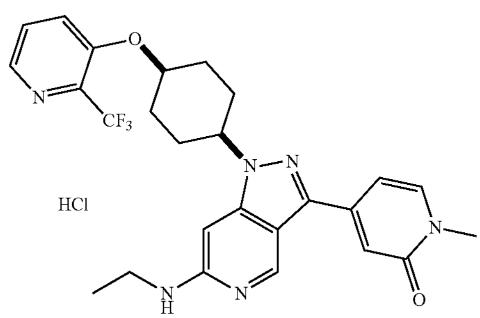 | 4-(6-(ethylamino)-1-((1s,4s)-4-((2-(trifluoromethyl)pyridin-3-yl)oxy)cyclohexyl)-1H-pyrazolo[4,3-c]pyridin-3-yl)-1-methylpyridin-2(1H)-one hydrochloride | Mass spectrum (apci) m/z = 513.2 |
| 220 | 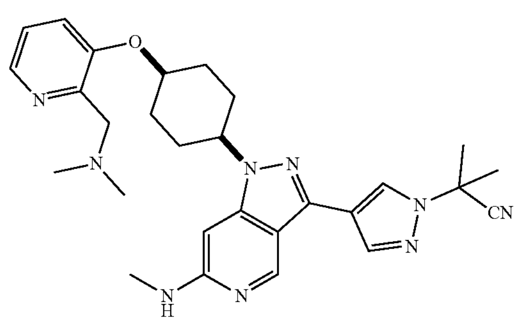 | 2-(4-(1-((1s,4s)-4-(2-((dimethylamino)methyl)pyridin-3-yl)oxy)cyclohexyl)-6-(methylamino)-1H-pyrazolo[4,3-c]pyridin-3-yl)-1H-pyrazol-1-yl)-2-methylpropanenitrile | Mass spectrum (apci) m/z = 514.2 |

| Example | Structure | Name | Data |
|---|---|---|---|
| 221 | 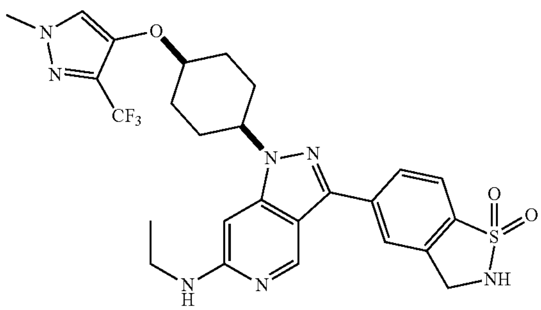 | 5-(6-(ethylamino)-1-((1s,4s)-4-((1-methyl-3-(trifluoromethyl)-1H-pyrazol-4-yl)oxy)cyclohexyl)-1H-pyrazolo[4,3-c]pyridin-3-yl)-2,3-dihydrobenzo[d]isothiazole 1,1-dioxide | Mass spectrum (apci) m/z = 576.2 |
| 222 | 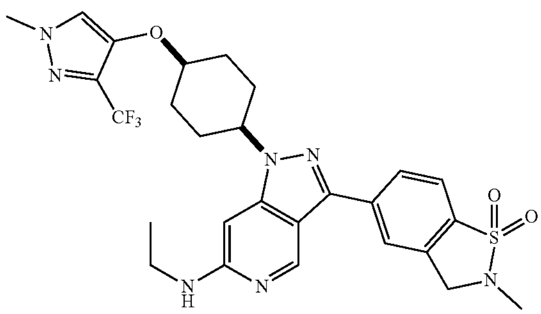 | 5-(6-(ethylamino)-1-((1s,4s)-4-((1-methyl-3-(trifluoromethyl)-1H-pyrazol-4-yl)oxy)cyclohexyl)-1H-pyrazolo[4,3-c]pyridin-3-yl)-2-methyl-2,3-dihydrobenzo[d]isothiazole 1,1-dioxide | Mass spectrum (apci) m/z = 590.2 |
| 223 | 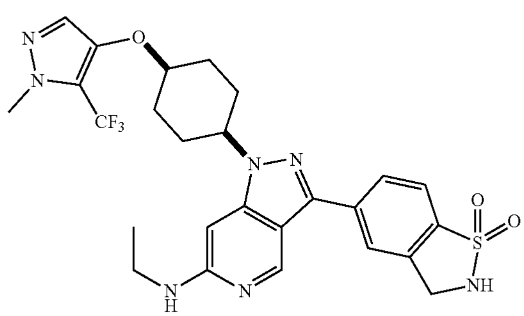 | 5-(6-(ethylamino)-1-((1s,4s)-4-((1-methyl-5-(trifluoromethyl)-1H-pyrazol-4-yl)oxy)cyclohexyl)-1H-pyrazolo[4,3-c]pyridin-3-yl)-2,3-dihydrobenzo[d]isothiazole 1,1-dioxide | Mass spectrum (apci) m/z = 576.2 |
| 224 | 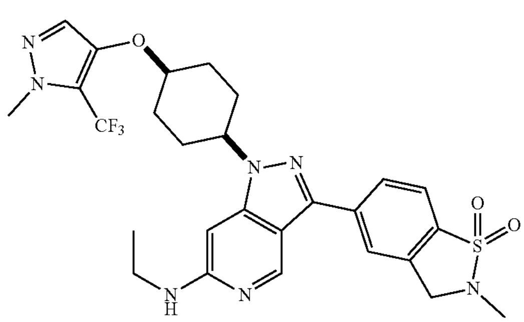 | 5-(6-(ethylamino)-1-((1s,4s)-4-((1-methyl-5-(trifluoromethyl)-1H-pyrazol-4-yl)oxy)cyclohexyl)-1H-pyrazolo[4,3-c]pyridin-3-yl)-2-methyl-2,3-dihydrobenzo[d]isothiazole 1,1-dioxide | Mass spectrum (apci) m/z = 590.2 |

Example 225

N-ethyl-1-((1s,4s)-4-((1-ethyl-1H-1,2,3-triazol-5-yl)oxy)cyclohexyl)-3-(1-methyl-1H-pyrazol-4-yl)-1H-pyrazolo[4,3-c]pyridin-6-amine

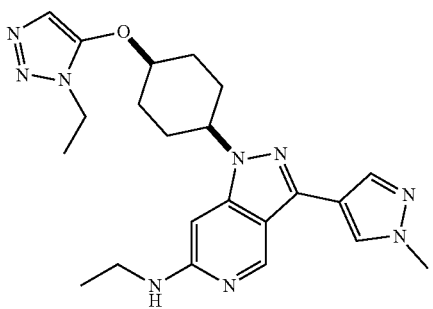

Step A: tert-butyl (3-bromo-1H-pyrazolo[4,3-c]pyridin-6-yl)(ethyl)carbamate (40 mg, 0.117 mmol) and (1r,4r)-4-((1-ethyl-1H-1,2,3-triazol-5-yl)oxy)cyclohexyl 4-methylbenzenesulfonate (64.3 mg, 0.18 mmol) were dissolved in DMF (0.5 mL) and $Cs_2CO_3$ (76.4 mg, 0.23 mmol) was added and heated to 100° C. overnight. The mixture was partitioned between water and EtOAc, extracted with EtOAc, dried over sodium sulfate, filtered and concentrated. The residue was purified over silica gel (0-70% EtOAc in DCM) to afford tert-butyl (3-bromo-1-((1s,4s)-4-((1-ethyl-1H-1,2,3-triazol-5-yl)oxy)cyclohexyl)-1H-pyrazolo[4,3-c]pyridin-6-yl)(ethyl)carbamate (31.9 mg, 51% yield).

Step B: tert-butyl (3-bromo-1-((1s,4s)-4-((1-ethyl-1H-1,2,3-triazol-5-yl)oxy)cyclohexyl)-1H-pyrazolo[4,3-c]pyridin-6-yl)(ethyl)carbamate (0.031 g, 0.058 mmol) and 1-methyl-4-(4,4,5,5-tetramethyl-1,3,2-dioxaborolan-2-yl)-1H-pyrazole (0.0302 g, 0.145 mmol) were dissolved in 0.6 mL of dioxane, under a nitrogen atmosphere. To this was added $K_2CO_3$ (0.087 mL, 3 eq. 2M aq. Solution), and $Pd(PPh_3)_4$ (0.006 g, 0.0058 mmol) and heated to 100° C. overnight. The mixture was partitioned between water/EtOAc, extracted with EtOAc, dried over sodium sulfate, filtered and concentrated. The residue was dissolved in 1 mL of DCM, 2 mL of 4M HCl/dioxane, stirred for 2 h and concentrated. The residue was purified over C-18 column (5-95% ACN in water with 0.1% TFA) to afford N-ethyl-1-((1s,4s)-4-((1-ethyl-1H-1,2,3-triazol-5-yl)oxy)cyclohexyl)-3-(1-methyl-1H-pyrazol-4-yl)-1H-pyrazolo[4,3-c]pyridin-6-amine bis(2,2,2-trifluoroacetate) (18.1 mg, 47% yield). Mass spectrum (apci) m/z=436.2 (M+H). 1H NMR (CD3OD) δ 8.87 (s, 1H), 8.30 (s, 1H), 8.05 (s, 1H), 7.30 (s, 1H), 6.86 (s, 1H), 4.69 (m, 2H), 4.36 (q, J=7.2 Hz, 2H), 4.00 (s, 3H), 3.43 (q, J=7.2 Hz, 2H), 2.49-2.31 (m, 4H), 2.02-1.90 (m, 4H), 1.56 (t, J=7.2 Hz, 3H), 1.37 (t, J=7.2 Hz, 3H).

Using the procedure described for the preparation of Example 225, the following compounds were also synthesized:

| Example | Structure | Name | Data |
| --- | --- | --- | --- |
| 226 | 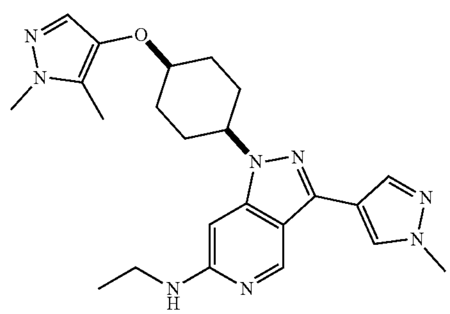 | 1-((1s,4s)-4-((1,5-dimethyl-1H-pyrazol-4-yl)oxy)cyclohexyl)-N-ethyl-3-(1-methyl-1H-pyrazol-4-yl)-1H-pyrazolo[4,3-c]pyridin-6-amine | Mass spectrum (apci) m/z = 435.2 |
| 227 | 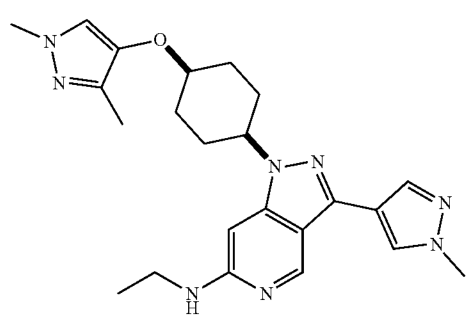 | 1-((1s,4s)-4-((1,3-dimethyl-1H-pyrazol-4-yl)oxy)cyclohexyl)-N-ethyl-3-(1-methyl-1H-pyrazol-4-yl)-1H-pyrazolo[4,3-c]pyridin-6-amine | Mass spectrum (apci) m/z = 435.3 |

-continued

| Example | Name | Data |
|---|---|---|
| 228 | 1-((1s,4s)-4-((3-cyclopropyl-1-methyl-1H-pyrazol-4-yl)oxy)cyclohexyl)-N-ethyl-3-(1-methyl-1H-pyrazol-4-yl)-1H-pyrazolo[4,3-c]pyridin-6-amine | Mass spectrum (apci) m/z = 461.3 |
| 229 | 1-((1s,4s)-4-((1,3-dimethyl-1H-pyrazol-4-yl)oxy)cyclohexyl)-N-ethyl-3-(4-((4-methylpiperazin-1-yl)methyl)phenyl)-1H-pyrazolo[4,3-c]pyridin-6-amine | Mass spectrum (apci) m/z = 543.3 |
| 230 | 5-(1-((1s,4s)-4-((1,3-dimethyl-1H-pyrazol-4-yl)oxy)cyclohexyl)-6-(ethylamino)-1H-pyrazolo[4,3-c]pyridin-3-yl)isoindolin-1-one | Mass spectrum (apci) m/z = 486.2 |
| 231 | N-cyclopropyl-4-(1-((1s,4s)-4-((1,3-dimethyl-1H-pyrazol-4-yl)oxy)cyclohexyl)-6-(ethylamino)-1H-pyrazolo[4,3-c]pyridin-3-yl)benzamide | Mass spectrum (apci) m/z = 514.3 |
| 232 | N-methyl-1-((1s,4s)-4-((1-methyl-1H-pyrazol-4-yl)oxy)cyclohexyl)-3-(4-((4-methylpiperazin-1-yl)methyl)phenyl)-1H-pyrazolo[4,3-c]pyridin-6-amine | Mass spectrum (apci) m/z = 515.3 |

| Example | Structure | Name | Data |
|---|---|---|---|
| 233 | 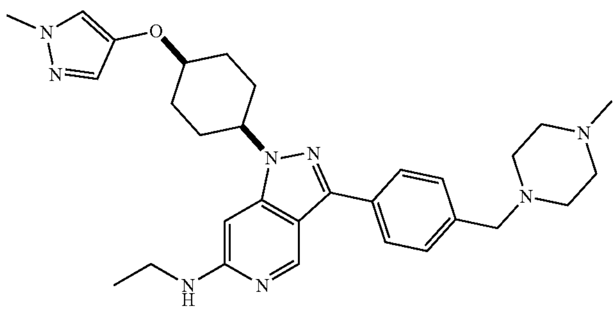 | N-ethyl-1-((1s,4s)-4-((1-methyl-1H-pyrazol-4-yl)oxy)cyclohexyl)-3-(4-((4-methylpiperazin-1-yl)methyl)phenyl)-1H-pyrazolo[4,3-c]pyridin-6-amine | Mass spectrum (apci) m/z = 529.2 |

Example 234

(R)-3-(4-(6-(ethylamino)-1-((1s,4S)-4-((3-fluoro-4-(trifluoromethyl)pyridin-2-yl)oxy)cyclohexyl)-1H-pyrazolo[4,3-c]pyridin-3-yl)-1H-pyrazol-1-yl)propane-1,2-diol

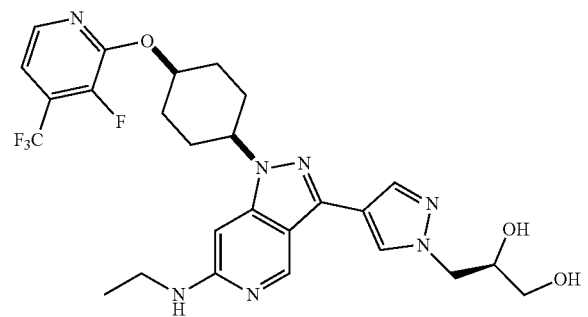

Step A: A solution of triphenylphosphine (1.34 g, 5.1 mmol) in THF (25 mL) was cooled to 0° C. and treated with DIAD (1.0 mL, 5.12 mmol). The mixture was stirred for 15 min, then tert-butyl (3-bromo-1-((1r,4r)-4-hydroxycyclohexyl)-1H-pyrazolo[4,3-c]pyridin-6-yl)(ethyl)carbamate (1.5 g, 3.41 mmol) was added as a solid, followed by a solution of 3-fluoro-4-(trifluoromethyl)pyridin-2-ol (1.24 g, 6.83 mmol) in THF (10 mL) over 5 min. The mixture was allowed to warm slowly to room temperature overnight. The mixture was partitioned between water (100 mL) and EtOAc (100 mL) and the aqueous layer was extracted with EtOAc (2×30 mL). The combined organic phases were washed with brine (30 mL), dried over Na₂SO₄, filtered and concentrated. The residue was purified over silica gel (10-40% EtOAc/hexanes) to afford tert-butyl (3-bromo-1-((1s,4s)-4-((3-fluoro-4-(trifluoromethyl)pyridin-2-yl)oxy)cyclohexyl)-1H-pyrazolo[4,3-c]pyridin-6-yl)(ethyl)carbamate (1.07 g, 52% yield).

Step B: tert-butyl (3-bromo-1-((1s,4s)-4-((3-fluoro-4-(trifluoromethyl)pyridin-2-yl)oxy)cyclohexyl)-1H-pyrazolo[4,3-c]pyridin-6-yl)(ethyl)carbamate (1.07 g, 1.78 mmol), (R)-1-((2,2-dimethyl-1,3-dioxolan-4-yl)methyl)-4-(4,4,5,5-tetramethyl-1,3,2-dioxaborolan-2-yl)-1H-pyrazole (1.09 g, 3.55 mmol) and Pd(PPh₃)₄ (205 mg, 0.18 mmol) were combined in dioxanes (15 mL) and treated with K₂CO₃ (2.66 mL, 2N, 5.33 mmol) and heated to 100° C. overnight. The reaction mixture was partitioned between water (50 mL) and EtOAc (50 mL) and the aqueous layer was extracted with EtOAc (2×30 mL). The combined organic phases were washed with brine (20 mL), dried over Na₂SO₄, filtered and concentrated. The residue was purified over silica gel (30-100% EtOAc in hexanes) to afford tert-butyl (3-(1-(((R)-2,2-dimethyl-1,3-dioxolan-4-yl)methyl)-1H-pyrazol-4-yl)-1-((1s,4S)-4-((3-fluoro-4-(trifluoromethyl)pyridin-2-yl)oxy)cyclohexyl)-1H-pyrazolo[4,3-c]pyridin-6-yl)(ethyl)carbamate (1.37 g, 110% yield).

Step C: To a solution of tert-butyl (3-(1-(((R)-2,2-dimethyl-1,3-dioxolan-4-yl)methyl)-1H-pyrazol-4-yl)-1-((1s,4S)-4-((3-fluoro-4-(trifluoromethyl)pyridin-2-yl)oxy)cyclohexyl)-1H-pyrazolo[4,3-c]pyridin-6-yl)(ethyl)carbamate (1.25 g, 1.78 mmol) in methanol (20 mL) was added concentrated HCl (444 μL, 5.33 mmol). The mixture was heated to reflux for 5 h and then room temperature overnight. The reaction mixture was concentrated to half volume then basified with 1N NaOH (5.33 mL), diluted with water (50 mL) and extracted with DCM (3×50 mL). The combined organic phases were washed with brine (30 mL), dried over Na₂SO₄, filtered and concentrated. The residue was purified over silica gel (0-10% MeOH in DCM) to afford (R)-3-(4-(6-(ethylamino)-1-((1s,4S)-4-((3-fluoro-4-(trifluoromethyl)pyridin-2-yl)oxy)cyclohexyl)-1H-pyrazolo[4,3-c]pyridin-3-yl)-1H-pyrazol-1-yl)propane-1,2-diol (660 mg, 65.9% yield). Mass spectrum (apci) m/z=564.2 (M+H). ¹H NMR (CDCl₃ with CD3OD) δ 8.65 (d, J=1.0 Hz, 1H), 8.05 (d, J=5.1 Hz, 1H), 8.04 (s, 1H), 8.02 (s, 1H), 7.07 (dd, J=4.9, 4.5 Hz, 1H), 6.17 (d, J=0.8 Hz, 1H), 5.52 (m, 1H), 4.44 (t, J=11.9, 3.9 Hz, 1H), 4.36 (dd, J=14.1, 4.7 Hz, 1H), 4.29 (dd, J=14.1, 6.5 Hz, 1H), 4.09 (m, 1H), 3.63-3.54 (m, 2H), 3.29 (q, J=7.2 Hz, 2H), 2.57 (m, 2H), 2.35 (m, 2H), 1.96 (m, 2H), 1.86 (m, 2H), 1.35 (t, J=7.2 Hz, 3H).

Example 235

(S)-3-(4-(6-(ethylamino)-1-((1s,4R)-4-((3-fluoro-4-(trifluoromethyl)pyridin-2-yl)oxy)cyclohexyl)-1H-pyrazolo[4,3-c]pyridin-3-yl)-1H-pyrazol-1-yl)propane-1,2-diol

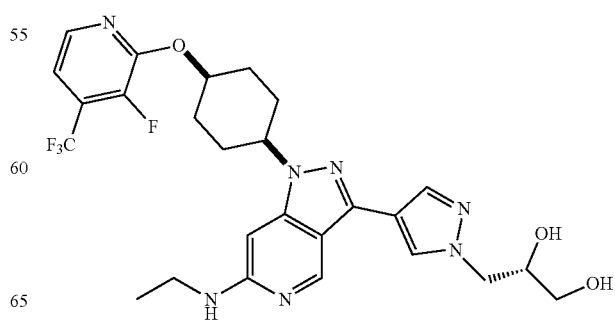

Step A: A solution of triphenylphosphine (2.24 g, 8.54 mmol) in THF (50 mL) was cooled to 0° C. and treated with DIAD (1.68 mL, 8.54 mmol). The mixture was stirred for 15 min (a pale yellow precipitate formed) then tert-butyl (3-bromo-1-((1r,4r)-4-hydroxycyclohexyl)-1H-pyrazolo[4,3-c]pyridin-6-yl)(ethyl)carbamate (2.5 g, 5.7 mmol) was added as a solid, followed by a solution of 3-fluoro-4-(trifluoromethyl)pyridin-2-ol (2.06 g, 11.38 mmol) in THF (10 mL) over 5 min. The mixture was allowed to warm slowly to room temperature overnight. The mixture was partitioned between water (200 mL) and EtOAc (200 mL) and the aqueous layer was extracted with EtOAc (2×50 mL). The combined organic phases were washed with brine (50 mL), dried over Na$_2$SO$_4$, filtered and concentrated. The residue was purified over silica gel (10-40% EtOAc/hexanes) to afford tert-butyl (3-bromo-1-((1s,4s)-4-((3-fluoro-4-(trifluoromethyl)pyridin-2-yl)oxy)cyclohexyl)-1H-pyrazolo[4,3-c]pyridin-6-yl)(ethyl)carbamate (2.25 g, 66% yield).

Step B: A solution of tert-butyl (3-bromo-1-((1s,4s)-4-((3-fluoro-4-(trifluoromethyl)pyridin-2-yl)oxy)cyclohexyl)-1H-pyrazolo[4,3-c]pyridin-6-yl)(ethyl)carbamate (5.95 g, 9.88 mmol) in CH2Cl2 (50 mL) was treated with 4N HCl/dioxanes (7.41 mL, 29.6 mmol) and stirred for 6 h. Additional 4N HCl in dioxane (4 mL) was added and the mixture stirred overnight. The mixture was concentrated, partitioned between 2N NaOH (30 mL), water (200 mL) and EtOAc (300 mL). The aqueous layer was extracted with EtOAc (2×200 mL) and the combined organic phases were washed with brine (100 mL), dried over Na$_2$SO$_4$, filtered and concentrated to afford 3-bromo-N-ethyl-1-((1s,4s)-4-((3-fluoro-4-(trifluoromethyl)pyridin-2-yl)oxy)cyclohexyl)-1H-pyrazolo[4,3-c]pyridin-6-amine (4.91 g, 99% yield).

Step C: 3-Bromo-N-ethyl-1-((1s,4s)-4-((3-fluoro-4-(trifluoromethyl)pyridin-2-yl)oxy)cyclohexyl)-1H-pyrazolo[4,3-c]pyridin-6-amine (5.54 g, 11.0 mmol), (S)-1-((2,2-dimethyl-1,3-dioxolan-4-yl)methyl)-4-(4,4,5,5-tetramethyl-1,3,2-dioxaborolan-2-yl)-1H-pyrazole (6.80 g, 22.1 mmol) and Pd(PPh$_3$)$_4$ (637 mg, 0.55 mmol) were combined in dioxane (110 mL) and treated with K$_2$CO$_3$ (16.5 mL, 2N, 33.1 mmol). The mixture was heated to 100° C. in a sealed vessel overnight. The cooled mixture was partitioned between water (200 mL) and EtOAc (200 mL) and the aqueous layer was extracted with EtOAc (2×100 mL). The combined organic phases were washed with brine (100 mL), dried over Na$_2$SO$_4$, filtered and concentrated. The residue was purified over silica gel (20-100% EtOAc/hexanes) to afford 3-(1-(((S)-2,2-dimethyl-1,3-dioxolan-4-yl)methyl)-1H-pyrazol-4-yl)-N-ethyl-1-((1s,4R)-4-((3-fluoro-4-(trifluoromethyl)pyridin-2-yl)oxy)cyclohexyl)-1H-pyrazolo[4,3-c]pyridin-6-amine (6.14 g, 91% yield).

Step D: To a solution of 3-(1-(((S)-2,2-dimethyl-1,3-dioxolan-4-yl)methyl)-1H-pyrazol-4-yl)-N-ethyl-1-((1s,4R)-4-((3-fluoro-4-(trifluoromethyl)pyridin-2-yl)oxy)cyclohexyl)-1H-pyrazolo[4,3-c]pyridin-6-amine (7.88 g, 13.1 mmol) in THF (200 mL) was added 0.3N HCl (65.3 mL, 19.6 mmol). The mixture was stirred at 60° C. overnight. The cooled mixture was basified with 2N NaOH (12 mL) and partitioned between water (200 mL) and EtOAc (200 mL). The aqueous layer was extracted with EtOAc (2×100 mL) and the combined organic phases were washed with brine (200 mL), dried over Na$_2$SO$_4$, filtered and concentrated to afford a solid. The solid was recrystallized from methanol (500 mL), filtered, washed with methanol and dried in vacuo to afford (S)-3-(4-(6-(ethylamino)-1-((1s,4R)-4-((3-fluoro-4-(trifluoromethyl)pyridin-2-yl)oxy)cyclohexyl)-1H-pyrazolo[4,3-c]pyridin-3-yl)-1H-pyrazol-1-yl)propane-1,2-diol (5.20 g, 71% yield) Mass spectrum (apci) m/z=564.3 (M+H). $^1$H NMR (CDCl$_3$ with CD3OD) δ 8.65 (d, J=0.8 Hz, 1H), 8.07-8.01 (m, 3H), 7.07 (m, 1H), 6.17 (s, 1H), 5.52 (m, 1H), 4.44 (t, J=11.9, 3.9 Hz, 1H), 4.36 (dd, J=14.1, 4.7 Hz, 1H), 4.28 (dd, J=14.1, 6.5 Hz, 1H), 4.08 (m, 1H), 3.63-3.52 (m, 2H), 3.28 (q, J=7.2 Hz, 2H), 2.57 (m, 2H), 2.35 (m, 2H), 1.96 (m, 2H), 1.87 (m, 2H), 1.35 (t, J=7.2 Hz, 3H).

Using the procedure described for the preparation of Example 234, the following compounds were also synthesized:

| Example | Structure | Name | Data |
|---|---|---|---|
| 236 | 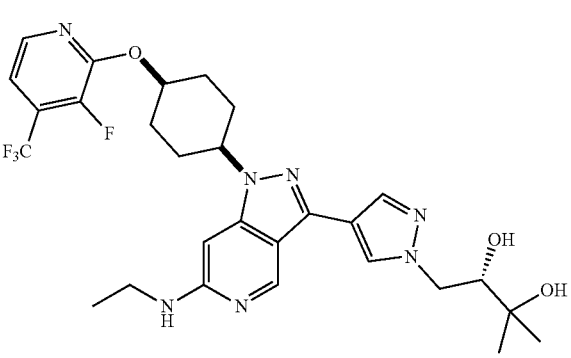 | (S)-1-(4-(6-(ethylamino)-1-((1s,4R)-4-((3-fluoro-4-(trifluoromethyl)pyridin-2-yl)oxy)cyclohexyl)-1H-pyrazolo[4,3-c]pyridin-3-yl)-1H-pyrazol-1-yl)-3-methylbutane-2,3-diol | Mass spectrum (apci) m/z = 592.3 |

| Example | Structure | Name | Data |
|---|---|---|---|
| 237 | 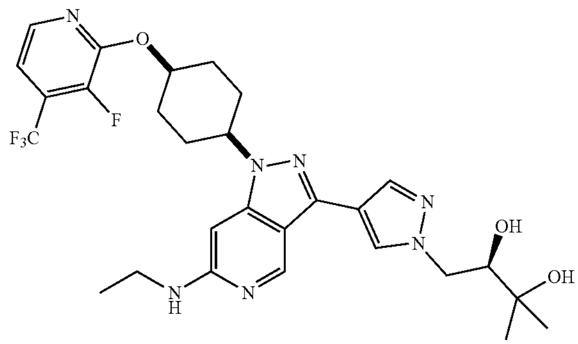 | (R)-1-(4-(6-(ethylamino)-1-((1s,4R)-4-((3-fluoro-4-(trifluoromethyl)pyridin-2-yl)oxy)cyclohexyl)-1H-pyrazolo[4,3-c]pyridin-3-yl)-1H-pyrazol-1-yl)-3-methylbutane-2,3-diol | Mass spectrum (apci) m/z = 592.3 |
| 238 | 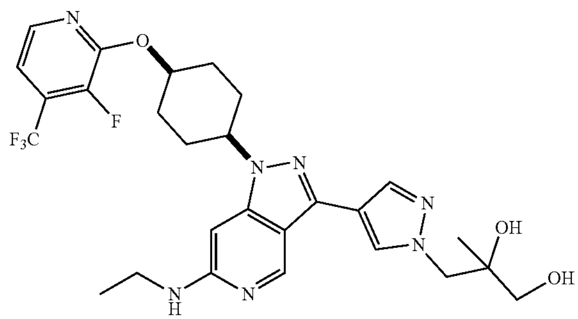 | 3-(4-(6-(ethylamino)-1-((1s,4s)-4-((3-fluoro-4-(trifluoromethyl)pyridin-2-yl)oxy)cyclohexyl)-1H-pyrazolo[4,3-c]pyridin-3-yl)-1H-pyrazol-1-yl)-2-methylpropane-1,2-diol | Mass spectrum (apci) m/z = 578.2 |
| 239 | 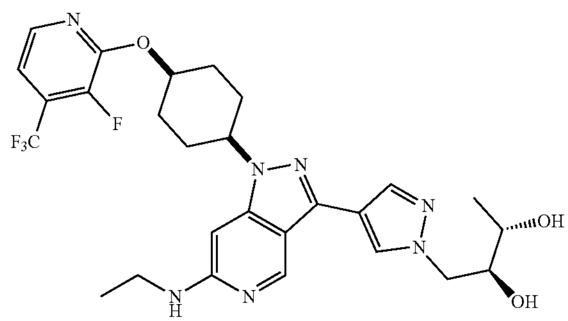 | (2S,3S)-1-(4-(6-(ethylamino)-1-((1s,4R)-4-((3-fluoro-4-(trifluoromethyl)pyridin-2-yl)oxy)cyclohexyl)-1H-pyrazolo[4,3-c]pyridin-3-yl)-1H-pyrazol-1-yl)butane-2,3-diol | Mass spectrum (apci) m/z = 578.2 |

Example 240

(R)-3-(4-(1-((1s,4S)-4-((5-chloro-3-fluoropyridin-2-yl)oxy)cyclohexyl)-6-(ethylamino)-1H-pyrazolo[4,3-c]pyridin-3-yl)-1H-pyrazol-1-yl)propane-1,2-diol

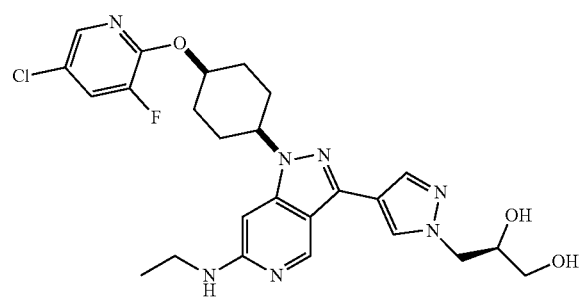

Step A tert-butyl (3-bromo-1-((1r,4r)-4-hydroxycyclohexyl)-1H-pyrazolo[4,3-c]pyridin-6-yl)(ethyl)carbamate (1.0 g, 2.28 mmol), (R)-1-((2,2-dimethyl-1,3-dioxolan-4-yl)methyl)-4-(4,4,5,5-tetramethyl-1,3,2-dioxaborolan-2-yl)-1H-pyrazole (1.40 g, 4.55 mmol) and Pd(PPh₃)₄ (263 mg, 0.23 mmol) were combined in dioxanes (15 mL) and treated with K₂CO₃ (3.41 mL, 2N, 6.83 mmol) and heated to 100° C. overnight. The reaction mixture was partitioned between water (50 mL) and EtOAc (50 mL) and the aqueous layer was extracted with EtOAc (2×30 mL). The combined organic phases were washed with brine (20 mL), dried over Na₂SO₄, filtered and concentrated. The residue was purified over silica gel (30-100% EtOAc/hexanes) to afford tert-butyl (3-(1-(((R)-2,2-dimethyl-1,3-dioxolan-4-yl)methyl)-1H-pyrazol-4-yl)-1-((1r,4R)-4-hydroxycyclohexyl)-1H-pyrazolo[4,3-c]pyridin-6-yl)(ethyl)carbamate (1.30 g, 106% yield).

Step B: A solution of triphenylphosphine (37 mg, 0.14 mmol) in THF (1 mL) was treated with DIAD (28 μL, 0.14 mmol). After stirring for 15 min, tert-butyl (3-(1-(((R)-2,2-dimethyl-1,3-dioxolan-4-yl)methyl)-1H-pyrazol-4-yl)-1-((1r,4R)-4-hydroxycyclohexyl)-1H-pyrazolo[4,3-c]pyridin-6-yl)(ethyl)carbamate (50 mg, 0.09 mmol) was added as a solid, followed by 5-chloro-3-fluoropyridin-2-ol (41 mg, 0.28 mmol) and stirred overnight. The reaction mixture was partitioned between water (10 mL) and EtOAc (10 mL) and the aqueous layer was extracted with EtOAc (2×10 mL). The combined organic phases were washed with brine (10 mL), dried over $Na_2SO_4$, filtered and concentrated. The residue was purified over silica gel (30-80% EtOAc in hexanes) to afford tert-butyl (1-((1s,4S)-4-((5-chloro-3-fluoropyridin-2-yl)oxy)cyclohexyl)-3-(1-(((R)-2,2-dimethyl-1,3-dioxolan-4-yl)methyl)-1H-pyrazol-4-yl)-1H-pyrazolo[4,3-c]pyridin-6-yl)(ethyl)carbamate (54 mg, 87.1% yield).

Step C: A solution of tert-butyl (1-((1s,4S)-4-((5-chloro-3-fluoropyridin-2-yl)oxy)cyclohexyl)-3-(1-(((R)-2,2-dimethyl-1,3-dioxolan-4-yl)methyl)-1H-pyrazol-4-yl)-1H-pyrazolo[4,3-c]pyridin-6-yl)(ethyl)carbamate (54 mg, 0.08 mmol) in MeOH (2 mL) was treated with 4N HCl/dioxanes (2 mL). After 2 h, the reaction was concentrated and the residue purified on preparative HPLC (5-95% ACN/$H_2O$/ 0.1% TFA over 20 min). Clean fractions were combined, concentrated to ½ volume then partitioned between 2N NaOH and DCM, dried over sodium sulfate, filtered and concentrated to afford (R)-3-(4-(1-((1s,4S)-4-((5-chloro-3-fluoropyridin-2-yl)oxy)cyclohexyl)-6-(ethylamino)-1H-pyrazolo[4,3-c]pyridin-3-yl)-1H-pyrazol-1-yl)propane-1,2-diol (15 mg, 35% yield). Mass spectrum (apci) m/z=530.2 (M+H). $^1$H NMR ($CDCl_3$ with $CD3OD$) δ 8.65 (s, 1H), 8.03 (s, 1H), 8.02 (s, 1H), 7.91 (d, J=2.2 Hz, 1H), 7.42 (dd, J=9.4, 2.2 Hz, 1H), 6.14 (s, 1H), 5.43 (m, 1H), 4.45-4.26 (m, 3H), 4.10 (m, 1H), 3.64-3.54 (m, 2H), 3.28 (q, J=7.0 Hz, 2H), 2.53 (m, 2H), 2.33 (m, 2H), 1.93 (m, 2H), 1.83 (m, 2H), 1.35 (t, J=7.0 Hz, 3H).

Using the procedure described for the preparation of Example 240, the following compounds were also synthesized:

| Example | Structure | Name | Data |
|---|---|---|---|
| 241 | 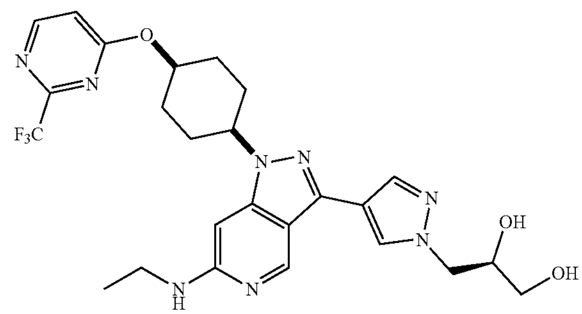 | (R)-3-(4-(6-(ethylamino)-1-((1s,4S)-4-((2-(trifluoromethyl)pyrimidin-4-yl)oxy)cyclohexyl)-1H-pyrazolo[4,3-c]pyridin-3-yl)-1H-pyrazol-1-yl)propane-1,2-diol | Mass spectrum (apci) m/z = 547.3 |
| 242 | 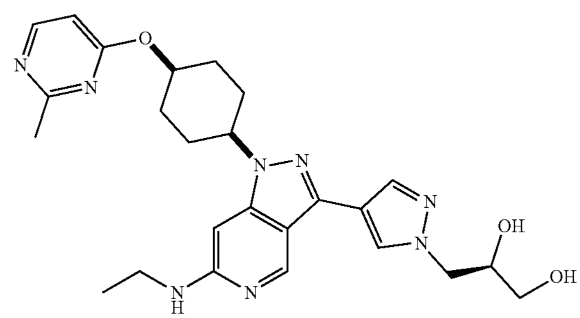 | (R)-3-(4-(6-(ethylamino)-1-((1s,4S)-4-((2-methylpyrimidin-4-yl)oxy)cyclohexyl)-1H-pyrazolo[4,3-c]pyridin-3-yl)-1H-pyrazol-1-yl)propane-1,2-diol | Mass spectrum (apci) m/z = 493.2 |
| 243 | 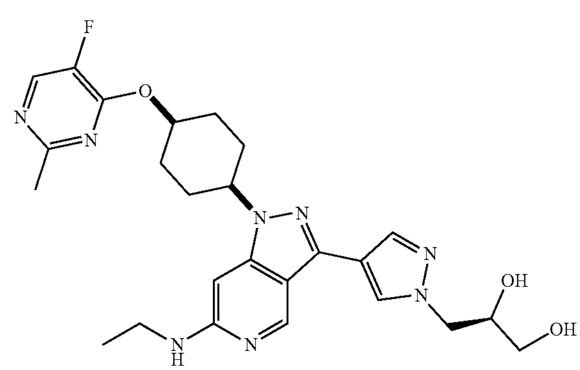 | (R)-3-(4-(6-(ethylamino)-1-((1s,4S)-4-((5-fluoro-2-methylpyrimidin-4-yl)oxy)cyclohexyl)-1H-pyrazolo[4,3-c]pyridin-3-yl)-1H-pyrazol-1-yl)propane-1,2-diol | Mass spectrum (apci) m/z = 511.3 |

-continued

| Example | Structure | Name | Data |
|---|---|---|---|
| 244 | 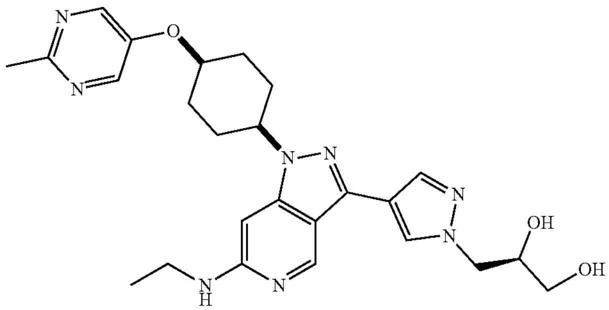 | (R)-3-(4-(6-(ethylamino)-1-((1s,4S)-4-((2-methylpyrimidin-5-yl)oxy)cyclohexyl)-1H-pyrazolo[4,3-c]pyridin-3-yl)-1H-pyrazol-1-yl)propane-1,2-diol | Mass spectrum (apci) m/z = 493.2 |
| 245 | 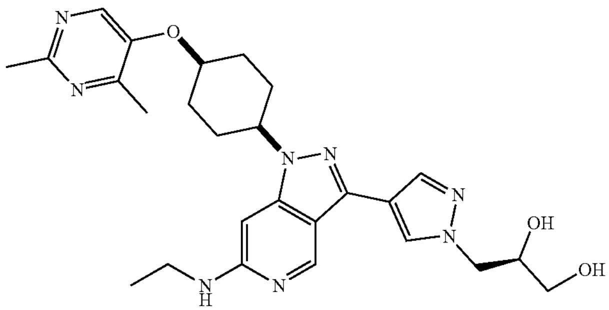 | (R)-3-(4-(1-((1s,4S)-4-((2,4-dimethylpyrimidin-5-yl)oxy)cyclohexyl)-6-(ethylamino)-1H-pyrazolo[4,3-c]pyridin-3-yl)-1H-pyrazol-1-yl)propane-1,2-diol | Mass spectrum (apci) m/z = 507.3 |
| 246 | 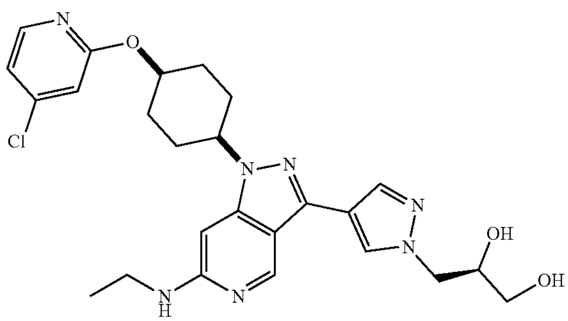 | (R)-3-(4-(1-((1s,4S)-4-((4-chloropyridin-2-yl)oxy)cyclohexyl)-6-(ethylamino)-1H-pyrazolo[4,3-c]pyridin-3-yl)-1H-pyrazol-1-yl)propane-1,2-diol | Mass spectrum (apci) m/z = 512.2 |
| 247 | 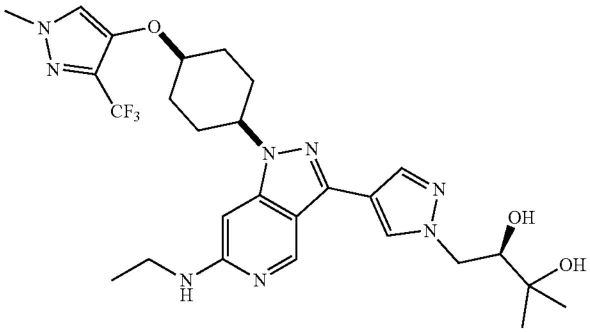 | (R)-1-(4-(6-(ethylamino)-1-((1s,4S)-4-((1-methyl-3-(trifluoromethyl)-1H-pyrazol-4-yl)oxy)cyclohexyl)-1H-pyrazolo[4,3-c]pyridin-3-yl)-1H-pyrazol-1-yl)-3-methylbutane-2,3-diol | Mass spectrum (apci) m/z = 577.3 |

Example 248

2-(4-(6-(ethylamino)-1-((1s,4s)-4-((3-fluoro-4-(trifluoromethyl)pyridin-2-yl)oxy)cyclohexyl)-1H-pyrazolo[4,3-c]pyridin-3-yl)-1H-pyrazol-1-yl)acetamide

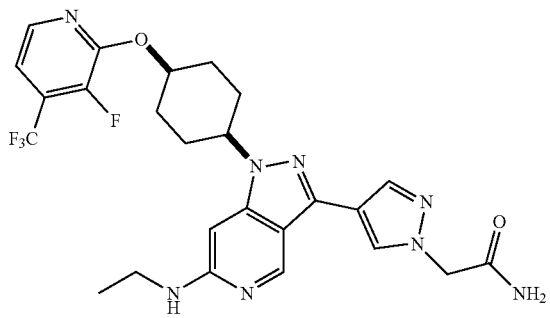

Step A: A solution of triphenylphosphine (896 mg, 3.41 mmol) in THF (20 mL) was cooled to 0° C. and treated with DIAD (673 µL, 3.41 mmol). The mixture was stirred for 15 min, then tert-butyl (3-bromo-1-((1r,4r)-4-hydroxycyclohexyl)-1H-pyrazolo[4,3-c]pyridin-6-yl)(ethyl)carbamate (1.0 g, 2.28 mmol) was added as a solid, followed by a solution of 3-fluoro-4-(trifluoromethyl)pyridin-2-ol (824 mg, 4.55 mmol) in THF (5 mL) over 5 min. The mixture was allowed to warm slowly to RT overnight. The reaction mixture was partitioned between water (100 mL) and EtOAc (100 mL) and the aqueous layer was extracted with EtOAc (2×30 mL). The combined organic phases were washed with brine (30 mL), dried over $Na_2SO_4$, filtered and concentrated. The residue was purified over silica gel (10-40% EtOAc/hexanes) to afford tert-butyl (3-bromo-1-((1s,4s)-4-((3-fluoro-4-(trifluoromethyl)pyridin-2-yl)oxy)cyclohexyl)-1H-pyrazolo[4,3-c]pyridin-6-yl)(ethyl)carbamate (729 mg, 53.2% yield).

Step B: tert-butyl (3-bromo-1-((1s,4s)-4-((3-fluoro-4-(trifluoromethyl)pyridin-2-yl)oxy)cyclohexyl)-1H-pyrazolo[4,3-c]pyridin-6-yl)(ethyl)carbamate (50 mg, 0.083 mmol), 2-(4-(4,4,5,5-tetramethyl-1,3,2-dioxaborolan-2-yl)-1H-pyrazol-1-yl)acetamide (42 mg, 0.166 mmol) and $Pd(PPh_3)_4$ (10 mg, 0.0083 mmol) were combined in dioxane (2 mL) and treated with $K_2CO_3$ (125 µL, 0.249 mmol) and heated to 100° C. overnight. The reaction mixture was partitioned between water (50 mL) and EtOAc (30 mL) and the aqueous layer was extracted with EtOAc (2×30 mL). The combined organic phases were washed with brine (100 mL), dried over $Na_2SO_4$, filtered and concentrated. The residue was purified over silica gel (0-8% MeOH in DCM) to afford tert-butyl (3-(1-(2-amino-2-oxoethyl)-1H-pyrazol-4-yl)-1-((1s,4s)-4-((3-fluoro-4-(trifluoromethyl)pyridin-2-yl)oxy)cyclohexyl)-1H-pyrazolo[4,3-c]pyridin-6-yl)(ethyl)carbamate (36.5 mg, 68% yield).

Step C: tert-butyl (3-(1-(2-amino-2-oxoethyl)-1H-pyrazol-4-yl)-1-((1s,4s)-4-((3-fluoro-4-(trifluoromethyl)pyridin-2-yl)oxy)cyclohexyl)-1H-pyrazolo[4,3-c]pyridin-6-yl)(ethyl)carbamate (36.5 mg, 0.0564 mmol) was dissolved in MeOH (2 mL) and treated with 4N HCl/dioxane (2 mL). After 1 h the reaction was concentrated and purified by reverse phase chromatography (5 to 95% ACN in water with 0.1% TFA). The product containing fractions were partitioned between 2 N NaOH and DCM, extracted with DCM (3×15 mL), washed with brine (15 mL), dried over sodium sulfate, filtered and concentrated to afford 2-(4-(6-(ethylamino)-1-((1s,4s)-4-((3-fluoro-4-(trifluoromethyl)pyridin-2-yl)oxy)cyclohexyl)-1H-pyrazolo[4,3-c]pyridin-3-yl)-1H-pyrazol-1-yl)acetamide (7.8 mg, 25% yield). Mass spectrum (apci) m/z=547.2 (M+H). $^1$H NMR ($CDCl_3$ with $CD_3OD$) δ 8.66 (d, J=0.8 Hz, 1H), 8.11 (s, 1H), 8.09 (s, 1H), 8.05 (d, J=5.3 Hz, 1H), 7.07 (m, 1H), 6.17 (s, 1H), 5.52 (m, 1H), 4.90 (s, 2H), 4.44 (m, 1H), 3.29 (q, J=7.2 Hz, 2H), 2.57 (m, 2H), 2.36 (m, 2H), 2.00-1.82 (m, 4H), 1.36 (t, J=7.2 Hz, 3H).

Using the procedure described for the preparation of Example 248, the following compounds were also synthesized:

| Example | Structure | Name | Data |
|---|---|---|---|
| 249 | 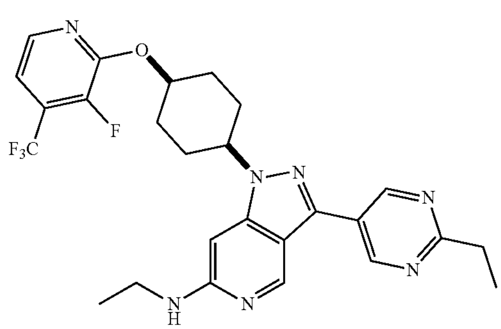 | N-ethyl-3-(2-ethylpyrimidin-5-yl)-1-((1s,4s)-4-((3-fluoro-4-(trifluoromethyl)pyridin-2-yl)oxy)cyclohexyl)-1H-pyrazolo[4,3-c]pyridin-6-amine | Mass spectrum (apci) m/z = 530.2 |

| Example | Name | Data |
|---|---|---|
| 250 | 3-(2-ethoxypyrimidin-5-yl)-N-ethyl-1-((1s,4s)-4-((3-fluoro-4-(trifluoromethyl)pyridin-2-yl)oxy)cyclohexyl)-1H-pyrazolo[4,3-c]pyridin-6-amine | Mass spectrum (apci) m/z = 546.2 |
| 251 | N-ethyl-1-((1s,4s)-4-((3-fluoro-4-(trifluoromethyl)pyridin-2-yl)oxy)cyclohexyl)-3-(2-(isopropylamino)pyrimidin-5-yl)-1H-pyrazolo[4,3-c]pyridin-6-amine | Mass spectrum (apci) m/z = 559.2 |
| 252 | N-ethyl-1-((1s,4s)-4-((3-fluoro-4-(trifluoromethyl)pyridin-2-yl)oxy)cyclohexyl)-3-(2-((2-methoxyethyl)amino)pyrimidin-5-yl)-1H-pyrazolo[4,3-c]pyridin-6-amine | Mass spectrum (apci) m/z = 575.2 |
| 253 | 3-(2-(dimethylamino)pyrimidin-5-yl)-N-ethyl-1((1s,4s)-4-((3-fluoro-4-(trifluoromethyl)pyridin-2-yl)oxy)cyclohexyl)-1H-pyrazolo[4,3-c]pyridin-6-amine | Mass spectrum (apci) m/z = 545.2 |
| 254 | 6-(6-(ethylamino)-1-((1s,4s)-4-(3-fluoro-4-(trifluoromethyl)pyridin-2-yl)oxy)cyclohexyl)-1H-pyrazolo[4,3-c]pyridin-3-yl)-2-methylpyridazin-3(2H)-one hydrochloride | Mass spectrum (apci) m/z = 532.2 |

-continued

| Example | Name | Data |
|---|---|---|
| 255 | tert-butyl ethyl(1-((1s,4s)-4-((3-fluoro-4-(trifluoromethyl)pyridin-2-yl)oxy)cyclohexyl)-3-(1-methyl-1,2,3,6-tetrahydropyridin-4-yl)-1H-pyrazolo[4,3-c]pyridin-6-yl)carbamate | Mass spectrum (apci) m/z = 519.2 |
| 256 | 5-(6-(ethylamino)-1-((1s,4s)-4-((3-fluoro-4-(trifluoromethyl)pyridin-2-yl)oxy)cyclohexyl)-1H-pyrazolo[4,3-c]pyridin-3-yl)-1-methylpyrimidin-2(1H)-one | Mass spectrum (apci) m/z = 519.2 |
| 257 | 5-(6-(ethylamino)-1-((1s,4s)-4-((3-fluoro-4-(trifluoromethyl)pyridin-2-yl)oxy)cyclohexyl)-1H-pyrazolo[4,3-c]pyridin-3-yl)-1-methylpyrazin-2(1H)-one | Mass spectrum (apci) m/z = 532.2 |
| 258 | 2-(4-(6-(ethylamino)-1-((1s,4s)-4-((3-fluoro-4-(trifluoromethyl)pyridin-2-yl)oxy)cyclohexyl)-1H-pyrazolo[4,3-c]pyridin-3-yl)-1H-pyrazol-1-yl)-N-methylacetamide | Mass spectrum (apci) m/z = 561.2 |
| 259 | 2-(4-(6-(ethylamino)-1-((1s,4s)-4-((3-fluoro-4-(trifluoromethyl)pyridin-2-yl)oxy)cyclohexyl)-1H-pyrazolo[4,3-c]pyridin-3-yl)-1H-pyrazol-1-yl)-N,N-dimethylacetamide | Mass spectrum (apci) m/z = 575.2 |

-continued

| Example | Structure | Name | Data |
|---|---|---|---|
| 260 | 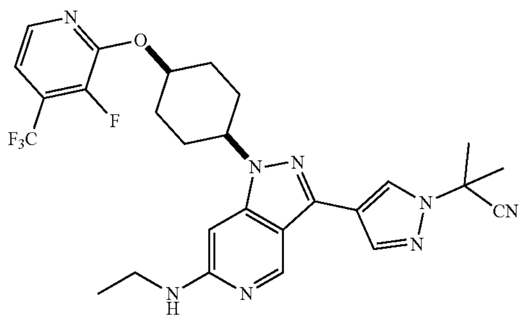 | 2-(4-(6-(ethylamino)-1-((1s,4s)-4-((3-fluoro-4-(trifluoromethyl)pyridin-2-yl)oxy)cyclohexyl)-1H-pyrazolo[4,3-c]pyridin-3-yl)-1H-pyrazol-1-yl)-2-methylpropanenitrile | Mass spectrum (apci) m/z = 557.2 |
| 261 | 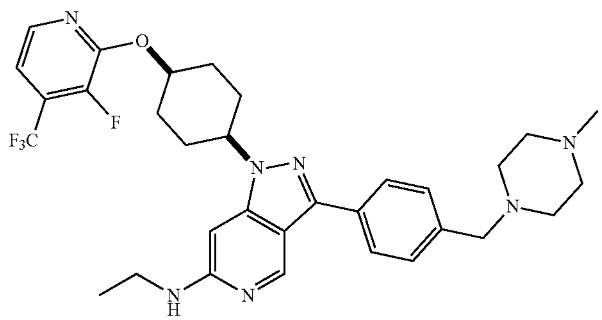 | N-ethyl-1-((1s,4s)-4-((3-fluoro-4-(trifluoromethyl)pyridin-2-yl)oxy)cyclohexyl)-3-(4-((4-methylpiperazin-1-yl)methyl)phenyl)-1H-pyrazolo[4,3-c]pyridin-6-amine | Mass spectrum (apci) m/z = 612.3 |
| 262 | 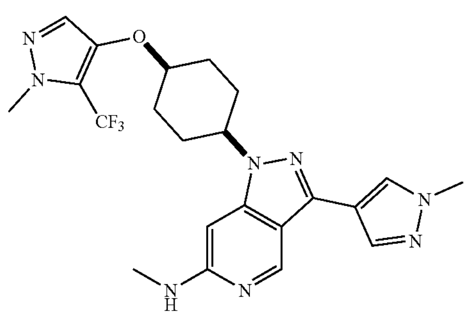 | N-methyl-3-(1-methyl-1H-pyrazol-4-yl)-1-((1s,4s)-4-((1-methyl-5-(trifluoromethyl)-1H-pyrazol-4-yl)oxy)cyclohexyl)-1H-pyrazolo[4,3-c]pyridin-6-amine | Mass spectrum (apci) m/z = 475.2 |
| 263 | 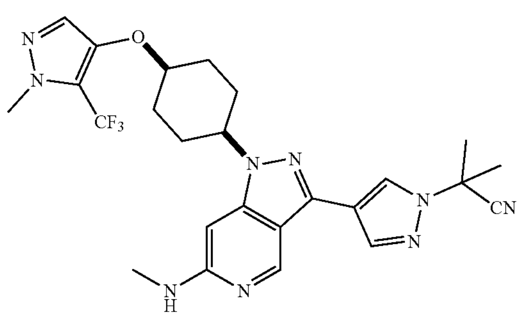 | 2-methyl-2-(4-(1-((1s,4s)-4-((1-methyl-5-(trifluoromethyl)-1H-pyrazol-4-yl)oxy)cyclohexyl)-6-(methylamino)-1H-pyrazolo[4,3-c]pyridin-3-yl)-1H-pyrazol-1-yl)propanenitrile | Mass spectrum (apci) m/z = 528.2 |
| 264 | 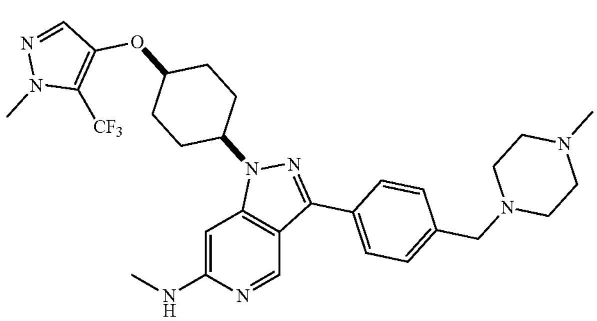 | N-methyl-1-((1s,4s)-4-((1-methyl-5-(trifluoromethyl)-1H-pyrazol-4-yl)oxy)cyclohexyl)-3-(4-((4-methylpiperazin-1-yl)methyl)phenyl)-1H-pyrazolo[4,3-c]pyridin-6-amine | Mass spectrum (apci) m/z = 583.3 |

| Example | Structure | Name | Data |
|---|---|---|---|
| 265 | 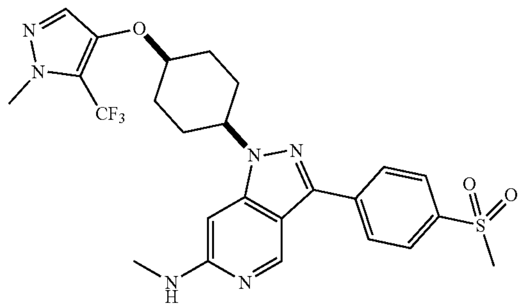 | N-methyl-1-((1s,4s)-4-((1-methyl-5-(trifluoromethyl)-1H-pyrazol-4-yl)oxy)cyclohexyl)-3-(4-(methylsulfonyl)phenyl)-1H-pyrazolo[4,3-c]pyridin-6-amine | Mass spectrum (apci) m/z = 549.2 |
| 266 | 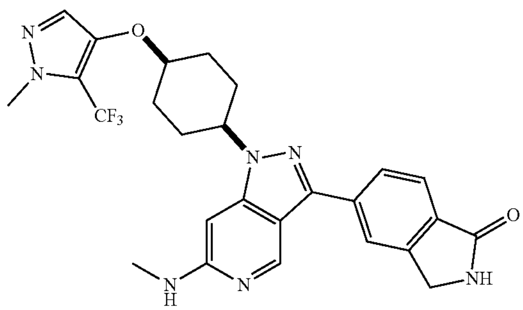 | 5-(1-((1s,4s)-4-((1-methyl-5-(trifluoromethyl)-1H-pyrazol-4-yl)oxy)cyclohexyl)-6-(methylamino)-1H-pyrazolo[4,3-c]pyridin-3-yl)isoindolin-1-one | Mass spectrum (apci) m/z = 526.2 |
| 267 | 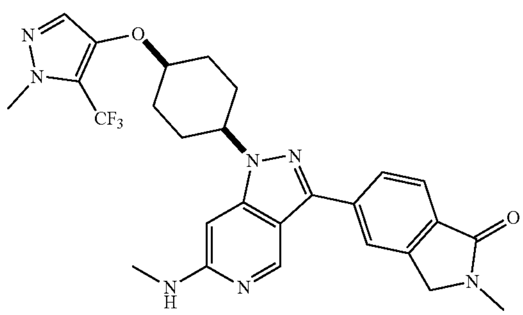 | 2-methyl-5-(1-((1s,4s)-4-((1-methyl-5-(trifluoromethyl)-1H-pyrazol-4-yl)oxy)cyclohexyl)-6-(methylamino)-1H-pyrazolo[4,3-c]pyridin-3-yl)isoindolin-1-one | Mass spectrum (apci) m/z = 540.2 |
| 268 | 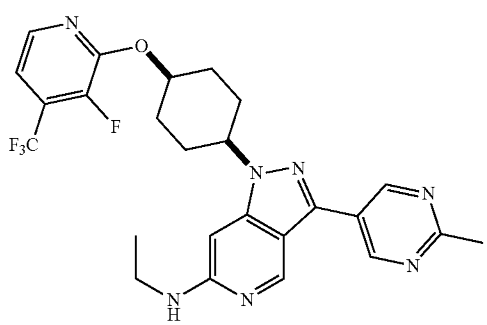 | N-ethyl-1-((1s,4s)-4-((3-fluoro-4-(trifluoromethyl)pyridin-2-yl)oxy)cyclohexyl)-3-(2-methylpyrimidin-5-yl)-1H-pyrazolo[4,3-c]pyridin-6-amine | Mass spectrum (apci) m/z = 516.2 |
| 269 | 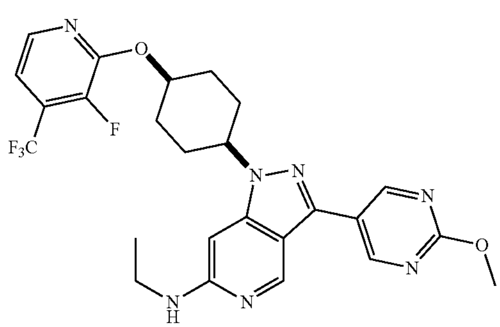 | N-ethyl-1-((1s,4s)-4-((3-fluoro-4-(trifluoromethyl)pyridin-2-yl)oxy)cyclohexyl)-3-(2-methoxypyrimidin-5-yl)-1H-pyrazolo[4,3-c]pyridin-6-amine | Mass spectrum (apci) m/z = 532.2 |

| Example | Structure | Name | Data |
|---|---|---|---|
| 270 | 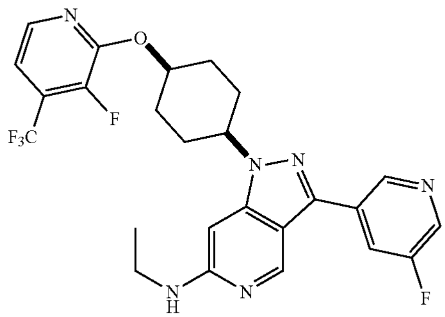 | N-ethyl-1-((1s,4s)-4-((3-fluoro-4-(trifluoromethyl)pyridin-2-yl)oxy)cyclohexyl)-3-(5-fluoropyridin-3-yl)-1H-pyrazolo[4,3-c]pyridin-6-amine | Mass spectrum (apci) m/z = 519.2 |
| 271 | 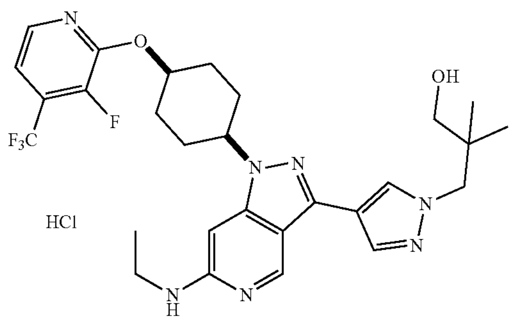 | 3-(4-(6-(ethylamino)-1-((1s,4s)-4-((3-fluoro-4-(trifluoromethyl)pyridin-2-yl)oxy)cyclohexyl)-1H-pyrazolo[4,3-c]pyridin-3-yl)-1H-pyrazol-1-yl)-2,2-dimethylpropan-1-ol hydrochloride | Mass spectrum (apci) m/z = 576.3 |
| 272 | 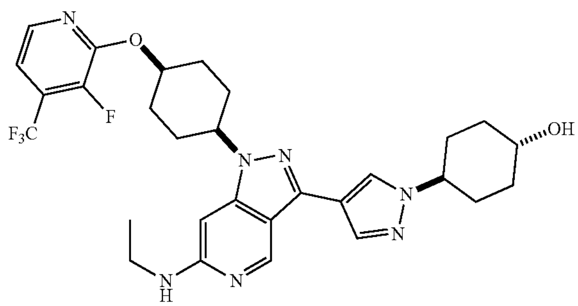 | (1R,4r)-4-(4-(6-(ethylamino)-1-((1s,4S)-4-((3-fluoro-4-(trifluoromethyl)pyridin-2-yl)oxy)cyclohexyl)-1H-pyrazolo[4,3-c]pyridin-3-yl)-1H-pyrazol-1-yl)cyclohexan-1-ol | Mass spectrum (apci) m/z = 588.3 |
| 273 | 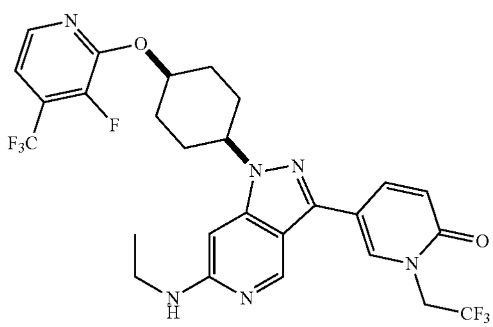 | 5-(6-(ethylamino)-1-((1s,4s)-4-((3-fluoro-4-(trifluoromethyl)pyridin-2-yl)oxy)cyclohexyl)-1H-pyrazolo[4,3-c]pyridin-3-yl)-1-(2,2,2-trifluoroethyl)pyridin-2(1H)-one | Mass spectrum (apci) m/z = 599.2 |
| 274 | 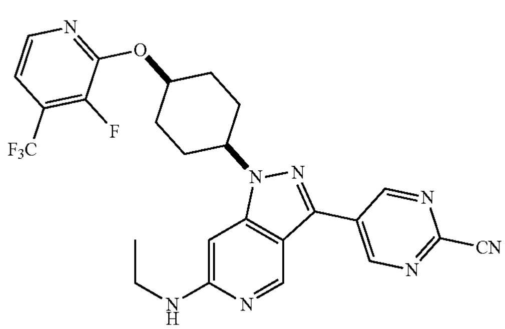 | 5-(6-(ethylamino)-1-((1s,4s)-4-((3-fluoro-4-(trifluoromethyl)pyridin-2-yl)oxy)cyclohexyl)-1H-pyrazolo[4,3-c]pyridin-3-yl)pyrimidine-2-carbonitrile | Mass spectrum (apci) m/z = 527.2 |

Example 275

(3-(((1s,4s)-4-(3-(1-methyl-1H-pyrazol-4-yl)-6-(methylamino)-1H-pyrazolo[4,3-c]pyridin-1-yl)cyclohexyl)oxy)pyridin-2-yl)methanol

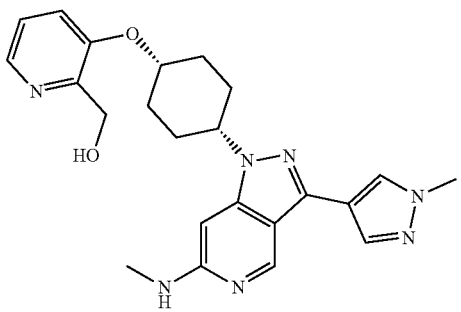 [SMILES: CNc1cc2c(cn1)c(-c1cnn(C)c1)nn2[C@H]1CC[C@@H](Oc2cccnc2CO)CC1]

NaBH$_4$ (0.0017 g, 0.046 mmol) was added to methyl 3-(((1s,4s)-4-(3-(1-methyl-1H-pyrazol-4-yl)-6-(methylamino)-1H-pyrazolo[4,3-c]pyridin-1-yl)cyclohexyl)oxy)picolinate (0.021 g, 0.046 mmol) in MeOH (0.46 mL) and stirred overnight. An additional equivalent of NaBH$_4$ was added stirred for 2 h. The reaction mixture was partitioned between DCM and water, washed with brine, dried over Na$_2$SO$_4$, filtered and concentrated. The residue was purified on preparative HPLC (water:ACN 5-95% with 0.1% TFA). The product containing fractions were partitioned between DCM and saturated NaHCO$_3$, washed with brine, dried over sodium sulfate, filtered and concentrated to afford (3-(((1s,4s)-4-(3-(1-methyl-1H-pyrazol-4-yl)-6-(methylamino)-1H-pyrazolo[4,3-c]pyridin-1-yl)cyclohexyl)oxy)pyridin-2-yl)methanol (0.004 g, 0.0092 mmol, 20% yield). Mass spectrum (apci) m/z=434.3 (M+H). $^1$H NMR (CDCl$_3$) δ 8.65 (s, 1H), 8.19 (dd, J=4.1, 1.4 Hz, 1H), 7.98 (s, 1H), 7.97 (s, 1H), 7.23-7.16 (m, 2H), 6.07 (s, 1H), 4.98 (s, 2H), 4.74 (m, 1H), 4.36 (tt, J=11.9, 3.9 Hz, 1H), 4.01 (s, 3H), 2.98 (s, 3H), 2.50 (m, 2H), 2.31 (m, 2H), 1.95-1.77 (m, 4H).

Example 276

N-methyl-3-(((1s,4s)-4-(3-(1-methyl-1H-pyrazol-4-yl)-6-(methylamino)-1H-pyrazolo[4,3-c]pyridin-1-yl)cyclohexyl)oxy)picolinamide

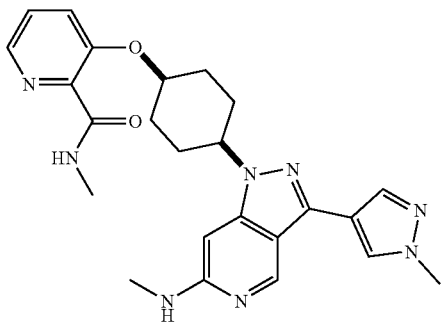

Step A: tert-butyl (1-((1r,4r)-4-hydroxycyclohexyl)-3-(1-methyl-1H-pyrazol-4-yl)-1H-pyrazolo[4,3-c]pyridin-6-yl)(methyl)carbamate (65 mg, 0.15 mmol), methyl 3-hydroxypicolinate (30 mg, 0.20 mmol) and PPh$_3$ (44 mg, 0.17 mmol) were diluted with THF (1 mL) followed by the addition of DIAD (33 μL, 0.17 mmol). After stirring for 12 hours, the reaction was partitioned between ethyl acetate and water, dried over MgSO$_4$, filtered and concentrated. The residue was purified over silica gel (10-60% ethyl acetate/hexanes) to afford methyl 3-(((1s,4s)-4-(6-((tert-butoxycarbonyl)(methyl)amino)-3-(1-methyl-1H-pyrazol-4-yl)-1H-pyrazolo[4,3-c]pyridin-1-yl)cyclohexyl)oxy)picolinate (68 mg, 0.12 mmol, 79% yield).

Step B: methyl 3-(((1s,4s)-4-(6-((tert-butoxycarbonyl)(methyl)amino)-3-(1-methyl-1H-pyrazol-4-yl)-1H-pyrazolo[4,3-c]pyridin-1-yl)cyclohexyl)oxy)picolinate (33 mg, 0.059 mmol) was diluted with methanol (300 μL) followed by the addition of 2M LiOH (176 μL, 0.35 mmol). After stirring for 12 hours, the reaction was diluted with 176 μL of 2N HCl. The reaction mixture was concentrated to afford 3-(((1s,4s)-4-(6-((tert-butoxycarbonyl)(methyl)amino)-3-(1-methyl-1H-pyrazol-4-yl)-1H-pyrazolo[4,3-c]pyridin-1-yl)cyclohexyl)oxy)picolinic acid (32 mg, 0.058 mmol, 99% yield) which was used crude in the next step.

Step C: 3-(((1s,4s)-4-(6-((tert-butoxycarbonyl)(methyl)amino)-3-(1-methyl-1H-pyrazol-4-yl)-1H-pyrazolo[4,3-c]pyridin-1-yl)cyclohexyl)oxy)picolinic acid (12 mg, 0.022 mmol), HATU (10.0 mg, 0.026 mmol) and 2M dimethylamine (22 μL, 0.044 mmol) were dissolved in DMF (0.5 mL) followed by the addition of DIEA (11 μL, 0.066 mmol). After 12 h, the reaction was partitioned between ethyl acetate and water, dried over MgSO$_4$, filtered and concentrated to afford tert-butyl (1-((1s,4s)-4-((2-(dimethylcarbamoyl)pyridin-3-yl)oxy)cyclohexyl)-3-(1-methyl-1H-pyrazol-4-yl)-1H-pyrazolo[4,3-c]pyridin-6-yl)(methyl)carbamate (13 mg, 0.023 mmol, 103% yield) which was used crude in the next step.

Step D: tert-butyl methyl(3-(1-methyl-1H-pyrazol-4-yl)-1-((1s,4s)-4-((2-(methylcarbamoyl)pyridin-3-yl)oxy)cyclohexyl)-1H-pyrazolo[4,3-c]pyridin-6-yl)carbamate (10 mg, 0.018 mmol) was diluted with DCM (1 mL) followed by the addition of TFA (1 mL). After stirring for 3 hours, the reaction was concentrated. The reaction mixture was partitioned between ethyl acetate and saturated sodium bicarbonate, dried over MgSO$_4$, filtered and concentrated. The residue was purified over silica gel (10% methanol/DCM) to afford N-methyl-3-(((1s,4s)-4-(3-(1-methyl-1H-pyrazol-4-yl)-6-(methylamino)-1H-pyrazolo[4,3-c]pyridin-1-yl)cyclohexyl)oxy)picolinamide (5.0 mg, 0.011 mmol, 61% yield). Mass spectrum (apci) m/z=461.2 (M+H). $^1$H NMR (CDCl$_3$) δ 8.69 (s, 1H), 8.24 (dd, J=4.3, 1.0 Hz, 1H), 7.98 (s, 1H), 7.87 (s, 1H), 7.77 (br s, 1H), 7.43 (dd, J=8.2, 1.2 Hz, 1H), 7.38 (dd, J=8.2, 4.1 Hz, 1H), 6.60 (s, 1H), 4.79 (m, 1H), 4.46 (tt, J=12.1, 3.9 Hz, 1H), 3.99 (s, 3H), 3.05 (m, 6H), 2.70 (m, 2H), 2.34 (m, 2H), 1.94 (m, 2H), 1.81 (m, 2H).

Using the procedure described for the preparation of Example 276, the following compound was also synthesized:

| Example | Structure | Name | Data |
|---|---|---|---|
| 277 | 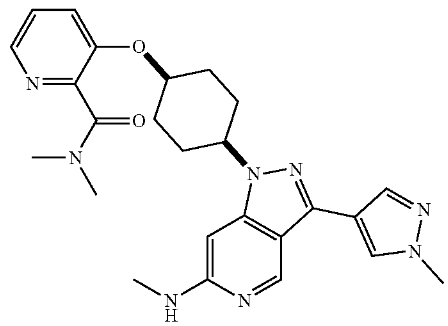 | N,N-dimethyl-3-(((1s,4s)-4-(3-(1-methyl-1H-pyrazol-4-yl)-6-(methylamino)-1H-pyrazolo[4,3-c]pyridin-1-yl)cyclohexyl)oxy)picolinamide | Mass spectrum (apci) m/z = 475.3 |

Example 278

2-methyl-2-(4-(1-((1s,4s)-4-((1-methyl-1H-pyrazol-4-yl)oxy)cyclohexyl)-6-(methylamino)-1H-pyrazolo[4,3-c]pyridin-3-yl)-1H-pyrazol-1-yl)propanenitrile

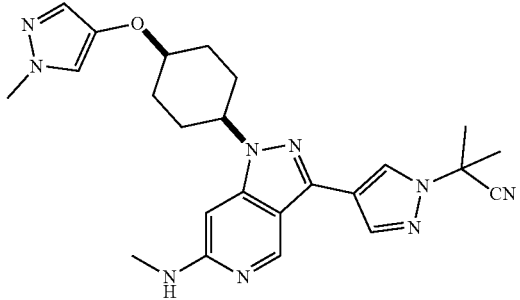

Step A: tert-butyl (3-bromo-1H-pyrazolo[4,3-c]pyridin-6-yl)(methyl)carbamate (0.5155 g, 1.576 mmol) was dissolved in DMF (7.8 mL) and Cs$_2$CO$_3$ (1.027 g, 3.151 mmol) was added and stirred for 30 minutes. (1r,4r)-4-((1-methyl-1H-pyrazol-4-yl)oxy)cyclohexyl 4-methylbenzenesulfonate (0.6073 g, 1.733 mmol) was added and heated to 60° C. overnight. The reaction mixture was filtered through GF filter paper, diluted with MTBE (40 mL), washed with brine (3×20 mL), dried over MgSO$_4$, filtered and concentrated. The residue was purified over silica gel (0-10% MeOH in DCM) to afford tert-butyl (3-bromo-1-((1s,4s)-4-((1-methyl-1H-pyrazol-4-yl)oxy)cyclohexyl)-1H-pyrazolo[4,3-c]pyridin-6-yl)(methyl)carbamate (778 mg, 97.7% yield).

Step B: To a mixture of tert-butyl (3-bromo-1-((1s,4s)-4-((1-methyl-1H-pyrazol-4-yl)oxy)cyclohexyl)-1H-pyrazolo[4,3-c]pyridin-6-yl)(methyl)carbamate (0.778 g, 1.539 mmol) and 2-methyl-2-(4-(4,4,5,5-tetramethyl-1,3,2-dioxaborolan-2-yl)-1H-pyrazol-1-yl)propanenitrile (0.4221 g, 1.616 mmol) in dioxane (7.7 mL) was added tetrakis(triphenylphosphine)palladium (0) (0.1779 g, 0.1539 mmol) followed by 2M K$_2$CO$_3$ (4.618 mL, 9.236 mmol). The reaction mixture was heated to 90° C. for 4 h. The reaction mixture was partitioned between DCM and brine, dried over MgSO$_4$, filtered and concentrated. The residue was purified over silica gel (0-10% MeOH in DCM) to afford tert-butyl (3-(1-(2-cyanopropan-2-yl)-1H-pyrazol-4-yl)-1-((1s,4s)-4-((1-methyl-1H-pyrazol-4-yl)oxy)cyclohexyl)-1H-pyrazolo[4,3-c]pyridin-6-yl)(methyl)carbamate (801 mg, 93% yield).

Step C: tert-butyl (3-(1-(2-cyanopropan-2-yl)-1H-pyrazol-4-yl)-1-((1s,4s)-4-((1-methyl-1H-pyrazol-4-yl)oxy)cyclohexyl)-1H-pyrazolo[4,3-c]pyridin-6-yl)(methyl)carbamate (0.8012 g, 1.432 mmol) was dissolved into CH$_2$Cl$_2$ (5 mL) then 4N HCl in dioxane was added (5 mL) and stirred for 4 h. The reaction mixture was concentrated and partitioned between DCM and 2M Na$_2$CO$_3$, dried over MgSO$_4$, filtered and concentrated. The residue was purified over silica gel (0-10% MeOH in DCM) to afford 2-methyl-2-(4-(1-((1s,4s)-4-((1-methyl-1H-pyrazol-4-yl)oxy)cyclohexyl)-6-(methylamino)-1H-pyrazolo[4,3-c]pyridin-3-yl)-1H-pyrazol-1-yl)propanenitrile (182 mg, 27.8% yield). Mass spectrum (apci) m/z=460.2 (M+H). $^1$H NMR (CDCl$_3$) δ 8.71 (d, J=0.8 Hz, 1H), 8.16 (s, 1H), 8.10 (s, 1h), 7.28 (s, 1H), 7.14 (s, 1H), 6.07 (d, J=0.8 Hz, 1H), 4.79 (q, J=5.3 Hz, 1H), 4.33 (tt, J=11.7, 3.9 Hz, 1H), 4.23 (m, 1H), 3.83 (s, 3H), 2.97 (d, J=5.3 Hz, 3H), 2.52 (m, 2H), 2.31 (m, 2H), 2.07 (s, 6H), 1.88 (m, 2H), 1.71 (m, 2H).

Using the procedure described for the preparation of Example 278, the following compounds were also synthesized:

| Example | Structure | Name | Data |
|---|---|---|---|
| 279 | 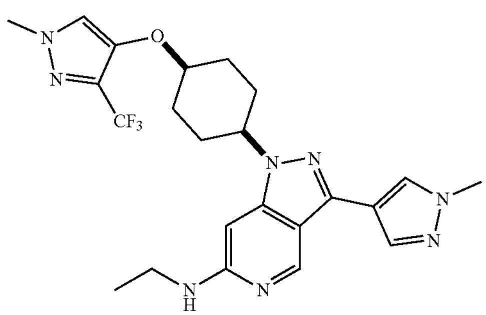 | N-ethyl-3-(1-methyl-1H-pyrazol-4-yl)-1-((1s,4s)-4-((1-methyl-3-(trifluoromethyl)-1H-pyrazol-4-yl)oxy)cyclohexyl)-1H-pyrazolo[4,3-c]pyridin-6-amine | Mass spectrum (apci) m/z = 489.2 |

| Example | Structure | Name | Data |
|---|---|---|---|
| 280 | 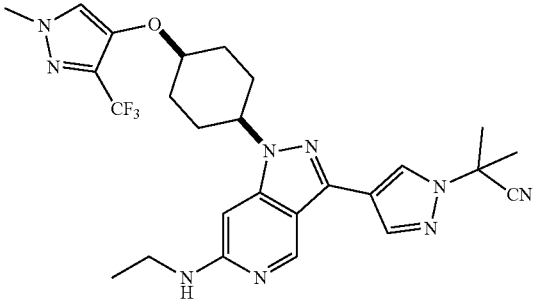 | 2-(4-(6-(ethylamino)-1-((1s,4s)-4-((1-methyl-3-(trifluoromethyl)-1H-pyrazol-4-yl)oxy)cyclohexyl)-1H-pyrazolo[4,3-c]pyridin-3-yl)-1H-pyrazol-1-yl)-2-methylpropanenitrile | Mass spectrum (apci) m/z = 542.2 |
| 281 | 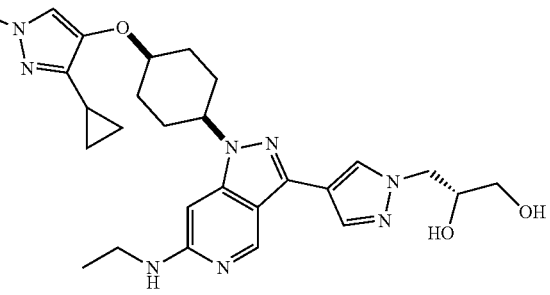 | ®-3-(4-(1-((1s,4S)-4-((3-cyclopropyl-1-methyl-1H-pyrazol-4-yl)oxy)cyclohexyl)-6-(ethylamino)-1H-pyrazolo[4,3-c]pyridin-3-yl)-1H-pyrazol-1-yl)propane-1,2-diol | Mass spectrum (apci) m/z = 521.3 |
| 282 | 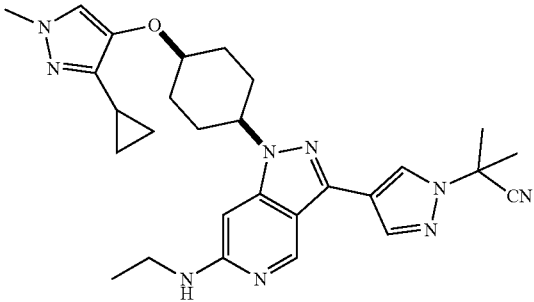 | 2-(4-(1-((1s,4s)-4-((3-cyclopropyl-1-methyl-1H-pyrazol-4-yl)oxy)cyclohexyl)-6-(ethylamino)-1H-pyrazolo[4,3-c]pyridin-3-yl)-1H-pyrazol-1-yl)-2-methylpropanenitrile | Mass spectrum (apci) m/z = 514.3 |
| 283 | 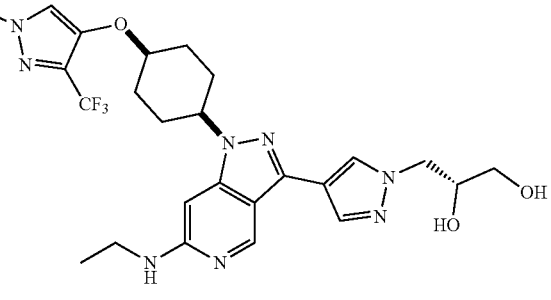 | ®-3-(4-(6-(ethylamino)-1-((1s,4S)-4-((1-methyl-3-(trifluoromethyl)-1H-pyrazol-4-yl)oxy)cyclohexyl)-1H-pyrazolo[4,3-c]pyridin-3-yl)-1H-pyrazol-1-yl)propane-1,2-diol | Mass spectrum (apci) m/z = 549.2 |
| 284 | 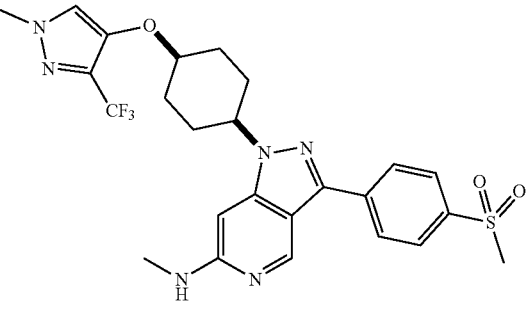 | N-methyl-1-((1s,4s)-4-((1-methyl-3-(trifluoromethyl)-1H-pyrazol-4-yl)oxy)cyclohexyl)-3-(4-(methylsulfonyl)phenyl)-1H-pyrazolo[4,3-c]pyridin-6-amine | Mass spectrum (apci) m/z = 549.2 |

| Example | Structure | Name | Data |
|---|---|---|---|
| 285 | 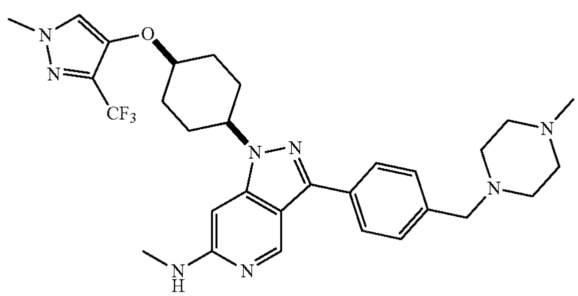 | N-methyl-1-((1s,4s)-4-((1-methyl-3-(trifluoromethyl)-1H-pyrazol-4-yl)oxy)cyclohexyl)-3-(4-((4-methylpiperazin-1-yl)methyl)phenyl)-1H-pyrazolo[4,3-c]pyridin-6-amine | Mass spectrum (apci) m/z = 583.3 |
| 286 | 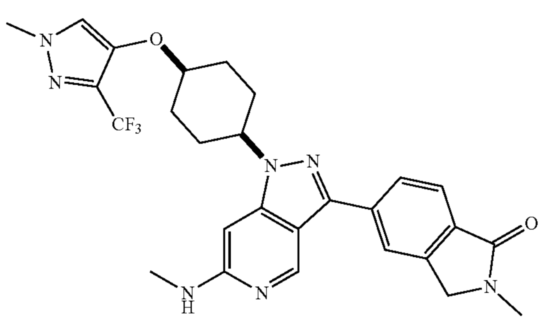 | 2-methyl-5-(1-((1s,4s)-4-((1-methyl-3-(trifluoromethyl)-1H-pyrazol-4-yl)oxy)cyclohexyl)-6-(methylamino)-1H-pyrazolo[4,3-c]pyridin-3-yl)isoindolin-1-one | Mass spectrum (apci) m/z = 540.2 |

Example 287

6-(6-(ethylamino)-1-((1s,4s)-4-((1-methyl-3-(trifluoromethyl)-1H-pyrazol-4-yl)oxy)cyclohexyl)-1H-pyrazolo[4,3-c]pyridin-3-yl)isoindolin-1-one

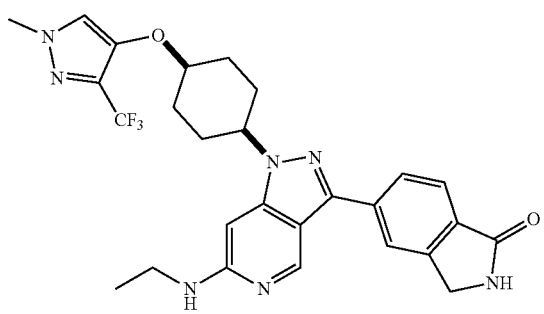

Step A: DIAD (0.1662 mL, 0.8431 mmol) was added to Ph₃P (0.2211 g, 0.8431 mmol) in THF (4.0 mL). To this was added 1-methyl-3-(trifluoromethyl)-1H-pyrazol-4-ol (0.1734 g, 1.044 mmol), followed by (1r,4r)-4-(3-bromo-6-(ethylamino)-1H-pyrazolo[4,3-c]pyridin-1-yl)cyclohexan-1-ol (0.2724 g, 0.8030 mmol) and stirred at 60° C. overnight. The reaction mixture was concentrated and partitioned between DCM and brine, dried over MgSO₄, filtered, then concentrated. The residue was purified over silica gel (0-10% MeOH/DCM) to afford 3-bromo-N-ethyl-1-((1s,4s)-4-((1-methyl-3-(trifluoromethyl)-1H-pyrazol-4-yl)oxy)cyclohexyl)-1H-pyrazolo[4,3-c]pyridin-6-amine (319 mg, 81% yield).

Step B: To a mixture of 3-bromo-N-ethyl-1-((1s,4s)-4-((1-methyl-3-(trifluoromethyl)-1H-pyrazol-4-yl)oxy)cyclohexyl)-1H-pyrazolo[4,3-c]pyridin-6-amine (0.1064 g, 0.2183 mmol) and 5-(4,4,5,5-tetramethyl-1,3,2-dioxaborolan-2-yl)isoindolin-1-one (0.1131 g, 0.4367 mmol) in dioxane (1.1 mL) was added tetrakis(triphenylphosphine)palladium (0) (0.02523 g, 0.02183 mmol) followed by aqueous 2M K₂CO₃ (0.6550 mL, 1.310 mmol) and heated to 90° C. overnight. The reaction mixture was partitioned between DCM and brine, dried over MgSO₄, filtered, then concentrated. The residue was purified over silica gel (0510% MeOH in DCM) to afford 6-(6-(ethylamino)-1-((1s,4s)-4-((1-methyl-3-(trifluoromethyl)-1H-pyrazol-4-yl)oxy)cyclohexyl)-1H-pyrazolo[4,3-c]pyridin-3-yl)isoindolin-1-one (17.1 mg, 14.5% yield). Mass spectrum (apci) m/z=540.2 (M+H). $^1$H NMR (CDCl₃) δ 8.88 (s, 1H), 8.08 (m, 2H), 7.99 (d, J=8.4 Hz, 1H), 7.15 (s, 1H), 6.30 (br s, 1H), 6.16 (s, 1H), 4.70 (m, 1H), 4.55 (s, 2H), 4.44 (tt, J=11.9, 3.7 Hz, 1H), 4.25 (I, 1H), 3.90 (s, 3H), 3.31 (m, 2H), 2.58 (m, 2H), 2.33 (m, 2H), 1.93 (m, 2H), 1.75 (m, 2H), 1.35 (t, J=7.2 Hz, 3H).

Using the procedure described for the preparation of Example 287, the following compounds were also synthesized:

| Example | Structure | Name | Data |
|---|---|---|---|
| 288 | 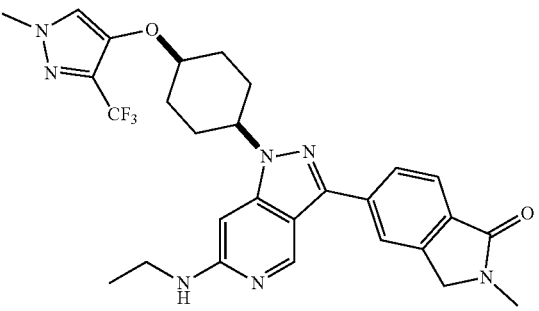 | 5-(6-(ethylamino)-1-((1s,4s)-4-((1-methyl-3-(trifluoromethyl)-1H-pyrazol-4-yl)oxy)cyclohexyl)-1H-pyrazolo[4,3-c]pyridin-3-yl)-2-methylisoindolin-1-one | Mass spectrum (apci) m/z = 554.2 |
| 289 | 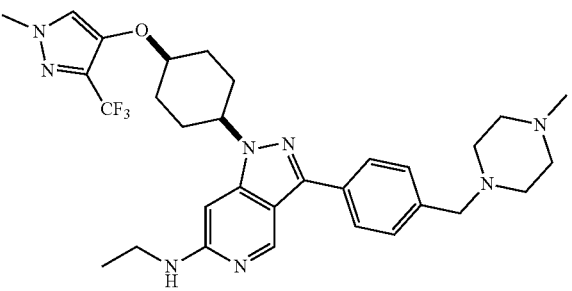 | N-ethyl-1-((1s,4s)-4-((1-methyl-3-(trifluoromethyl)-1H-pyrazol-4-yl)oxy)cyclohexyl)-3-(4-((4-methylpiperazin-1-yl)methyl)phenyl)-1H-pyrazolo[4,3-c]pyridin-6-amine | Mass spectrum (apci) m/z = 597.3 |
| 290 | 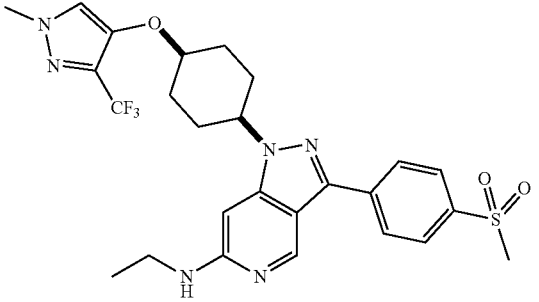 | N-ethyl-1-((1s,4s)-4-((1-methyl-3-(trifluoromethyl)-1H-pyrazol-4-yl)oxy)cyclohexyl)-3-(4-(methylsulfonyl)phenyl)-1H-pyrazolo[4,3-c]pyridin-6-amine | Mass spectrum (apci) m/z = 563.2 |
| 291 | 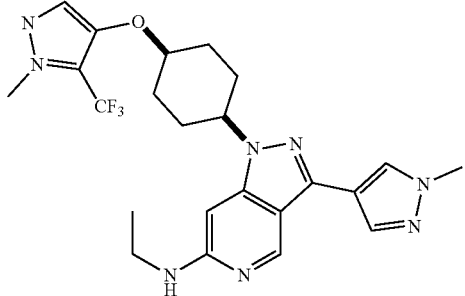 | N-ethyl-3-(1-methyl-1H-pyrazol-4-yl)-1-((1s,4s)-4-((1-methyl-5-(trifluoromethyl)-1H-pyrazol-4-yl)oxy)cyclohexyl)-1H-pyrazolo[4,3-c]pyridin-6-amine | Mass spectrum (apci) m/z = 489.2 |
| 292 | 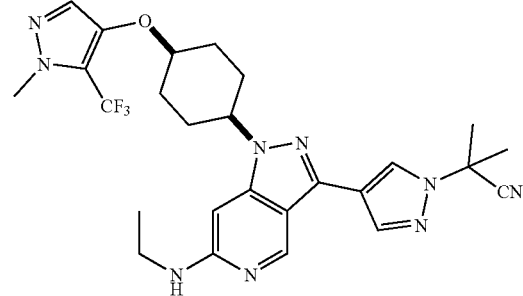 | 2-(4-(6-(ethylamino)-1-((1s,4s)-4-((1-methyl-5-(trifluoromethyl)-1H-pyrazol-4-yl)oxy)cyclohexyl)-1H-pyrazolo[4,3-c]pyridin-3-yl)-1H-pyrazol-1-yl)-2-methylpropanenitrile | Mass spectrum (apci) m/z = 542.3 |

| Example | Structure | Name | Data |
|---|---|---|---|
| 293 | 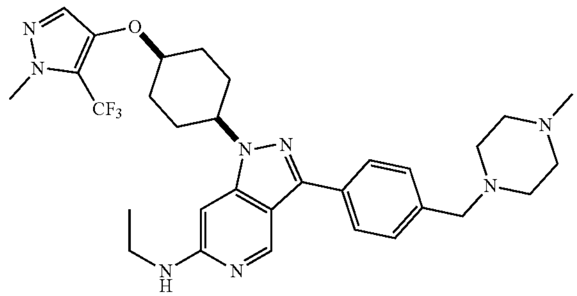 | N-ethyl-1-((1s,4s)-4-((1-methyl-5-(trifluoromethyl)-1H-pyrazol-4-yl)oxy)cyclohexyl)-3-(4-((4-methylpiperazin-1-yl)methyl)phenyl)-1H-pyrazolo[4,3-c]pyridin-6-amine | Mass spectrum (apci) m/z = 597.3 |
| 294 | 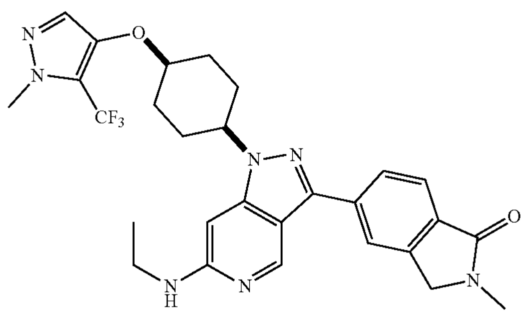 | 5-(6-(ethylamino)-1-((1s,4s)-4-((1-methyl-5-(trifluoromethyl)-1H-pyrazol-4-yl)oxy)cyclohexyl)-1H-pyrazolo[4,3-c]pyridin-3-yl)-2-methylisoindolin-1-one | Mass spectrum (apci) m/z = 554.2 |
| 295 | 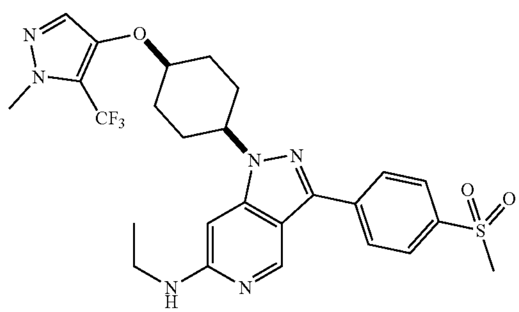 | N-ethyl-1-((1s,4s)-4-((1-methyl-5-(trifluoromethyl)-1H-pyrazol-4-yl)oxy)cyclohexyl)-3-(4-(methylsulfonyl)phenyl)-1H-pyrazolo[4,3-c]pyridin-6-amine | Mass spectrum (apci) m/z = 563.1 |
| 296 | 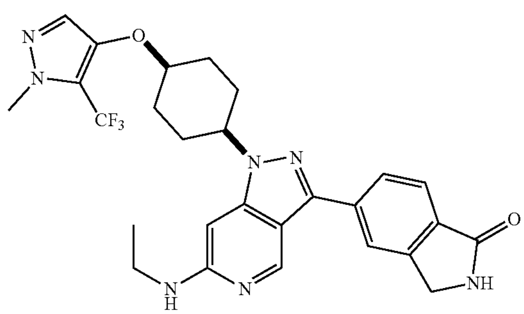 | 5-(6-(ethylamino)-1-((1s,4s)-4-((1-methyl-5-(trifluoromethyl)-1H-pyrazol-4-yl)oxy)cyclohexyl)-1H-pyrazolo[4,3-c]pyridin-3-yl)isoindolin-1-one | Mass spectrum (apci) m/z = 540.2 |
| 297 | 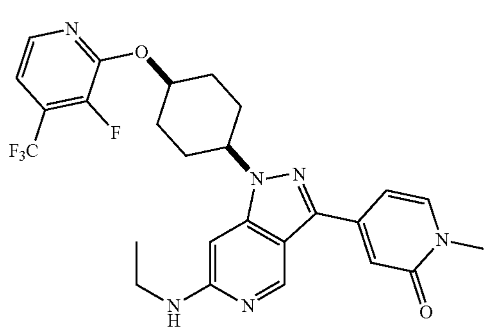 | 4-(6-(ethylamino)-1-((1s,4s)-4-((3-fluoro-4-(trifluoromethyl)pyridin-2-yl)oxy)cyclohexyl)-1H-pyrazolo[4,3-c]pyridin-3-yl)-1-methylpyridin-2(1H)-one | Mass spectrum (apci) m/z = 531.2 |

| Example | Structure | Name | Data |
|---|---|---|---|
| 298 | 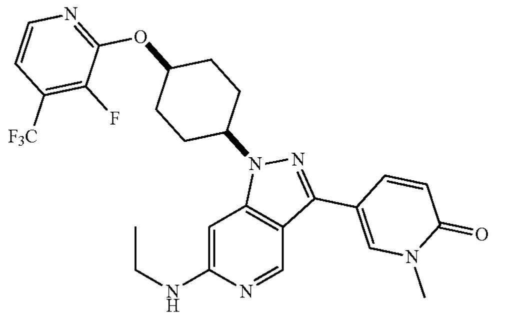 | 5-(6-(ethylamino)-1-((1s,4s)-4-((3-fluoro-4-(trifluoromethyl)pyridin-2-yl)oxy)cyclohexyl)-1H-pyrazolo[4,3-c]pyridin-3-yl)-1-methylpyridin-2(1H)-one | Mass spectrum (apci) m/z = 531.2 |
| 299 | 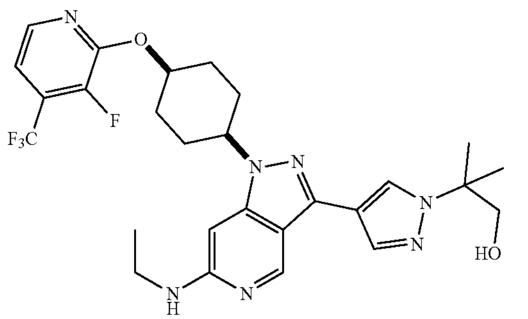 | 2-(4-(6-(ethylamino)-1-((1s,4s)-4-((3-fluoro-4-(trifluoromethyl)pyridin-2-yl)oxy)cyclohexyl)-1H-pyrazolo[4,3-c]pyridin-3-yl)-1H-pyrazol-1-yl)-2-methylpropan-1-ol | Mass spectrum (apci) m/z = 562.2 |
| 300 | 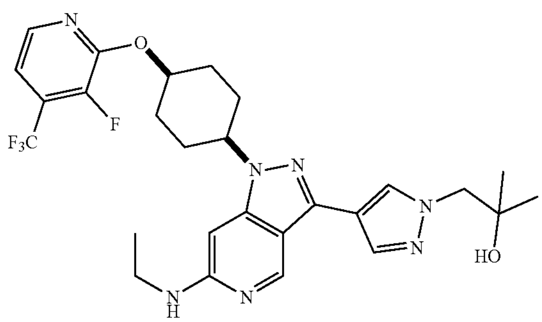 | 1-(4-(6-(ethylamino)-1-((1s,4s)-4-((3-fluoro-4-(trifluoromethyl)pyridin-2-yl)oxy)cyclohexyl)-1H-pyrazolo[4,3-c]pyridin-3-yl)-1H-pyrazol-1-yl)-2-methylpropan-2-ol | Mass spectrum (apci) m/z = 562.3 |

Example 301

1-((1s,4s)-4-((6-methoxypyridin-2-yl)oxy)cyclohexyl)-N-methyl-3-(1-methyl-1H-pyrazol-4-yl)-1H-pyrazolo[4,3-c]pyridin-6-amine

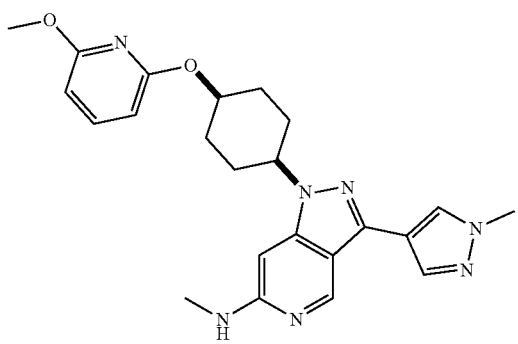

Step A: DIAD (0.0363 mL, 0.1846 mmol) was added to Ph₃P (0.0484 g, 0.1846 mmol), tert-butyl (1-((1r,4r)-4-hydroxycyclohexyl)-3-(1-methyl-1H-pyrazol-4-yl)-1H-pyrazolo[4,3-c]pyridin-6-yl)(methyl)carbamate (0.075 g, 0.1758 mmol) and 6-(benzyloxy)pyridin-2-ol (0.0460 g, 0.228 mmol) in THF (1.75 mL) and heated to 60° C. overnight. The mixture was concentrated and purified over silica gel (1-10% MeOH in DCM) to afford tert-butyl (1-((1s,4s)-4-((6-(benzyloxy)pyridin-2-yl)oxy)cyclohexyl)-3-(1-methyl-1H-pyrazol-4-yl)-1H-pyrazolo[4,3-c]pyridin-6-yl)(methyl)carbamate (0.080 g, 0.1312 mmol, 74.62% yield).

Step B: tert-butyl (1-((1s,4s)-4-((6-(benzyloxy)pyridin-2-yl)oxy)cyclohexyl)-3-(1-methyl-1H-pyrazol-4-yl)-1H-pyrazolo[4,3-c]pyridin-6-yl)(methyl)carbamate (0.200 g, 0.328 mmol) and 10% Pd/C (0.0349 g, 0.328 mmol) was stirred in MeOH (5 mL) under H2 balloon at room temperature overnight. The reaction mixture was filtered and concentrated. The residue was purified over silica gel (1-14% MeOH in DCM) to afford tert-butyl methyl(3-(1-methyl-1H-pyrazol-4-yl)-1-((1s,4s)-4-((6-oxo-1,6-dihydropyridin-2-yl)oxy)cyclohexyl)-1H-pyrazolo[4,3-c]pyridin-6-yl)carbamate (0.070 g, 0.135 mmol, 41.1% yield).

Step C: NaH (60% in mineral oil, 0.0063 g, 0.158 mmol) was added to tert-butyl methyl(3-(1-methyl-1H-pyrazol-4-yl)-1-((1s,4s)-4-((6-oxo-1,6-dihydropyridin-2-yl)oxy)cyclohexyl)-1H-pyrazolo[4,3-c]pyridin-6-yl)carbamate (0.055 g, 0.105 mmol) in THF (1.0 mL). Methyl 4-methylbenzenesulfonate (0.023 mL, 0.158 mmol) was then added and heated to 50° C. overnight. The reaction mixture was concentrated and diluted with DCM (1 mL) and TFA (1 mL) added and stirred for 1 h. The reaction mixture was concentrated and purified on C18 HPLC (water:ACN 5-95% with 1% TFA). The faster eluting product was collected and partitioned between DCM and aqueous NaHCO₃, dried over sodium sulfate, filtered and concentrated to afford 1-((1s, 4s)-4-((6-methoxypyridin-2-yl)oxy)cyclohexyl)-N-methyl-3-(1-methyl-1H-pyrazol-4-yl)-1H-pyrazolo[4,3-c]pyridin-6-amine (0.006 g, 79% yield). Mass spectrum (apci) m/z=434.2 (M+H). ¹H NMR (CDCl₃) δ 8.54 (s, 1H), 7.6 (s, 1H), 7.88 (s, 1H), 7.52 (t, J=7.8 Hz, 1H), 6.40 (d, J=8.0 Hz, 1H), 6.30 (d, J=7.8 Hz, 1H), 6.14 (s, 1H), 5.37 (m, 1H), 4.35 (tt, J=11.7, 4.1 Hz, 1H), 4.01 (s, 3H), 3.90 (s, 3H), 3.00 (s, 3H), 2.53 (m, 2H), 2.37 (m, 2H), 1.91 (m, 2H), 1.81 (m, 2H).

Using the procedure described for the preparation of Example 301, the following compound was also synthesized:

was extracted with EtOAc (2×25 mL), washed with water (2×50 mL), brine (50 mL), dried over Na₂SO₄, filtered and concentrated. The residue was purified over silica gel (10-70% EtOAc in hexanes) to afford 1-((1r,4r)-4-((tert-butyldimethylsilyl)oxy)cyclohexyl)-6-chloro-3-(1-methyl-1H-pyrazol-4-yl)-1H-pyrazolo[4,3-c]pyridine (0.83 g, 1.86 mmol, 78.8% yield).

Step B: To a solution of 1-((1r,4r)-4-((tert-butyldimethylsilyl)oxy)cyclohexyl)-6-chloro-3-(1-methyl-1H-pyrazol-4-yl)-1H-pyrazolo[4,3-c]pyridine (0.83 g, 1.86 mmol), Pd₂(dba)₃ (0.682 g, 0.744 mmol), 2-(Dicyclohexylphosphino)-2,4,6-Triisopropylbiphenyl (0.710 g, 1.49 mmol) and sodium tert-butoxide (0.536 g, 5.58 mmol) in dioxane (18.6 mL) was added aniline (1.70 mL, 18.6 mmol). The reaction mixture was purged with nitrogen for 5 minutes and then heated to 100° C. for 2 h. The reaction mixture was

| Example | Structure | Name | Data |
|---|---|---|---|
| 302 | 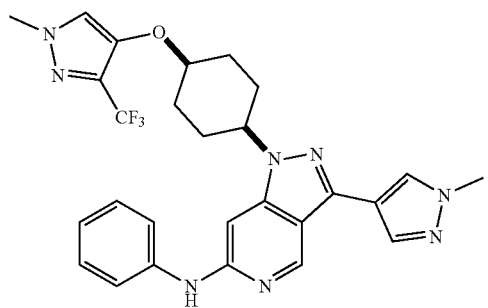 | N-methyl-3-(1-methyl-1H-pyrazol-4-yl)-1-((1s,4s)-4-((6-(2,2,2-trifluoroethoxy)pyridin-2-yl)oxy)cyclohexyl)-1H-pyrazolo[4,3-c]pyridin-6-amine | Mass spectrum (apci) m/z = 502.2 |

Example 303

3-(1-methyl-1H-pyrazol-4-yl)-1-((1s,4s)-4-((1-methyl-3-(trifluoromethyl)-1H-pyrazol-4-yl)oxy)cyclohexyl)-N-phenyl-1H-pyrazolo[4,3-c]pyridin-6-amine Step A: 3-bromo-1-((1r,4r)-4-((tert-butyldimethylsilyl)oxy)cyclohexyl)-6-chloro-1H-pyrazolo[4,3-c]pyridine (1.05 g, 2.36 mmol), 1-methyl-4-(4,4,5,5-tetramethyl-1,3,2-dioxaborolan-2-yl)-1H-pyrazole (0.638 g, 3.07 mmol), Pd(PPh₃)₄ (0.136 g, 0.118 mmol) and 2M Na₂CO₃ (2.36 mL, 4.72 mmol) were stirred in dioxane (23.6 mL) and heated to 90° C. for 23 hrs. The reaction mixture was partitioned between water (50 mL) and EtOAc (50 mL). The reaction mixture partitioned between water and EtOAc, the biphasic mixture was filtered over GF/F paper and then separated. The remaining organics in the water phase were extracted with EtOAc (2×25 mL), washed with water (2×50 mL), brine (50 mL), dried with Na₂SO₄, filtered and concentrated. The residue was purified over silica gel (10-100% EtOAc: hexanes) to afford 1-((1r,4r)-4-((tert-butyldimethylsilyl)oxy)cyclohexyl)-3-(1-methyl-1H-pyrazol-4-yl)-N-phenyl-1H-pyrazolo[4,3-c]pyridin-6-amine (0.66 g, 1.31 mmol, 70.6% yield).

Step C: 1-((1r,4r)-4-((tert-butyldimethylsilyl)oxy)cyclohexyl)-3-(1-methyl-1H-pyrazol-4-yl)-N-phenyl-1H-pyrazolo[4,3-c]pyridin-6-amine (0.66 g, 1.31 mmol) was diluted with THF (6.5 mL), followed by the addition of 1M TBAF (2.63 mL, 2.63 mmol) and heated to 70° C. overnight. The reaction mixture was partitioned between EtOAc and water, washed with water, brine, dried over sodium sulfate, filtered and concentrated. The residue was purified over silica gel (5-50% EtOAc in hexanes) to afford (1r,4r)-4-(3-(1-methyl-1H-pyrazol-4-yl)-6-(phenylamino)-1H-pyrazolo[4,3-c]pyridin-1-yl)cyclohexan-1-ol (0.315 g, 0.811 mmol, 61.8% yield).

Step D: To a solution of Ph₃P (0.02701 g, 0.1030 mmol), (1r,4r)-4-(3-(1-methyl-1H-pyrazol-4-yl)-6-(phenylamino)-1H-pyrazolo[4,3-c]pyridin-1-yl)cyclohexan-1-ol (0.020 g, 0.05148 mmol) and 1-methyl-3-(trifluoromethyl)-1H-pyrazol-4-ol (0.02565 g, 0.1545 mmol) in THF (0.5 mL) was added DIAD (0.02029 mL, 0.1030 mmol) and stirred for 30 min. The reaction mixture was partitioned between water and EtOAc, dried over sodium sulfate, filtered and concentrated. The residue was purified over C18 preparative HPLC (5-60% ACN in water with 0.2% TFA modifier). The product fractions were partitioned between DCM and saturated NaHCO$_3$, extracted with DCM, washed with brine, dried over sodium sulfate, filtered and concentrated to afford 3-(1-methyl-1H-pyrazol-4-yl)-1-((1s,4s)-4-((1-methyl-3-(trifluoromethyl)-1H-pyrazol-4-yl)oxy)cyclohexyl)-N-phenyl-1H-pyrazolo[4,3-c]pyridin-6-amine (0.0049 g, 0.009132 mmol, 17.74% yield). Mass spectrum (apci) m/z=537.2 (M+H). $^1$H NMR (CDCl$_3$) δ 8.83 (s, 1H), 8.02 (s, 1H), 7.90 (s, 1H), 7.40-7.34 (m, 4H), 7.12 (s, 1H), 7.07 (m, 1H), 6.77 (s, 1H), 6.63 (s, 1H), 4.29 (tt, J=11.5, 3.9 Hz, 1H), 4.20 (m, 1H), 4.04 (s, 3H), 3.88 (s, 3H), 2.51 (m, 2H), 2.28 (m, 2H). 1.86 (m, 2H), 1.69 (m, 2H).

Using the procedure described for the preparation of Example 303, the following compounds were also synthesized:

| Example | Structure | Name | Data |
|---|---|---|---|
| 304 | 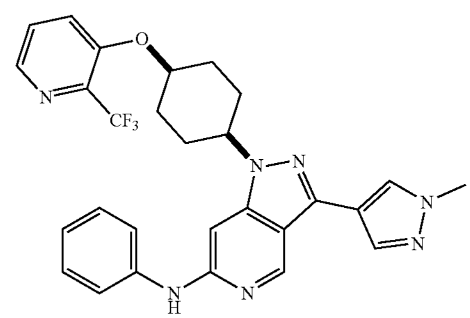 | 3-(1-methyl-1H-pyrazol-4-yl)-N-phenyl-1-((1s,4s)-4-((2-(trifluoromethyl)pyridin-3-yl)oxy)cyclohexyl)-1H-pyrazolo[4,3-c]pyridin-6-amine | Mass spectrum (apci) m/z = 534.2 |
| 305 | 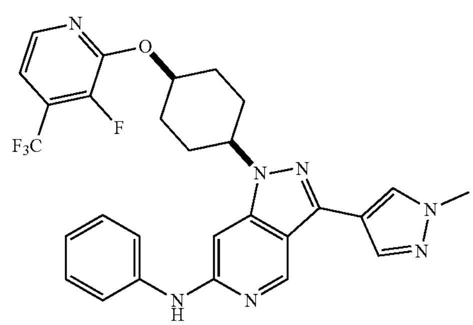 | 1-((1s,4s)-4-((3-fluoro-4-(trifluoromethyl)pyridin-2-yl)oxy)cyclohexyl)-3-(1-methyl-1H-pyrazol-4-yl)-N-phenyl-1H-pyrazolo[4,3-c]pyridin-6-amine | Mass spectrum (apci) m/z = 552.2 |

| Example | Structure | Name | Data |
|---|---|---|---|
| 306 | 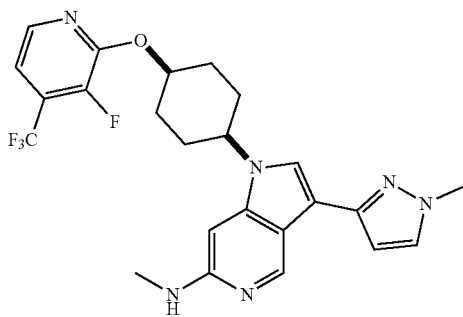 | 3-(1-methyl-1H-pyrazol-4-yl)-N-phenyl-1-((1s,4s)-4-((3-(trifluoromethyl)pyridin-2-yl)oxy)cyclohexyl)-1H-pyrazolo[4,3-c]pyridin-6-amine | Mass spectrum (apci) m/z = 534.2 |

Example 307

1-((1s,4s)-4-((3-fluoro-4-(trifluoromethyl)pyridin-2-yl)oxy)cyclohexyl)-N-methyl-3-(1-methyl-1H-pyrazol-3-yl)-1H-pyrrolo[3,2-c]pyridin-6-amine

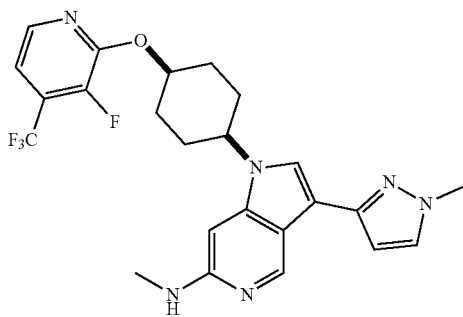

tert-Butyl (1-((1r,4r)-4-hydroxycyclohexyl)-3-(1-methyl-1H-pyrazol-3-yl)-1H-pyrrolo[3,2-c]pyridin-6-yl)(methyl)carbamate (0.037 g, 0.087 mmol),3-fluoro-4-(trifluoromethyl)pyridin-2-ol (0.0472 g, 0.261 mmol), PPh$_3$ (0.0684 g, 0.261 mmol) were dissolved in THF (1 mL) and then DIAD (0.0527 g, 0.261 mmol) was added and the reaction was stirred overnight. The reaction mixture was concentrated and then dissolved in DCM (1 mL) and 4M HCl in dioxane (2 mL) was added and stirred for 2 h. The reaction mixture was concentrated and purified by C18 preparative HPLC (5-95% ACN in water with 0.2% TFA) to afford 1-((1s,4s)-4-((3-fluoro-4-(trifluoromethyl)pyridin-2-yl)oxy)cyclohexyl)-N-methyl-3-(1-methyl-1H-pyrazol-3-yl)-1H-pyrrolo[3,2-c]pyridin-6-amine bis(2,2,2-trifluoroacetate) (12 mg, 19.3% yield). Mass spectrum (apci) m/z=489.2 (M+H). $^1$H NMR (CD3OD) δ 8.77 (s, 1H), 8.14 (d, 1H), 7.89 (s, 1H), 7.61 (s, 1H), 7.21 (m, 1H), 6.87 (s, 1H), 6.64 (s, 1H), 5.56 (s, 1H), 5.00 (m, 1H), 4.55 (m, 1H), 3.95 (s, 3H), 3.05 (s, 3H), 2.42-2.24 (m, 4H), 2.09-1.95 (m, 4H).

Example 308

N-ethyl-1-((1s,4s)-4-((3-fluoro-4-(trifluoromethyl)pyridin-2-yl)oxy)cyclohexyl)-3-(2-methyloxazol-5-yl)-1H-pyrazolo[4,3-c]pyridin-6-amine

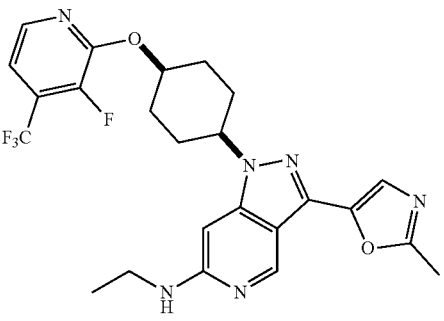

Step A: 3-bromo-1-((1r,4r)-4-((tert-butyldimethylsilyl)oxy)cyclohexyl)-N-ethyl-1H-pyrazolo[4,3-c]pyridin-6-amine (250 mg, 0.55 mmol) was dissolved in dioxane (5 mL) and 2-methyl-5-(4,4,5,5-tetramethyl-1,3,2-dioxaborolan-2-yl)oxazole (230 mg, 1.10 mmol) and 2M K$_2$CO$_3$ (0.83 mL, 1.65 mmol) were added and nitrogen bubbled through the reaction. Pd(PPh$_3$)$_4$ was added and the reaction was heated to 100° C. overnight. The reaction mixture was partitioned between water and EtOAc, dried over sodium sulfate, filtered and concentrated. The residue was purified over silica gel (0-75% EtOAc in DCM) to afford 1-((1r,4r)-4-((tert-butyldimethylsilyl)oxy)cyclohexyl)-N-ethyl-3-(2-methyloxazol-5-yl)-1H-pyrazolo[4,3-c]pyridin-6-amine (15.4 mg, 6.1% yield).

Step B: 1-((1r,4r)-4-((tert-butyldimethylsilyl)oxy)cyclohexyl)-N-ethyl-3-(2-methyloxazol-5-yl)-1H-pyrazolo[4,3-c]pyridin-6-amine (15 mg, 0.033 mmol) was dissolved in 1M THF (0.17 mL, 0.17 mmol) and heated to 50° C. for 1.5 h. The reaction mixture was diluted with EtOAc, washed several times with 10% aq. K₂CO₃, dried over sodium sulfate, filtered and concentrated to afford (1r,4r)-4-(6-(ethylamino)-3-(2-methyloxazol-5-yl)-1H-pyrazolo[4,3-c]pyridin-1-yl)cyclohexan-1-ol (10.1 mg, 90% yield).

Step C: (1r,4r)-4-(6-(ethylamino)-3-(2-methyloxazol-5-yl)-1H-pyrazolo[4,3-c]pyridin-1-yl)cyclohexan-1-ol (0.0101 g, 0.0296 mmol), 3-fluoro-4-(trifluoromethyl)pyridin-2-ol (0.0161 g, 0.0887 mmol), PPh₃ (0.0233 g, 0.0887 mmol) were dissolved in THF (0.5 mL) and then DIAD (0.0179 g, 0.0887 mmol) was added and stirred overnight and then concentrated. The residue was purified over preparative HPLC (5-95% ACN in water with 0.2% TFA) and concentrated to afford N-ethyl-1-((1s,4s)-4-((3-fluoro-4-(trifluoromethyl)pyridin-2-yl)oxy)cyclohexyl)-3-(2-methyl-oxazol-5-yl)-1H-pyrazolo[4,3-c]pyridin-6-amine bis(2,2,2-trifluoroacetate) (5.6 mg, 25.8% yield). Mass spectrum (apci) m/z=505.2 (M+H). ¹H NMR (CD3OD) δ 8.91 (s, 1H), 8.13 (d, 1H), 7.70 (s, 1H), 7.20 (m, 1H), 6.82 (s, 1H), 5.53 (s, 1H), 4.99 (m, 1H), 4.70 (m, 1H), 3.42 (q, J=7.0 Hz, 2H), 2.61 (s, 3H), 2.53-2.30 (m, 4H), 1.96 (m, 4H), 1.36 (t, J=7.0 Hz, 3H).

Using the procedure described for the preparation of Example 308, the following compound was also synthesized:

| Example | Structure | Name | Data |
|---|---|---|---|
| 309 | 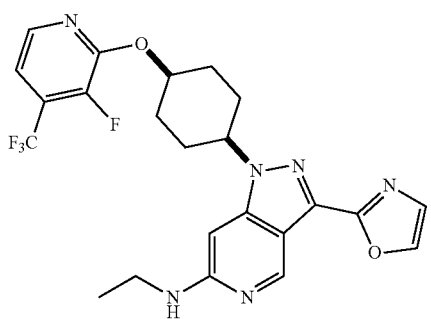 | N-ethyl-1-((1s,4s)-4((3-fluoro-4-(trifluoromethyl)pyridin-2-yl)oxy)cyclohexyl)-3-(3-methylisoxazol-5-yl)-1H-pyrazolo[4,3-c]pyridin-6-amine bis(2,2,2-trifluoroacetate) | Mass spectrum (apci) m/z = 534.2 |

Example 310

N-ethyl-1-((1s,4s)-4-((3-fluoro-4-(trifluoromethyl)pyridin-2-yl)oxy)cyclohexyl)-3-(oxazol-2-yl)-1H-pyrazolo[4,3-c]pyridin-6-amine Step A: tert-butyl (3-bromo-1-((1r,4r)-4-((tert-butyldimethylsilyl)oxy)cyclohexyl)-1H-pyrazolo[4,3-c]pyridin-6-yl)(ethyl)carbamate (250 mg, 0.45 mmol) was dissolved in toluene (4.5 mL) and 2-(tributylstannyl)oxazole (323 mg, 0.90 mmol) and CuI (8.6 mg, 0.045 mmol) were added and purged with nitrogen. Pd(PPh₃)₄ was added and the reaction was heated to 100° C. overnight. The reaction mixture was partitioned between EtOAc and 10% K₂CO₃, dried over sodium sulfate, filtered and concentrated. The residue was purified over silica gel (10-75% EtOAc in hexanes) to afford tert-butyl (1-((1r,4r)-4-((tert-butyldimethylsilyl)oxy)cyclohexyl)-3-(oxazol-2-yl)-1H-pyrazolo[4,3-c]pyridin-6-yl)(ethyl)carbamate (160 mg, 65.4% yield).

Step B: tert-butyl (1-((1r,4r)-4-((tert-butyldimethylsilyl)oxy)cyclohexyl)-3-(oxazol-2-yl)-1H-pyrazolo[4,3-c]pyridin-6-yl)(ethyl)carbamate (160 mg, 0.29 mmol) was dissolved in THF (1.5 mL) and 1M TBAF (1.5 mL, 1.5 mmol) was added and the reaction was heated to 50° C. for 2.5 h. The reaction mixture was partitioned between EtOAc and water, washed with 10% K₂CO₃, dried over sodium sulfate, filtered and concentrated to afford tert-butyl ethyl(1-((1r,4r)-4-hydroxycyclohexyl)-3-(oxazol-2-yl)-1H-pyrazolo[4,3-c]pyridin-6-yl)carbamate (130 mg, 103% yield).

Step C: tert-butyl ethyl(1-((1r,4r)-4-hydroxycyclohexyl)-3-(oxazol-2-yl)-1H-pyrazolo[4,3-c]pyridin-6-yl)carbamate (50 mg, 0.12 mmol) was dissolved in THF (1 mL) and 3-fluoro-4-(trifluoromethyl)pyridin-2-ol (63.5 mg, 0.35 mmol) and PPh₃ (92 mg, 0.35 mmol) were added, followed by DIAD (0.069 mL, 0.35 mmol) and stirred overnight. The reaction mixture was concentrated and dissolved in DCM (1 mL) and 4M HCl in dioxane (2 mL) was added. After 2 h, the reaction was concentrated and purified by preparative HPLC (5 to 95% ACN in water with 0.2% TFA) to afford N-ethyl-1-((1s,4s)-4-((3-fluoro-4-(trifluoromethyl)pyridin-2-yl)oxy)cyclohexyl)-3-(oxazol-2-yl)-1H-pyrazolo[4,3-c]pyridin-6-amine bis(2,2,2-trifluoroacetate) (17.2 mg, 20.5% yield). Mass spectrum (apci) m/z=491.1 (M+H). ¹H NMR (CD3OD) δ 9.05 (d, J=0.8 Hz, 1H), 8.14 (m, 2H), 7.46 (d, J=0.8 Hz, 1H), 7.20 (t, J=4.7 Hz, 1H), 6.92 (s, 1H), 5.55 (m, 1H), 4.77 (m, 1H), 3.44 (q, J=7.0 Hz, 2H), 2.51 (m, 2H), 2.36 (m, 2H), 2.05-1.95 (m, 4H), 1.38 (t, J=7.0 Hz, 3H).

Example 311

N-ethyl-3-(1-methyl-1H-pyrazol-4-yl)-1-((1s,4s)-4-((3-(trifluoromethyl)-1H-pyrazol-4-yl)oxy)cyclohexyl)-1H-pyrazolo[4,3-c]pyridin-6-amine

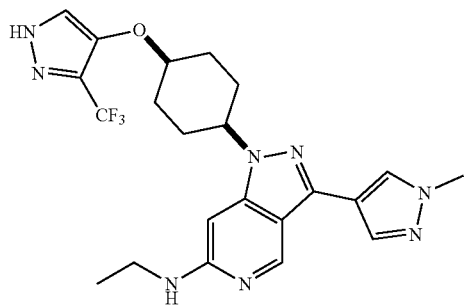

Step A: triphenylphosphane (46.23 mg, 0.1762 mmol) was dissolved in THF (1 mL) at RT. Diisopropyl (R)-diazene-1,2-dicarboxylate (34.74 µL, 0.1762 mmol) was added and stirred for 10 min. (1r,4r)-4-(6-(ethylamino)-3-(1-methyl-1H-pyrazol-4-yl)-1H-pyrazolo[4,3-c]pyridin-1-yl)cyclohexan-1-ol (40 mg, 0.1175 mmol) was added, followed by crude 3-(trifluoromethyl)-1-((2-(trimethylsilyl)ethoxy)methyl)-1H-pyrazol-4-ol (66.35 mg, 0.2350 mmol) and stirred overnight. Additional 3-(trifluoromethyl)-1-((2-(trimethylsilyl)ethoxy)methyl)-1H-pyrazol-4-ol (66.35 mg, 0.2350 mmol) and triphenylphosphane (46.23 mg, 0.1762 mmol) added, then diisopropyl (R)-diazene-1,2-dicarboxylate (34.74 µL, 0.1762 mmol) added dropwise and heated to 35° C. for 4 h. The reaction mixture was partitioned between EtOAc and water, dried over sodium sulfate, filtered and concentrated. The residue was purified over silica gel (100% EtOAc) to afford N-ethyl-3-(1-methyl-1H-pyrazol-4-yl)-1-((1s,4s)-4-((3-(trifluoromethyl)-1-((2-(trimethylsilyl)ethoxy)methyl)-1H-pyrazol-4-yl)oxy)cyclohexyl)-1H-pyrazolo[4,3-c]pyridin-6-amine (67 mg, 0.1108 mmol, 94.29% yield) as a mixture of compounds in which the SEM protecting group was on different nitrogen atoms of the pyrazole ring.

Step B: Crude N-ethyl-3-(1-methyl-1H-pyrazol-4-yl)-1-((1s,4s)-4-((3-(trifluoromethyl)-1-((2-(trimethylsilyl)ethoxy)methyl)-1H-pyrazol-4-yl)oxy)cyclohexyl)-1H-pyrazolo[4,3-c]pyridin-6-amine (66 mg, 0.11 mmol) mixture was diluted with ethylenediamine (73 µL, 1.1 mmol) and 1M TBAF (327 µL, 0.33 mmol) was added and heated to 50° C. for 5 h. The reaction mixture was concentrated and partitioned between EtOAc and water. The organic layer was with water and brine, dried over sodium sulfate, filtered and concentrated. The residue was purified over silica gel (10% MeOH in DCM) to afford N-ethyl-3-(1-methyl-1H-pyrazol-4-yl)-1-((1s,4s)-4-((3-(trifluoromethyl)-1H-pyrazol-4-yl)oxy)cyclohexyl)-1H-pyrazolo[4,3-c]pyridin-6-amine (14 mg, 0.030 mmol, 27% yield). Mass spectrum (apci) m/z=475.2 (M+H). $^1$H NMR (CDCl$_3$) δ 8.63 (s, 1H), 7.96 (s, 1H), 7.87 (s, 1H), 7.29 (s, 1H), 6.10 (s, 1H), 4.35 (tt, J=11.9, 3.7 Hz, 1H), 4.26 (m, 1H), 3.97 (s, 3H), 3.25 (q, J=7.0 Hz, 2H), 2.51 (m, 2H), 2.29 (m, 2H), 1.86 (m, 2H), 1.71 (m, 2H), 1.31 (t, J=7.2 Hz, 3H).

Example 312

2-(4-(6-(ethylamino)-1-((1s,4s)-4-((5-(trifluoromethyl)-1H-pyrazol-4-yl)oxy)cyclohexyl)-1H-pyrazolo[4,3-c]pyridin-3-yl)-1H-pyrazol-1-yl)-2-methylpropanenitrile

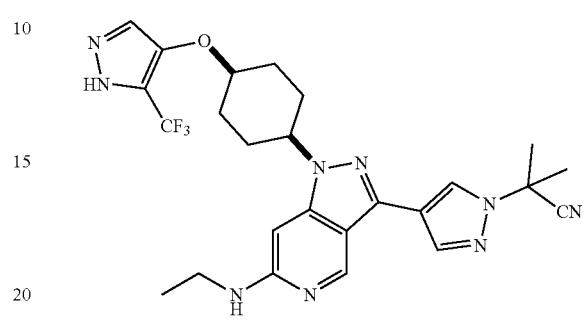

Step A: PPh$_3$ (275 mg, 1.049 mmol) was dissolved in THF (7 mL) at 0° C. tert-butyl (3-bromo-1-((1r,4r)-4-hydroxycyclohexyl)-1H-pyrazolo[4,3-c]pyridin-6-yl)(ethyl)carbamate (307 mg, 0.699 mmol) was added, followed by 5-(trifluoromethyl)-1-((2-(trimethylsilyl)ethoxy)methyl)-1H-pyrazol-4-ol (395 mg, 1.399 mmol). The solution was treated with DIAD (207 µL, 1.049 mmol) and stirred at room temperature overnight. The mixture was diluted with water (25 mL), extracted with EtOAc (3×15 mL), and brine (15 mL), dried over sodium sulfate, filtered and concentrated. The residue was purified over silica gel (0-50% EtOAc/hexanes) to afford tert-butyl (3-bromo-1-((1s,4s)-4-((5-(trifluoromethyl)-1-((2-(trimethylsilyl)ethoxy)methyl)-1H-pyrazol-4-yl)oxy)cyclohexyl)-1H-pyrazolo[4,3-c]pyridin-6-yl)(ethyl)carbamate (548 mg, 111O % yield).

Step B: tert-butyl (3-bromo-1-((1s,4s)-4-((5-(trifluoromethyl)-1-((2-(trimethylsilyl)ethoxy)methyl)-1H-pyrazol-4-yl)oxy)cyclohexyl)-1H-pyrazolo[4,3-c]pyridin-6-yl)(ethyl)carbamate (100 mg, 0.142 mmol), 2-methyl-2-(4-(4,4,5,5-tetramethyl-1,3,2-dioxaborolan-2-yl)-1H-pyrazol-1-yl)propanenitrile (74 mg, 0.284 mmol) and Pd(PPh$_3$)$_4$ (16 mg, 0.0142 mmol) were combined in dioxanes (2 mL) and treated with 2M K$_2$CO$_3$ (213 µL, 0.426 mmol). The reaction mixture was heated to 100° C. overnight. The mixture was partitioned between water (20 mL) and EtOAc (15 mL) and the aqueous layer was extracted with EtOAc (2×15 mL). The combined organic phases were washed with brine (20 mL), dried over Na$_2$SO$_4$, filtered and concentrated. The residue was purified over silica gel (0-30% EtOAc/hexanes) to afford tert-butyl (3-(1-(2-cyanopropan-2-yl)-1H-pyrazol-4-yl)-1-((1s,4s)-4-((5-(trifluoromethyl)-1-((2-(trimethylsilyl)ethoxy)methyl)-1H-pyrazol-4-yl)oxy)cyclohexyl)-1H-pyrazolo[4,3-c]pyridin-6-yl)(ethyl)carbamate (56.8 mg, 52.7% yield).

Step C: tert-butyl (3-(1-(2-cyanopropan-2-yl)-1H-pyrazol-4-yl)-1-((1s,4s)-4-((5-(trifluoromethyl)-1-((2-(trimethylsilyl)ethoxy)methyl)-1H-pyrazol-4-yl)oxy)cyclohexyl)-1H-pyrazolo[4,3-c]pyridin-6-yl)(ethyl)carbamate (56.8 mg, 0.0749 mmol) was dissolved in THF (1 mL) and 1M TBAF (138 µL, 0.187 mmol) was added and the reaction was heated to reflux overnight. The reaction mixture was partitioned between 0.2M NaOH (10 mL) and EtOAc (3×15 mL), washed with brine (20 mL), dried over sodium sulfate, filtered and concentrated. The residue was purified over silica gel (40-100% EtOAc/hexanes) to afford tert-butyl (3-(1-(2-cyanopropan-2-yl)-1H-pyrazol-4-yl)-1-((1s,4s)-4-((5-(trifluoromethyl)-1H-pyrazol-4-yl)oxy)cyclohexyl)-1H-pyrazolo[4,3-c]pyridin-6-yl)(ethyl)carbamate (10.5 mg, 22.3% yield).

Step D: tert-butyl (3-(1-(2-cyanopropan-2-yl)-1H-pyrazol-4-yl)-1-((1s,4s)-4-((5-(trifluoromethyl)-1H-pyrazol-4-yl)oxy)cyclohexyl)-1H-pyrazolo[4,3-c]pyridin-6-yl)(ethyl)carbamate (10.5 mg, 0.0167 mmol) was dissolved in DCM (2 mL) and treated with 4N HCl/dioxane (2 mL) and stirred for 1 h. The reaction mixture was concentrated and purified by preparative HPLC (5 to 95% ACN in water with 0.2% TFA). The product containing fractions were partitioned between 2 N NaOH and DCM, dried over sodium sulfate, filtered and concentrated to afford 2-(4-(6-(ethylamino)-1-((1s,4s)-4-((5-(trifluoromethyl)-1H-pyrazol-4-yl)oxy)cyclohexyl)-1H-pyrazolo[4,3-c]pyridin-3-yl)-1H-pyrazol-1-yl)-2-methylpropanenitrile (3.9 mg, 44.2% yield). Mass spectrum (apci) m/z=528.3 (M+H). $^1$H NMR (CDCl$_3$) δ 8.70 (d, J=0.8 Hz, 1H), 8.15 (s, 1H), 8.20 (s, 1H), 7.33 (m, 1H), 6.12 (s, 1H), 4.85 (br s, 1H), 4.39 (tt, J=11.7, 3.7 Hz, 1H), 4.30 (m, 1H), 3.30 (q, J=7.2 Hz, 2H), 2.56 (m, 2H), 1.33 (m, 2H), 2.07 (s, 6H), 1.90 (m, 2H), 1.75 (m, 2H), 1.35 (t, J=7.2 Hz, 3H).

Example 313

N-ethyl-3-(1-methylpiperidin-4-yl)-1-((1s,4s)-4-((5-(trifluoromethyl)-1H-pyrazol-4-yl)oxy)cyclohexyl)-1H-pyrazolo[4,3-c]pyridin-6-amine

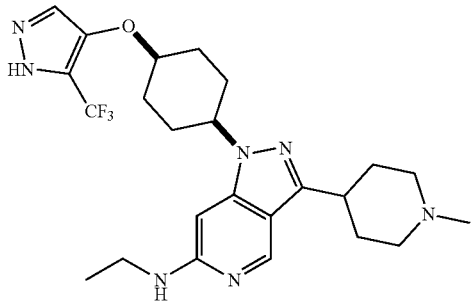

Step A: tert-butyl (3-bromo-1-((1s,4s)-4-((5-(trifluoromethyl)-1-((2-(trimethylsilyl)ethoxy)methyl)-1H-pyrazol-4-yl)oxy)cyclohexyl)-1H-pyrazolo[4,3-c]pyridin-6-yl)(ethyl)carbamate (100 mg, 0.142 mmol), 1-methyl-4-(4,4,5,5-tetramethyl-1,3,2-dioxaborolan-2-yl)-1,2,3,6-tetrahydropyridine (63 mg, 0.284 mmol) and Pd(PPh$_3$)$_4$ (16 mg, 0.0142 mmol) were combined in dioxane (2 mL) and treated with 2M K$_2$CO$_3$ (213 μL, 0.426 mmol) and heated to 100° C. overnight. The reaction mixture was partitioned between water (20 mL) and EtOAc (15 mL), extracted with EtOAc (2×15 mL), washed with brine (20 mL), dried over Na$_2$SO$_4$, filtered and concentrated. The residue was purified over silica gel (0-50% EtOAc in hexanes) to afford tert-butyl ethyl(3-(1-methyl-1,2,3,6-tetrahydropyridin-4-yl)-1-((1s,4s)-4-((5-(trifluoromethyl)-1-((2-(trimethylsilyl)ethoxy)methyl)-1H-pyrazol-4-yl)oxy)cyclohexyl)-1H-pyrazolo[4,3-c]pyridin-6-yl)carbamate (43.8 mg, 42.8% yield).

Step B: A solution of tert-butyl ethyl(3-(1-methyl-1,2,3,6-tetrahydropyridin-4-yl)-1-((1s,4s)-4-((5-(trifluoromethyl)-1-((2-(trimethylsilyl)ethoxy)methyl)-1H-pyrazol-4-yl)oxy)cyclohexyl)-1H-pyrazolo[4,3-c]pyridin-6-yl)carbamate (43.8 mg, 0.0608 mmol) in MeOH (2 mL) was treated with 10% Pd/C (wet, Degussa type, 10 mg) and hydrogenated under a balloon atmosphere overnight. The mixture was filtered through GF paper and concentrated to afford a tan foam which was used directly without purification.

Step C: tert-butyl ethyl(3-(1-methylpiperidin-4-yl)-1-((1s,4s)-4-((5-(trifluoromethyl)-1-((2-(trimethylsilyl)ethoxy)methyl)-1H-pyrazol-4-yl)oxy)cyclohexyl)-1H-pyrazolo[4,3-c]pyridin-6-yl)carbamate (40.1 mg, 0.0555 mmol) was dissolved in THF (1 mL) and 1M TBAF (139 μL, 0.139 mmol) was added and the reaction was heated to reflux overnight. The reaction mixture was partitioned between 0.2 M NaOH (10 mL) and EtOAc (3×15 mL), brine (20 mL) dried over sodium sulfate, filtered and concentrated. The residue was purified over silica gel (8-20% MeOH in DCM) to afford tert-butyl ethyl(3-(1-methylpiperidin-4-yl)-1-((1s,4s)-4-((5-(trifluoromethyl)-1H-pyrazol-4-yl)oxy)cyclohexyl)-1H-pyrazolo[4,3-c]pyridin-6-yl)carbamate (13.2 mg, 40.2% yield).

Step D: tert-butyl ethyl(3-(1-methylpiperidin-4-yl)-1-((1s,4s)-4-((5-(trifluoromethyl)-1H-pyrazol-4-yl)oxy)cyclohexyl)-1H-pyrazolo[4,3-c]pyridin-6-yl)carbamate (13.2 mg, 0.0223 mmol) was dissolved in MeOH (2 mL) and treated with 4N HCl/dioxane (2 mL) and stirred for 1 h. The reaction mixture was concentrated and purified by preparative HPLC (5 to 95% ACN in water with 0.2% TFA). The product containing fractions were partitioned between 2N NaOH and DCM, dried over sodium sulfate, filtered and concentrated to afford N-ethyl-3-(1-methylpiperidin-4-yl)-1-((1s,4s)-4-((5-(trifluoromethyl)-1H-pyrazol-4-yl)oxy)cyclohexyl)-1H-pyrazolo[4,3-c]pyridin-6-amine (6.9 mg, 62.9% yield). Mass spectrum (apci) m/z=492.3 (M+H). $^1$H NMR (CDCl$_3$) δ 8.62 (d, J=1.0 Hz, 1H), 7.35 (m, 1H), 6.08 (s, 1H), 4.74 (br s, 1H), 4.36-4.25 (m, 2H), 3.26 (q, J=7.2 Hz, 2H), 3.05-2.92 (m, 3H), 2.48 (m, 2H), 2.36 (s, 3H), 2.30 (m, 2H), 2.21-2.01 (m, 6H), 1.85 (m, 2H), 1.71 (m, 2H), 1.32 (t, J=7.2 Hz, 3H).

Example 314

(5-(((1s,4s)-4-(6-(ethylamino)-3-(1-methyl-1H-pyrazol-4-yl)-1H-pyrazolo[4,3-c]pyridin-1-yl)cyclohexyl)oxy)-1-methyl-H-pyrazol-3-yl)methanol

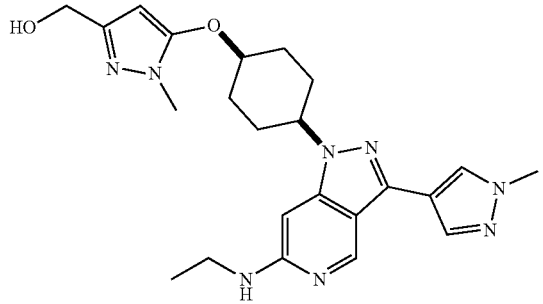

Step A: To a stirred solution of tert-butyl ethyl(1-((1r,4r)-4-hydroxycyclohexyl)-3-(1-methyl-1H-pyrazol-4-yl)-1H-pyrazolo[4,3-c]pyridin-6-yl)carbamate (44 mg, 0.09988 mmol), methyl 5-hydroxy-1-methyl-1H-pyrazole-3-carboxylate (19.5 mg, 0.125 mmol) and triphenylphosphine (32.75 mg, 0.1248 mmol) in 500 μL of THF at room temperature under nitrogen was added DIAD (24.58 μL, 0.1248 mmol) dropwise by syringe and stirred overnight. The reaction mixture was concentrated and purified over silica gel (0% to 60% ethyl acetate in hexanes) to afford methyl 5-(((1s,4s)-4-(6-((tert-butoxycarbonyl)(ethyl)amino)-3-(1-methyl-1H-pyrazol-4-yl)-1H-pyrazolo[4,3-c]pyridin-1-yl)cyclohexyl)oxy)-1-methyl-1H-pyrazole-3-carboxylate (32 mg, 55.4% yield).

Step B: To a stirred solution of methyl 5-(((1s,4s)-4-(6-((tert-butoxycarbonyl)(ethyl)amino)-3-(1-methyl-1H-pyrazol-4-yl)-1H-pyrazolo[4,3-c]pyridin-1-yl)cyclohexyl)oxy)-1-methyl-1H-pyrazole-3-carboxylate (32 mg, 0.055 mmol)

in 550 µL of methanol at room temperature in a reaction vial under nitrogen was added 1M LiAlH$_4$ (276 µL, 276 mmol). The reaction mixture was stirred for 1 h, partitioned between DCM and saturated NH$_4$Cl. The organic layer was extracted with DCM, dried over MgSO$_4$, filtered and concentrated to afford crude tert-butyl ethyl(1-((1s,4s)-4-((3-(hydroxymethyl)-1-methyl-1H-pyrazol-5-yl)oxy)cyclohexyl)-3-(1-methyl-1H-pyrazol-4-yl)-1H-pyrazolo[4,3-c]pyridin-6-yl)carbamate (30 mg, 100% yield), which was used in the next step without further purification Step C: tert-butyl ethyl(1-((1s,4s)-4-((3-(hydroxymethyl)-1-methyl-1H-pyrazol-5-yl)oxy)cyclohexyl)-3-(1-methyl-1H-pyrazol-4-yl)-1H-pyrazolo[4,3-c]pyridin-6-yl)carbamate (30 mg, 0.0545 mmol) was dissolved in 420 µL of dichloromethane and TFA (420 µL, 5.45 mmol) was added and stirred for 1 h. The reaction mixture was concentrated and purified by reverse phase HPLC (5% to 95% acetonitrile with 0.02% TFA). The fractions containing the product were partitioned between DCM and aqueous NaHCO$_3$, extracted (2×15 mL) with dichloromethane, dried over MgSO$_4$, filtered and concentrated to afford (5-(((1s,4s)-4-(6-(ethylamino)-3-(1-methyl-1H-pyrazol-4-yl)-1H-pyrazolo[4,3-c]pyridin-1-yl)cyclohexyl)oxy)-1-methyl-1H-pyrazol-3-yl)methanol (4.0 mg, 16.3% yield). Mass spectrum (apci) m/z=451.2 (M+H). $^1$H NMR (CDCl$_3$) δ 8.68 (s, 1H), 7.97 (d, J=0.6 Hz, 1H), 7.85 (s, 1H), 6.03 (s, 1H), 5.56 (s, 1H), 4.75 (br s, 1H), 4.59 (s, 2H), 4.49 (m, 1H), 4.32 (tt, J=tt, 11.5, 3.9 Hz, 1H), 4.00 (s, 3H), 3.73 (s, 3H), 3.28 (q, J=7.2 Hz, 2H), 2.47 (m, 2H), 2.35 (m, 2H), 1.93 (m, 2H), 1.80 (m, 2H), 1.34 (t, J=7.2 Hz, 3H).

Example 315

N-ethyl-1-((1s,4s)-4-((3-fluoro-4-(trifluoromethyl)pyridin-2-yl)oxy)cyclohexyl)-3-isopropyl-1H-pyrazolo[4,3-c]pyridin-6-amine dihydrochloride

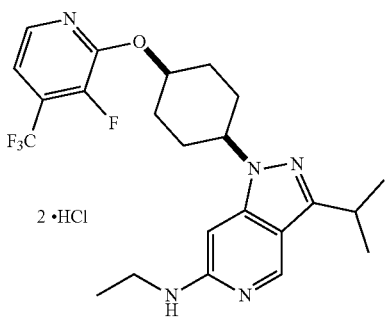

2 ·HCl

Step A: tert-butyl (3-bromo-1-((1s,4s)-4-((3-fluoro-4-(trifluoromethyl)pyridin-2-yl)oxy)cyclohexyl)-1H-pyrazolo[4,3-c]pyridin-6-yl)(ethyl)carbamate (50 mg, 0.08 mmol), 4,4,5,5-tetramethyl-2-(prop-1-en-2-yl)-1,3,2-dioxaborolane (56 mg, 0.33 mmol) and Pd(PPh$_3$)$_4$ (10 mg, 0.008 mmol) were combined in dioxane (1 mL) and treated with K$_2$CO$_3$ (120 µL, 2N, 0.25 mmol). The reaction mixture was heated to 100° C. overnight. Additional Pd(PPh$_3$)$_4$ (10 mg) and boronate (100 mg) were added and the reaction mixture was stirred at 100° C. overnight. The reaction mixture was partitioned between water (10 mL) and EtOAc (10 mL) and the aqueous layer was extracted with EtOAc (2×10 mL). The combined organic phases were washed with brine (10 mL), dried over Na$_2$SO$_4$, filtered and concentrated. The residue was purified over silica gel (5-60% EtOAc/hexanes) to afford tert-butyl ethyl(1-((1s,4s)-4-((3-fluoro-4-(trifluoromethyl)pyridin-2-yl)oxy)cyclohexyl)-3-(prop-1-en-2-yl)-1H-pyrazolo[4,3-c]pyridin-6-yl)carbamate (40 mg, 86% yield).

Step B: A solution of tert-butyl ethyl(1-((1s,4s)-4-((3-fluoro-4-(trifluoromethyl)pyridin-2-yl)oxy)cyclohexyl)-3-(prop-1-en-2-yl)-1H-pyrazolo[4,3-c]pyridin-6-yl)carbamate (40 mg, 0.07 mmol) in methanol (3 mL) was treated with 10% Pd/C (wet, Degussa type, 10 mg) and hydrogenated under balloon pressure overnight. The mixture was filtered through GF paper and concentrated to afford tert-butyl ethyl(1-((1s,4s)-4-((3-fluoro-4-(trifluoromethyl)pyridin-2-yl)oxy)cyclohexyl)-3-isopropyl-1H-pyrazolo[4,3-c]pyridin-6-yl)carbamate (38 mg, 95% yield) which was used without purification.

Step C: A solution of tert-butyl ethyl(1-((1s,4s)-4-((3-fluoro-4-(trifluoromethyl)pyridin-2-yl)oxy)cyclohexyl)-3-isopropyl-1H-pyrazolo[4,3-c]pyridin-6-yl)carbamate (38 mg, 0.07 mmol) in DCM (2 mL) was treated with 4N HCl/dioxanes (2 mL) and stirred for 2 h. The mixture was concentrated, triturated with EtOAc, filtered and dried to afford N-ethyl-1-((1s,4s)-4-((3-fluoro-4-(trifluoromethyl)pyridin-2-yl)oxy)cyclohexyl)-3-isopropyl-1H-pyrazolo[4,3-c]pyridin-6-amine dihydrochloride (12 mg, 33% yield). Mass spectrum (apci) m/z=466.2 (M+H). $^1$H NMR (CDCl$_3$) δ 8.37 (s, 1H), 8.05 (d, J=5.1 Hz, 1H), 7.55 (s, 1H), 7.07 (m, 1H), 6.22 (s, 1H), 5.52 (m, 1H), 4.39 (m, 1H), 3.36-3.23 (m, 3H), 2.50 (m, 2H), 2.35 (m, 2H), 1.93 (m, 2H), 1.84 (m, 2H), 1.41 (m, 9H).

Using the procedure described for the preparation of Example 315, the following compounds were also synthesized:

| Example | Structure | Name | Data |
| --- | --- | --- | --- |
| 316 | 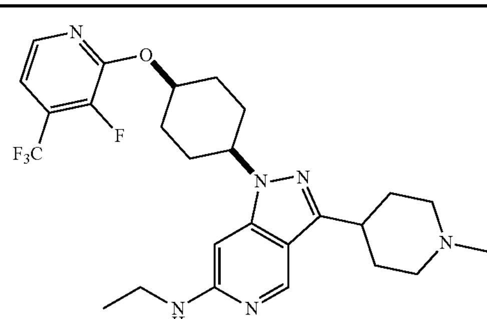 | N-ethyl-1-((1s,4s)-4-((3-fluoro-4-(trifluoromethyl)pyridin-2-yl)oxy)cyclohexyl)-3-(1-methylpiperidin-4-yl)-1H-pyrazolo[4,3-c]pyridin-6-amine | Mass spectrum (apci) m/z = 521.3 |

-continued

| Example | Structure | Name | Data |
|---|---|---|---|
| 317 | 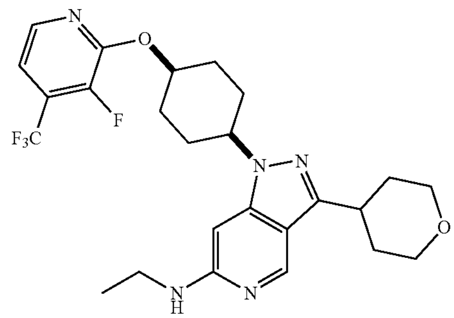 | N-ethyl-1-((1s,4s)-4-((3-fluoro-4-(trifluoromethyl)pyridin-2-yl)oxy)cyclohexyl)-3-(tetrahydro-2H-pyran-4-yl)-1H-pyrazolo[4,3-c]pyridin-6-amine | Mass spectrum (apci) m/z = 508.2 |
| 318 | 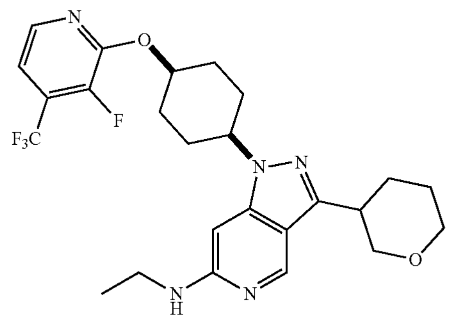 | N-ethyl-1-((1s,4s)-4-((3-fluoro-4-(trifluoromethyl)pyridin-2-yl)oxy)cyclohexyl)-3-(tetrahydro-2H-pyran-3-yl)-1H-pyrazolo[4,3-c]pyridin-6-amine | Mass spectrum (apci) m/z = 508.2 |
| 319 | 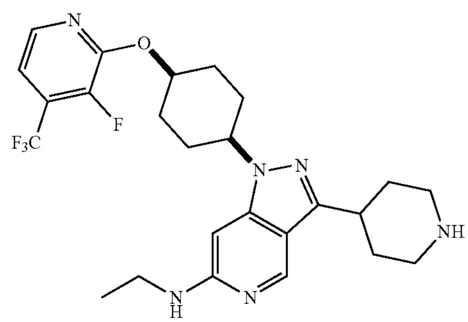 | N-ethyl-1-((1s,4s)-4-((3-fluoro-4-(trifluoromethyl)pyridin-2-yl)oxy)cyclohexyl)-3-(piperidin-4-yl)-1H-pyrazolo[4,3-c]pyridin-6-amine | Mass spectrum (apci) m/z = 507.2 |
| 320 | 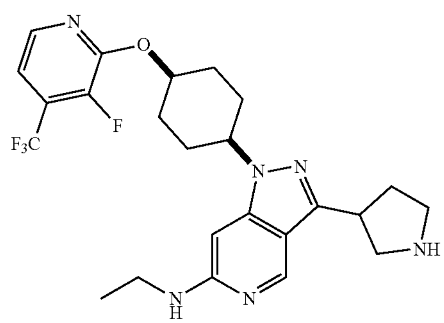 | N-ethyl-1-((1s,4s)-4-((3-fluoro-4-(trifluoromethyl)pyridin-2-yl)oxy)cyclohexyl)-3-(pyrrolidin-3-yl)-1H-pyrazolo[4,3-c]pyridin-6-amine | Mass spectrum (apci) m/z = 493.2 |
| 321 | 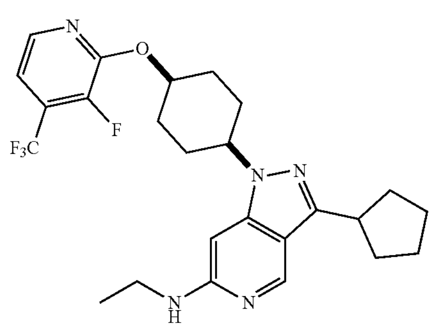 | 3-cyclopentyl-N-ethyl-1-((1s,4s)-4-((3-fluoro-4-(trifluoromethyl)pyridin-2-l)oxy)cyclohexyl)-1H-pyrazolo[4,3-c]pyridin-6-amine | Mass spectrum (apci) m/z = 492.2 |

-continued

| Example | Structure | Name | Data |
|---|---|---|---|
| 322 | 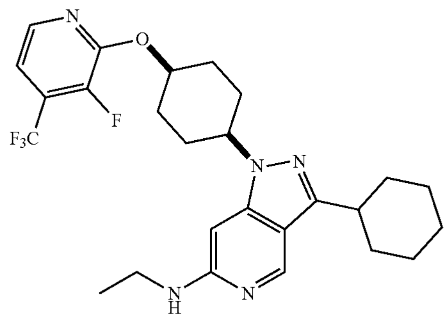 | 3-cyclohexyl-N-ethyl-1-((1s,4s)-4-((3-fluoro-4-(trifluoromethyl)pyridin-2-yl)oxy)cyclohexyl)-1H-pyrazolo[4,3-c]pyridin-6-amine | Mass spectrum (apci) m/z = 506.2 |
| 323 | 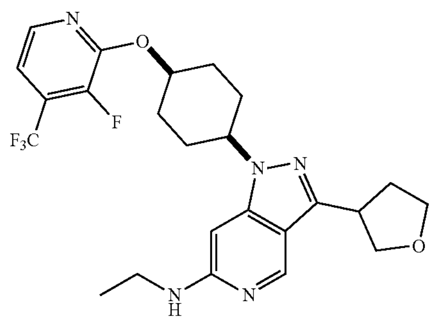 | N-ethyl-1-((1s,4s)-4-((3-fluoro-4-(trifluoromethyl)pyridin-2-yl)oxy)cyclohexyl)-3-(tetrahydrofuran-3-yl)-1H-pyrazolo[4,3-c]pyridin-6-amine | Mass spectrum (apci) m/z = 494.2 |
| 324 | 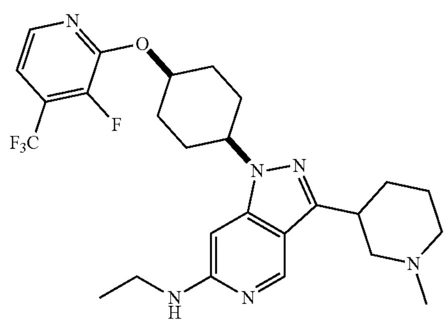 | N-ethyl-1-((1s,4s)-4-((3-fluoro-4-(trifluoromethyl)pyridin-2-yl)oxy)cyclohexyl)-3-(1-methylpiperidin-3-yl)-1H-pyrazolo[4,3-c]pyridin-6-amine | Mass spectrum (apci) m/z = 521.3 |

Example 325

N-ethyl-1-((1s,4s)-4-((3-fluoro-4-(trifluoromethyl)pyridin-2-yl)oxy)cyclohexyl)-3-(1-methylpyrrolidin-3-yl)-1H-pyrazolo[4,3-c]pyridin-6-amine

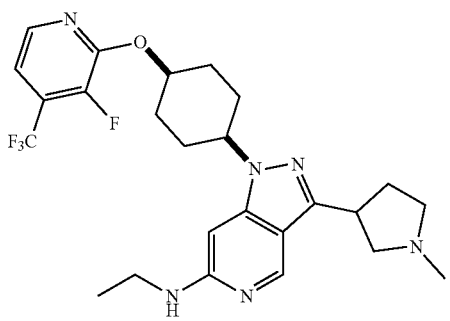

To a suspension of N-ethyl-1-((1s,4s)-4-((3-fluoro-4-(trifluoromethyl)pyridin-2-yl)oxy)cyclohexyl)-3-(pyrrolidin-3-yl)-1H-pyrazolo[4,3-c]pyridin-6-amine trihydrochloride (61.5 mg, 0.10 mmol) in DCE (2 mL) was added formaldehyde (37% in water, 42 mg, 0.51 mmol) followed by NaBH(OAc)$_3$ (54 mg, 0.26 mmol). The mixture was stirred overnight and partitioned between 2N Na$_2$CO$_3$ (10 mL) and DCM, extracted with DCM (3×10 mL), washed with brine (10 mL), dried over Na$_2$SO$_4$, filtered and concentrated. The residue was purified over silica gel (0-20% MeOH/DCM with 2% NH4OH) to afford N-ethyl-1-((1s,4s)-4-((3-fluoro-4-(trifluoromethyl)pyridin-2-yl)oxy)cyclohexyl)-3-(1-methylpyrrolidin-3-yl)-1H-pyrazolo[4,3-c]pyridin-6-amine (10.9 mg, 21% yield). Mass spectrum (apci) m/z=507.2 (M+H). $^1$H NMR (CDCl$_3$) δ 8.67 (s, 1H), 8.04 (d, J=5.3 Hz, 1H), 7.04 (m, 1H), 6.12 (s, 1H), 5.49 (m, 1H), 4.63 (s, 1H), 4.38 (tt, J=12.1, 4.1 Hz, 1H), 3.75 (m, 1H), 3.28 (m, 2H), 3.08 (t, J=8.6 Hz, 1H), 2.81 (m, 2H), 2.71 (m, 1H), 2.53 (m, 2H), 2.45 (s, 3H), 2.40 (m, 1H), 2.32 (m, 2H), 2.21 (m, 1H), 1.92 (m, 2H), 1.81 (m, 2H), 1.33 (t, J=7.2 Hz, 3H).

Using the procedure described for the preparation of Example 325, the following compounds were also synthesized:

| Example | Structure | Name | Data |
|---|---|---|---|
| 326 | 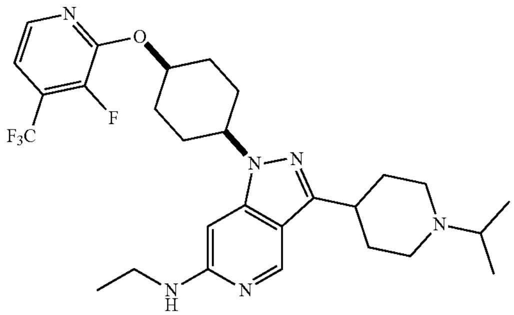 | N-ethyl-1-((1s,4s)-4-((3-fluoro-4-(trifluoromethyl)pyridin-2-yl)oxy)cyclohexyl)-3-(1-isopropylpiperidin-4-yl)-1H-pyrazolo[4,3-c]pyridin-6-amine | Mass spectrum (apci) m/z = 549.3 |
| 327 | 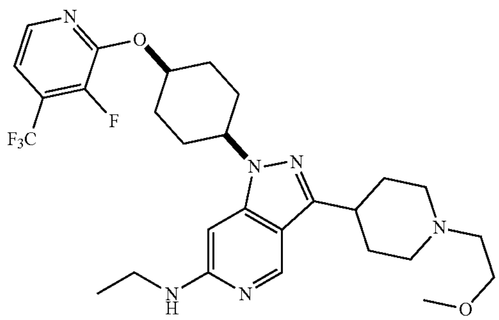 | N-ethyl-1-((1s,4s)-4-((3-fluoro-4-(trifluoromethyl)pyridin-2-yl)oxy)cyclohexyl)-3-(1-(2-methoxyethyl)piperidin-4-yl)-1H-pyrazolo[4,3-c]pyridin-6-amine | Mass spectrum (apci) m/z = 565.3 |
| 328 | 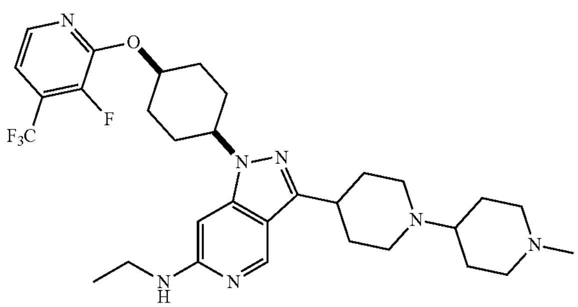 | N-ethyl-1-((1s,4s)-4-((3-fluoro-4-(trifluoromethyl)pyridin-2-yl)oxy)cyclohexyl)-3-(1'-methyl-[1,4'-bipiperidin]-4-yl)-1H-pyrazolo[4,3-c]pyridin-6-amine | Mass spectrum (apci) m/z = 604.3 |

Example 329

1-(4-(6-(ethylamino)-1-((1s,4s)-4-((3-fluoro-4-(trifluoromethyl)pyridin-2-yl)oxy)cyclohexyl)-1H-pyrazolo[4,3-c]pyridin-3-yl)piperidin-1-yl)-2-methylpropan-1-one

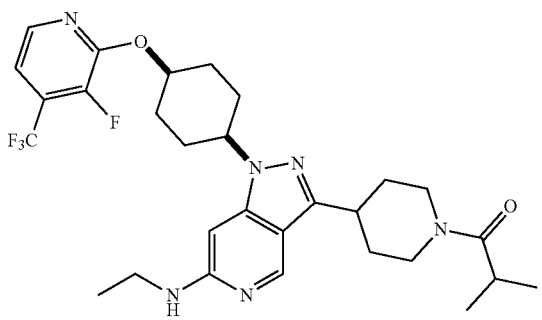

To a solution of N-ethyl-1-((1s,4s)-4-((3-fluoro-4-(trifluoromethyl)pyridin-2-yl)oxy)cyclohexyl)-3-(piperidin-4-yl)-1H-pyrazolo[4,3-c]pyridin-6-amine trihydrochloride (30 mg, 0.05 mmol) and DIEA (43 µL, 0.24 mmol) in DCM (2 mL) was added isobutyryl chloride (10 µL, 0.10 mmol). The reaction mixture was stirred overnight, treated with 2N Na$_2$CO$_3$ (10 mL), extracted with DCM (3×10 mL), washed with brine (10 mL), dried over Na$_2$SO$_4$, filtered and concentrated. The residue was purified by preparative HPLC (5-95% ACN/water/0.1% TFA) and fractions containing the product were partitioned between 1N NaOH and DCM, dried over sodium sulfate, filtered and concentrated to afford 1-(4-(6-(ethylamino)-1-((1s,4s)-4-((3-fluoro-4-(trifluoromethyl)pyridin-2-yl)oxy)cyclohexyl)-1H-pyrazolo[4,3-c]pyridin-3-yl)piperidin-1-yl)-2-methylpropan-1-one (4.8 mg, 17% yield). Mass spectrum (apci) m/z=577.3 (M+H). $^1$H NMR (CDCl$_3$) δ 8.53 (s, 1H), 8.04 (s, J=5.1 Hz, 1H), 7.05 (m, 1H), 6.12 (s, 1H), 5.50 (m, 1H). 4.85 (br s, 1H), 4.68 (m, 1H), 4.37 (tt, J=11.7, 3.9 Hz, 1H), 4.08 (m, 1H), 3.31-3.19 (m, 4H), 2.91-2.79 (m, 2H), 2.52 (m, 2H), 2.32 (m, 2H), 2.10 (m, 2H), 2.02-1.76 (m, 6H), 1.33 (t, J=7.2 Hz, 3H), 1.16 (m, 6H).

Example 330

N-ethyl-1-((1s,4s)-4-((3-fluoro-4-(trifluoromethyl)pyridin-2-yl)oxy)cyclohexyl)-3-morpholino-1H-pyrazolo[4,3-c]pyridin-6-amine

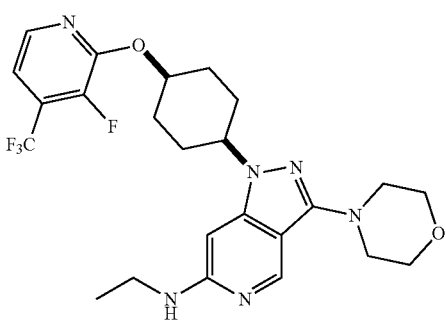

Step A: tert-butyl (3-bromo-1-((1s,4s)-4-((3-fluoro-4-(trifluoromethyl)pyridin-2-yl)oxy)cyclohexyl)-1H-pyrazolo[4,3-c]pyridin-6-yl)(ethyl)carbamate (50 mg, 0.083 mmol), $Cs_2CO_3$ (81 mg, 0.249 mmol), BINAP (8 mg, 0.012 mmol), $Pd_2(dba)_3$ (4 mg, 0.004 mmol) were combined in THF (2 mL). Morpholine (22 µL, 0.249 mmol) was added and purged with argon for 5 minutes. The tube was sealed and heated at 80° C. overnight. The reaction mixture was partitioned between water (20 mL) and EtOAc (15 mL), extracted with EtOAc (2×15 mL), washed with brine (20 mL), dried over $Na_2SO_4$, filtered and concentrated. The residue was purified over silica gel (20-40% EtOAc in hexanes) to afford tert-butyl ethyl(1-((1s,4s)-4-((3-fluoro-4-(trifluoromethyl)pyridin-2-yl)oxy)cyclohexyl)-3-morpholino-1H-pyrazolo[4,3-c]pyridin-6-yl)carbamate (42.8 mg, 84.7% yield).

Step B: tert-butyl ethyl(1-((1s,4s)-4-((3-fluoro-4-(trifluoromethyl)pyridin-2-yl)oxy)cyclohexyl)-3-morpholino-1H-pyrazolo[4,3-c]pyridin-6-yl)carbamate (42.8 mg, 0.0703 mmol) was dissolved in MeOH (2 mL) and treated with 4N HCl/dioxane (2 mL) and stirred for 1 h. The reaction mixture was concentrated and purified over preparative HPLC (5 to 95% ACN in water with 0.1% TFA). Fractions containing the product were partitioned between 2 N NaOH and DCM, extracted with DCM (3×10 mL), washed with brine (15 mL), dried over sodium sulfate, filtered and concentrated to afford N-ethyl-1-((1s,4s)-4-((3-fluoro-4-(trifluoromethyl)pyridin-2-yl)oxy)cyclohexyl)-3-morpholino-1H-pyrazolo[4,3-c]pyridin-6-amine (24.2 mg, 68% yield). Mass spectrum (apci) m/z=509.2 (M+H). $^1$H NMR ($CDCl_3$) δ 8.52 (d, J=0.6 Hz, 1H), 8.03 (d, J=5.1 Hz, 1H), 7.04 (m, 1H), 6.01 (s, 1H), 5.47 (m, 1H), 4.62 (br s, 1H), 4.23 (tt, J=11.7, 4.1 Hz, 1H), 3.90 (m, 4H), 3.44 (m, 4H), 3.26 (m, 2H), 2.48 (m, 2H), 2.30 (m, 2H), 1.91-1.75 (m, 4H), 1.32 (t, J=7.2 Hz, 3H).

Using the procedure described for the preparation of Example 330, the following compounds were also synthesized:

| Example | Structure | Name | Data |
| --- | --- | --- | --- |
| 331 | 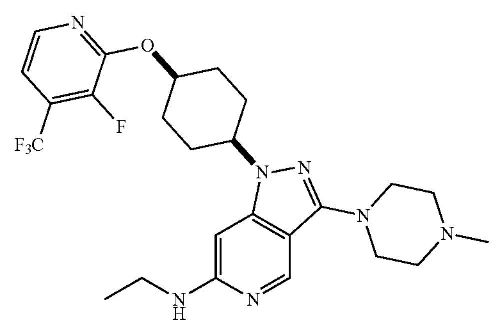 | N-ethyl-1-((1s,4s)-4((3-fluoro-4-(trifluoromethyl)pyridin-2-yl)oxy)cyclohexyl)-3-(4-methylpiperazin-1-yl)-1H-pyrazolo[4,3-c]pyridin-6-amine | Mass spectrum (apci) m/z = 522.3 |
| 332 | 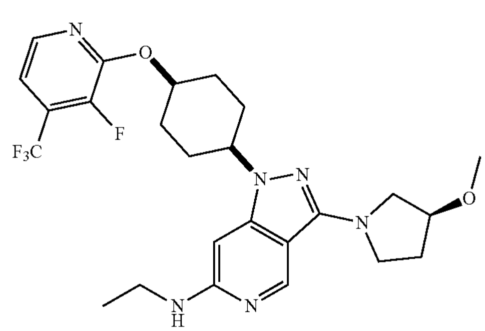 | N-ethyl-1-((1s,4R)-4-((3-fluoro-4-(trifluoromethyl)pyridin-2-yl)oxy)cyclohexyl)-3-((S)-3-methoxypyrrolidin-1-yl)-1H-pyrazolo[4,3-c]pyridin-6-amine | Mass spectrum (apci) m/z = 523.2 |

-continued

| Example | Structure | Name | Data |
|---|---|---|---|
| 333 | 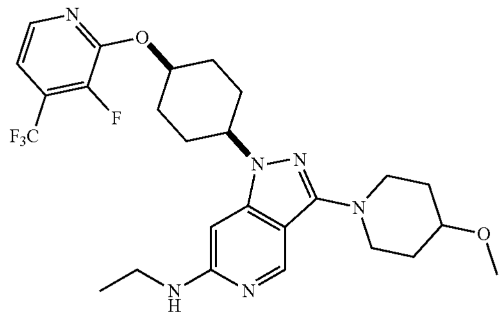 | N-ethyl-1-((1s,4s)-4((3-fluoro-4-(trifluoromethyl)pyridin-2-yl)oxy)cyclohexyl)-3-(4-methoxypiperidin-1-yl)-1H-pyrazolo[4,3-c]pyridin-6-amine | Mass spectrum (apci) m/z = 537.3 |
| 334 | 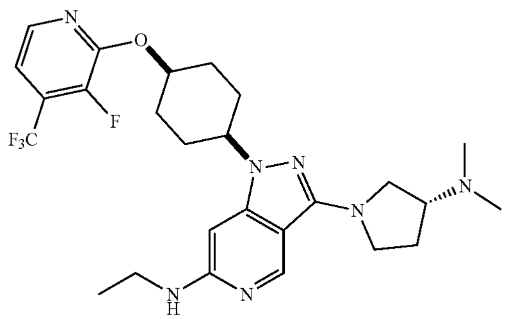 | 3-((R)-3-(dimethylamino)pyrrolidin-1-yl)-N-ethyl-1-((1s,4S)-4-((3-fluoro-4-(trifluoromethyl)pyridin-2-yl)oxy)cyclohexyl)-1H-pyrazolo[4,3-c]pyridin-6-amine | Mass spectrum (apci) m/z = 536.3 |
| 335 | 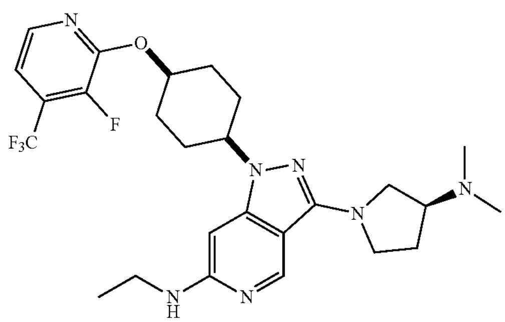 | 3-((S)-3-(dimethylamino)pyrrolidin-1-yl)-N-ethyl-1-((1s,4R)-4-((3-fluoro-4-(trifluoromethyl)pyridin-2-yl)oxy)cyclohexyl)-1H-pyrazolo[4,3-c]pyridin-6-amine | Mass spectrum (apci) m/z = 536.2 |
| 336 | 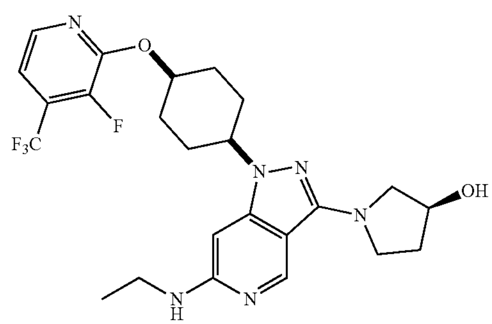 | (S)-1-(6-(ethylamino)-1-((1s,4R)-4-((3-fluoro-4-(trifluoromethyl)pyridin-2-yl)oxy)cyclohexyl)-1H-pyrazolo[4,3-c]pyridin-3-yl)pyrrolidin-3-ol | Mass spectrum (apci) m/z = 509.2 |
| 337 | 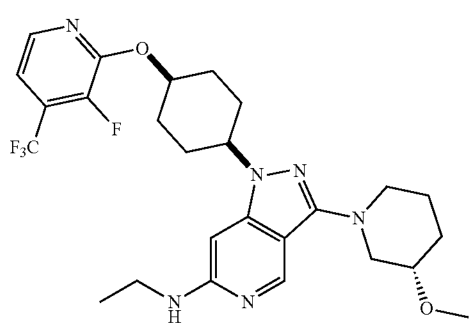 | N-ethyl-1-((1s,4R)-4-((3-fluoro-4-(trifluoromethyl)pyridin-2-yl)oxy)cyclohexyl)-3-((S)-3-methoxypiperidin-1-yl)-1H-pyrazolo[4,3-c]pyridin-6-amine | Mass spectrum (apci) m/z = 537.3 |

| Example | Structure | Name | Data |
|---|---|---|---|
| 338 | 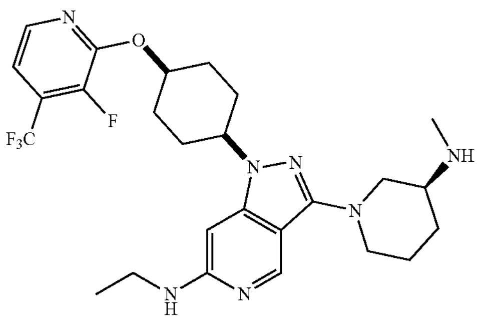 | N-ethyl-1-((1s,4R)-4-((3-fluoro-4-(trifluoromethyl)pyridin-2-yl)oxy)cyclohexyl)-3-((S)-3-(methylamino)piperidin-1-yl)-1H-pyrazolo[4,3-c]pyridin-6-amine | Mass spectrum (apci) m/z = 536.3 |
| 339 | 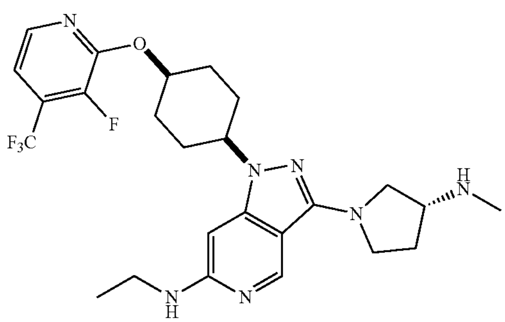 | N-ethyl-1-((1s,4S)-4-((3-fluoro-4-(trifluoromethyl)pyridin-2-yl)oxy)cyclohexyl)-3-((R)-3-(methylamino)pyrrolidin-1-yl)-1H-pyrazolo[4,3-c]pyridin-6-amine | Mass spectrum (apci) m/z = 522.2 |
| 340 | 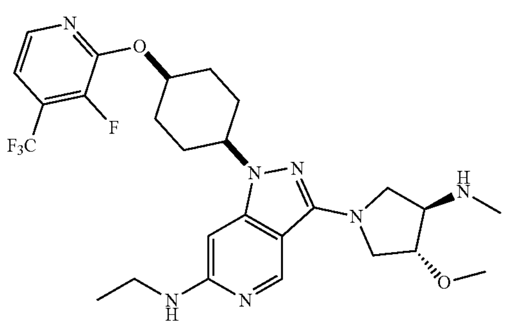 | 3-((3R,4R)-3,4-dimethoxypyrrolidin-1-yl)-N-ethyl-1-((1s,4S)-4-((3-fluoro-4-(trifluoromethyl)pyridin-2-yl)oxy)cyclohexyl)-1H-pyrazolo[4,3-c]pyridin-6-amine | Mass spectrum (apci) m/z = 553.3 |
| 341 | 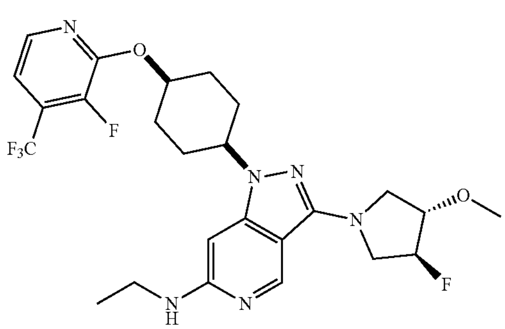 | N-ethyl-1-((1s,4R)-4-((3-fluoro-4-(trifluoromethyl)pyridin-2-yl)oxy)cyclohexyl)-3-((3S,4S)-3-fluoro-4-methoxypyrrolidin-1-yl)-1H-pyrazolo[4,3-c]pyridin-6-amine | Mass spectrum (apci) m/z = 541.3 |

-continued

| Example | Structure | Name | Data |
|---|---|---|---|
| 342 | 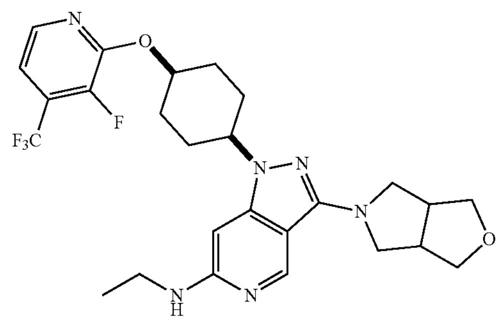 | N-ethyl-1-((1s,4s)-4((3-fluoro-4-(trifluoromethyl)pyridin-2-yl)oxy)cyclohexyl)-3-(tetrahydro-1H-furo[3,4-c]pyrrol-5(3H)-yl)-1H-pyrazolo[4,3-c]pyridin-6-amine | Mass spectrum (apci) m/z = 535.2 |
| 343 | 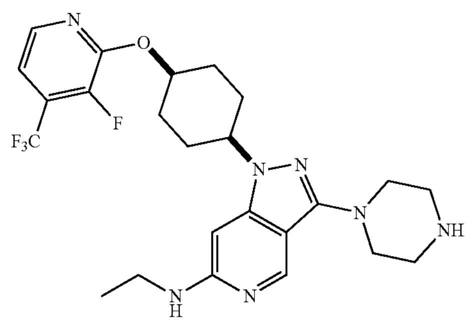 | N-ethyl-1-((1s,4s)-4((3-fluoro-4-(trifluoromethyl)pyridin-2-yl)oxy)cyclohexyl)-3-(piperazin-1-yl)-1H-pyrazolo[4,3-c]pyridin-6-amine | Mass spectrum (apci) m/z = 508.2 |
| 344 | 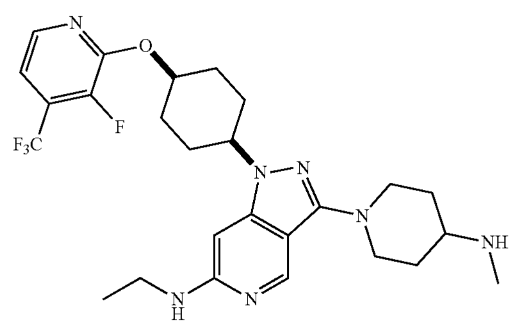 | N-ethyl-1-((1s,4s)-4((3-fluoro-4-(trifluoromethyl)pyridin-2-yl)oxy)cyclohexyl)-3-(4-(methylamino)piperidin-1-yl)-1H-pyrazolo[4,3-c]pyridin-6-amine | Mass spectrum (apci) m/z = 536.3 |
| 345 | 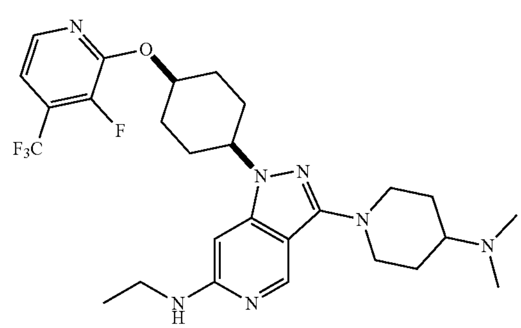 | 3-(4-(dimethylamino)piperidin-1-yl)-N-ethyl-1-((1s,4s)-4-((3-fluoro-4-(trifluoromethyl)pyridin-2-yl)oxy)cyclohexyl)-1H-pyrazolo[4,3-c]pyridin-6-amine | Mass spectrum (apci) m/z = 550.3 |

Example 346

N-ethyl-1-((1s,4s)-4-((3-fluoro-4-methylpyridin-2-yl)oxy)cyclohexyl)-3-(1-methyl-1H-pyrazol-4-yl)-1H-pyrazolo[4,3-c]pyridin-6-amine

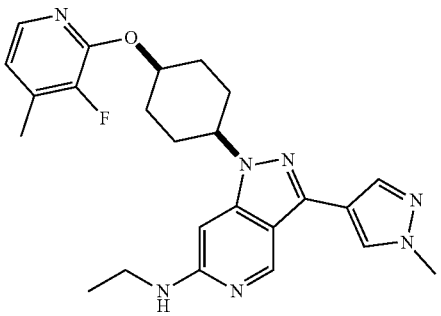

Step A: To a solution of Ph₃P (0.2679 g, 1.021 mmol), tert-butyl ethyl(1-((1r,4r)-4-hydroxycyclohexyl)-3-(1-methyl-1H-pyrazol-4-yl)-1H-pyrazolo[4,3-c]pyridin-6-yl)carbamate (0.150 g, 0.3405 mmol) and 3-fluoro-4-iodopyridin-2(1H)-one (0.1627 g, 0.6810 mmol) in THF (3.4 mL) was added DIAD (0.2013 mL, 1.021 mmol). After 1 h, EtOAc (15 mL) and water (15 mL) were added and the biphasic mixture was separated. The organic layer was washed with brine (2×15 mL), dried over Na₂SO₄, filtered and concentrated. The residue was purified over silica gel (10-100% EtOAc in hexanes) to afford tert-butyl ethyl(1-((1s,4s)-4-((3-fluoro-4-iodopyridin-2-yl)oxy)cyclohexyl)-3-(1-methyl-1H-pyrazol-4-yl)-1H-pyrazolo[4,3-c]pyridin-6-yl)carbamate (0.187 g, 0.2827 mmol, 83.02% yield).

Step B: A mixture of tert-butyl ethyl(1-((1s,4s)-4-((3-fluoro-4-iodopyridin-2-yl)oxy)cyclohexyl)-3-(1-methyl-1H-pyrazol-4-yl)-1H-pyrazolo[4,3-c]pyridin-6-yl)carbamate (25 mg, 0.038 mmol), Trimethylboroxine (9.5 mg, 0.076 mmol), Pd(PPh₃)₄ (0.0022 g, 0.0019 mmol) and 2M K₂CO₃ (40 µL, 0.080 mmol) in DMF (380 µL) was heated to 90° C. for 16 hrs. The reaction mixture was partitioned between EtOAc (15 mL) and water (15 mL), washed with water (25 mL) and brine (25 mL), dried over Na₂SO₄, filtered and concentrated. The material was dissolved in DCM (0.5 mL) and TFA (0.5 mL) was added and stirred for 2 h. The reaction mixture was concentrated and partitioned between 2M Na₂CO₃ and DCM, extracted with DCM (×2), washed with brine, dried over sodium sulfate, filtered and concentrated. The residue was purified over silica gel (50-100% EtOAc in hexanes) to afford N-ethyl-1-((1s,4s)-4-((3-fluoro-4-methylpyridin-2-yl)oxy)cyclohexyl)-3-(1-methyl-1H-pyrazol-4-yl)-1H-pyrazolo[4,3-c]pyridin-6-amine (3.5 mg, 21% yield). Mass spectrum (apci) m/z=450.2 (M+H). ¹H NMR (CDCl₃) δ 8.69 (s, 1H), 7.99 (s, 1H), 7.88 (s, 1H), 7.77 (d, J=5.1 Hz, 1H), 6.71 (t, J=4.9 Hz, 1H), 6.19 (s, 1H), 5.44 (m, 1H), 4.75 (br s, 1H), 4.42 (tt, J=11.9, 4.1 Hz, 1H), 4.00 (s, 3H), 3.32 (m, 2H), 2.59 (m, 2H), 2.37-2.29 (m, 5H), 1.93 (m, 2H), 1.81 (m, 2H), 1.36 (t, J=7.0 Hz, 3H).

Using the procedure described for the preparation of Example 346, the following compound was also synthesized:

| Example | Structure | Name | Data |
|---|---|---|---|
| 347 | 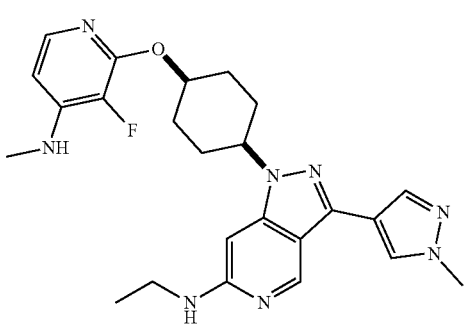 | (R)-3-(4-(6-(ethylamino)-1-((1s,4S)-4-((3-fluoro-4-methylpyridin-2-yl)oxy)cyclohexyl)-1H-pyrazolo[4,3-c]pyridin-3-yl)-1H-pyrazol-1-yl)propane-1,2-diol | Mass spectrum (apci) m/z = 510.2 |

Example 348

N-ethyl-1-((1s,4s)-4-((3-fluoro-4-(methylamino)pyridin-2-yl)oxy)cyclohexyl)-3-(1-methyl-1H-pyrazol-4-yl)-1H-pyrazolo[4,3-c]pyridin-6-amine A pressure tube was charged with tert-butyl ethyl(1-((1s,4s)-4-((3-fluoro-4-iodopyridin-2-yl)oxy)cyclohexyl)-3-(1-methyl-1H-pyrazol-4-yl)-1H-pyrazolo[4,3-c]pyridin-6-yl)carbamate (25 mg, 0.038 mmol), 2M MeNH$_2$ (0.076 mL, 0.15 mmol) and 1 mL of dioxane under a nitrogen atmosphere. To this was added dicyclohexyl(2',6'-diisopropoxy-[1,1'-biphenyl]-2-yl)phosphane (7.1 mg, 0.015 mmol), sodium t-butoxide (7.3 mg, 0.076 mmol), and Pd2dba3 (6.9 mg, 0.0076 mmol). The tube was sealed and heated to 100° C. for 1 h. The reaction mixture was partitioned between EtOAc and water, extracted with EtOAc, washed with brine, dried over sodium sulfate, filtered and concentrated. The residue was dissolved in DCM (0.5 mL) and TFA (0.5 mL) was added and stirred for 2 h. The reaction mixture was concentrated and partitioned between DCM and 2M Na$_2$CO$_3$, extracted with DCM, dried over sodium sulfate, filtered and concentrated. The residue was purified over silica gel (0 to 10% MeOH in DCM) to afford N-ethyl-1-((1s,4s)-4-((3-fluoro-4-(methylamino)pyridin-2-yl)oxy)cyclohexyl)-3-(1-methyl-1H-pyrazol-4-yl)-1H-pyrazolo[4,3-c]pyridin-6-amine (5.3 mg, 28% yield). Mass spectrum (apci) m/z=465.2 (M+H). $^1$H NMR (CDCl$_3$) δ 8.69 (s, 1H), 7.99 (s, 1H), 7.88 (s, 1H), 7.69 (s, J=5.7 Hz, 1H), 6.31 (t, J=5.7 Hz, 1H), 6.17 (s, 1H), 5.39 (m, 1H), 4.75 (br s, 1H), 4.45-4.32 (m, 2H), 3.99 (s, 3H), 3.31 (m, 2H), 2.93 (d, J=5.3 Hz, 3H), 2.59 (m, 2H), 2.31 (m, 2H), 1.92 (m, 2H), 1.79 (m, 2H), 1.35 (t, J=7.2 Hz, 3H).

Using the procedure described for the preparation of Example 348, the following compounds were also synthesized:

Example 351

3-((1s,4S)-4-(dimethylamino)cyclohexyl)-N-ethyl-1-((1s,4S)-4-((3-fluoro-4-(trifluoromethyl)pyridin-2-yl)oxy)cyclohexyl)-1H-pyrazolo[4,3-c]pyridin-6-amine

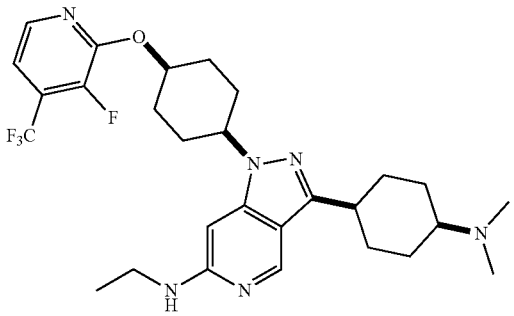

Step A: tert-butyl (3-bromo-1-((1s,4s)-4-((3-fluoro-4-(trifluoromethyl)pyridin-2-yl)oxy)cyclohexyl)-1H-pyrazolo[4,3-c]pyridin-6-yl)(ethyl)carbamate (300 mg, 0.498 mmol), 4,4,5,5-tetramethyl-2-(1,4-dioxaspiro[4.5]dec-7-en-8-yl)-1,3,2-dioxaborolane (318 mg, 1.20 mmol) and Pd(PPh$_3$)$_4$ (58 mg, 0.05 mmol) were combined in dioxane (5 mL) and treated with 2M K$_2$CO$_3$ (747 μL, 1.49 mmol) and heated to 100° C. overnight under nitrogen. The reaction mixture was partitioned between water (20 mL) and EtOAc (20 mL), extracted with EtOAc (2×10 mL), washed with brine (10 mL), dried over Na$_2$SO$_4$, filtered and concentrated. The residue was purified over silica gel (0-30% EtOAc in

| Example | Structure | Name | Data |
|---|---|---|---|
| 349 | 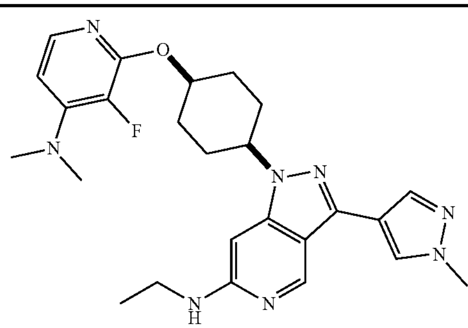 | 1-((1s,4s)-4-((4-(dimethylamino)-3-fluoropyridin-2-yl)oxy)cyclohexyl)-N-ethyl-3-(1-methyl-1H-pyrazol-4-yl)-1H-pyrazolo[4,3-c]pyridin-6-amine | Mass spectrum (apci) m/z = 479.3 |
| 350 | | 1-((1s,4s)-4-((3-(dimethylamino)-4-(trifluoromethyl)pyridin-2-yl)oxy)cyclohexyl)-N-ethyl-3-(1-methyl-1H-pyrazol-4-yl)-1H-pyrazolo[4,3-c]pyridin-6-amine | Mass spectrum (apci) m/z = 529.2 | hexanes) to afford tert-butyl ethyl(1-((1s,4s)-4-((3-fluoro-4-(trifluoromethyl)pyridin-2-yl)oxy)cyclohexyl)-3-(1,4-dioxaspiro[4.5]dec-7-en-8-yl)-1H-pyrazolo[4,3-c]pyridin-6-yl)carbamate (336 mg, 102% yield).

Step B: To a solution of tert-butyl ethyl(1-((1s,4s)-4-((3-fluoro-4-(trifluoromethyl)pyridin-2-yl)oxy)cyclohexyl)-3-(1,4-dioxaspiro[4.5]dec-7-en-8-yl)-1H-pyrazolo[4,3-c]pyridin-6-yl)carbamate (330 mg, 0.50 mmol) in methanol (10 mL) was added 10% Pd/C (wet, Degussa type, 50 mg). The mixture was hydrogenated under a double-walled balloon of hydrogen overnight. The reaction mixture was filtered and concentrated to afford tert-butyl ethyl(1-((1s,4s)-4-((3-fluoro-4-(trifluoromethyl)pyridin-2-yl)oxy)cyclohexyl)-3-(1,4-dioxaspiro[4.5]decan-8-yl)-1H-pyrazolo[4,3-c]pyridin-6-yl)carbamate (333 mg, 101% yield).

Step C: To a solution of tert-butyl ethyl(1-((1s,4s)-4-((3-fluoro-4-(trifluoromethyl)pyridin-2-yl)oxy)cyclohexyl)-3-(1,4-dioxaspiro[4.5]decan-8-yl)-1H-pyrazolo[4,3-c]pyridin-6-yl)carbamate (330 mg, 0.497 mmol) in THF (5 mL) was added 2N HCl (5 mL) and stirred at 50° C. overnight. The reaction mixture was partitioned between 2N $Na_2CO_3$ and EtOAc, extracted with EtOAc, washed with brine, dried over $Na_2SO_4$, filtered and concentrated to afford 4-(6-(ethylamino)-1-((1s,4s)-4-((3-fluoro-4-(trifluoromethyl)pyridin-2-yl)oxy)cyclohexyl)-1H-pyrazolo[4,3-c]pyridin-3-yl)cyclohexan-1-one (235 mg, 91% yield).

Step D: To a suspension of 4-(6-(ethylamino)-1-((1s,4s)-4-((3-fluoro-4-(trifluoromethyl)pyridin-2-yl)oxy)cyclohexyl)-1H-pyrazolo[4,3-c]pyridin-3-yl)cyclohexan-1-one (100 mg, 0.19 mmol) in DCE (4 mL) was added dimethylamine (2N/THF, 962 µL, 1.92 mmol) followed by NaBH(OAc)$_3$ (102 mg, 0.48 mmol). The mixture was stirred overnight. The reaction mixture was partitioned between 2N $Na_2CO_3$ (10 mL) and DCM, extracted with DCM (3×10 mL), washed with brine (10 mL), dried over $Na_2SO_4$, filtered and concentrated. The residue was purified over silica gel (0-20% MeOH in DCM with 0.5% $NH_3$), followed by preparative HPLC (5-95% ACN in water with 0.1% TFA). The fractions containing the product were partitioned between 1N NaOH and DCM, dried over sodium sulfate, filtered and concentrated to afford 3-((1s,4S)-4-(dimethylamino)cyclohexyl)-N-ethyl-1-((1s,4S)-4-((3-fluoro-4-(trifluoromethyl)pyridin-2-yl)oxy)cyclohexyl)-1H-pyrazolo[4,3-c]pyridin-6-amine (6 mg, 6% yield). Mass spectrum (apci) m/z=549.3 (M+H). $^1$H NMR (CDCl$_3$) δ 8.58 (s, 1H), 8.03 (d, J=5.3 Hz, 1H), 7.04 (m, 1H), 6.10 (s, 1H), 5.49 (m, 1H), 4.61 (br s, 1H), 4.37 (tt, J=11.3, 3.9 Hz, 1H), 3.26 (m, 3H), 2.53 (m, 2H), 2.36-2.20 (m, 10H), 1.97-1.74 (m, 8H), 1.66 (m, 2H), 1.33 (t, J=7.2 Hz, 3H).

Example 352

2-(((1s,4s)-4-(6-(ethylamino)-3-(1-methyl-1H-pyrazol-4-yl)-1H-pyrazolo[4,3-c]pyridin-1-yl)cyclohexyl)oxy)-3-fluoroisonicotinonitrile

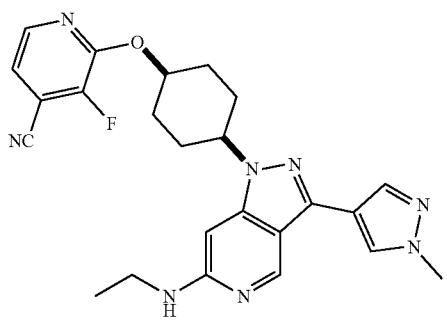

A solution of tert-butyl ethyl(1-((1s,4s)-4-((3-fluoro-4-iodopyridin-2-yl)oxy)cyclohexyl)-3-(1-methyl-1H-pyrazol-4-yl)-1H-pyrazolo[4,3-c]pyridin-6-yl)carbamate (0.025 g, 0.038 mmol) and copper(I) cyanide (0.0068 g, 0.076 mmol) in propionitrile (0.38 mL) was heated to 100° C. for 1 h. NMP (0.4 mL) was added and the reaction mixture was heated to 150° C. overnight. The reaction mixture was cooled, DCM (2 mL) and TFA (5 mL) were added and the reaction mixture was stirred for 1 h. The reaction mixture was concentrated and purified by preparative HPLC (5-75% ACN in water with 0.2% TFA). The fractions containing the product were partitioned between saturated NaHCO$_3$ and DCM, extracted with DCM (×2), washed with brine, dried over Na$_2$SO$_4$, filtered and concentrated to afford 2-(((1s,4s)-4-(6-(ethylamino)-3-(1-methyl-1H-pyrazol-4-yl)-1H-pyrazolo[4,3-c]pyridin-1-yl)cyclohexyl)oxy)-3-fluoroisonicotinonitrile (0.0018 g, 0.0039 mmol, 10% yield). Mass spectrum (apci) m/z=461.2 (M+H). $^1$H NMR (CDCl$_3$) δ 8.69 (s, 1H), 8.04 (d, J=4.9 Hz, 1H), 7.98 (s, 1H), 7.88 (s, 1H), 7.04 (dd, J=5.1, 3.9 Hz, 1H), 6.12 (s, 1H), 5.51 (m, 1H), 4.41 (tt, J=11.5, 3.9 Hz, 1H), 4.00 (s, 3H), 3.31 (q, J=7.0 Hz, 2H), 2.55 (m, 2H), 2.34 (m, 2H), 1.96 (m, 2H), 1.86 (m, 2H), 1.37 (t, J=7.0 Hz, 3H).

Example 353

1-((1s,4s)-4-(2-fluorophenoxy)cyclohexyl)-N-methyl-3-(1-methyl-1H-pyrazol-4-yl)-1H-pyrazolo[4,3-c]pyridin-6-amine

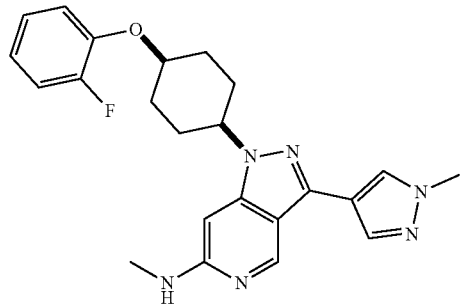

DIAD (0.01213 mL, 0.06154 mmol) was added to Ph$_3$P (0.01614 g, 0.06154 mmol) in THF (0.6 mL). To this was added tert-butyl (1-((1r,4r)-4-hydroxycyclohexyl)-3-(1-methyl-1H-pyrazol-4-yl)-1H-pyrazolo[4,3-c]pyridin-6-yl)(methyl)carbamate (0.025 g, 0.05861 mmol) followed by 2-fluorophenol (0.007060 mL, 0.07620 mmol) and heated to 60° C. overnight. The reaction mixture was partitioned between water and DCM, washed with brine, dried over sodium sulfate, filtered and concentrated. The residue was dissolved in DCM (0.5 mL) and TFA (1 mL) was added. After 1 h, the reaction was concentrated and purified on preparative HPLC (5 to 95% ACN in water with 0.1% TFA). The fractions containing the product were partitioned between saturated NaHCO$_3$ and DCM, dried over sodium sulfate, filtered and concentrated to afford 1-((1s,4s)-4-(2-fluorophenoxy)cyclohexyl)-N-methyl-3-(1-methyl-1H-pyrazol-4-yl)-1H-pyrazolo[4,3-c]pyridin-6-amine (0.0108 g, 0.02568 mmol, 43.82% yield). Mass spectrum (apci) m/z=421.2 (M+H). $^1$H NMR (CDCl$_3$) δ 8.70 (d, J=1.0 Hz, 1H), 7.99 (s, 1H), 7.88 (s, 1H), 7.15-7.04 (m, 3H), 6.94 (m, 1H), 6.20 (d, J=0.8 Hz, 1H), 4.77 (m, 1H), 4.65 (m, 1H), 4.42 (tt, J=11.9, 3.9 Hz, 1H), 3.99 (s, 3H), 2.99 (d, J=5.3 Hz, 3H), 2.65 (m, 2H), 2.31 (m, 2H), 1.91 (m, 2H), 1.76 (m, 2H).

Using the procedure described for the preparation of Example 354, the following compounds were also synthesized:

| Example | Structure | Name | Data |
|---|---|---|---|
| 354 | 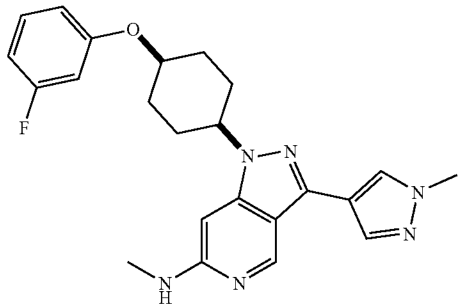 | 1-((1s,4s)-4-(3-fluorophenoxy)cyclohexyl)-N-methyl-3-(1-methyl-1H-pyrazol-4-yl)-1H-pyrazolo[4,3-c]pyridin-6-amine | Mass spectrum (apci) m/z = 421.2 |
| 355 | 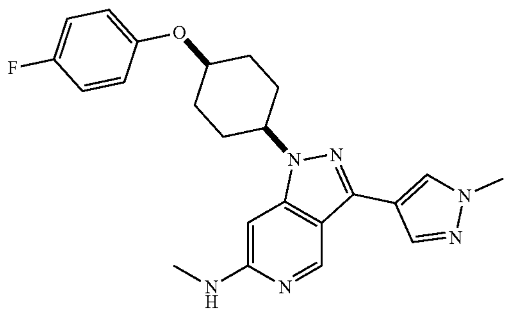 | 1-((1s,4s)-4-(4-fluorophenoxy)cyclohexyl)-N-methyl-3-(1-methyl-1H-pyrazol-4-yl)-1H-pyrazolo[4,3-c]pyridin-6-amine | Mass spectrum (apci) m/z = 421.2 |
| 356 | 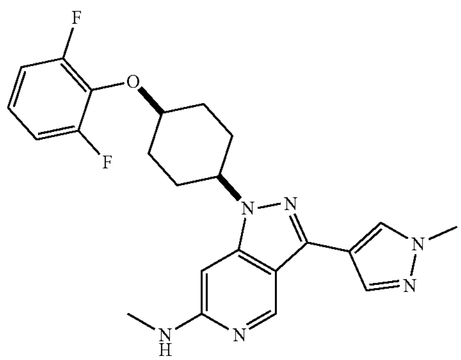 | 1-((1s,4s)-4-(2,6-difluorophenoxy)cyclohexyl)-N-methyl-3-(1-methyl-1H-pyrazol-4-yl)-1H-pyrazolo[4,3-c]pyridin-6-amine | Mass spectrum (apci) m/z = 439.2 |
| 357 | 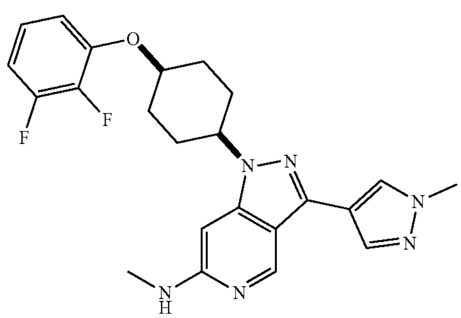 | 1-((1s,4s)-4-(2,3-difluorophenoxy)cyclohexyl)-N-methyl-3-(1-methyl-1H-pyrazol-4-yl)-1H-pyrazolo[4,3-c]pyridin-6-amine | Mass spectrum (apci) m/z = 439.2 |
| 358 | 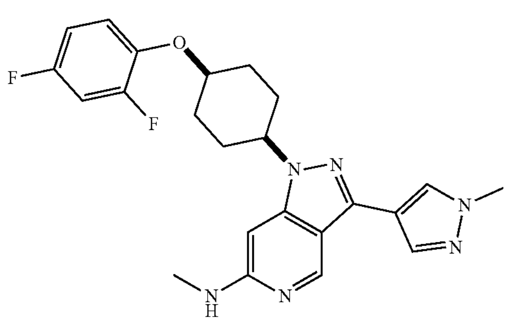 | 1-((1s,4s)-4-(2,4-difluorophenoxy)cyclohexyl)-N-methyl-3-(1-methyl-1H-pyrazol-4-yl)-1H-pyrazolo[4,3-c]pyridin-6-amine | Mass spectrum (apci) m/z = 439.2 |

| Example | Structure | Name | Data |
|---|---|---|---|
| 359 | 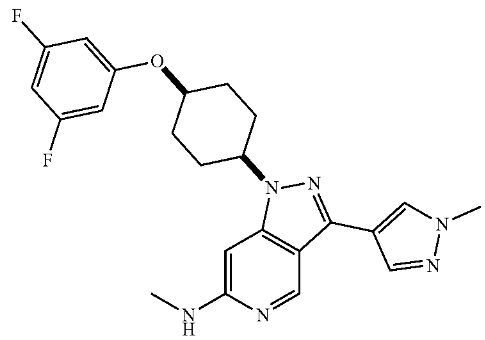 | 1-((1s,4s)-4-(3,5-difluorophenoxy)cyclohexyl)-N-methyl-3-(1-methyl-1H-pyrazol-4-yl)-1H-pyrazolo[4,3-c]pyridin-6-amine | Mass spectrum (apci) m/z = 439.2 |
| 360 | 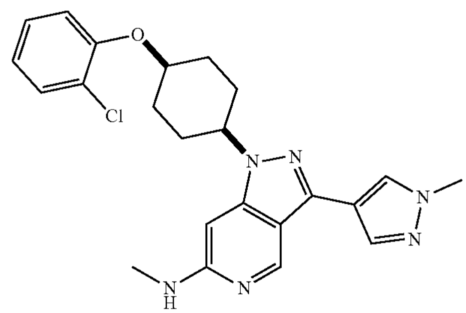 | 1-((1s,4s)-4-(2-chlorophenoxy)cyclohexyl)-N-methyl-3-(1-methyl-1H-pyrazol-4-yl)-1H-pyrazolo[4,3-c]pyridin-6-amine | Mass spectrum (apci) m/z = 437.2 |
| 361 | 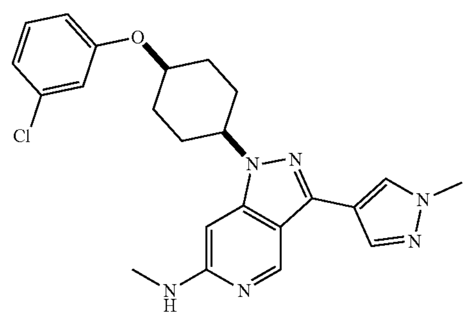 | 1-((1s,4s)-4-(3-chlorophenoxy)cyclohexyl)-N-methyl-3-(1-methyl-1H-pyrazol-4-yl)-1H-pyrazolo[4,3-c]pyridin-6-amine | Mass spectrum (apci) m/z = 437.2 |
| 362 | 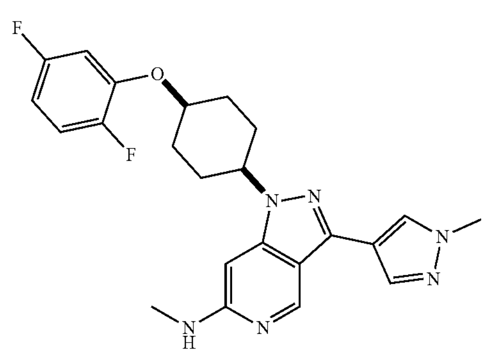 | 1-((1s,4s)-4-(2,5-difluorophenoxy)cyclohexyl)-N-methyl-3-(1-methyl-1H-pyrazol-4-yl)-1H-pyrazolo[4,3-c]pyridin-6-amine | Mass spectrum (apci) m/z = 439.2 |

-continued

| Example | Structure | Name | Data |
|---|---|---|---|
| 363 | 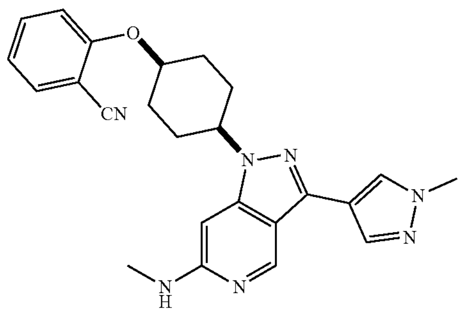 | 2-(((1s,4s)-4-(3-(1-methyl-1H-pyrazol-4-yl)-6-(methylamino)-1H-pyrazolo[4,3-c]pyridin-1-yl)cyclohexyl)oxy)benzonitrile | Mass spectrum (apci) m/z = 428.2 |
| 364 | 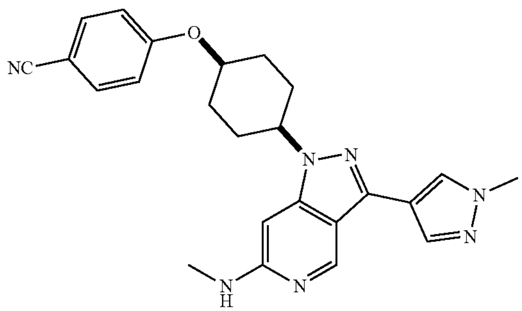 | 4-(((1s,4s)-4-(3-(1-methyl-1H-pyrazol-4-yl)-6-(methylamino)-1H-pyrazolo[4,3-c]pyridin-1-yl)cyclohexyl)oxy)benzonitrile | Mass spectrum (apci) m/z = 428.2 |
| 366 | 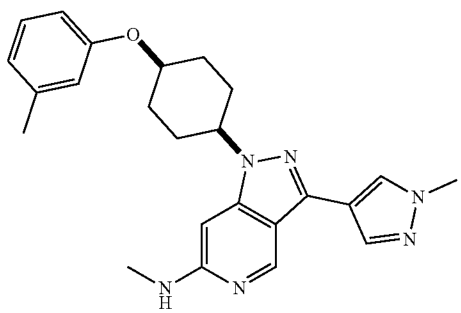 | N-methyl-3-(1-methyl-1H-pyrazol-4-yl)-1-((1s,4s)-4-(m-tolyloxy)cyclohexyl)-1H-pyrazolo[4,3-c]pyridin-6-amine | Mass spectrum (apci) m/z = 417.2 |
| 367 | 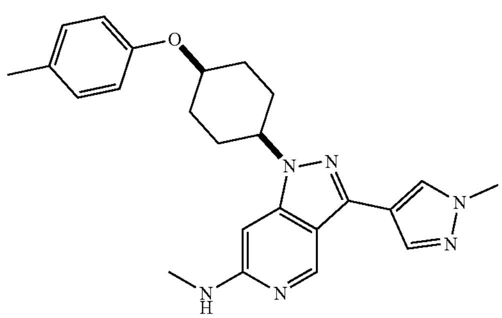 | N-methyl-3-(1-methyl-1H-pyrazol-4-yl)-1-((1s,4s)-4-(p-tolyloxy)cyclohexyl)-1H-pyrazolo[4,3-c]pyridin-6-amine | Mass spectrum (apci) m/z = 417.2 |
| 368 | 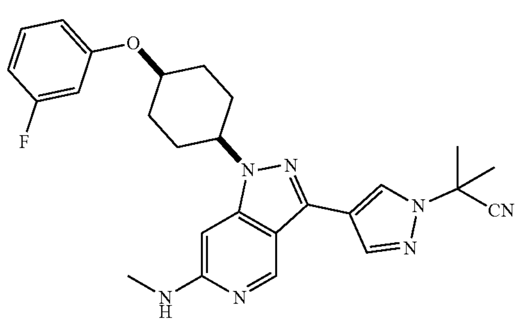 | 2-(4-(1-((1s,4s)-4-(3-fluorophenoxy)cyclohexyl)-6-(methylamino)-1H-pyrazolo[4,3-c]pyridin-3-yl)-1H-pyrazol-1-yl)-2-methylpropanenitrile | Mass spectrum (apci) m/z = 474.2 |

| Example | Structure | Name | Data |
|---|---|---|---|
| 369 | 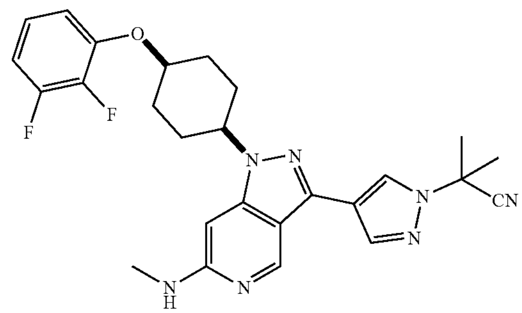 | 2-(4-(1-((1s,4s)-4-(2,3-difluorophenoxy)cyclohexyl)-6-(methylamino)-1H-pyrazolo[4,3-c]pyridin-3-yl)-1H-pyrazol-1-yl)-2-methylpropanenitrile | Mass spectrum (apci) m/z = 492.2 |
| 370 | 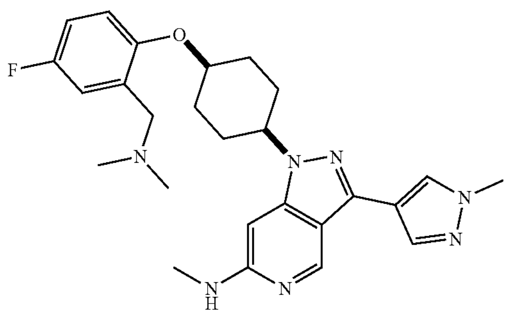 | 1-((1s,4s)-4-(2-((dimethylamino)methyl)-4-fluorophenoxy)cyclohexyl)-N-methyl-3-(1-methyl-1H-pyrazol-4-yl)-1H-pyrazolo[4,3-c]pyridin-6-amine | Mass spectrum (apci) m/z = 478.2 |

Example 371

N-methyl-1-methyl-1H-pyrazol-4-yl)-1-((1 s,4s)-4-phenoxycyclohexyl)-1H-pyrazolo[4,3-c]pyridin-6-amine

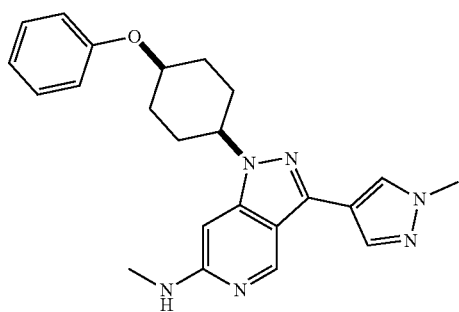

Step A: tert-butyl (1-((1r,4r)-4-hydroxycyclohexyl)-3-(1-methyl-1H-pyrazol-4-yl)-1H-pyrazolo[4,3-c]pyridin-6-yl)(methyl)carbamate (30 mg, 0.070 mmol), phenol (8.6 mg, 0.091 mmol) and triphenylphosphine (20 mg, 0.077 mmol) were diluted with THF (300 µL) followed by the addition of DIAD (15 µL, 0.077 mmol). After stirring for 12 hours, the reaction was partitioned between ethyl acetate and saturated sodium carbonate, dried over MgSO$_4$, filtered and concentrated. The residue was purified over silica gel (10-50% ethyl acetate/hexanes) to afford tert-butyl methyl(3-(1-methyl-1H-pyrazol-4-yl)-1-((1s,4s)-4-phenoxycyclohexyl)-1H-pyrazolo[4,3-c]pyridin-6-yl)carbamate (20 mg, 0.040 mmol, 57% yield).

Step B: tert-butyl methyl(3-(1-methyl-1H-pyrazol-4-yl)-1-((1s,4s)-4-phenoxycyclohexyl)-1H-pyrazolo[4,3-c]pyridin-6-yl)carbamate (20 mg, 0.040 mmol) was diluted with DCM (1 mL) followed by the addition of TFA (1 mL). After stirring for 3 hours, the reaction was concentrated, partitioned between DCM and saturated sodium bicarbonate, dried over MgSO$_4$, filtered and concentrated. The residue was purified over silica gel (1-10% methanol/DCM) to afford N-methyl-3-(1-methyl-1H-pyrazol-4-yl)-1-((1s,4s)-4-phenoxycyclohexyl)-1H-pyrazolo[4,3-c]pyridin-6-amine (13 mg, 0.032 mmol, 81% yield). Mass spectrum (apci) m/z=403.2 (M+H). $^1$H NMR (d6-DMSO) δ 8.79 (d, J=0.8 Hz, 1H), 8.35 (s, 1H), 7.96 (d, J=0.6 Hz, 1H), 7.31 (m, 2H), 7.03 (m, 2H), 6.93 (m, 1H), 6.39 (m, 1H), 6.26 (s, 1H), 4.69 (m, 1H), 4.52 (tt, J=11.3, 3.5 Hz, 1H), 3.92 (s, 3H), 2.81 (d, J=5.1 Hz, 3H), 2.29 (m, 2H), 2.11 (m, 2H), 1.89-1.72 (m, 4H).

Using the procedure described for the preparation of Example 371, the following compounds were also synthesized:

| Example | Structure | Name | Data |
|---|---|---|---|
| 372 | 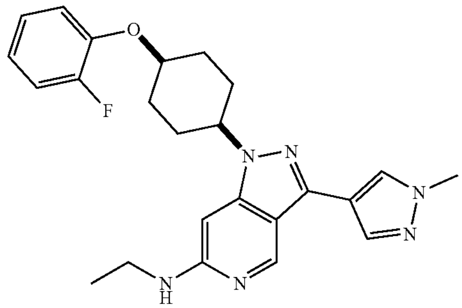 | tert-butyl ethyl(1-((1s,4s)-4-(2-fluorophenoxy)cyclohexyl)-3-(1-methyl-1H-pyrazol-4-yl)-1H-pyrazolo[4,3-c]pyridin-6-yl)carbamate | Mass spectrum (apci) m/z = 435.2 |
| 373 | 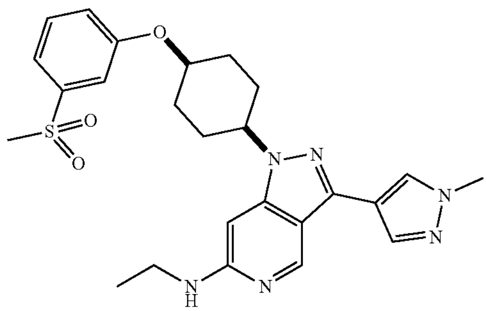 | N-ethyl-3-(1-methyl-1H-pyrazol-4-yl)-1-((1s,4s)-4-(3-(methylsulfonyl)phenoxy)cyclohexyl)-1H-pyrazolo[4,3-c]pyridin-6-amine | Mass spectrum (apci) m/z = 495.2 |
| 374 | 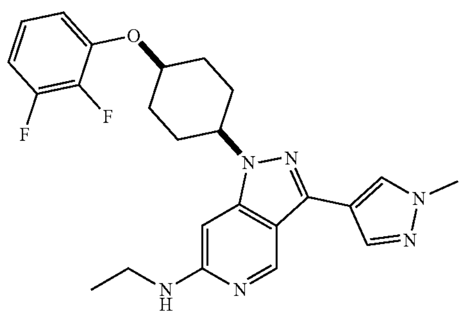 | 1-((1s,4s)-4-(2,3-difluorophenoxy)cyclohexyl)-N-ethyl-3-(1-methyl-1H-pyrazol-4-yl)-1H-pyrazolo[4,3-c]pyridin-6-amine | Mass spectrum (apci) m/z = 453.2 |
| 375 | 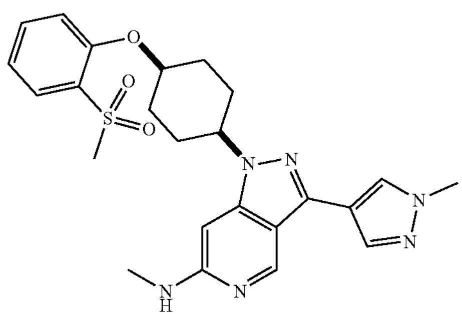 | N-methyl-3-(1-methyl-1H-pyrazol-4-yl)-1-((1s,4s)-4-(2-(methylsulfonyl)phenoxy)cyclohexyl)-1H-pyrazolo[4,3-c]pyridin-6-amine | Mass spectrum (apci) m/z = 481.2 |
| 376 | 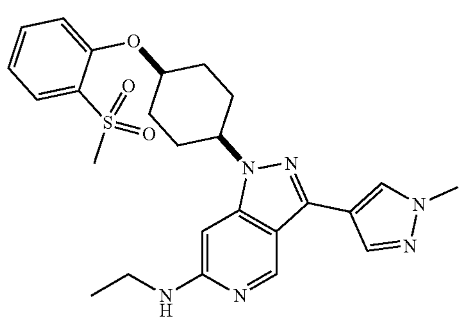 | N-ethyl-3-(1-methyl-1H-pyrazol-4-yl)-1-((1s,4s)-4-(2-(methylsulfonyl)phenoxy)cyclohexyl)-1H-pyrazolo[4,3-c]pyridin-6-amine | Mass spectrum (apci) m/z = 495.2 |

-continued

| Example | Structure | Name | Data |
|---|---|---|---|
| 377 | 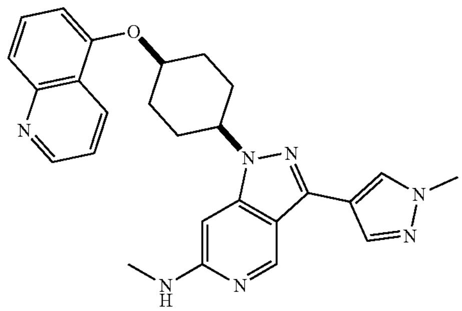 | N-methyl-3-(1-methyl-1H-pyrazol-4-yl)-1-((1s,4s)-4-(quinolin-5-yloxy)cyclohexyl)-1H-pyrazolo[4,3-c]pyridin-6-amine | Mass spectrum (apci) m/z = 454.2 |
| 378 | 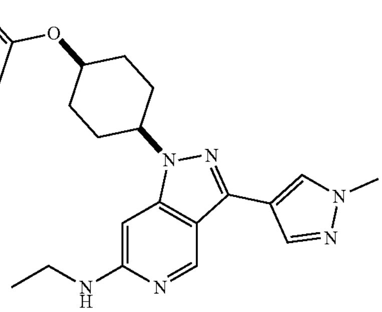 | 3-(((1s,4s)-4-(6-(ethylamino)-3-(1-methyl-1H-pyrazol-4-yl)-1H-pyrazolo[4,3-c]pyridin-1-yl)cyclohexyl)oxy)benzonitrile | Mass spectrum (apci) m/z = 442.2 |
| 379 | 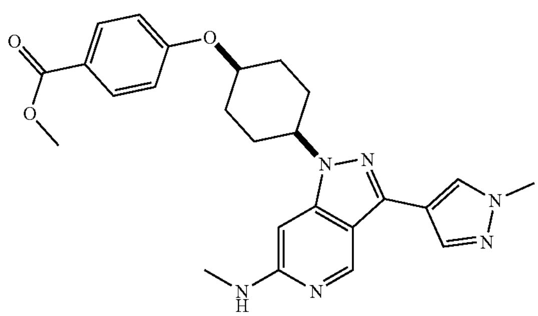 | methyl 4-(((1s,4s)-4-(3-(1-methyl-1H-pyrazol-4-yl)-6-(methylamino)-1H-pyrazolo[4,3-c]pyridin-1-yl)cyclohexyl)oxy)benzoate | Mass spectrum (apci) m/z = 461.2 |
| 380 | 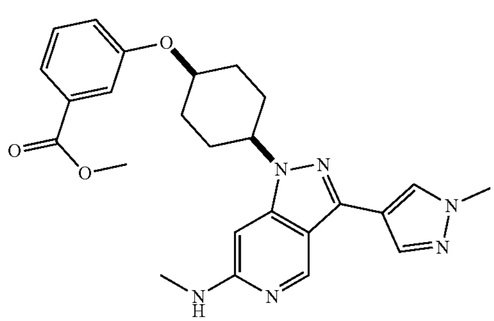 | methyl 3-(((1s,4s)-4-(3-(1-methyl-1H-pyrazol-4-yl)-6-(methylamino)-1H-pyrazolo[4,3-c]pyridin-1-yl)cyclohexyl)oxy)benzoate | Mass spectrum (apci) m/z = 461.2 |
| 381 | 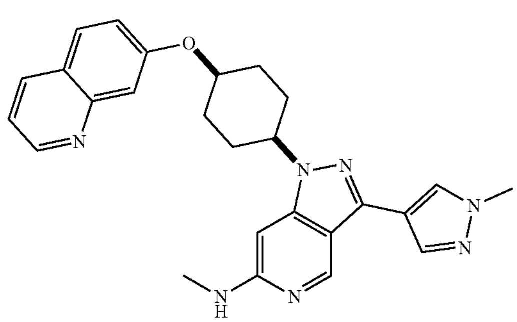 | N-methyl-3-(1-methyl-1H-pyrazol-4-yl)-1-((1s,4s)-4-(quinolin-7-yloxy)cyclohexyl)-1H-pyrazolo[4,3-c]pyridin-6-amine | Mass spectrum (apci) m/z = 454.2 |

-continued

| Example | Structure | Name | Data |
|---|---|---|---|
| 382 | 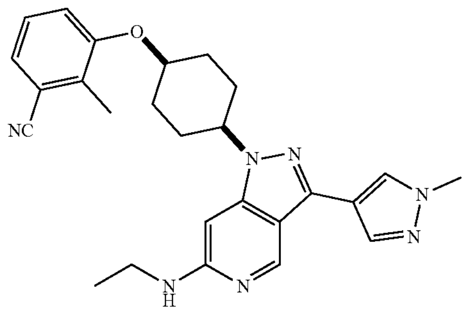 | 3-(((1s,4s)-4-(6-(ethylamino)-3-(1-methyl-1H-pyrazol-4-yl)-1H-pyrazolo[4,3-c]pyridin-1-yl)cyclohexyl)oxy)-2-methylbenzonitrile | Mass spectrum (apci) m/z = 456.3 |
| 383 | 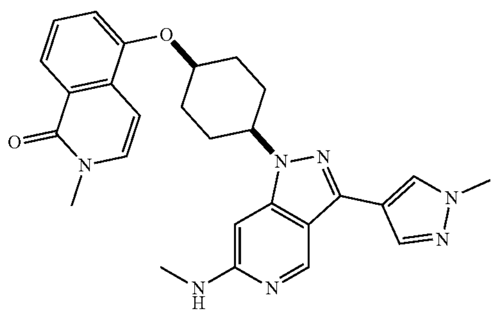 | 2-methyl-5-(((1s,4s)-4-(3-(1-methyl-1H-pyrazol-4-yl)-6-(methylamino)-1H-pyrazolo[4,3-c]pyridin-1-yl)cyclohexyl)oxy)isoquinolin-1(2H)-one | Mass spectrum (apci) m/z = 484.2 |
| 384 | 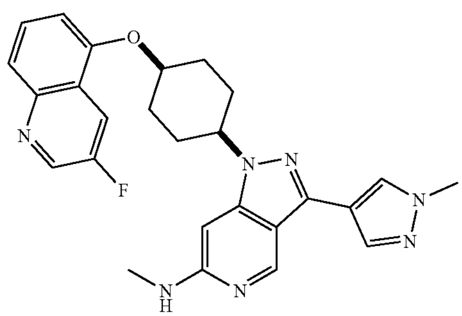 | 1-((1,4s)-4-((3-fluoroquinolin-5-yl)oxy)cyclohexyl)-N-methyl-3-(1-methyl-1H-pyrazol-4-yl)-1H-pyrazolo[4,3-c]pyridin-6-amine | Mass spectrum (apci) m/z = 472.2 |
| 385 | 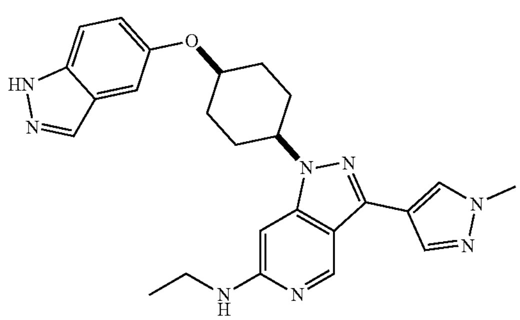 | 1-((1s,4s)-4-((1H-indazol-5-yl)oxy)cyclohexyl)-N-ethyl-3-(1-methyl-1H-pyrazol-4-yl)-1H-pyrazolo[4,3-c]pyridin-6-amine | Mass spectrum (apci) m/z = 457.2 |
| 386 | 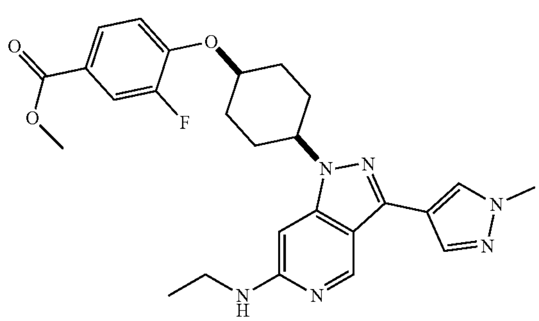 | methyl 4-(((1s,4s)-4-(6-(ethylamino)-3-(1-methyl-1H-pyrazol-4-yl)-1H-pyrazolo[4,3-c]pyridin-1-yl)cyclohexyl)oxy)-3-fluorobenzoate | Mass spectrum (apci) m/z = 493.2 |

-continued

| Example | Structure | Name | Data |
|---|---|---|---|
| 387 | 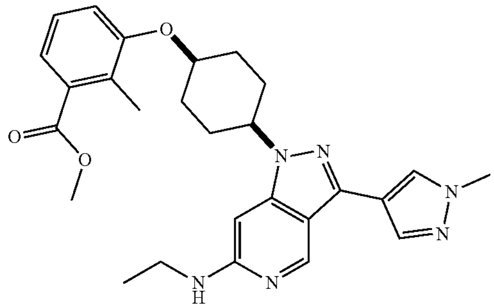 | methyl 3-(((1s,4s)-4-(6-(ethylamino)-3-(1-methyl-1H-pyrazol-4-yl)-1H-pyrazolo[4,3-c]pyridin-1-yl)cyclohexyl)oxy)-2-methylbenzoate | Mass spectrum (apci) m/z = 489.2 |
| 388 | 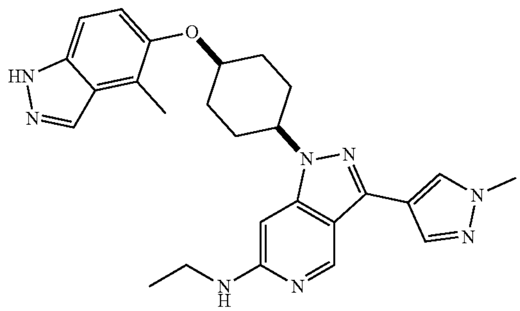 | N-ethyl-1-((1s,4s)-4-((4-methyl-1H-indazol-5-yl)oxy)cyclohexyl)-3-(1-methyl-1H-pyrazol-4-yl)-1H-pyrazolo[4,3-c]pyridin-6-amine | Mass spectrum (apci) m/z = 471.3 |
| 389 | 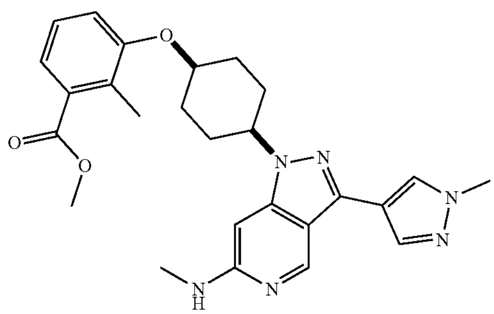 | methyl 2-methyl-3-(((1s,4s)-4-(3-(1-methyl-1H-pyrazol-4-yl)-6-(methylamino)-1H-pyrazolo[4,3-c]pyridin-1-yl)cyclohexyl)oxy)benzoate | Mass spectrum (apci) m/z = 475.2 |
| 390 | 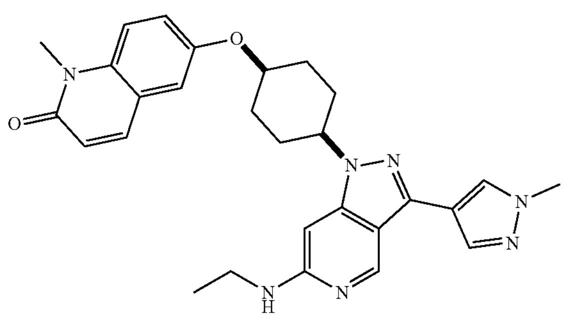 | 6-(((1s,4s)-4-(6-(ethylamino)-3-(1-methyl-1H-pyrazol-4-yl)-1H-pyrazolo[4,3-c]pyridin-1-yl)cyclohexyl)oxy)-1-methylquinolin-2(1H)-one | Mass spectrum (apci) m/z = 498.3 |
| 391 | 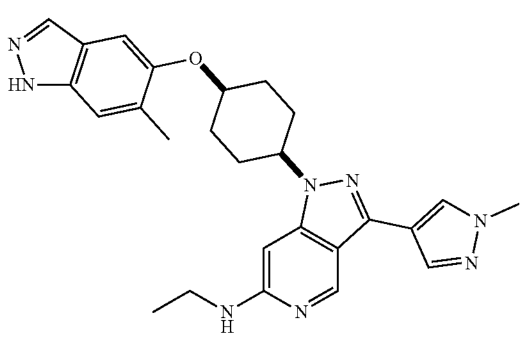 | N-ethyl-1-((1s,4s)-4-((6-methyl-1H-indazol-5-yl)oxy)cyclohexyl)-3-(1-methyl-1H-pyrazol-4-yl)-1H-pyrazolo[4,3-c]pyridin-6-amine | Mass spectrum (apci) m/z = 471.3 |

| Example | Structure | Name | Data |
|---|---|---|---|
| 392 | 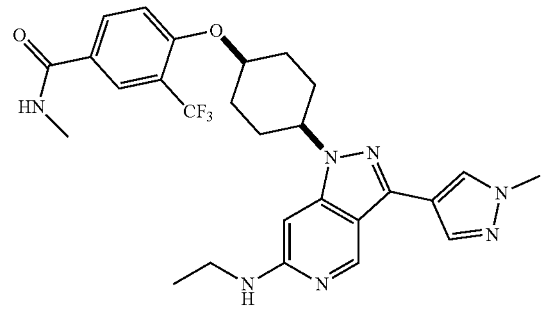 | 4-(((1s,4s)-4-(6-(ethylamino)-3-(1-methyl-1H-pyrazol-4-yl)-1H-pyrazolo[4,3-c]pyridin-1-yl)cyclohexyl)oxy)-N-methyl-3-(trifluoromethyl)benzamide | Mass spectrum (apci) m/z = 542.2 |
| 393 | 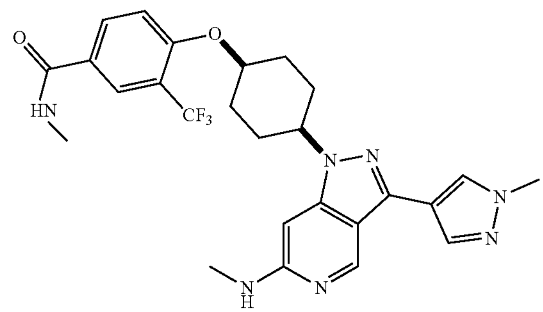 | N-methyl-4-(((1s,4s)-4-(3-(1-methyl-1H-pyrazol-4-yl)-6-(methylamino)-1H-pyrazolo[4,3-c]pyridin-1-yl)cyclohexyl)oxy)-3-(trifluoromethyl)benzamide | Mass spectrum (apci) m/z = 528.2 |

Example 394

2-(4-(1-((1s,4s)-4-(2-fluorophenoxy)cyclohexyl)-6-(methylamino)-1H-pyrazolo[4,3-c]pyridin-3-yl)-1H-pyrazol-1-yl)-2-methylpropanenitrile

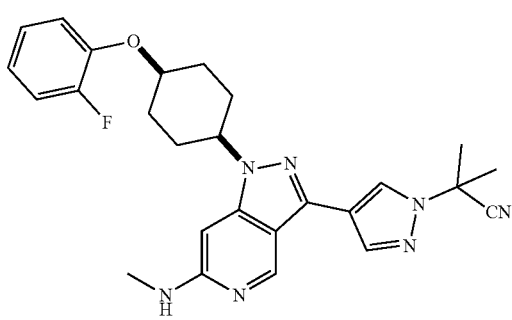

Step A: DIAD (0.1216 mL, 0.6172 mmol) was added to Ph₃P (0.1619 g, 0.6172 mmol) in THF (5.9 mL) at 0° C. To this was added tert-butyl (3-bromo-1-((1r,4r)-4-hydroxycyclohexyl)-1H-pyrazolo[4,3-c]pyridin-6-yl)(methyl)carbamate (0.250 g, 0.5878 mmol) followed by 2-fluorophenol (0.07079 mL, 0.7641 mmol) at 0° C. The reaction mixture was warmed to room temperature overnight. The reaction mixture was partitioned between water (10 mL) and EtOAc (10 mL), extracted with EtOAc (3×10 mL), washed with water (2×20 mL) and brine (20 mL), dried over Na₂SO₄, filtered and concentrated. The residue was purified over silica gel (5-60% EtOAc in hexanes) to afford tert-butyl (3-bromo-1-((1s,4s)-4-(2-fluorophenoxy)cyclohexyl)-1H-pyrazolo[4,3-c]pyridin-6-yl)(methyl)carbamate (0.078 g, 0.1502 mmol, 25.55% yield).

Step B: tert-butyl (3-bromo-1-((1s,4s)-4-(2-fluorophenoxy)cyclohexyl)-1H-pyrazolo[4,3-c]pyridin-6-yl)(methyl)carbamate (0.020 g, 0.0385 mmol), 2-methyl-2-(4-(4,4,5,5-tetramethyl-1,3,2-dioxaborolan-2-yl)-1H-pyrazol-1-yl)propanenitrile (0.012 g, 0.046 mmol) and Pd(PPh₃)₄ (0.00222 g, 0.00193 mmol) were diluted with dioxane (0.4 mL). 2M Na₂CO₃ (0.0674 mL, 0.135 mmol) was then added and the reaction was heated to 85° C. overnight. The reaction mixture was diluted with DCM (2 mL), filtered through a syringe filter and TFA (2 mL) was added. After 1 h, the reaction was concentrated and purified by preparative HPLC (5-70% ACN in water with 0.2% TFA). The fractions containing the product were partitioned between saturated NaHCO₃ and DCM, dried over sodium sulfate, filtered and concentrated to afford 2-(4-(1-((1s,4s)-4-(2-fluorophenoxy)cyclohexyl)-6-(methylamino)-1H-pyrazolo[4,3-c]pyridin-3-yl)-1H-pyrazol-1-yl)-2-methylpropanenitrile (0.0133 g, 0.0281 mmol, 72.9% yield). Mass spectrum (apci) m/z=474.2 (M+H). $^1$H NMR (CDCl₃) δ 8.68 (s, 1H), 8.16 (s, 1H), 8.10 (s, 1H), 7.16-7.06 (m, 3H), 6.95 (m, 1H), 6.22 (s, 1H), 4.65 (m, 1H), 4.43 (tt, J=12.3, 3.9 Hz, 1H), 3.00 (s, 3H), 2.65 (m, 2H), 2.32 (m, 2H), 2.08 (s, 6H), 1.92 (m, 2H), 1.77 (m, 2H).

Using the procedure described for the preparation of Example 394, the following compounds were also synthesized:

| Example | Structure | Name | Data |
|---|---|---|---|
| 395 | 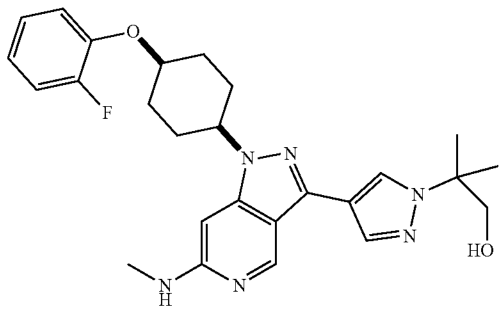 | 2-(4-(1-((1s,4s)-4-(2-fluorophenoxy)cyclohexyl)-6-(methylamino)-1H-pyrazolo[4,3-c]pyridin-3-yl)-1H-pyrazol-1-yl)-2-methylpropan-1-ol | Mass spectrum (apci) m/z = 479.3 |
| 396 | 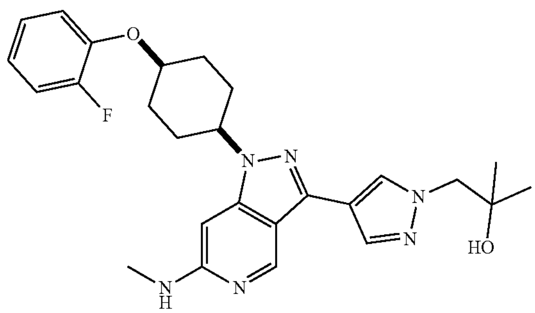 | 1-(4-(1-((1s,4s)-4-(2-fluorophenoxy)cyclohexyl)-6-(methylamino)-1H-pyrazolo[4,3-c]pyridin-3-yl)-1H-pyrazol-1-yl)-2-methylpropan-2-ol | Mass spectrum (apci) m/z = 479.2 |
| 397 | 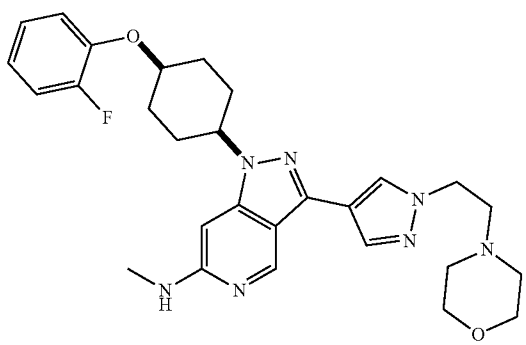 | 1-((1s,4s)-4-(2-fluorophenoxy)cyclohexyl)-N-methyl-3-(1-(2-morpholinoethyl)-1H-pyrazol-4-yl)-1H-pyrazolo[4,3-c]pyridin-6-amine | Mass spectrum (apci) m/z = 520.3 |
| 398 | 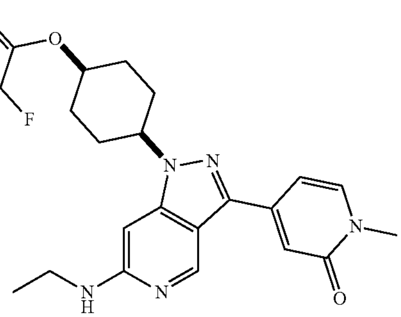 | 4-(6-(ethylamino)-1-((1s,4s)-4-(2-fluorophenoxy)cyclohexyl)-1H-pyrazolo[4,3-c]pyridin-3-yl)-1-methylpyridin-2(1H)-one | Mass spectrum (apci) m/z = 462.2 |
| 399 | 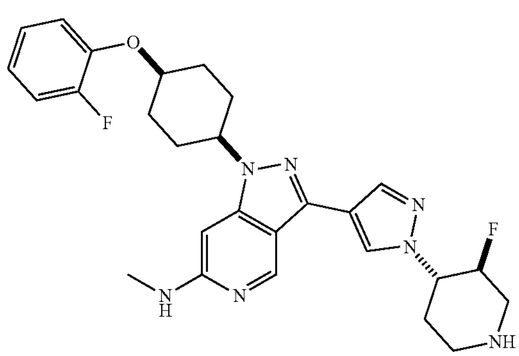 | 1-((1s,4R)-4-(2-fluorophenoxy)cyclohexyl)-3-(1-((3S,4S)-3-fluoropiperidin-4-yl)-1H-pyrazol-4-yl)-N-methyl-1H-pyrazolo[4,3-c]pyridin-6-amine | Mass spectrum (apci) m/z = 508.2 |

| Example | Structure | Name | Data |
|---|---|---|---|
| 400 | 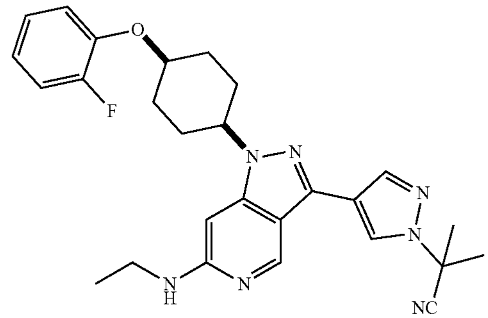 | 2-(4-(6-(ethylamino)-1-((1s,4s)-4-(2-fluorophenoxy)cyclohexyl)-1H-pyrazolo[4,3-c]pyridin-3-yl)-1H-pyrazol-1-yl)-2-methylpropanenitrile | Mass spectrum (apci) m/z = 488.3 |
| 401 | 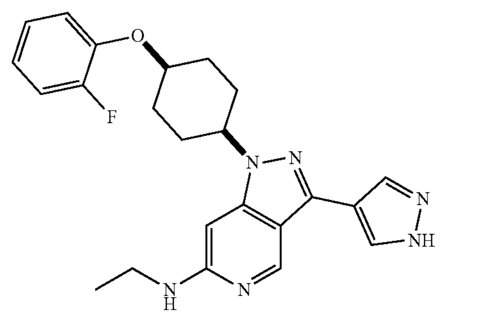 | N-ethyl-1-((1s,4s)-4-(2-fluorophenoxy)cyclohexyl)-3-(1H-pyrazol-4-yl)-1H-pyrazolo[4,3-c]pyridin-6-amine | Mass spectrum (apci) m/z = 421.2 |

Example 402

N-(2-cyclopropylethyl)-1-((1s,4s)-4-(2-fluorophenoxy)cyclohexyl)-3-(1-methyl-1H-pyrazol-4-yl)-1H-pyrazolo[4,3-c]pyridin-6-amine

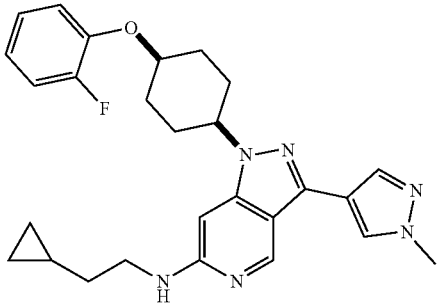

Step A: 3-bromo-6-chloro-1-((1r,4r)-4-((tetrahydro-2H-pyran-2-yl)oxy)cyclohexyl)-1H-pyrazolo[4,3-c]pyridine (5.3 g, 12.8 mmol), 1-methyl-4-(4,4,5,5-tetramethyl-1,3,2-dioxaborolan-2-yl)-1H-pyrazole (2.92 g, 14.1 mmol) and Pd(PPh$_3$)$_4$ (0.738 g, 0.639 mmol) were diluted with dioxane (60 mL) followed by the addition of 2M Na$_2$CO$_3$ (22.4 mL, 44.7 mmol). The reaction mixture was purged with argon, heated to 85° C. and stirred for 12 hours. The reaction mixture was partitioned between ethyl acetate and water, extracted with ethyl acetate, dried over MgSO$_4$, filtered and concentrated. The residue was purified over silica gel (40-100% ethyl acetate/hexanes) to afford 6-chloro-3-(1-methyl-1H-pyrazol-4-yl)-1-((1r,4r)-4-((tetrahydro-2H-pyran-2-yl)oxy)cyclohexyl)-1H-pyrazolo[4,3-c]pyridine (4.21 g, 10.1 mmol, 79.2% yield).

Step B: 6-chloro-3-(1-methyl-1H-pyrazol-4-yl)-1-((1r,4r)-4-((tetrahydro-2H-pyran-2-yl)oxy)cyclohexyl)-1H-pyrazolo[4,3-c]pyridine (250 mg, 0.601 mmol) was diluted with DCM (1 mL) followed by the addition of TFA (1 mL). After stirring for 3 hours, the reaction was concentrated and partitioned between DCM and saturated aqueous sodium bicarbonate, dried over MgSO$_4$, filtered and concentrated. The residue was purified over silica gel (20-80% ethyl acetate/hexanes) to afford (1r,4r)-4-(6-chloro-3-(1-methyl-1H-pyrazol-4-yl)-1H-pyrazolo[4,3-c]pyridin-1-yl)cyclohexan-1-ol (140 mg, 0.422 mmol, 70.2% yield).

Step C: (1r,4r)-4-(6-chloro-3-(1-methyl-1H-pyrazol-4-yl)-1H-pyrazolo[4,3-c]pyridin-1-yl)cyclohexan-1-ol (140 mg, 0.422 mmol), triphenylphosphine (122 mg, 0.464 mmol) and 2-fluorophenol (51.2 µL, 0.549 mmol) were diluted with THF (3 mL) followed by the addition of DIAD (90.2 µL, 0.464 mmol). After stirring for 12 hours, the reaction was partitioned between ethyl acetate and saturated sodium bicarbonate, dried over MgSO$_4$, filtered and concentrated. The residue was purified over silica gel (10-60% ethyl acetate/hexanes) to afford 6-chloro-1-((1s,4s)-4-(2-fluorophenoxy)cyclohexyl)-3-(1-methyl-1H-pyrazol-4-yl)-1H-pyrazolo[4,3-c]pyridine (135 mg, 0.317 mmol, 75.1% yield).

Step D: 6-chloro-1-((1s,4s)-4-(2-fluorophenoxy)cyclohexyl)-3-(1-methyl-1H-pyrazol-4-yl)-1H-pyrazolo[4,3-c]pyridine (20 mg, 0.047 mmol) was diluted with DMA (200 µL) followed by the addition of 2-cyclopropylethan-1-amine (40 mg, 0.47 mmol). The reaction mixture was sealed, heated to 140° C. and stirred for 36 hours. The reaction mixture was partitioned between ethyl acetate and water, dried over MgSO$_4$, filtered and concentrated. The residue was purified over silica gel (1-10% methanol/DCM) to afford N—(2-cyclopropylethyl)-1-((1s,4s)-4-(2-fluorophenoxy)cyclohexyl)-3-(1-methyl-1H-pyrazol-4-yl)-1H-pyrazolo[4,3-c]pyridin-6-amine (4 mg, 0.0084 mmol, 18% yield). Mass spectrum (apci) m/z=475.3 (M+H). ¹H NMR (CDCl₃) δ 8.67 (s, 1H), 7.99 (s, 1H), 7.88 (s, 1H), 7.14-7.04 (m, 3H), 6.94 (m, 1H), 6.22 (s, 1H), 4.65 (m, 1H), 4.41 (tt, J=11.7, 3.7 Hz, 1H), 3.99 (s, 3H), 3.36 (t, J=7.0 Hz, 2H), 2.64 (m, 2H), 2.31 (m, 2H), 1.91 (m, 2H), 1.76 (m, 2H), 1.63 (q, J=6.8 Hz, 2H), 0.84 (m, 1H), 0.52 (m, 2H), 0.15 (m, 2H).

Example 403

1-((1s,4s)-4-(2-fluorophenoxy)cyclohexyl)-3-(1-methyl-1H-pyrazol-4-yl)-N-(2,2,2-trifluoroethyl)-1H-pyrazolo[4,3-c]pyridin-6-amine

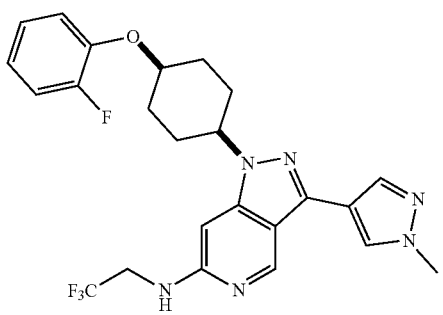

Step A: 6-chloro-1-((1s,4s)-4-(2-fluorophenoxy)cyclohexyl)-3-(1-methyl-1H-pyrazol-4-yl)-1H-pyrazolo[4,3-c]pyridine (25 mg, 0.059 mmol), 2-(Dicyclohexylphosphino)-2',4',6'-tri-1-propyl-1,1'-biphenyl (28 mg, 0.059 mmol), Cs₂CO₃ (96 mg, 0.29 mmol) and Pd2(dba)₃ (27 mg, 0.029 mmol) were diluted with dioxane (200 μL) followed by the addition of tert-butyl (2,2,2-trifluoroethyl)carbamate (117 mg, 0.59 mmol). The reaction mixture was purged with argon, sealed and heated to 95° C. for 12 h. The reaction mixture was partitioned between ethyl acetate and water, dried over MgSO₄, filtered and concentrated. The residue was purified over silica gel (10-50% ethyl acetate/hexanes) to afford tert-butyl (1-((1s,4s)-4-(2-fluorophenoxy)cyclohexyl)-3-(1-methyl-1H-pyrazol-4-yl)-1H-pyrazolo[4,3-c]pyridin-6-yl)(2,2,2-trifluoroethyl)carbamate (4.5 mg, 0.0076 mmol, 13% yield).

Step B: tert-butyl (1-((1s,4s)-4-(2-fluorophenoxy)cyclohexyl)-3-(1-methyl-1H-pyrazol-4-yl)-1H-pyrazolo[4,3-c]pyridin-6-yl)(2,2,2-trifluoroethyl)carbamate (4.5 mg, 0.0076 mmol) was diluted with DCM (500 μL) followed by the addition of TFA (500 μL). After stirring for 3 hours, the reaction was concentrated, partitioned between ethyl acetate and saturated sodium carbonate, dried over MgSO₄, filtered and concentrated. The residue was purified over silica gel (10% methanol/DCM) to afford 1-((1s,4s)-4-(2-fluorophenoxy)cyclohexyl)-3-(1-methyl-1H-pyrazol-4-yl)-N-(2,2,2-trifluoroethyl)-1H-pyrazolo[4,3-c]pyridin-6-amine (2.0 mg, 0.0041 mmol, 54% yield). Mass spectrum (apci) m/z=489.1 (M+H). ¹H NMR (CDCl₃) δ 9.40 (m, 1H), 8.97 (s, 1H), 8.10 (s, 1H), 8.08 (s, 1H), 7.20-7.05 (m, 3H), 6.97 (m, 1H), 6.60 (s, 1H), 4.70 (m, 1H), 4.50 (m, 1H), 4.08-4.00 (m, 5H), 2.61 (m, 2H), 2.35 (m, 2H), 1.94 (m, 2H), 1.79 (m, 2H).

Using the procedure described for the preparation of Example 403, the following compounds were also synthesized:

| Example | Structure | Name | Data |
|---|---|---|---|
| 404 | 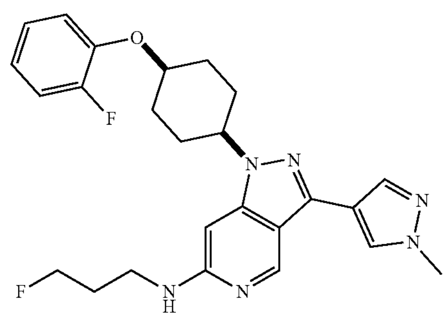 | 1-((1s,4s)-4-(2-fluorophenoxy)cyclohexyl)-N-(3-fluoropropyl)-3-(1-methyl-1H-pyrazol-4-yl)-1H-pyrazolo[4,3-c]pyridin-6-amine | Mass spectrum (apci) m/z = 467.3 |
| 405 | 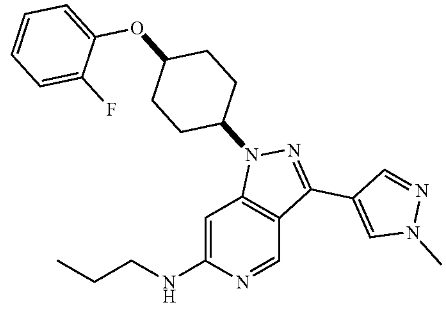 | 1-((1s,4s)-4-(2-fluorophenoxy)cyclohexyl)-3-(1-methyl-1H-pyrazol-4-yl)-N-propyl-1H-pyrazolo[4,3-c]pyridin-6-amine | Mass spectrum (apci) m/z = 449.2 |

| Example | Structure | Name | Data |
|---|---|---|---|
| 406 | 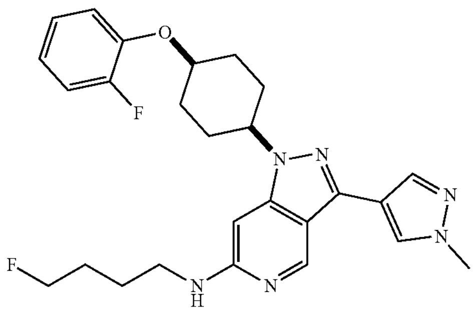 | N-(4-fluorobutyl)-1-((1s,4s)-4-(2-fluorophenoxy)cyclohexyl)-3-(1-methyl-1H-pyrazol-4-yl)-1H-pyrazolo[4,3-c]pyridin-6-amine bis(2,2,2-trifluoroacetate) | Mass spectrum (apci) m/z = 481.3 |

Example 407

N-ethyl-3-(1-methyl-1H-pyrazol-4-yl)-1-((1 r,4r)-4-phenoxycyclohexyl)-1H-pyrazolo[4,3-c]pyridin-6-amine

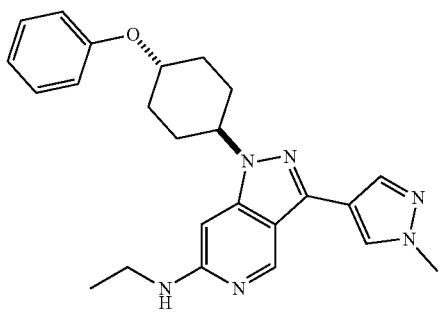

Step A: 3-bromo-6-chloro-1H-pyrazolo[4,3-c]pyridine (110 mg, 0.473 mmol), (1s,4s)-4-phenoxycyclohexyl 4-methylbenzenesulfonate (213 mg, 0.615 mmol) and Cs₂CO₃ (324 mg, 0.994 mmol) were diluted with DMA (3 mL) and heated to 90° C. After 12 h, the reaction was partitioned between ethyl acetate and water, dried over MgSO₄, filtered and concentrated. The residue was purified over silica gel (10-50% ethyl acetate/hexanes) to afford 3-bromo-6-chloro-1-((1r,4r)-4-phenoxycyclohexyl)-1H-pyrazolo[4,3-c]pyridine (65 mg, 0.160 mmol, 33.8% yield).

Step B: 3-bromo-6-chloro-1-((1r,4r)-4-phenoxycyclohexyl)-1H-pyrazolo[4,3-c]pyridine (65 mg, 0.16 mmol), 1-methyl-4-(4,4,5,5-tetramethyl-1,3,2-dioxaborolan-2-yl)-1H-pyrazole (37 mg, 0.18 mmol) and Pd(PPh₃)₄ (9.2 mg, 0.0080 mmol) were diluted with dioxane (700 µL) followed by the addition of 2M Na₂CO₃ (240 µL, 0.48 mmol). The reaction mixture was purged with argon, sealed and heated to 90° C. After 12 h, the reaction was partitioned between ethyl acetate and water, dried over MgSO₄, filtered and concentrated. The residue was purified over silica gel (10-60% ethyl acetate/hexanes) to afford 6-chloro-3-(1-methyl-1H-pyrazol-4-yl)-1-((1r,4r)-4-phenoxycyclohexyl)-1H-pyrazolo[4,3-c]pyridine (50 mg, 0.12 mmol, 77% yield).

Step C: 6-chloro-3-(1-methyl-1H-pyrazol-4-yl)-1-((1r,4r)-4-phenoxycyclohexyl)-1H-pyrazolo[4,3-c]pyridine (25 mg, 0.061 mmol), 2-(Dicyclohexylphosphino)-2',4',6'-tri-1-propyl-1,1'-biphenyl (29 mg, 0.061 mmol), Cs₂CO₃ (80 mg, 0.25 mmol) and Pd2(dba)₃ (28 mg, 0.031 mmol) were diluted with dioxane (500 µL), followed by the addition of tert-butyl ethylcarbamate (89 mg, 0.61 mmol). The reaction mixture was purged with argon, sealed and heated to 95° C. After 12 h, the reaction was partitioned between ethyl acetate and water, dried over MgSO₄, filtered and concentrated. The residue was purified over silica gel (10-60% ethyl acetate/hexanes) to afford tert-butyl ethyl(3-(1-methyl-1H-pyrazol-4-yl)-1-((1r,4r)-4-phenoxycyclohexyl)-1H-pyrazolo[4,3-c]pyridin-6-yl)carbamate (20 mg, 0.039 mmol, 63% yield).

Step D: tert-butyl ethyl(3-(1-methyl-1H-pyrazol-4-yl)-1-((1r,4r)-4-phenoxycyclohexyl)-1H-pyrazolo[4,3-c]pyridin-6-yl)carbamate (20 mg, 0.039 mmol) was diluted with DCM (1 mL) followed by the addition of TFA (1 mL). After stirring for 4 hours, the reaction was concentrated, partitioned between saturated sodium carbonate and ethyl acetate, dried over sodium sulfate, filtered and concentrated. The residue was purified over silica gel (10% methanol/DCM) to afford N-ethyl-3-(1-methyl-1H-pyrazol-4-yl)-1-((1r,4r)-4-phenoxycyclohexyl)-1H-pyrazolo[4,3-c]pyridin-6-amine (7 mg, 0.017 mmol, 43% yield). Mass spectrum (apci) m/z=417.2 (M+H). $^1$H NMR (CDCl₃) δ 8.68 (d, J=1.0 Hz, 1H), 7.98 (s, 1H), 7.85 (s, 1H), 7.30 (m, 2H), 6.96 (m, 3H), 6.02 (d, J=0.8 Hz, 1H), 4.70 (br s, 1H), 4.39 (tt, J=10.5, 4.3 Hz, 1H), 4.29 (tt, J=11.3, 4.2 Hz, 1H), 4.00 (s, 3H), 3.30 (m, 2H), 2.38 (m, 2H), 2.24 (m, 2H), 2.13 (m, 2H), 1.70 (m, 2H), 1.35 (t, J=7.2 Hz, 3H).

Example 408

2-(4-(1-((1s,4s)-4-(2-fluorophenoxy)cyclohexyl)-6-(methylamino)-1H-pyrazolo[4,3-c]pyridin-3-yl)-1H-pyrazol-1-yl)propane-1,3-diol

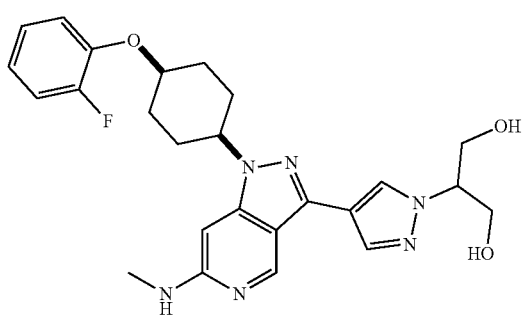

Step A: tert-butyl (3-bromo-1-((1r,4r)-4-((tert-butyldimethylsilyl)oxy)cyclohexyl)-1H-pyrazolo[4,3-c]pyridin-6-yl)(methyl)carbamate (520 mg, 0.964 mmol), tert-butyl 4-(4,4,5,5-tetramethyl-1,3,2-dioxaborolan-2-yl)-1H-pyrazole-1-carboxylate (567 mg, 1.93 mmol) and Pd(PPh$_3$)$_4$ (111 mg, 0.10 mmol) were combined in dioxanes (10 mL) and treated with 2M K$_2$CO$_3$ (1.45 mL, 2.89 mmol) and heated to 100° C. in a sealed tube overnight. 100 mg of the boronate and 50 mg of Pd(PPh$_3$)$_4$ were added and the mixture heated overnight again, partitioned between water (30 mL) and EtOAc (30 mL), extracted with EtOAc (2×20 mL), washed with brine (20 mL), dried over Na$_2$SO$_4$, filtered and concentrated. The residue was purified over silica gel (20-100% EtOAc/hexanes) to afford tert-butyl (1-((1r,4r)-4-((tert-butyldimethylsilyl)oxy)cyclohexyl)-3-(1H-pyrazol-4-yl)-1H-pyrazolo[4,3-c]pyridin-6-yl)(methyl)carbamate (584 mg, 115% yield).

Step B: A solution of tert-butyl (1-((1r,4r)-4-((tert-butyldimethylsilyl)oxy)cyclohexyl)-3-(1H-pyrazol-4-yl)-1H-pyrazolo[4,3-c]pyridin-6-yl)(methyl)carbamate (340 mg, 0.65 mmol) in DMA (5 mL) was treated with Cs$_2$CO$_3$ (421 mg, 1.29 mmol) followed by (2s,5s)-2-phenyl-1,3-dioxan-5-yl methanesulfonate (500 mg, 1.94 mmol). The mixture was stirred at 100° C. overnight, partitioned between water (10 mL) and EtOAc (10 mL), extracted with EtOAc (2×10 mL), washed with water (4×10 mL) and brine (10 mL), dried over Na$_2$SO$_4$, filtered and concentrated. The residue was purified over silica gel (5-50% EtOAc/hexanes) to afford tert-butyl (1-((1r,4R)-4-((tert-butyldimethylsilyl)oxy)cyclohexyl)-3-(1-((2R,5r)-2-phenyl-1,3-dioxan-5-yl)-1H-pyrazol-4-yl)-1H-pyrazolo[4,3-c]pyridin-6-yl)(methyl)carbamate (109 mg, 24.5% yield).

Step C: To a solution of tert-butyl (1-((1r,4R)-4-((tert-butyldimethylsilyl)oxy)cyclohexyl)-3-(1-((2R,5r)-2-phenyl-1,3-dioxan-5-yl)-1H-pyrazol-4-yl)-1H-pyrazolo[4,3-c]pyridin-6-yl)(methyl)carbamate (109 mg, 0.16 mmol) in THF (5 mL) was added 1M TBAF (475 µL, 0.475 mmol). The mixture was stirred over the weekend, partitioned between saturated NaHCO$_3$(10 mL) and EtOAc (10 mL), extracted with EtOAc (2×10 mL), washed with brine (10 mL), dried over Na$_2$SO$_4$, filtered and concentrated to afford crude tert-butyl (1-((1r,4R)-4-hydroxycyclohexyl)-3-(1-((2R,5r)-2-phenyl-1,3-dioxan-5-yl)-1H-pyrazol-4-yl)-1H-pyrazolo[4,3-c]pyridin-6-yl)(methyl)carbamate (102 mg, 112% yield).

Step D: To a solution of tert-butyl (1-((1r,4R)-4-hydroxycyclohexyl)-3-(1-((2R,5r)-2-phenyl-1,3-dioxan-5-yl)-1H-pyrazol-4-yl)-1H-pyrazolo[4,3-c]pyridin-6-yl)(methyl)carbamate (30 mg, 0.05 mmol) and 2-fluorophenol (18 mg, 0.16 mmol) in THF (3 mL) was added PPh$_3$ (41 mg, 0.16 mmol) followed by DIAD (31 µL, 0.17 mmol). The mixture was warmed to 60° C. for 2 h. The reaction mixture was partitioned between water (10 mL) and EtOAc (10 mL) and the aqueous layer was extracted with EtOAc (2×10 mL), washed with brine (10 mL), dried over Na$_2$SO$_4$, filtered and concentrated. The residue was purified over silica gel (20-80% EtOAc/hexanes) to afford tert-butyl (1-((1s,4S)-4-(2-fluorophenoxy)cyclohexyl)-3-(1-((2R,5r)-2-phenyl-1,3-dioxan-5-yl)-1H-pyrazol-4-yl)-1H-pyrazolo[4,3-c]pyridin-6-yl)(methyl)carbamate (35 mg, 100% yield).

Step E: To a solution of tert-butyl (1-((1s,4S)-4-(2-fluorophenoxy)cyclohexyl)-3-(1-((2R,5r)-2-phenyl-1,3-dioxan-5-yl)-1H-pyrazol-4-yl)-1H-pyrazolo[4,3-c]pyridin-6-yl)(methyl)carbamate (35 mg, 0.05 mmol) in MeOH (2 mL) was added concentrated HCl (3 drops). The mixture was stirred at reflux for 3 h. The reaction mixture was concentrated and purified on preparative HPLC (5-95% ACN in water/0.1% TFA). Clean fractions were combined, concentrated to half volume then partitioned between 1N NaOH/10% MeOH/DCM, dried over sodium sulfate, filtered and concentrated to afford 2-(4-(1-((1s,4s)-4-(2-fluorophenoxy)cyclohexyl)-6-(methylamino)-1H-pyrazolo[4,3-c]pyridin-3-yl)-H-pyrazol-1-yl)propane-1,3-diol (6 mg, 24% yield). Mass spectrum (apci) m/z=481.2 (M+H). $^1$H NMR (CDCl$_3$) δ 8.62 (s, 1H), 8.07 (s, 1H), 8.05 (s, 1H). 7.15-7.04 (m, 3H), 6.94 (i, 1H), 6.17 (s, 1H), 4.95 (br s, 1H), 4.64 (m, 1H), 4.40 (m, 2H), 4.15 (d, J=5.1 Hz, 4H), 2.97 (s, 3H), 2.63 (m, 2H), 2.30 (m, 2H), 1.89 (m, 2H), 1.75 (in, 2H).

Using the procedure described for the preparation of Example 408, the following compounds were also synthesized:

| Example | Structure | Name | Data |
|---|---|---|---|
| 409 | 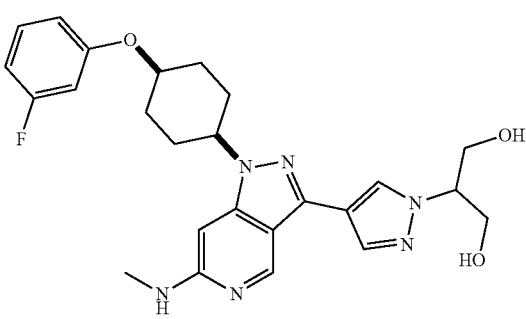 | 2-(4-(1-((1s,4s)-4-(3-fluorophenoxy)cyclohexyl)-6-(methylamino)-1H-pyrazolo[4,3-c]pyridin-3-yl)-1H-pyrazol-1-yl)propane-1,3-diol | Mass spectrum (apci) m/z = 481.3 |

| Example | Structure | Name | Data |
|---|---|---|---|
| 410 | 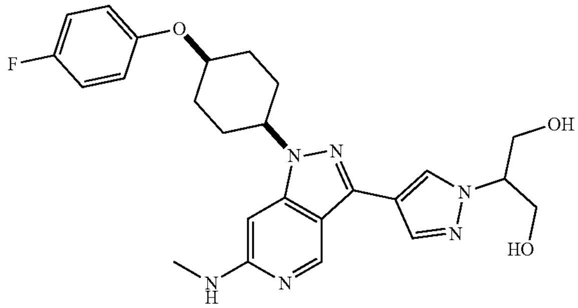 | 2-(4-(1-((1s,4s)-4-(4-fluorophenoxy)cyclohexyl)-6-(methylamino)-1H-pyrazolo[4,3-c]pyridin-3-yl)-1H-pyrazol-1-yl)propane-1,3-diol | Mass spectrum (apci) m/z = 481.2 |
| 411 | 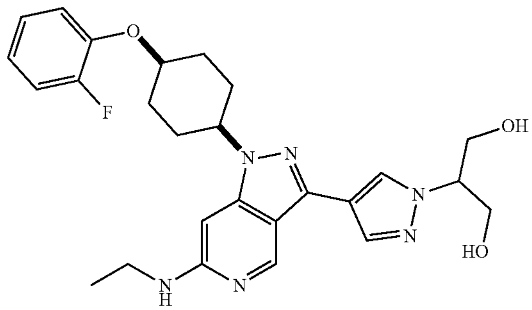 | 2-(4-(6-(ethylamino)-1-((1s,4s)-4-(2-fluorophenoxy)cyclohexyl)-1H-pyrazolo[4,3-c]pyridin-3-yl)-1H-pyrazol-1-yl)propane-1,3-diol | Mass spectrum (apci) m/z = 495.2 |
| 412 | 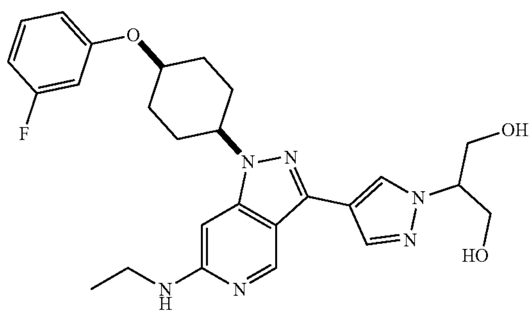 | 2-(4-(6-(ethylamino)-1-((1s,4s)-4-(3-fluorophenoxy)cyclohexyl)-1H-pyrazolo[4,3-c]pyridin-3-yl)-1H-pyrazol-1-yl)propane-1,3-diol | Mass spectrum (apci) m/z = 495.2 |
| 413 | 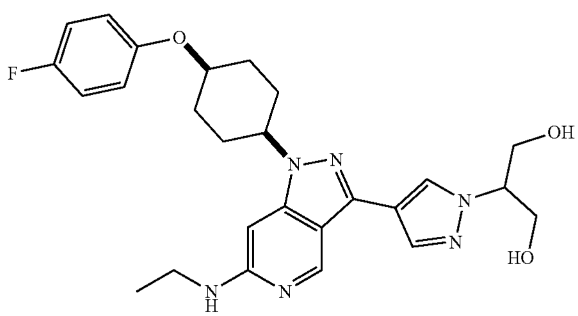 | 2-(4-(6-(ethylamino)-1-((1s,4s)-4-fluorophenoxy(cyclohexyl)-1H-pyrazolo[4,3-c]pyridin-3-yl)-1H-pyrazol-1-yl)propane-1,3-diol | Mass spectrum (apci) m/z = 495.2 |
| 414 | 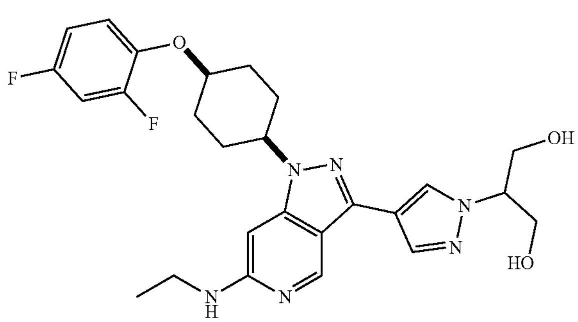 | 2-(4-(1-((1s,4s)-4-(2,4-difluorophenoxy)cyclohexyl)-6-(ethylamino)-1H-pyrazolo[4,3-c]pyridin-3-yl)-1H-pyrazol-1-yl)propane-1,3-diol | Mass spectrum (apci) m/z = 513.2 |

-continued

| Example | Structure | Name | Data |
|---|---|---|---|
| 415 | 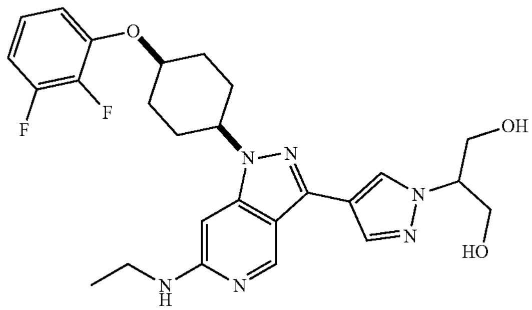 | 2-(4-(1-((1s,4s)-4-(2,3-difluorophenoxy)cyclohexyl)-6-(ethylamino)-1H-pyrazolo[4,3-c]pyridin-3-yl)-1H-pyrazol-1-yl)propane-1,3-diol | Mass spectrum (apci) m/z = 513.2 |
| 416 | 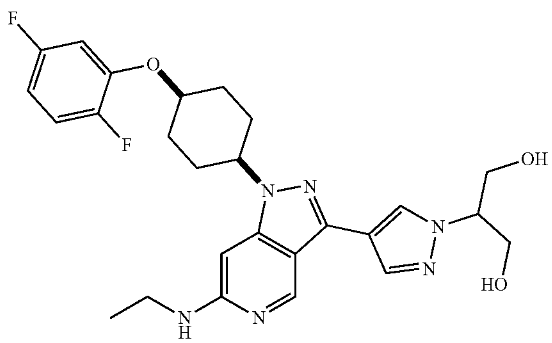 | 2-(4-(1-((1s,4s)-4-(2,5-difluorophenoxy)cyclohexyl)-6-(ethylamino)-1H-pyrazolo[4,3-c]pyridin-3-yl)-1H-pyrazol-1-yl)propane-1,3-diol | Mass spectrum (apci) m/z = 513.2 |
| 417 | 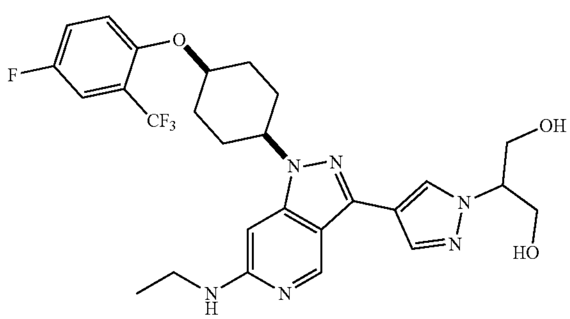 | 2-(4-(6-(ethylamino)-1-((1s,4s)-4-(4-fluoro-2-(trifluoromethyl)phenoxy)-cyclohexyl)-1H-pyrazolo[4,3-c]pyridin-3-yl)-1H-pyrazol-1-yl)propane-1,3-diol | Mass spectrum (apci) m/z = 563.2 |
| 418 | 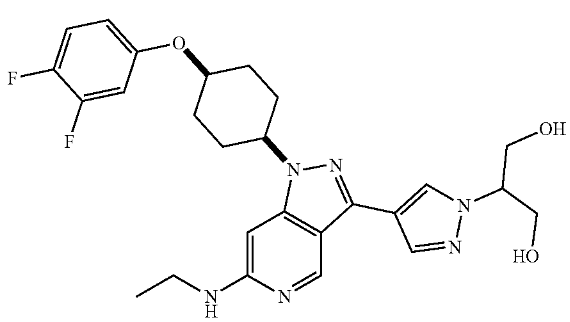 | 2-(4-(1-((1s,4s)-4-(3,4-difluorophenoxy)cyclohexyl)-6-(ethylamino)-1H-pyrazolo[4,3-c]pyridin-3-yl)-1H-pyrazol-1-yl)propane-1,3-diol | Mass spectrum (apci) m/z = 513.2 |
| 419 | 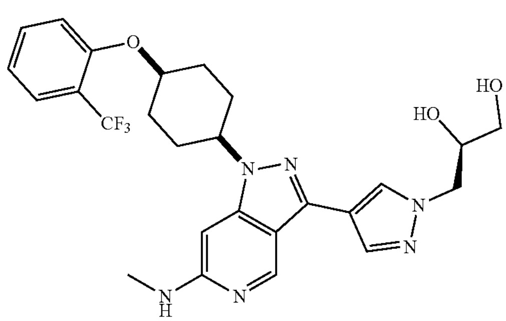 | (R)-3-(4-(6-(methylamino)-1-((1s,4S)-4-(2-(trifluoromethyl)phenoxy)-cyclohexyl)-1H-pyrazolo[4,3-c]pyridin-3-yl)-1H-pyrazol-1-yl)propane-1,2-diol | Mass spectrum (apci) m/z = 531.2 |

| Example | Structure | Name | Data |
|---|---|---|---|
| 420 | 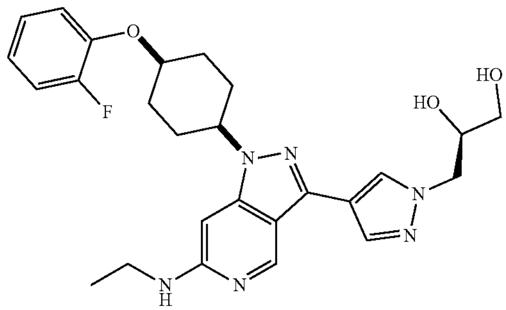 | (R)-3-(4-(6-(ethylamino)-1-((1s,4S)-4-(2-fluorophenoxy)cyclohexyl)-1H-pyrazolo[4,3-c]pyridin-3-yl)-1H-pyrazol-1-yl)propane-1,2-diol | Mass spectrum (apci) m/z = 495.1 |
| 421 | 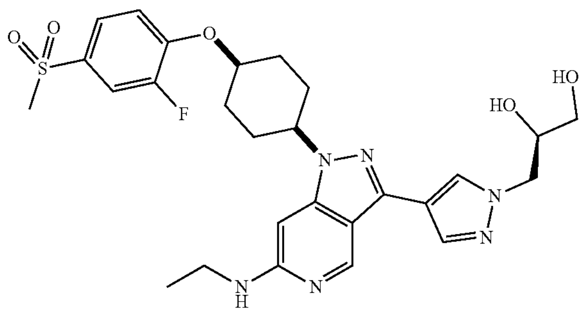 | (R)-3-(4-(6-(ethylamino)-1-((1s,4S)-4-(2-fluoro-4-(methylsulfonyl)phenoxy)-cyclohexyl)-1H-pyrazolo[4,3-c]pyridin-3-yl)-1H-pyrazol-1-yl)propane-1,2-diol | Mass spectrum (apci) m/z = 573.2 |
| 422 | 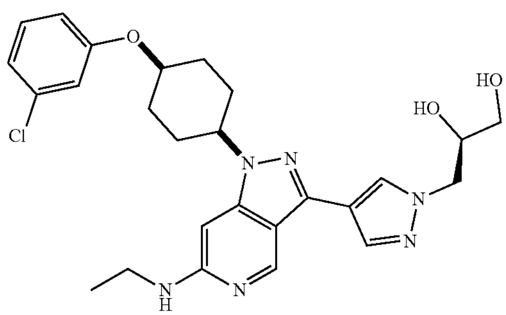 | (R)-3-(4-(1-((1s,4S)-4-(3-chlorophenoxy)cyclohexy])-6-(ethylamino)-1H-pyrazolo[4,3-c]pyridin-3-yl)-1H-pyrazol-1-yl)propane-1,2-diol | Mass spectrum (apci) m/z = 511.1 |
| 423 | 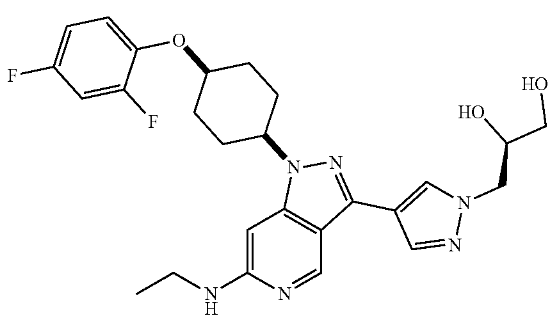 | (R)-3-(4-(1-((1s,4S)-4-(2,4-difluorophenoxy)cyclohexyl)-6-(ethylamino)-1H-pyrazolo[4,3-c]pyridin-3-yl)-1H-pyrazol-1-yl)propane-1,2-diol | Mass spectrum (apci) m/z = 513.1 |
| 424 | 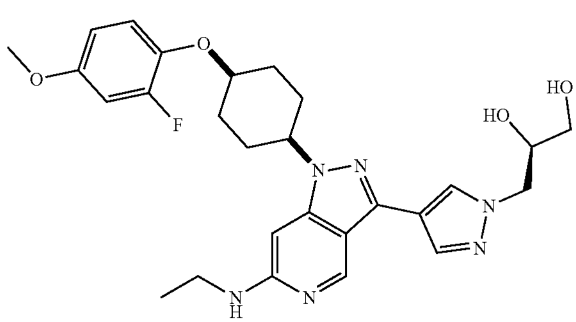 | (R)-3-(4-(6-(ethylamino)-1-((1s,4S)-4-(2-fluoro-4-methoxyphenoxy)cyclohexyl)-1H-pyrazolo[4,3-c]pyridin-3-yl)-1H-pyrazol-1-yl)propane-1,2-diol | Mass spectrum (apci) m/z = 525.2 |

-continued

| Example | Structure | Name | Data |
|---|---|---|---|
| 425 | 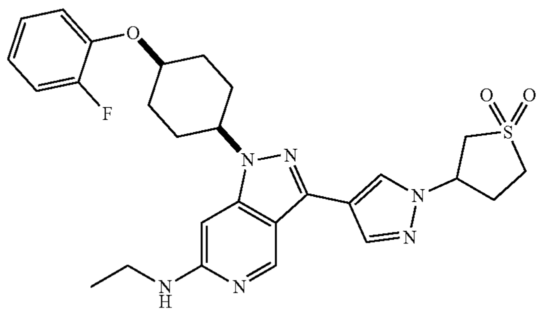 | 3-(4-(6-(ethylamino)-1-((1s,4s)-4-(2-fluorophenoxy)cyclohexyl)-1H-pyrazolo[4,3-c]pyridin-3-yl)-1H-pyrazol-1-yl)tetrahydrothiophene 1,1-dioxide | Mass spectrum (apci) m/z = 539.1 |
| 426 | 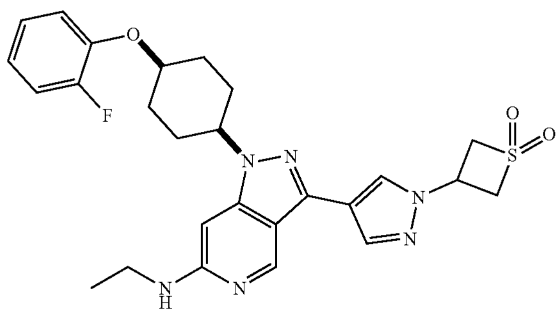 | 3-(4-(6-(ethylamino)-1-((1s,4s)-4-(2-fluorophenoxy)cyclohexyl)-1H-pyrazolo[4,3-c]pyridin-3-yl)-1H-pyrazol-1-yl)thietane 1,1-dioxide | Mass spectrum (apci) m/z = 525.1 |
| 427 | 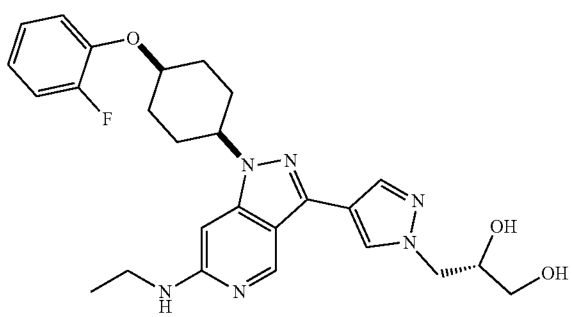 | (S)-3-(4-(6-(ethylamino)-1-((1s,4R)-4-(2-fluorophenoxy)cyclohexyl)-1H-pyrazolo[4,3-c]pyridin-3-yl)-1H-pyrazol-1-yl)propane-1,2-diol | Mass spectrum (apci) m/z = 495.1 |
| 428 | 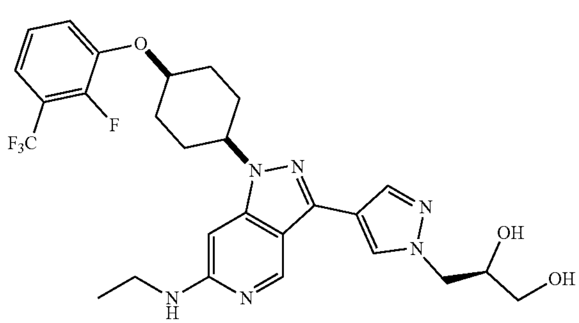 | (R)-3-(4-(6-(ethylamino)-1-((1s,4S)-4-(2-fluoro-3-(trifluoromethyl)phenoxy)-cyclohexyl)-1H-pyrazolo[4,3-c]pyridin-3-yl)-1H-pyrazol-1-yl)propane-1,2-diol | Mass spectrum (apci) m/z = 563.2 |

Example 429

(R)-3-(4-(1-((1s,4S)-4-(2,3-difluorophenoxy)cyclohexyl)-6-(ethylamino)-1H-pyrazolo[4,3-c]pyridin-3-yl)-1H-pyrazol-1-yl)propane-1,2-diol

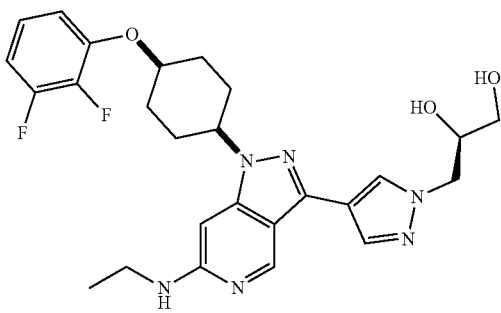

Step A: A solution of PPh₃ (99 mg, 0.376 mmol) in THF (3 mL) at 0° C. was treated with DIAD (74 µL, 0.376 mmol). After stirring for 10 min, tert-butyl (3-bromo-1-((1r,4r)-4-hydroxycyclohexyl)-1H-pyrazolo[4,3-c]pyridin-6-yl)(ethyl)carbamate (110 mg, 0.251 mmol) was added, followed by 2,3-difluorophenol (98 mg, 0.751 mmol). The reaction mixture was heated to 60° C. for 1 h, partitioned between EtOAc and water, extracted with EtOAc (3×15 mL), washed with brine (20 mL), dried over sodium sulfate and concentrated. The residue was purified over silica gel (0-25% EtOAc in hexanes) to afford tert-butyl (3-bromo-1-((1s,4s)-4-(2,3-difluorophenoxy)cyclohexyl)-1H-pyrazolo[4,3-c]pyridin-6-yl)(ethyl)carbamate (82.4 mg, 59.6% yield).

Step B: tert-butyl (3-bromo-1-((1s,4s)-4-(2,3-difluorophenoxy)cyclohexyl)-1H-pyrazolo[4,3-c]pyridin-6-yl)(ethyl)carbamate (82.4 mg, 0.149 mmol), 1-((2,2-dimethyl-1,3-dioxolan-4-yl)methyl)-4-(4,4,5,5-tetramethyl-1,3,2-dioxaborolan-2-yl)-1H-pyrazole (81 mg, 0.262 mmol) and Pd(PPh₃)₄ (17 mg, 0.0149 mmol) were combined in dioxane (2 mL) and treated with 2M K₂CO₃ (224 µL, 0.448 mmol). The reaction mixture was heated to 100° C. in a sealed tube overnight, partitioned between water (30 mL) and EtOAc (35 mL), extracted with EtOAc (2×35 mL), washed with brine (20 mL), dried over Na₂SO₄, filtered and concentrated. The residue was purified over silica gel (25-60% EtOAc in hexanes) to afford tert-butyl (1-((1s,4S)-4-(2,3-difluorophenoxy)cyclohexyl)-3-(1-(((R)-2,2-dimethyl-1,3-dioxolan-4-yl)methyl)-1H-pyrazol-4-yl)-1H-pyrazolo[4,3-c]pyridin-6-yl)(ethyl)carbamate (77.4 mg, 79.4% yield).

Step C: To a solution of tert-butyl (1-((1s,4S)-4-(2,3-difluorophenoxy)cyclohexyl)-3-(1-(((R)-2,2-dimethyl-1,3-dioxolan-4-yl)methyl)-1H-pyrazol-4-yl)-1H-pyrazolo[4,3-c]pyridin-6-yl)(ethyl)carbamate (77.4 mg, 0.119 mmol) in MeOH (3 mL) was added 12M HCl (6 drops). The reaction mixture was heated to reflux for 2 h. The reaction mixture was concentrated and purified by preparative HPLC (5 to 95% ACN in water with 0.1% TFA). The product containing fractions were partitioned between 2N NaOH and DCM, extracted with DCM (×3), dried over sodium sulfate, filtered and concentrated to afford (R)-3-(4-(1-((1s,4S)-4-(2,3-difluorophenoxy)cyclohexyl)-6-(ethylamino)-1H-pyrazolo[4,3-c]pyridin-3-yl)-1H-pyrazol-1-yl)propane-1,2-diol (43.9 mg, 72.2% yield). Mass spectrum (apci) m/z=513.1 (M+H). ¹H NMR (CDCl₃) δ 8.65 (d, J=1.0 Hz, 1H), 8.05 (s, 1H), 8.02 (s, 1H), 7.01 (m, 1H), 6.88-6.78 (m, 2H), 6.18 (s, 1H), 4.68 (m, 1H), 4.45-4.25 (m, 3H), 4.08 (m, 1H), 3.63-3.53 (m, 2H), 3.40 (m, 1H), 3.30 (q, J=7.2 Hz, 2H), 2.60 (m, 2H), 1.31 (m, 2H), 1.91 (m, 2H), 1.79 (m, 2H), 1.45 (t, J=7.0 Hz, 3H).

Using the procedure described for the preparation of Example 429, the following compounds were also synthesized:

| Example | Structure | Name | Data |
| --- | --- | --- | --- |
| 430 | 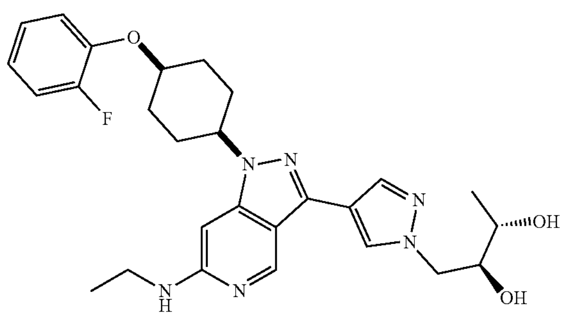 | (2S,3S)-1-(4-(6-(ethylamino)-1-((1s,4R)-4-(2-fluorophenoxy)cyclohexyl)-1H-pyrazolo[4,3-c]pyridin-3-yl)-1H-pyrazol-1-yl)butane-2,3-diol | Mass spectrum (apci) m/z = 509.3 |
| 431 | 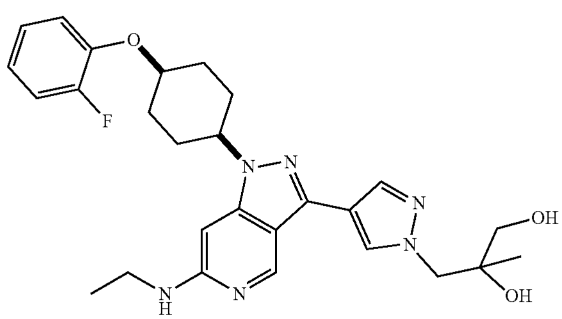 | 3-(4-(6-(ethylamino)-1-((1s,4s)-4-(2-fluorophenoxy)cyclohexyl)-1H-pyrazolo[4,3-c]pyridin-3-yl)-1H-pyrazol-1-yl)-2-methylpropane-1,2-diol | Mass spectrum (apci) m/z = 509.3 |

-continued

| Example | Structure | Name | Data |
|---|---|---|---|
| 432 | 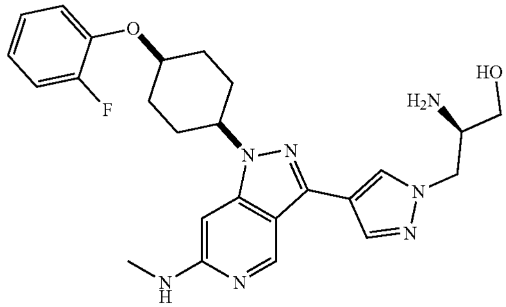 | (R)-2-amino-3-(4-(1-((1s,4S)-4-(2-fluorophenoxy)cyclohexyl)-6-(methylamino)-1H-pyrazolo[4,3-c]pyridin-3-yl)-1H-pyrazol-1-yl)propan-1-ol | Mass spectrum (apci) m/z = 480.2 |
| 433 | 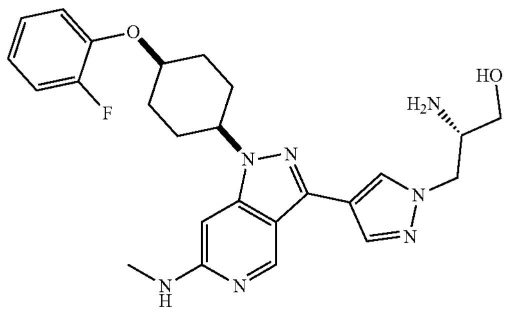 | (S)-2-amino-3-(4-(1-((1s,4S)-4-(2-fluorophenoxy)cyclohexyl)-6-(methylamino)-1H-pyrazolo[4,3-c]pyridin-3-yl)-1H-pyrazol-1-yl)propan-1-ol | Mass spectrum (apci) m/z = 480.2 |

Example 434

(R)-3-(4-(1-((1s,4S)-4-(3-chloro-2-fluorophenoxy)cyclohexyl)-6-(ethylamino)-1H-pyrazolo[4,3-c]pyridin-3-yl)-1H-pyrazol-1-yl)propane-1,2-diol

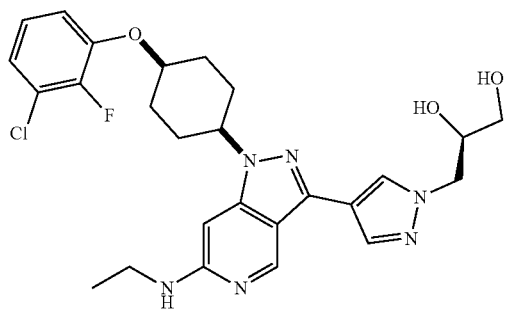

Step A: tert-butyl (3-bromo-1-((1r,4r)-4-hydroxycyclohexyl)-1H-pyrazolo[4,3-c]pyridin-6-yl)(ethyl)carbamate (1.0 g, 2.28 mmol), 1-((2,2-dimethyl-1,3-dioxolan-4-yl)methyl)-4-(4,4,5,5-tetramethyl-1,3,2-dioxaborolan-2-yl)-1H-pyrazole (1.40 g, 4.55 mmol) and Pd(PPh$_3$)$_4$ (263 mg, 0.23 mmol) were combined in dioxane (15 mL) and treated with 2M K$_2$CO$_3$ (3.41 mL, 6.83 mmol). The reaction mixture was heated to 100° C. in a sealed tube overnight, partitioned between water (50 mL) and EtOAc (50 mL), extracted with EtOAc (2×30 mL), washed with brine (20 mL), dried over Na$_2$SO$_4$, filtered and concentrated. The residue was purified over silica gel (30-100% EtOAc in hexanes) to afford tert-butyl (3-(1-(((R)-2,2-dimethyl-1,3-dioxolan-4-yl)methyl)-1H-pyrazol-4-yl)-1-((1r,4R)-4-hydroxycyclohexyl)-1H-pyrazolo[4,3-c]pyridin-6-yl)(ethyl)carbamate (1.3 g, 106% yield).

Step B: A solution of triphenylphosphine (37 mg, 0.14 mmol) in THF (1 mL) was treated with DIAD (27 µL, 0.14 mmol). After stirring for 15 min, tert-butyl (3-(1-(((R)-2,2-dimethyl-1,3-dioxolan-4-yl)methyl)-1H-pyrazol-4-yl)-1-((1r,4R)-4-hydroxycyclohexyl)-1H-pyrazolo[4,3-c]pyridin-6-yl)(ethyl)carbamate (50 mg, 0.09 mmol) was added, followed by 3-chloro-2-fluorophenol (41 mg, 0.28 mmol) and stirred overnight. The reaction mixture was partitioned between water (10 mL) and EtOAc (10 mL), extracted with EtOAc (2×10 mL), washed with brine (10 mL), dried over Na$_2$SO$_4$, filtered and concentrated. The residue was purified over silica gel (50-100% EtOAc/hexanes) to afford tert-butyl (1-((1s,4S)-4-(3-chloro-2-fluorophenoxy)cyclohexyl)-3-(1-(((R)-2,2-dimethyl-1,3-dioxolan-4-yl)methyl)-1H-pyrazol-4-yl)-1H-pyrazolo[4,3-c]pyridin-6-yl)(ethyl)carbamate (36 mg, 58% yield).

Step C: A solution of tert-butyl (1-((1s,4S)-4-(3-chloro-2-fluorophenoxy)cyclohexyl)-3-(1-(((R)-2,2-dimethyl-1,3-dioxolan-4-yl)methyl)-1H-pyrazol-4-yl)-1H-pyrazolo[4,3-c]pyridin-6-yl)(ethyl)carbamate (36 mg, 0.05 mmol) in MeOH (2 mL) was treated with 4N HCl/dioxanes (2 mL). After 2 h, the reaction was concentrated and the residue purified on preparative HPLC (5-95% ACN/H$_2$O/0.1% TFA). Product containing fractions were combined, concentrated to ½ volume, partitioned between 2N NaOH and DCM, dried over sodium sulfate, filtered and concentrated to afford (R)-3-(4-(1-((1s,4S)-4-(3-chloro-2-fluorophenoxy)cyclohexyl)-6-(ethylamino)-1H-pyrazolo[4,3-c]pyridin-3-yl)-1H-pyrazol-1-yl)propane-1,2-diol (15 mg, 53% yield). Mass spectrum (apci) m/z=529.2 (M+H). $^1$H NMR (CDCl$_3$) δ 8.66 (s, 1H), 8.02 (s, 2H), 7.05-6.95 (m, 3H), 6.19 (s, 1H), 4.66 (m, 1H), 4.45-4.26 (m, 3H), 4.10 (m, 1H), 3.60 (m, 2H), 3.31 (q, J=7.0 Hz, 2H), 2.60 (m, 2H), 2.30 (m, 2H), 1.91 (m, 2H), 1.78 (m, 2H), 1.36 (t, J=7.0 Hz, 3H).

Using the procedure described for the preparation of Example 434, the following compounds were also synthesized:

| Example | Structure | Name | Data |
|---|---|---|---|
| 435 | 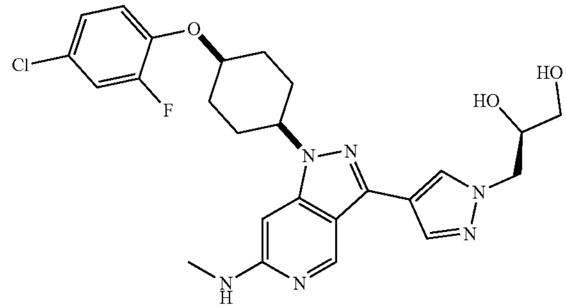 | (R)-3-(4-(1-(((1s,4S)-4-(4-chloro-2-fluorophenoxy)cyclohexyl)-6-(ethylamino)-1H-pyrazolo[4,3-c]pyridin-3-yl)-1H-pyrazol-1-yl)propane-1,2-diol | Mass spectrum (apci) m/z = 529.2 |
| 436 | 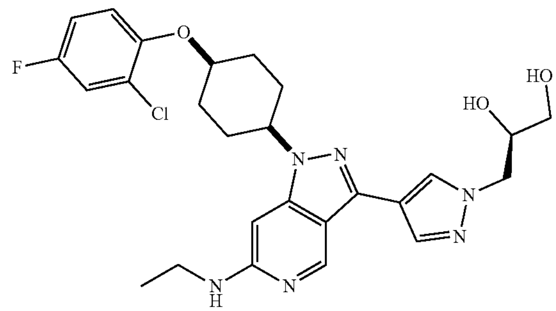 | (R)-3-(4-(1-(((1s,4S)-4-(2-chloro-4-fluorophenoxy)cyclohexyl)-6-(ethylamino)-1H-pyrazolo[4,3-c]pyridin-3-yl)-1H-pyrazol-1-yl)propane-1,2-diol | Mass spectrum (apci) m/z = 529.2 |
| 437 | 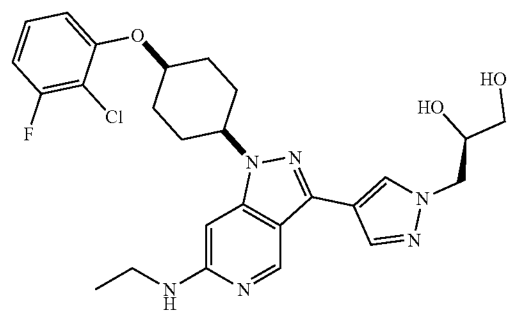 | (R)-3-(4-(1-(((1s,4S)-4-(2-chloro-3-fluorophenoxy)cyclohexyl)-6-(ethylamino)-1H-pyrazolo[4,3-c]pyridin-3-yl)-1H-pyrazol-1-yl)propane-1,2-diol | Mass spectrum (apci) m/z = 529.2 |
| 438 | 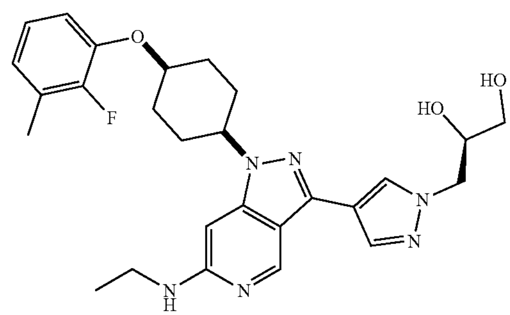 | (R)-3-(4-(6-(ethylamino)-1-((1s,4S)-4-(2-fluoro-3-methylphenoxy)cyclohexyl)-1H-pyrazolo[4,3-c]pyridin-3-yl)-1H-pyrazol-1-yl)propane-1,2 diol | Mass spectrum (apci) m/z = 509.2 |
| 439 | 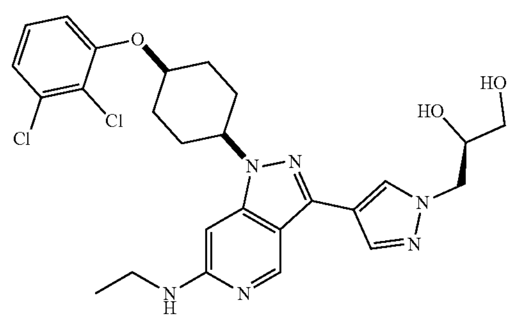 | (R)-3-(4-(1-((1s,4S)-4-(2,3-dichiorophenoxy)cyclohexyl)-6-(ethylamino)-1H-pyrazolo[4,3-c]pyridin-3-yl)-1H-pyrazol-1-yl(propane-1,2-diol | Mass spectrum (apci) m/z = 545.2 |

-continued

| Example | Structure | Name | Data |
|---|---|---|---|
| 440 | 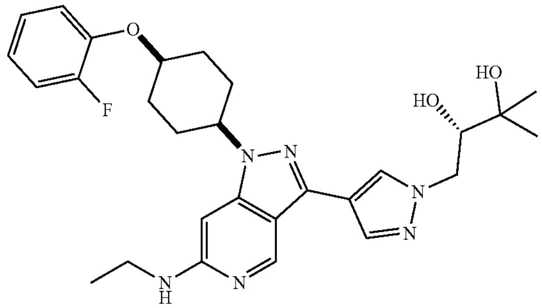 | (S)-1-(4-(6-(ethylamino)-1-((1s,4R)-4-(2-fluorophenoxy)cyclohexyl)-1H-pyrazolo[4,3-c]pyridin-3-yl)-1H-pyrazol-1-yl)-3-methylbutane-2,3-diol | Mass spectrum (apci) m/z = 523.3 |
| 441 | 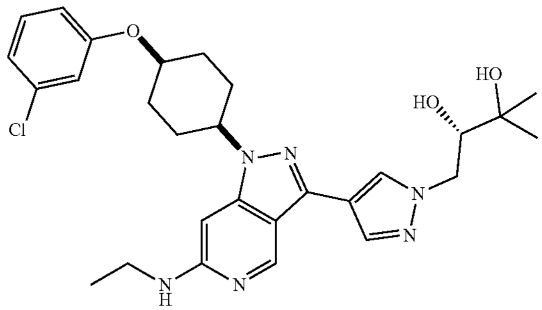 | (S)-1-(4-(1-((1s,4R)-4-(3-chlorophenoxy)cyclohexyl)-6-(ethylamino)-1H-pyrazolo[4,3-c]pyridin-3-yl)-1H-pyrazol-1-yl)-3-methylbutane-2,3-diol | Mass spectrum (apci) m/z = 539.3 |
| 442 | 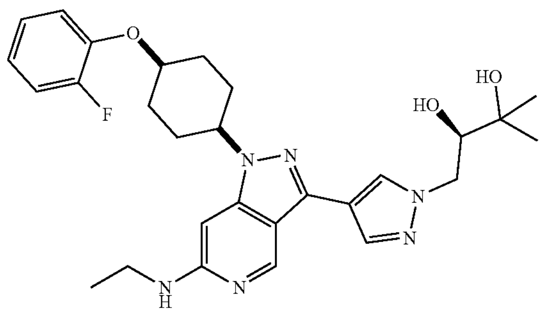 | (R)-1-(4-(6-(ethylamino)-1-((1s,4S)-4-(2-fluorophenoxy)cyclohexyl)-1H-pyrazolo[4,3-c]pyridin-3-yl)-1H-pyrazol-1-yl)-3-methylbutane-2,3-diol | Mass spectrum (apci) m/z = 523.3 |
| 443 | 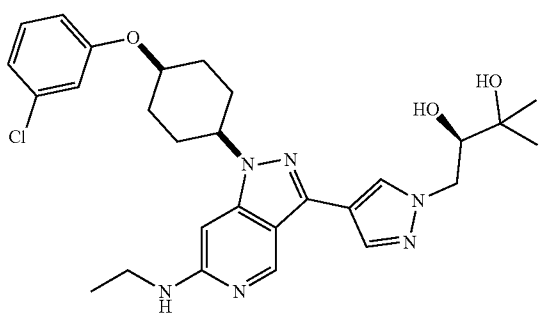 | (R)-1-(4-(1-((1s,4S)-4-(3-chlorophenoxy)cyclohexyl)-6-(ethylamino)-1H-pyrazolo[4,3-c]pyridin-3-yl)-1H-pyrazol-1-yl)-3-methylbutane-2,3-diol | Mass spectrum (apci) m/z = 539.2 |
| 444 | 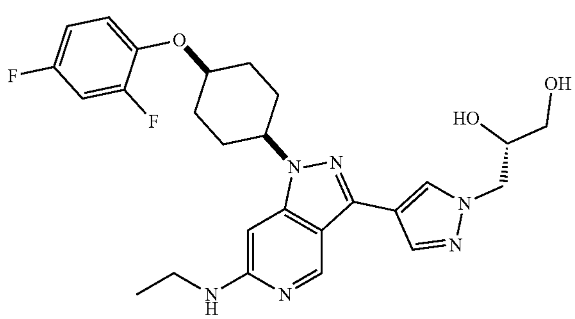 | (S)-3-(4-(1-((1s,4R)-4-(2,4-difluorophenoxy)cyclohexyl)-6-(ethylamino)-1H-pyrazolo[4,3-c]pyridin-3-yl)-1H-pyrazol-1-yl)propane-1,2-diol | Mass spectrum (apci) m/z = 513.3 |

| Example | Structure | Name | Data |
|---|---|---|---|
| 445 | 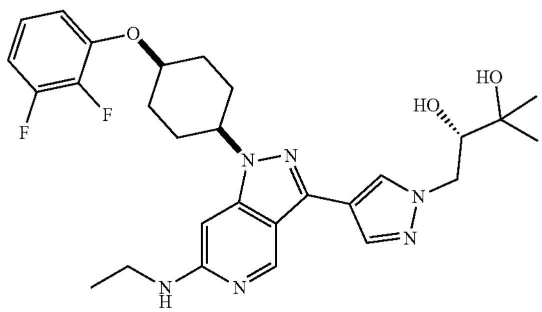 | (S)-1-(4-(1-((1s,4R)-4-(2,3-difluorophenoxy)cyclohexyl)-6-(ethylamino)-1H-pyrazolo[4,3-c]pyridin-3-yl)-1H-pyrazol-1-yl)-3-methylbutane-2,3-diol | Mass spectrum (apci) m/z = 541.3 |
| 446 | 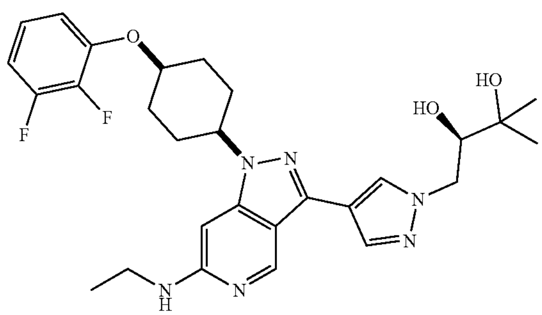 | (R)-1-(4-(1-((1s,4S)-4-(2,3-difluorophenoxy)cyclohexyl)-6-(ethylamino)-1H-pyrazolo[4,3-c]pyridin-3-yl)-1H-pyrazol-1-yl)-3-methylbutane-2,3-diol | Mass spectrum (apci) m/z = 541.3 |
| 447 | 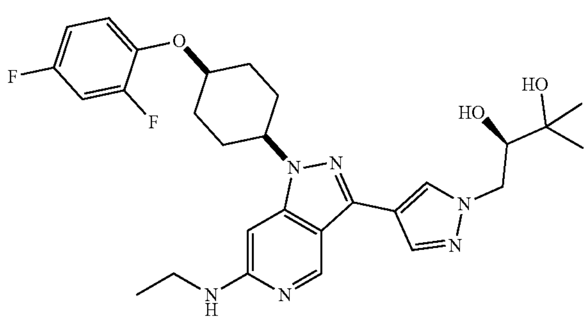 | (R)-1-(4-(1-((1s,4S)-4-(2,4-difluorophenoxy)cyclohexyl)-6-(ethylamino)-1H-pyrazolo[4,3-c]pyridin-3-yl)-1H-pyrazol-1-yl)-3-methylbutane-2,3-diol | Mass spectrum (apci) m/z = 541.3 |
| 448 | 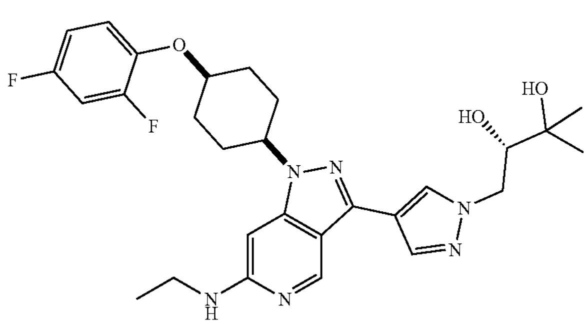 | (S)-1-(4-(1-((1s,4S)-4-(2,4-difluorophenoxy)cyclohexyl)-6-(ethylamino)-1H pyrazolo[4,3-c]pyridin-3-yl)-1H-pyrazol-1-yl)-3-methylbutane-2,3-diol | Mass spectrum (apci) m/z = 541.3 |

Example 449

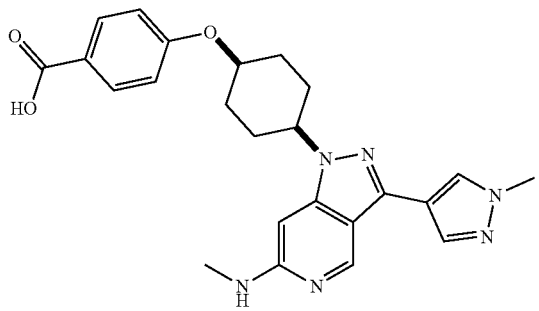

4-(((1s,4s)-4-(3-(1-methyl-1H-pyrazol-4-yl)-6-(methylamino)-1H-pyrazolo[4,3-c]pyridin-1-yl)cyclohexyl)oxy)benzoic acid Methyl 4-(((1s,4s)-4-(6-((tert-butoxycarbonyl)(methyl)amino)-3-(1-methyl-1H-pyrazol-4-yl)-1H-pyrazolo[4,3-c]pyridin-1-yl)cyclohexyl)oxy)benzoate (460 mg, 0.820 mmol) was diluted with methanol (5 mL) followed by the addition of 2M LiOH (1641 µL, 3.28 mmol). After stirring for 12 hours, the reaction was diluted with 2N HCl until the pH was about 5 and then the material was extracted with ethyl acetate, dried over MgSO₄, filtered and concentrated to afford 4-(((1s,4s)-4-(6-((tert-butoxycarbonyl)(methyl)amino)-3-(1-methyl-1H-pyrazol-4-yl)-1H-pyrazolo[4,3-c]pyridin-1-yl)cyclohexyl)oxy)benzoic acid (400 mg, 0.732 mmol, 89.2% yield).

Step B: 4-(((1s,4s)-4-(6-((tert-butoxycarbonyl)(methyl)amino)-3-(1-methyl-1H-pyrazol-4-yl)-1H-pyrazolo[4,3-c]pyridin-1-yl)cyclohexyl)oxy)benzoic acid (25 mg, 0.046 mmol) was diluted with DCM (1 mL) and TFA (1 mL). After stirring for 3 hours, the reaction was concentrated. The material was purified on preparative HPLC (5-95% ACN/water with 0.1% TFA) to afford 4-(((1s,4s)-4-(3-(1-methyl-1H-pyrazol-4-yl)-6-(methylamino)-1H-pyrazolo[4,3-c]pyridin-1-yl)cyclohexyl)oxy)benzoic acid (5.0 mg, 0.011 mmol, 24% yield). Mass spectrum (apci) m/z=447.2 (M+H). 1H NMR (d6-DMSO) δ 12.60 (br s, 1H), 9.01 (s, 1H), 8.47 (s, 1H), 8.10 (s, 1H), 7.91 (m, 2H), 7.12 (m, 2H), 6.82 (s, 1H), 4.85 (m, 1H), 4.73 (m, 1H), 3.94 (s, 3H), 2.93 (s, 3H), 2.35-2.11 (m, 4H), 1.94-1.76 (m, 4H).

Using the procedure described for the preparation of Example 449, the following compounds were also synthesized:

| Example | Structure | Name | Data |
| --- | --- | --- | --- |
| 450 | 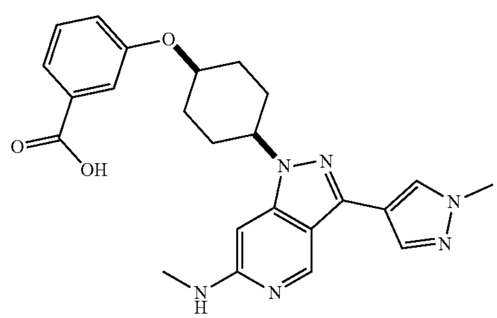 | 3-(((1s,4s)-4-(3-(1-methyl-1H-pyrazol-4-yl)-6-(methyl amino)-1H-pyrazolo[4,3-c]pyridin-1-yl)cyclohexyl)oxy)benzoic acid | Mass spectrum (apci) m/z = 447.2 |
| 451 | 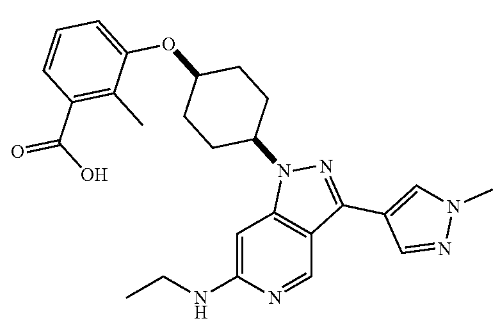 | 3-(((1s,4s)-4-(6-(ethylamino)-3-(1-methyl-1H-pyrazol-4-yl)-1H-pyrazolo[4,3-c]pyridin-1-yl)cyclohexyl)oxy)-2-methylbenzoic acid | Mass spectrum (apci) m/z = 475.2 |

Example 452

N-methyl-3-(((1s,4s)-4-(3-(1-methyl-1H-pyrazol-4-yl)-6-(methylamino)-1H-pyrazolo[4,3-c]pyridin-1-yl)cyclohexyl)oxy)benzamide

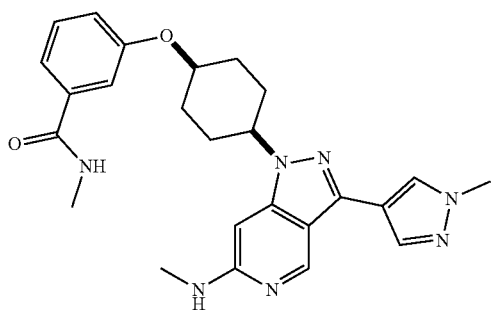

Step A: 3-(((1s,4s)-4-(6-((tert-butoxycarbonyl)(methyl)amino)-3-(1-methyl-1H-pyrazol-4-yl)-1H-pyrazolo[4,3-c]pyridin-1-yl)cyclohexyl)oxy)benzoic acid (25 mg, 0.046 mmol) and HATU (19 mg, 0.050 mmol) were diluted with DMF (300 μL) followed by the addition of methylamine hydrochloride (4.0 mg, 0.059 mmol) and DIEA (24 μL, 0.14 mmol). After 12 h, the reaction was partitioned between ethyl acetate and water, dried over MgSO$_4$, filtered and concentrated to afford tert-butyl methyl(3-(1-methyl-1H-pyrazol-4-yl)-1-((1s,4s)-4-(3-(methylcarbamoyl)phenoxy)cyclohexyl)-1H-pyrazolo[4,3-c]pyridin-6-yl)carbamate (25 mg, 0.045 mmol, 98% yield).

Step B: tert-butyl methyl(3-(1-methyl-1H-pyrazol-4-yl)-1-((1s,4s)-4-(3-(methylcarbamoyl)phenoxy)cyclohexyl)-1H-pyrazolo[4,3-c]pyridin-6-yl)carbamate (25 mg, 0.045 mmol) was diluted with DCM (1 mL) and TFA (1 mL). After 3 h, the reaction was concentrated and purified by preparative HPLC (5-95% ACN/water with 0.1% TFA). The product containing fractions were partitioned between ethyl acetate and saturated sodium bicarbonate, dried over MgSO$_4$, filtered and concentrated to afford N-methyl-3-(((1s,4s)-4-(3-(1-methyl-1H-pyrazol-4-yl)-6-(methylamino)-1H-pyrazolo[4,3-c]pyridin-1-yl)cyclohexyl)oxy)benzamide (4.0 mg, 0.0087 mmol, 19% yield). Mass spectrum (apci) m/z=460.2 (M+H). $^1$H NMR (CDCl$_3$) δ 8.67 (s, 1H), 7.99 (s, 1H), 7.89 (s, 1H), 7.47 (m, 1H), 7.35 (m, 1H), 7.25 (m, 1H), 7.12 (m, 1H), 6.13 (br s, 1H), 6.07 (s, 1H), 4.72 (m, 1H), 4.35 (tt, J=11.9, 3.9 Hz, 1H), 4.00 (s, 3H), 3.03 (d, J=4.9 Hz, 3H), 2.98 (s, 3H), 2.54 (m, 2H), 2.31 (m, 2H), 1.90 (m, 2H), 1.79 (m, 2H).

Using the procedure described for the preparation of Example 452, the following compounds were also synthesized:

| Example | Structure | Name | Data |
|---|---|---|---|
| 453 | 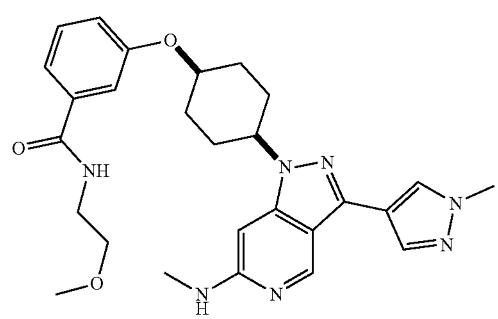 | N-(2-methoxyethyl)-3-(((1s,4s)-4-(3-(1-methyl-1H-pyrazol-4-yl)-6-(methylamino)-1H-pyrazolo[4,3-c]pyridin-1-yl)cyclohexyl)oxy)benzamide | Mass spectrum (apci) m/z = 504.2 |
| 454 | 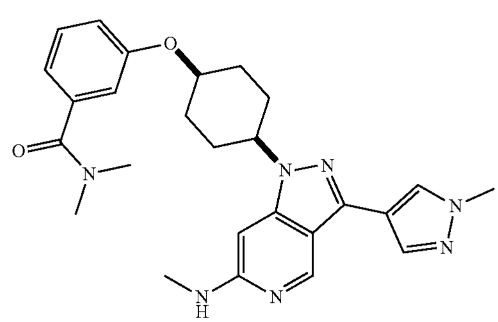 | N,N-dimethyl-3-((1s,4s)-4-(3-(1-methyl-1H-pyrazol-4-yl)-6-(methylamino)-1H-pyrazolo[4,3-c]pyridin-1-yl)cyclohexyl)oxy)benzamide | Mass spectrum (apci) m/z = 474.2 |

| Example | Structure | Name | Data |
|---|---|---|---|
| 455 | 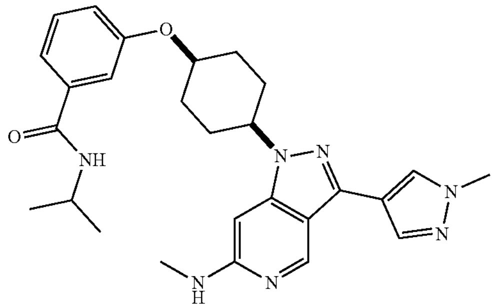 | N-isopropyl-3-(((1s,4s)-4-(3-(1-methyl-1H-pyrazol-4-yl)-6-(methylamino)-1H-pyrazolo[4,3-c]pyridin-1-yl)cyclohexyl)oxy)benzamide | Mass spectrum (apci) m/z = 488.3 |
| 456 | 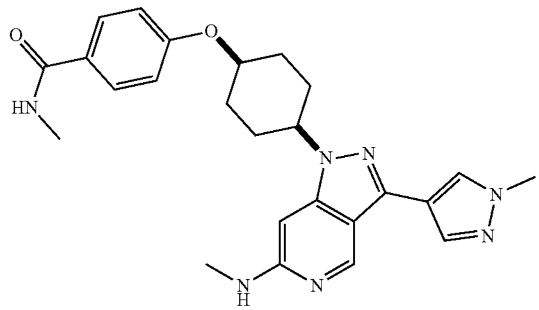 | N-methyl-4-(((1s,4s)-4-(3-(1-methyl-1H-pyrazol-4-yl)-6-(methylamino)-1H-pyrazolo[4,3-c]pyridin-1-yl)cyclohexyl)oxy)benzamide | Mass spectrum (apci) m/z = 460.1 |
| 457 | 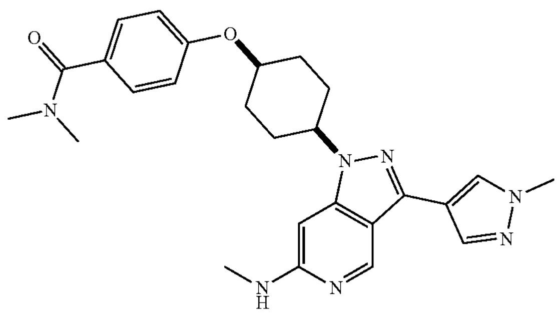 | N,N-dimethyl-4-(((1s,4s)-4-(3-(1-methyl-1H-pyrazol-4-yl)-6-(methylamino)-1H-pyrazolo[4,3-c]pyridin-1-yl)cyclohexyl)oxy)benzamide | Mass spectrum (apci) m/z = 474.2 |
| 458 | 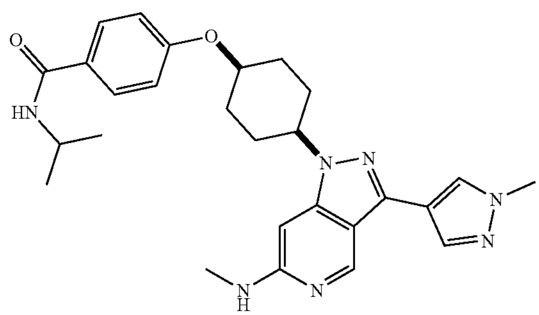 | N-isopropyl-4-(((1s,4s)-4-(3-(1-methyl-1H-pyrazol-4-yl)-6-(methylamino)-1H-pyrazolo[4,3-c]pyridin-1-yl)cyclohexyl)oxy)benzamide | Mass spectrum (apci) m/z = 488.2 |
| 459 | 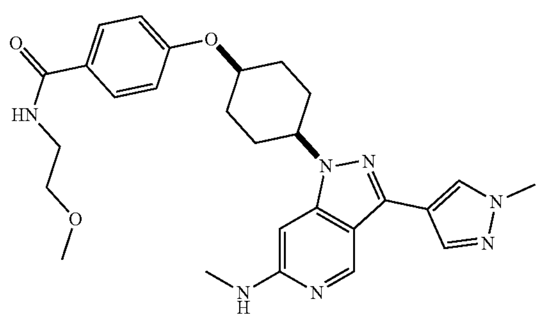 | N-(2-methoxyethyl)-4-(((1s,4s)-4-(3-(1-methyl-1H-pyrazol-4-yl)-6-(methylamino)-1H-pyrazolo[4,3-c]pyridin-1-yl)cyclohexyl)oxy)benzamide | Mass spectrum (apci) m/z = 504.2 |

| Example | Name | Data |
|---|---|---|
| 460 | 4-(((1s,4S)-4-(6-(ethylamino)-3-(1-methyl-1H-pyrazol-4-yl)-1H-pyrazolo[4,3-c]pyridin-1-yl)cyclohexyl)oxy)-3-fluoro-N-methylbenzamide | Mass spectrum (apci) m/z = 492.2 |
| 461 | 4-(((1s,4S)-4-(6-(ethylamino)-3-(1-methyl-1H-pyrazol-4-yl)-1H-pyrazolo[4,3-c]pyridin-1-yl)cyclohexyl)oxy)-3-fluoro-N,N-dimethylbenzamide | Mass spectrum (apci) m/z = 506.2 |
| 462 | 4-(((1s,4S)-4-(6-(ethylamino)-3-(1-methyl-1H-pyrazol-4-yl)-1H-pyrazolo[4,3-c]pyridin-1-yl)cyclohexyl)oxy)-3-fluoro-N-isopropylbenzamide | Mass spectrum (apci) m/z = 520.2 |
| 463 | 2-fluoro-N-methyl-3-(((1s,4s)-4-(3-(1-methyl-1H-pyrazol-4-yl)-6-(methylamino)-1H-pyrazolo[4,3-c]pyridin-1-yl)cyclohexyl)oxy)benzamide | Mass spectrum (apci) m/z = 478.2 |
| 464 | N-ethyl-2-fluoro-3-(((1s,4s)-4-(3-(1-methyl-1H-pyrazol-4-yl)-6-(methylamino)-1H-pyrazolo[4,3-c]pyridin-1-yl)cyclohexyl)oxy)benzamide | Mass spectrum (apci) m/z = 492.2 |

-continued

| Example | Structure | Name | Data |
|---|---|---|---|
| 465 | 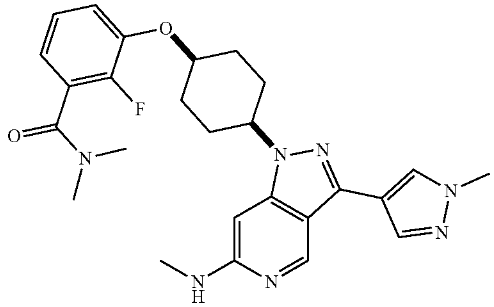 | 2-fluoro-N,N-dimethyl-3-(((1s,4s)-4-(3-(1-methyl-1H-pyrazol-4-yl)-6-(methylamino)-1H-pyrazolo[4,3-c]pyridin-1-yl)cyclohexyl)oxy)benzamide | Mass spectrum (apci) m/z = 492.2 |
| 466 | 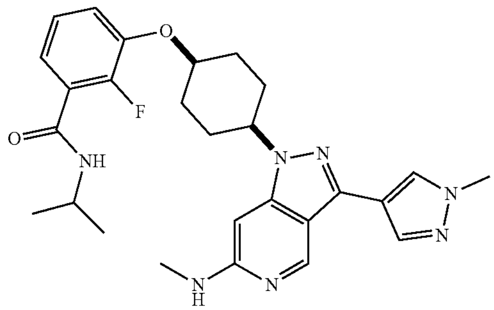 | 2-fluoro-N-isopropyl-3-(((1s,4s)-4-(3-(1-methyl-1H-pyrazol-4-yl)-6-(methylamino)-1H-pyrazolo[4,3-c]pyridin-1-yl)cyclohexyl)oxy)benzamide | Mass spectrum (apci) m/z = 506.2 |
| 467 | 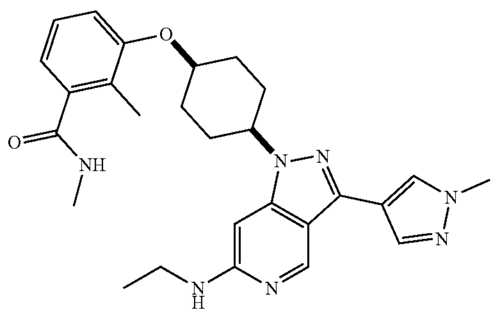 | 3-(((1s,4s)-4-(6-(ethylamino)-3-(1-methyl-1H-pyrazol-4-yl)-1H-pyrazolo[4,3-c]pyridin-1-yl)cyclohexyl)oxy)-N,2-dimethylbenzamide | Mass spectrum (apci) m/z = 488.2 |
| 468 | 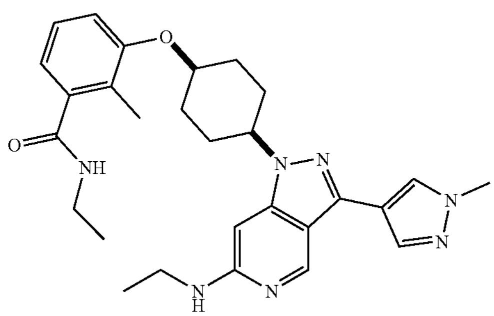 | N-ethyl-3-(((1s,4s)-4-(6-(ethylamino)-3-(1-methyl-1H-pyrazol-4-yl)-1H-pyrazolo[4,3-c]pyridin-1-yl)cyclohexyl)oxy)-2-methylbenzamide | Mass spectrum (apci) m/z = 502.2 |
| 469 | 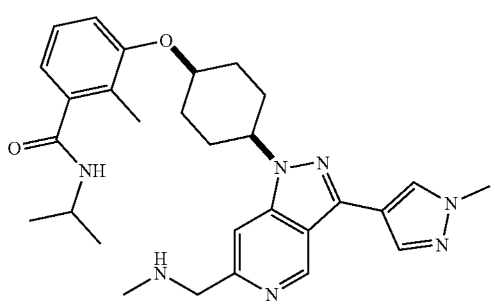 | 3-(((1s,4s)-4-(6-(ethylamino)-3-(1-methyl-1H-pyrazol-4-yl)-1H-pyrazolo[4,3-c]pyridin-1-yl)cyclohexyl)oxy)-N-isopropyl-2-methylbenzamide | Mass spectrum (apci) m/z = 516.2 |

Example 470

Racemic-(1S,2S,5R)-5-(3-(1-methyl-1H-pyrazol-4-yl)-6-(methylamino)-1H-pyrazolo[4,3-c]pyridin-1-yl)-2-phenoxycyclohexan-1-ol

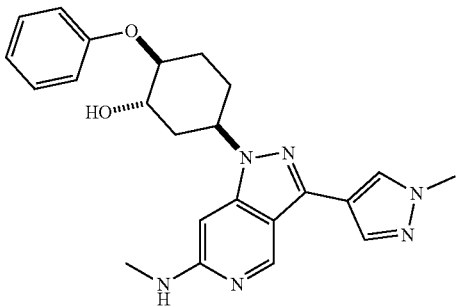

Step A: A solution of 3-bromo-6-chloro-1H-pyrazolo[4,3-c]pyridine (8.00 g, 34.4 mmol, 1.0 eq.), methyl cyclohex-3-ene-1-sulfonate (13.9 g, 79.1 mmol, 2.3 eq) and cesium carbonate (33.6 g, 103 mmol, 3.00 eq) in dimethylformamide (100 mL) was stirred at 110° C. for 12 hours. The mixture was diluted with ethyl acetate (200 mL), washed with water (200 mL×2), brine (100 mL), dried over sodium sulfate and concentrated. The residue was purified over silica gel (2-10% EtOAc in hexanes) to afford 3-bromo-6-chloro-1-cyclohex-3-en-1-yl-pyrazolo[4,3-c]pyridine (6.80 g, 63% yield).

Step B: To a solution of 3-bromo-6-chloro-1-(cyclohex-3-en-1-yl)-1H-pyrazolo[4,3-c]pyridine (156 mg, 0.5 mmol) in 1.5 mL of dichloromethane at 0° C. under nitrogen was added mCPBA (115 mg, 0.50 mmol). After 1 h, the reaction was warmed to room temperature overnight. The reaction mixture was partitioned between DCM and saturated NaHCO$_3$, dried over sodium sulfate, filtered and concentrated. The residue was purified over silica gel (0 to 30% EtOAc in hexanes) to afford 2 isomers. The first eluting peak was 1-((1S,3R,6R)-7-oxabicyclo[4.1.0]heptan-3-yl)-3-bromo-6-chloro-1H-pyrazolo[4,3-c]pyridine (90 mg, 55% yield).

Step C: To a stirred solution of 1-((1S,3R,6R)-7-oxabicyclo[4.1.0]heptan-3-yl)-3-bromo-6-chloro-1H-pyrazolo[4,3-c]pyridine (90 mg, 0.274 mmol) and phenol (38.7 mg, 0.411 mmol) in 1 mL of DMF was added Cs$_2$CO$_3$ (201 mg, 0.616 mmol). The reaction mixture was capped and heated to 100° C. overnight, partitioned between ethyl acetate (15 mL) and water (15 mL), washed 3×15 mL with water and 1×15 mL with brine, dried over MgSO$_4$, filtered and concentrated. The residue was purified over silica gel (0% to 30% ethyl acetate in hexanes) to afford (1S,2S,5R)-5-(3-bromo-6-chloro-1H-pyrazolo[4,3-c]pyridin-1-yl)-2-phenoxycyclohexan-1-ol (96 mg, 82.9% yield).

Step D: To a solution of (1S,2S,5R)-5-(3-bromo-6-chloro-1H-pyrazolo[4,3-c]pyridin-1-yl)-2-phenoxycyclohexan-1-ol (96 mg, 0.227 mmol) in 670 μL of dioxane was added 1-methyl-4-(4,4,5,5-tetramethyl-1,3,2-dioxaborolan-2-yl)-1H-pyrazole (51.9 mg, 0.249 mmol) followed by 2M Na$_2$CO$_3$ (227 μL, 0.454 mmol). The reaction mixture was sparged with argon for 5 minutes and then Pd(PPh$_3$)$_4$ (26.2 mg, 0.022 mmol) was added, sealed and heated to 100° C. overnight. The reaction mixture was partitioned between ethyl acetate (15 mL) and water (15 mL), dried over MgSO$_4$, filtered and concentrated. The residue was purified over silica gel (0% to 30% ethyl acetate in hexanes) to afford (1S,2S)-5-(6-chloro-3-(1-methyl-1H-pyrazol-4-yl)-1H-pyrazolo[4,3-c]pyridin-1-yl)-2-phenoxycyclohexan-1-ol (78 mg, 81% yield).

Step E: To a stirred solution of (1S,2S,5R)-5-(6-chloro-3-(1-methyl-1H-pyrazol-4-yl)-1H-pyrazolo[4,3-c]pyridin-1-yl)-2-phenoxycyclohexan-1-ol (78 mg, 0.18 mmol) and tert-butyl methylcarbamate (121 mg, 0.92 mmol) in 600 μL of dioxane was added Cs$_2$CO$_3$ (120 mg, 0.37 mmol) followed by 2-Dicyclohexylphosphino-2',6'-diisopropoxybiphenyl (34 mg, 0.074 mmol). The reaction mixture was sparged with argon for 5 minutes and then Pd2(dba)$_3$ (34 mg, 0.037 mmol) was added and the vial was capped and heated to 100° C. overnight. The reaction mixture was partitioned between dichloromethane (15 mL) and water (15 mL), extracted 3×15 mL with dichloromethane, dried over MgSO$_4$, filtered and concentrated. The residue was purified over silica gel (0% to 75% ethyl acetate in hexanes) to afford tert-butyl (1-((1R,3S,4S)-3-hydroxy-4-phenoxycyclohexyl)-3-(1-methyl-1H-pyrazol-4-yl)-1H-pyrazolo[4,3-c]pyridin-6-yl)(methyl)carbamate (30 mg, 31% yield).

Step F: To a solution of tert-butyl (1-((1R,3S,4S)-3-hydroxy-4-phenoxycyclohexyl)-3-(1-methyl-1H-pyrazol-4-yl)-1H-pyrazolo[4,3-c]pyridin-6-yl)(methyl)carbamate (30 mg, 0.0578 mmol) in 1 mL of dichloromethane was added TFA (446 μL, 5.78 mmol). After 2 h, the reaction was concentrated then redissolved in 3 mL of dichloromethane and treated with saturated sodium bicarbonate (3 mL), dried over MgSO$_4$, filtered and concentrated. The residue was purified on preparative HPLC (5% to 95% acetonitrile in water with 0.1% TFA) the product containing fractions were partitioned between saturated sodium bicarbonate and DCM, dried over MgSO$_4$, filtered and concentrated to afford (1S,2S,5R)-5-(3-(1-methyl-1H-pyrazol-4-yl)-6-(methylamino)-1H-pyrazolo[4,3-c]pyridin-1-yl)-2-phenoxycyclohexan-1-ol (13 mg, 53.7% yield). Mass spectrum (apci) m/z=419.3 (M+H). $^1$H NMR (CDCl$_3$) δ 8.69 (s, 1H), 7.99 (s, 1H), 7.87 (s, 1H), 7.30 (m, 3H), 6.99 (m, 3H), 6.06 (s, 1H), 4.85-4.70 (m, 2H), 4.48 (m, 1H), 4.39 (q, J=4.3 Hz, 1H), 3.99 (s, 3H), 2.95 (d, J=4.9 Hz, 3H), 2.76 (m, 1H), 2.39 (m, 1H), 2.13 (m, 2H), 2.04 (m, 1H), 1.87 (m, 1H).

Examples 471A and 471B (1S,2S,5R)-5-(3-(1-methyl-1H-pyrazol-4-yl)-6-(methylamino)-1H-pyrazolo[4,3-c]pyridin-1-yl)-2-phenoxycyclohexan-1-ol and (1R,2R,5S)-5-(3-(1-methyl-1H-pyrazol-4-yl)-6-(methylamino)-1H-pyrazolo[4,3-c]pyridin-1-yl)-2-phenoxycyclohexan-1-ol

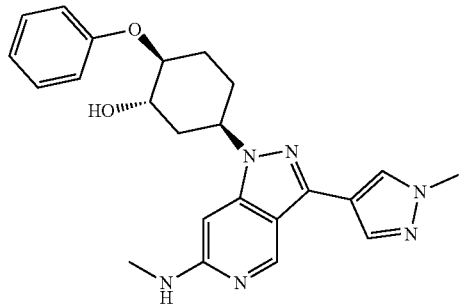

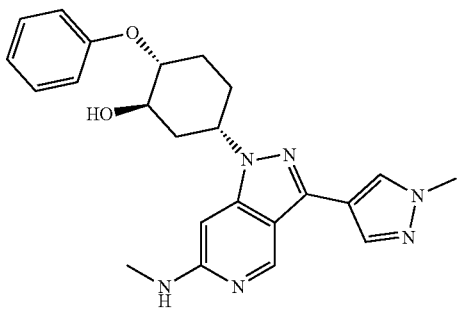

Racemic (1S,2S,5R)-5-(3-(1-methyl-1H-pyrazol-4-yl)-6-(methylamino)-1H-pyrazolo[4,3-c]pyridin-1-yl)-2-phenoxycyclohexan-1-ol (Example 470) was purified by chiral SFC chromatography (IA chiral tech column, 4.6 mm×250 mm, 4 mL/min, MeOH:IPA:DEA (80:20:1))

Example 472

1-((1s,4s)-4-(2-fluorophenoxy)cyclohexyl)-N-methyl-3-(1-methyl-1H-pyrazol-3-yl)-1H-pyrazolo[4,3-c]pyridin-6-amine

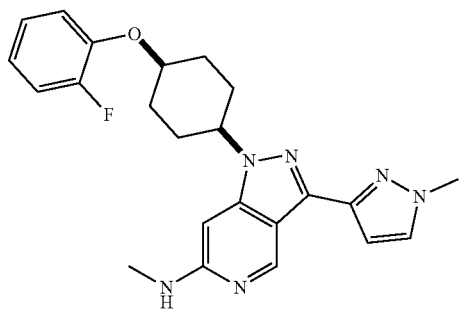

Step A: 3-bromo-1-((1r,4r)-4-((tert-butyldimethylsilyl)oxy)cyclohexyl)-6-chloro-1H-pyrazolo[4,3-c]pyridine (0.25 g, 0.56 mmol) was dissolved in dioxane (6 mL), 1-methyl-3-(4,4,5,5-tetramethyl-1,3,2-dioxaborolan-2-yl)-1H-pyrazole (0.13 g, 0.62 mmol), 2M $K_2CO_3$ (0.84 mL, 1.7 mmol) and Pd(PPh$_3$)$_4$ (0.065 g, 0.056 mmol) were added. The reaction mixture was purged with argon for 5 minutes, sealed and heated to 100° C. overnight. The reaction mixture was partitioned between EtOAc and water, extracted with EtOAc, dried over sodium sulfate, filtered and concentrated. The residue was purified over silica gel (0-60% EtOAc in DCM) to afford 1-((1r,4r)-4-((tert-butyldimethylsilyl)oxy)cyclohexyl)-6-chloro-3-(1-methyl-1H-pyrazol-3-yl)-1H-pyrazolo[4,3-c]pyridine (100 mg, 40% yield).

Step B: 1-((1r,4r)-4-((tert-butyldimethylsilyl)oxy)cyclohexyl)-6-chloro-3-(1-methyl-1H-pyrazol-3-yl)-1H-pyrazolo[4,3-c]pyridine (100 mg, 0.22 mmol) was dissolved in dioxane (1 mL) and tert-butyl methylcarbamate (120 mg, 0.90 mmol) and sodium t-butoxide (43 mg, 0.45 mmol) were added and the reaction bubbled through with nitrogen. Pd2(dba)$_3$ (41 mg, 0.045 mmol) and dicyclohexyl(2',6'-diisopropoxy-[1,1'-biphenyl]-2-yl)phosphane (42 mg, 0.090 mmol) were added and the reaction sealed and heated to 100° C. overnight. The reaction mixture was partitioned between EtOAc and water, extracted with EtOAc, dried over sodium sulfate, filtered and concentrated. The residue was purified over silica gel to afford tert-butyl (1-((1r,4r)-4-((tert-butyldimethylsilyl)oxy)cyclohexyl)-3-(1-methyl-1H-pyrazol-3-yl)-1H-pyrazolo[4,3-c]pyridin-6-yl)(methyl)carbamate (87 mg, 72% yield).

Step C: tert-butyl (1-((1r,4r)-4-((tert-butyldimethylsilyl)oxy)cyclohexyl)-3-(1-methyl-1H-pyrazol-3-yl)-1H-pyrazolo[4,3-c]pyridin-6-yl)(methyl)carbamate (87 mg, 0.16 mmol) was dissolved in DCM (1 mL) and 4M HCl/dioxane (2 mL) added. After 2 h, the reaction was concentrated, partitioned between EtOAc and 10% $K_2CO_3$, extracted with EtOAc, dried over sodium sulfate and concentrated to afford (1r,4r)-4-(3-(1-methyl-1H-pyrazol-3-yl)-6-(methylamino)-1H-pyrazolo[4,3-c]pyridin-1-yl)cyclohexan-1-ol (53 mg, 101% yield).

Step D: (1r,4r)-4-(3-(1-methyl-1H-pyrazol-3-yl)-6-(methylamino)-1H-pyrazolo[4,3-c]pyridin-1-yl)cyclohexan-1-ol (0.015 g, 0.046 mmol), 2-fluorophenol (0.008 g, 0.069 mmol), PPh$_3$ (0.018 g, 0.069 mmol) were dissolved in THF (0.5 mL) and DIAD (0.014 g, 0.069 mmol) was added and heated to 50° C. overnight, concentrated and purified by preparative HPLC (5 to 95% ACN in water with 0.1% TFA) to afford 1-((1s,4s)-4-(2-fluorophenoxy)cyclohexyl)-N-methyl-3-(1-methyl-1H-pyrazol-3-yl)-1H-pyrazolo[4,3-c]pyridin-6-amine bis(2,2,2-trifluoroacetate). Mass spectrum (apci) m/z=421.2 (M+H). $^1$H NMR (CD3OD) δ 9.04 (d, J=0.6 Hz, 1H), 7.69 (d, J=2.3 Hz, 1H), 7.22-7.08 (m, 3H), 6.97 (m, 1H), 6.87 (d, J=2.3 Hz, 1H), 6.82 (s, 1H), 4.70-4.62 (m, 2H), 4.01 (s, 3H), 3.05 (s, 3H), 2.26 (m, 2H), 2.27 (m, 2H), 1.90 (m, 4H).

Example 473

(R)-3-(4-(6-(ethylamino)-1-((1s,4S)-4-(2-fluorophenoxy)cyclohexyl)-1H-pyrrolo[3,2-c]pyridin-3-yl)-1H-pyrazol-1-yl)propane-1,2-diol dihydrochloride

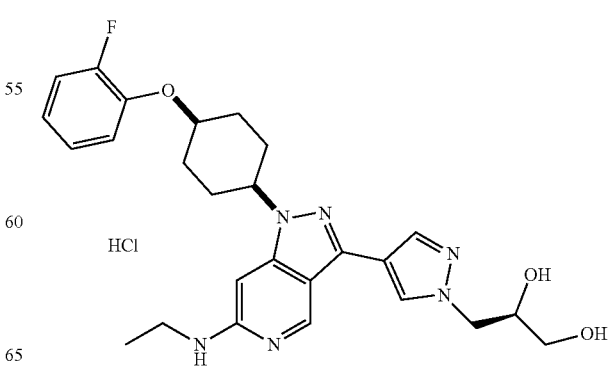

Step A: 3-bromo-6-chloro-1H-pyrrolo[3,2-c]pyridine (65 mg, 0.28 mmol) was dissolved in DMA (2 mL). Cs₂CO₃ (180 mg, 0.56 mmol) and (1r,4r)-4-(2-fluorophenoxy)cyclohexyl 4-methylbenzenesulfonate (200 mg, 0.56 mmol) were added and the reaction was heated to 100° C. overnight. The reaction mixture was partitioned between EtOAc and water, extracted with EtOAc, washed with brine, dried over sodium sulfate, filtered and concentrated. The residue was purified over silica gel (5-50% EtOAc in hexanes) to afford 3-bromo-6-chloro-1-((1s,4s)-4-(2-fluorophenoxy)cyclohexyl)-1H-pyrrolo[3,2-c]pyridine (75 mg, 63% yield).

Step B: 3-bromo-6-chloro-1-((1s,4s)-4-(2-fluorophenoxy)cyclohexyl)-1H-pyrrolo[3,2-c]pyridine (75 mg, 0.18 mmol), (R)-1-((2,2-dimethyl-1,3-dioxolan-4-yl)methyl)-4-(4,4,5,5-tetramethyl-1,3,2-dioxaborolan-2-yl)-1H-pyrazole (60 mg, 0.19 mmol) were dissolved in dioxane (2 mL) and 2M K₂CO₃ (0.27 mL, 0.53 mmol) and Pd(PPh₃)₄ (20 mg, 0.018 mmol) were added, placed under a nitrogen atmosphere and heated to 100° C. overnight. The reaction mixture was partitioned between EtOAc and water, extracted with EtOAc, dried over sodium sulfate, filtered and concentrated. The residue was purified over silica gel (10-100% EtOAc in hexanes) to afford 6-chloro-3-(1-(((R)-2,2-dimethyl-1,3-dioxolan-4-yl)methyl)-1H-pyrazol-4-yl)-1-((1s,4S)-4-(2-fluorophenoxy)cyclohexyl)-1H-pyrrolo[3,2-c]pyridine (26 mg, 28% yield).

Step C: 6-chloro-3-(1-(((R)-2,2-dimethyl-1,3-dioxolan-4-yl)methyl)-1H-pyrazol-4-yl)-1-((1s,4S)-4-(2-fluorophenoxy)cyclohexyl)-1H-pyrrolo[3,2-c]pyridine (0.026 g, 0.05 mmol), tert-butyl ethylcarbamate (0.029 g, 0.20 mmol) were dissolved in dioxane (0.5 mL). dicyclohexyl(2',6'-diisopropoxy-[1,1'-biphenyl]-2-yl)phosphane (0.009 g, 0.02 mmol), sodium t-butoxide (0.0095 g, 0.099 mmol) and Pd₂dba₃ (0.0091 g, 0.0099 mmol) were added and placed under a nitrogen atmosphere. The reaction mixture was sealed and heated to 100° C. overnight, partitioned between EtOAc and water, extracted with EtOAc, dried over sodium sulfate, filtered and concentrated. The residue was purified over silica gel (0-100% EtOAc in DCM) to afford tert-butyl (3-(1-(((R)-2,2-dimethyl-1,3-dioxolan-4-yl)methyl)-1H-pyrazol-4-yl)-1-((1s,4S)-4-(2-fluorophenoxy)cyclohexyl)-1H-pyrrolo[3,2-c]pyridin-6-yl)(ethyl)carbamate (13 mg, 41% yield).

Step D: (3-(1-(((R)-2,2-dimethyl-1,3-dioxolan-4-yl)methyl)-1H-pyrazol-4-yl)-1-((1s,4S)-4-(2-fluorophenoxy)cyclohexyl)-1H-pyrrolo[3,2-c]pyridin-6-yl)(ethyl)carbamate (0.012 g, 0.019 mmol) was dissolved with 1 mL of methanol. To this was added a few drops of concentrated HCl and the mixture stirred at 3 h, then concentrated to afford (R)-3-(4-(6-(ethylamino)-1-((1s,4S)-4-(2-fluorophenoxy)cyclohexyl)-1H-pyrrolo[3,2-c]pyridin-3-yl)-1H-pyrazol-1-yl)propane-1,2-diol dihydrochloride (11 mg, 100% yield). Mass spectrum (apci) m/z=494.2 (M+H). ¹H NMR (CD3OD) δ 8.49 (s, 1H), 8.22 (s, 1H), 8.05 (s, 1H), 7.77 (s, 1H), 7.21 (t, J=8.4 Hz, 1H), 7.13 (m, 2H), 6.98 (m, 1H), 6.90 (s, 1H), 4.70 (m, 1H), 4.56-4.38 (m, 2H), 4.25 (m, 1H), 4.07 (m, 1H), 3.57 (m, 2H), 3.43 (m, 2H), 2.40-2.22 (m, 4H), 1.94 (m, 4H), 1.37 (t, J=5.3 Hz, 3H).

Example 474

N-ethyl-1-((1r,4r)-4-(4-fluorophenoxy)cyclohexyl)-3-(1-methyl-1H-pyrazol-4-yl)-1H-pyrazolo[4,3-c]pyridin-6-amine

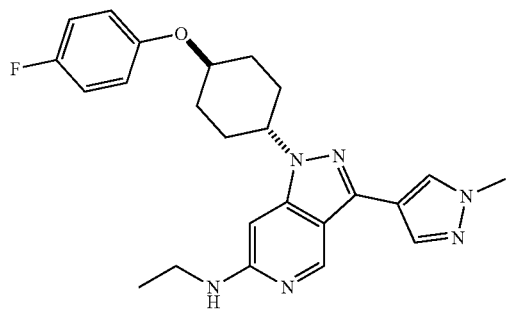

Step A: To a stirred solution of tert-butyl ethyl(3-(1-methyl-1H-pyrazol-4-yl)-1H-pyrazolo[4,3-c]pyridin-6-yl)carbamate (45 mg, 0.13 mmol) in 600 μL of DMF was added (1s,4s)-4-(4-fluorophenoxy)cyclohexyl 4-methylbenzenesulfonate (47 mg, 0.13 mmol), followed by Cs2CO3 (85 mg, 0.26 mmol). The reaction mixture was capped and heated to 100° C. overnight. Another 1 equivalent of (1s,4s)-4-(4-fluorophenoxy)cyclohexyl 4-methylbenzenesulfonate was added and the reaction was reheated to 100° C. overnight again, partitioned between ethyl acetate (15 mL) and water (15 mL), washed 3×15 mL with water and 1×15 mL with brine, dried over MgSO₄, filtered and concentrated. The residue was purified over silica gel (30% to 75% ethyl acetate in hexanes) to afford tert-butyl ethyl(1-((1r,4r)-4-(4-fluorophenoxy)cyclohexyl)-3-(1-methyl-1H-pyrazol-4-yl)-1H-pyrazolo[4,3-c]pyridin-6-yl)carbamate (26 mg, 37% yield).

Step B: To a solution of tert-butyl ethyl(1-((1r,4r)-4-(4-fluorophenoxy)cyclohexyl)-3-(1-methyl-1H-pyrazol-4-yl)-1H-pyrazolo[4,3-c]pyridin-6-yl)carbamate (26 mg, 0.0486312 mmol) in 1 mL of dichloromethane was added TFA (936 μL, 12.1 mmol). After stirring for 2 h, the reaction was concentrated, redissolved in 15 mL of dichloromethane and washed with saturated sodium bicarbonate, extracted 2×15 mL with dichloromethane, dried over MgSO₄, filtered and concentrated to afford N-ethyl-1-((r,4r)-4-(4-fluorophenoxy)cyclohexyl)-3-(1-methyl-1H-pyrazol-4-yl)-1H-pyrazolo[4,3-c]pyridin-6-amine (20 mg, 89.9% yield). Mass spectrum (apci) m/z=435.2 (M+H). ¹H NMR (CDCl₃) δ 8.67 (s, 1H), 7.97 (s, 1H), 7.85 (s, 1H), 6.98 (m, 2H), 6.88 (m, 2H), 6.02 (s, 1H), 4.73 (br s, 1H), 4.28 (m, 2H), 3.99 (s, 3H), 3.30 (m, 2H), 2.34 (m, 2H), 2.28-2.08 (m, 4H), 1.68 (m, 2H), 1.35 (t, J=7.2 Hz, 3H).

Using the procedure described for the preparation of Example 474, the following compounds were also synthesized:

| Example | Structure | Name | Data |
|---|---|---|---|
| 475 | 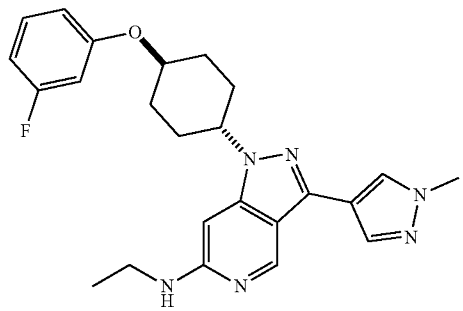 | N-ethyl-1-((1r,4r)-4-(3-fluorophenoxy)cyclohexyl)-3-(1-methyl-1H-pyrazol-4-yl)-1H-pyrazolo[4,3-c]pyridin-6-amine | Mass spectrum (apci) m/z = 435.2 |
| 476 | 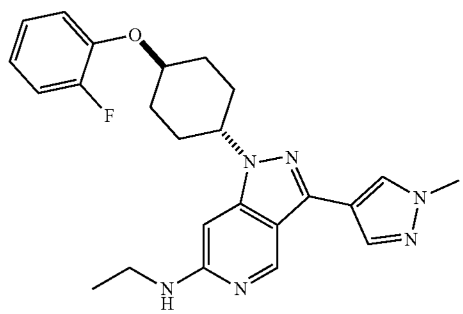 | N-ethyl-1-((1r,4r)-4-(2-fluorophenoxy)cyclohexyl)-3-(1-methyl-1H-pyrazol-4-yl)-1H-pyrazolo[4,3-c]pyridin-6-amine | Mass spectrum (apci) m/z = 435.2 |
| 477 | 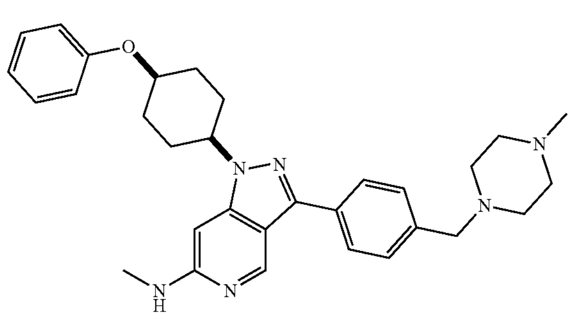 | N-methyl-3-(4-((4-methylpiperazin-1-yl)methyl)phenyl)-1-((1s,4s)-4-phenoxycyclohexyl)-1H-pyrazolo[4,3-c]pyridin-6-amine | Mass spectrum (apci) m/z = 511.3 |
| 478 | 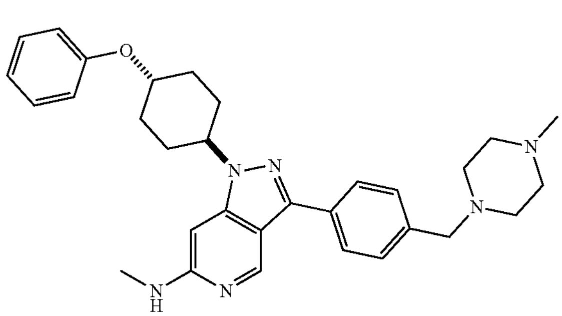 | N-methyl-3-(4-((4-methylpiperazin-1-yl)methyl)phenyl)-1-((1r,4r)-4-phenoxycyclohexyl)-1H-pyrazolo[4,3-c]pyridin-6-amine | Mass spectrum (apci) m/z = 511.3 |

Example 479

3-((1s,4s)-4-(2-fluorophenoxy)cyclohexyl)-N-methyl-1-(1-methyl-1H-pyrazol-4-yl)-1H-pyrazolo[3,4-c]pyridin-5-amine

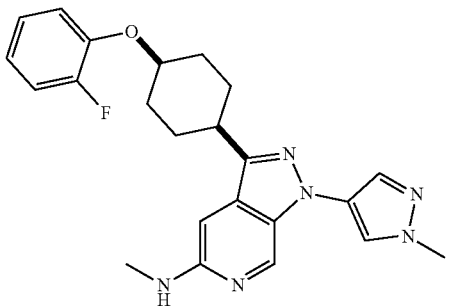

Step A: 3-bromo-5-chloro-1H-pyrazolo[3,4-c]pyridine (0.977 g, 4.2 mmol) was dissolved in DMF (17 mL) and cooled to 0° C. NaH (252 mgs, 6.3 mmol, 60% dispersion in mineral oil) was added and stirred for 20 min. (2-(chloromethoxy)ethyl)trimethylsilane (0.841 g, 5.04 mmol) was then added and warmed to room temperature overnight. The reaction mixture was partitioned between EtOAc and water, extracted with EtOAc, washed with brine, dried over sodium sulfate, filtered and concentrated. The residue was purified over silica gel (10-30% EtOAc in hexanes) to afford 3-bromo-5-chloro-1-((2-(trimethylsilyl)ethoxy)methyl)-1H-pyrazolo[3,4-c]pyridine (988 mg, 64.8% yield).

Step B: 3-bromo-5-chloro-1-((2-(trimethylsilyl)ethoxy)methyl)-1H-pyrazolo[3,4-c]pyridine (750 mg, 2.07 mmol) and 4,4,5,5-tetramethyl-2-(1,4-dioxaspiro[4.5]dec-7-en-8-yl)-1,3,2-dioxaborolane (605 mg, 2.27 mmol) were dissolved in dioxane (20 mL) and 2.0 M $K_2CO_3$ (3.1 mL, 6.2 mmol) and Pd(PPh$_3$)$_4$ were added and purged with argon for 5 minutes, tube sealed and warmed to 100° C. overnight. The reaction mixture was partitioned between EtOAc and water, extracted with EtOAc, dried over sodium sulfate, filtered and concentrated. The residue was purified over silica gel (10-50% EtOAc in hexanes) to afford 5-chloro-3-(1,4-dioxaspiro[4.5]dec-7-en-8-yl)-1-((2-(trimethylsilyl)ethoxy)methyl)-1H-pyrazolo[3,4-c]pyridine (713 mg, 81.7% yield).

Step C: 5-chloro-3-(1,4-dioxaspiro[4.5]dec-7-en-8-yl)-1-((2-(trimethylsilyl)ethoxy)methyl)-1H-pyrazolo[3,4-c]pyridine (775 mg, 1.84 mmol) was dissolved in dioxane (18 mL) and tert-butyl methylcarbamate (964 mg, 7.35 mmol), dicyclohexyl(2',6'-diisopropoxy-[1,1'-biphenyl]-2-yl)phosphane (343 mg, 0.735 mmol), Pd2dba3 (336 mg, 0.367 mmol) and sodium t-butoxide (353 mg, 3.67 mmol) were added and purged with nitrogen. The tube was sealed and heated to 100° C. overnight, partitioned between EtOAc and water, extracted with EtOAc, dried over sodium sulfate, filtered and concentrated. The residue was purified over silica gel (10-50% EtOAc in hexanes) to afford tert-butyl (3-(1,4-dioxaspiro[4.5]dec-7-en-8-yl)-1-((2-(trimethylsilyl)ethoxy)methyl)-1H-pyrazolo[3,4-c]pyridin-5-yl)(methyl)carbamate (731 mg, 77% yield).

Step D: tert-butyl (3-(1,4-dioxaspiro[4.5]dec-7-en-8-yl)-1-((2-(trimethylsilyl)ethoxy)methyl)-1H-pyrazolo[3,4-c]pyridin-5-yl)(methyl)carbamate (0.73 g, 1.41 mmol) was dissolved in methanol (10 mL) and 500 mg of 10% Pd/C (degussa type) was added and placed under a balloon of hydrogen while be being heated to 30° C. for 4h. The reaction mixture was filtered and concentrated to afford tert-butyl (3-(1,4-dioxaspiro[4.5]decan-8-yl)-1-((2-(trimethylsilyl)ethoxy)methyl)-1H-pyrazolo[3,4-c]pyridin-5-yl)(methyl)carbamate (538 mg, 73.3% yield).

Step E: tert-butyl (3-(1,4-dioxaspiro[4.5]decan-8-yl)-1-((2-(trimethylsilyl)ethoxy)methyl)-1H-pyrazolo[3,4-c]pyridin-5-yl)(methyl)carbamate (0.538 g, 1.04 mmol) was dissolved in THF (10 mL) and TBAF (5.2 mL, 5.2 mmol, 1M in THF) was added and heated to 50° C. overnight. The reaction mixture was partitioned between EtOAc and water, washed with 10% $K_2CO_3$, dried over sodium sulfate, filtered and concentrated. The residue was purified over silica gel (0-20% MeOH in DCM) to afford tert-butyl (3-(1,4-dioxaspiro[4.5]decan-8-yl)-1H-pyrazolo[3,4-c]pyridin-5-yl)(methyl)carbamate (306 mg, 75.9% yield).

Step F: tert-butyl (3-(1,4-dioxaspiro[4.5]decan-8-yl)-1H-pyrazolo[3,4-c]pyridin-5-yl)(methyl)carbamate (0.15 g, 0.386 mmol) was dissolved in DMSO (4 mL) and 4-iodo-1-methyl-1H-pyrazole (0.12 g, 0.579 mmol), N1,N2-dimethylethane-1,2-diamine (0.043 g, 0.502 mmol), cesium carbonate (0.315 g, 0.965 mmol) and Cu(I) iodide (0.0368 g, 0.193 mmol) were added and purged with nitrogen. The tube was sealed and heated to 100° C. overnight. The reaction mixture was partitioned between EtOAc and water, extracted with EtOAc, washed with brine, dried over sodium sulfate, filtered and concentrated. The residue was purified over silica gel (0-10% MeOH in DCM) to afford tert-butyl methyl(1-(1-methyl-1H-pyrazol-4-yl)-3-(1,4-dioxaspiro[4.5]decan-8-yl)-1H-pyrazolo[3,4-c]pyridin-5-yl)carbamate (105 mg, 58% yield).

Step G: tert-butyl methyl(1-(1-methyl-1H-pyrazol-4-yl)-3-(1,4-dioxaspiro[4.5]decan-8-yl)-1H-pyrazolo[3,4-c]pyridin-5-yl)carbamate (0.105 g, 0.224 mmol) was dissolved in dioxane (2 mL) and 6M HCl (2 mL) was added and the reaction was heated to 50° C. overnight. The reaction mixture was partitioned between 10% $K_2CO_3$ and EtOAc, dried over sodium sulfate, filtered and concentrated to afford 4-(1-(1-methyl-1H-pyrazol-4-yl)-5-(methylamino)-1H-pyrazolo[3,4-c]pyridin-3-yl)cyclohexan-1-one (63 mg, 86% yield).

Step H: 4-(1-(1-methyl-1H-pyrazol-4-yl)-5-(methylamino)-1H-pyrazolo[3,4-c]pyridin-3-yl)cyclohexan-1-one (0.063 g, 0.194 mmol) was dissolved in DCM (2 mL). To this was added BOC anhydride (0.106 g, 0.486 mmol) and DMAP (0.005 g, 0.039 mmol) and stirred overnight. Another 0.5 eq of BOC anhydride added followed by another 0.2 eq of DMAP and heated to 35° C. for 3 h and concentrated. The residue was purified over silica gel (0-5% MeOH in DCM) to afford tert-butyl methyl(1-(1-methyl-1H-pyrazol-4-yl)-3-(4-oxocyclohexyl)-1H-pyrazolo[3,4-c]pyridin-5-yl)carbamate (36.5 mg, 44.3% yield).

Step I: tert-butyl methyl(1-(1-methyl-1H-pyrazol-4-yl)-3-(4-oxocyclohexyl)-1H-pyrazolo[3,4-c]pyridin-5-yl)carbamate (0.036 g, 0.085 mmol) was dissolved in methanol (1 mL). Sodium borohydride (0.01 g, 0.25 mmol) was added, stirred for 2 h and concentrated. The crude material partitioned between aqueous ammonium chloride and EtOAc, extracted with EtOAc, dried over sodium sulfate, filtered and concentrated to afford a 5:1 mix of tert-butyl (3-((1s,4s)-4-hydroxycyclohexyl)-1-(1-methyl-1H-pyrazol-4-yl)-1H-pyrazolo[3,4-c]pyridin-5-yl)(methyl)carbamate and tert-butyl (3-((1r,4r)-4-hydroxycyclohexyl)-1-(1-methyl-1H-pyrazol-4-yl)-1H-pyrazolo[3,4-c]pyridin-5-yl)(methyl)carbamate (0.031 g, 0.073 mmol, 86% yield).

Step J: Crude mixture of tert-butyl (3-((1s,4s)-4-hydroxycyclohexyl)-1-(1-methyl-1H-pyrazol-4-yl)-1H-pyrazolo[3, 4-c]pyridin-5-yl)(methyl)carbamate and tert-butyl (3-((1r,4r)-4-hydroxycyclohexyl)-1-(1-methyl-1H-pyrazol-4-yl)-1H-pyrazolo[3,4-c]pyridin-5-yl)(methyl)carbamate (0.031 g, 0.073 mmol) was dissolved in THF (1 mL). 2-fluorophenol (0.012 g, 0.109 mmol) and triphenylphosphine (0.028 g, 0.109 mmol) were added, followed by DIAD (0.022 g, 0.109 mmol) and heated to 70° C. overnight. The reaction mixture was concentrated and the crude material was taken up in DCM (1 mL) and 4M HCl/dioxane (2 mL), stirred for 2 h and concentrated. The residue was purified by preparative HPLC (5 to 95% ACN in water with 0.1% TFA) to afford 3-((1r,4r)-4-(2-fluorophenoxy)cyclohexyl)-N— methyl-1-(1-methyl-1H-pyrazol-4-yl)-1H-pyrazolo[3,4-c]pyridin-5-amine bis(2,2,2-trifluoroacetate) (9.3 mg, 19% yield). Mass spectrum (apci) m/z=421.2 (M+H). $^1$H NMR (CD3OD) δ 8.62 (d, J=1.0 Hz, 1H), 8.16 (s, 1H), 7.90 (s, 1H), 7.27 (s, 1H), 7.20-7.06 (m, 3H), 6.94 (m, 1H), 4.72 (m, 1H), 4.00 (s, 3H), 3.05 (s, 3H), 2.35-2.15 (m, 5H), 1.95-1.80 (m, 4H).

Example 480

N-ethyl-3-((1s,4s)-4-(2-fluorophenoxy)cyclohexyl)-1-(1-methyl-1H-pyrazol-4-yl)-1H-pyrazolo[3,4-c]pyridin-5-amine

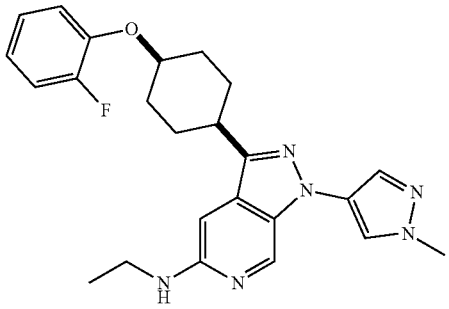

Step A: PPh$_3$ (12.4 g, 47.4 mmol) was dissolved in THF (160 mL) and cooled to 0° C. DIAD (9.6 g, 47.4 mmol) was added by syringe and the mixture was stirred for 30 min. 1,4-dioxaspiro[4.5]decan-8-ol (5.0 g, 31.6 mmol) was added followed by 2-fluorophenol (10.6 g, 94.8 mmol, in 10 mL of THF) and allowed to warm to room temperature overnight. The reaction mixture was partitioned between EtOAc and 10% K$_2$CO$_3$, washed 2× with 10% K$_2$CO$_3$ and brine, dried over sodium sulfate, filtered and concentrated. The residue was purified over silica gel (5-20% EtOAc in hexane) to afford 8-(2-fluorophenoxy)-1,4-dioxaspiro[4.5]decane (5.34 g, 67% yield).

Step B: 8-(2-fluorophenoxy)-1,4-dioxaspiro[4.5]decane (5.3 g, 21.0 mmol) was dissolved in DCM (40 mL), TFA (10 mL) and water (5 mL) and stirred for 4 h. The mixture was poured into 2M aq. NaOH (500 mL) and extracted 2× with DCM, dried over sodium sulfate, filtered and concentrated to afford 4-(2-fluorophenoxy)cyclohexan-1-one (4.15 g, 95% yield).

Step C: 4-(2-fluorophenoxy)cyclohexan-1-one (4.15 g, 19.93 mmol) was dissolved in THF (100 mL) and cooled to −78° C. LiHMDS (22 mL, 22 mmol, 1M in THF) was added by syringe and the mixture was stirred at −78° C. for 1 h. 1,1,2,2,3,3,4,4,4-nonafluorobutane-1-sulfonyl fluoride (6.62 g, 22 mmol) was added portionwise by syringe. Once the addition was complete, the mixture was allowed to warm to room temperature and stirred for one hour. The reaction mixture was quenched with saturated ammonium chloride solution and partitioned between water and EtOAc, extracted 2× with EtOAc, washed with brine, dried over sodium sulfate, filtered and concentrated. The residue was purified over silica gel (0-10% EtOAc in hexane) to afford 4-(2-fluorophenoxy)cyclohex-1-en-1-yl 1,1,2,2,3,3,4,4,4-nonafluorobutane-1-sulfonate (6.2 g, 63.4% yield).

Step D: 4-(2-fluorophenoxy)cyclohex-1-en-1-yl 1,1,2,2,3,3,4,4,4-nonafluorobutane-1-sulfonate (6.2 g, 12.6 mmol), 4,4,4',4',5,5,5',5'-octamethyl-2,2'-bi(1,3,2-dioxaborolane) (3.53 g, 13.9 mmol) and KOAc (3.72 g, 37.9 mmol) were dissolved in dioxane (63 mL) under a nitrogen atmosphere. PdCl$_2$(dppf) dichloromethane adduct (516 mg, 0.63 mmol) was added and the reaction was heated to 100° C. overnight. The reaction mixture was partitioned between EtOAc and water, extracted with EtOAc, washed with brine, dried over sodium sulfate, filtered and concentrated. The residue was purified over silica gel (100% DCM) to afford 2-(4-(2-fluorophenoxy)cyclohex-1-en-1-yl)-4,4,5,5-tetramethyl-1,3,2-dioxaborolane (2.32 g, 57.7% yield)

Step E: 3-Bromo-5-chloro-1-((2-(trimethylsilyl)ethoxy)methyl)-1H-pyrazolo[3,4-c]pyridine (920 mg, 2.5 mmol) and 2-(4-(2-fluorophenoxy)cyclohex-1-en-1-yl)-4,4,5,5-tetramethyl-1,3,2-dioxaborolane (890 mg, 2.8 mmol) were dissolved in dioxane (25 mL) under a nitrogen atmosphere. Pd(PPh$_3$)$_4$ (290 mg, 0.25 mmol) was added and the reaction mixture was heated to 100° C. overnight. The reaction mixture was partitioned between EtOAc and water, extracted with EtOAc, dried over sodium sulfate, filtered and concentrated. The residue was purified over silica gel (10-30% EtOAc in hexane) to afford 5-chloro-3-(4-(2-fluorophenoxy)cyclohex-1-en-1-yl)-1-((2-(trimethylsilyl)ethoxy)methyl)-1H-pyrazolo[3,4-c]pyridine (750 mg, 62% yield).

Step F: 5-chloro-3-(4-(2-fluorophenoxy)cyclohex-1-en-1-yl)-1-((2-(trimethylsilyl)ethoxy)methyl)-1H-pyrazolo[3,4-c]pyridine (0.75 g, 1.58 mmol) and tert-butyl ethylcarbamate (0.92 g, 6.33 mmol) were dissolved in dioxane (16 mL) and dicyclohexyl(2',6'-diisopropoxy-[1,1'-biphenyl]-2-yl)phosphane (0.29 g, 0.63 mmol), sodium t-butoxide (0.30 g, 3.2 mmol) and Pd2dba3 (0.29 g, 0.32 mmol) were added and purged with nitrogen. The tube was sealed and heated to 100° C. overnight, partitioned between EtOAc and water, extracted with EtOAc, dried over sodium sulfate, filtered and concentrated. The residue was purified over silica gel (10-30% EtOAc in hexanes) to afford tert-butyl ethyl(3-(4-(2-fluorophenoxy)cyclohex-1-en-1-yl)-1-((2-(trimethylsilyl)ethoxy)methyl)-1H-pyrazolo[3,4-c]pyridin-5-yl)carbamate (615 mg, 66.7% yield).

Step G: tert-butyl ethyl(3-(4-(2-fluorophenoxy)cyclohex-1-en-1-yl)-1-((2-(trimethylsilyl)ethoxy)methyl)-1H-pyrazolo[3,4-c]pyridin-5-yl)carbamate (0.615 g, 1.06 mmol) was dissolved in methanol (11 mL), and 600 mg of 10% Pd/C (Degussa type, 50% water) was added and hydrogenated under a balloon of nitrogen at 30° C. for 1 h. The reaction mixture was filtered, concentrated and purified over silica gel (15-70% EtOAc in hexanes) to afford tert-butyl ethyl(3-((1s,4s)-4-(2-fluorophenoxy)cyclohexyl)-1-((2-(trimethylsilyl)ethoxy)methyl)-1H-pyrazolo[3,4-c]pyridin-5-yl)carbamate (358 mg, 58% yield).

Step H: tert-butyl ethyl(3-((1s,4s)-4-(2-fluorophenoxy)cyclohexyl)-1-((2-(trimethylsilyl)ethoxy)methyl)-1H-pyrazolo[3,4-c]pyridin-5-yl)carbamate (355 mg, 0.607 mmol) was dissolved in THF (6 mL), ethane-1,2-diamine (0.41 mL, 6.0 mmol) and TBAF (3.0 mL, 3.0 mmol, 1M in THF) were added, tube sealed and heated to 70° C. for 5 h. The reaction mixture was diluted with EtOAc, washed 3× with 10%

$K_2CO_3$, dried over sodium sulfate, filtered and concentrated to afford tert-butyl ethyl(3-((1s,4s)-4-(2-fluorophenoxy)cyclohexyl)-1H-pyrazolo[3,4-c]pyridin-5-yl)carbamate (230 mg, 83% yield).

Step I: tert-butyl ethyl(3-((1s,4s)-4-(2-fluorophenoxy)cyclohexyl)-1H-pyrazolo[3,4-c]pyridin-5-yl)carbamate (75 mg, 0.16 mmol) was dissolved in DMSO (1.5 mL) and 4-iodo-1-methyl-1H-pyrazole (34 mg, 0.16 mmol), N1,N2-dimethylethane-1,2-diamine (0.023 mL, 0.21 mmol), $Cs_2CO_3$ (130 mg, 0.41 mmol) and copper(I) iodide (16 mg, 0.08 mmol) were added and purged with nitrogen. The tube was sealed and heated to 100° C. for 4 h. Another equivalent of 4-iodo-1-methyl-1H-pyrazole was added, followed by another 0.5 eq. of CuI and the reaction mixture was heated overnight at 100° C. The reaction mixture was partitioned between EtOAc and water, extracted with EtOAc, dried over sodium sulfate, filtered and concentrated. The residue was purified over silica gel (50% EtOAc in hexanes) to afford tert-butyl ethyl(3-((1s,4s)-4-(2-fluorophenoxy)cyclohexyl)-1-(1-methyl-1H-pyrazol-4-yl)-1H-pyrazolo[3,4-c]pyridin-5-yl)carbamate (55 mg, 62% yield).

Step J: tert-butyl ethyl(3-((1s,4s)-4-(2-fluorophenoxy)cyclohexyl)-1-(1-methyl-1H-pyrazol-4-yl)-1H-pyrazolo[3,4-c]pyridin-5-yl)carbamate (55 mg, 0.10 mmol) was dissolved in DCM (0.5 mL) and 4M HCl/dioxane (1 mL) was added and stirred 2 h and concentrated. The residue was purified by preparative HPLC (5 to 95% ACN in water with 0.1% TFA) to afford N-ethyl-3-((1s,4s)-4-(2-fluorophenoxy)cyclohexyl)-1-(1-methyl-1H-pyrazol-4-yl)-1H-pyrazolo[3,4-c]pyridin-5-amine bis(2,2,2-trifluoroacetate) (45 mg, 66% yield). Mass spectrum (apci) m/z=435.2 (M+H). $^1$H NMR (CD3OD) δ 8.63 (d, J=1.1 Hz, 1H), 8.15 (s, 1H), 7.90 (s, 1H), 7.30 (d, J=0.8 Hz, 1H), 7.20-7.06 (m, 3H), 6.94 (m, 1H), 4.71 (m, 1H), 3.99 (s, 3H), 3.43 (q, J=7.2 Hz, 2H), 2.35-2.15 (m, 4H), 1.95-1.80 (m, 4H), 1.36 (t, J=7.2 Hz, 3H).

Using the procedure described for the preparation of Example 480, the following compounds were also synthesized:

| Example | Structure | Name | Data |
|---|---|---|---|
| 481 | 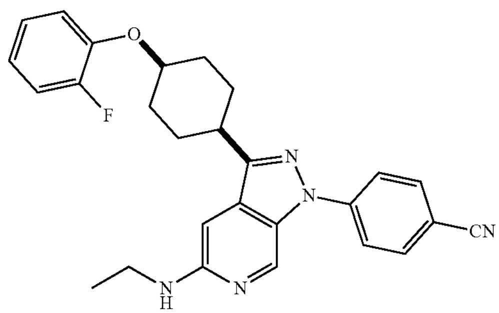 | 4-(5-(ethylamino)-3-((1s,4s)-4-(2-fluorophenoxy)cyclohexyl)-1H-pyrazolo[3,4-c]pyridin-1-yl)benzonitrile | Mass spectrum (apci) m/z = 456.2 |
| 482 | 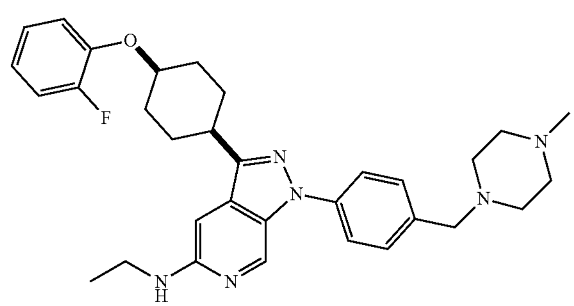 | N-ethyl-3-((1s,4s)-4-(2-fluorophenoxy)cyclohexyl)-1-(4-((4-methylpiperazin-1-yl)methyl)phenyl)-1H-pyrazolo[3,4-c]pyridin-5-amine | Mass spectrum (apci) m/z = 543.3 |
| 483 | 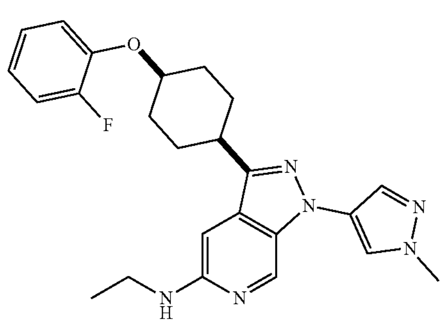 | 2-methyl-6-(((1s,4s)-4-(1-(1-methyl-1H-pyrazol-4-yl)-5-(methylamino)-1H-pyrazolo[3,4-c]pyridin-3-yl)cyclohexyl)oxy)pyridazin-3(2H)-one | Mass spectrum (apci) m/z = 435.2 |

Example 484

(R)-3-(4-(6-amino-1-((1s,4S)-4-(2-fluorophenoxy)
cyclohexyl)-1H-pyrazolo[4,3-c]pyridin-3-yl)-1H-
pyrazol-1-yl)propane-1,2-diol

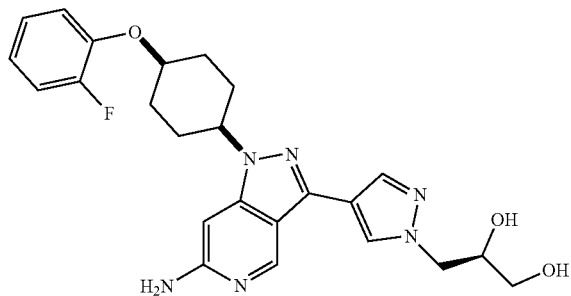

Step A: 3-bromo-1-((1r,4r)-4-((tert-butyldimethylsilyl)oxy)cyclohexyl)-6-chloro-1H-pyrazolo[4,3-c]pyridine (500 mg, 1.12 mmol), (R)-1-((2,2-dimethyl-1,3-dioxolan-4-yl)methyl)-4-(4,4,5,5-tetramethyl-1,3,2-dioxaborolan-2-yl)-1H-pyrazole (381 mg, 1.24 mmol) and Pd(PPh$_3$)$_4$ (130 mg, 0.112 mmol) were combined in dioxane (6 mL) and treated with 2M K$_2$CO$_3$ (1.69 mL, 3.37 mmol) and heated to 100° C. overnight. The reaction mixture was partitioned between water (50 mL) and EtOAc (35 mL), extracted with EtOAc (2×35 mL), washed with brine (40 mL), dried over Na$_2$SO$_4$, filtered and concentrated. The residue was purified over silica gel (10-40% EtOAc in hexanes) to afford 1-((1r,4R)-4-((tert-butyldimethylsilyl)oxy)cyclohexyl)-6-chloro-3-(1-(((R)-2,2-dimethyl-1,3-dioxolan-4-yl)methyl)-1H-pyrazol-4-yl)-1H-pyrazolo[4,3-c]pyridine (502 mg, 81.8% yield).

Step B: 1-((1r,4R)-4-((tert-butyldimethylsilyl)oxy)cyclohexyl)-6-chloro-3-(1-(((R)-2,2-dimethyl-1,3-dioxolan-4-yl)methyl)-1H-pyrazol-4-yl)-1H-pyrazolo[4,3-c]pyridine (503 mg, 0.92 mmol), Cs$_2$CO$_3$ (600 mg, 1.84 mmol), X-PHOS (88 mg, 0.18 mmol) and Pd2(dba)$_3$ (84 mg, 0.092 mmol) were combined in dioxane (6 mL) and treated with tert-butyl carbamate (647 mg, 5.52 mmol). The mixture was purged with nitrogen and heated in a sealed tube at 100° C. overnight. The reaction mixture was partitioned between water (60 mL) and EtOAc (50 mL), extracted with EtOAc (2×25 mL), washed with brine (10 mL), dried over Na$_2$SO$_4$, filtered and concentrated. The residue was purified over silica gel (20-50% EtOAc in hexanes) to afford tert-butyl (1-((1r,4R)-4-((tert-butyldimethylsilyl)oxy)cyclohexyl)-3-(1-(((R)-2,2-dimethyl-1,3-dioxolan-4-yl)methyl)-1H-pyrazol-4-yl)-1H-pyrazolo[4,3-c]pyridin-6-yl)carbamate (182 mg, 31.5% yield).

Step C: To a solution of tert-butyl (1-((1r,4R)-4-((tert-butyldimethylsilyl)oxy)cyclohexyl)-3-(1-(((R)-2,2-dimethyl-1,3-dioxolan-4-yl)methyl)-1H-pyrazol-4-yl)-1H-pyrazolo[4,3-c]pyridin-6-yl)carbamate (182 mg, 0.291 mmol) in THF (3 mL) was added 1M TBAF in THF (872 μL, 0.872 mmol) and stirred overnight. The reaction mixture was partitioned between saturated NaHCO$_3$ (65 mL) and EtOAc (25 mL), extracted with EtOAc (2×25 mL), washed with brine (40 mL), dried over Na$_2$SO$_4$, filtered and concentrated. The residue was purified over silica gel (50-100% EtOAc in hexanes) to afford tert-butyl (3-(1-(((R)-2,2-dimethyl-1,3-dioxolan-4-yl)methyl)-1H-pyrazol-4-yl)-1-((1r,4R)-4-hydroxycyclohexyl)-1H-pyrazolo[4,3-c]pyridin-6-yl)carbamate (121 mg, 81% yield).

Step D: A solution of PPh$_3$ (93 mg, 0.354 mmol) in THF (3 mL) was treated with DIAD (70 μL, 0.354 mmol). After stirring for 10 min, tert-butyl (3-(1-(((R)-2,2-dimethyl-1,3-dioxolan-4-yl)methyl)-1H-pyrazol-4-yl)-1-((1r,4R)-4-hydroxycyclohexyl)-1H-pyrazolo[4,3-c]pyridin-6-yl)carbamate (121 mg, 0.236 mmol) was added, followed by 2-fluorophenol (63 μL, 0.708 mmol) and stirred overnight. The reaction mixture was partitioned between EtOAc and water, extracted with EtOAc (3×15 mL), washed with brine (20 mL), dried over sodium sulfate, filtered and concentrated. The residue was purified over silica gel (30-70% EtOAc in hexanes) to afford tert-butyl (3-(1-(((R)-2,2-dimethyl-1,3-dioxolan-4-yl)methyl)-1H-pyrazol-4-yl)-1-((1s,4S)-4-(2-fluorophenoxy)cyclohexyl)-1H-pyrazolo[4,3-c]pyridin-6-yl)carbamate (206 mg, 144% yield).

Step E: The impure mixture of tert-butyl (3-(1-(((R)-2,2-dimethyl-1,3-dioxolan-4-yl)methyl)-1H-pyrazol-4-yl)-1-((1s,4S)-4-(2-fluorophenoxy)cyclohexyl)-1H-pyrazolo[4,3-c]pyridin-6-yl)carbamate (206 mg, 0.340 mmol) was dissolved in MeOH (4 mL) and treated with 4N HCl/dioxane (7 mL) and stirred overnight. The reaction mixture was concentrated and purified by preparative HPLC (5 to 95% ACN in water with 0.1% TFA). The fractions containing the product were partitioned between 2N NaOH and DCM, extracted with DCM (3×30 mL), washed with brine (40 mL), dried over sodium sulfate, filtered and concentrated to afford (R)-3-(4-(6-amino-1-((1s,4S)-4-(2-fluorophenoxy)cyclohexyl)-1H-pyrazolo[4,3-c]pyridin-3-yl)-1H-pyrazol-1-yl)propane-1,2-diol (59.8 mg, 37% yield). Mass spectrum (apci) m/z=467.2 (M+H). $^1$H NMR (CDCl$_3$) δ 8.71 (d, J=0.8 Hz, 1H), 8.05 (s, 1H), 7.98 (s, 1H), 7.16-7.05 (m, 3H), 6.95 (m, 1H), 6.52 (d, J=0.6 Hz, 1H), 4.65 (m, 1H), 4.51 (br s, 1H), 4.44-4.34 (m, 3H), 4.17 (m, 1H), 3.67 (m, 2H), 2.61 (m, 2H), 2.30 (m, 2H), 1.89 (m, 2H), 1.73 (m, 2H).

Example 485

N-ethyl-1-((1s,4s)-4-(2-fluorophenoxy)cyclohexyl)-
3-(4-methyl-1H-imidazol-1-yl)-1H-pyrazolo[4,3-c]
pyridin-6-amine

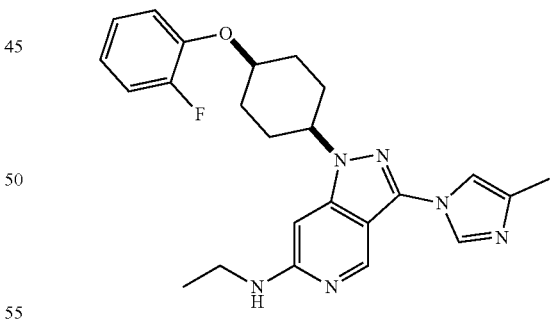

Step A: To a solution of tert-butyl (3-bromo-1-((1s,4s)-4-(2-fluorophenoxy)cyclohexyl)-1H-pyrazolo[4,3-c]pyridin-6-yl)(ethyl)carbamate (35 mg, 0.0656 mmol) in 300 μL of toluene was added 4-methyl-1H-imidazole (10.8 mg, 0.131 mmol) followed by K$_3$PO$_4$ (69.6 mg, 0.328 mmol) and N,N'-dimethylethylenediamine (2.82 μL, 0.0262 mmol). Cu(I)I (2.50 mg, 0.0131 mmol) was then added and the reaction was capped and heated to 115° C. for 48 h. 300 μL of DMSO was added and the reaction was allowed to heat for another 24 hours. The reaction mixture was partitioned between dichloromethane and water, washed with water, dried over MgSO₄, filtered and concentrated. The crude product was purified over silica gel (0% to 10% methanol) to afford tert-butyl ethyl(1-((1s,4s)-4-(2-fluorophenoxy)cyclohexyl)-3-(4-methyl-1H-imidazol-1-yl)-1H-pyrazolo[4,3-c]pyridin-6-yl)carbamate (13 mg, 37% yield).

Step B: To a solution of tert-butyl ethyl(1-((1s,4s)-4-(2-fluorophenoxy)cyclohexyl)-3-(4-methyl-1H-imidazol-1-yl)-1H-pyrazolo[4,3-c]pyridin-6-yl)carbamate (13 mg, 0.0243 mmol) in 500 μL of dichloromethane was added TFA (468 μL, 6.08 mmol). After 2 h the reaction was concentrated and purified by preparative HPLC (5 to 95% ACN in water with 0.1% TFA). The fractions containing the product were partitioned between DCM and saturated NaHCO₃, extracted with DCM (×2), dried over MgSO₄, filtered and concentrated to afford N-ethyl-1-((1s,4s)-4-(2-fluorophenoxy)cyclohexyl)-3-(4-methyl-1H-imidazol-1-yl)-1H-pyrazolo[4,3-c]pyridin-6-amine (8 mg, 74% yield). Mass spectrum (apci) m/z=435.2 (M+H). 1H NMR (CDCl₃) δ 8.65 (s, 1H), 8.05 (s, 1H), 7.29 (s, 1H), 7.15-7.05 (m, 3H), 6.95 (m, 1H), 6.13 (s, 1H), 4.76 (m, 1H), 4.63 (m, 1H), 4.33 (tt, J=11.9, 3.9 Hz, 1H), 3.31 (m, 2H), 2.59 (m, 2H), 2.55-2.26 (m, 5H), 1.91 (m, 2H), 1.76 (m, 2H), 1.35 (t, J=7.2 Hz, 3H).

Example 486

1-((1s,4s)-4-(2,3-difluorophenoxy)cyclohexyl)-3-(1-methyl-1H-pyrazol-4-yl)-N-phenyl-1H-pyrazolo[4,3-c]pyridin-6-amine

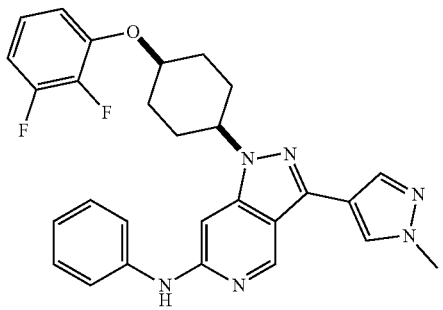

Step A: To a solution of 1-((1r,4r)-4-((tert-butyldimethylsilyl)oxy)cyclohexyl)-6-chloro-3-(1-methyl-1H-pyrazol-4-yl)-1H-pyrazolo[4,3-c]pyridine (0.83 g, 1.86 mmol), Pd₂(dba)₃ (0.682 g, 0.744 mmol), 2-(Dicyclohexylphosphino)-2,4,6-Triisopropylbiphenyl (0.710 g, 1.49 mmol) and sodium tert-butoxide (0.536 g, 5.58 mmol) in 1,4-dioxane (18.6 mL) was added aniline (1.70 mL, 18.6 mmol). The reaction mixture was purged with nitrogen for 5 minutes and heated to 100° C. for 2 h. The reaction mixture was partitioned between EtOAc and hexanes, filtered through GF/F paper, extracted with EtOAc, washed with water and brine, dried over sodium sulfate, filtered and concentrated. The residue was purified over silica gel (10-100% EtOAc in hexanes) to afford 1-((1r,4r)-4-((tert-butyldimethylsilyl)oxy)cyclohexyl)-3-(1-methyl-1H-pyrazol-4-yl)-N-phenyl-1H-pyrazolo[4,3-c]pyridin-6-amine (0.66 g, 1.31 mmol, 70.6% yield).

Step B: 1-((1r,4r)-4-((tert-butyldimethylsilyl)oxy)cyclohexyl)-3-(1-methyl-1H-pyrazol-4-yl)-N-phenyl-1H-pyrazolo[4,3-c]pyridin-6-amine (0.66 g, 1.31 mmol) was diluted with THF (6.5 mL), followed by the addition of 1M TBAF in THF (2.63 mL, 2.63 mmol) and heated to 70° C. overnight. The reaction mixture was partitioned between EtOAc and water, washed with water and brine, dried over Na₂SO₄, filtered and concentrated. The residue was purified over silica gel (5-50% EtOAc in hexanes) to afford (1r,4r)-4-(3-(1-methyl-1H-pyrazol-4-yl)-6-(phenylamino)-1H-pyrazolo[4,3-c]pyrazol-1-yl)cyclohexan-1-ol (0.315 g, 0.811 mmol, 61.8% yield)

Step C: To a solution of Ph₃P (0.0276 g, 0.105 mmol), (1r,4r)-4-(3-(1-methyl-1H-pyrazol-4-yl)-6-(phenylamino)-1H-pyrazolo[4,3-c]pyridin-1-yl)cyclohexan-1-ol (0.0205 g, 0.0527 mmol) and 2,3-difluorophenol (0.0137 g, 0.105 mmol) in THF (0.5 mL) was added DIAD (0.0208 mL, 0.105 mmol) and stirred for 30 minutes. The reaction mixture was diluted with dichloromethane (2 mL) and TFA (5 mL) was added and stirred for 2 h. The reaction mixture was concentrated and purified by preparative HPLC (5-60% ACN in water with 0.2% TFA). The fractions containing the product were partitioned between saturated NaHCO₃ and DCM, extracted with DCM (2×15 mL), washed with brine (15 mL), dried over Na2SO4, filtered and concentrated to afford 1-((1s,4s)-4-(2,3-difluorophenoxy)cyclohexyl)-3-(1-methyl-1H-pyrazol-4-yl)-N-phenyl-1H-pyrazolo[4,3-c]pyridin-6-amine (0.0175 g, 0.03496 mmol, 66.25% yield). Mass spectrum (apci) m/z=501.2 (M+H). ¹H NMR (CDCl₃) δ 8.82 (d, J=1.0 Hz, 1H), 8.02 (s, 1H), 7.92 (s, 1H), 7.40-7.33 (m, 4H), 7.07 (m, 1H), 6.97 (m, 1H), 6.85-6.76 (m, 3H), 6.65 (s, 1H), 4.61 (m, 1H), 4.32 (tt, J=11.7, 3.9 Hz, 1H), 4.01 (s, 3H), 2.57 (m, 2H), 2.28 (m, 2H), 1.89 (m, 2H), 1.75 (m, 2H).

Example 487

2-(((1S,4s)-4-(3-(1-((R)-2,3-dihydroxypropyl)-1H-pyrazol-4-yl)-6-(ethylamino)-1H-pyrazolo[4,3-c]pyridin-1-yl)cyclohexyl)oxy)-3-fluoroisonicotinonitrile

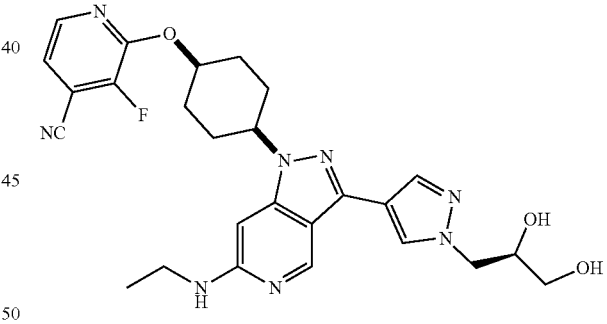

Step A: To a solution of Ph₃P (0.4465 g, 1.702 mmol), (1R,4r)-4-(3-(1-(((R)-2,2-dimethyl-1,3-dioxolan-4-yl)methyl)-1H-pyrazol-4-yl)-6-(ethylamino)-1H-pyrazolo[4,3-c]pyridin-1-yl)cyclohexan-1-ol (0.250 g, 0.5675 mmol) and 3-fluoro-4-iodopyridin-2(1H)-one (0.1763 g, 0.7377 mmol) in THF (5.6 mL) was added DIAD (0.3355 ml, 1.702 mmol) at 0° C. The reaction mixture was allowed to warm to room temperature and was stirred for 1 h. EtOAc (15 mL) and water (15 mL) were added and the biphasic mixture was separated. The organic layer was washed with brine (2×15 mL), dried with Na₂SO₄, filtered and concentrated in vacuo. The residue was purified over silica gel (10-100% EtOAc in hexanes) to afford 3-(1-(((R)-2,2-dimethyl-1,3-dioxolan-4-yl)methyl)-1H-pyrazol-4-yl)-N— ethyl-1-((1s,4S)-4-((3-fluoro-4-iodopyridin-2-yl)oxy)cyclohexyl)-1H-pyrazolo[4,3-c]pyridin-6-amine (0.094 g, 0.1421 mmol, 25.04% yield).

Step B: A solution of 3-(1-(((R)-2,2-dimethyl-1,3-dioxolan-4-yl)methyl)-1H-pyrazol-4-yl)-N-ethyl-1-((1s,4S)-4-((3-fluoro-4-iodopyridin-2-yl)oxy)cyclohexyl)-1H-pyrazolo[4,3-c]pyridin-6-amine (0.032 g, 0.048 mmol) and copper(I) cyanide (0.022 g, 0.24 mmol) in NMP (0.0047 ml, 0.048 mmol) was heated to 150° C. for 17 hours. A solution (1.5 mL) of 60:40 ACN:water with 2% TFA modifier was added and the mixture was syringe-filtered (×2). The product was purified by HPLC (5-75% ACN in water with 0.2% TFA modifier). The product fractions were free-based with saturated NaHCO₃(15 mL) and mixture was extracted with DCM. The combined organic layers were washed with brine (15 mL), dried over Na$_2$SO$_4$, filtered and concentrated to obtain 2-(((1S,4s)-4-(3-(1-((R)-2,3-dihydroxypropyl)-1H-pyrazol-4-yl)-6-(ethylamino)-1H-pyrazolo[4,3-c]pyridin-1-yl)cyclohexyl)oxy)-3-fluoroisonicotinonitrile (0.0055 g, 0.011 mmol, 22% yield). Mass spectrum (apci) m/z=521.2 (M+H). 1H NMR (d6-DMSO) δ 8.79 (s, 1H), 8.26 (s, 1H), 8.20 (d, J=5.3 Hz, 1H), 7.98 (s, 1H), 7.47 (m, 1H), 6.31 (t, J=5.5 Hz, 1H), 6.28 (s, 1H), 5.43 (m, 1H), 5.00 (d, J=5.5 Hz, 1H), 4.75 (t, J=5.9 Hz, 1H), 4.53 (m, 1H), 4.28 (dd, J=13.5, 3.7 Hz, 1H), 4.07 (dd, J=13.3, 5.7 Hz, 1H), 3.87 (m, 1H), 3.37 (m, 2H), 3.23 (m, 2H), 2.35-2.15 (m, 4H), 1.99-1.77 (m, 4H), 1.20 (t, J=7.0 Hz, 3H).

Using the procedure described for the preparation of Example 330, the following compounds were also synthesized:

| Example | Structure | Name | Data |
|---|---|---|---|
| 488 | 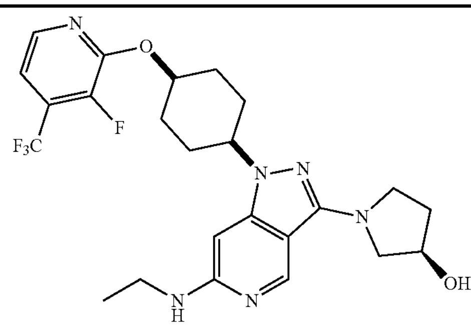 | (R)-1-(6-(ethylamino)-1-((1s,4S)-4-((3-fluoro-4-(trifluoromethyl)pyridin-2-yl)oxy)cyclohexyl)-1H-pyrazolo[4,3-c]pyridin-3-yl)pyrrolidin-3-ol | Mass spectrum (apci) m/z = 509.2 |
| 489 | 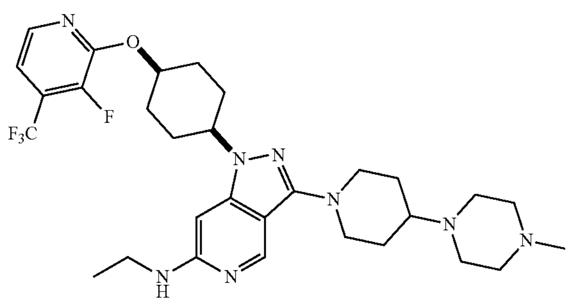 | N-ethyl-1-((1s,4s)-4-((3-fluoro-4-(trifluoromethyl)pyridin-2-yl)oxy)cyclohexyl)-3-(4-(4-methylpiperazin-1-yl)piperidin-1-yl)-1H-pyrazolo[4,3-c]pyridin-6-amine | Mass spectrum (apci) m/z = 605.3 |
| 490 | 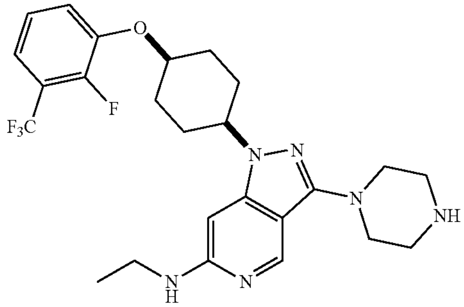 | N-ethyl-1-((1s,4s)-4-(2-fluoro-3-(trifluoromethyl)phenoxy)cyclohexyl)-3-(piperazin-1-yl)-1H-pyrazolo[4,3-c]pyridin-6-amine | Mass spectrum (apci) m/z = 507.2 |
| 491 | 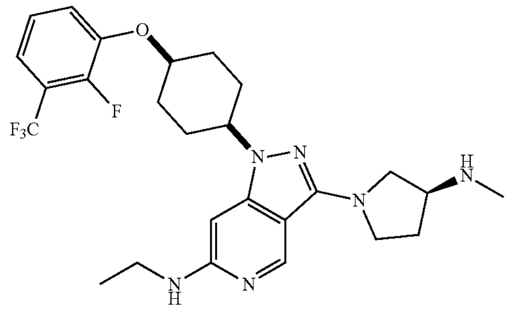 | N-ethyl-1-((1s,4R)-4-(2-fluoro-3-(trifluoromethyl)phenoxy)cyclohexyl)-3-((S)-3-(methylamino)pyrrolidin-1-yl)-1H-pyrazolo[4,3-c]pyridin-6-amine | Mass spectrum (apci) m/z = 521.3 |

-continued

| Example | Name | Data |
|---------|------|------|
| 492 | N-ethyl-1-((1s,4S)-4-(2-fluoro-3-(trifluoromethyl)phenoxy)cyclohexyl)-3-((R)-3-(methylamino)pyrrolidin-1-yl)-1H-pyrazolo[4,3-c]pyridin-6-amine | Mass spectrum (apci) m/z = 521.2 |
| 493 | 3-((S)-3-aminopyrrolidin-1-yl)-N-ethyl-1-((1s,4R)-4-((3-fluoro-4-(trifluoromethyl)pyridin-2-yl)oxy)cyclohexyl)-1H-pyrazolo[4,3-c]pyridin-6-amine | Mass spectrum (apci) m/z = 508.2 |
| 494 | 3-((R)-3-aminopyrrolidin-1-yl)-N-ethyl-1-((1s,4S)-4-((3-fluoro-4-(trifluoromethyl)pyridin-2-yl)oxy)cyclohexyl)-1H-pyrazolo[4,3-c]pyridin-6-amine | Mass spectrum (apci) m/z = 508.2 |
| 495 | 1-((1s,4s)-4-((3-fluoro-4-(trifluoromethyl)pyridin-2-yl)oxy)cyclohexyl)-N-methyl-3-(piperazin-1-yl)-1H-pyrazolo[4,3-c]pyridin-6-amine | Mass spectrum (apci) m/z = 494.2 |

Using the procedure described for the preparation of Example 248, the following compound was also synthesized:

| Example | Structure | Name | Data |
|---|---|---|---|
| 496 | 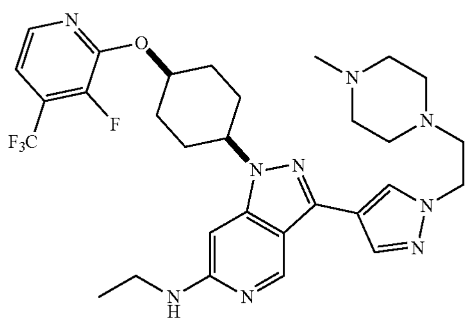 | N-ethyl-1-((1s,4s)-4((3-fluoro-4-(trifluoromethyl)pyridin-2-yl)oxy)cyclohexyl)-3-(1-(2-(4-methylpiperazin-1-yl)ethyl)-1H-pyrazol-4-yl)-1H-pyrazolo[4,3-c]pyridin-6-amine | Mass spectrum (apci) m/z = 616.3 |

Using the procedure described for the preparation of Example 371, the following compound was also synthesized:

| Example | Structure | Name | Data |
|---|---|---|---|
| 497 | 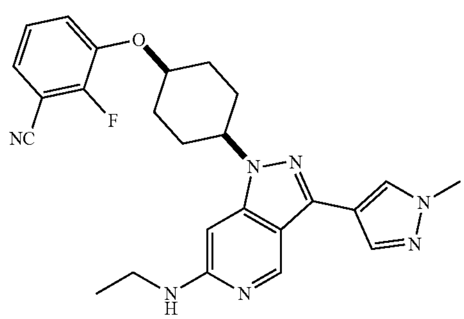 | 3-(((1s,4s)-4-(6-(ethylamino)-3-(1-methyl-1H-pyrazol-4-yl)-1H-pyrazolo[4,3-c]pyridin-1-yl)cyclohexyl)oxy)-2-fluorobenzonitrile | Mass spectrum (apci) m/z = 460.2 |

Using the procedure described for the preparation of Example 429, the following compounds were also synthesized:

| Example | Structure | Name | Data |
|---|---|---|---|
| 498 | 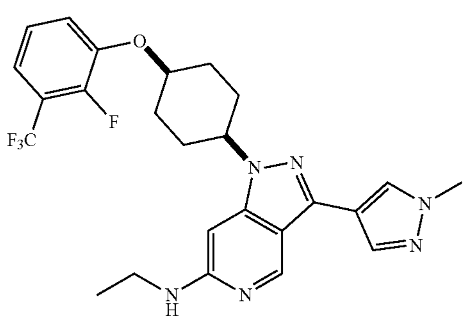 | N-ethyl-1-((1s,4s)-4-(2-fluoro-3-(trifluoromethyl)phenoxy)cyclohexyl)-3-(1-methyl-1H-pyrazol-4-yl)-1H-pyrazolo[4,3-c]pyridin-6-amine | Mass spectrum (apci) m/z = 503.2 |

-continued

| Example | Structure | Name | Data |
|---|---|---|---|
| 499 | 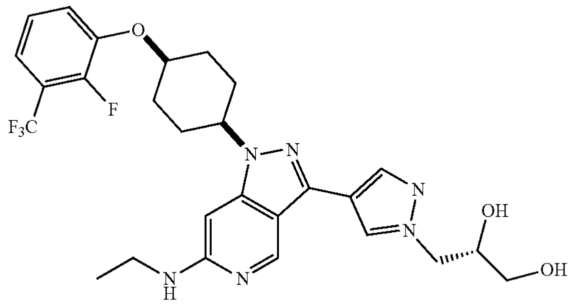 | (S)-3-(4-(6-(ethylamino)-1-((1s,4R)-4-(2-fluoro-3-(trifluoromethyl)phenoxy)cyclohexyl)-1H-pyrazolo[4,3-c]pyridin-3-yl)-1H-pyrazol-1-yl)propane-1,2-diol | Mass spectrum (apci) m/z = 563.3 |

Using the procedure described for the preparation of Example 434, the following compounds were also synthesized:

| Example | Structure | Name | Data |
|---|---|---|---|
| 500 | 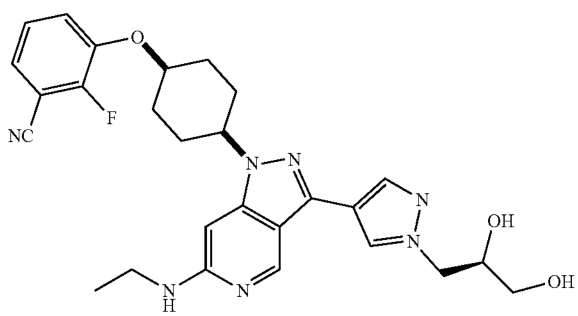 | 3-(((1S,4s)-4-(3-(1-((R)-2,3-dihydroxypropyl)-1H-pyrazol-4-yl)-6-(ethylamino)-1H-pyrazolo[4,3-c]pyridin-1-yl)cyclohexyl)oxy)-2-fluorobenzonitrile | Mass spectrum (apci) m/z = 520.2 |
| 501 | 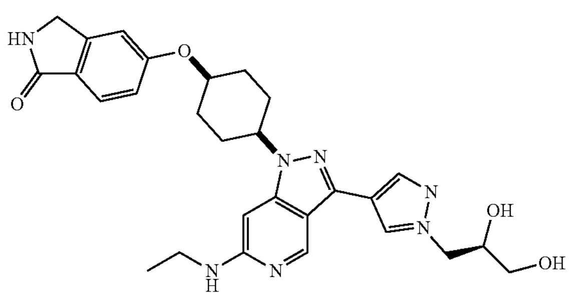 | 5-(((1S,4s)-4-(3-(1-((R)-2,3-dihydroxypropyl)-1H-pyrazol-4-yl)-6-(ethylamino)-1H-pyrazolo[4,3-c]pyridin-1-yl)cyclohexyl)oxy)isoindolin-1-one | Mass spectrum (apci) m/z = 532.2 |
| 502 | 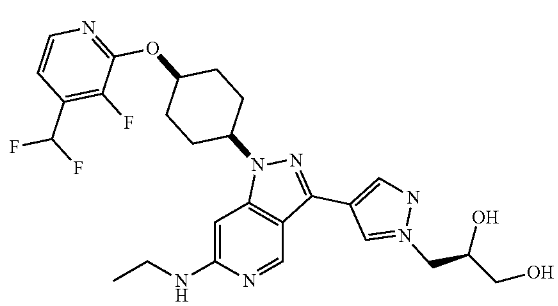 | (R)-3-(4-(1-((1s,4S)-4-((4-(difluoromethyl)-3-fluoropyridin-2-yl)oxy)cyclohexyl)-6-(ethylamino)-1H-pyrazolo[4,3-c]pyridin-3-yl)-1H-pyrazol-1-yl)propane-1,2-diol | Mass spectrum (apci) m/z = 546.3 |

| Example | Structure | Name | Data |
|---|---|---|---|
| 503 | 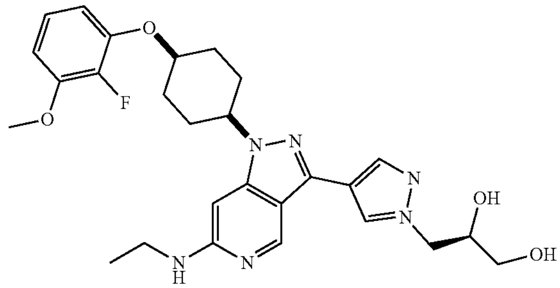 | (R)-3-(4-(6-(ethylamino)-1-((1s,4S)-4-(2-fluoro-3-methoxyphenoxy)cyclohexyl)-1H-pyrazolo[4,3-c]pyridin-3-yl)-1H-pyrazol-1-yl)propane-1,2-diol | Mass spectrum (apci) m/z = 525.3 |

Example 504

(S)-3-(4-(6-amino-1-((1s,4R)-4-((3-fluoro-4-(trifluoromethyl)pyridin-2-yl)oxy)cyclohexyl)-1H-pyrazolo[4,3-c]pyridin-3-yl)-1H-pyrazol-1-yl)propane-1,2-diol

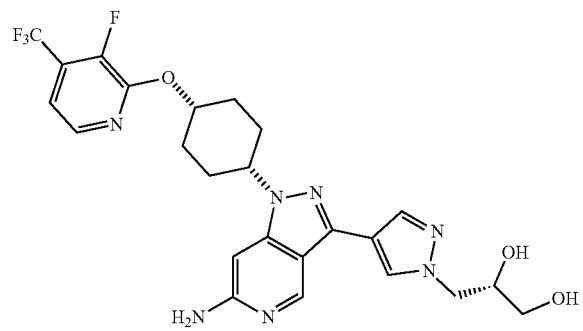

Step A: 1-((1r,4S)-4-((tert-butyldimethylsilyl)oxy)cyclohexyl)-6-chloro-3-(1-(((S)-2,2-dimethyl-1,3-dioxolan-4-yl)methyl)-1H-pyrazol-4-yl)-1H-pyrazolo[4,3-c]pyridine (283.2 mg, 0.519 mmol), Cs$_2$CO$_3$ (338 mg, 1.84 mmol), XPHOS (49 mg, 0.104 mmol) and Pd2(dba)$_3$ (48 mg, 0.0519 mmol) were combined in dioxanes (6 mL) and treated with tert-butyl carbamate (365 mg, 3.111 mmol). The mixture was purged briefly with N2 then heated in a sealed tube at 100° C. overnight. The cooled mixture was partitioned between water (60 mL) and EtOAc (40 mL) and the aqueous layer was extracted with EtOAc (2×20 mL). The combined organic phases were washed with brine (10 mL), dried over Na$_2$SO$_4$, filtered and concentrated. The residue was purified over silica gel (20-50% EtOAc in hexanes) to afford tert-butyl (1-((1r,4S)-4-((tert-butyldimethylsilyl)oxy)cyclohexyl)-3-(1-(((S)-2,2-dimethyl-1,3-dioxolan-4-yl)methyl)-1H-pyrazol-4-yl)-1H-pyrazolo[4,3-c]pyridin-6-yl)carbamate (84.8 mg, 26% yield).

Step B: To a solution of tert-butyl (1-((1r,4S)-4-((tert-butyldimethylsilyl)oxy)cyclohexyl)-3-(1-(((S)-2,2-dimethyl-1,3-dioxolan-4-yl)methyl)-1H-pyrazol-4-yl)-1H-pyrazolo[4,3-c]pyridin-6-yl)carbamate (84.8 mg, 0.135 mmol) in THF (2 mL) was added TBAF (406 µL, 1.0 M, 0.406 mmol). The mixture was stirred at room temperature overnight. The mixture was partitioned between 0.1 N NaOH (5 mL) and EtOAc (10 mL) and the aqueous layer was extracted with EtOAc (2×10 mL). The combined organic phases were washed with brine (30 mL), dried over Na$_2$SO$_4$, filtered and concentrated. The residue was purified over silica gel (50-100% EtOAc in hexanes) to afford tert-butyl (3-(1-(((S)-2,2-dimethyl-1,3-dioxolan-4-yl)methyl)-1H-pyrazol-4-yl)-1-((1r,4S)-4-hydroxycyclohexyl)-1H-pyrazolo[4,3-c]pyridin-6-yl)carbamate (50.9 mg, 73.4% yield).

Step C: A solution of triphenylphosphine (39 mg, 0.149 mmol) in THF (1 mL) at room temperature was treated with DIAD (29 µL, 0.149 mmol). The mixture was stirred for 10 min and then tert-butyl (3-(1-(((S)-2,2-dimethyl-1,3-dioxolan-4-yl)methyl)-1H-pyrazol-4-yl)-1-((1r,4S)-4-hydroxycyclohexyl)-1H-pyrazolo[4,3-c]pyridin-6-yl)carbamate (50.9 mg, 0.099 mmol) was added in THF (1 mL), followed by 3-fluoro-4-(trifluoromethyl)pyridin-2-ol (36 mg, 0.199 mmol). The mixture stirred overnight and partitioned between water (15 mL) and EtOAc (10 mL). The aqueous layer was extracted with EtOAc (2×10 mL). The combined organic phases were washed with brine (30 mL), dried over Na$_2$SO$_4$, filtered and concentrated. The residue was purified over silica gel (20-70% EtOAc in hexanes) to afford tert-butyl (3-(1-(((S)-2,2-dimethyl-1,3-dioxolan-4-yl)methyl)-1H-pyrazol-4-yl)-1-((1s,4R)-4-((3-fluoro-4-(trifluoromethyl)pyridin-2-yl)oxy)cyclohexyl)-1H-pyrazolo[4,3-c]pyridin-6-yl)carbamate (77.7 mg, 115% yield).

Step D: Tert-butyl (3-(1-(((S)-2,2-dimethyl-1,3-dioxolan-4-yl)methyl)-1H-pyrazol-4-yl)-1-((1s,4R)-4-((3-fluoro-4-(trifluoromethyl)pyridin-2-yl)oxy)cyclohexyl)-1H-pyrazolo[4,3-c]pyridin-6-yl)carbamate (40.6 mg, 0.0601 mmol) was dissolved in MeOH (2 mL) and treated with 4N HCl/dioxane (3 mL). The reaction mixture was stirred at room temperature for 2 h. Additional 4N HCl in dioxane (2 mL) was added and the reaction mixture was stirred for 3 h. The reaction was concentrated and purified via C18 reverse phase chromatography (5-95% ACN in water with 0.1% TFA). The purified fractions were partitioned between 2 N NaOH and DCM (3×10 mL), washed with brine (15 mL), dried over sodium sulfate, filtered and concentrated to afford (S)-3-(4-(6-amino-1-((1s,4R)-4-((3-fluoro-4-(trifluoromethyl)pyridin-2-yl)oxy)cyclohexyl)-1H-pyrazolo[4,3-c]pyridin-3-yl)-1H-pyrazol-1-yl)propane-1,2-diol (14.4 mg, 44.8% yield) as a yellow foam. Mass spectrum (apci) m/z=536.2 (M+H). $^1$H NMR (CDCl$_3$) δ 8.72 (s, 1H), 8.04 (m, 2H), 7.98 (s, 1H), 7.05 (t, J=4.4 Hz, 1H), 6.43 (s, 1H), 5.51 (m, 1H), 4.53 (br s, 2H), 4.43-4.34 (m, 3H), 4.17 (m, 1H), 3.67 (m, 2H), 2.55 (m, 2H), 2.34 (m, 2H), 1.95 (m, 2H), 1.83 (in, 2H).

Following the procedure in Example 504, the following compound was also synthesized:

| Ex. | Structure | Name | Data |
|---|---|---|---|
| 505 | 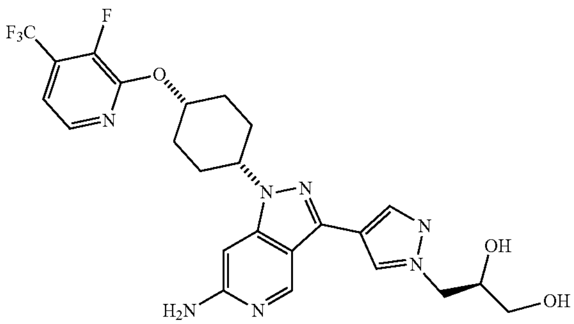 | (R)-3-(4-(6-amino-1-((1s,4S)-4-((3-fluoro-4-(trifluoromethyl)pyridin-2-yl)oxy)cyclohexyl)-1H-pyrazolo[4,3-c]pyridin-3-yl)-1H-pyrazol-1-yl)propane-1,2-diol | Mass spectrum (apci) m/z = 536.2 |

Using the procedures in Example 346, the following compound was also synthesized:

| Ex. | Structure | Name | Data |
|---|---|---|---|
| 506 | 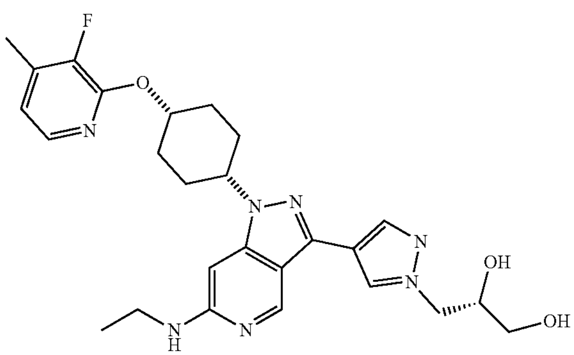 | (S)-3-(4-(6-(ethylamino)-1-((1s,4R)-44(3-fluoro-4-methylpyridin-2-yl)oxy)cyclohexyl)-1H-pyrazolo[4,3-c]pyridin-3-yl)-1H-pyrazol-1-yl)propane-1,2-diol | Mass spectrum (apci) m/z = 510.3 |

Using the procedures in Example 487, the following compound was also synthesized:

| Ex. | Structure | Name | Data |
|---|---|---|---|
| 507 | 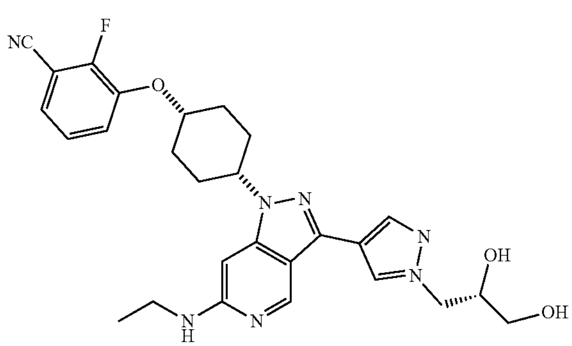 | 3-(((1R,4s)-4-(3-(1-((S)-2,3-dihydroxypropyl)-1H-pyrazol-4-yl)-6-(ethylamino)-1H-pyrazolo[4,3-c]pyridin-1-yl)cyclohexyl)oxy)-2-fluorobenzonitrile | Mass spectrum (apci) m/z = 520.2 |

Using the procedures in Example 434, the following compound was also synthesized:

| Ex. | Structure | Name | Data |
|---|---|---|---|
| 508 | 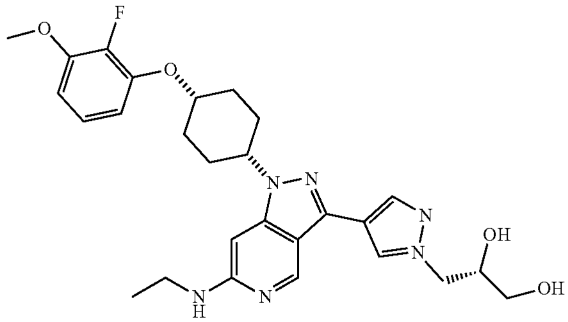 | (S)-3-(4-(6-(ethylamino)-1-((1s,4R)-4-(2-fluoro-3-methoxyphenoxy)cyclohexyl)-1H-pyrazolo[4,3-c]pyridin-3-yl)-1H-pyrazol-1-yl)propane-1,2-diol | Mass spectrum (apci) m/z = 525.3 |

Using procedures described herein, the following compounds were also synthesized:

| Ex. | Structure | Name | Data |
|---|---|---|---|
| 509 | 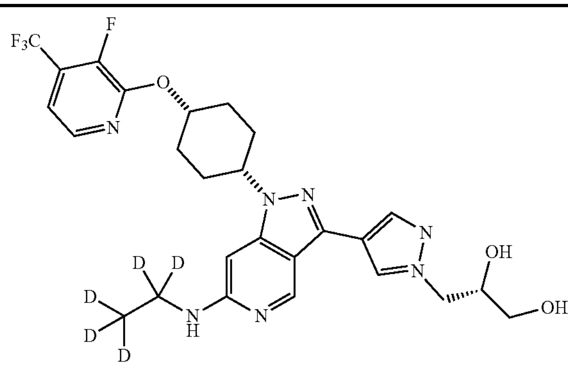 | (S)-3-(4-(6-((ethyl-d5)amino)-1-((1s,4R)-4-((3-fluoro-4-(trifluoromethyl)pyridin-2-yl)oxy)cyclohexyl)-1H-pyrazolo[4,3-c]pyridin-3-yl)-1H-pyrazol-1-yl)propane-1,2-diol | Mass spectrum (apci) m/z = 568.6 |
| 510 | 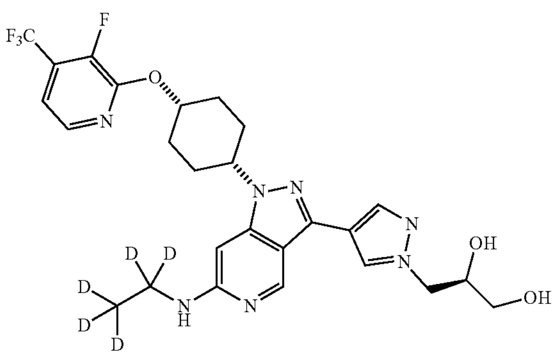 | (R)-3-(4-(6-((ethyl-d5)amino)-1-((1s,4S)-4-((3-fluoro-4-(trifluoromethyl)pyridin-2-yl)oxy)cyclohexyl)-1H-pyrazolo[4,3-c]pyridin-3-yl)-1H-pyrazol-1-yl)propane-1,2-diol | Mass spectrum (apci) m/z = 568.6 |

Abbreviations:

| | |
|---|---|
| ACN | acetonitrile |
| AcOH | acetic acid |
| Boc, BOC | tert-butyl carboxylate group |
| DCE | 1,2-Dichloroethane |
| DCM | Dichloromethane |
| DIAD | Diisopropyl azodicarboxylate |
| DIEA | N,N-Diisopropylethylamine |
| DI water | Deionized water |
| DMA | N,N-Dimethylacetamide |
| DMAP | 4-Dimethylaminopyridine |
| DMF | N,N-Dimethylformamide |

-continued

Abbreviations:

| | |
|---|---|
| DMSO | Dimethylsulfoxide |
| Et$_2$O | Diethyl Ether |
| EtOAc | Ethyl Acetate |
| EtOH | Ethanol |
| eq | equivalent |
| GF/F paper | GF/F glass microfiber filter paper |
| h | hour, hours |
| HATU | 1-[Bis(dimethylamino)methylene]-1H-1,2,3-triazolo[4,5-b]pyridinium 3-oxide |

-continued

| | Abbreviations: |
|---|---|
| | hexafluorophosphate or 2-(7-Aza-1H-benzotriazole-1-yl)-1,1,3,3-tetramethyluronium hexafluorophosphate |
| HOAc | Acetic Acid |
| IPA | Isopropyl alcohol |
| i-PrMgCl | Isopropyl magnesium chloride |
| LiHMDS | Lithium Hexamethyldisilazide |
| mCPBA | meta-chloroperoxybenzoic acid |
| min | minute, minutes |
| MTBE | Methyl tert-Butyl Ether |
| NB | SN-Bromosuccinimide |
| 10% Pd/C | Palladium 10 wt. % (dry basis), active carbon, wet, Degussa |
| Pd(PPh$_3$)$_4$ | Tetrakis(triphenylphosphine)palladium (0) |
| Pd$_2$(dba)$_3$ | tris(dibenzylideneacetone)dipalladium (0) |
| PdCl$_2$(dppf)•CH$_2$Cl$_2$ | 1,1'-Bis(diphenylphosphino)ferrocene-palladium(II)dichloride dichloromethane complex |
| Pd$_2$(dba)$_3$ | tris(dibenzylideneacetone)dipalladium (0) |
| PPh$_3$ | Triphenylphosphine |
| rt, RT | Room temperature |
| SEM | 2-(trimethylsilyl)ethoxymethyl |
| TBAF | Tetra-n-butylammonium fluoride |
| TFA | Trifluoroacetic acid |
| THF | tetrahydrofuran |
| TsCl | 4-Toluenesulfonyl chloride |
| X-PHOS | dicyclohexyl(2',4',6'-triisopropyl-[1,1'-biphenyl]-2-yl)phosphine |

What is claimed is:
1. A compound of the Formula I:

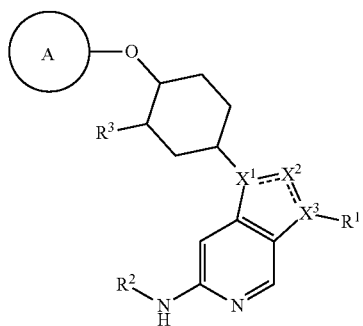

and stereoisomers, tautomers and pharmaceutically acceptable salts thereof, wherein:
one of the dashed lines in Formula I is a single bond and the other dashed line is a double bond;
$X^1$ is N, $X^2$ is N, and $X^3$ is C, or
$X^1$ is C, $X^2$ is N and $X^3$ is N, or
$X^1$ is N, $X^2$ is CH and $X^3$ is C;
Ring A is hetAr$^1$, hetAr$^2$ or Ar$^1$;
hetAr$^1$ is a 5-6 membered heteroaryl ring having 1-3 ring nitrogen atoms or a 9-10 membered bicyclic heteroaryl having 1-2 ring nitrogen atoms, wherein one or more ring carbon atoms is optionally substituted with a substituent independently selected from (a) C1-C6 alkyl, (b) C1-C6 fluoroalkyl, (c) C1-C6 alkoxy, (d) C1-C6 fluoroalkoxy, (e) C1-C6 hydroxyalkyl, (f) halogen, (g) cyano, (h) hydroxyl, (i) R'R"N(CH$_2$)$_n$— wherein n is 0 or 1 and R' and R" are independently H or C1-C6 alkyl, (j) (C1-C6 alkoxy)C(=O)—, (k) R'R"NC(=O)— wherein R' and R" are independently H or C1-C6 alkyl, (l) hetCyc$^a$CH$_2$—, (m) C3-C6 cycloalkyl, (n) acetylenyl, and (o) benzyloxy;
hetAr$^2$ is a 6-membered heteroaryl ring having 1-2 ring nitrogen atoms, wherein one ring carbon atom of said heteroaryl ring is substituted with oxo and one of said ring nitrogen atoms is substituted with (a) C1-C6 alkyl, (b) C1-C6 fluoroalkyl, (c) (C1-C6 alkoxy)C1-C6 alkyl-, (d) (R'R"N)C1-C6 alkyl- wherein R' and R" are independently H or C1-C6 alkyl, or (e) Ar$^a$CH$_2$— wherein Ar$^a$ is phenyl optionally substituted with C1-C6 alkoxy, wherein one or more of the remaining ring carbon atoms is optionally substituted with one or two substituents independently selected from C1-C6 alkyl and C1-C6 fluoroalkyl;
Ar$^1$ is phenyl optionally substituted with one or more substituents independently selected from (a) halogen, (b) cyano, (c) C1-C6 alkyl, (d) C1-C6 fluoroalkyl, (e) C1-C6 alkoxy, (f) C3-C6 cycloalkyl, (g) R'R"N(CH$_2$)$_n$— wherein n is 0 or 1 and R' and R" are independently H or C1-C6 alkyl, (h) (C1-C6 alkyl) SO$_2$—, (i) (C1-C6 alkoxy)C(=O)—, (j) HOC(=O)—, and (k) R'R"NC(=O)— wherein R' and R" are independently H, C1-C6 alkyl or (C1-C6 alkoxy)C1-C6 alkyl-, or Ar$^1$ is phenyl fused to a 6-membered heteroaryl ring having a ring nitrogen atom, wherein said ring nitrogen atom is substituted with C1-C6 alkyl and one ring carbon atom of said heteroaryl ring is substituted with oxo, or Ar$^1$ is phenyl fused to a 5-6 membered heterocyclic ring having a ring nitrogen and one ring carbon atom of said heteroaryl ring is substituted with oxo;
when $X^3$ is N, then $R^1$ is Ar$^2$, hetAr$^3$, hetAr$^4$, hetCyc$^1$, Cyc$^1$, or C1-C6 alkyl, and
when $X^3$ is C, then $R^1$ is Ar$^2$, hetAr$^3$, hetAr$^4$, hetCyc$^1$, Cyc$^1$, C1-C6 alkyl or Br;
Ar$^2$ is phenyl optionally substituted with one or more substituents independently selected from (a) halogen, (b) CN, (c) C1-C6 hydroxyalkyl, (d) C2-C6 dihydroxyalkyl, (e) C1-C6 alkoxy, (f) hetCyc$^a$(CH$_2$)$_n$— wherein n is 0, 1 or 2, (g) hetCyc$^a$-C(=O)—, (h) hetCyc$^a$-O—, (i) C3-C6 cycloalkyl optionally substituted with cyano or a 5-6 membered heterocyclic ring having 1-2 ring nitrogen atoms wherein said heterocyclic ring is optionally substituted with C1-C6 alkyl, (j) R'R"NC(=O)— wherein R' and R" are independently H, C1-C6 alkyl, C1-C6 hydroxyalkyl, or C3-C6 cycloalkyl, (k) (C1-C6 alkyl)C(=O)NHCH$_2$—, (l) (C1-C6 alkyl)SO$_2$—, and (m) R'R"NSO$_2$— wherein R' and R" are independently H or C1-C6 alkyl,
or Ar$^2$ is phenyl fused to a 5-6 membered saturated heterocyclic ring having 1-2 ring heteroatoms independently selected from N and S wherein said S is optionally oxidized to SO$_2$, wherein said heterocyclic ring is optionally substituted with oxo and is further optionally substituted with C1-C6 alkyl;
each hetCyc$^a$ is independently a 5-6 membered heterocyclic ring having 1-2 ring heteroatoms independently selected from N and O, wherein said ring is optionally substituted with one or more substituents independently selected from halogen, cyano, hydroxyl, C1-C6 alkyl, C1-C6 hydroxyalkyl, C1-C6 alkoxy, (C1-C6 alkoxy)C1-C6 alkyl-, (C1-C6 alkoxy)C1-C6 alkoxy-, and R'R"N— wherein R' and R" are independently H or C1-C6 alkyl;
hetAr$^3$ is a 5-6 membered heteroaryl ring having 1-2 ring heteroatoms independently selected from N and O, wherein said heteroaryl ring is optionally substituted with one or more substituents independently selected from (a) halogen, (b) cyano, (c) C1-C6 alkyl, (d) C1-C6 fluoroalkyl, (e) C1-C6 hydroxyalkyl wherein said alkyl portion is optionally substituted with R'R"N— wherein R' and R" are independently H or C1-C6 alkyl, (f) C2-C6 dihydroxyalkyl, (g) C1-C6 cyanoalkyl, (h) C1-C6 alkoxy, (i) R'R"N— wherein R' and R" are independently H, C1-C6 alkyl, or (C1-C6 alkoxy)C1-C6 alkyl-, (k) (C1-C6 alkylSO$_2$)C1-C6 alkyl-, (l) C3-C6 cycloalkyl optionally substituted with hydroxyl, (m) R'R"NC(=O)C1-C6 alkyl- wherein R' and R" are independently H or C1-C6 alkyl, and (n) hetCyc$^b$(CH$_2$)$_n$— wherein n is 0, 1 or 2;

hetCyc$^b$ is a 4-6 membered heterocyclic ring having 1-2 ring heteroatoms independently selected from N, O and S, wherein said S is optionally oxidized to SO$_2$, and wherein said ring is optionally substituted with one or more substituents independently selected from halogen, C1-C6 alkyl, and (C1-C6 alkoxy)C1-C6 alkyl-;

hetAr$^4$ is a 6-membered heteroaryl ring having 1-2 ring nitrogen atoms, wherein a ring carbon atom of said heteroaryl ring is substituted with oxo and wherein one of said ring nitrogen atoms is substituted with C1-C6 alkyl or C1-C6 fluoroalkyl;

hetCyc$^1$ is a 5-6 membered saturated or partially unsaturated monocyclic heterocyclic ring having 1-2 ring heteroatoms independently selected from N and O or a 8-10 membered fused saturated heterocyclic ring having 1-2 ring heteroatoms independently selected from N and O, wherein said heterocyclic rings are optionally substituted with one or more substituents independently selected from (a) halogen, C1-C6 alkyl, (b) C1-C6 alkoxy, (c) (C1-C6 alkoxy)C1-C6 alkyl-, (d) (C1-C6 alkyl)C(=O)—, (e) hydroxyl, and (f) R'R"N— wherein R' and R" are independently H or C1-C6 alkyl;

Cyc$^1$ is 3-6 membered cycloalkyl ring optionally substituted with R'R"N— wherein R' and R" are independently H or C1-C6 alkyl;

R$^2$ is H, C1-C6 alkyl, C1-C6 fluoroalkyl, C3-C6 cycloalkyl, (C3-C6 cycloalkyl)C1-C6 alkyl-, phenyl optionally substituted with one or more substituents independently selected from cyano and halogen, or C1-C6 alkyl wherein 2-5 hydrogens are replaced by deuterium; and R$^3$ is hydrogen or hydroxyl.

2. A compound according to claim 1 or a pharmaceutically acceptable salt thereof, wherein X$^1$ is N, X$^2$ is N, and X$^3$ is C.

3. A compound according to claim 2 or a pharmaceutically acceptable salt thereof, wherein Ring A is Ar$^1$.

4. A compound according to claim 3 or a pharmaceutically acceptable salt thereof, wherein R$^1$ is Ar$^2$.

5. A compound according to claim 3 or a pharmaceutically acceptable salt thereof, wherein R$^1$ is hetAr$^3$.

6. A compound according to claim 2 or a pharmaceutically acceptable salt thereof, wherein Ring A is hetAr$^1$.

7. A compound according to claim 6 or a pharmaceutically acceptable salt thereof, wherein R$^1$ is Ar$^2$.

8. A compound according to claim 6 or a pharmaceutically acceptable salt thereof, wherein R$^1$ is hetAr$^3$.

9. A compound according to claim 6 or a pharmaceutically acceptable salt thereof, wherein R$^1$ is hetAr$^4$.

10. A compound according to claim 6 or a pharmaceutically acceptable salt thereof, wherein R$^1$ is hetCyc$^1$.

11. A compound according to claim 2 or a pharmaceutically acceptable salt thereof, wherein Ring A is hetAr$^2$.

12. A compound according to claim 11 or a pharmaceutically acceptable salt thereof, wherein R$^2$ is hetAr$^3$.

13. A compound according to claim 1 or a pharmaceutically acceptable salt thereof, wherein X$^1$ is C, X$^2$ is N, and X$^3$ is N.

14. A compound according to claim 1 or a pharmaceutically acceptable salt thereof, wherein X$^1$ is N, X$^2$ is CH, and X$^3$ is C.

15. A compound according to claim 1 or a pharmaceutically acceptable salt thereof, wherein R$^2$ is C1-C6 alkyl.

16. A compound according to claim 1 or a pharmaceutically acceptable salt thereof, wherein R$^2$ is C1-C6 fluoroalkyl.

17. A compound according to claim 1 or a pharmaceutically acceptable salt thereof, wherein R$^3$ is hydrogen.

18. A compound according to claim 1, selected from

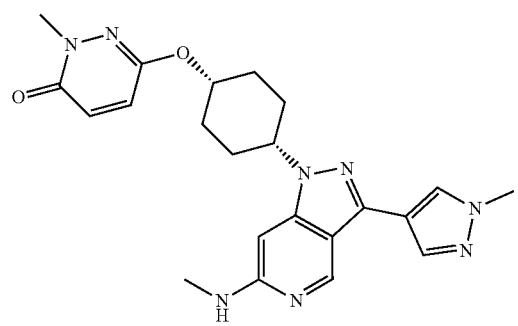

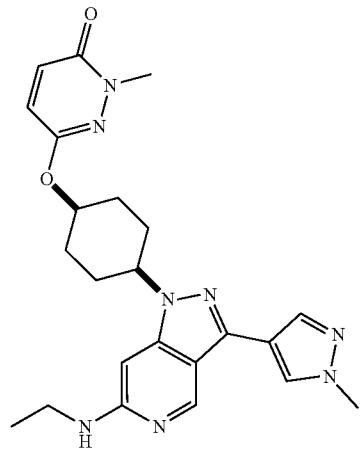

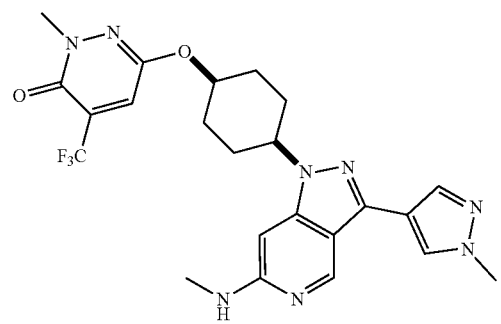

685
-continued
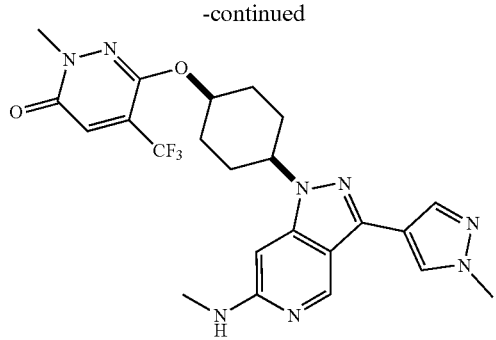
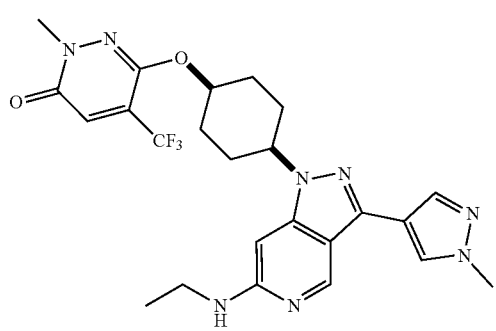
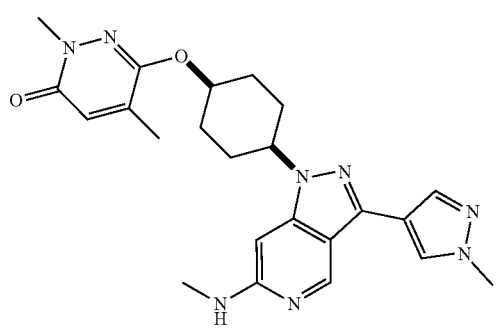
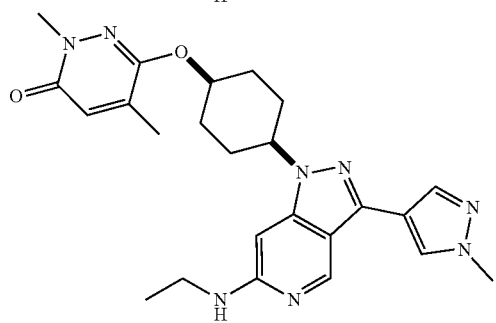
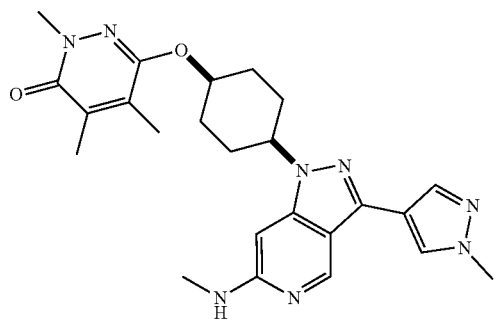
686
-continued
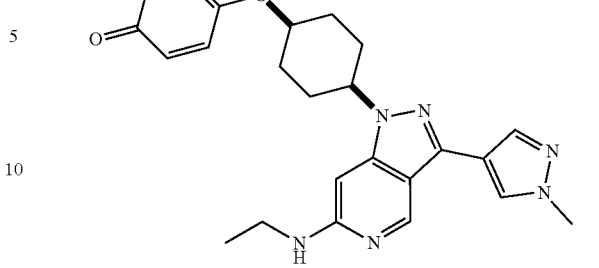
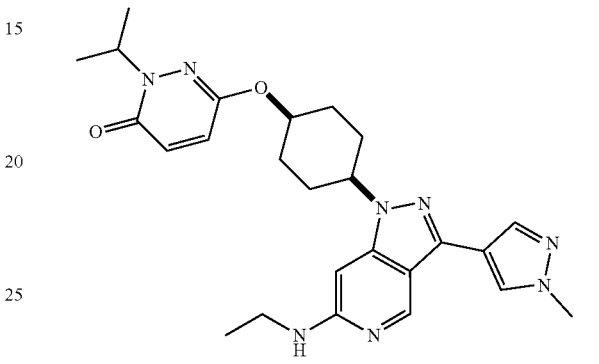
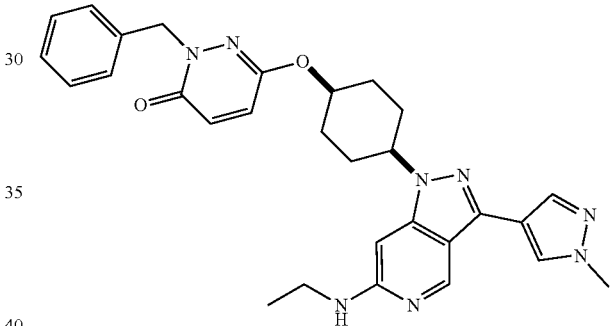
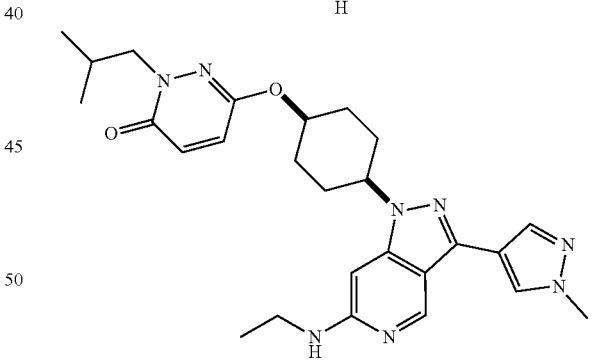
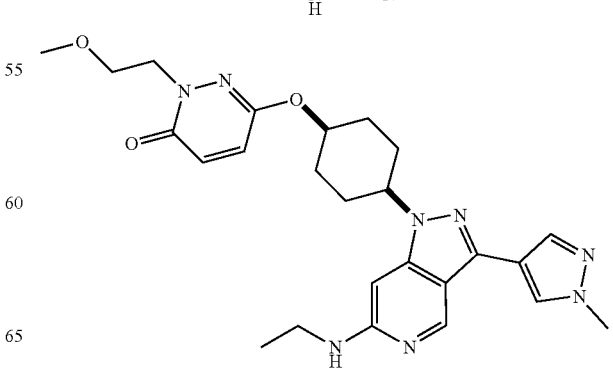

687
-continued
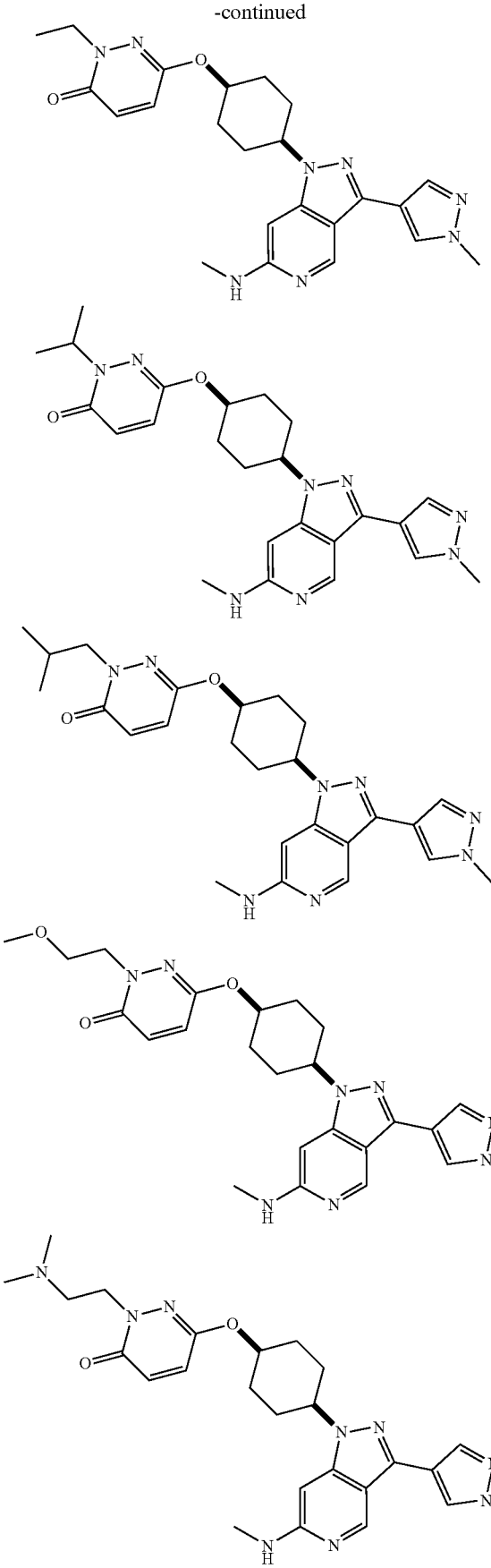
688
-continued
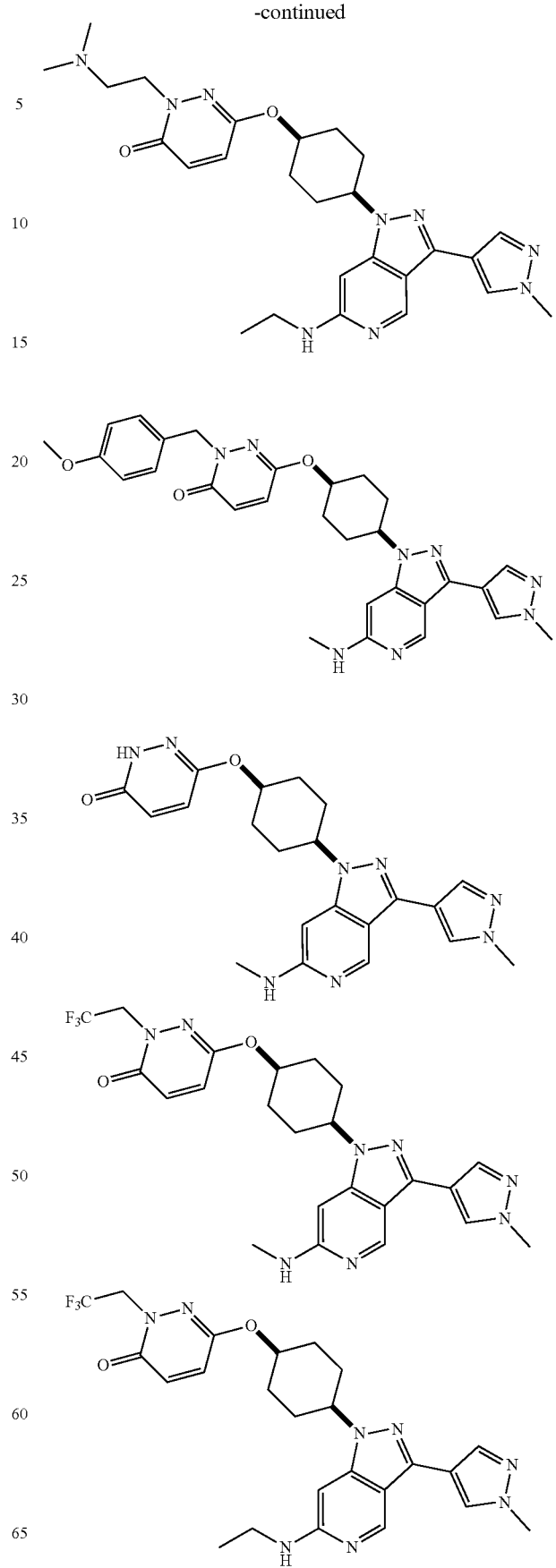

-continued
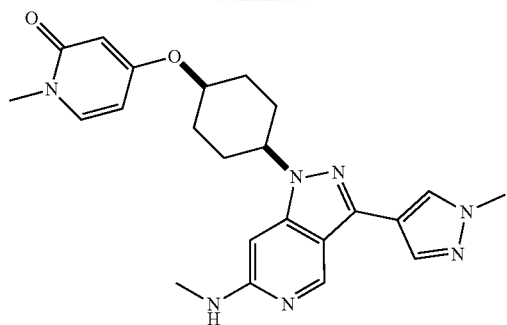
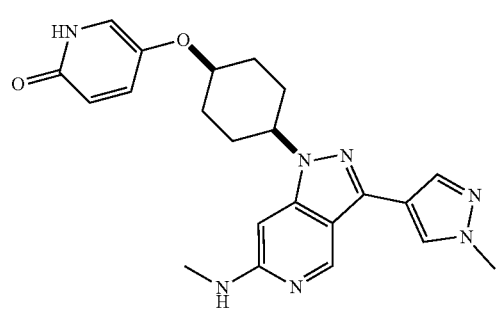
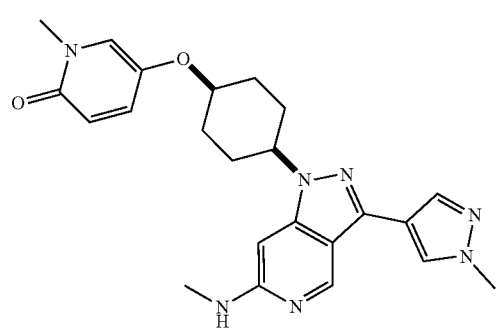
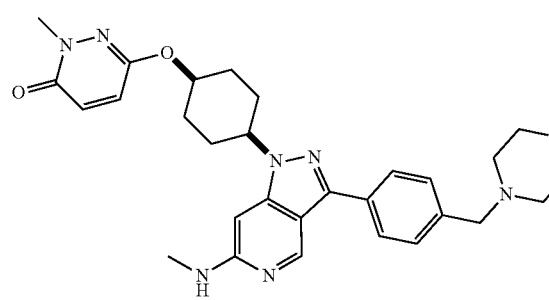
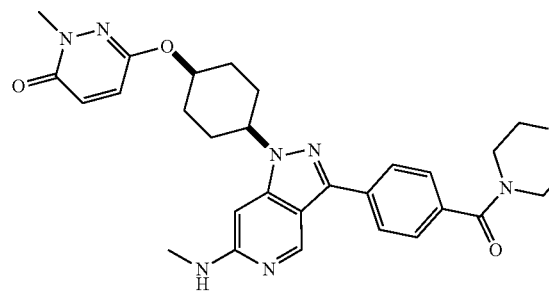
-continued
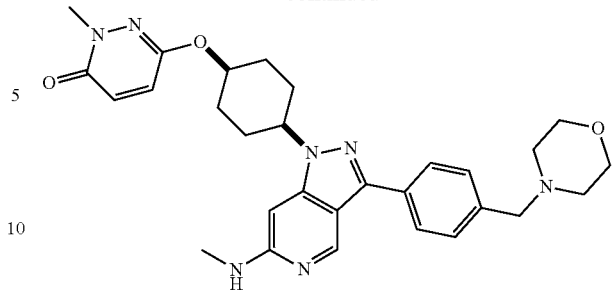
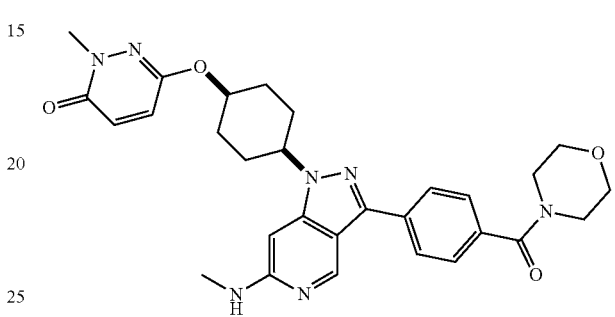
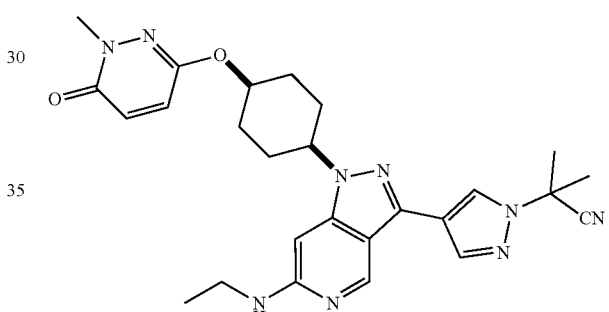
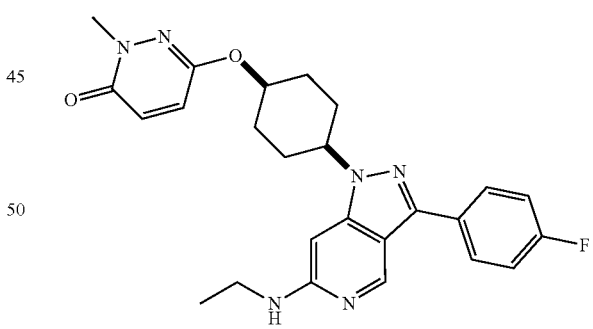
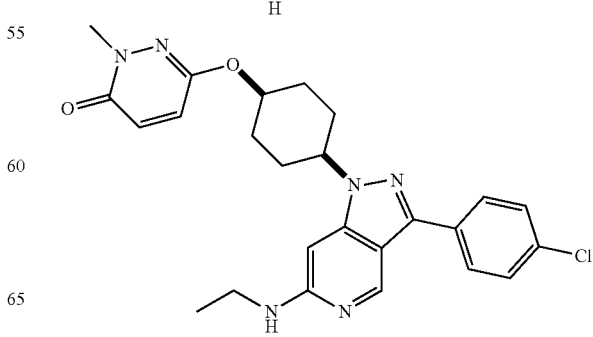

691
-continued
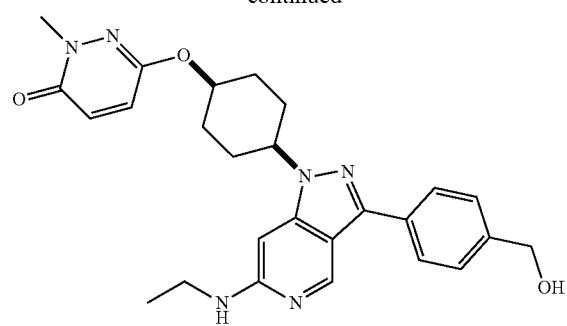
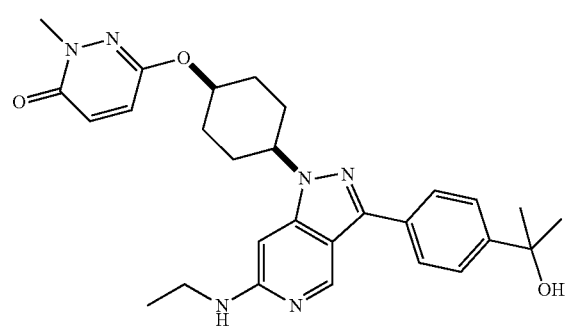
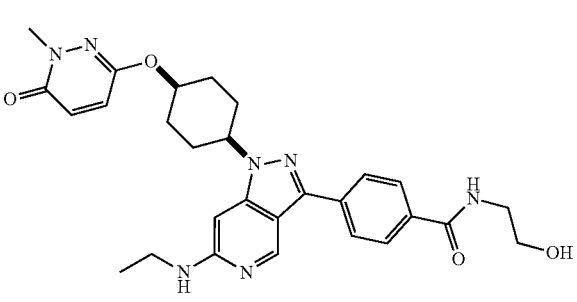
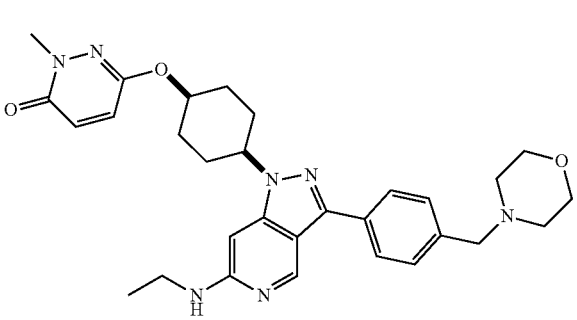
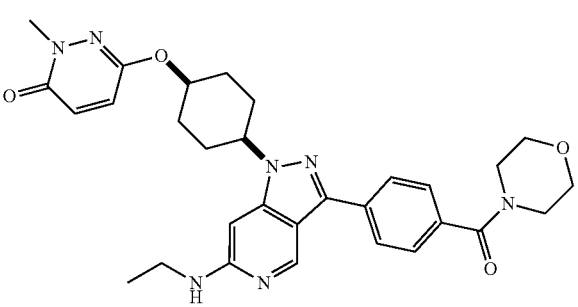
692
-continued
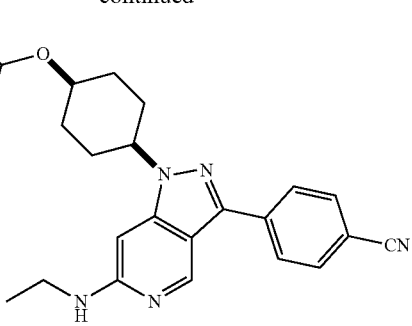
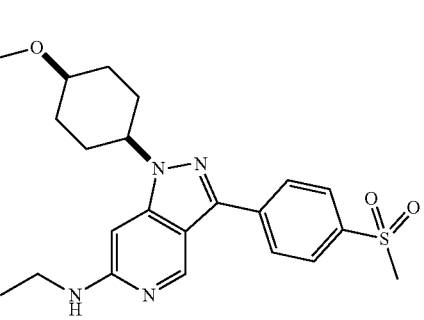
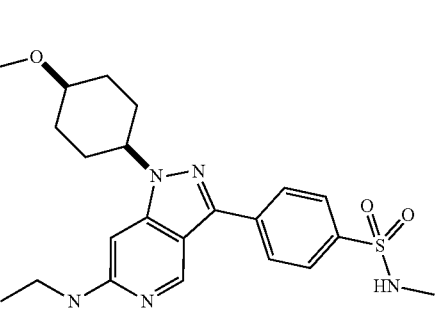
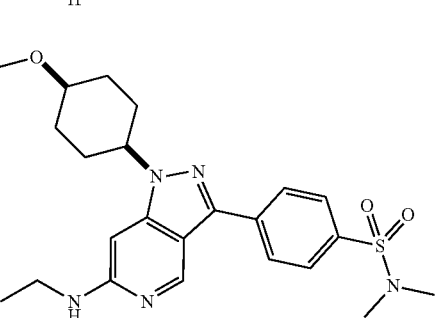
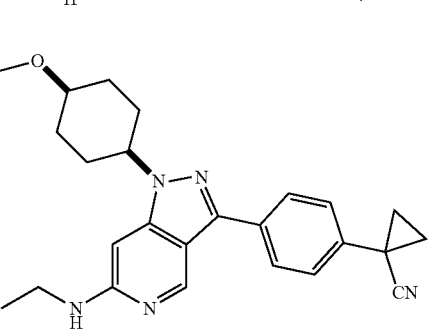

693
-continued
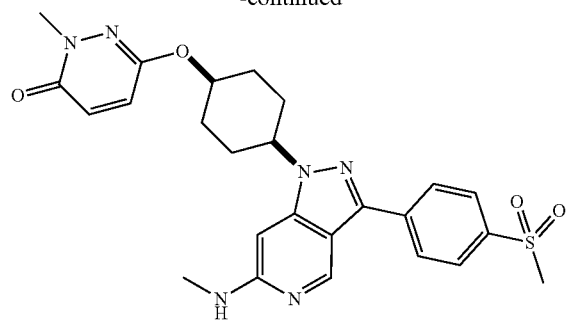
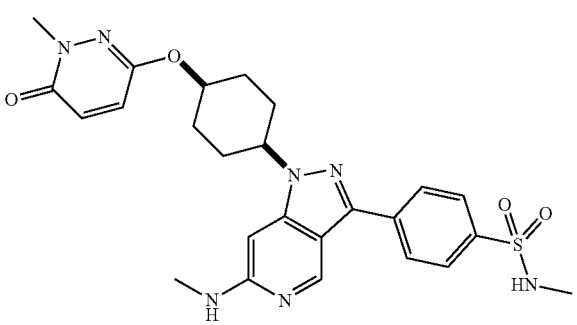
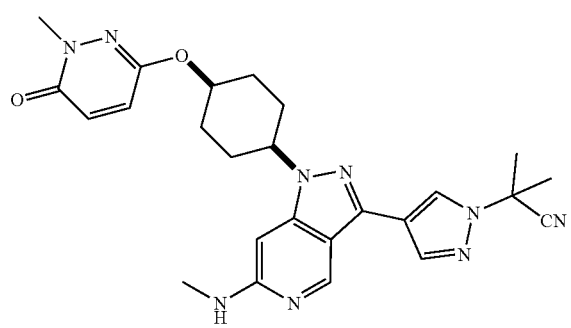
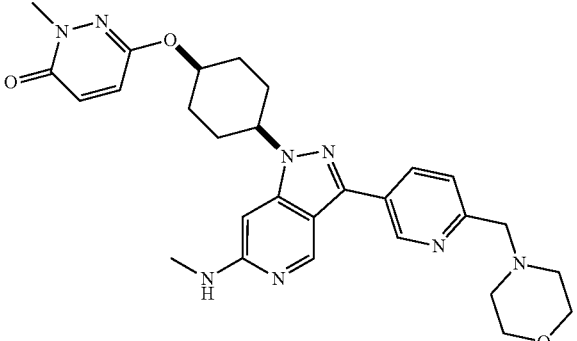
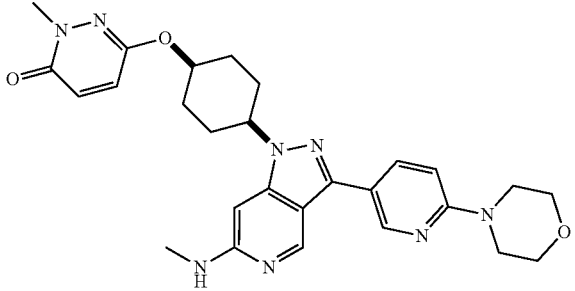
694
-continued
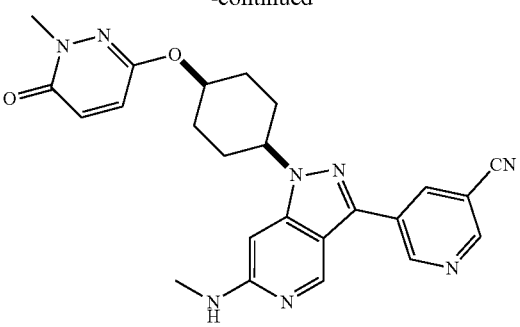
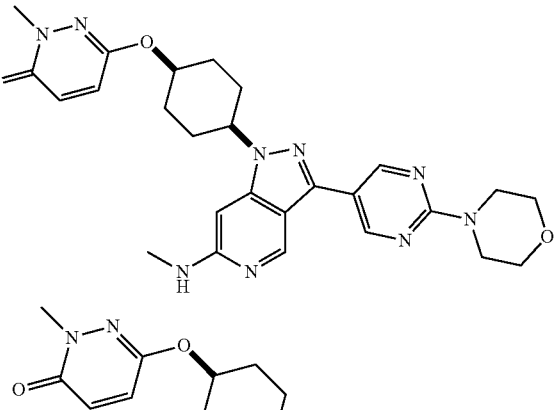
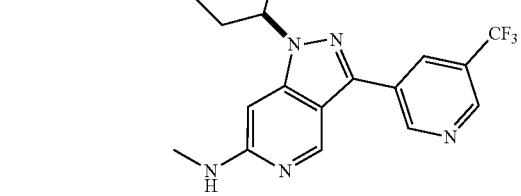
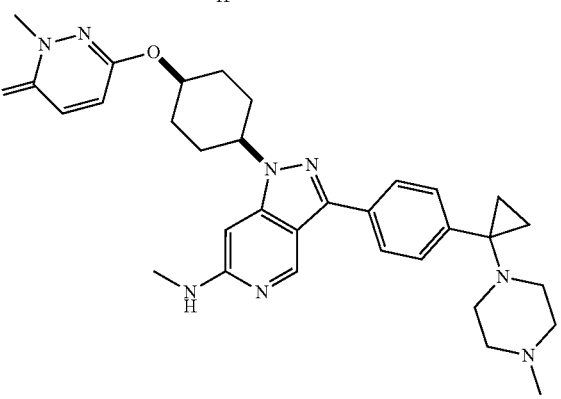
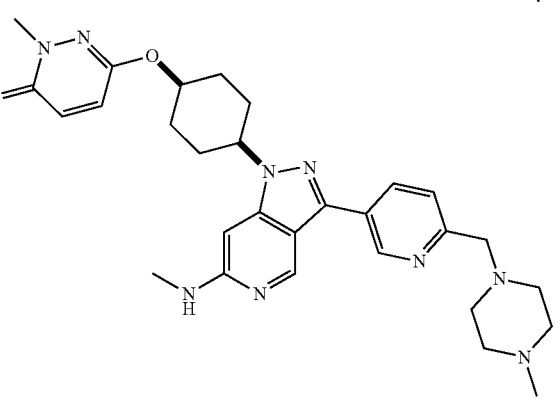

695
-continued
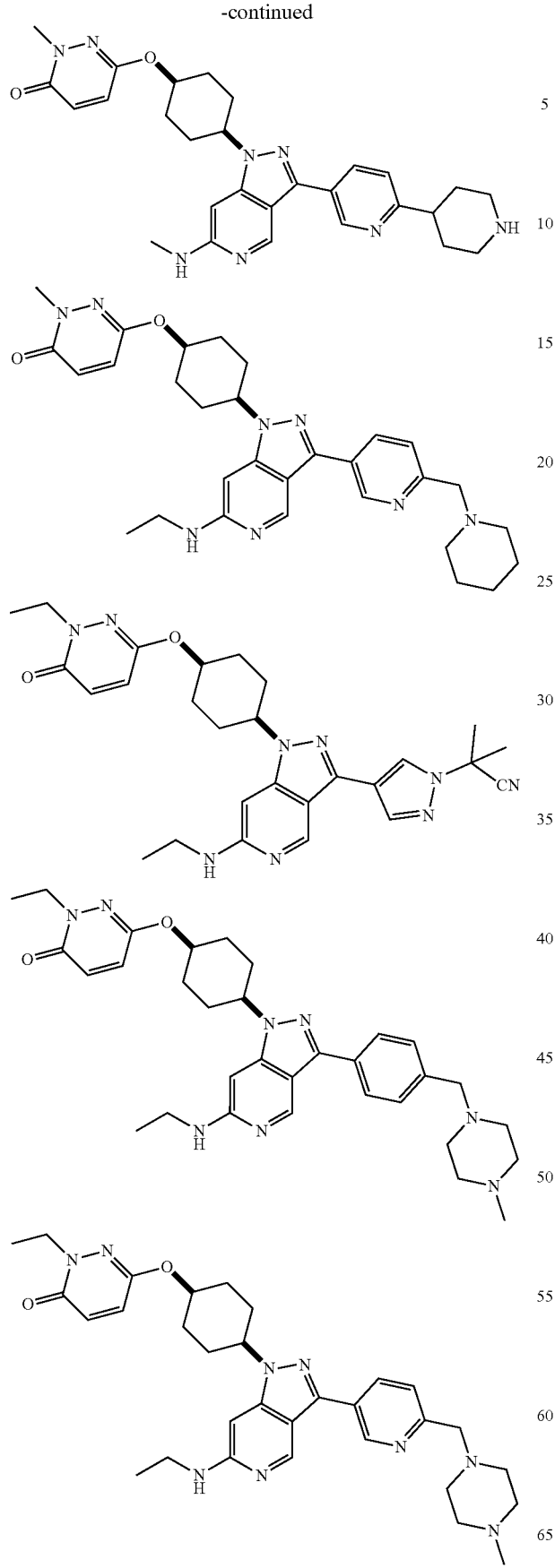
696
-continued
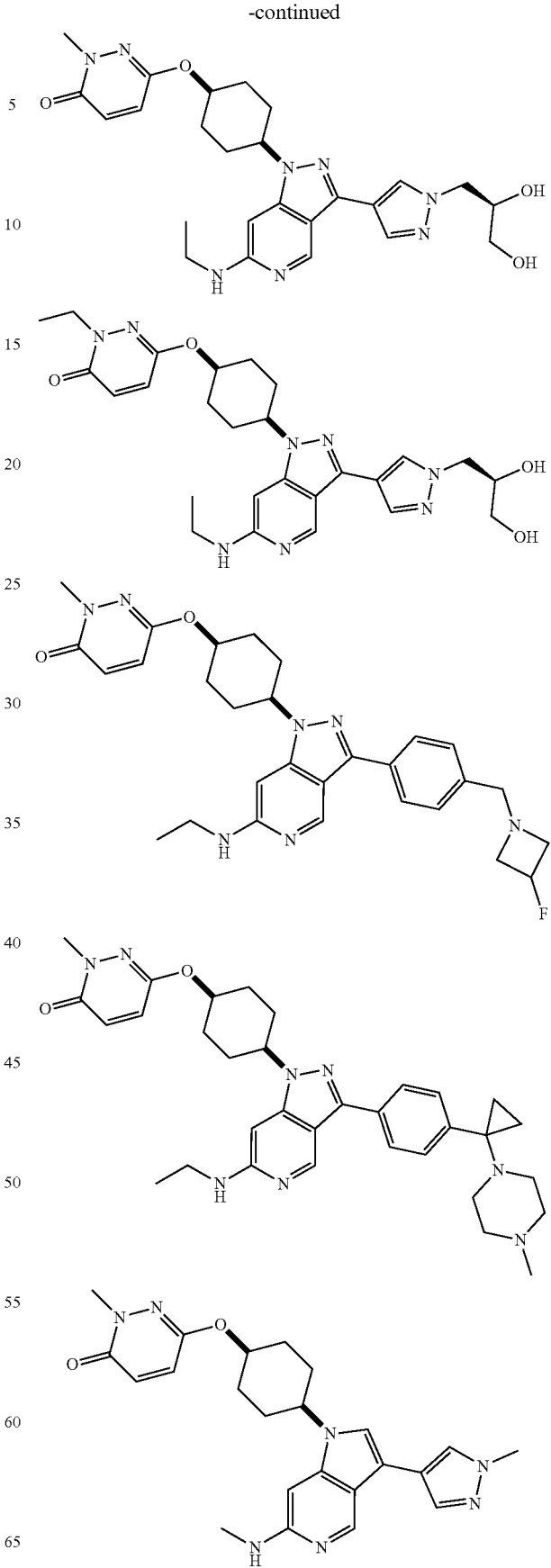

697
-continued
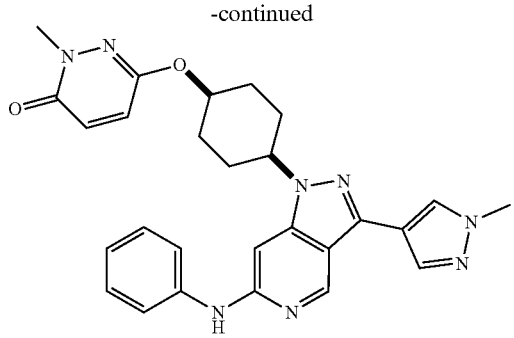
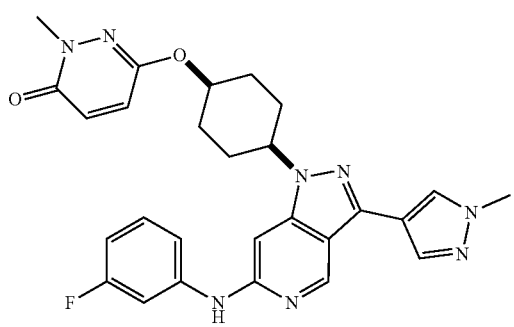
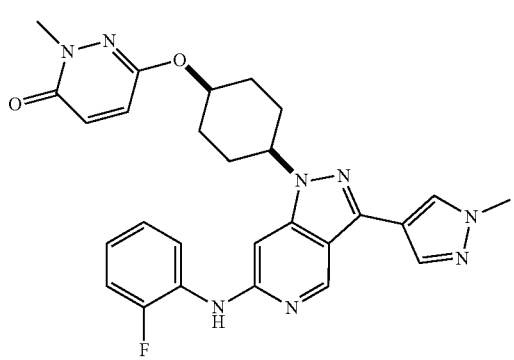
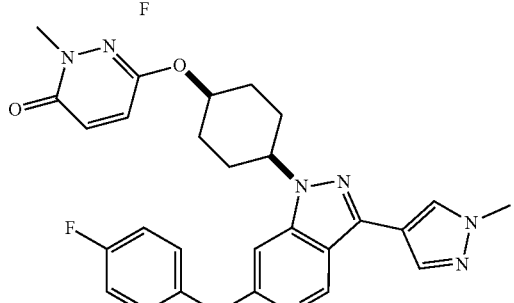
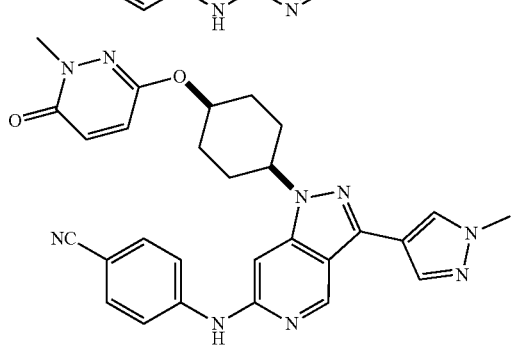
698
-continued
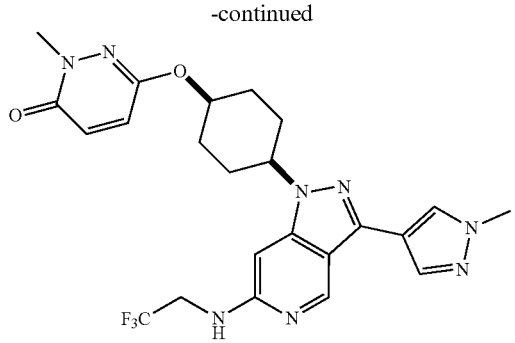
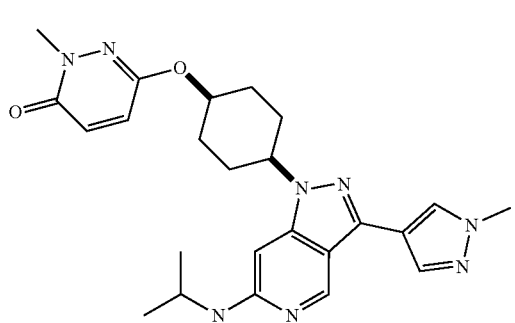
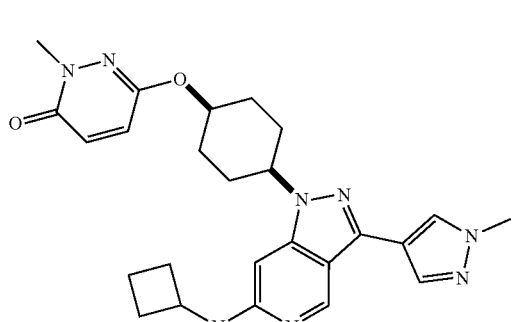
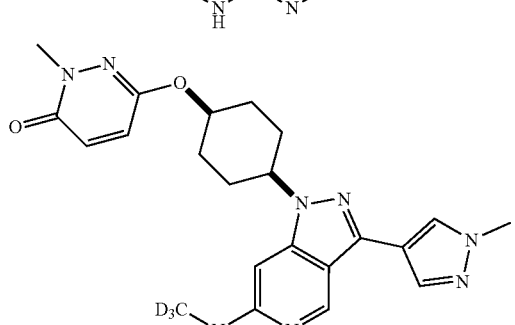
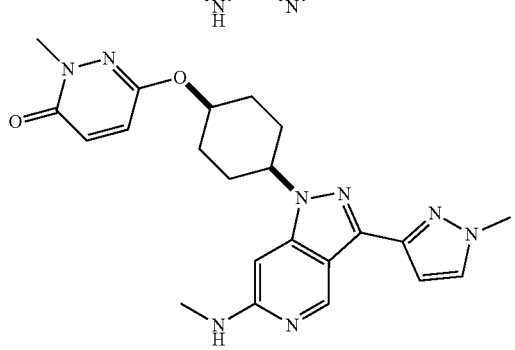

699
-continued
700
-continued
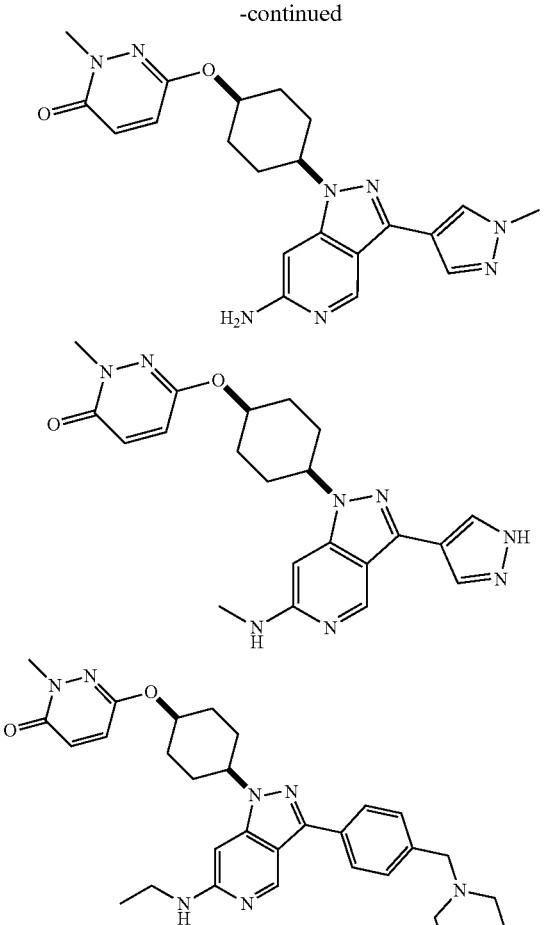
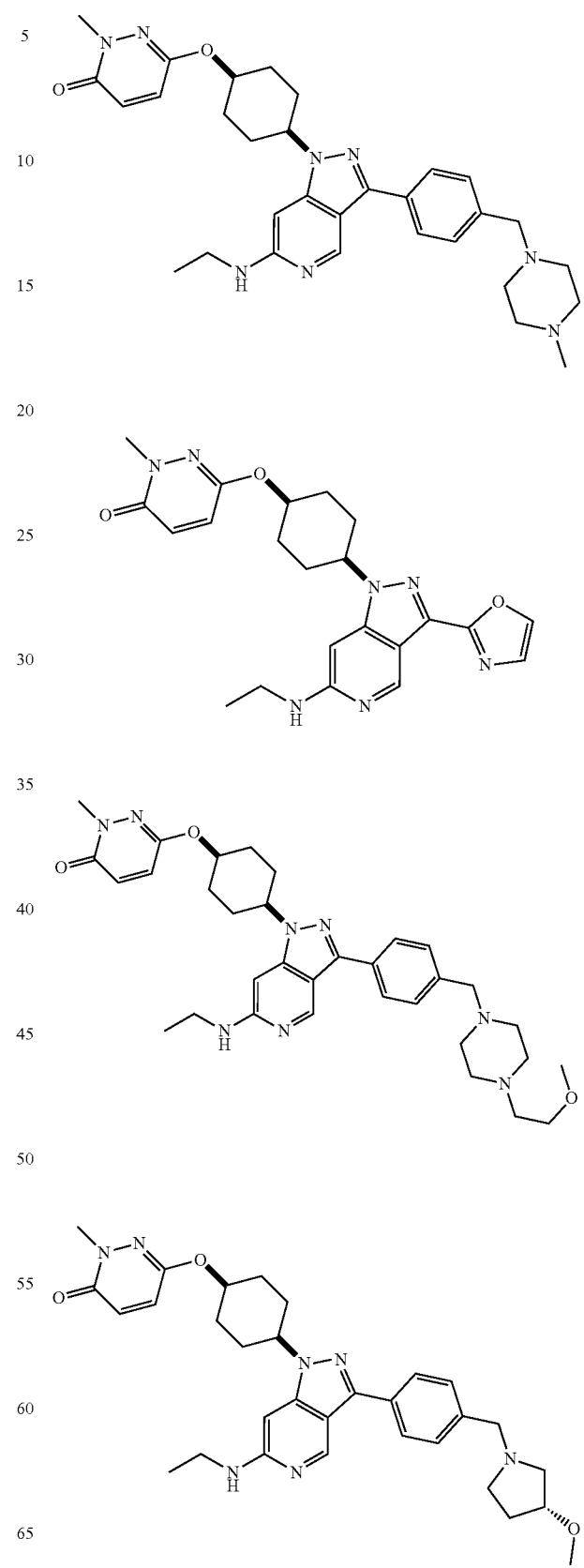

701
-continued
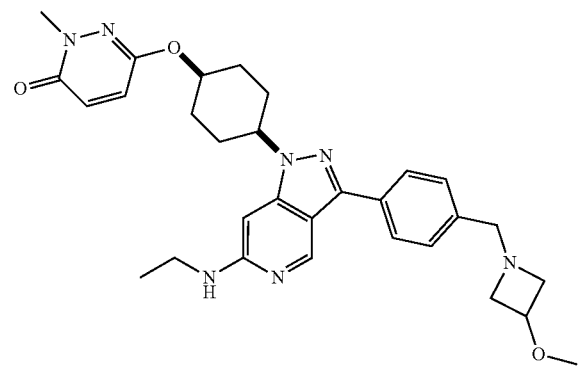
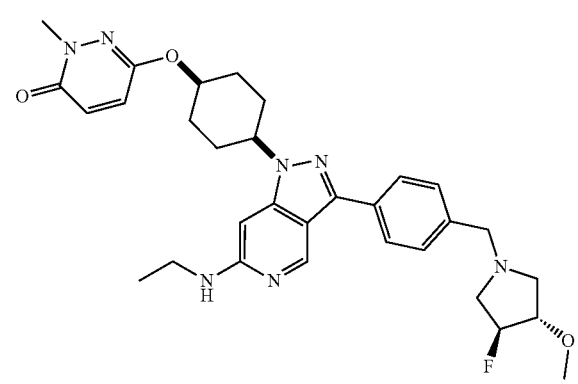
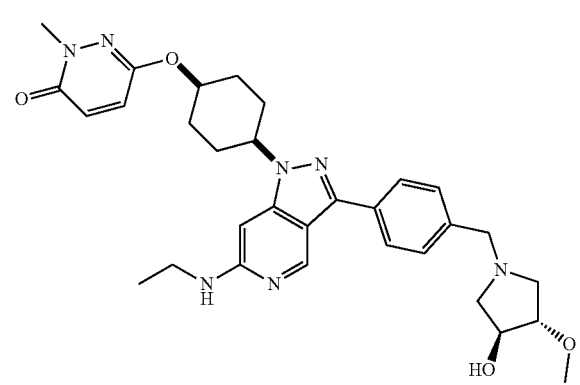
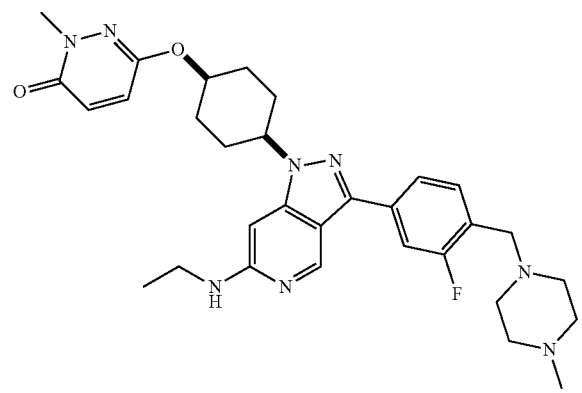
702
-continued
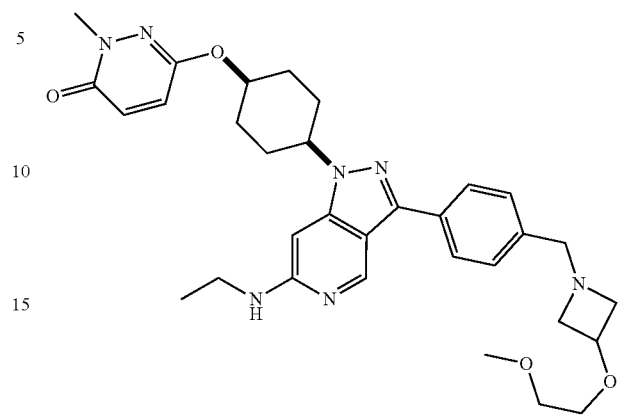
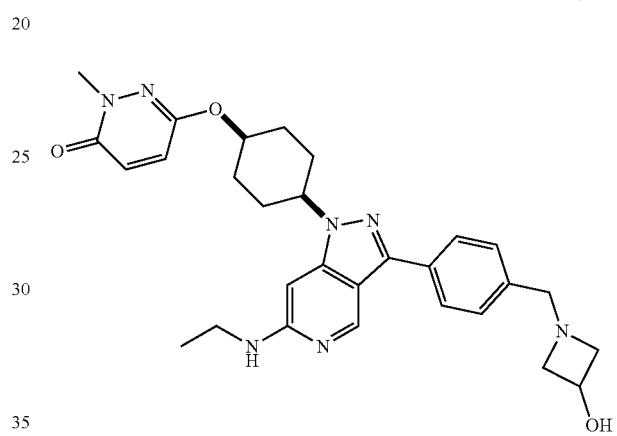
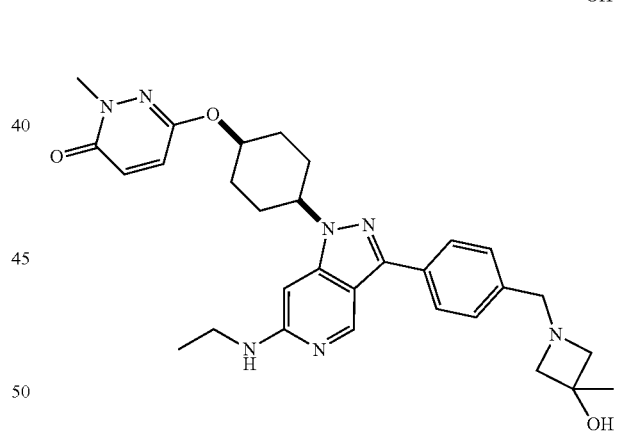
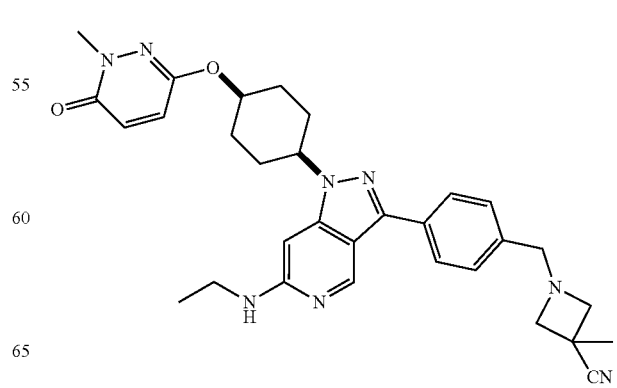

703
-continued
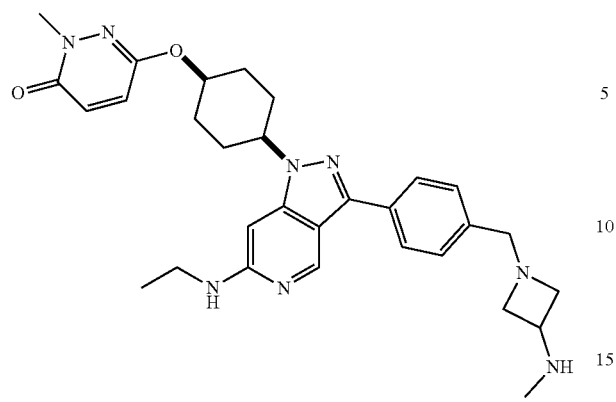
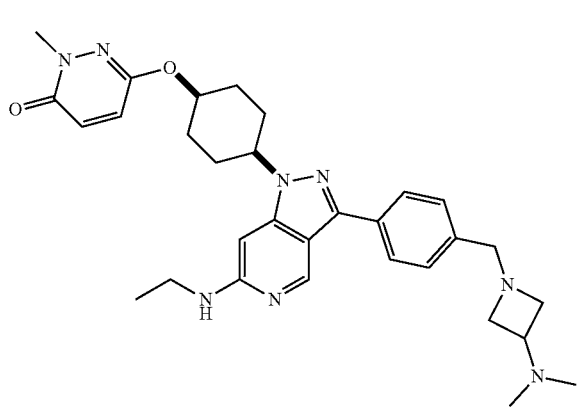
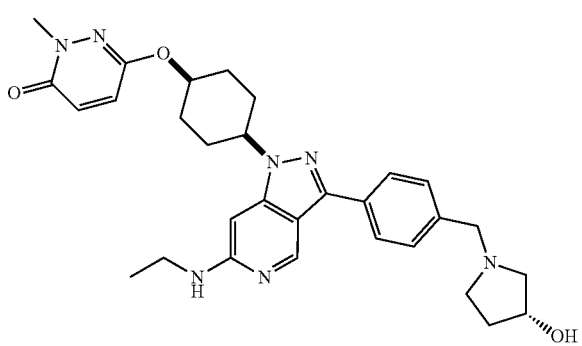
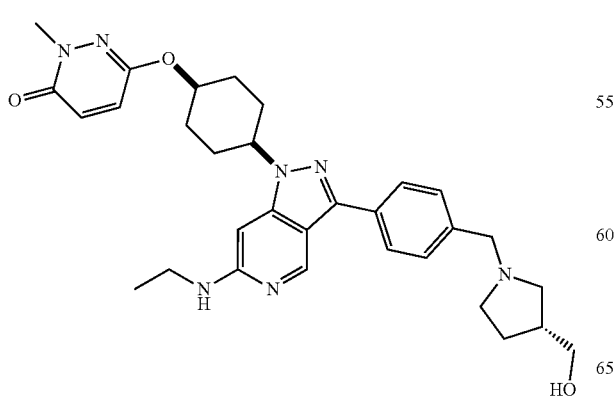
704
-continued
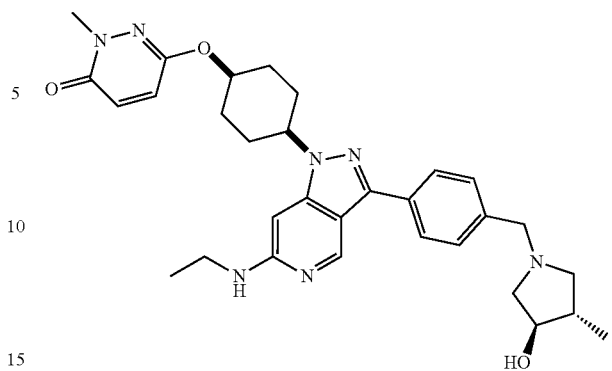
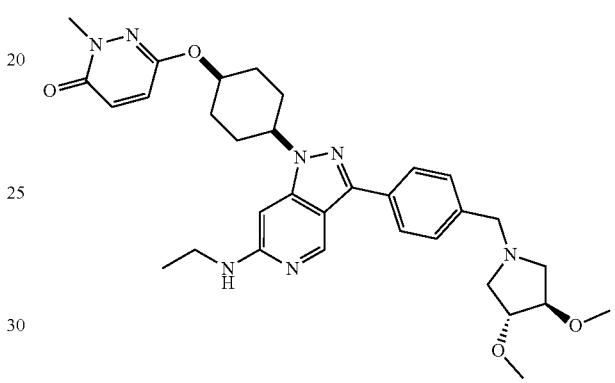
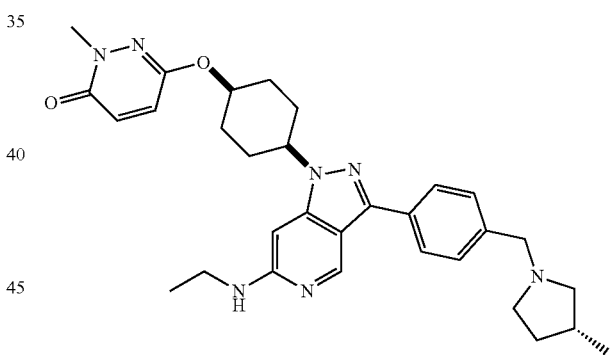
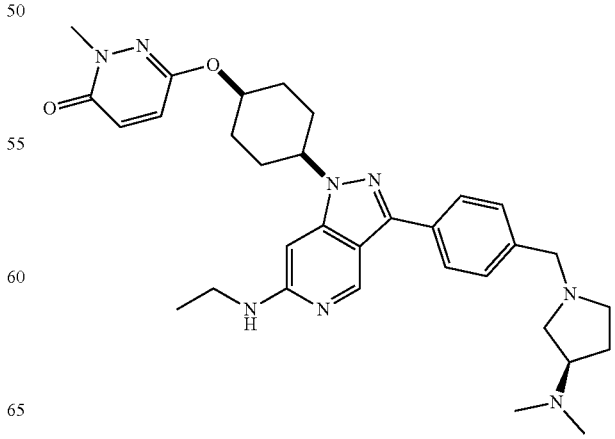

705
-continued
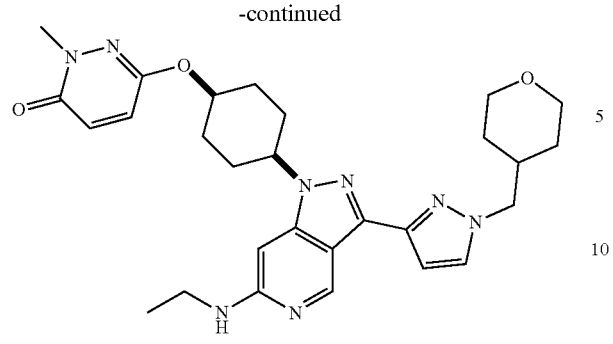
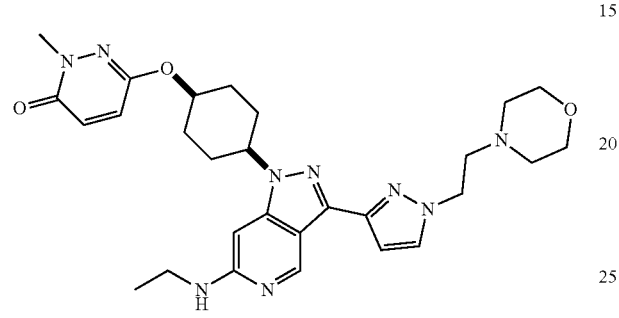
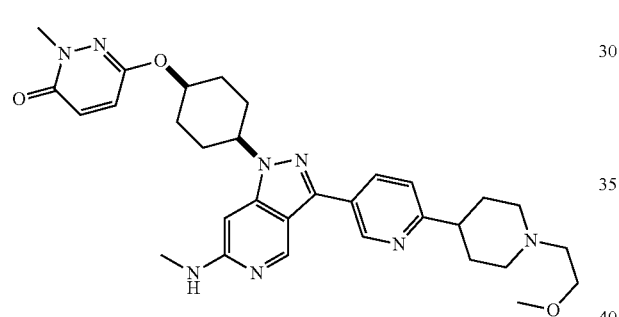
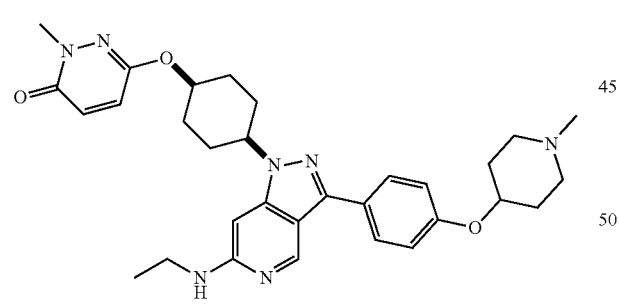
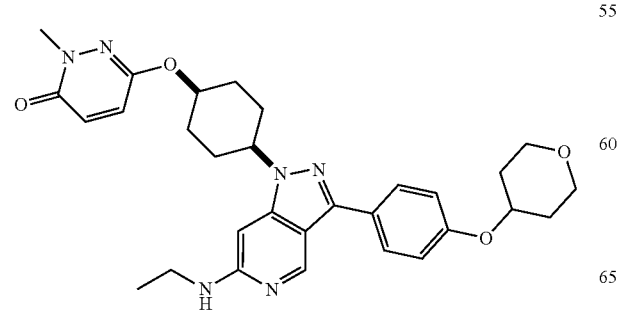
706
-continued
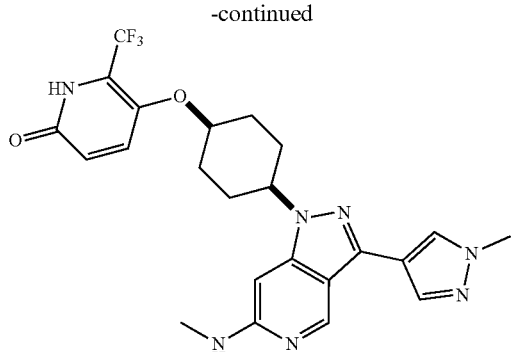
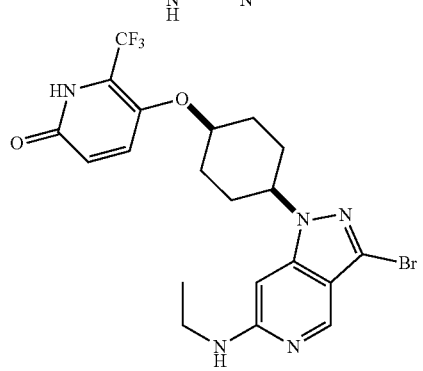
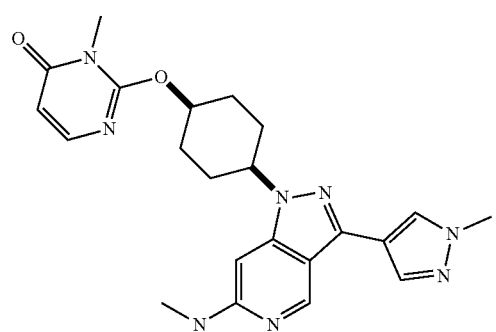
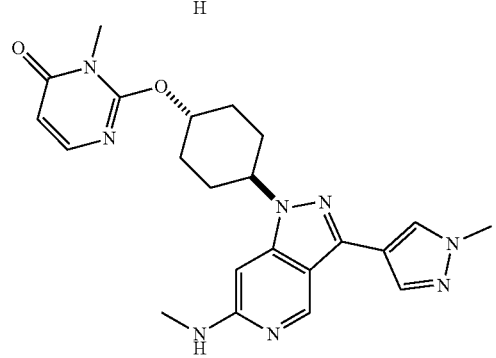
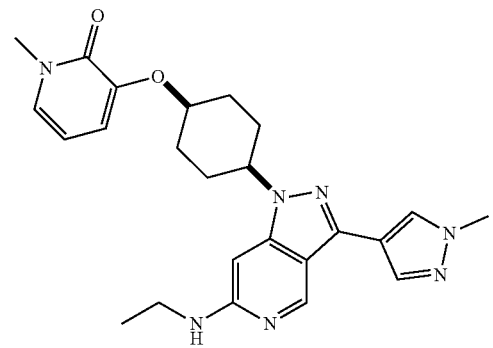

707
-continued
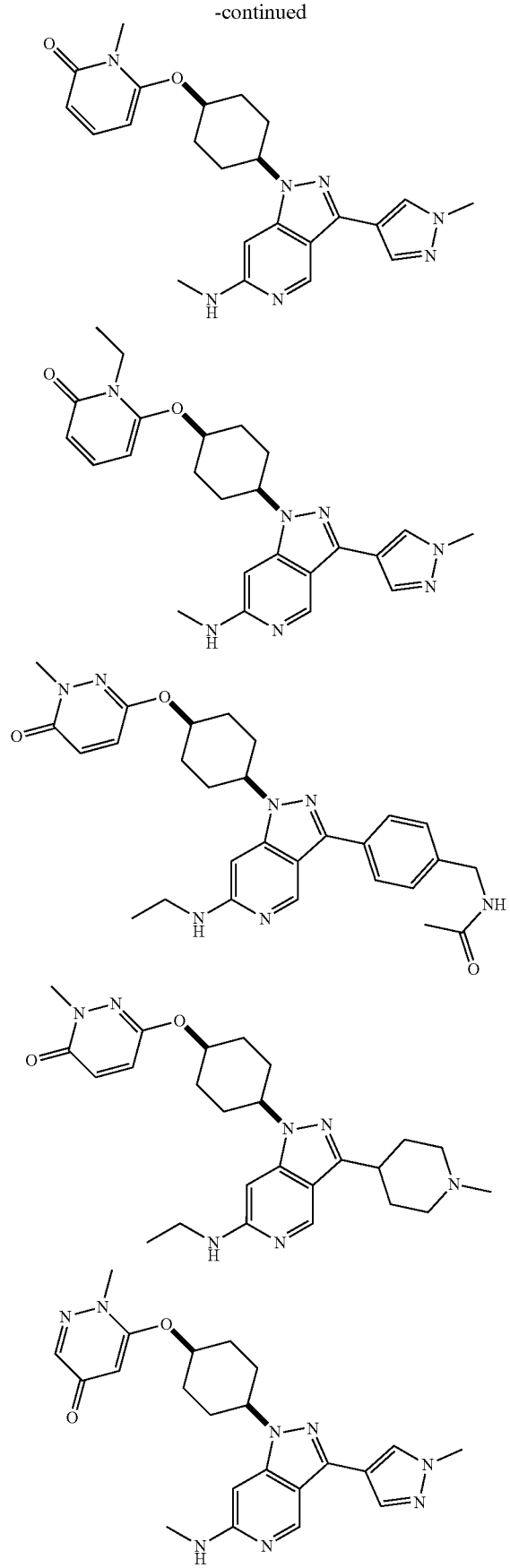
708
-continued
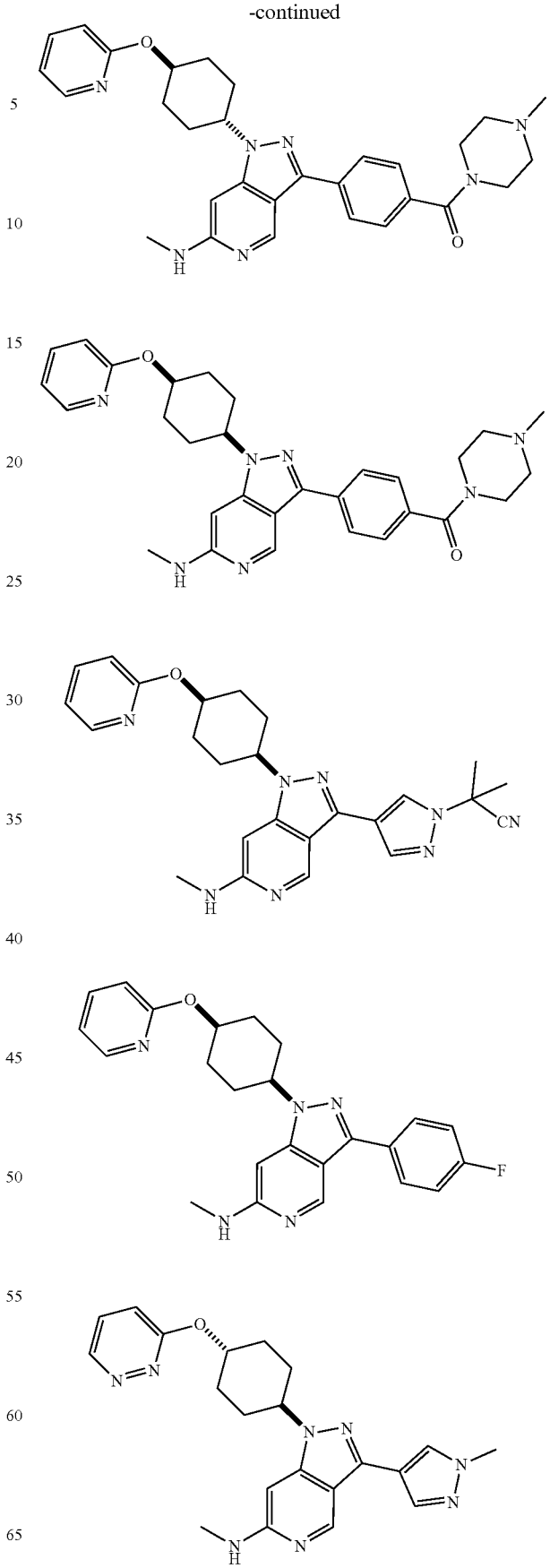

709
-continued
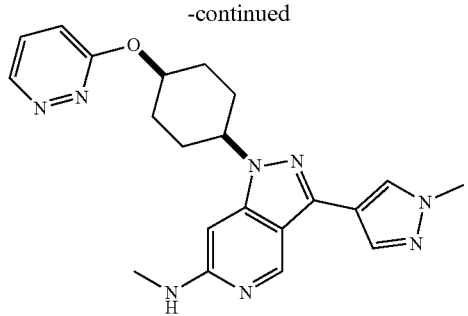
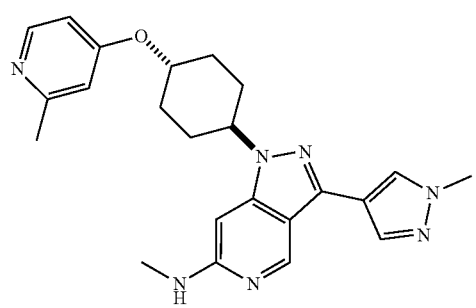
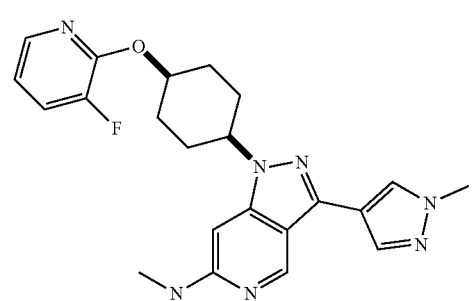
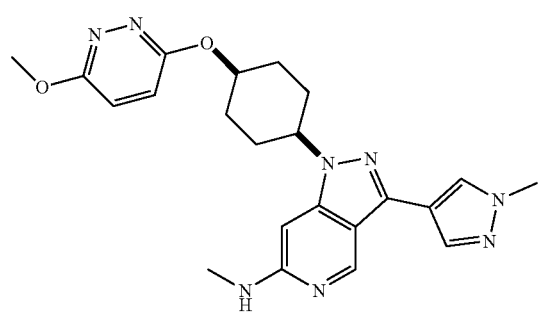
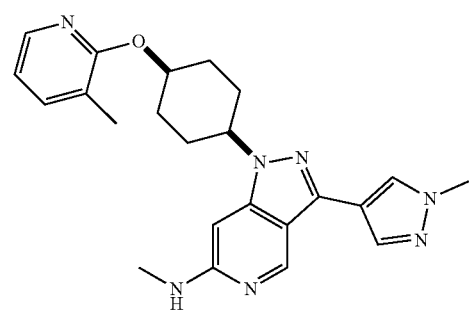
710
-continued
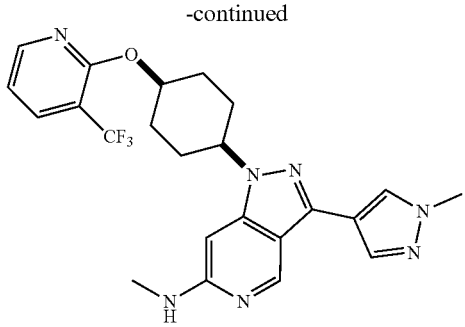
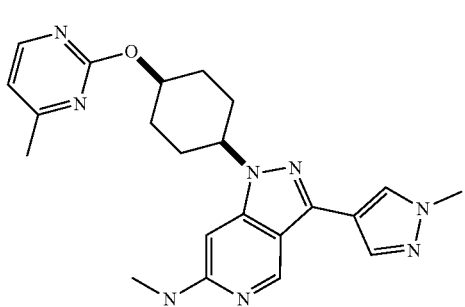
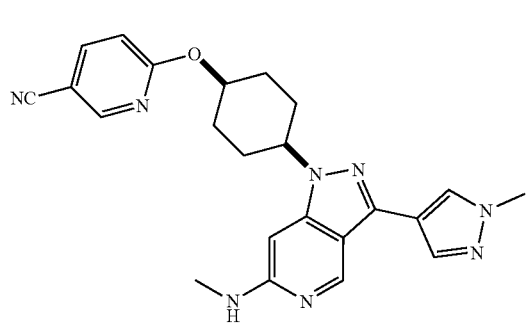
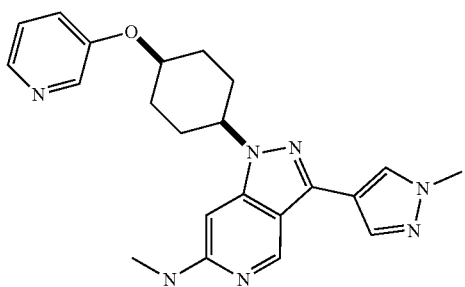
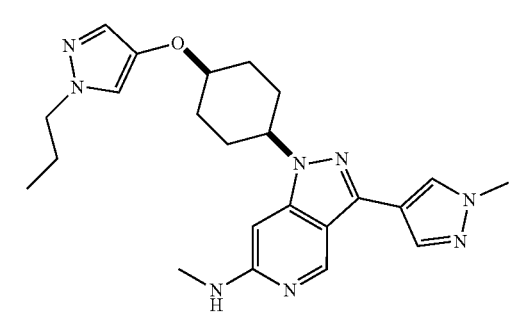

711
-continued
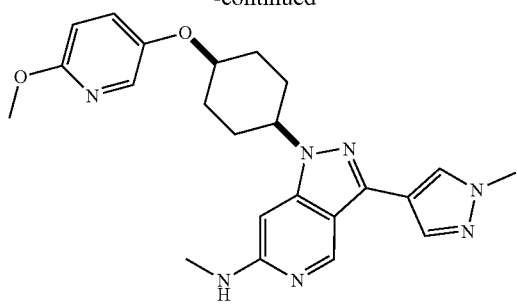
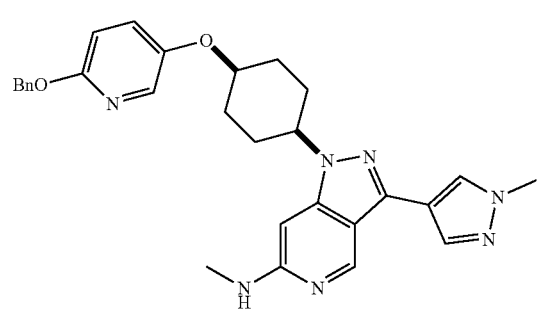
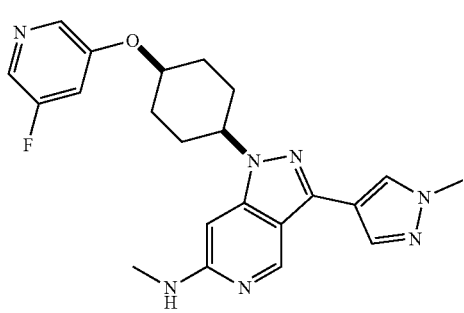
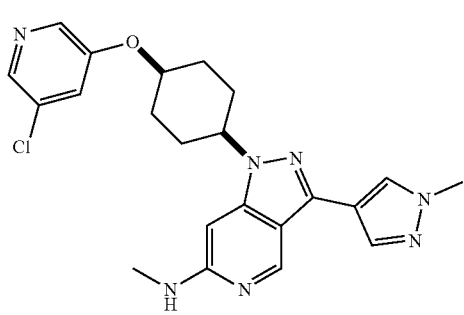
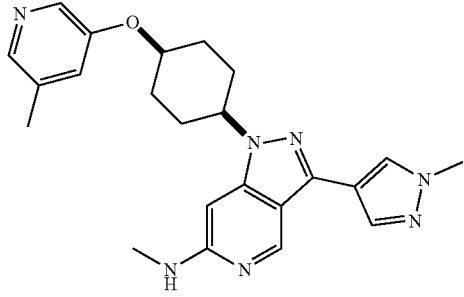
712
-continued
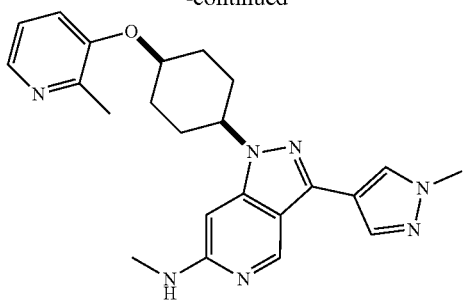
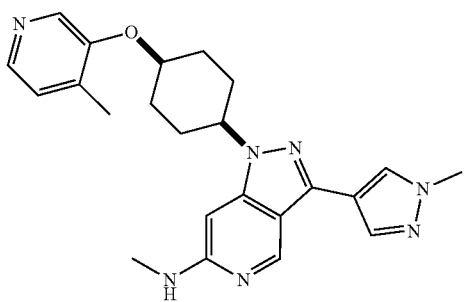
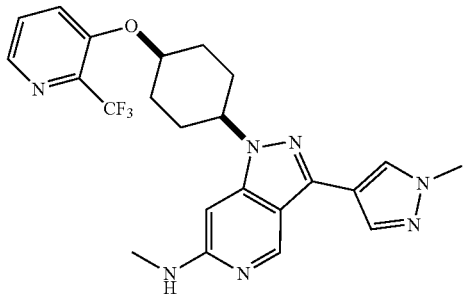
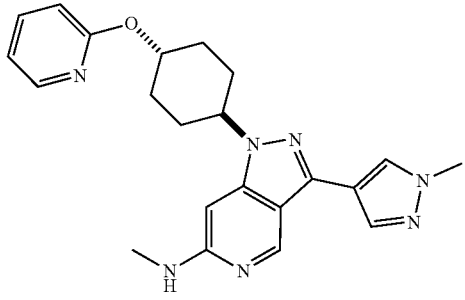
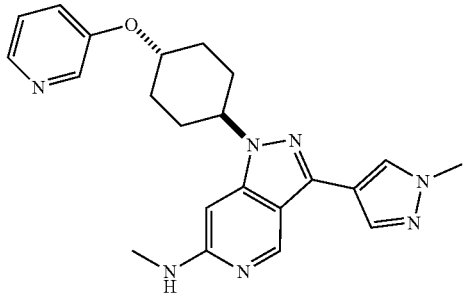

713
-continued
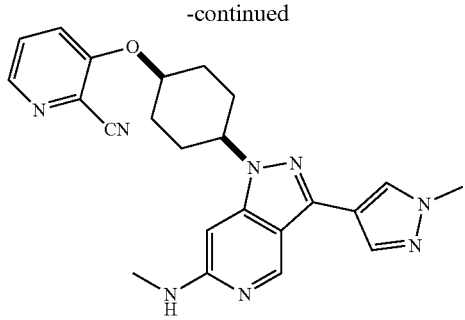
714
-continued
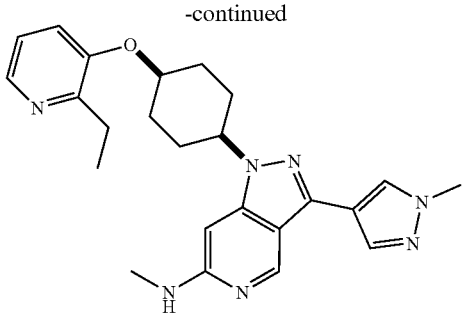
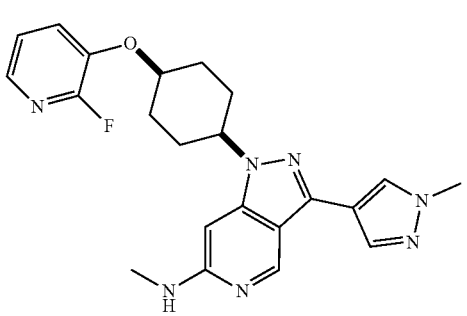
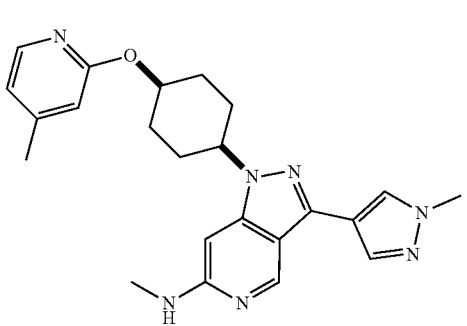

715
-continued
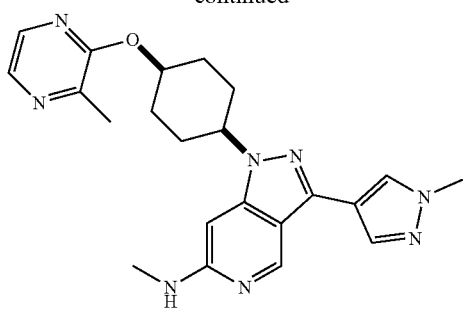
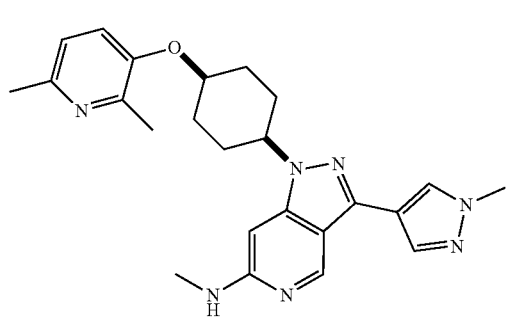
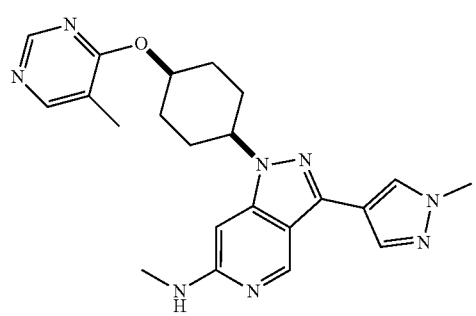
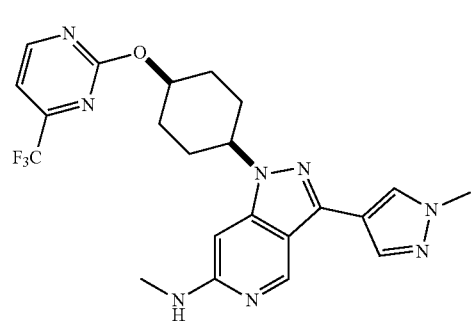
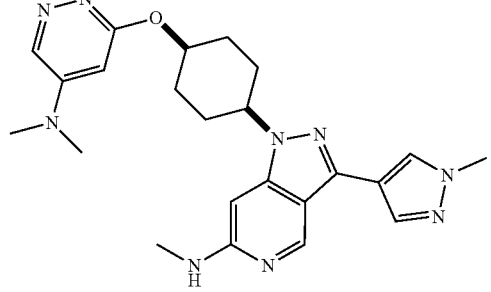
716
-continued
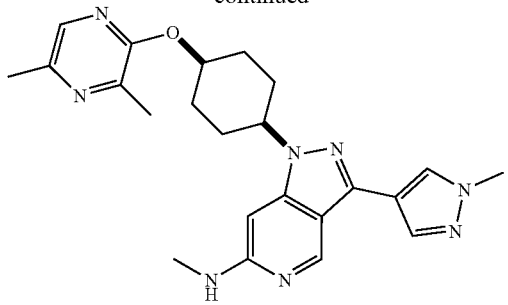
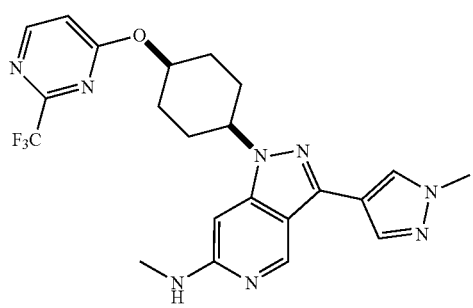
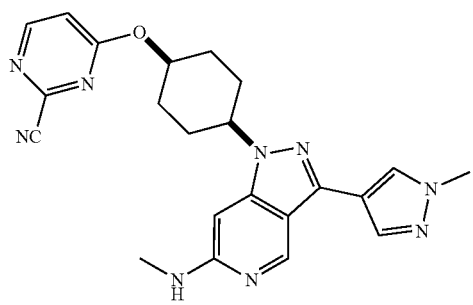
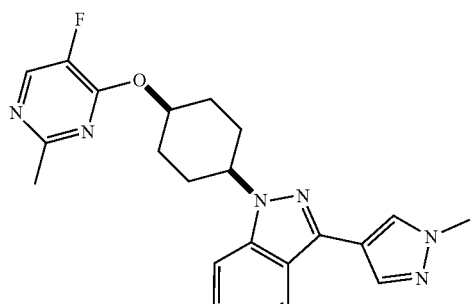
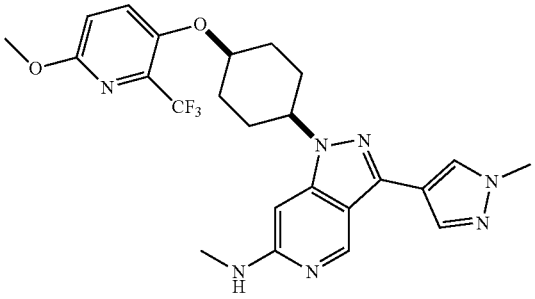

717
-continued
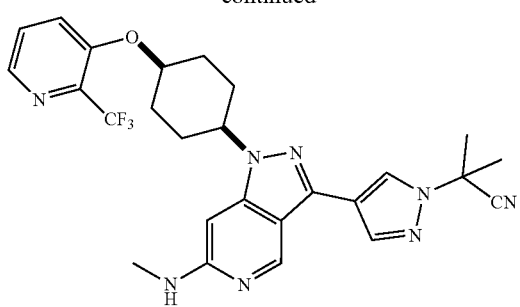
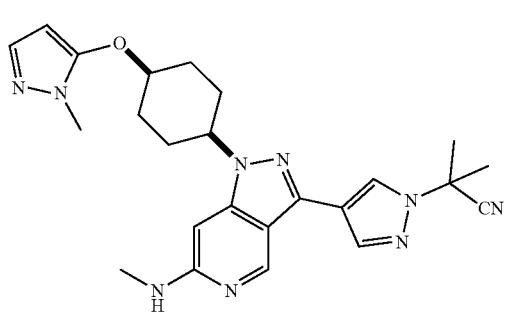
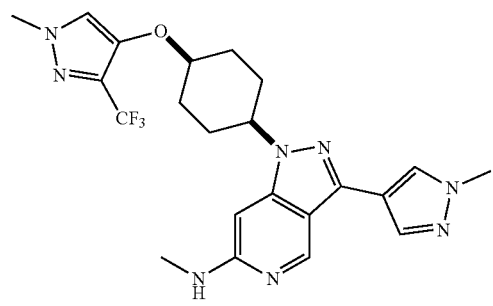
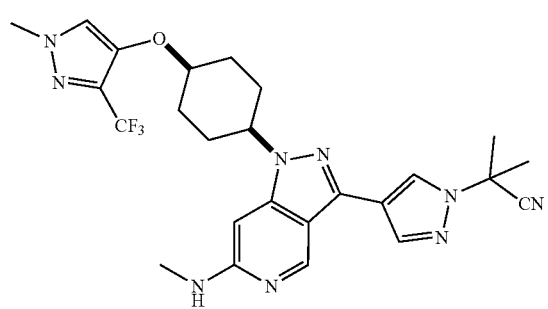
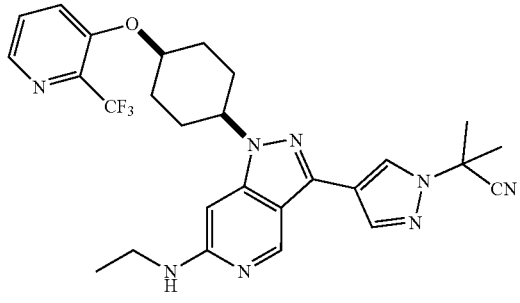
718
-continued
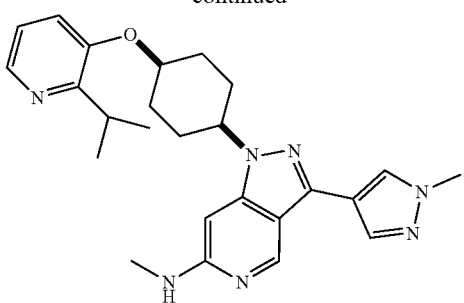
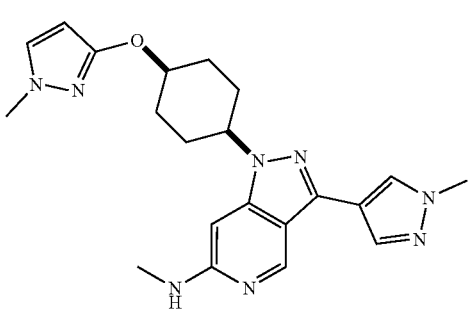
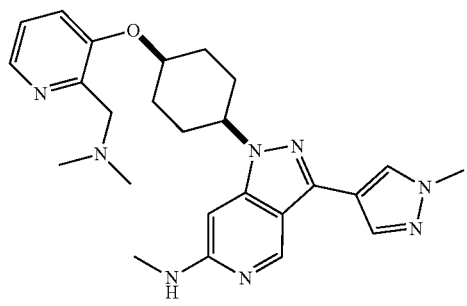
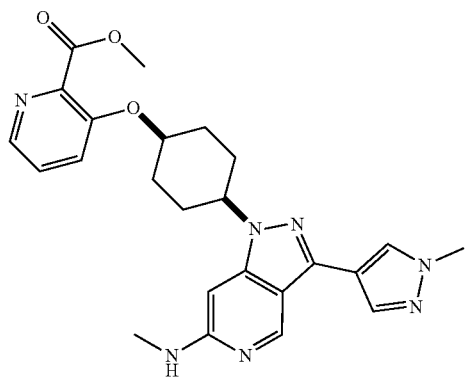
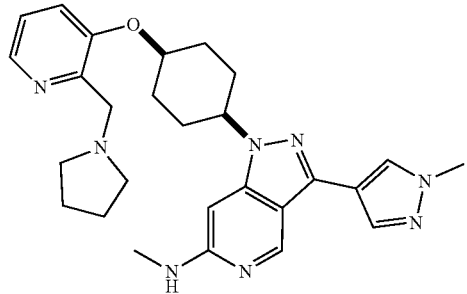

719
-continued
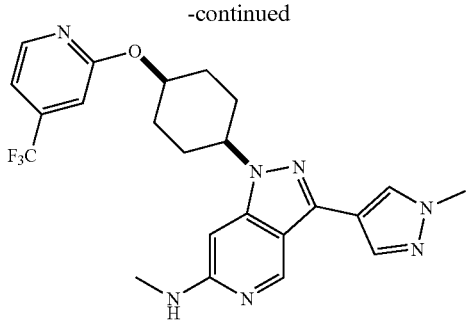
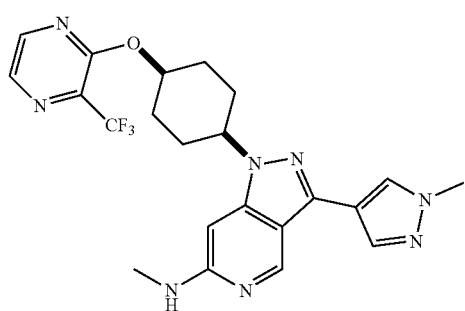
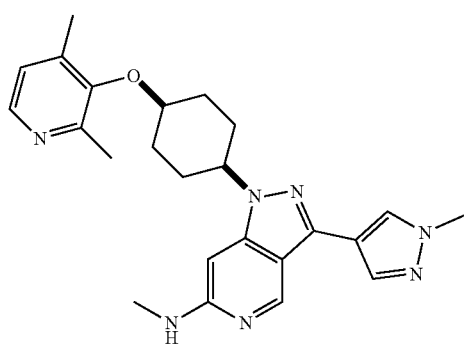
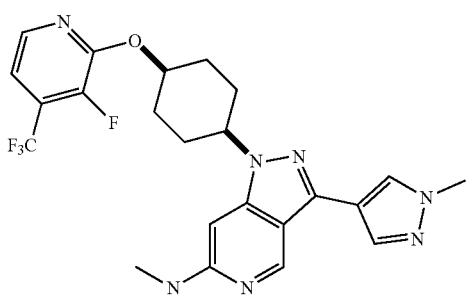
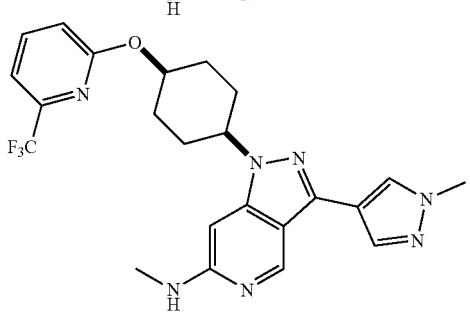
720
-continued
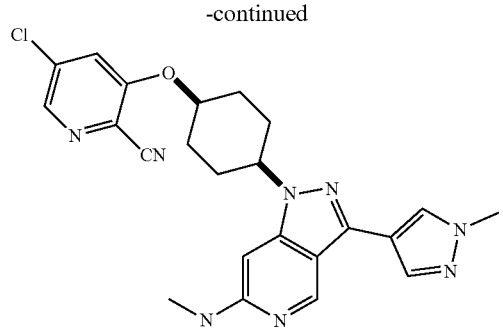
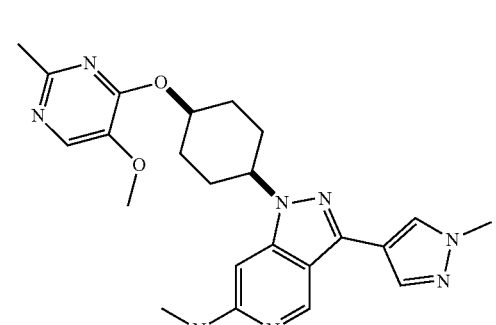
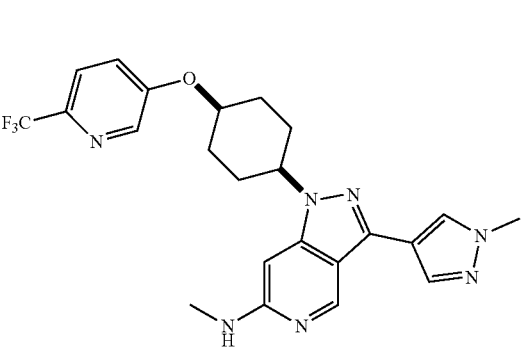
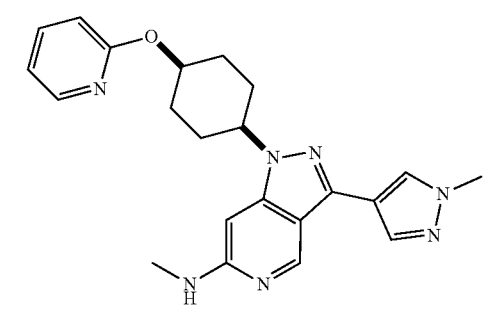
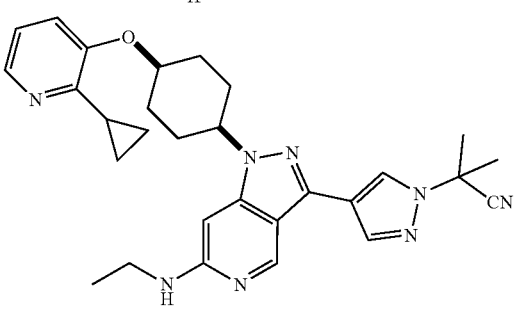

| 721 -continued | 722 -continued |
|---|---|
| 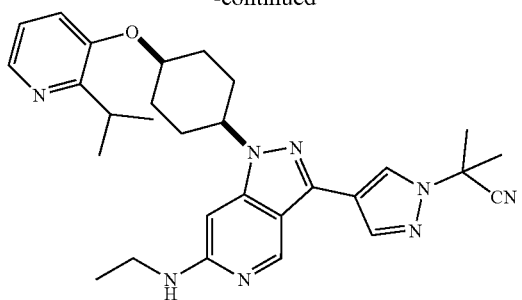 | 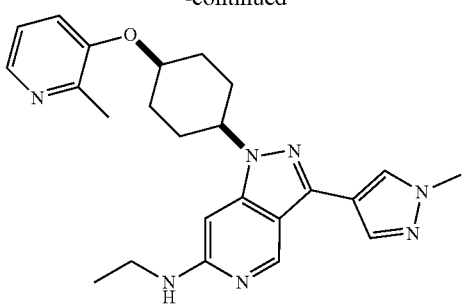 |
| 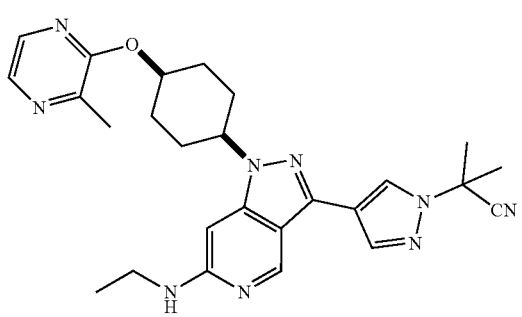 | 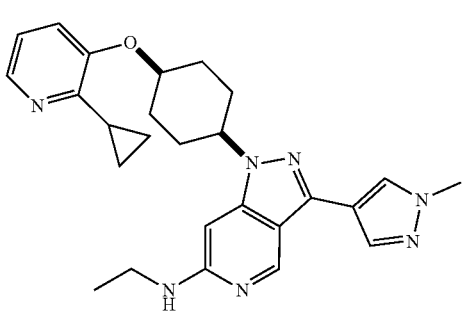 |
| 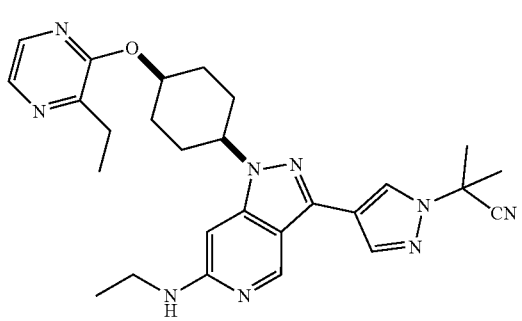 | 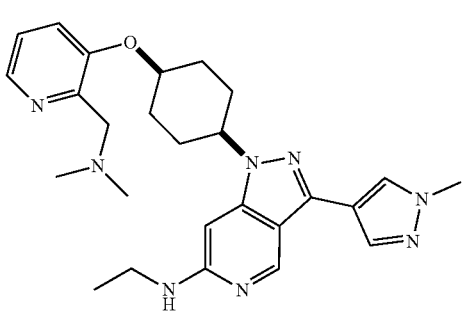 |
| 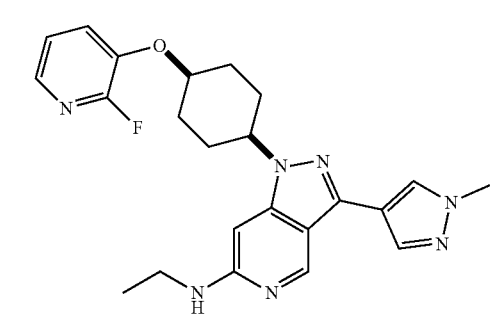 | 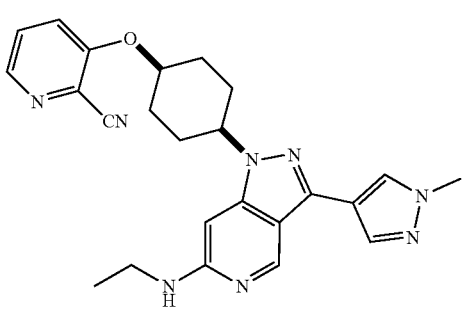 |
| 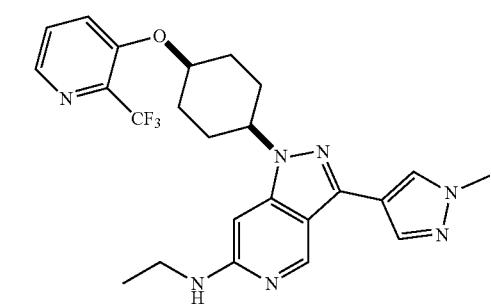 | 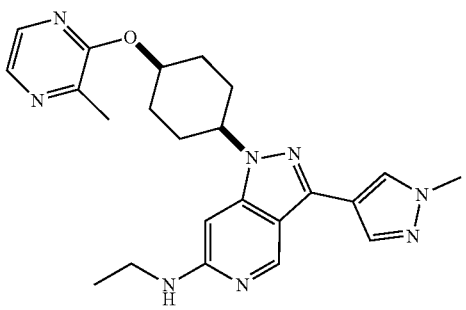 |

723
-continued
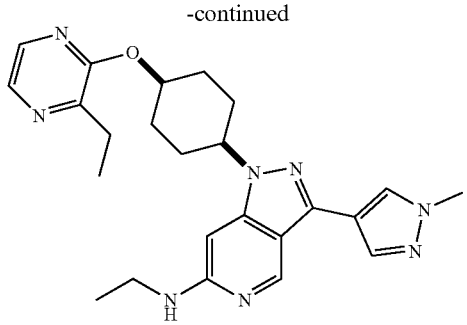
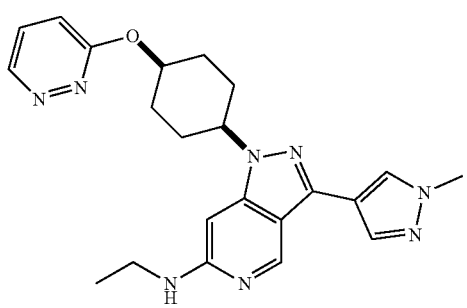
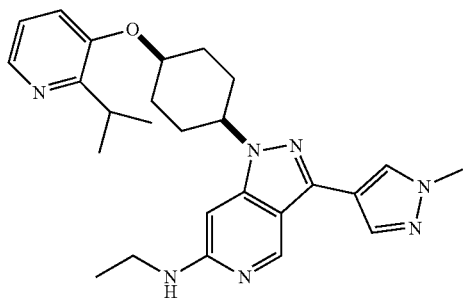
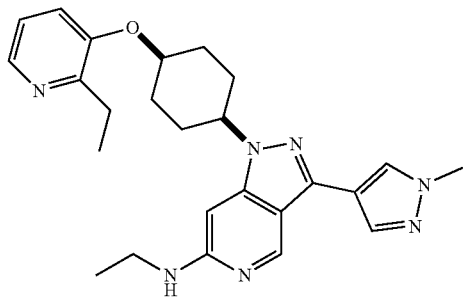
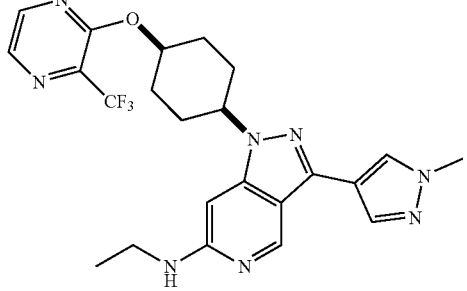
724
-continued
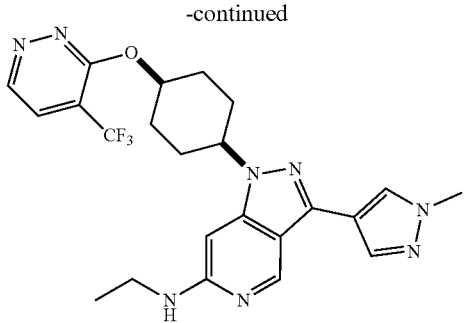
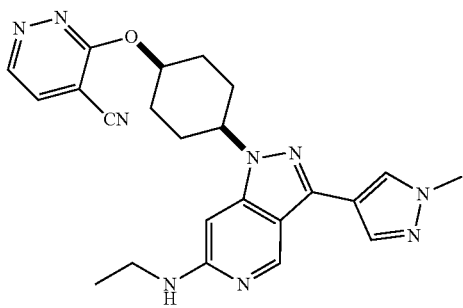
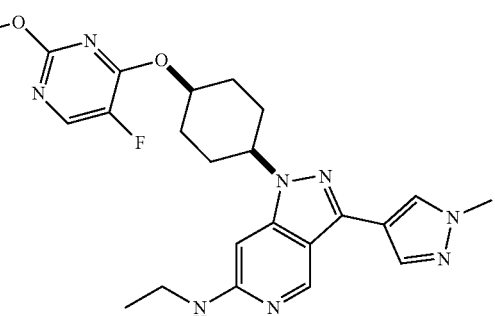
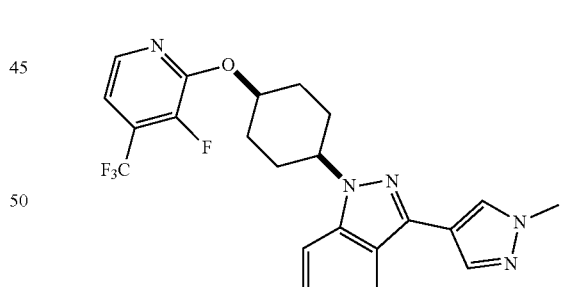
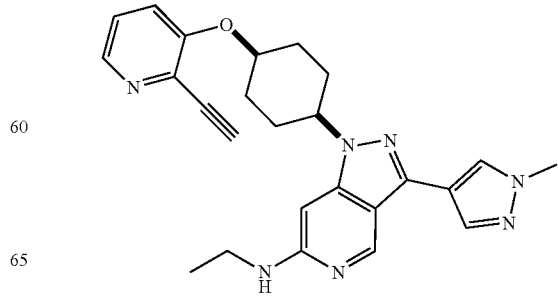

725
-continued
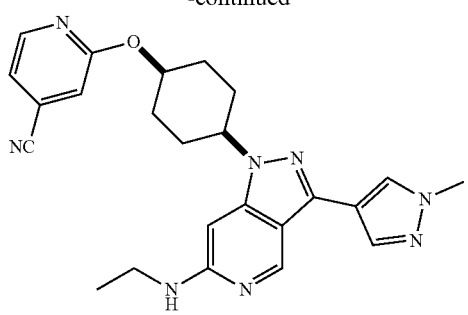
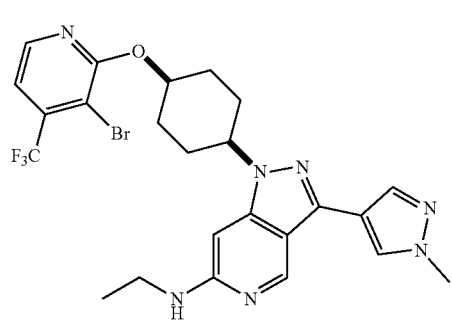
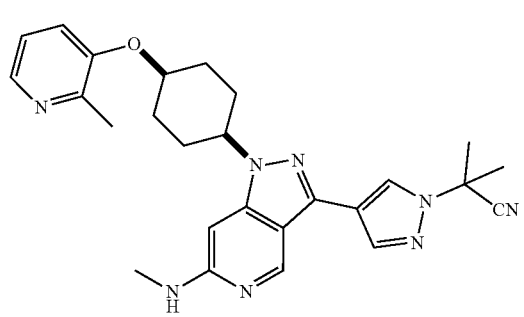
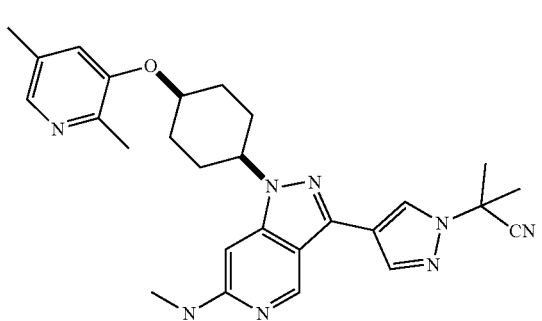
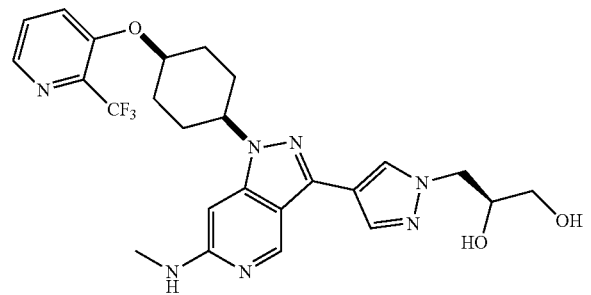
726
-continued
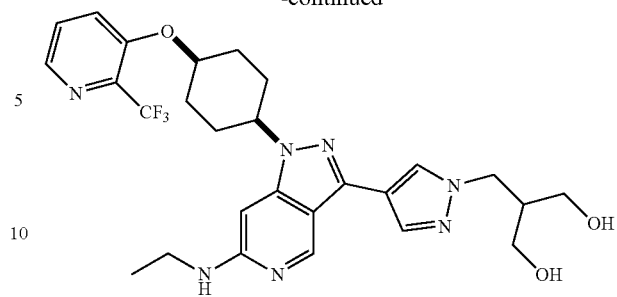
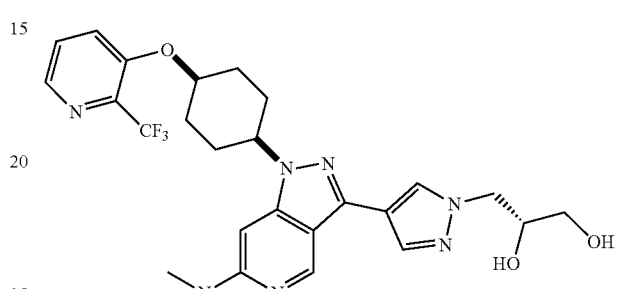
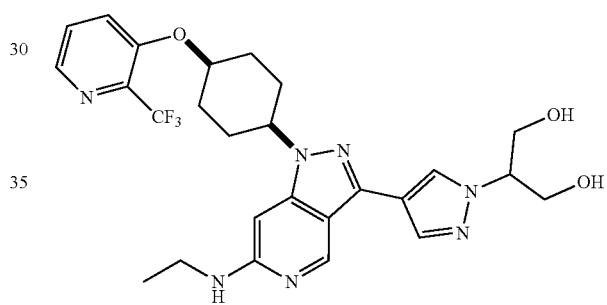
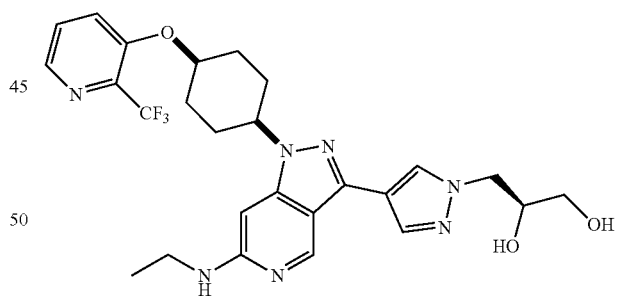
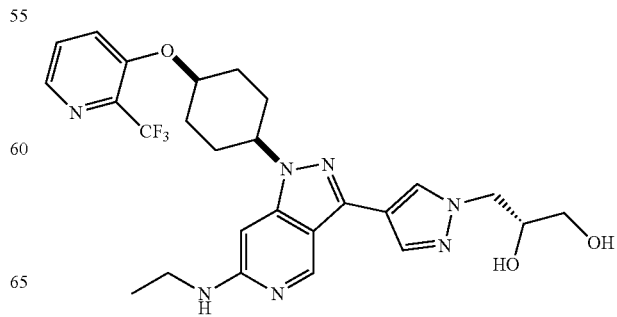

727
-continued
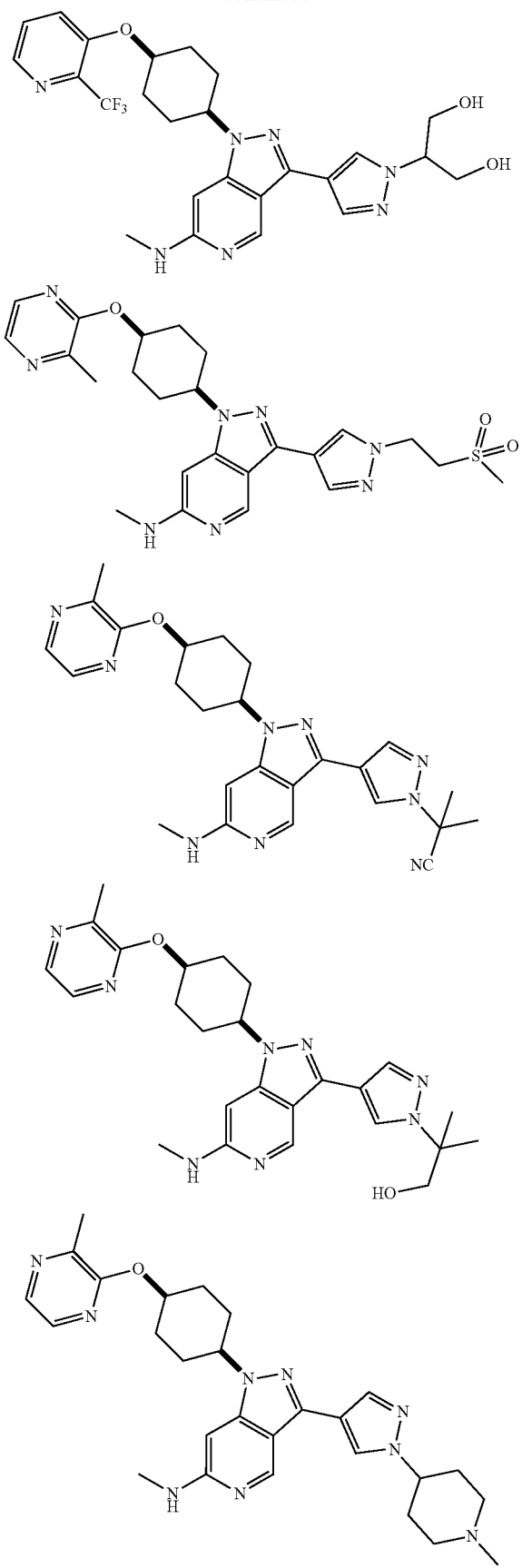
728
-continued
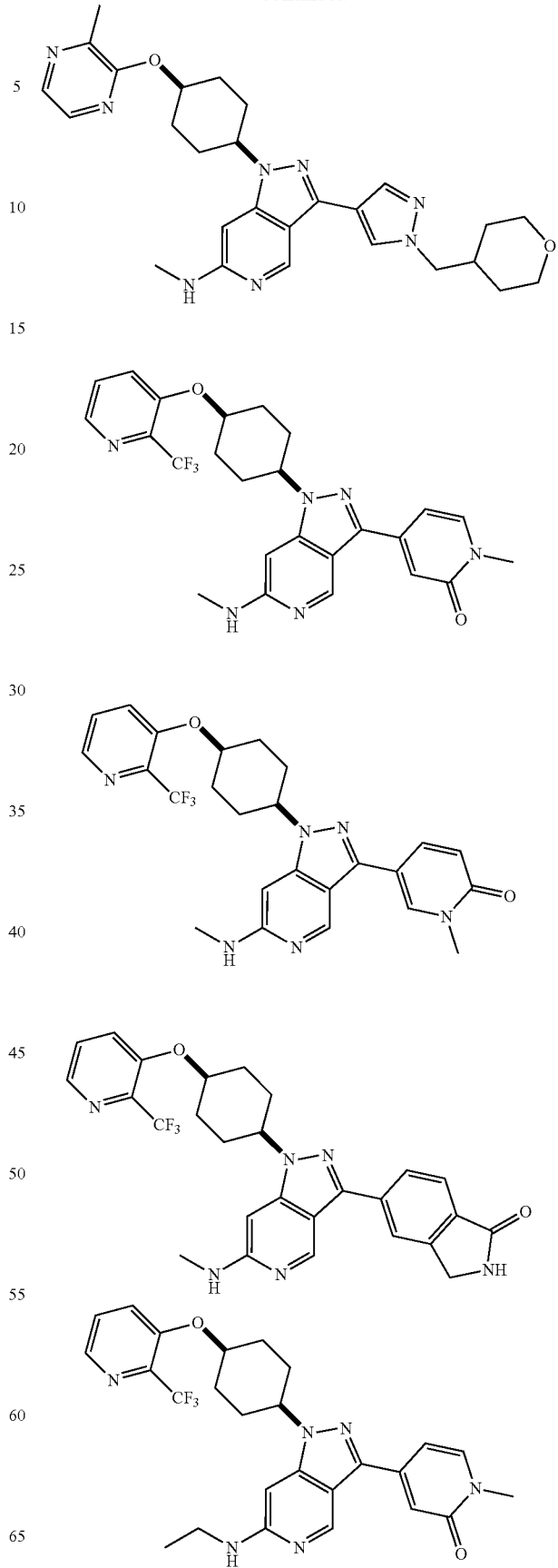

729
-continued
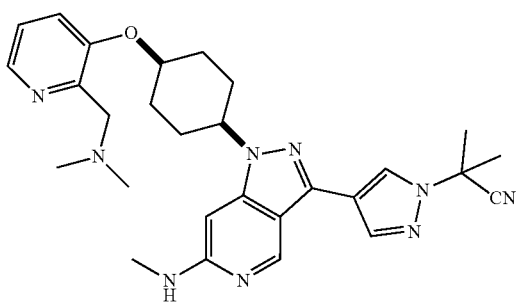
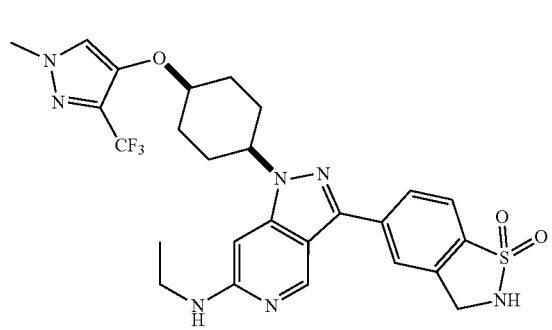
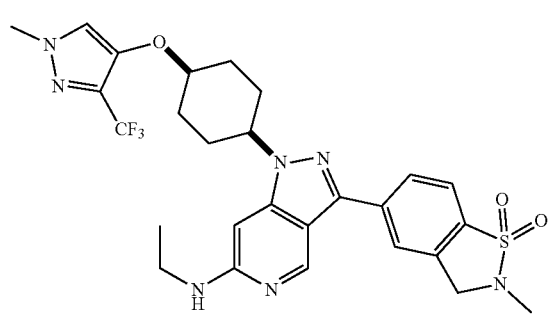
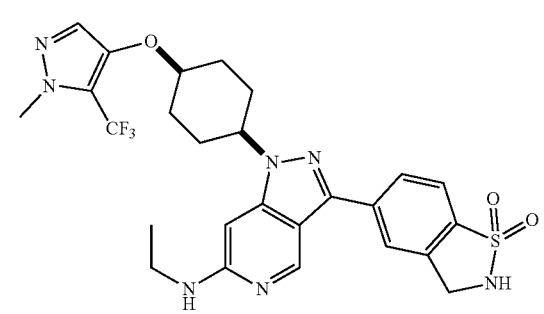
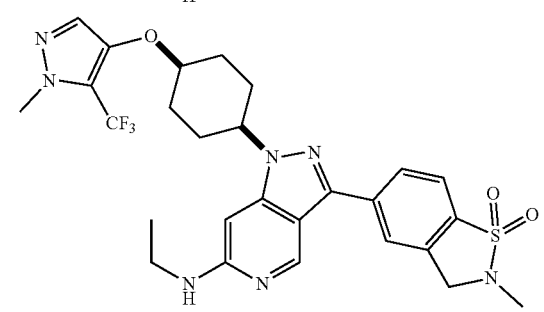
730
-continued
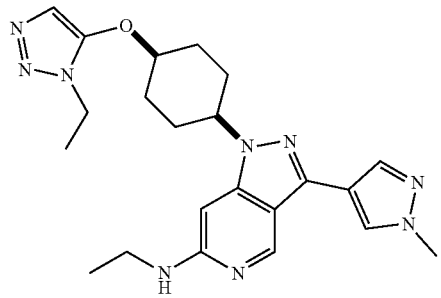
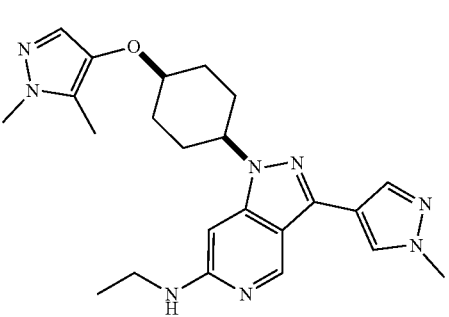
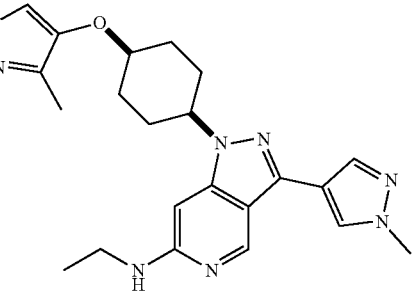
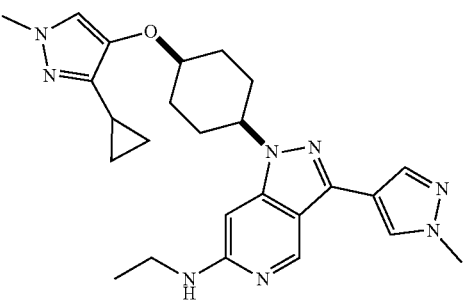
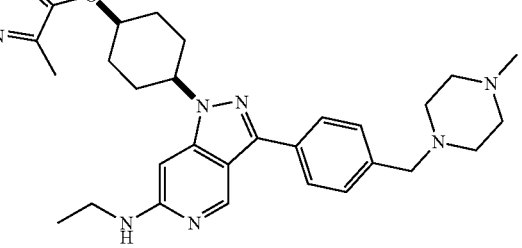

731
-continued
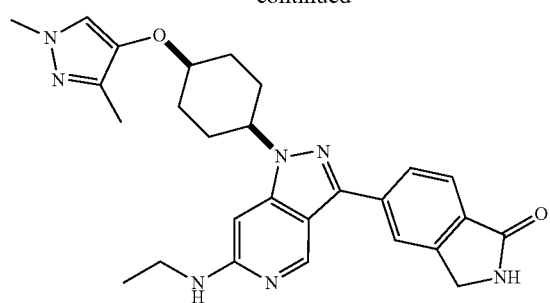
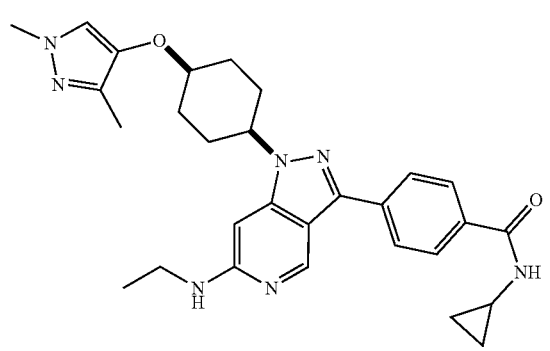
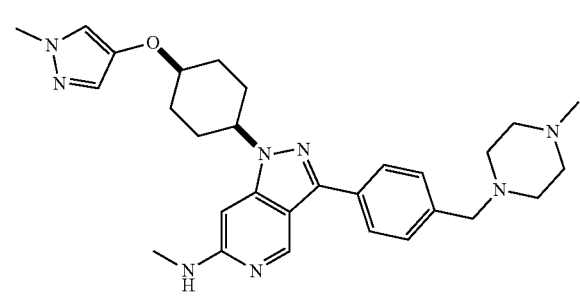
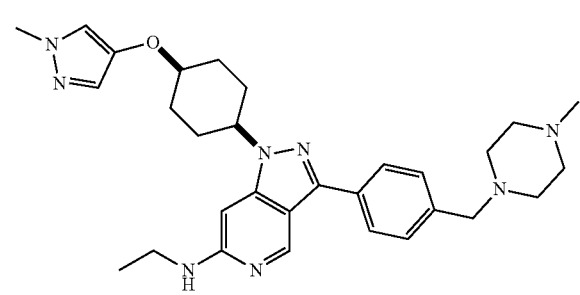
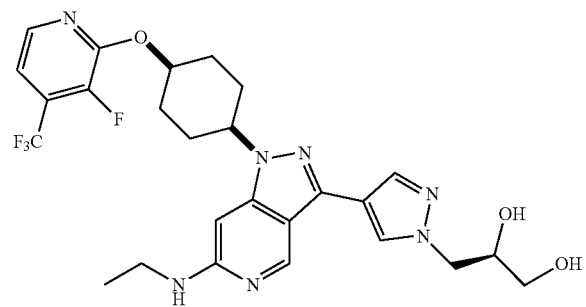
732
-continued
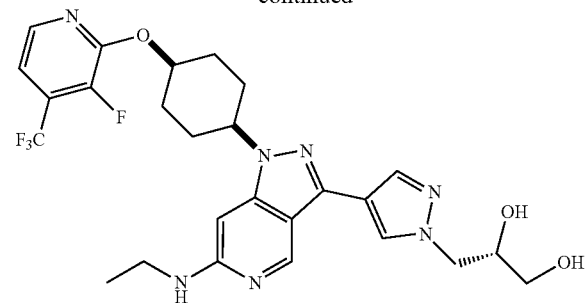
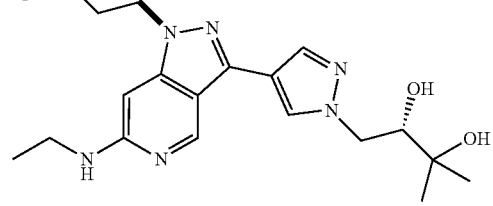
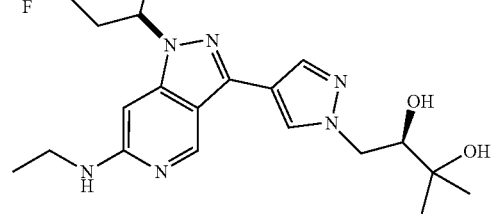
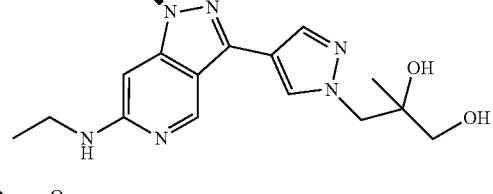
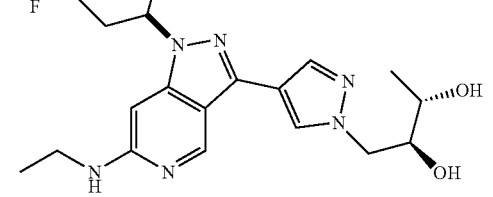

733
-continued
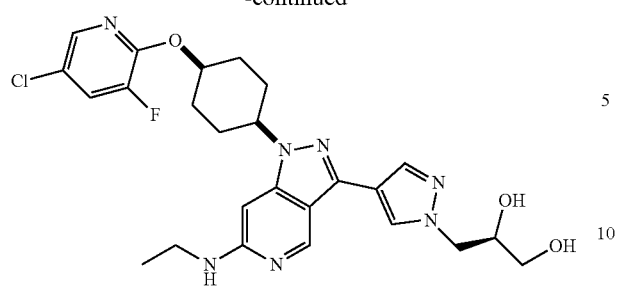
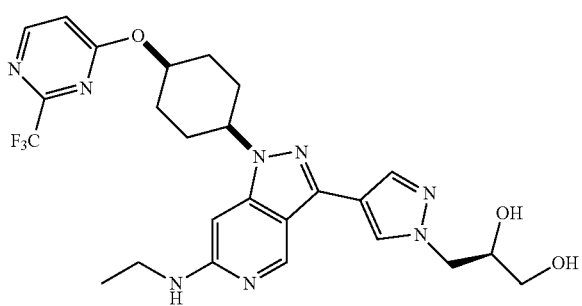
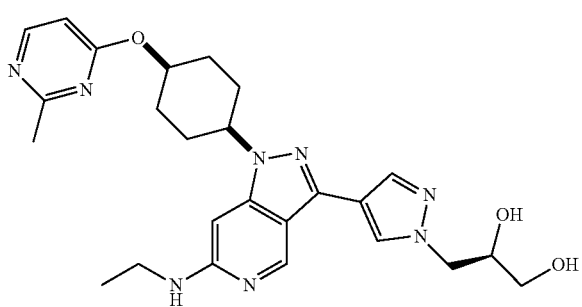
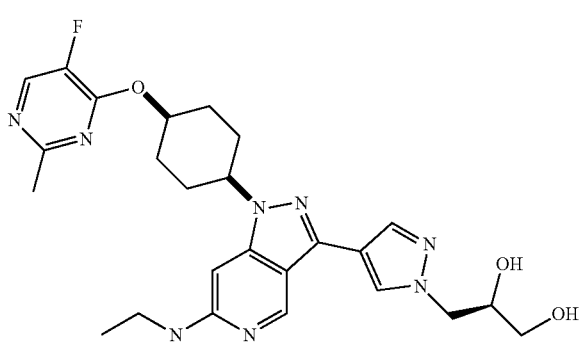
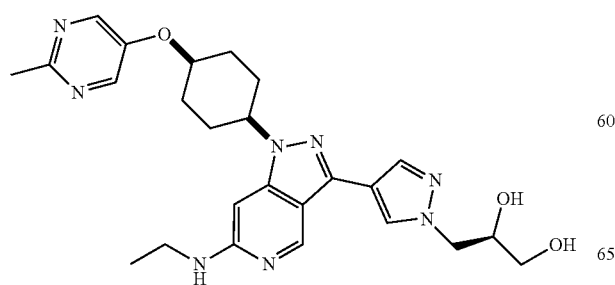
734
-continued
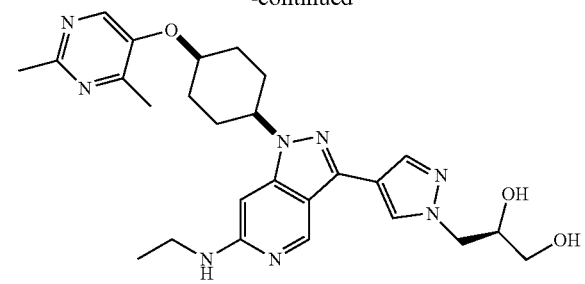
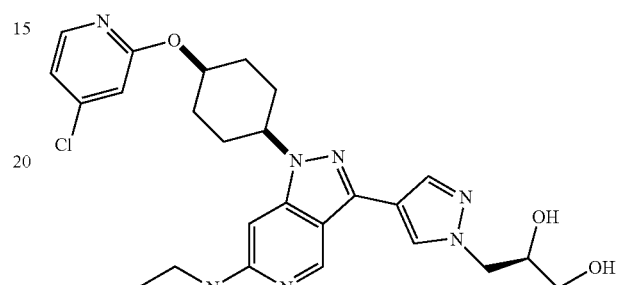
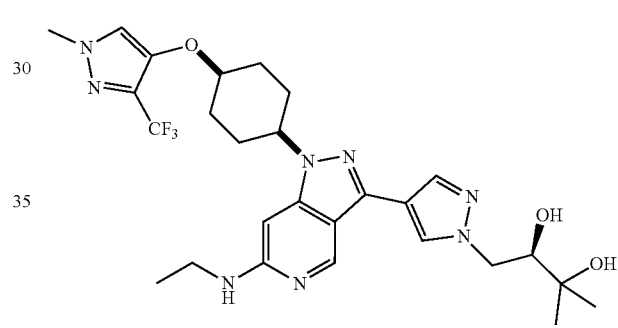
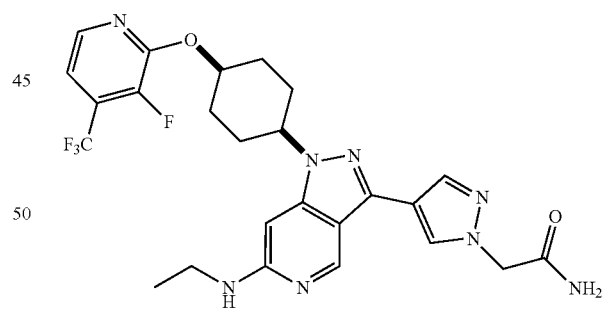
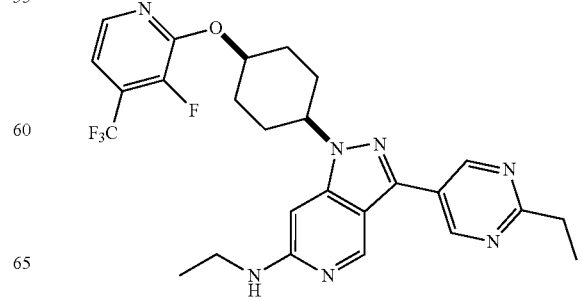

| 735 -continued | 736 -continued |
|---|---|
| 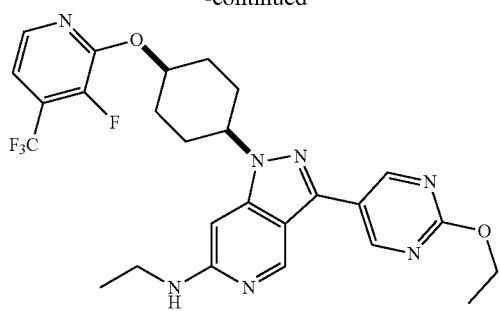 | 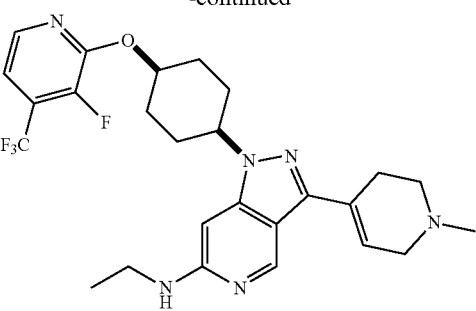 |
| 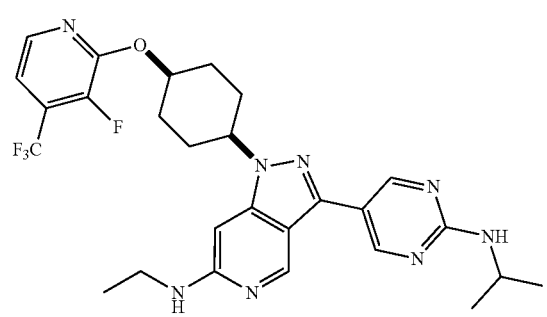 | 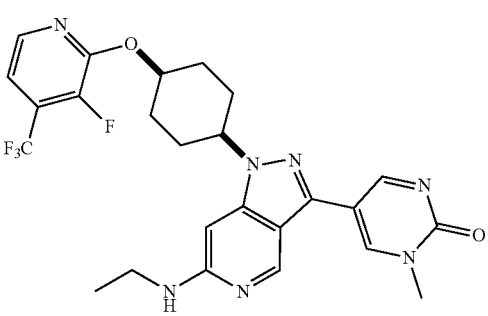 |
| 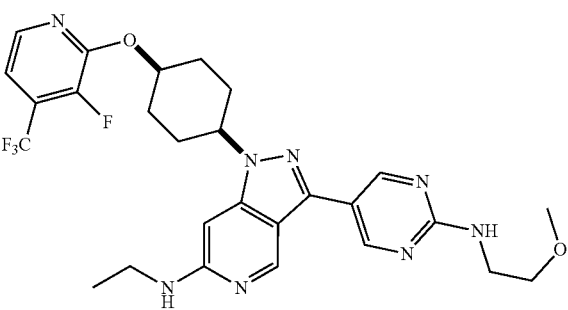 | 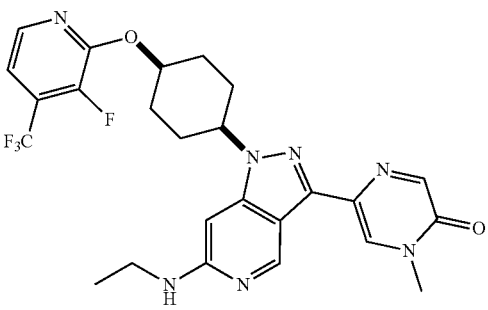 |
| 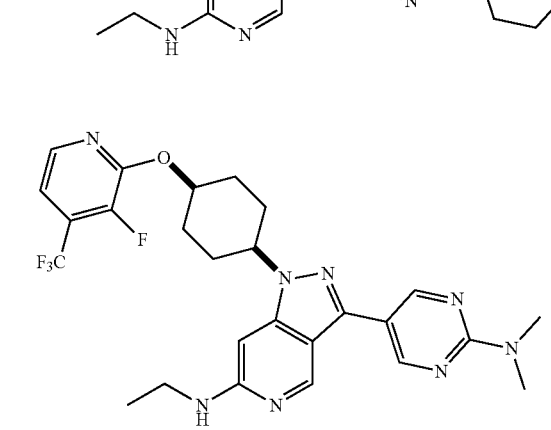 | 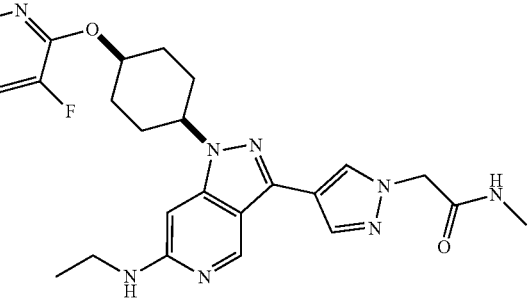 |
| 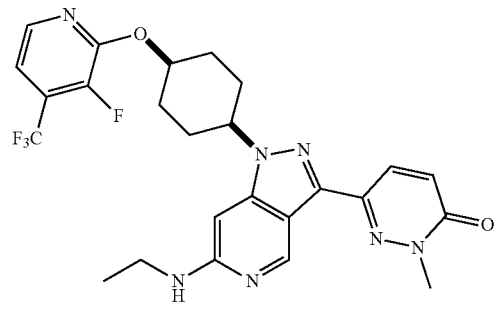 | 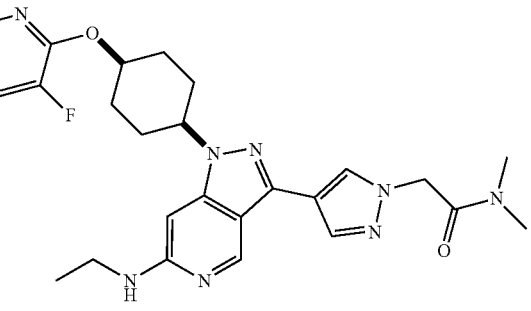 |

737
-continued
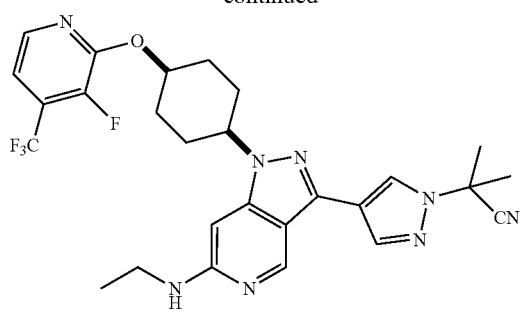
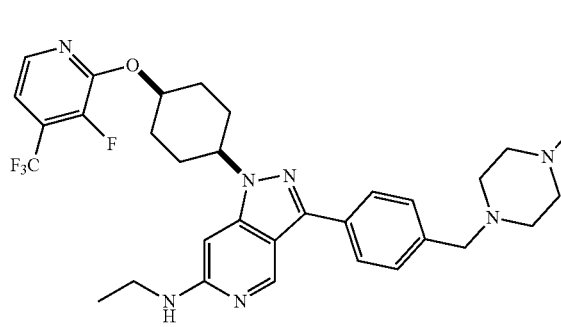
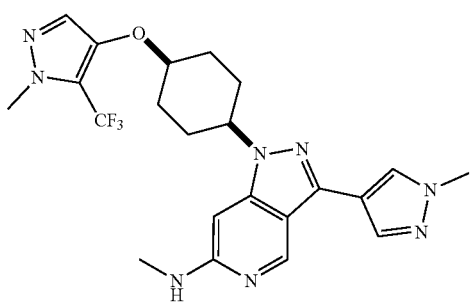
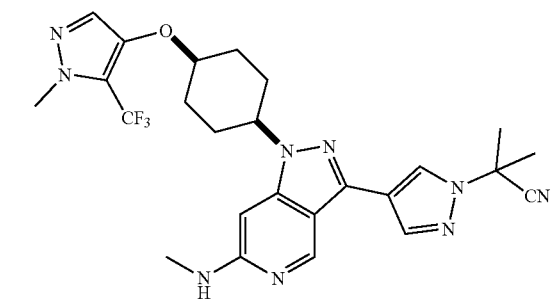
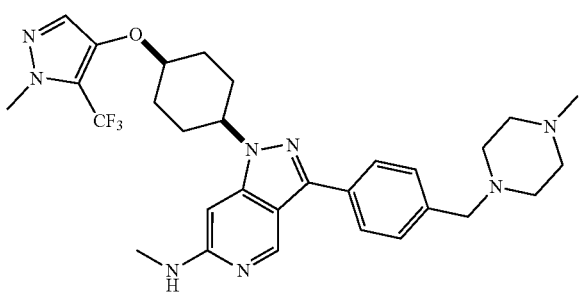
738
-continued
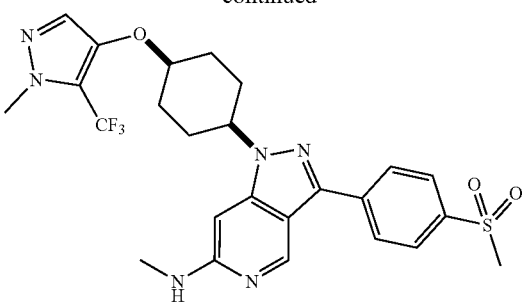
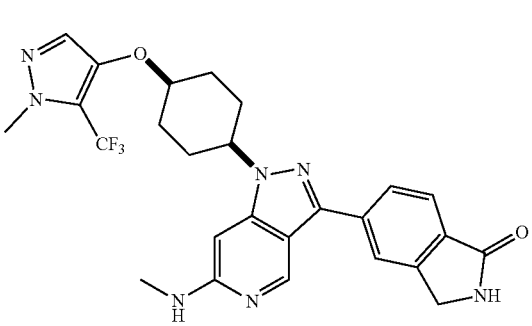
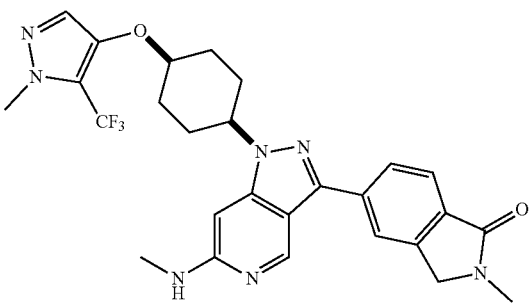
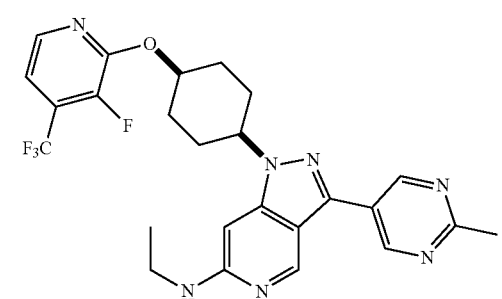
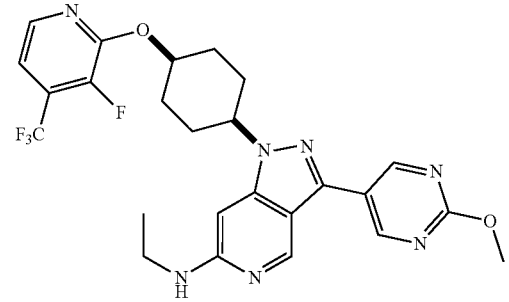

| 739 -continued | 740 -continued |
|---|---|
| 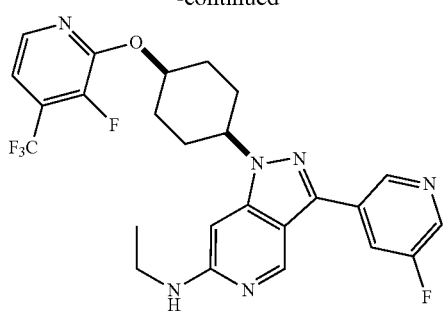 | 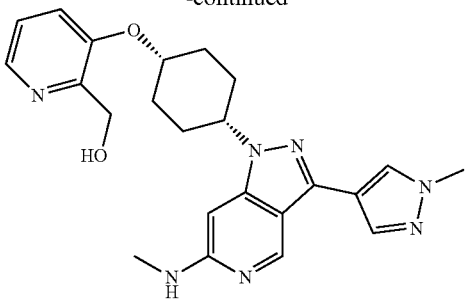 |
| 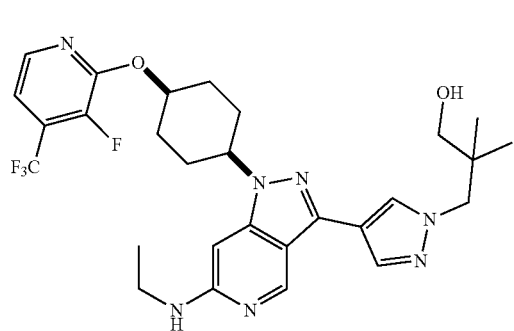 | 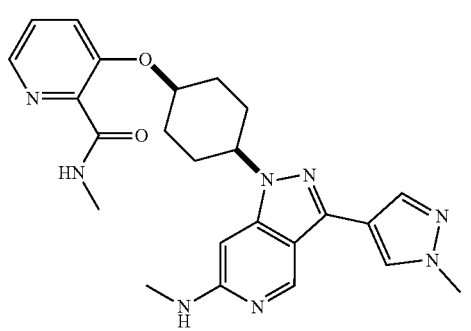 |
| 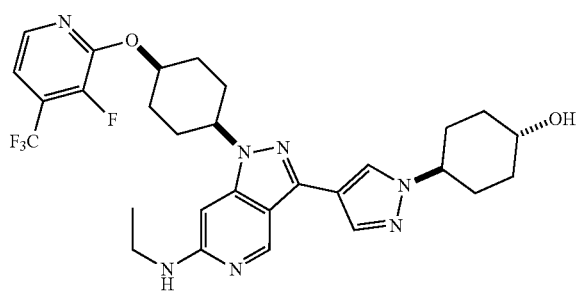 | 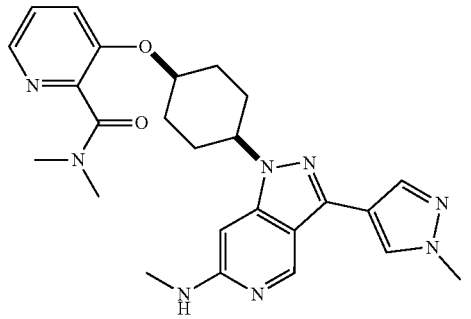 |
| 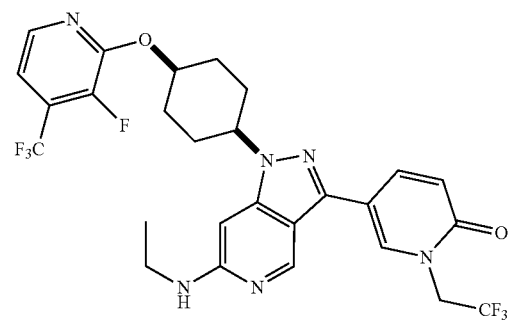 | 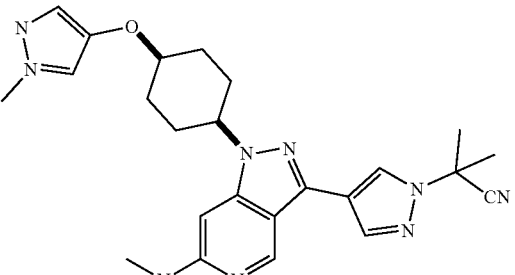 |
| 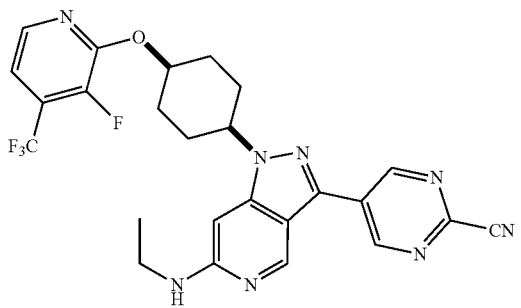 | 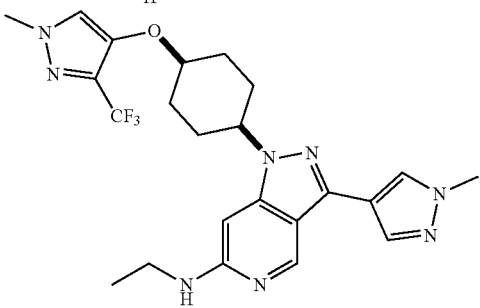 |

741
-continued
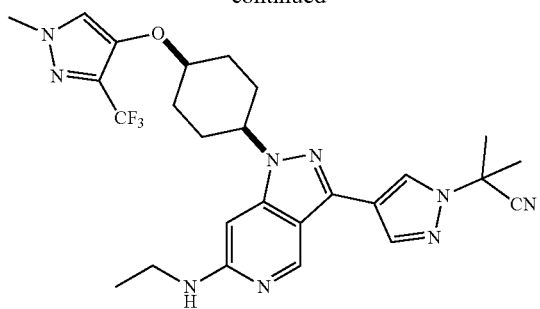
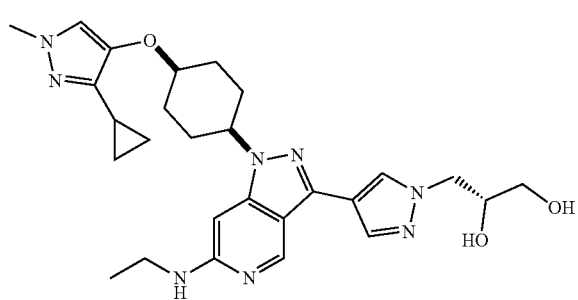
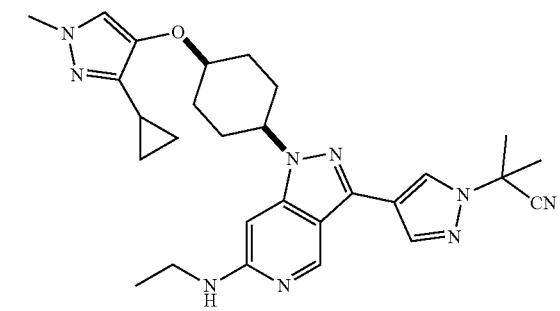
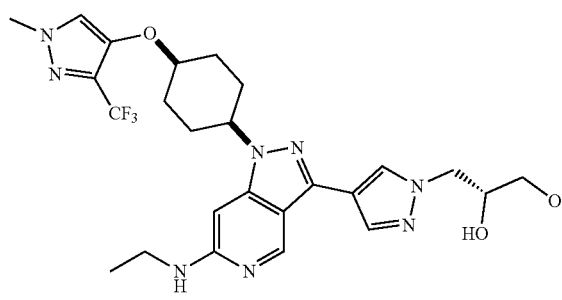
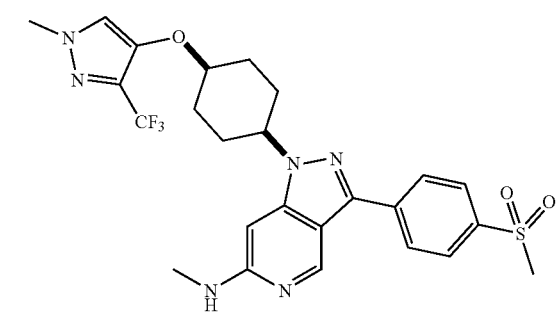
742
-continued
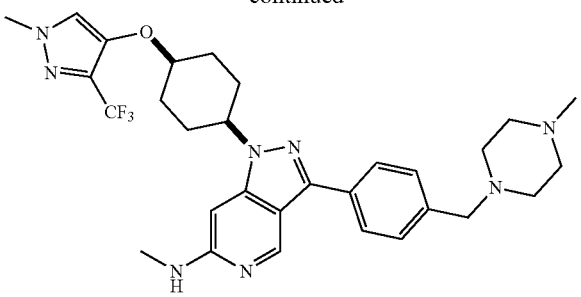
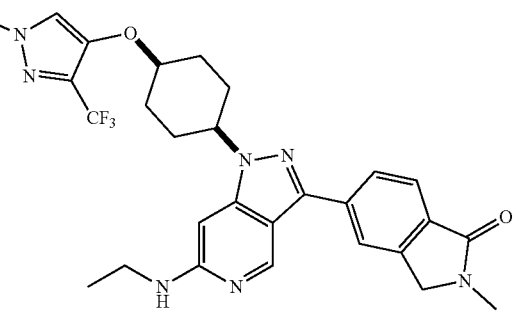
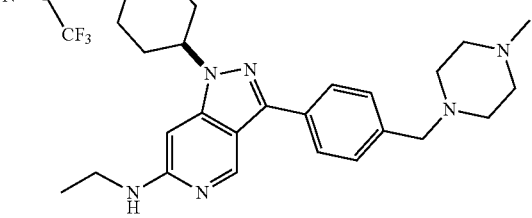

743
-continued
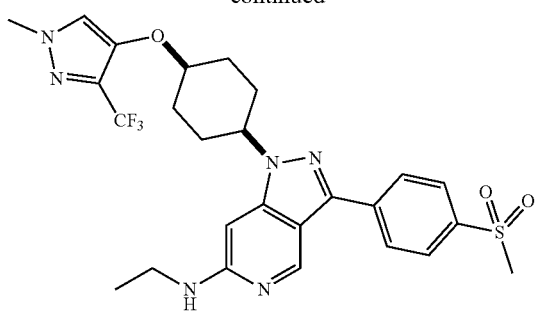
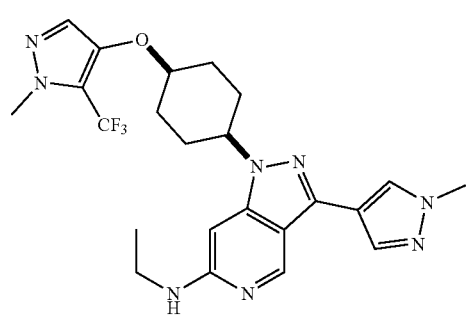
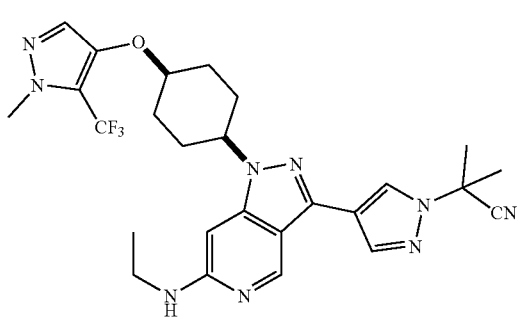
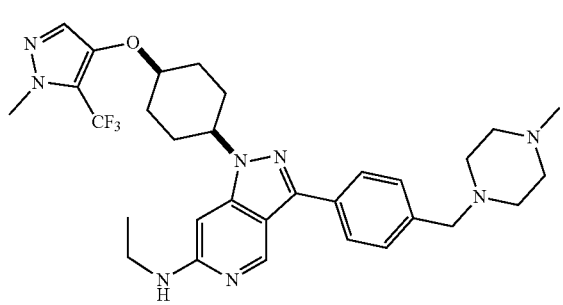
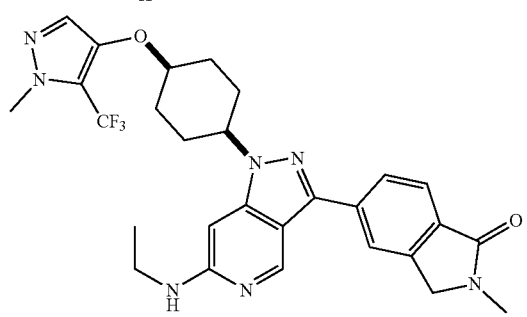
744
-continued
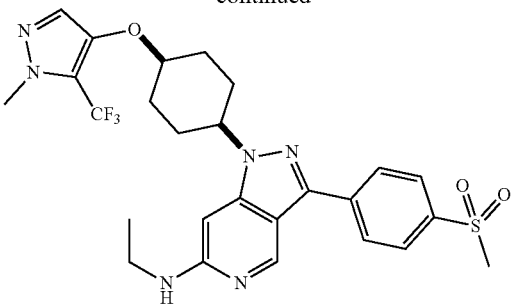
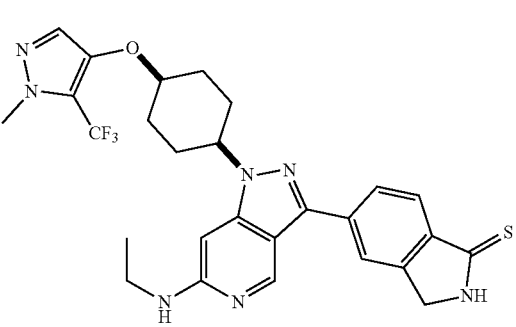
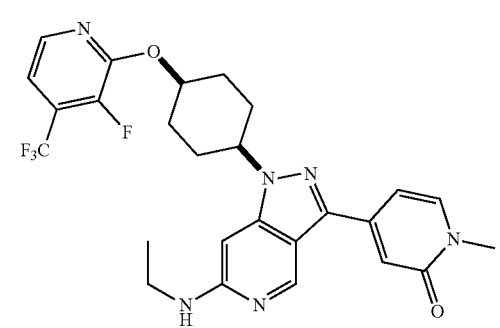
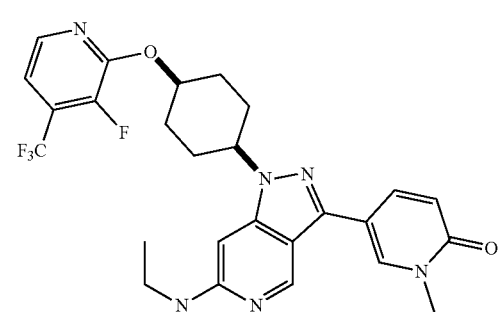
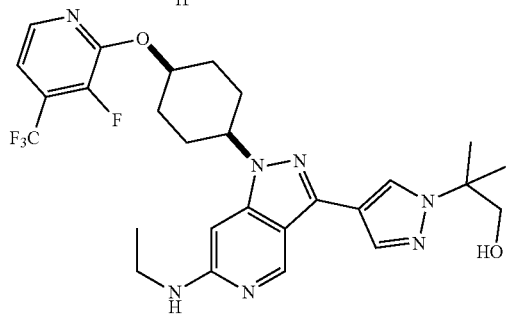

745
-continued
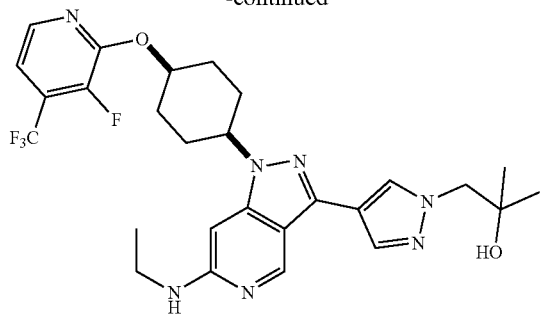
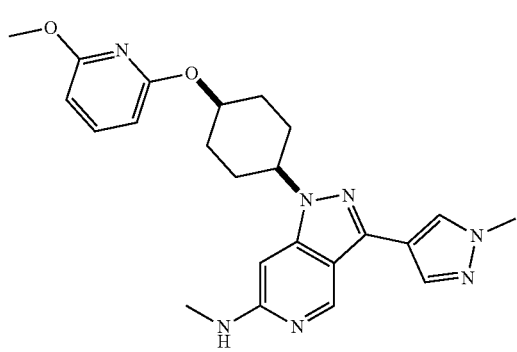
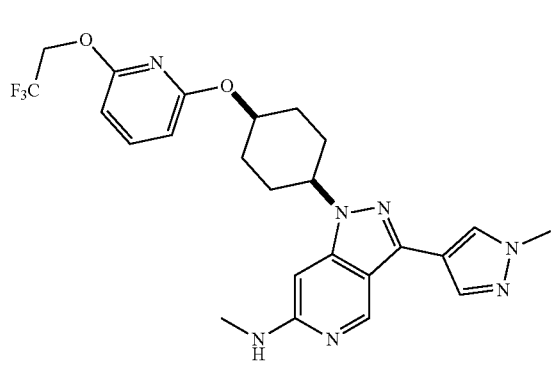
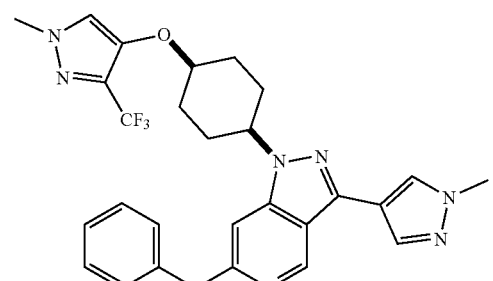
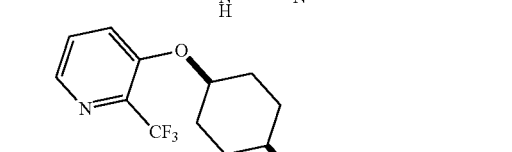
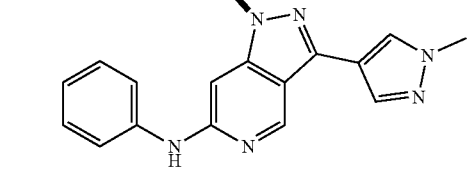
746
-continued
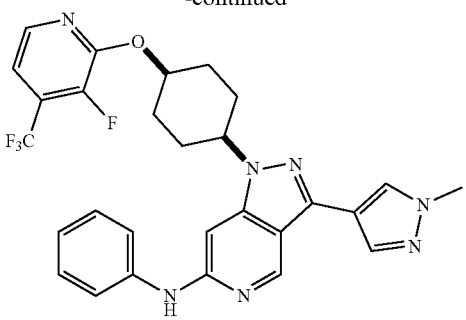
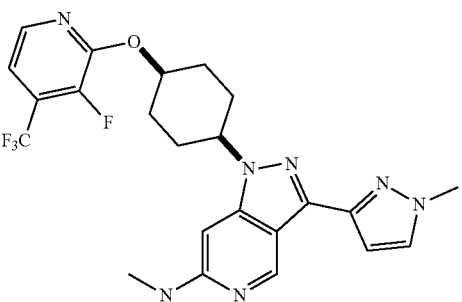
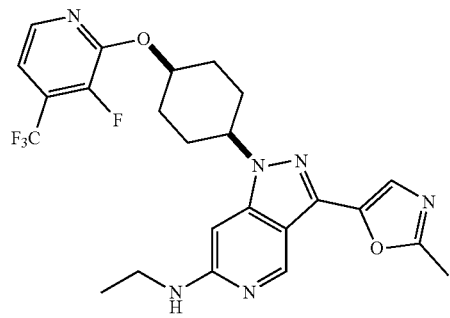
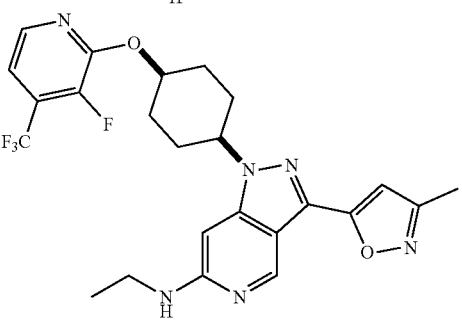

747 748
-continued -continued
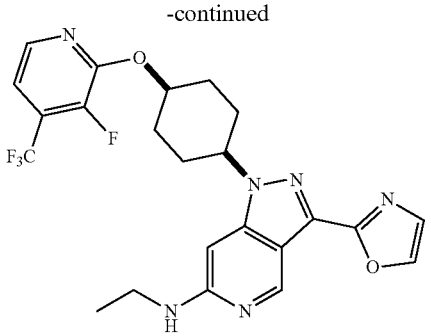
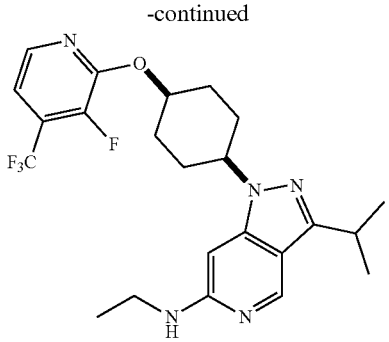
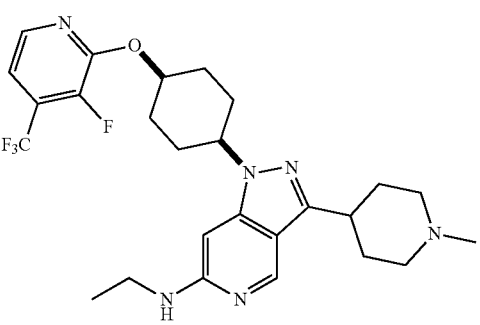
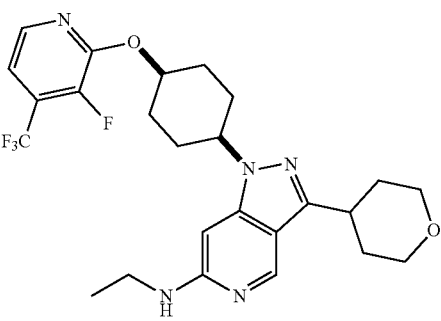
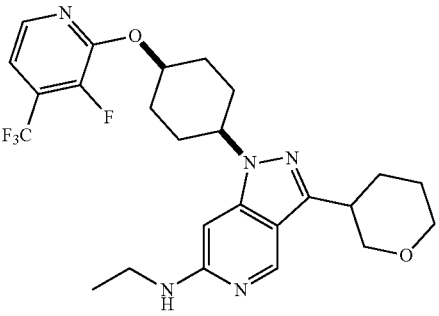
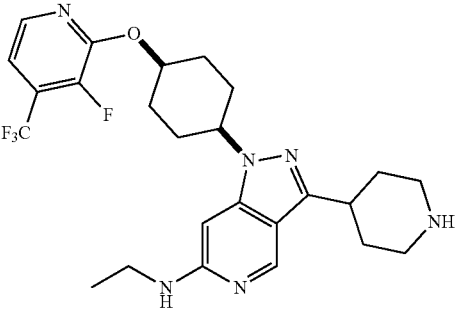

749
-continued
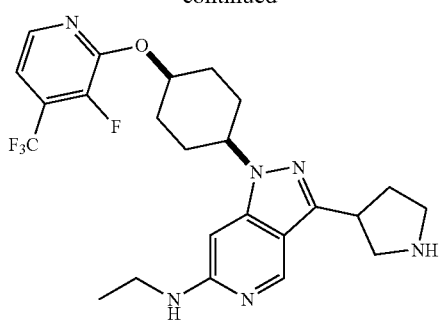
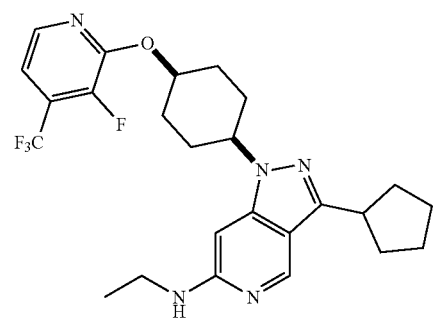
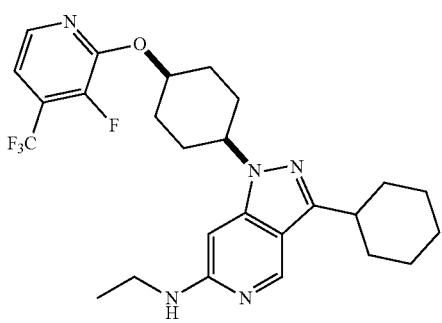
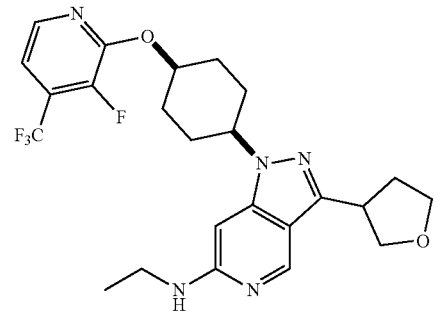
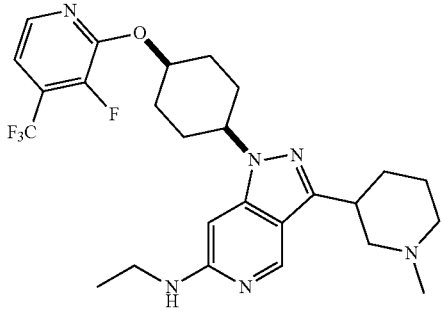
750
-continued
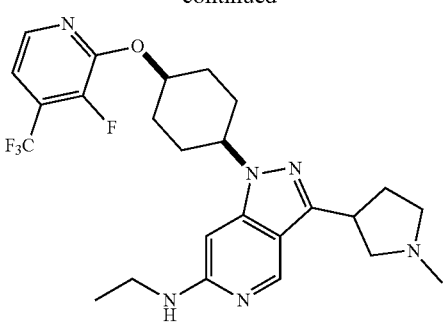
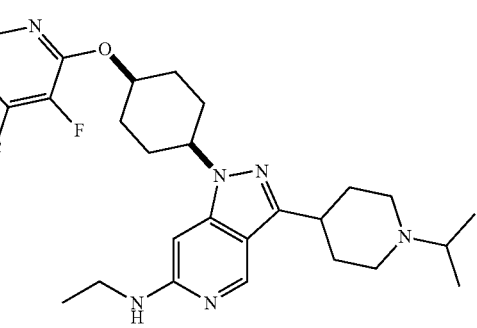
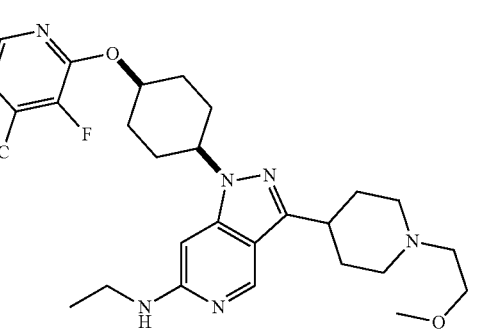
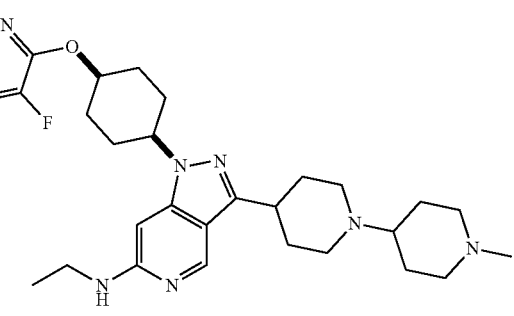
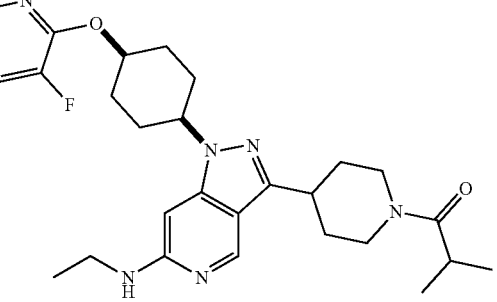

751
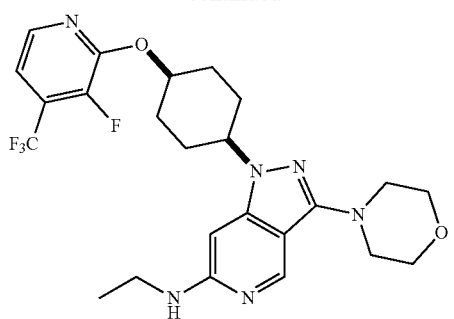
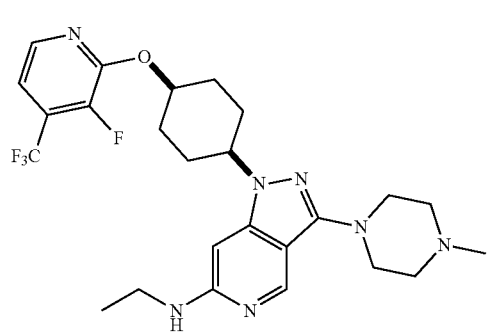
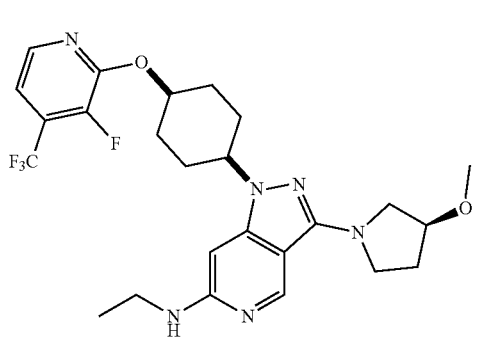
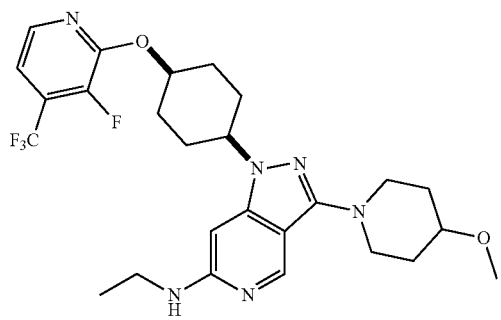
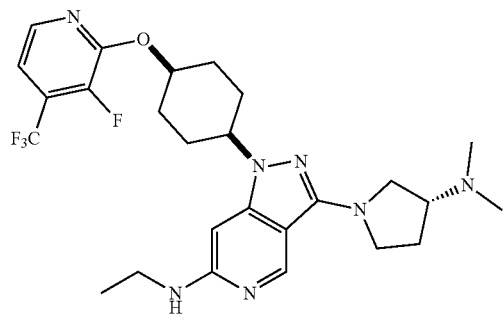
752
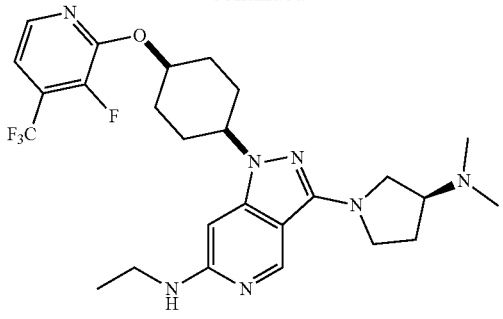
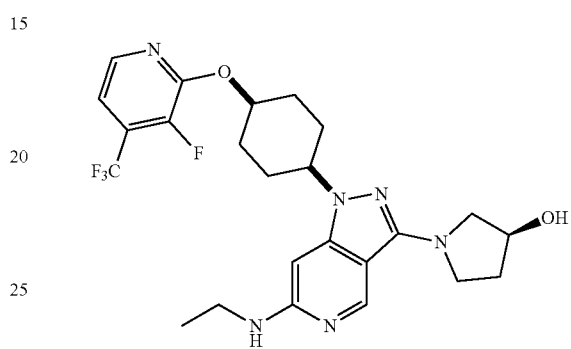
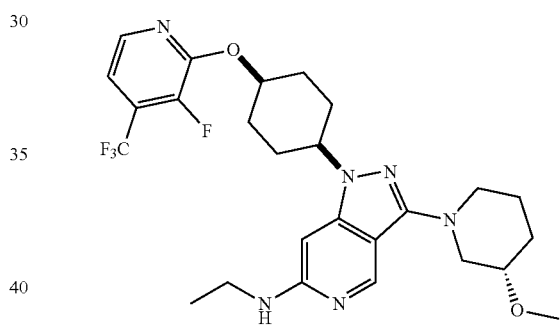
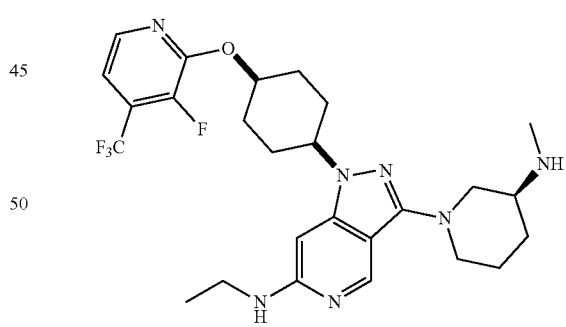
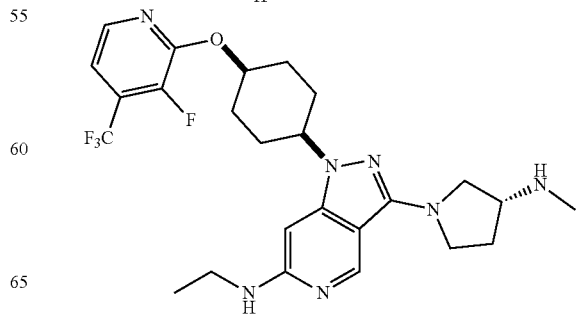

753
-continued
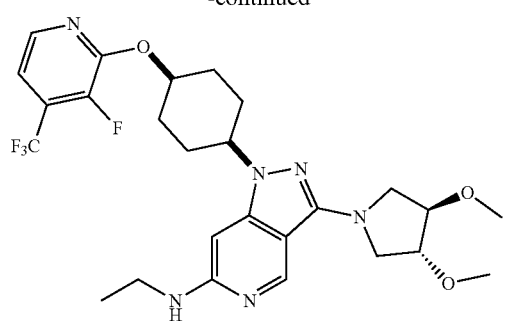
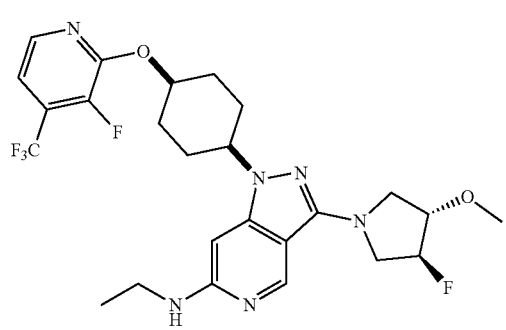
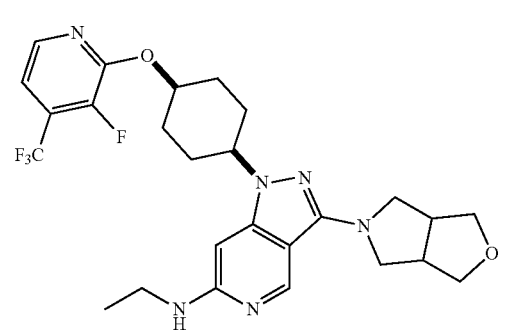
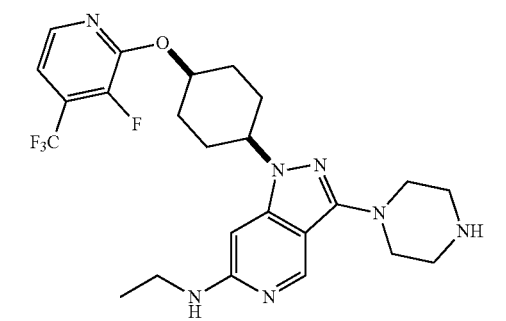
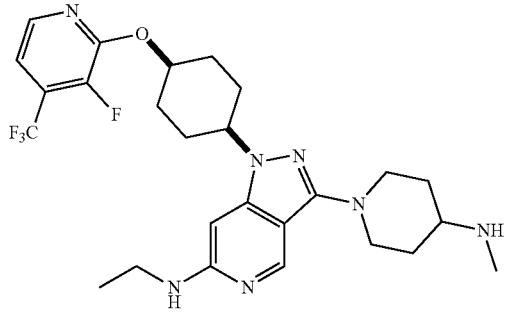
754
-continued
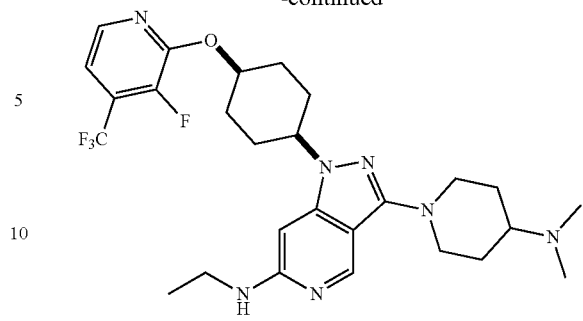
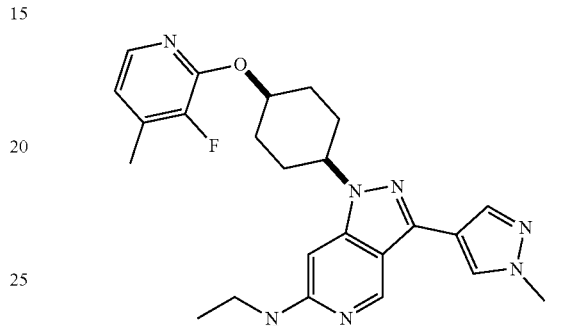
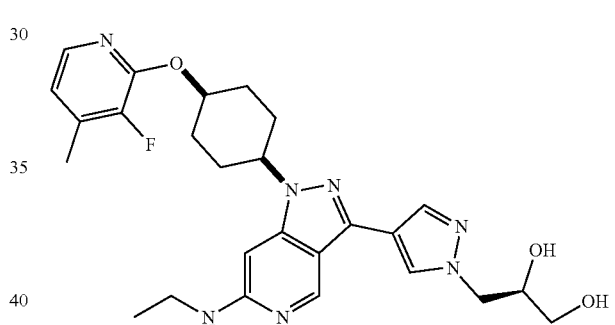
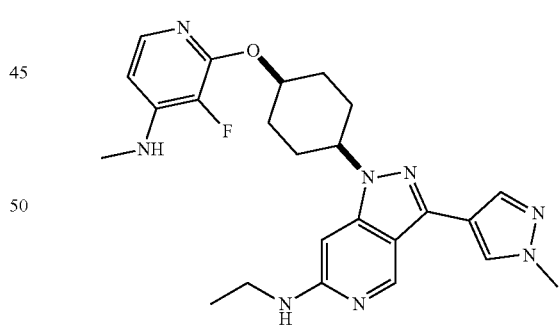
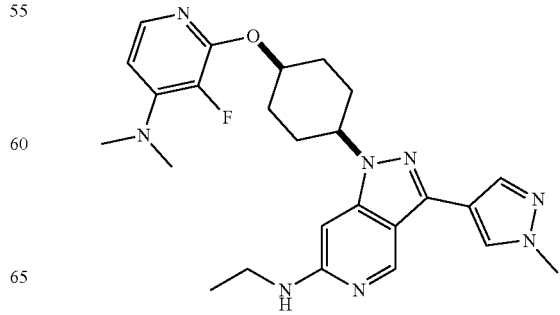

755
-continued
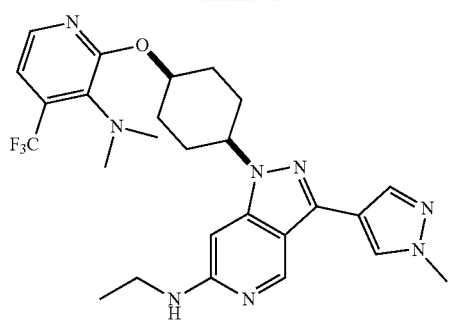
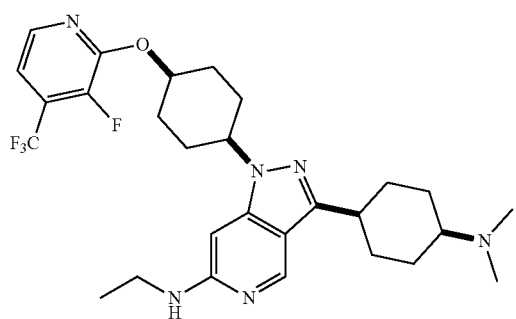
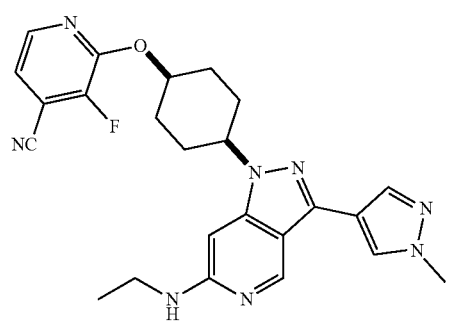
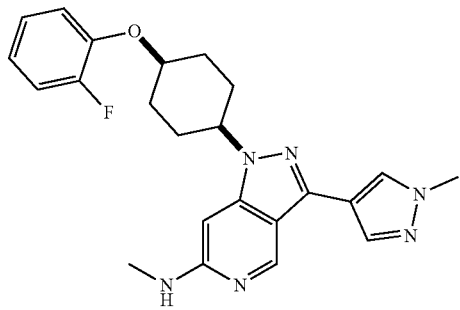
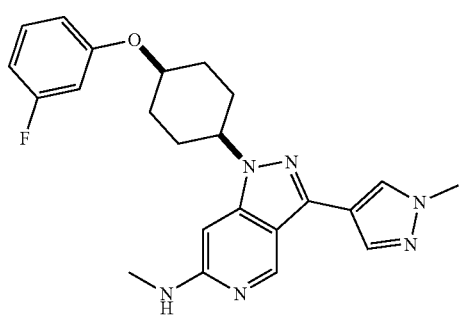
756
-continued
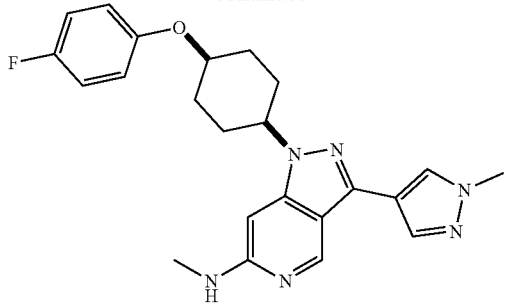
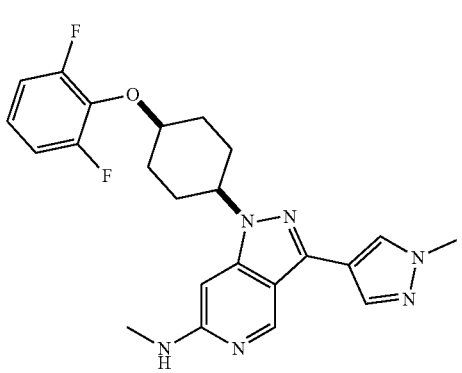
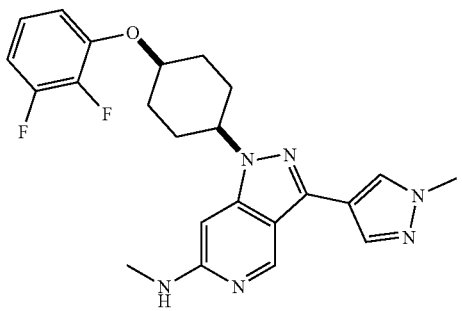
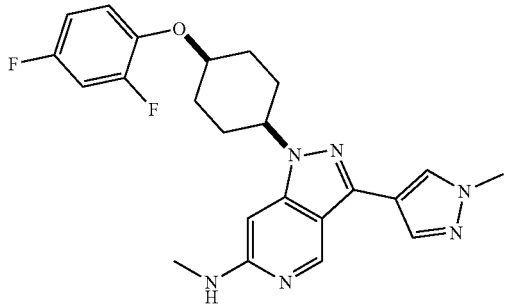
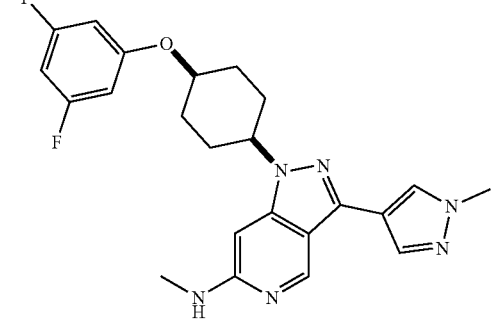

757
-continued
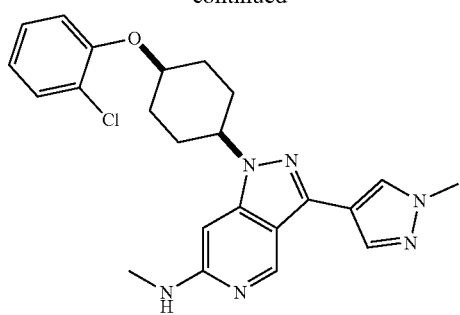
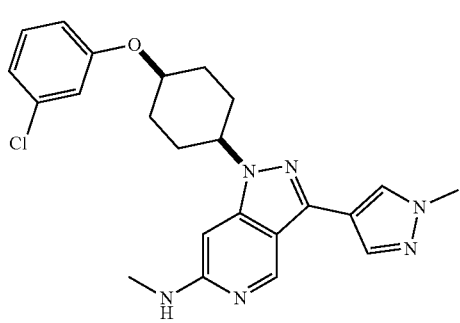
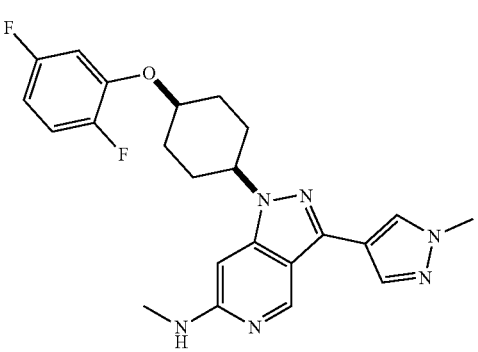
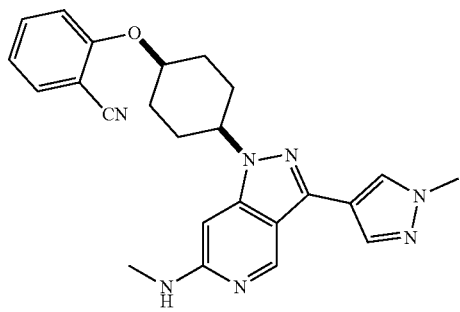
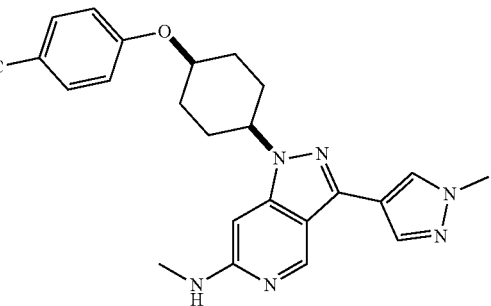
758
-continued
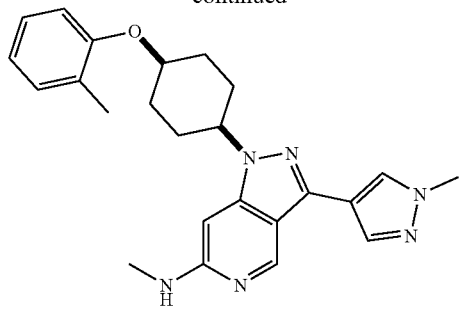
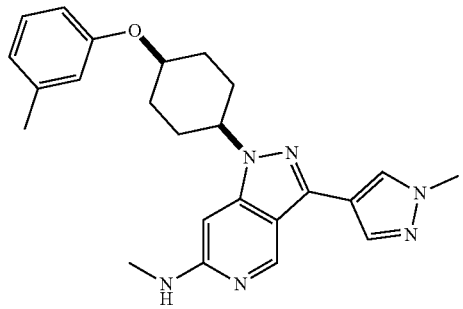
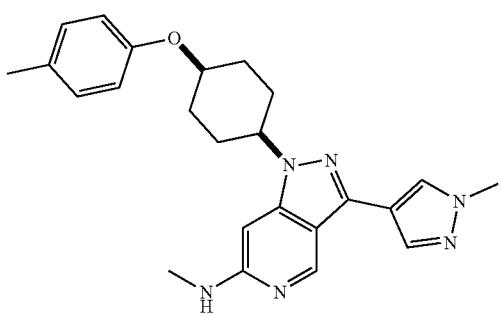
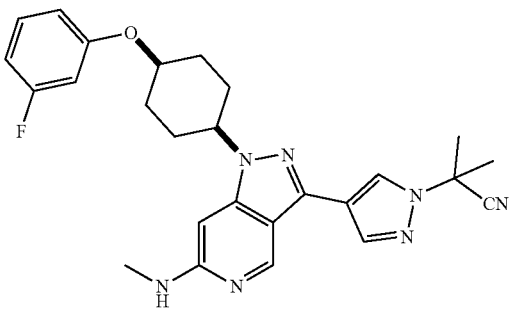
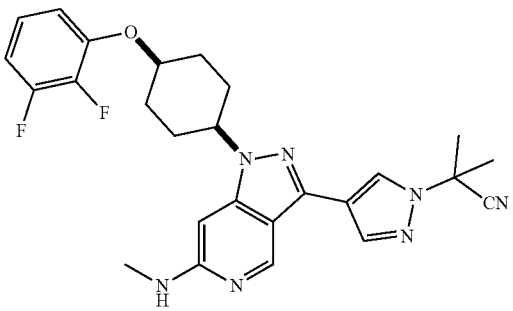

759
-continued
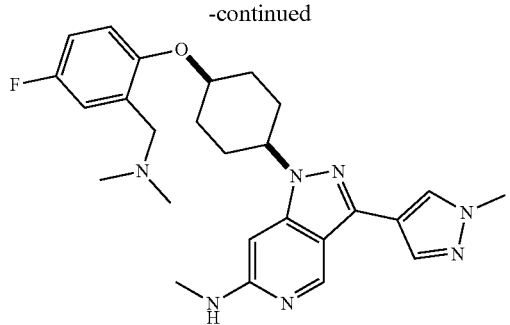
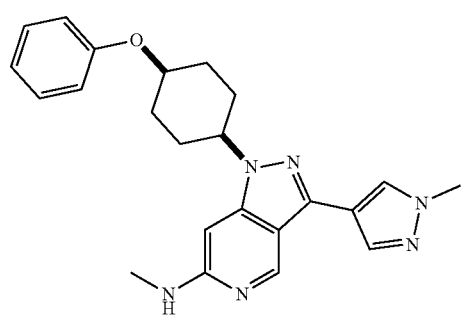
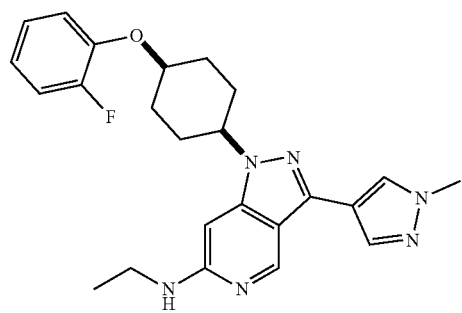
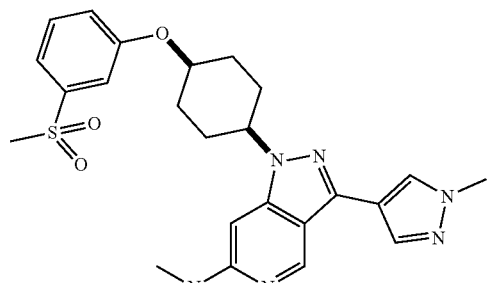
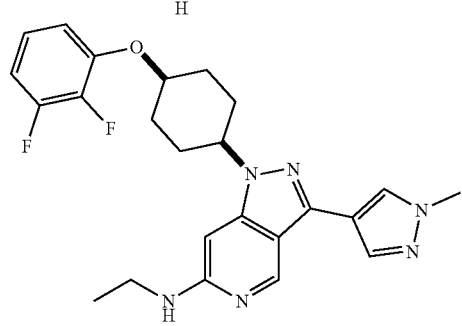
760
-continued
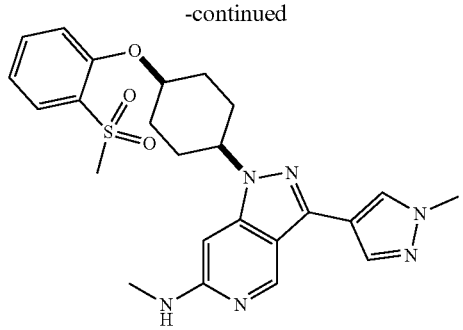
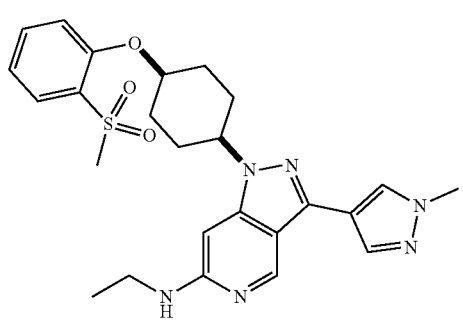
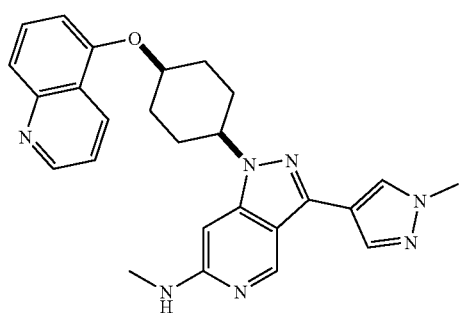
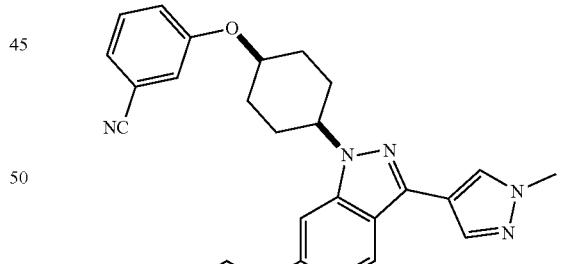
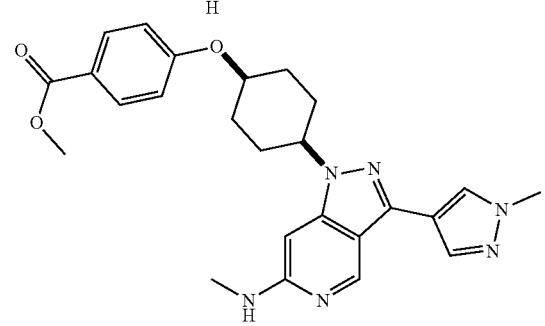

761
-continued
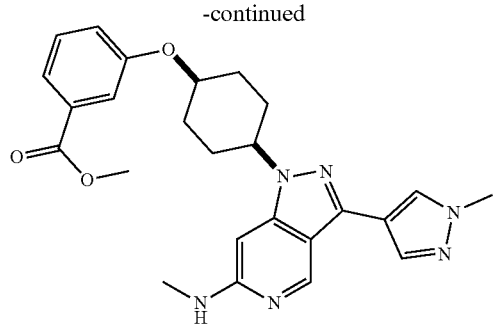
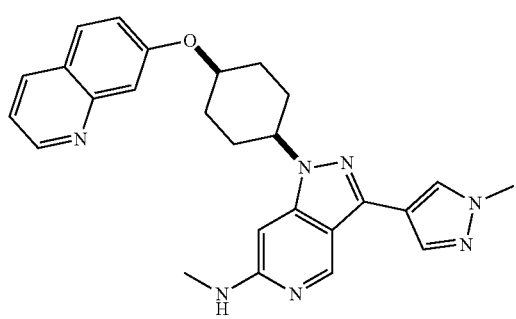
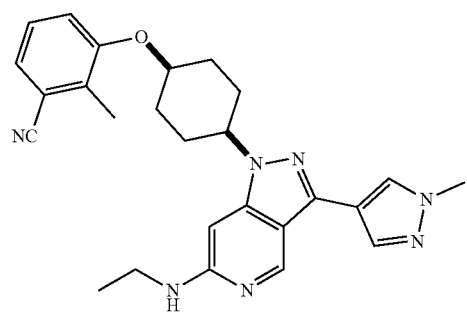
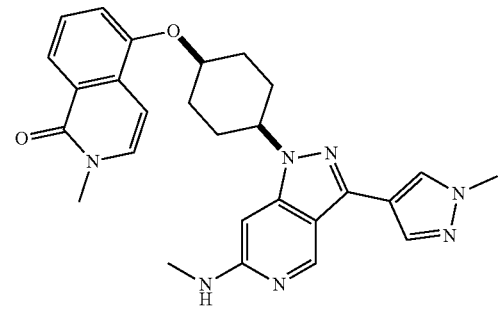
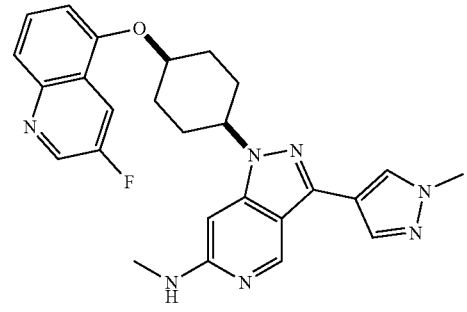
762
-continued
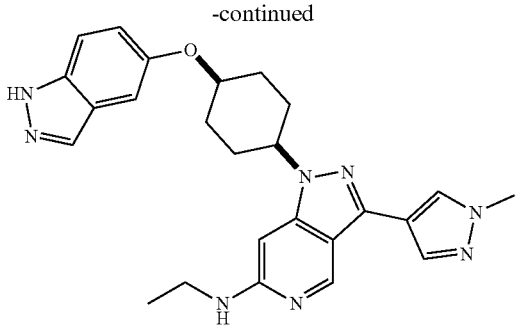
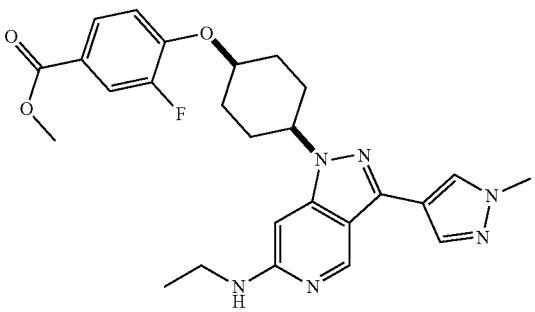
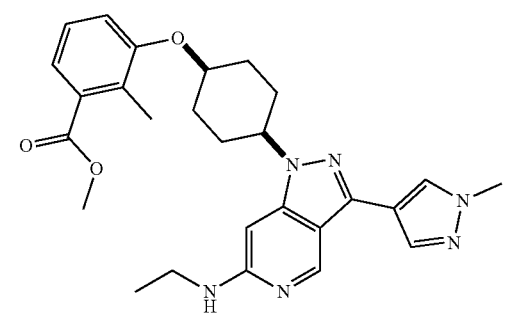
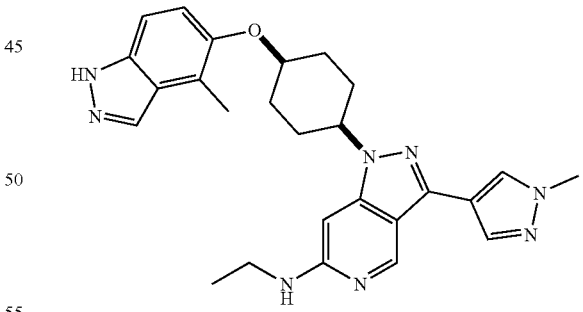
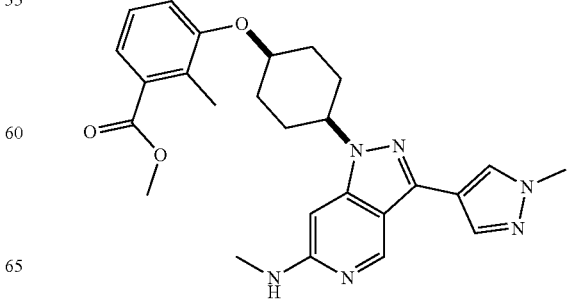

| 763 | 764 |
|---|---|
| -continued | -continued |
| 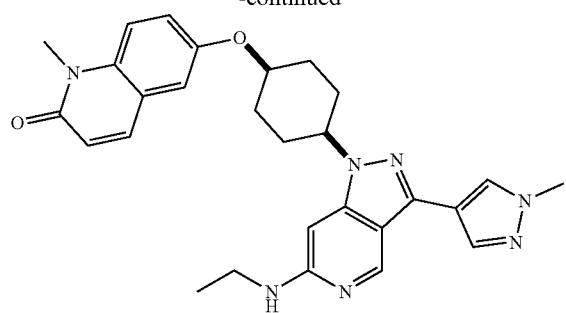 | 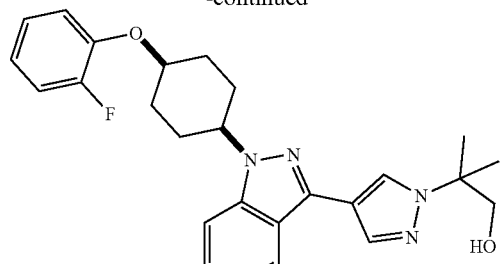 |
| 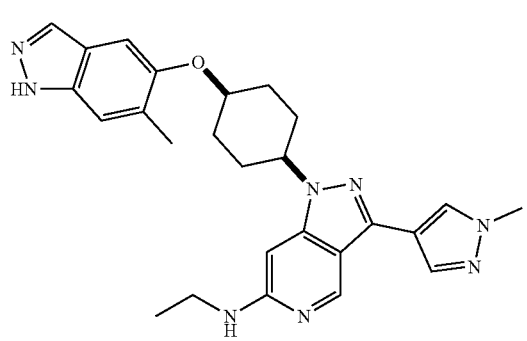 | 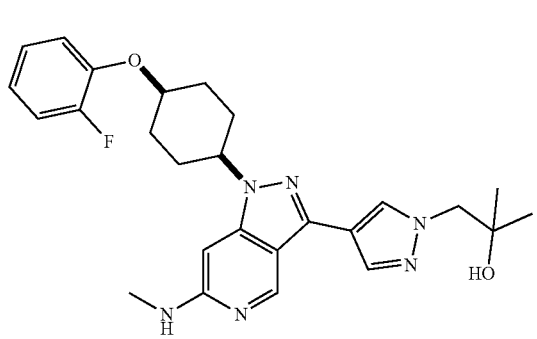 |
| 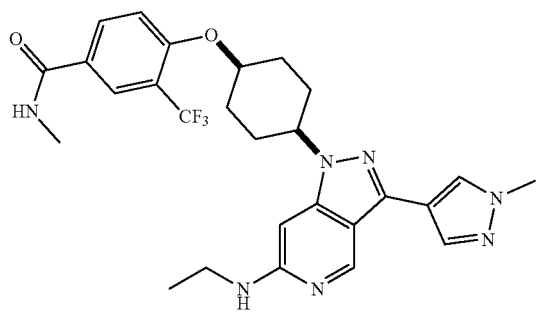 | 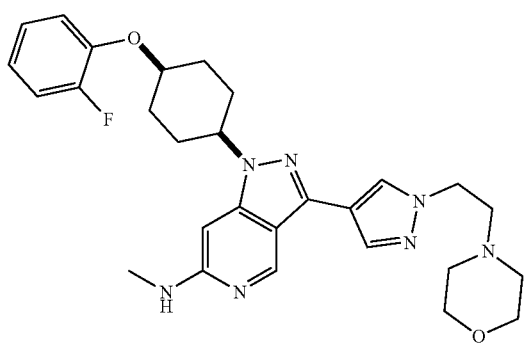 |
| 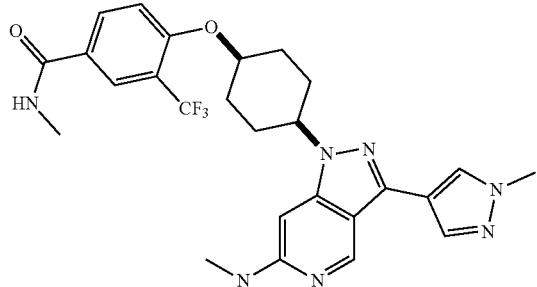 | 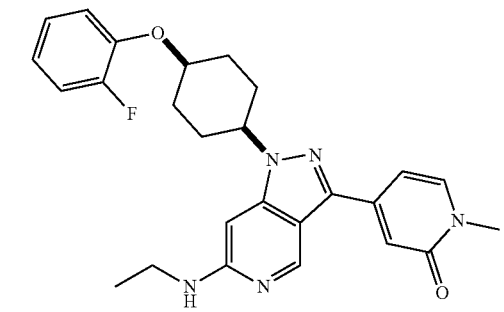 |
| 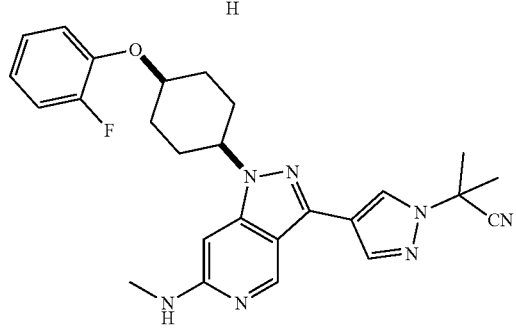 | 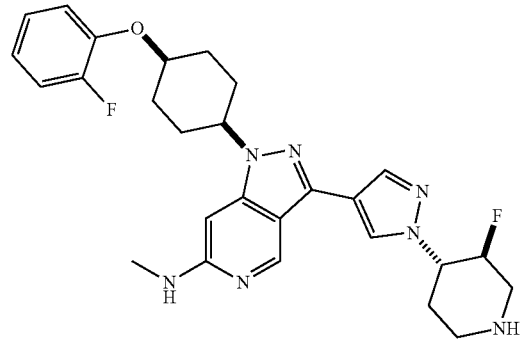 |

765
-continued
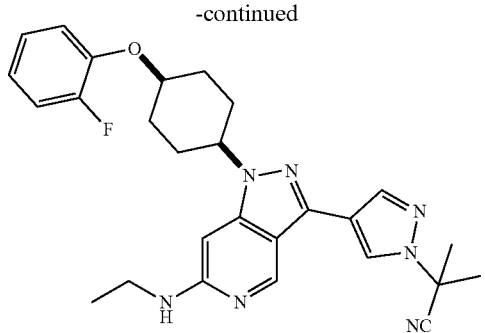
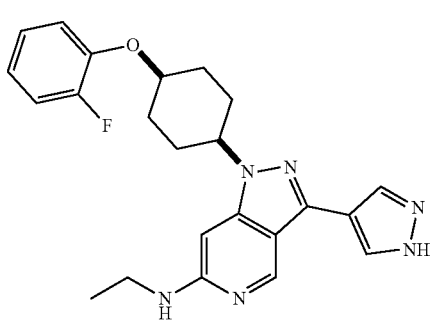
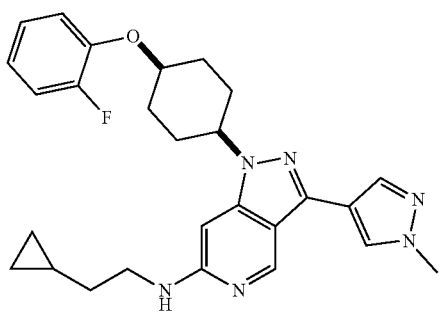
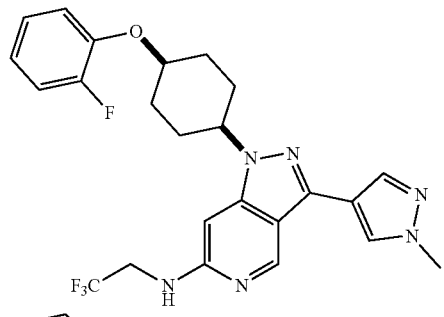
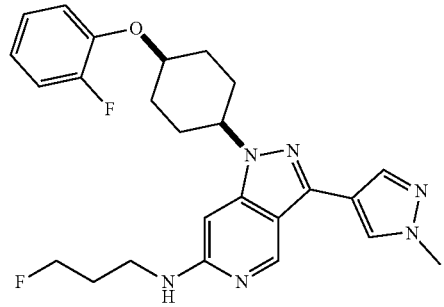
766
-continued
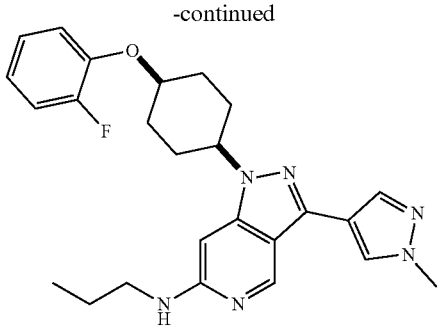
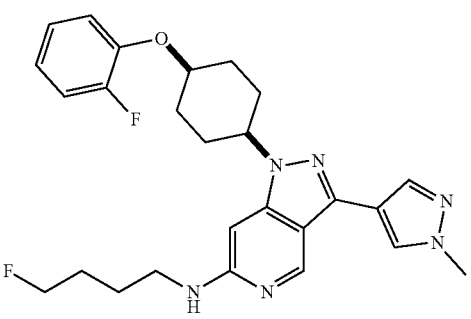
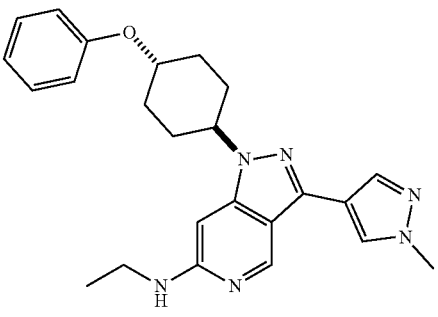
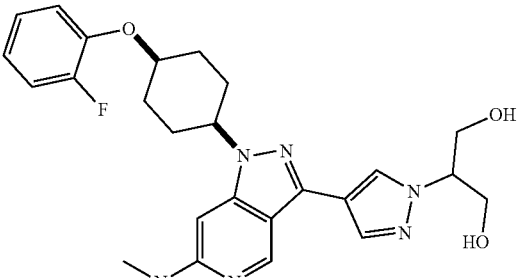
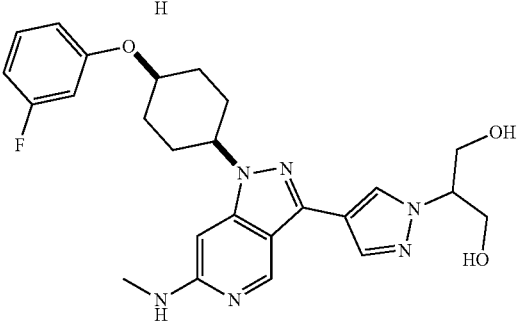

767 -continued
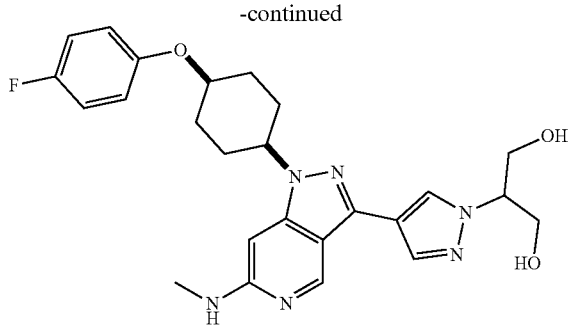
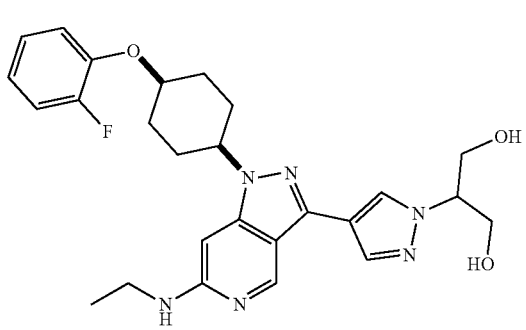
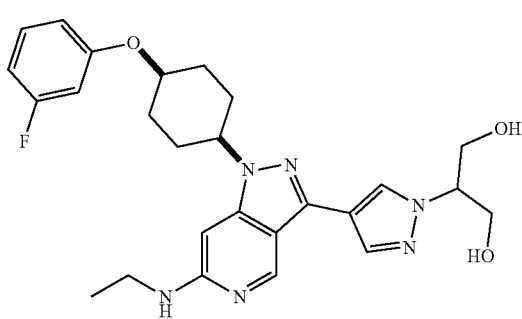
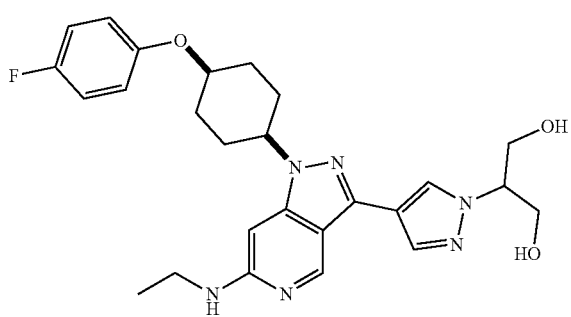
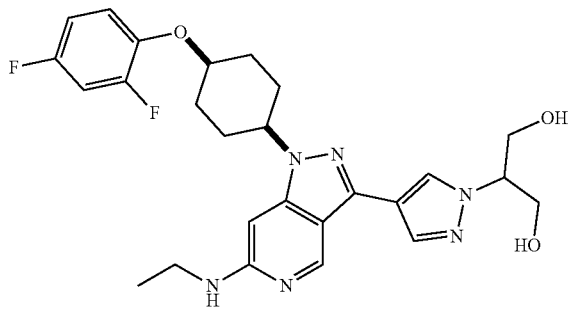
768 -continued
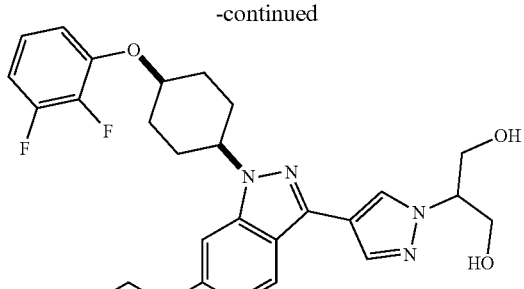
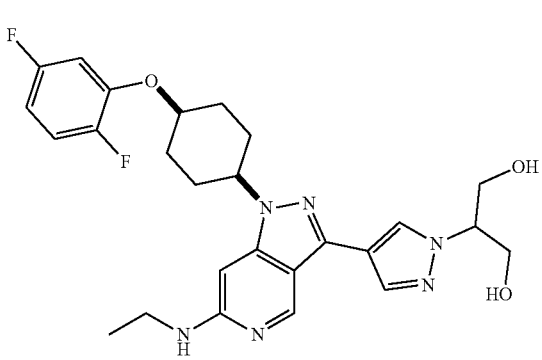
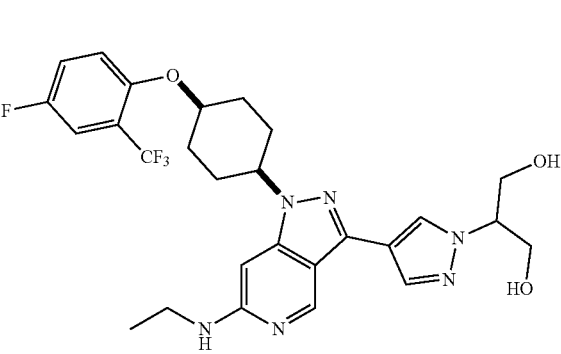
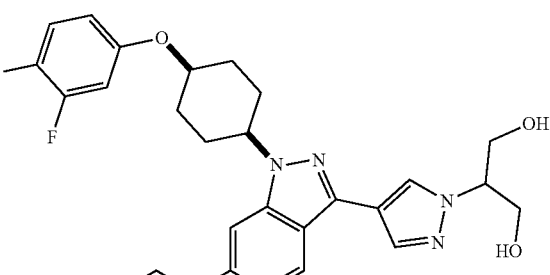
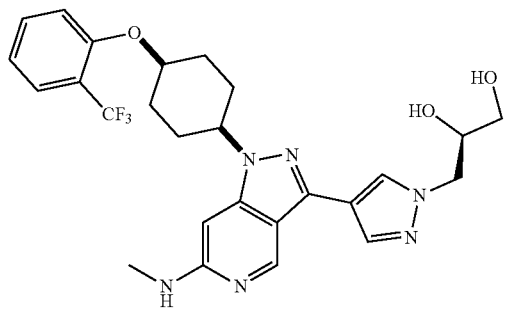

769
-continued
770
-continued
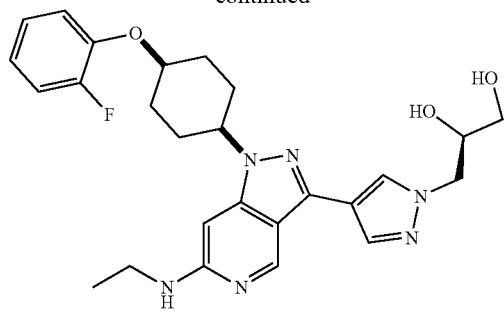
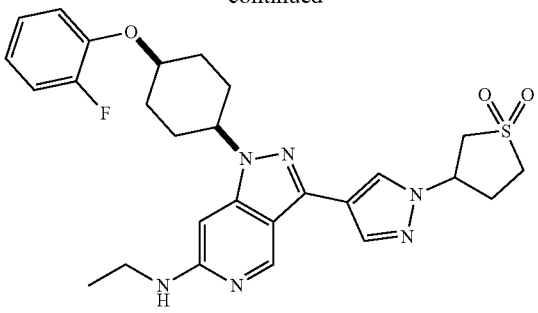
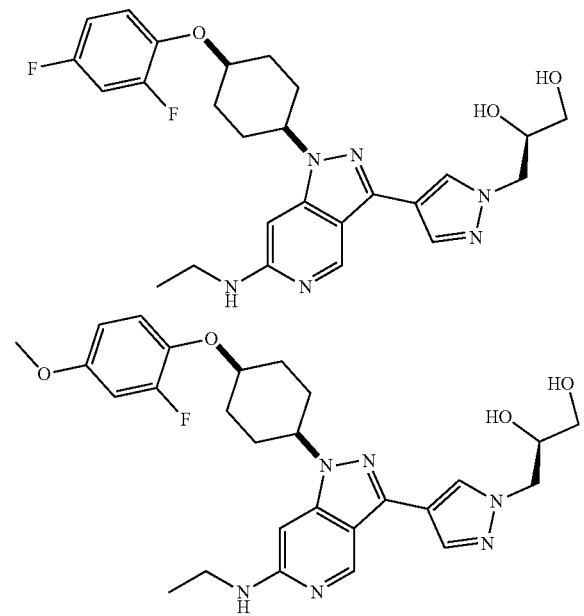
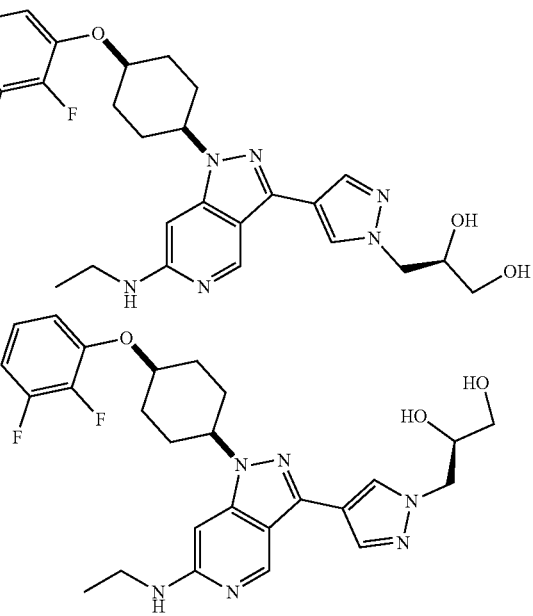

771
-continued
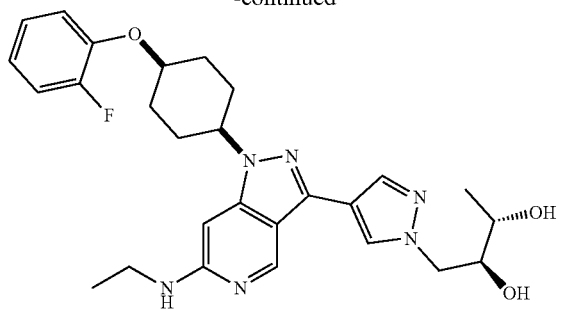
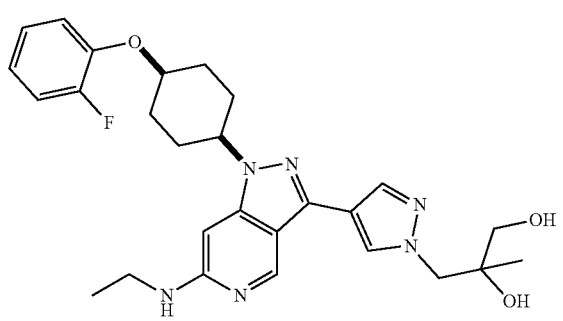
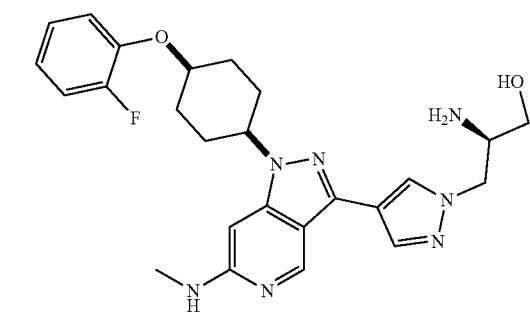
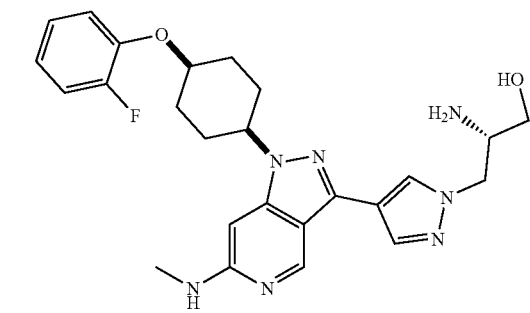
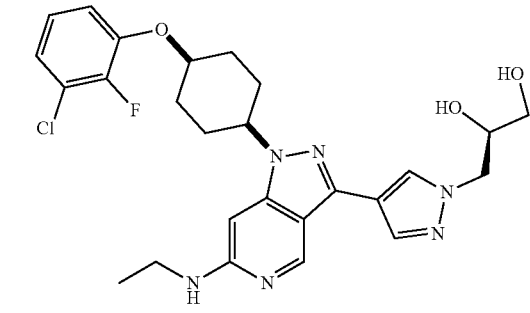
772
-continued
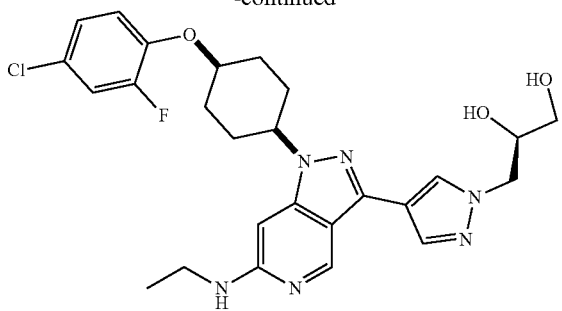
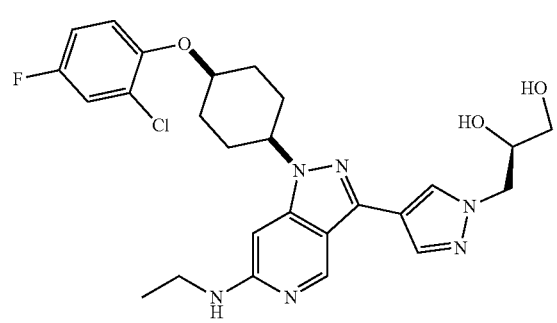
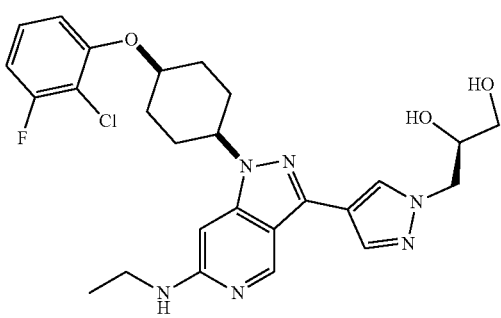
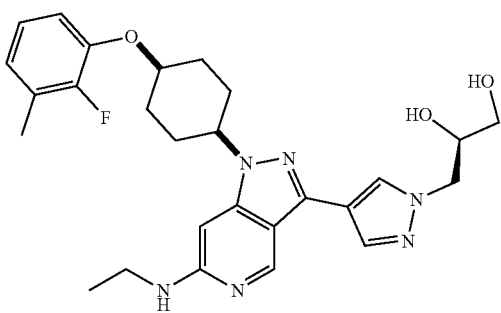
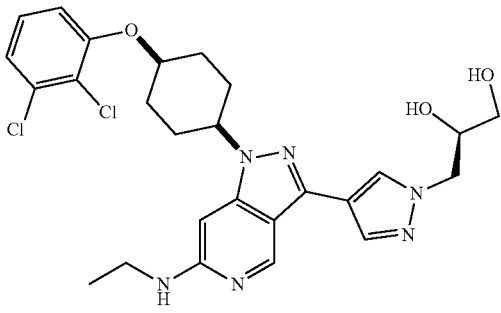

773
-continued
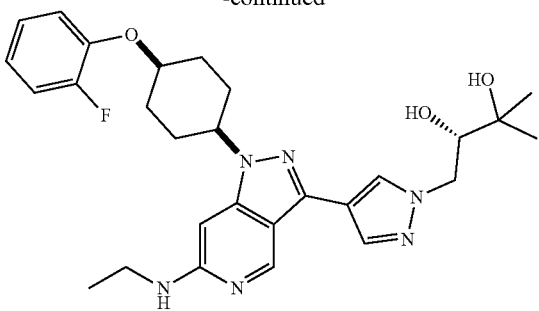
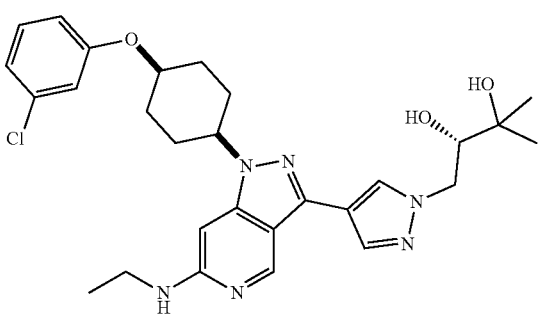
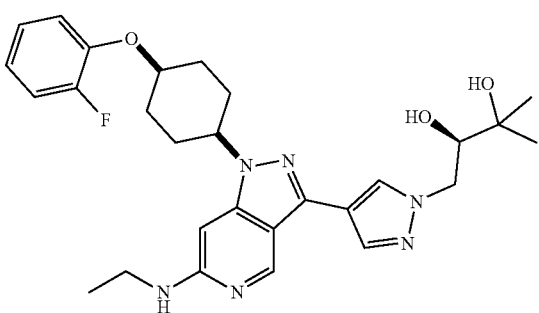
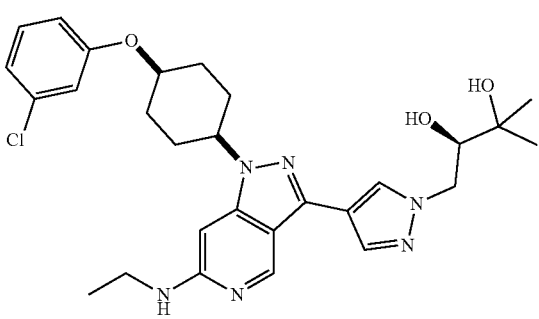
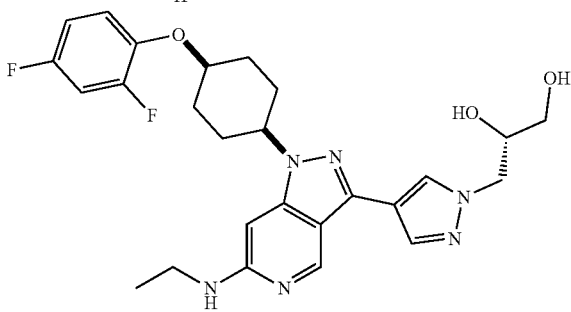
774
-continued
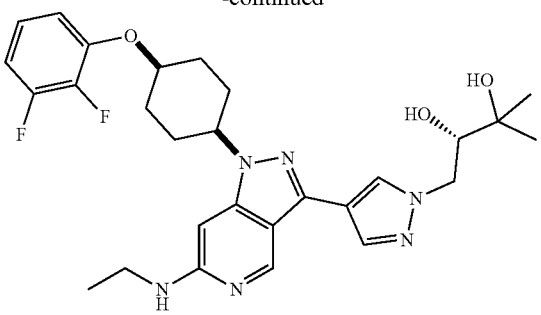
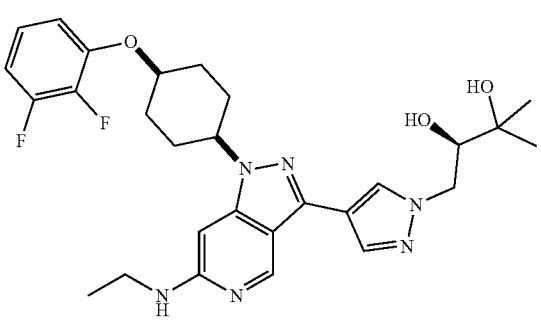
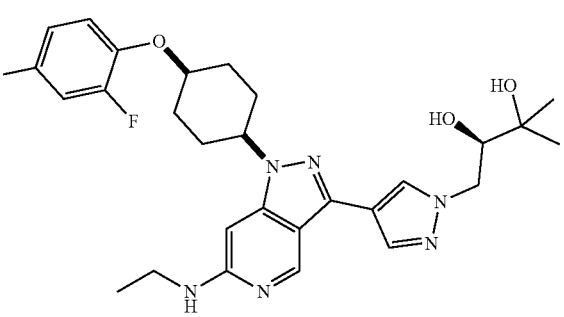
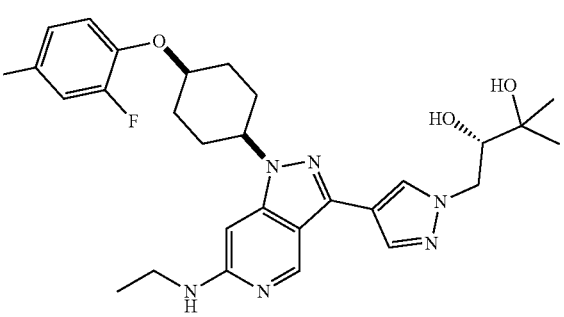
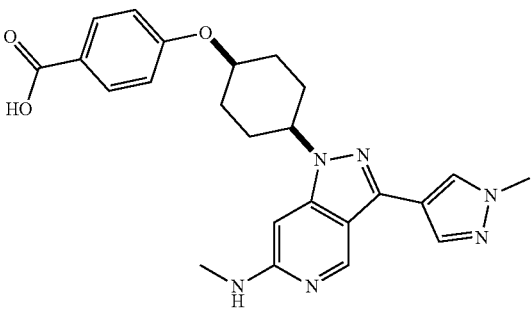

775
-continued
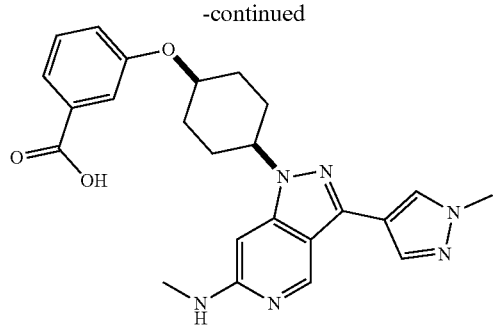
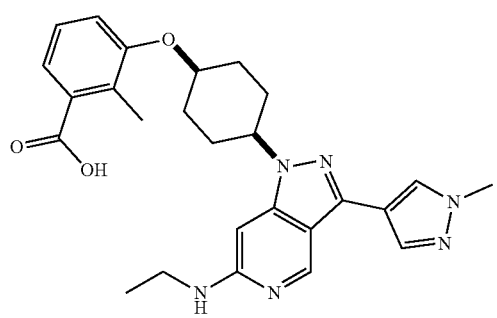
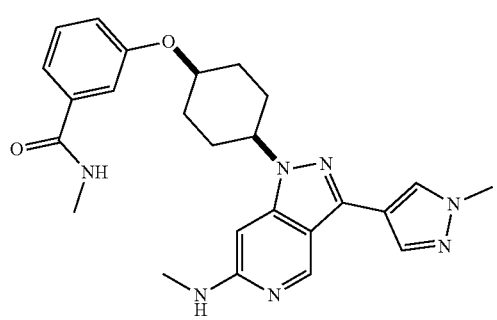
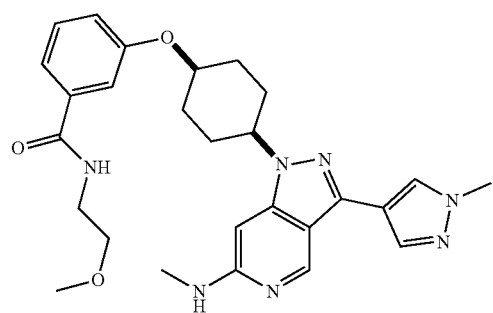
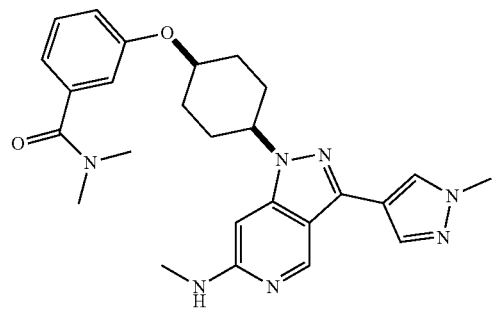
776
-continued
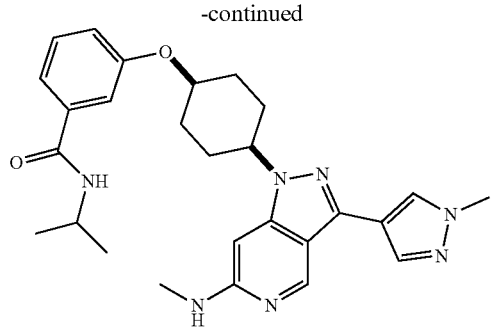
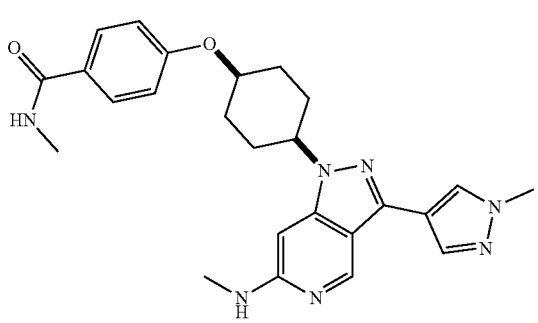
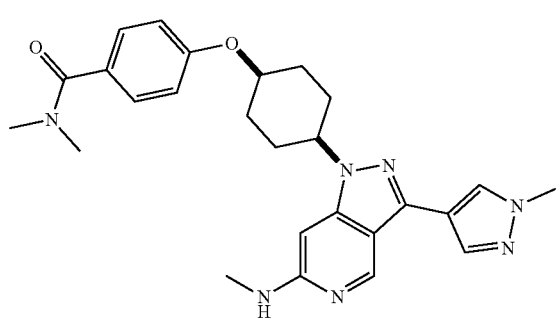
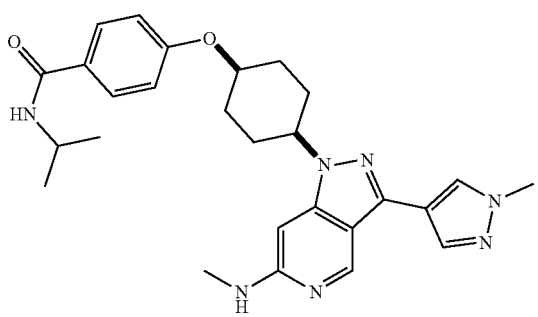
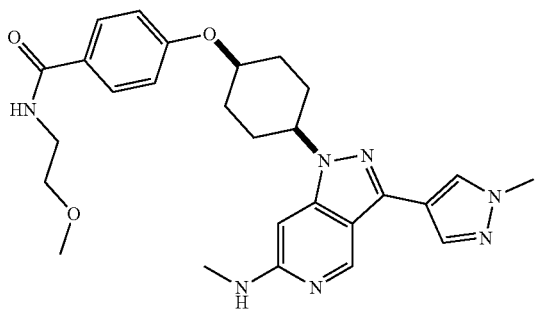

777
-continued
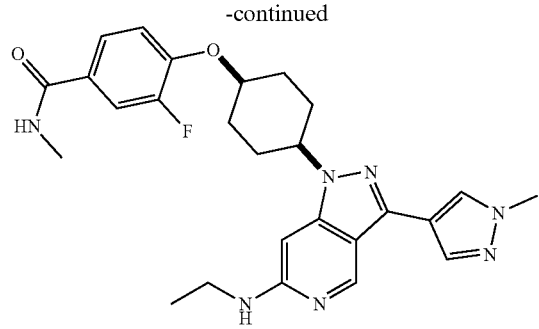
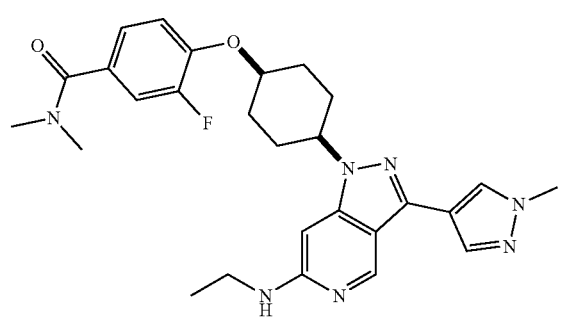
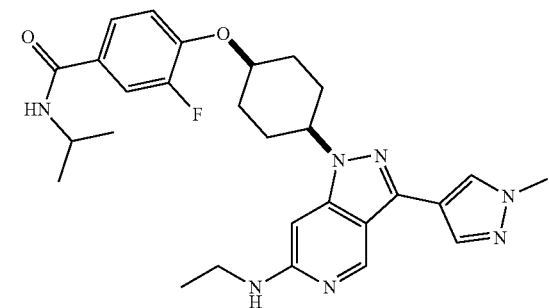
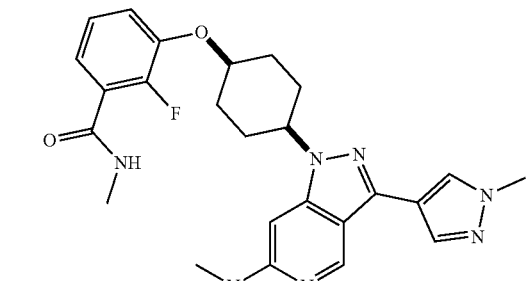
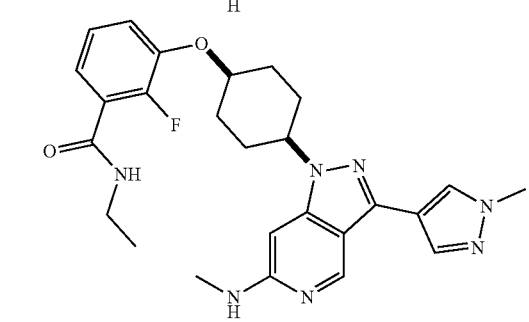
778
-continued
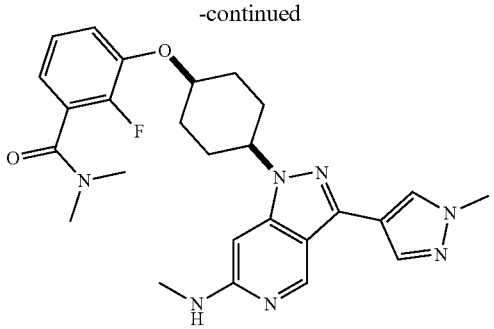
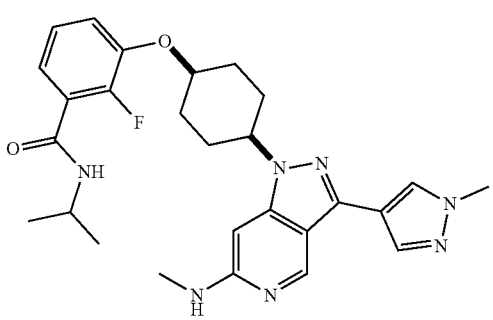
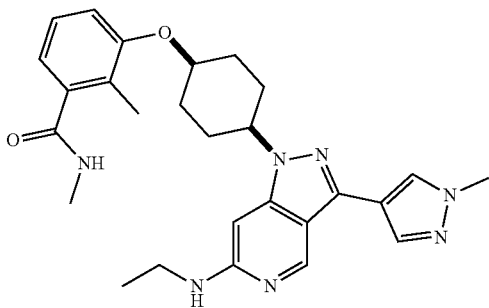
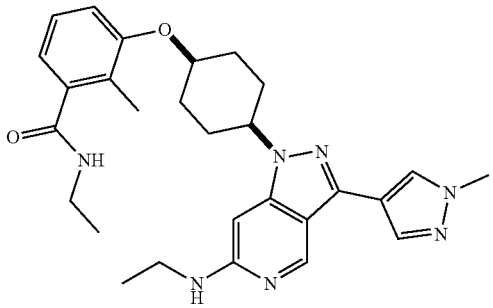
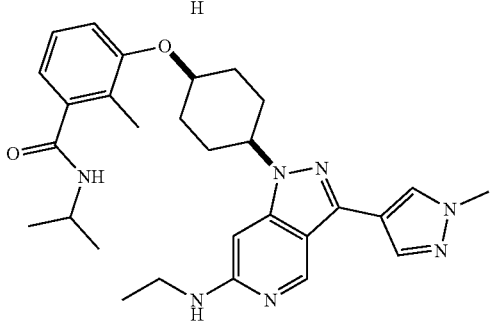

779
-continued
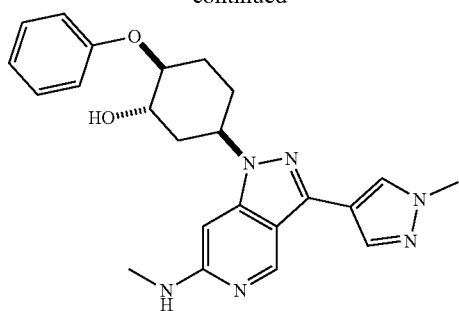
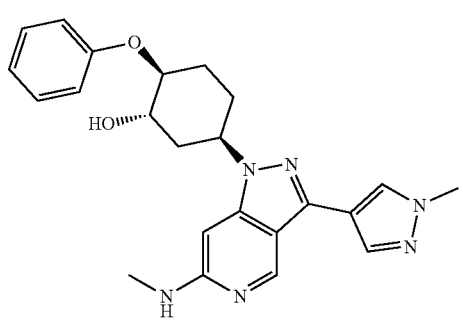
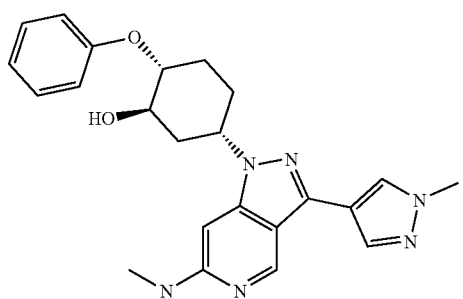
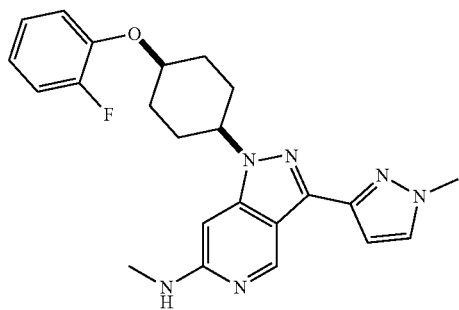
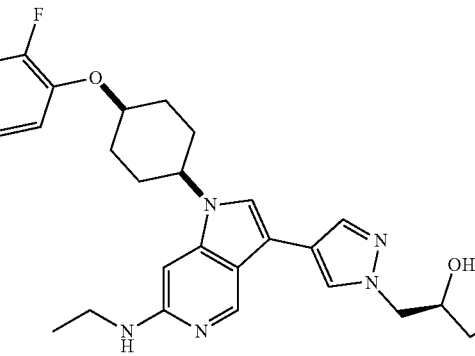
780
-continued
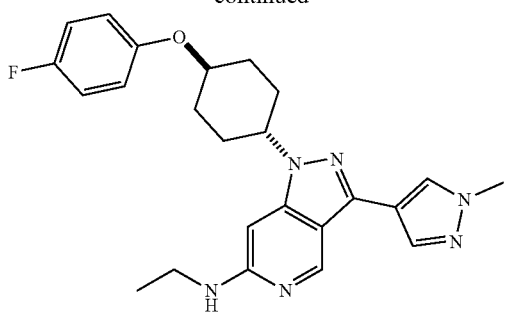
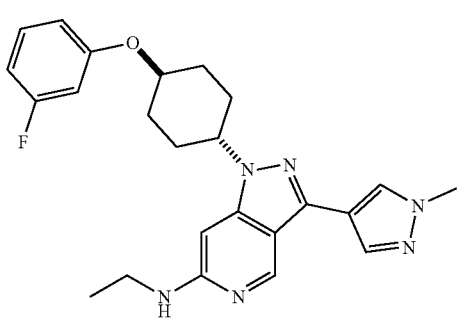
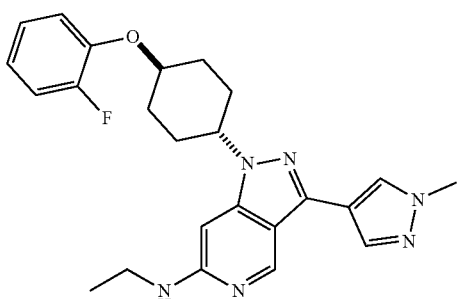
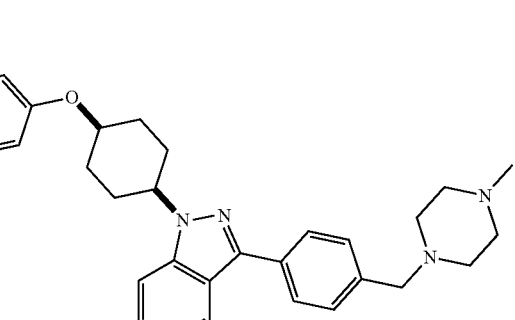
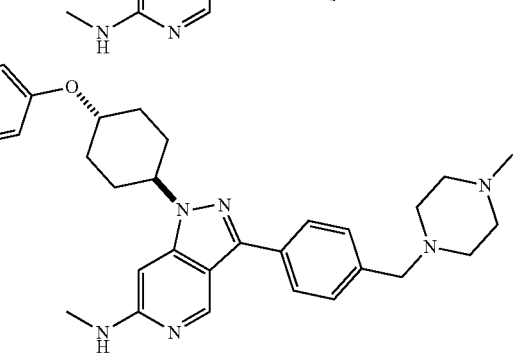

781
-continued
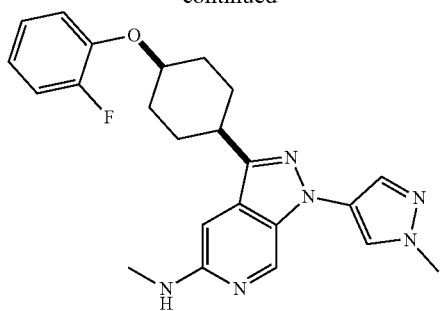
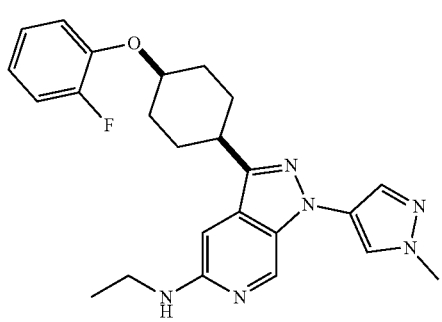
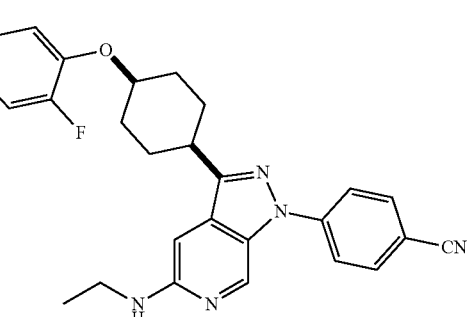
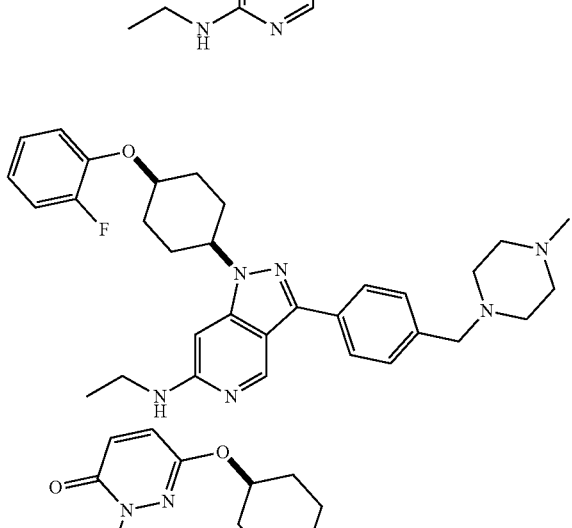
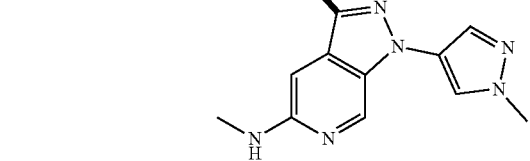
782
-continued
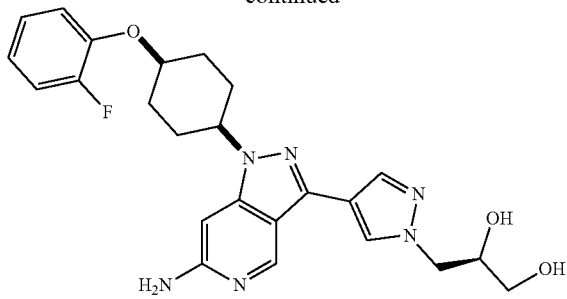
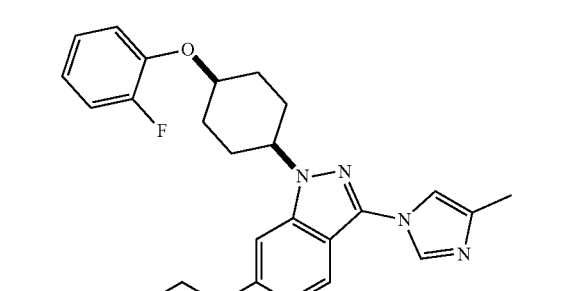
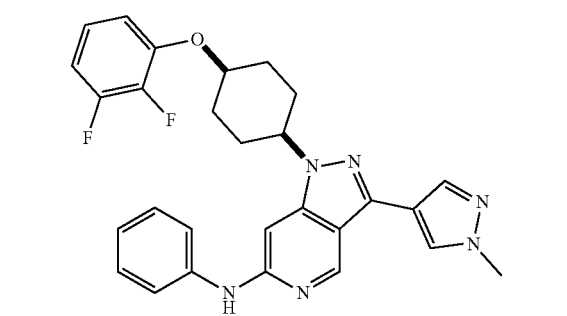
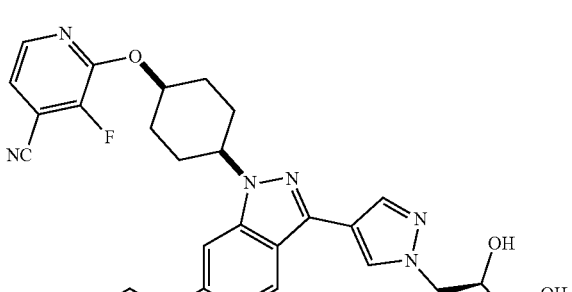
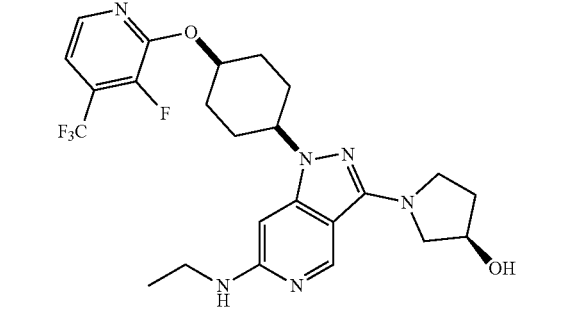

783
-continued
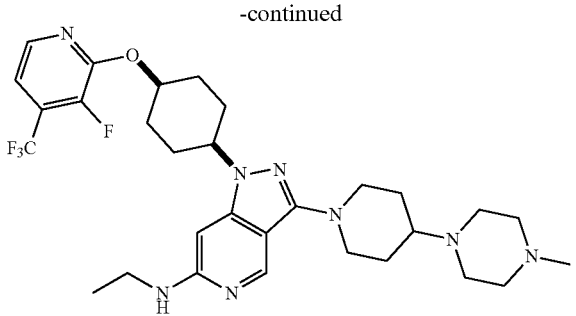
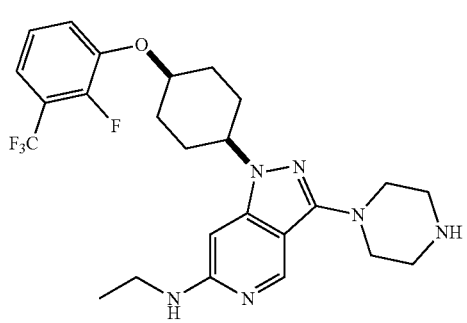
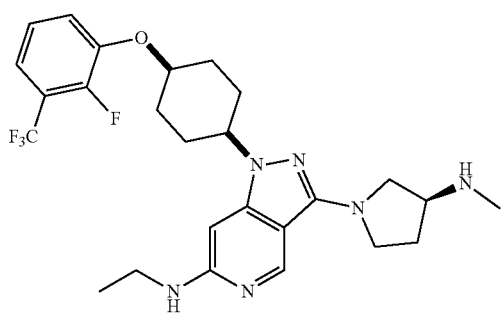
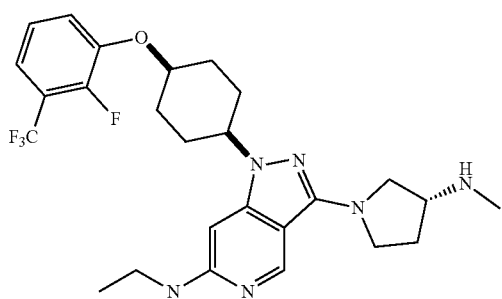
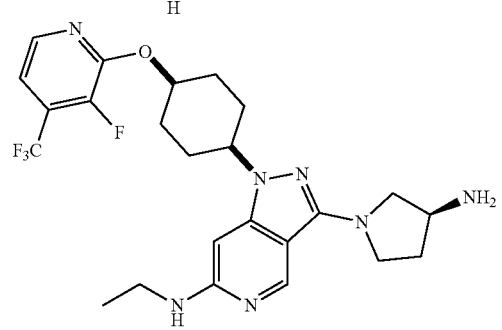
784
-continued
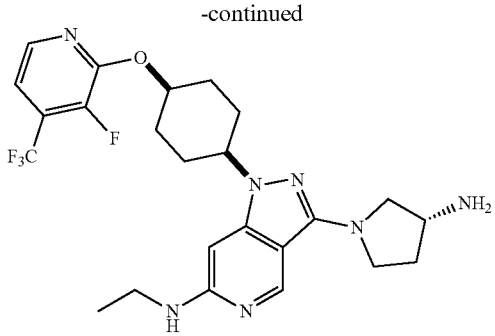
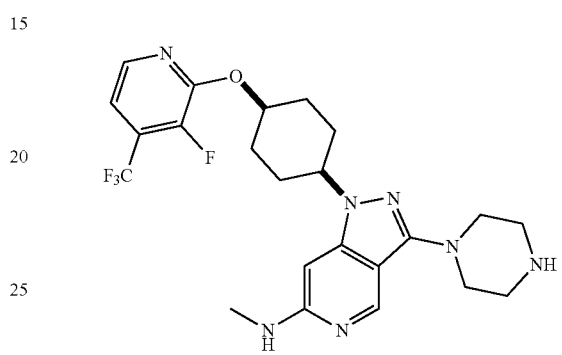
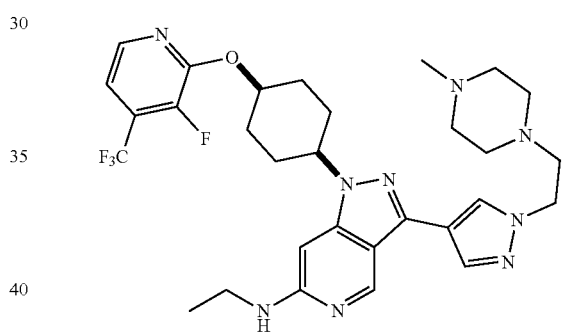
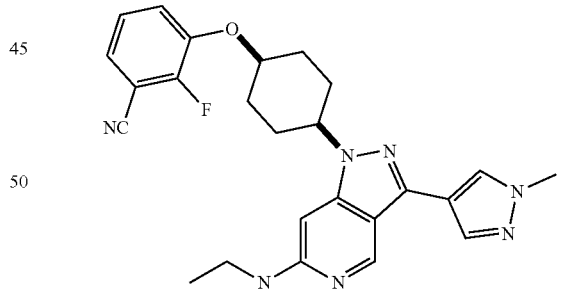
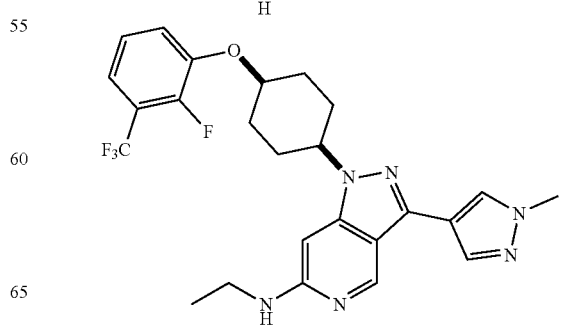

785
-continued
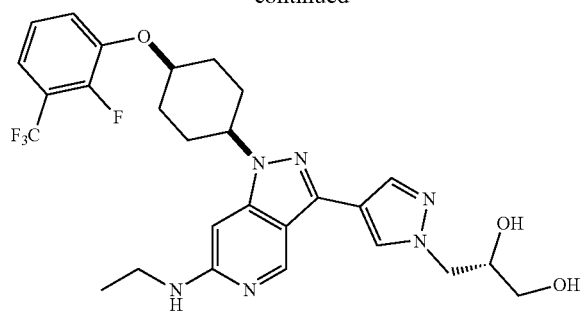
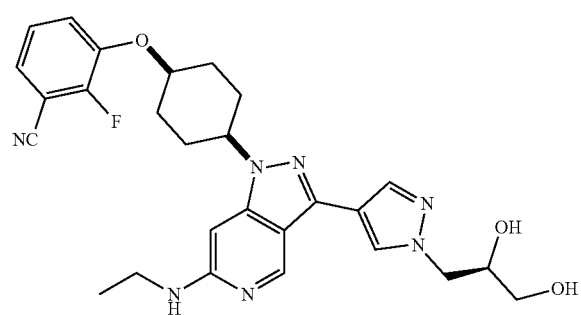
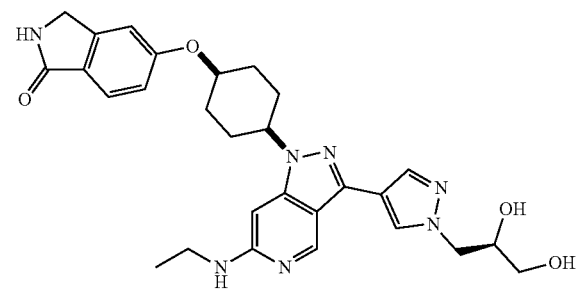
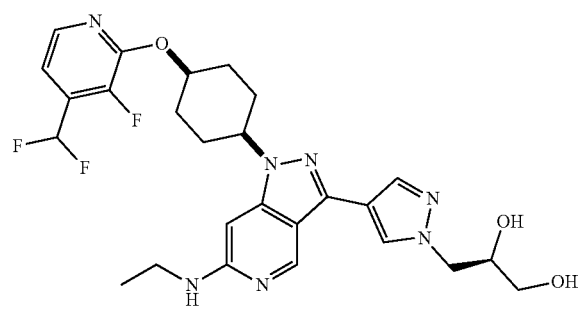
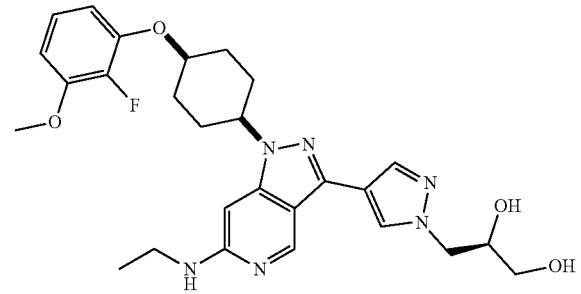
786
-continued
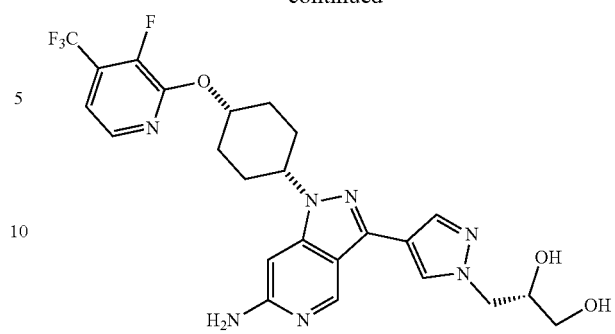
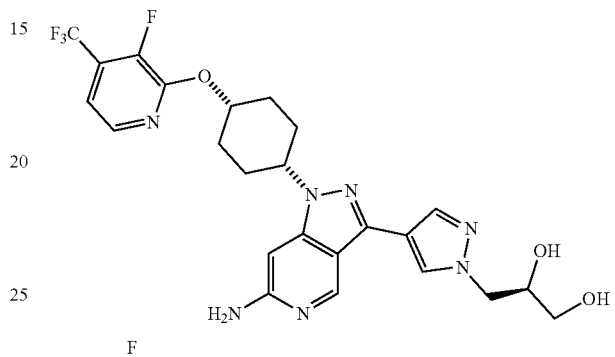
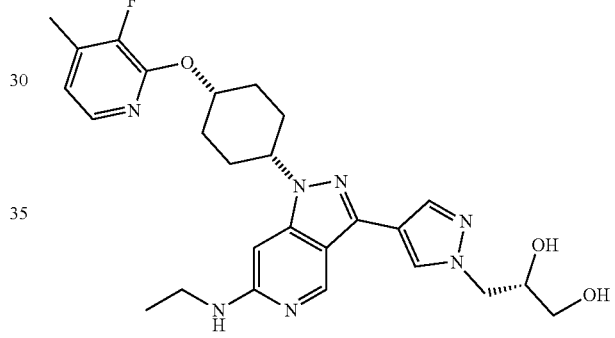
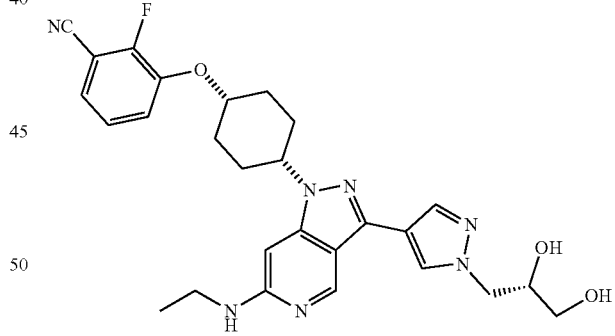
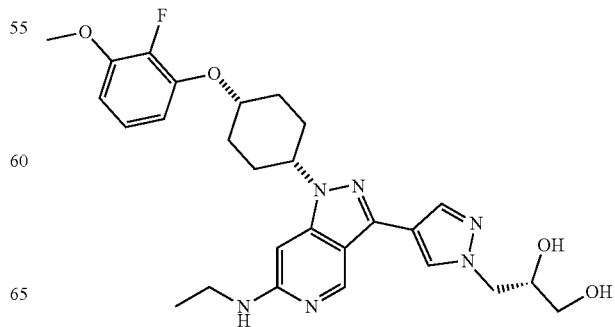

or a pharmaceutically acceptable salt thereof.

19. A pharmaceutical composition, comprising a compound of claim 1 or a pharmaceutically acceptable salt thereof, and a pharmaceutically acceptable diluent or carrier.

20. A process for preparing a compound of Formula I according to claim 1, comprising:
(a) for a compound of Formula I wherein $X^1$ is N, $X^2$ is N or CH, $X^3$ is C, $R^3$ is H, and Ring A, $R^1$ and $R^2$ are as defined in claim 1, reacting a corresponding compound of formula 5 wherein $X^2$ is N, $R^3$ is hydrogen, and $R^1$ and $R^2$ are as defined in claim 1, with a reagent having the formula C wherein Ring A is a defined in claim 1, in the presence of triphenylphosphine and diisopropyl azodicarboxylate; or
(b) for a compound of Formula I wherein $X^1$ is N, $X^2$ is N or CH, $X^3$ is C, $R^3$ is H, and Ring A, $R^1$ and $R^2$ are as defined in claim 1, reacting a corresponding compound of formula 11 wherein $X^2$ is N, $R^3$ is hydrogen, and $R^1$, $R^2$ and Ring A are as defined in claim 1, with a reagent having the formula $R^2$—$NH_2$ wherein $R^2$ is as defined in claim 1, at elevated temperature; or
(c) for a compound of Formula I wherein $X^1$ is N, $X^2$ is N or CH, $X^3$ is C, $R^3$ is H, and Ring A, $R^1$ and $R^2$ are as defined in claim 1, reacting a corresponding compound of formula 11 wherein $X^2$ is N, $R^3$ is hydrogen, and $R^1$, $R^2$ and Ring A are as defined in claim 1, with a reagent having the formula $R^2$—NH—$P^2$ wherein $P^2$ is an amino protecting group and $R^2$ is as defined in claim 1, in the presence of a palladium catalyst, followed by removal of the amino protecting group $P^2$; or (d) for a compound of Formula I wherein $X^1$ is N, $X^2$ is N or CH, $X^3$ is C, $R^3$ is H, and Ring A, $R^1$ and $R^2$ are as defined in claim 1, reacting a corresponding compound of formula 12a or 12b

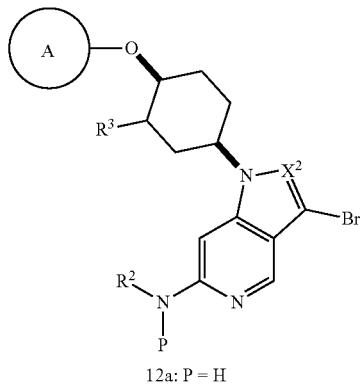

12a: P = H wherein P of compound 12a is hydrogen, $P^2$ of compound 12b is an amino protecting group, $R^3$ is hydrogen, $X^2$ is nitrogen, and Ring A and $R^2$ are as defined in claim 1, with a boronic ester having the formula $R^1$—$B(OR^x)(OR^y)$, where $R^1$ is as defined in claim 1 and $R^x$ and $R^y$ are H or C1-C6 alkyl, or $R^x$ and $R^y$ together with the atoms to which they are connected form a 5-6 membered ring optionally substituted with 1-4 substituents selected from C1-C3 alkyl, in the presence of a palladium catalyst; or (e) for a compound of Formula I wherein $X^1$ is N, $X^2$ is N or CH, $X^3$ is C, $R^3$ is H, and Ring A, $R^1$ and $R^2$ are as defined in claim 1, reacting a corresponding compound of formula 12b 12b: P = $P^2$ wherein $P^2$ is an amino protecting group, $R^3$ is hydrogen, $X^2$ is nitrogen, and Ring A and $R^2$ are as defined in claim 1, with a boronic ester having the formula $R^1$—$B(OR^x)(OR^y)$, where $R^1$ is as defined in claim 1 and $R^x$ and $R^y$ are H or C1-C6 alkyl, or $R^x$ and $R^y$ together with the atoms to which they are connected form a 5-6 membered ring optionally substituted with 1-4 substituents selected from C1-C3 alkyl, in the presence of a palladium catalyst, followed by removal of the amino protecting group; or (f) for a compound of Formula I wherein $X^1$ is N, $X^2$ is N or CH, $X^3$ is C, $R^3$ is H, and Ring A, $R^1$ and $R^2$ are as defined in claim 1, reacting a compound of formula 15

15 wherein $X^2$ is N, $P^2$ is an amino protecting group, and $R^1$ and $R^2$ are as defined in claim 1, with a compound having the formula 18

18 wherein $R^3$ is hydrogen and Ring A is as defined in claim 1, in the presence of a base, followed by removal of the amino protecting group $P^2$; or (g) for a compound of Formula I wherein $X^1$ is C, $X^2$ is N, $X^3$ is N, $R^3$ is H, and Ring A, $R^1$ and $R^2$ are as defined in claim 1, reacting a compound of formula 33

33 wherein $P^2$ is an amino protecting group, $R^3$ is hydrogen, and $R^3$ and Ring A are as defined in claim 1, with a reagent having the formula X—$R^1$ wherein X is a leaving group or atom, in the presence of a copper catalyst and a base, followed by removal of the $P^2$ protecting group; or (h) for a compound of Formula I wherein $X^1$ is N, $X^2$ is N or CH, $X^3$ is C, $R^3$ is hydroxyl, and $R^1$, $R^2$, and Ring A are as defined in claim 1, reacting a compound of formula 37

37 wherein $X^2$ is N or CH, and $R^1$ and Ring A are as defined in claim 1, with a reagent having the formula $R^2$—NH—$P^2$ wherein $R^2$ is as defined in claim 1 and $P^2$ is an amino protecting group, in the presence of a palladium catalyst, followed by removal of the $P^2$ protecting group; and removing any additional protecting groups if present and optionally forming a pharmaceutically acceptable salt thereof.

\* \* \* \* \*